US010683353B2

United States Patent
Wang et al.

(10) Patent No.: US 10,683,353 B2
(45) Date of Patent: Jun. 16, 2020

(54) COILED COIL IMMUNOGLOBULIN FUSION PROTEINS AND COMPOSITIONS THEREOF

(71) Applicant: THE SCRIPPS RESEARCH INSTITUTE, La Jolla, CA (US)

(72) Inventors: Feng Wang, Carlsbad, CA (US); Yong Zhang, Temple City, CA (US); Yan Liu, San Diego, CA (US); Peter G. Schultz, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 140 days.

(21) Appl. No.: 14/903,492

(22) PCT Filed: Jul. 11, 2014

(86) PCT No.: PCT/US2014/046419
§ 371 (c)(1),
(2) Date: Jan. 7, 2016

(87) PCT Pub. No.: WO2015/006736
PCT Pub. Date: Jan. 15, 2015

(65) Prior Publication Data
US 2016/0159920 A1 Jun. 9, 2016

Related U.S. Application Data

(60) Provisional application No. 62/017,713, filed on Jun. 26, 2014, provisional application No. 61/925,904, filed on Jan. 10, 2014, provisional application No. 61/845,280, filed on Jul. 11, 2013, provisional application No. 61/845,287, filed on Jul. 11, 2013.

(51) Int. Cl.
| | |
|---|---|
| *A61K 39/395* | (2006.01) |
| *C07K 16/28* | (2006.01) |
| *C07K 14/505* | (2006.01) |
| *C07K 14/535* | (2006.01) |
| *C07K 14/575* | (2006.01) |
| *C07K 14/435* | (2006.01) |
| *C07K 14/61* | (2006.01) |
| *C07K 16/10* | (2006.01) |
| *C07K 14/705* | (2006.01) |
| *A61K 47/65* | (2017.01) |
| *A61K 47/68* | (2017.01) |
| *C07K 16/32* | (2006.01) |
| *C07K 14/47* | (2006.01) |
| *C07K 14/605* | (2006.01) |
| *C07K 14/64* | (2006.01) |
| *C07K 14/81* | (2006.01) |
| *A61K 39/00* | (2006.01) |

(52) U.S. Cl.
CPC ........ *C07K 16/2863* (2013.01); *A61K 39/395* (2013.01); *A61K 47/65* (2017.08); *A61K 47/6889* (2017.08); *C07K 14/43522* (2013.01); *C07K 14/47* (2013.01); *C07K 14/505* (2013.01); *C07K 14/535* (2013.01); *C07K 14/5759* (2013.01); *C07K 14/57563* (2013.01); *C07K 14/605* (2013.01); *C07K 14/61* (2013.01); *C07K 14/64* (2013.01); *C07K 14/70503* (2013.01); *C07K 14/811* (2013.01); *C07K 16/1027* (2013.01); *C07K 16/2866* (2013.01); *C07K 16/32* (2013.01); *A61K 2039/505* (2013.01); *C07K 2317/24* (2013.01); *C07K 2317/565* (2013.01); *C07K 2317/76* (2013.01); *C07K 2317/92* (2013.01); *C07K 2318/10* (2013.01); *C07K 2319/00* (2013.01); *C07K 2319/30* (2013.01); *C07K 2319/33* (2013.01); *C07K 2319/50* (2013.01); *C07K 2319/55* (2013.01); *C07K 2319/73* (2013.01)

(58) Field of Classification Search
None
See application file for complete search history.

(56) References Cited

U.S. PATENT DOCUMENTS

| | | | |
|---|---|---|---|
| 5,677,171 | A | 10/1997 | Hudziak et al. |
| 5,770,195 | A | 6/1998 | Hudziak et al. |

(Continued)

FOREIGN PATENT DOCUMENTS

| | | | |
|---|---|---|---|
| EP | 1798240 A1 | 6/2007 | |
| JP | 2004538283 A | 12/2004 | |

(Continued)

OTHER PUBLICATIONS

Chen et al. (Advanced Drug Delivery Reviews 65, pp. 1357-1369, available online Sep. 29, 2012) (Year: 2012).*

(Continued)

*Primary Examiner* — Meera Natarajan
(74) *Attorney, Agent, or Firm* — Wilson Sonsini Goodrich & Rosati

(57) ABSTRACT

Disclosed herein are immunoglobulin fusion proteins comprising a first antibody region, a first therapeutic agent, and a first connecting peptide; wherein the first therapeutic agent is attached to the first antibody region by the connecting peptide; and wherein the connecting peptide does not comprise a region having beta strand secondary structure. The connecting peptide may comprise an extender peptide. The extender peptide may have an alpha helical secondary structure. The connecting peptide may comprise a linker peptide. The linker peptide may not comprise any secondary structure. Also disclosed herein are compositions comprising the immunoglobulin fusion proteins and methods for using the immunoglobulin fusion proteins for the treatment or prevention of a disease or condition in a subject.

13 Claims, 48 Drawing Sheets

Specification includes a Sequence Listing.

(56) References Cited

U.S. PATENT DOCUMENTS

| | | | |
|---|---|---|---|
| 5,772,997 | A | 6/1998 | Hudziak et al. |
| 6,294,654 | B1 | 9/2001 | Bogen et al. |
| 6,372,716 | B1 | 4/2002 | Bush et al. |
| 6,498,020 | B1 | 12/2002 | Walker et al. |
| 6,685,940 | B2 | 2/2004 | Andya et al. |
| 7,736,652 | B2 | 6/2010 | Penichet et al. |
| 2006/0182751 | A1 | 8/2006 | Gazzard et al. |
| 2007/0160617 | A1 | 7/2007 | Ma et al. |
| 2009/0214541 | A1* | 8/2009 | Gillies ............... C07K 16/2863 424/136.1 |
| 2010/0136032 | A1 | 6/2010 | Weinberg et al. |
| 2012/0128672 | A1 | 5/2012 | Keer |
| 2012/0302737 | A1 | 11/2012 | Christensen et al. |
| 2014/0022767 | A1 | 1/2014 | Martinez |
| 2014/0050720 | A1* | 2/2014 | Smider .................. C07K 16/00 424/133.1 |
| 2014/0086871 | A1 | 3/2014 | Smider et al. |
| 2014/0227267 | A1 | 8/2014 | Wang et al. |
| 2015/0011431 | A1 | 1/2015 | Smider et al. |
| 2015/0192971 | A1 | 7/2015 | Shah |
| 2016/0168231 | A1 | 6/2016 | De Los Rios et al. |
| 2016/0237156 | A1 | 8/2016 | Wang et al. |

FOREIGN PATENT DOCUMENTS

| | | | |
|---|---|---|---|
| JP | 2010540453 | A | 12/2010 |
| JP | 2011231085 | A | 11/2011 |
| TW | 200734354 | A | 9/2007 |
| WO | WO-9622377 | A1 | 7/1996 |
| WO | WO-2009132876 | A1 | 11/2009 |
| WO | WO-2012007167 | A1 | 1/2012 |
| WO | WO-2013055404 | A1 | 4/2013 |
| WO | WO-2015006744 | A1 | 1/2015 |
| WO | WO-2015017146 | A2 | 2/2015 |
| WO | WO-2015105741 | A1 | 7/2015 |
| WO | WO-2016015992 | A1 | 2/2016 |

OTHER PUBLICATIONS

Suzuki and Fujii (Tetrahedron Letters 40, 1999, pp. 6013-6017 (Year: 1999).*

Apostolovic, B. et al. Coiled Coils: attractive protein folding motifs for the fabrication of self-assembled, responsive and bioactive materials, Chem. Soc. Rev. 39:3541-3575 (2010).

Burkhard, P. et al. Coiled coils: a highly versatile protein folding motif, TRENDS in Cell Biology, 11(2):82-88 (Feb. 2001).

Gazi, A.D. et al. Coiled-coils in type III secretion systems: structural flexibility, disorder and biological implications, Cellular Microbiology 11(5):719-729 (2009).

Hadley, EB et al. An Antiparallel a-Helical Coiled-Coil Model System for Rapid Assessment of Side-Chain Recognition at the Hydrophobic Interface, J. Am. Chem. Soc. 128:16444-16445 (2006).

Harbury, P.B. et al. A Switch Between Two, Three, and Four-Stranded Coiled Coils in GCN4 Leucine Zipper Mutants, Science, New Series, 262(5138);1401-1407 (Nov. 26, 1993).

Hill, R.B. et al. De Novo Design of Helical Bundles as Models for Understanding Protein Folding and Function, Acc. Chem. Res. 33(11):745-754 (Nov. 2011).

Lopez et al. A single VH family and long CDR3s are the targets for hypermutation in bovine immunoglobulin heavy chains. Immunological Reviews, vol. 162, pp. 55-66 (1998).

Marsden, H.R. et al. Self-Assembly of Coiled Coils in Synthetic Biology: Inspiration and Progress, Angew. Chem. Int. Ed. (2010) 49:2988-3005.

Oakley, M.G. et. al. The design of antiparallel coiled coils, Current Opinion in Structural Biology, 11:450-457 (2011).

Peckman, M. Coiled coils and SAH domains in cytoskeletal molecular motors, Biochemical Society Transactions 39(5):1142-1148 (2011).

Pejchal et al., Structure and Function of Broadly Reactive Antibody PG16 Reveal an H3 Subdomain that Mediates Potent Neutralization of HIV-1. PNAS, 107(25)11483-11488 (2010).

Saini, et al. Exceptionally long CDR3H region with multiple cysteine residues in functional bovine IgM antibodies. EurJ Immunol. Aug. 1999;29(8):2420-2426.

Saphire et al., Crystal Structure of a Neutralizing Human IgG Against HIV-1: A Template for Vaccine Design, Science 293: 1155-1159 (2001).

Wang, et al., Reshaping Antibody Diversity. Cell 153: 1379-1393 (2013).

Woolfson, Derek N. The Design of Coiled-Coil Structures and Assemblies, Advances in Protein Chemistry, 70:79 (2005).

Zhang, et al. An Antibody CDR3-Erythropoietin Fusion Protein. ACS Chem. Biolo. 8:2117-2121 (2013).

Zhang, et al., Functional Antibody CDR3 fusion proteins with enhanced pharmacological properties. Angew. Chem. Int. Ed. 52: 8295-8298 (2013).

Altschul et al. Basic Local Alignment Search Tool. J. Mol. Biol. 215: 403-410 (1990).

Arndt, Katja M. et al. Helix-stabilized fv (hsfv) antibody fragments: substituting the constant domains of a fab fragment for a heterodimeric coiled-coil domain. Journal of Molecular Biology, .312(1):.221-228 (Sep. 7, 2001).

International Application No. PCT/US2014/046419 International Preliminary Report on Patentability dated Jan. 1, 2016.

International Application No. PCT/US2014/046419 International Search Report and Written Opinion dated Dec. 24, 2014.

Karlin, S. et al. Applications and statistics for multiple high-scoring segments in molecular sequences. Proc. Natl. Acad. Sci. USA 90:5873-5877 (1993).

Karlin, S. et al. Methods for assessing the statistical significance of molecular sequence features by using general scoring schemes. Proc. Natl. Acad. Sci. USA 87: 2264-2268 (1990).

Zhang, et al. An Antibody with a Variable-Region Coiled-Coil "Knob: Domain".Angew. Chem. Int. Ed. 53: 132-135 (2014).

Fornier et al., Update on the management of advanced breast cancer. Oncology. 13(5):67-658 (1999).

Fujiwara et al., Selection of inhibitory peptides for Aurora-A kinase from a phage-displayed library of helix-loop-helix peptides. Bioorganic and Medicinal Chemistry Letters. 20(5):1776-1778 (2010).

Maier et al., Requirements for the internalization of a murine monoclonal antibody directed against the HER-2/neu gene product c-erbB-2. Cancer Research. 51(19):5361-5369 (1991).

Rosenblum et al., Recombinant immunotoxins directed against the c-erb-2/HER2/neu oncogene product: in vitro cytotoxicity, pharmacokinetics, and in vivo efficacy studies in xenograft models. Clinical Cancer Research. 5(4):865-874 (1999).

* cited by examiner 210, 230 = extender peptide
220 = therapeutic agent
240, 250 = linker
260 = proteolytic cleavage

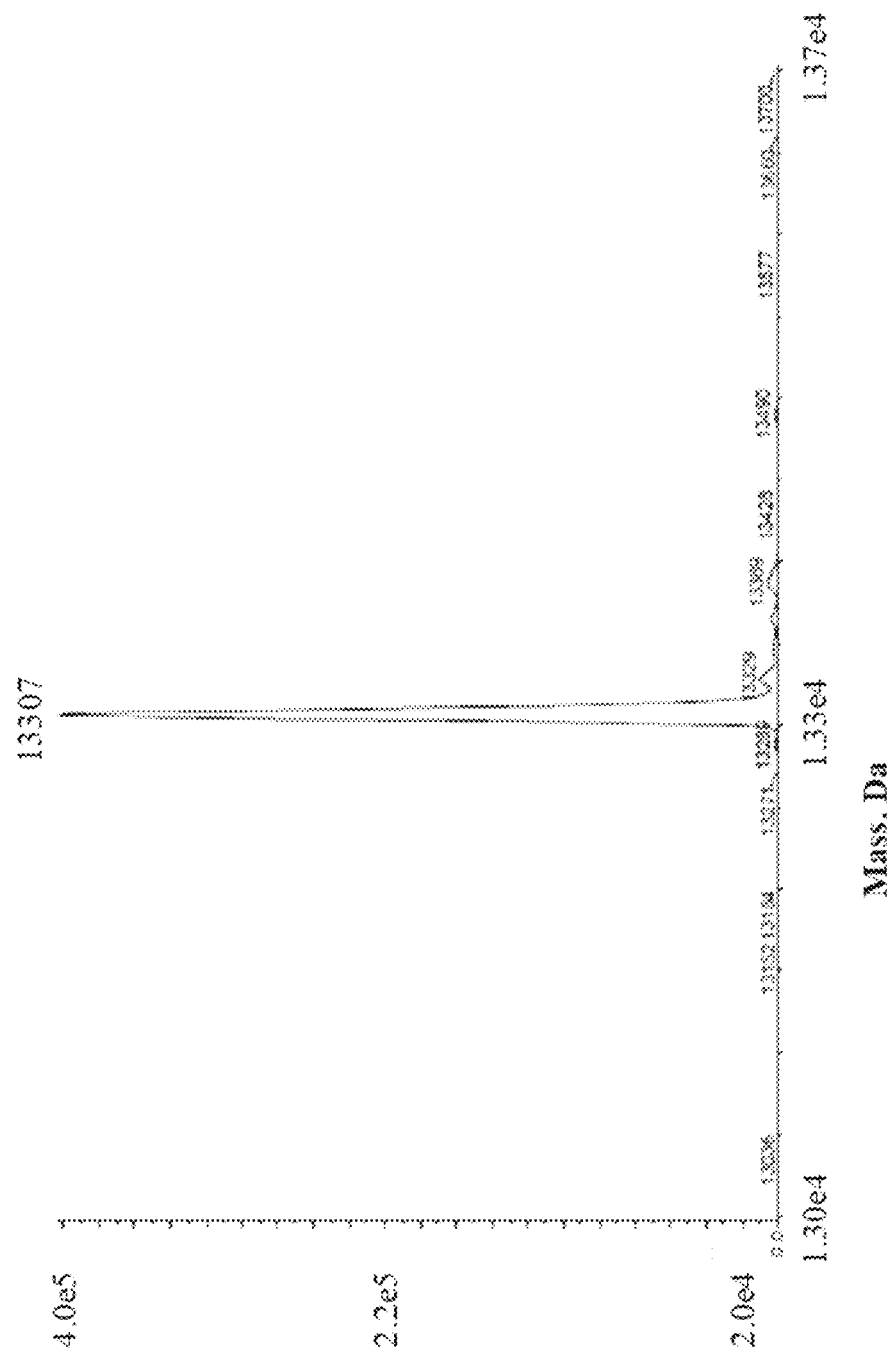

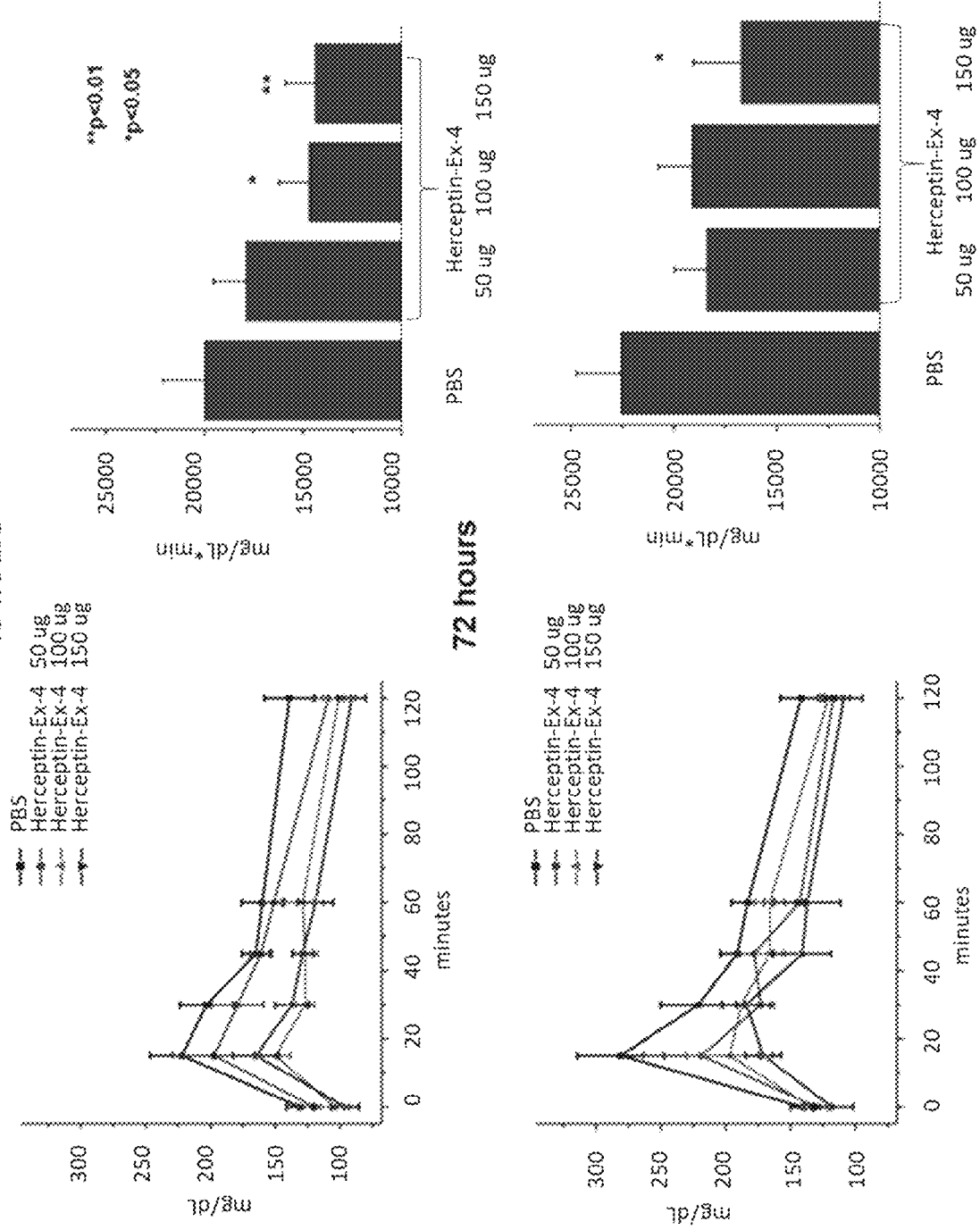

- hLeptin
- hAb-Leptin(H3)
- hAb-Leptin(H2)

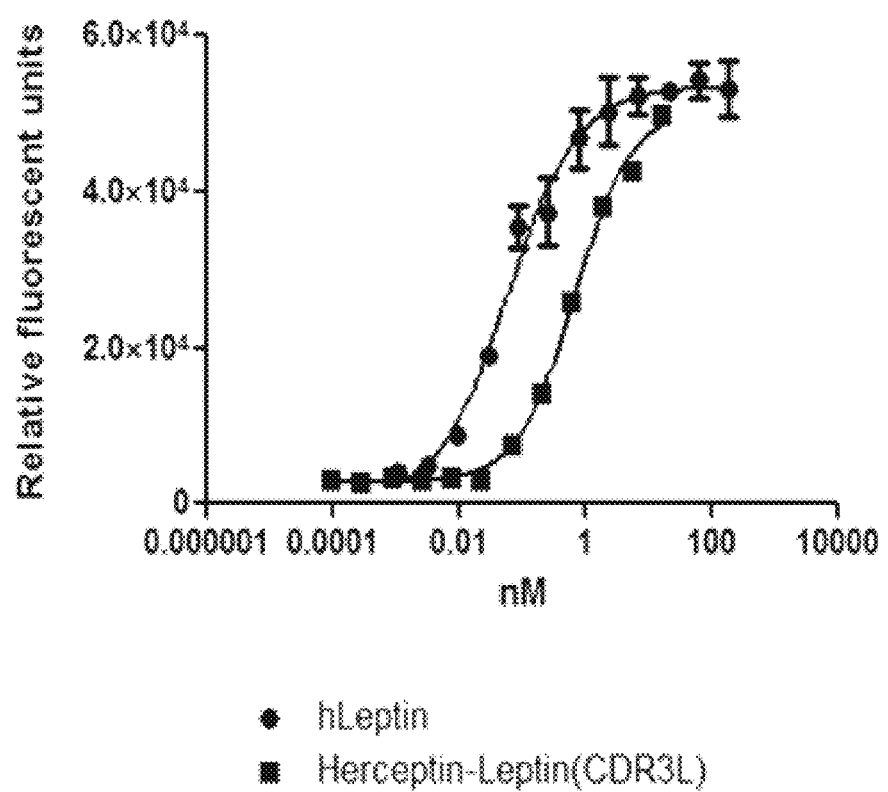

SEQUENCE LISTING

<160> NUMBER OF SEQ ID NOS: 279

<210> SEQ ID NO 1
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gacatccaga tgacccagtc tccatcctcc ctgtctgcat ctgtaggaga cagagtcacc    60
atcacttgcc gggcaagtca ggatgtgaat accgcggtcg catggtatca gcagaaacca   120
gggaaagccc ctaagctcct gatctattct gcatccttct tgtatagtgg ggtcccatca   180
aggttcagtg gcagtagatc tgggacagat ttcactctca ccatcagcag tctgcaacct   240
gaagattttg caacttacta ctgtcaacag cattacacta cccctccgac gttcggccaa   300
ggtaccaagc ttgagatcaa acgaactgtg gctgcaccat ctgtcttcat cttcccgcca   360
tctgatgagc agttgaaatc tggaactgcc tctgtcgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacc ctgacg  540 ctgagcaaag cagactacga aaacacaaa gtctacgcct gcgaagtcac ccatcagggc   600
ctgtcctcgc ccgtcacaaa gagcttcaac aggggagagt gt                      642
```

<210> SEQ ID NO 2
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

```
gacatccaga tgacccagtc tccatcctcc ctgtctgcat ctgtaggaga cagagtcacc    60
atcacttgcc gggcaagtca g                                              81
```

<210> SEQ ID NO 3
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
accgcggtcg catggtatca gcagaaacca gggaaagccc ctaagctcct gatctattct    60
gcatccttct tgtatagtgg ggtcccatca aggttcagtg gcagtagatc tgggacagat   120
ttcactctca ccatcagcag tctgcaacct gaagattttg caacttacta ctgtcaacag   180
cattacacta cccctccgac gttcggccaa ggtaccaagc ttgagatcaa acgaactgtg   240
gctgcaccat ctgtcttcat cttcccgcca tctgatgagc agttgaaatc tggaactgcc   300
tctgtcgtgt gcctgctgaa taacttctat cccagagagg ccaaagtaca gtggaaggtg   360
gataacgccc tccaatcggg taactcccag gagagtgtca cagagcagga cagcaaggac   420
agcacctaca gcctcagcag caccctgacg ctgagcaaag cagactacga aaacacaaa   480
```

```
gtctacgcct gcgaagtcac ccatcagggc ctgtcctcgc ccgtcacaaa gagcttcaac      540
aggggagagt gt                                                         552
```

<210> SEQ ID NO 4
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
gaagtgcagc tggtggaaag cggcggcggc ctggtgcagc cgggcggcag cctgcgcctg      60
agctgcgcgg cgagcggctt aacattaaa gatacctata ttcattgggt gcgccaggcg      120
ccgggcaaag gcctggaatg ggtggcgcgc atttatccga ccaacggcta tacccgctat     180
gcggatagcg tgaaaggccg ctttaccatt agcgcggata ccagcaaaaa caccgcgtat     240
ctgcagatga acagcctgcg cgcggaagat accgcggtgt attattgcag ccgctggggc     300
ggcgatggct tttatgcgat ggattattgg ggccaggca cctggtgac cgtgagcagc      360 gcgagcacca aggcccgag cgtgtttccg ctggcgccga gcagcaaag caccagcggc      420 ggcaccgcgg cgctgggctg cctggtgaaa gattattttc cggaaccggt gaccgtgagc     480
tggaacagcg gcgcgctgac cagcggcgtg cataccttc cggcggtgct gcagagcagc     540
ggcctgtata gcctgagcag cgtggtgacc gtgccgagca gcagcctggg cacccagacc     600
tatatttgca acgtgaacca taaaccagc aacaccaaag tggataaaaa agtggaaccg     660
ccgaaaagct gcgataaaac ccatacctgc ccgccgtgcc cggcgccgga actgctgggc     720
ggcccgagcg tgtttctgtt ccgccgaaa ccgaaagata ccctgatgat tagccgcacc     780
ccggaagtga cctgcgtggt ggtggatgtg agccatgaag atccggaagt gaaatttaac     840
tggtatgtgg atggcgtgga agtgcataac gcgaaaacca accgcgcga agaacagtat     900 aacagcacct atcgcgtggt gagcgtgctg accgtgctgc atcaggattg gctgaacggc     960
aaagaatata atgcaaagt gagcaacaaa gcgctgccgg cgccgattga aaaaaccatt     1020
agcaaagcga aaggccagcc gcgcgaaccg caggtgtata ccctgccgcc gagccgcgat     1080
gaactgacca aaaaccaggt gagcctgacc tgcctggtga aaggctttta tccgagcgat     1140
attgcggtgg aatgggaaag caacggccag ccggaaaaca actataaaac cacccccgccg     1200 gtgctggata gcgatggcag cttttttctg tatagcaaac tgaccgtgga taaaagccgc     1260
tggcagcagg gcaacgtgtt tagctgcagc gtgatgcatg aagcgctgca taaccattat     1320
acccagaaaa gcctgagcct gagcccgggc aaa                                  1353
```

<210> SEQ ID NO 5
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gaagtgcagc tggtggaaag cggcggcggc ctggtgcagc cgggcggcag cctgcgcctg      60
agctgcgcgg cgagcggctt aacattaaa gatacctata ttcattgggt gcgccaggcg      120
ccgggcaaag gcctggaatg ggtggcgcgc atttatccga ccaacggcta tacccgctat     180
gcggatagcg tgaaaggccg ctttaccatt agcgcggata ccagcaaaaa caccgcgtat     240
```

```
ctgcagatga acagcctgcg cgcggaagat accgcggtgt attattgcag ccgc         294
```

<210> SEQ ID NO 6
<211> LENGTH: 1032
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
gattattggg gccagggcac cctggtgacc gtgagcagcg cgagcaccaa aggcccgagc    60
gtgtttccgc tggcgccgag cagcaaaagc accagcggcg gcaccgcggc gctgggctgc   120
ctggtgaaag attattttcc ggaaccggtg accgtgagct ggaacagcgg cgcgctgacc   180
agcggcgtgc ataccttttcc ggcggtgctg cagagcagcg gcctgtatag cctgagcagc   240
gtggtgaccg tgccgagcag cagcctgggc acccagacct atatttgcaa cgtgaaccat   300
aaaccgagca acaccaaagt ggataaaaaa gtggaaccgc cgaaaagctg cgataaaacc   360
catacctgcc cgccgtgccc ggcgccggaa ctgctgggcg gcccgagcgt gtttctgttt   420
ccgccgaaac cgaaagatac cctgatgatt agccgcaccc cggaagtgac ctgcgtggtg   480
gtggatgtga gccatgaaga tccggaagtg aaatttaact ggtatgtgga tggcgtggaa   540
gtgcataacg cgaaaaccaa accgcgcgaa gaacagtata acagcaccta tcgcgtggtg   600
agcgtgctga ccgtgctgca tcaggattgg ctgaacggca agaatataa atgcaaagtg   660
agcaacaaag cgctgccggc gccgattgaa aaaaccatta gcaaagcgaa aggccagccg   720
cgcgaaccgc aggtgtatac cctgccgccg agccgcgatg aactgaccaa aaaccaggtg   780
agcctgacct gcctggtgaa aggctttat ccgagcgata ttgcggtgga atgggaaagc   840
aacggccagc cggaaaacaa ctataaaacc accccgccgg tgctggatag cgatggcagc   900
ttttttctgt atagcaaact gaccgtggat aaaagccgct ggcagcaggg caacgtgttt   960
agctgcagcg tgatgcatga agcgctgcat aaccattata cccagaaaag cctgagcctg  1020
agcccgggca aa                                                     1032
```

<210> SEQ ID NO 7
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
gaggtgcagc tggtggagtc tggaggaggc ttggtccagc ctggggggtc cctgagactc    60
tcctgtgcag cctctgggtt caatattaag gacacttaca tccactgggt ccgccaggct   120
ccagggaagg gctggagtg gtcgcacgt atttatccta ccaatggtta cacacgctac   180
gcagactccg tgaagggccg attcaccatc tccgcagaca cttccaagaa cacggcgtat   240
cttcaaatga acagcctgag agccgaggac acggccgtgt attactgttc gagatggggc   300
ggtgacggct ctatgccat ggactactgg ggccaaggaa ccctggtcac cgtctcctca   360
gcctccacca agggcccatc ggtcttcccc ctggcaccct cctccaagag cacctctggg   420
ggcacagcgg ccctgggctg cctggtcaag gactacttcc ccgaaccggt gacggtgtcg   480
tggaactcag gcgccctgac cagcggcgtg cacaccttcc cggctgtcct acagtcctca   540
```

| | |
|---|---|
| ggactctact ccctcagcag cgtggtgact gtgccctcta gcagcttggg cacccagacc | 600 |
| tacatctgca acgtgaatca caagcccagc aacaccaagg tggacaagaa agttgaaccc | 660 |
| aaatcttgcg acaaaactca cacatgccca ccgtgcccag cacctgaact cctgggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtgtacaccc tgcccccatc ccgggatgag | 1080 |
| ctgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctac agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggtaaa | 1350 |

<210> SEQ ID NO 8
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

| | |
|---|---|
| gaggtgcagc tggtggagtc tggaggaggc ttggtccagc ctgggggtc cctgagactc | 60 |
| tcctgtgcag cctctgggtt caatattaag gacacttaca tccactgggt ccgccaggct | 120 |
| ccagggaagg gctggagtg gtcgcacgt atttatccta ccaatggtta cacacgctac | 180 |
| gcagactccg tgaagggccg attcaccatc tccgcagaca cttccaagaa cacggcgtat | 240 |
| cttcaaatga acagcctgag agccgaggac acggccgtgt attactgttc gagatggggc | 300 |
| ggtgacggct tctatgccat ggactactgg ggccaaggaa ccctggtcac cgtctcctca | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgact gtgccctcta gcagcttggg cacccagacc | 600 |
| tacatctgca acgtgaatca caagcccagc aacaccaagg tggacaagaa agttgaaccc | 660 |
| aaatcttgcg acaaaactca cacatgccca ccgtgcccag cacctccagt cgccggaccg | 720 |
| tcagtcttcc tcttccctcc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacaacagc | 900 |
| acgtaccgtg tggtcagcgt cctcaccgtc ctgcaccagg actggctgaa tggcaaggag | 960 |
| tacaagtgca aggtctccaa caaggcctc ccaagctcca tcgagaaaac catctccaaa | 1020 |
| gccaaagggc agccccgaga accacaggtg tacaccctgc ctccatcccg ggatgagctg | 1080 |
| accaagaacc aggtcagcct gacctgcctg gtcaaaggct tctatcccag cgacatcgcc | 1140 |
| gtggagtggg agagcaatgg gcagccggag aacaactaca agaccacgcc tcccgtgctg | 1200 |

```
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 9
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
gaggtgcagc tggtggagtc tggaggaggc ttggtccagc ctggggggtc cctgagactc      60
tcctgtgcag cctctgggtt caatattaag gacacttaca tccactgggt ccgccaggct     120
ccagggaagg ggctggagtg ggtcgcacgt atttatccta ccaatggtta cacacgctac     180
gcagactccg tgaagggccg attcaccatc tccgcagaca cttccaagaa cacggcgtat     240
cttcaaatga acagcctgag agccgaggac acggccgtgt attactgttc gagatggggc     300
ggtgacggct ctatgccat ggactactgg ggccaaggaa ccctggtcac cgtctcctca     360
gccagcacta aggtccatc tgtgttccct ctggctcctt gcagccggag cacctccgag     420
tccacagccg ctctgggatg tctggtgaaa gattacttcc ccgagcccgt caccgtgagc     480
tggaatagcg gagcactgac ctccggcgtc cacacattcc ccgccgtgct ccaaagctcc     540
ggcctgtaca gcctctcctc cgtggtcacc gtgcccagca gctctctggg cacaaagacc     600
tatacctgta acgtggatca caagcctagc aacaccaaag tggataagcg ggtggagagc     660
aagtacggcc ctccctgtcc cccttgcccc gctcctgagg ccgctggcgg accttccgtg     720
ttcctgtttc cccctaagcc caaggacacc ctcatgatta gccggacacc cgaagtgacc     780
tgcgtggtcg tggatgtgtc ccaggaggac cctgaagtgc aatttaactg gtacgtggac     840
ggcgtcgagg tgcacaacgc caagaccaag cctcgggaag agcagttcaa cagcacctac     900
cgggtggtca gcgtgctgac agtgctgcac caggactggc tgaacggcaa ggagtacaag     960
tgcaaggtga gcaacaaggg cctgcccagc tccatcgaga agaccatcag caaggccaag    1020
ggccagccca gggaacccca ggtgtatacc ctgcccccta gccaggagga aatgaccaaa    1080
aaccaggtga gcctgacctg cctggtgaag ggcttctacc ccagcgacat cgccgtggag    1140
tgggagagca acggccagcc cgagaacaat tacaagacca cccctcctgt gctggacagc    1200
gacggctcct tctttctgta tagccggctg accgtggaca gagcaggtg gcaggagggc    1260 aacgtgttct cctgtagcgt gatgcacgag gccctgcaca accattacac ccagaagagc    1320
ttgagcctga gcctgggcaa a                                              1341
```

<210> SEQ ID NO 10
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
gacatccaga tgacccagtc cccctccacc ctgtccgcct ccgtgggcga ccgcgtgacc      60
atcacctgca gtgccagct gtccgtgggc tacatgcact ggtaccagca gaagcccggc     120
aaggccccca gctgctgat ctacgacacc tccaagctgg cctccggcgt gccctcccgc     180
```

```
ttctccggct ccggctccgg caccgagttc accctgacca tctcctccct gcagcccgac      240
gacttcgcca cctactactg cttccagggc tccggctacc ccttcacctt cggcggcggc      300
accaagctgg agatcaaacg aactgtggct gcaccatctg tcttcatctt cccgccatct      360
gatgagcagt tgaaatctgg aactgcctct gtcgtgtgcc tgctgaataa cttctatccc      420
agagaggcca agtacagtg gaaggtggat aacgccctcc aatcgggtaa ctcccaggag       480
agtgtcacag agcaggacag caaggacagc acctacagcc tcagcagcac cctgacgctg      540
agcaaagcag actacgagaa acacaaagtc tacgcctgcg aagtcaccca tcagggcctg      600
tcctcgcccg tcacaaagag cttcaacagg ggagagtgt                             639

<210> SEQ ID NO 11
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
caggtgaccc tgcgcgagtc cggccctgca ctggtgaagc ccacccagac cctgaccctg       60
acctgcacct tctccggctt ctccctgtcc acctccggca tgtccgtggg ctggatccgg      120
cagcctcccg gcaaggccct ggagtggctg gctgacatct ggtgggacga caagaaggac      180 tacaaccccct ccctgaagtc ccgcctgacc atctccaagg acacctccaa gaaccaggtg    240
gtgctgaagg tgaccaacat ggaccccgcc gacaccgcca cctactactg cgcccgc        297

<210> SEQ ID NO 12
<211> LENGTH: 1048
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gacgtgtggg gagccggtac caccgtgacc gtgtcttccg cctccaccaa gggcccatcg       60
gtcttccccc tggcaccctc ctccaagagc acctctgggg gcacagcggc cctgggctgc      120
ctggtcaagg actacttccc cgaaccggtg acggtgtcgt ggaactcagg cgccctgacc      180
agcggcgtgc acaccttccc ggctgtccta cagtcctcag gactctactc cctcagcagc      240
gtggtgactg tgccctctag cagcttgggc acccagacct acatctgcaa cgtgaatcac      300
aagcccagca acaccaaggt ggacaagaaa gttgaaccca aatcttgcga caaaactcac      360
acatgcccac cgtgcccagc acctccagtc gccggaccgt cagtcttcct cttccctcca      420
aaacccaagg acaccctcat gatctcccgg acccctgagg tcacatgcgt ggtggtggac      480
gtgagccacg aagaccctga ggtcaagttc aactggtacg tggacggcgt ggaggtgcat      540
aatgccaaga caaagccgcg ggaggagcag tacaacagca cgtaccgtgt ggtcagcgtc      600
ctcaccgtcc tgcaccagga ctggctgaat ggcaaggagt acaagtgcaa ggtctccaac      660
aaaggcctcc caagctccat cgagaaaacc atctccaaag ccaaagggca gccccgagaa      720
ccacaggtgt acaccctgcc tccatcccgg gatgagctga ccaagaacca ggtcagcctg      780
acctgcctgg tcaaaggctt ctatcccagc gacatcgccg tggagtggga gagcaatggg      840
cagccggaga acaactacaa gaccacgcct cccgtgctgg actccgacgg ctccttcttc      900
```

| ctctacagca agctcaccgt ggacaagagc aggtggcagc aggggaacgt cttctcatgc | 960 |
| tccgtgatgc atgaggctct gcacaaccac tacacgcaga agagcctctc cctgtctccg | 1020 |
| ggtaaatgat aagtgctagc tggccaga | 1048 |

<210> SEQ ID NO 13
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

| caggtgaccc tgcgcgagtc cggccccgcc ctggtgaagc ccacccagac cctgaccctg | 60 |
| acctgcacct tctccggctt ctccctgtcc acctccggca tgtccgtggg ctggatccgc | 120 |
| cagcccccg gcaaggccct ggagtggctg gccgacatct ggtgggacga caagaaggac | 180 |
| tacaacccct ccctgaagtc ccgcctgacc atctccaagg acacctccaa gaaccaggtg | 240 |
| gtgctgaagg tgaccaacat ggaccccgcc gacaccgcca cctactactg cgcccgctcc | 300 |
| atgatcacca actggtactt cgacgtgtgg ggcgccggca ccaccgtgac cgtgtcctcc | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgact gtgccctcta gcagcttggg cacccagacc | 600 |
| tacatctgca acgtgaatca caagcccagc aacaccaagg tggacaagaa agttgaaccc | 660 |
| aaatcttgcg acaaaactca cacatgccca ccgtgcccag cacctgaact cctgggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtgtacaccc tgcccccatc ccgggatgag | 1080 |
| ctgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctac agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggtaaa | 1350 |

<210> SEQ ID NO 14
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

| caggtgaccc tgcgcgagtc cggccccgcc ctggtgaagc ccacccagac cctgaccctg | 60 |
| acctgcacct tctccggctt ctccctgtcc acctccggca tgtccgtggg ctggatccgc | 120 |
| cagcccccg gcaaggccct ggagtggctg gccgacatct ggtgggacga caagaaggac | 180 |

```
tacaacccct ccctgaagtc ccgcctgacc atctccaagg acacctccaa gaaccaggtg    240
gtgctgaagg tgaccaacat ggaccccgcc gacaccgcca cctactactg cgcccgctcc    300
atgatcacca actggtactt cgacgtgtgg ggcgccggca ccaccgtgac cgtgtcctcc    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgact gtgccctcta gcagcttggg cacccagacc    600
tacatctgca acgtgaatca caagcccagc aacaccaagg tggacaagaa agttgaaccc    660
aaatcttgcg acaaaactca cacatgccca ccgtgcccag cacctccagt cgccggaccg    720
tcagtcttcc tcttccctcc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaaggcctc ccaagctcca tcgagaaaac catctccaaa    1020
gccaaagggc agccccgaga accacaggtg tacaccctgc ctccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                       1347
```

<210> SEQ ID NO 15
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
caggtgaccc tgcgcgagtc cggccccgcc ctggtgaagc ccacccagac cctgaccctg     60
acctgcacct tctccggctt ctccctgtcc acctccggca tgtccgtggg ctggatccgc    120
cagccccccg gcaaggccct ggagtggctg gccgacatct ggtgggacga caagaaggac    180
tacaacccct ccctgaagtc ccgcctgacc atctccaagg acacctccaa gaaccaggtg    240
gtgctgaagg tgaccaacat ggaccccgcc gacaccgcca cctactactg cgcccgctcc    300
atgatcacca actggtactt cgacgtgtgg ggcgccggca ccaccgtgac cgtgtcctcc    360
gccagcacta aggtccatc tgtgttccct ctggctcctt gcagccggag cacctccgag    420
tccacagccg ctctgggatg tctggtgaaa gattacttcc ccgagcccgt caccgtgagc    480
tggaatagcg gagcactgac ctccggcgtc cacacattcc ccgccgtgct ccaaagctcc    540
ggcctgtaca gcctctcctc cgtggtcacc gtgcccagca gctctctggg cacaaagacc    600
tatacctgta acgtggatca caagcctagc aacaccaaag tggataagcg ggtggagagc    660
aagtacggcc ctccctgtcc ccttgcccc gctcctgagg ccgctggcgg accttccgtg    720
ttcctgtttc cccctaagcc caaggacacc ctcatgatta gccggacacc cgaagtgacc    780
tgcgtggtcg tggatgtgtc ccaggaggac cctgaagtgc aatttaactg gtacgtggac    840
```

```
ggcgtcgagg tgcacaacgc caagaccaag cctcgggaag agcagttcaa cagcacctac    900
cgggtggtca gcgtgctgac agtgctgcac caggactggc tgaacggcaa ggagtacaag    960
tgcaaggtga gcaacaaggg cctgcccagc tccatcgaga agaccatcag caaggccaag   1020
ggccagcccc gggaacccca ggtgtatacc ctgccccta gccaggagga aatgaccaaa   1080
aaccaggtga gcctgacctg cctggtgaag ggcttctacc ccagcgacat cgccgtggag   1140
tgggagagca acggccagcc cgagaacaat tacaagacca cccctcctgt gctggacagc   1200
gacggctcct tctttctgta tagccggctg accgtggaca gagcaggtg gcaggagggc   1260 aacgtgttct cctgtagcgt gatgcacgag gccctgcaca accattacac ccagaagagc   1320
ttgagcctga gcctgggcaa a                                              1341

<210> SEQ ID NO 16
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
caggtccagc tgagagagag cggcccttca ctggtcaagc catcccagac actgagcctg     60
acatgcacag caagcgggtt ttcactgagc gacaaggcga tgggatgggt ccgacaggca    120
ccaggaaaag ccctggaatg gctgggcagc atcgataccg gcgggaacac agggtacaat    180
cccggactga gagcagact gtccattacc aaggacaact ctaaaagtca ggtgtcactg    240
agcgtgagct ccgtcaccac agaggatagt gcaacttact attgcacctc tgtgcaccag    300

<210> SEQ ID NO 17
<211> LENGTH: 1035
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
tggcatgtgg atgtctgggg acagggcctg ctggtgacag tctctagtgc ttccacaact     60
gcaccaaagg tgtaccccct gtcaagctgc tgtgggaca atcctctag taccgtgaca    120 ctgggatgcc tggtctcaag ctatatgccc gagcctgtga ctgtcacctg gaactcagga    180
gccctgaaaa gcggagtgca caccttccca gctgtgctgc agtcctctgg cctgtatagc    240
ctgagttcaa tggtgacagt ccccggcagt acttcagggc agaccttcac ctgtaatgtg    300
gcccatcctg ccagctccac caaagtggac aaagcagtgg aacccaaatc ttgcgacaaa    360
actcacacat gcccaccgtg cccagcacct gaactcctgg ggggaccgtc agtcttcctc    420
ttccccccaa aacccaagga caccctcatg atctcccgga cccctgaggt cacatgcgtg    480
gtggtggacg tgagccacga agaccctgag gtcaagttca actggtacgt ggacggcgtg    540
gaggtgcata atgccaagac aaagccgcgg gaggagcagt acaacagcac gtaccgtgtg    600
gtcagcgtcc tcaccgtcct gcaccaggac tggctgaatg gcaaggagta caagtgcaag    660
gtctccaaca aagccctccc agcccccatc gagaaaacca tctccaaagc caaagggcag    720
ccccgagaac cacaggtgta caccctgccc ccatcccggg atgagctgac caagaaccag    780
gtcagcctga cctgcctggt caaaggcttc tatcccagcg acatcgccgt ggagtgggag    840
```

```
agcaatgggc agccggagaa caactacaag accacgcctc ccgtgctgga ctccgacggc    900
tccttcttcc tctacagcaa gctcaccgtg gacaagagca ggtggcagca ggggaacgtc    960
ttctcatgct ccgtgatgca tgaggctctg cacaaccact acacgcagaa gagcctctcc   1020
ctgtctccgg gtaaa                                                    1035
```

<210> SEQ ID NO 18
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
caggccgtcc tgaaccagcc aagcagcgtc tccgggtctc tggggcagcg ggtctcaatc     60
acctgtagcg ggtcttcctc caatgtcggc aacggctacg tgtcttggta tcagctgatc    120
cctggcagtg ccccacgaac cctgatctac ggcgacacat ccagagcttc tggggtcccc    180
gatcggttct cagggagcag atccggaaac acagctactc tgaccatcag ctccctgcag    240
gctgaggacg aagcagatta tttctgcgca tctgccgagg actctagttc aaatgccgtg    300
tttggaagcg gcaccacact gacagtcctg ggcagcccca gagtccccc ttcagtgact     360 ctgttcccac cctctaccga ggaactgaac ggaaacaagg ccacactggt gtgtctgatc    420
agcgactttt accctggatc cgtcactgtg gtctggaagg cagatggcag cacaattact    480
aggaacgtgg aaactacccg cgcctccaag cagtctaata gtaaatacgc cgccagctcc    540
tatctgagcc tgacctctag tgattggaag tccaaagggt catatagctg cgaagtgacc    600
catgaaggct caaccgtgac taagactgtg aaaccatccg agtgctcc                 648
```

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln
            20                  25
```

<210> SEQ ID NO 21
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Thr Ala Val Ala Trp Tyr Gln Gln Lys Pro Gly Lys Ala Pro Lys Leu
1               5                   10                  15

Leu Ile Tyr Ser Ala Ser Phe Leu Tyr Ser Gly Val Pro Ser Arg Phe
            20                  25                  30

Ser Gly Ser Arg Ser Gly Thr Asp Phe Thr Leu Thr Ile Ser Ser Leu
        35                  40                  45

Gln Pro Glu Asp Phe Ala Thr Tyr Tyr Cys Gln Gln His Tyr Thr Thr
    50                  55                  60

Pro Pro Thr Phe Gly Gln Gly Thr Lys Leu Glu Ile Lys Arg Thr Val
65                  70                  75                  80

Ala Ala Pro Ser Val Phe Ile Phe Pro Pro Ser Asp Glu Gln Leu Lys
                85                  90                  95

Ser Gly Thr Ala Ser Val Val Cys Leu Leu Asn Asn Phe Tyr Pro Arg
            100                 105                 110

Glu Ala Lys Val Gln Trp Lys Val Asp Asn Ala Leu Gln Ser Gly Asn
        115                 120                 125

Ser Gln Glu Ser Val Thr Glu Gln Asp Ser Lys Asp Ser Thr Tyr Ser
    130                 135                 140

Leu Ser Ser Thr Leu Thr Leu Ser Lys Ala Asp Tyr Glu Lys His Lys
145                 150                 155                 160

Val Tyr Ala Cys Glu Val Thr His Gln Gly Leu Ser Ser Pro Val Thr
                165                 170                 175

Lys Ser Phe Asn Arg Gly Glu Cys
            180
```

```
<210> SEQ ID NO 22
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 23
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg

<210> SEQ ID NO 24
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Tyr Trp Gly Gln Gly Thr Leu Val Thr Val Ser Ser Ala Ser Thr
1               5                   10                  15

Lys Gly Pro Ser Val Phe Pro Leu Ala Pro Ser Ser Lys Ser Thr Ser
            20                  25                  30

Gly Gly Thr Ala Ala Leu Gly Cys Leu Val Lys Asp Tyr Phe Pro Glu
        35                  40                  45

Pro Val Thr Val Ser Trp Asn Ser Gly Ala Leu Thr Ser Gly Val His
    50                  55                  60

Thr Phe Pro Ala Val Leu Gln Ser Ser Gly Leu Tyr Ser Leu Ser Ser
65                  70                  75                  80

Val Val Thr Val Pro Ser Ser Ser Leu Gly Thr Gln Thr Tyr Ile Cys
                85                  90                  95
```

Asn Val Asn His Lys Pro Ser Asn Thr Lys Val Asp Lys Lys Val Glu
                100                 105                 110

Pro Pro Lys Ser Cys Asp Lys Thr His Thr Cys Pro Pro Cys Pro Ala
            115                 120                 125

Pro Glu Leu Leu Gly Gly Pro Ser Val Phe Leu Phe Pro Pro Lys Pro
        130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
210                 215                 220

Leu Pro Ala Pro Ile Glu Lys Thr Ile Ser Lys Ala Lys Gly Gln Pro
225                 230                 235                 240

Arg Glu Pro Gln Val Tyr Thr Leu Pro Pro Ser Arg Asp Glu Leu Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 25
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

```
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 26
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Gln Pro Gly Gly
```

-continued

```
1               5                   10                  15
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430
```

Ala Leu His Asn His Tyr Thr Gln Lys Ser Leu Ser Leu Ser Pro Gly
            435                 440                 445

Lys

<210> SEQ ID NO 27
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

-continued

```
Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 28
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 29
<211> LENGTH: 99
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 29

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg
```

<210> SEQ ID NO 30
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Asp Val Trp Gly Ala Gly Thr Thr Val Thr Val Ser Ser Ala Ser Thr
1               5                   10                  15

Lys Gly Pro Ser Val Phe Pro Leu Ala Pro Ser Ser Lys Ser Thr Ser
            20                  25                  30

Gly Gly Thr Ala Ala Leu Gly Cys Leu Val Lys Asp Tyr Phe Pro Glu
        35                  40                  45

Pro Val Thr Val Ser Trp Asn Ser Gly Ala Leu Thr Ser Gly Val His
50                  55                  60

Thr Phe Pro Ala Val Leu Gln Ser Ser Gly Leu Tyr Ser Leu Ser Ser
65                  70                  75                  80

Val Val Thr Val Pro Ser Ser Ser Leu Gly Thr Gln Thr Tyr Ile Cys
                85                  90                  95

Asn Val Asn His Lys Pro Ser Asn Thr Lys Val Asp Lys Lys Val Glu
            100                 105                 110

Pro Lys Ser Cys Asp Lys Thr His Thr Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Gly Leu Pro
    210                 215                 220
```

Ser Ser Ile Glu Lys Thr Ile Ser Lys Ala Lys Gly Gln Pro Arg Glu
225                 230                 235                 240

Pro Gln Val Tyr Thr Leu Pro Pro Ser Arg Asp Glu Leu Thr Lys Asn
            245                 250                 255

Gln Val Ser Leu Thr Cys Leu Val Lys Gly Phe Tyr Pro Ser Asp Ile
        260                 265                 270

Ala Val Glu Trp Glu Ser Asn Gly Gln Pro Glu Asn Asn Tyr Lys Thr
    275                 280                 285

Thr Pro Pro Val Leu Asp Ser Asp Gly Ser Phe Phe Leu Tyr Ser Lys
290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
            325                 330                 335

Ser Leu Ser Pro Gly Lys
            340

<210> SEQ ID NO 31
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly

```
                    225                 230                 235                 240
        Pro Ser Val Phe Leu Phe Pro Lys Pro Lys Asp Thr Leu Met Ile
                        245                 250                 255

Ser Arg Thr Pro Glu Val Thr Cys Val Val Asp Val Ser His Glu
                        260                 265                 270

Asp Pro Glu Val Lys Phe Asn Trp Tyr Val Asp Gly Val Glu Val His
                        275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                        340                 345                 350

Thr Leu Pro Pro Ser Arg Asp Glu Leu Thr Lys Asn Gln Val Ser Leu
                        355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                        420                 425                 430

Glu Ala Leu His Asn His Tyr Thr Gln Lys Ser Leu Ser Leu Ser Pro
                        435                 440                 445

Gly Lys
            450

<210> SEQ ID NO 32
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Thr Leu Arg Glu Ser Gly Pro Ala Leu Val Lys Pro Thr Gln
        1               5                   10                  15

Thr Leu Thr Leu Thr Cys Thr Phe Ser Gly Phe Ser Leu Ser Thr Ser
                        20                  25                  30

Gly Met Ser Val Gly Trp Ile Arg Gln Pro Pro Gly Lys Ala Leu Glu
                        35                  40                  45

Trp Leu Ala Asp Ile Trp Trp Asp Asp Lys Lys Asp Tyr Asn Pro Ser
            50                  55                  60

Leu Lys Ser Arg Leu Thr Ile Ser Lys Asp Thr Ser Lys Asn Gln Val
        65                  70                  75                  80

Val Leu Lys Val Thr Asn Met Asp Pro Ala Asp Thr Ala Thr Tyr Tyr
                        85                  90                  95

Cys Ala Arg Ser Met Ile Thr Asn Trp Tyr Phe Asp Val Trp Gly Ala
                        100                 105                 110

Gly Thr Thr Val Thr Val Ser Ser Ala Ser Thr Lys Gly Pro Ser Val
                        115                 120                 125
```

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 33
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

-continued

Gly Met Ser Val Gly Trp Ile Arg Gln Pro Pro Gly Lys Ala Leu Glu
        35                  40                  45

Trp Leu Ala Asp Ile Trp Trp Asp Asp Lys Asp Tyr Asn Pro Ser
 50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

```
<210> SEQ ID NO 34
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln
            100

<210> SEQ ID NO 35
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Trp His Val Asp Val Trp Gly Gln Gly Leu Leu Val Thr Val Ser Ser
1               5                   10                  15

Ala Ser Thr Thr Ala Pro Lys Val Tyr Pro Leu Ser Ser Cys Cys Gly
            20                  25                  30

Asp Lys Ser Ser Ser Thr Val Thr Leu Gly Cys Leu Val Ser Ser Tyr
        35                  40                  45

Met Pro Glu Pro Val Thr Val Thr Trp Asn Ser Gly Ala Leu Lys Ser
    50                  55                  60

Gly Val His Thr Phe Pro Ala Val Leu Gln Ser Ser Gly Leu Tyr Ser
65                  70                  75                  80

Leu Ser Ser Met Val Thr Val Pro Gly Ser Thr Ser Gly Gln Thr Phe
                85                  90                  95

Thr Cys Asn Val Ala His Pro Ala Ser Ser Thr Lys Val Asp Lys Ala
            100                 105                 110

Val Glu Pro Lys Ser Cys Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
```

```
                195                 200                 205
Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 36
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Ala Val Leu Asn Gln Pro Ser Ser Val Ser Gly Ser Leu Gly Gln
1               5                   10                  15

Arg Val Ser Ile Thr Cys Ser Gly Ser Ser Asn Val Gly Asn Gly
            20                  25                  30

Tyr Val Ser Trp Tyr Gln Leu Ile Pro Gly Ser Ala Pro Arg Thr Leu
        35                  40                  45

Ile Tyr Gly Asp Thr Ser Arg Ala Ser Gly Val Pro Asp Arg Phe Ser
    50                  55                  60

Gly Ser Arg Ser Gly Asn Thr Ala Thr Leu Thr Ile Ser Ser Leu Gln
65                  70                  75                  80

Ala Glu Asp Glu Ala Asp Tyr Phe Cys Ala Ser Ala Glu Asp Ser Ser
                85                  90                  95

Ser Asn Ala Val Phe Gly Ser Gly Thr Thr Leu Thr Val Leu Gly Gln
            100                 105                 110

Pro Lys Ser Pro Pro Ser Val Thr Leu Phe Pro Pro Ser Thr Glu Glu
        115                 120                 125

Leu Asn Gly Asn Lys Ala Thr Leu Val Cys Leu Ile Ser Asp Phe Tyr
    130                 135                 140

Pro Gly Ser Val Thr Val Val Trp Lys Ala Asp Gly Ser Thr Ile Thr
145                 150                 155                 160

Arg Asn Val Glu Thr Thr Arg Ala Ser Lys Gln Ser Asn Ser Lys Tyr
                165                 170                 175

Ala Ala Ser Ser Tyr Leu Ser Leu Thr Ser Ser Asp Trp Lys Ser Lys
            180                 185                 190

Gly Ser Tyr Ser Cys Glu Val Thr His Glu Gly Ser Thr Val Thr Lys
        195                 200                 205
```

Thr Val Lys Pro Ser Glu Cys Ser
    210                 215

<210> SEQ ID NO 37
<211> LENGTH: 1269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

| gacatccaga | tgacccagtc | tccatcctcc | ctgtctgcat | ctgtaggaga | cagagtcacc | 60   |
| atcacttgcc | gggcaagtca | gggcggaagc | ggagcaaagc | tcgccgcact | gaaagccaag | 120  |
| ctggccgctc | tgaagggggg | tggcggaagc | gccccaccac | gcctcatctg | tgacagccga | 180  |
| gtcctggaga | ggtacctctt | ggaggccaag | gaggccgaga | atatcacgac | gggctgtgct | 240  |
| gaacactgca | gcttgaatga | gaatatcact | gtcccagaca | ccaaagttaa | tttctatgcc | 300  |
| tggaagagga | tggaggtcgg | gcagcaggcc | gtagaagtct | ggcagggcct | ggccctgctg | 360  |
| tcggaagctg | tcctgcgggg | ccaggccctg | ttggtcaact | cttcccagcc | gtgggagccc | 420  |
| ctgcagctgc | atgtggataa | agccgtcagt | ggccttcgca | gcctcaccac | tctgcttcgg | 480  |
| gctctgggag | cccagaagga | agccatctcc | cctccagatg | cggcctcagc | tgctccactc | 540  |
| cgaacaatca | ctgctgacac | tttccgcaaa | ctcttccgag | tctactccaa | tttcctccgg | 600  |
| ggaaagctga | agctgtacac | aggggaggcc | tgcaggacag | ggacagagg  | cggaggtggg | 660  |
| agtgaactgg | ccgcactgga | agctgagctg | gctgccctcg | aagctggagg | ctctggaacc | 720  |
| gcggtcgcat | ggtatcagca | gaaaccaggg | aaagccccta | agctcctgat | ctattctgca | 780  |
| tccttcttgt | atagtggggt | cccatcaagg | ttcagtggca | gtagatctgg | gacagatttc | 840  |
| actctcacca | tcagcagtct | gcaacctgaa | gattttgcaa | cttactactg | tcaacagcat | 900  |
| tacactaccc | ctccgacgtt | cggccaaggt | accaagcttg | agatcaaacg | aactgtggct | 960  |
| gcaccatctg | tcttcatctt | cccgccatct | gatgagcagt | tgaaatctgg | aactgcctct | 1020 |
| gtcgtgtgcc | tgctgaataa | cttctatccc | agagaggcca | aagtacagtg | gaaggtggat | 1080 |
| aacgccctcc | aatcgggtaa | ctcccaggag | agtgtcacag | agcaggacag | caaggacagc | 1140 |
| acctacagcc | tcagcagcac | cctgacgctg | agcaaagcag | actacgagaa | acacaaagtc | 1200 |
| tacgcctgcg | aagtcaccca | tcagggcctg | tcctcgcccg | tcacaaagag | cttcaacagg | 1260 |
| ggagagtgt  |            |            |            |            |            | 1269 |

<210> SEQ ID NO 38
<211> LENGTH: 1983
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

| gaggtgcagc | tggtggagtc | tggaggaggc | ttggtccagc | ctgggggggtc | cctgagactc | 60  |
| tcctgtgcag | cctctgggtt | caatattaag | gacacttaca | tccactgggt | ccgccaggct | 120 |
| ccagggaagg | ggctggagtg | ggtcgcacgt | atttatccta | ccaatggtta | cacacgctac | 180 |
| gcagactccg | tgaagggccg | attcaccatc | tccgcagaca | cttccaagaa | cacggcgtat | 240 |
| cttcaaatga | acagcctgag | agccgaggac | acggccgtgt | attactgttc | gagaggcgga | 300 |

| | |
|---|---|
| agcggagcaa agctcgccgc actgaaagcc aagctggccg ctctgaaggg aggcggtggc | 360 |
| tccaccccc ttggccctgc ccgatccctg ccccagagct tcctgctcaa gtgcttagag | 420 |
| caagtgagga aaatccaggc tgatggcgcc gagctgcagg agaggctgtg tgccgcccac | 480 |
| aagctgtgcc acccggagga gctgatgctg ctcaggcact ctctgggcat cccccaggct | 540 |
| cccctaagca gctgctccag ccagtccctg cagctgacga gctgcctgaa ccaactacac | 600 |
| ggcggcctct ttctctacca gggcctcctg caggccctgg cgggcatctc cccagagctg | 660 |
| gcccccacct tggacacact gcagctggac gtcactgact ttgccacgaa catctggctg | 720 |
| cagatggagg acctggggc ggccccgct gtgcagccca ccagggcgc catgccgacc | 780 |
| ttcacttcag ccttccaacg cagagcagga ggggtcctgg ttgcttccca gctgcatcgt | 840 |
| ttcctggagc tggcataccg tggcctcgc taccttgctg agcccggcgg tggcggaagc | 900 |
| gaactggccg cactggaagc tgagctggct gccctcgaag ctggaggctc tggagactac | 960 |
| tggggccaag gaaccctggt caccgtctcc tcagcctcca ccaagggccc atcggtcttc | 1020 |
| cccctggcac cctcctccaa gagcacctct ggggcacac cggccctggg ctgcctggtc | 1080 |
| aaggactact cccccgaacc ggtgacggtg tcgtggaact caggcgccct gaccagcggc | 1140 |
| gtgcacacct tcccggctgt cctacagtcc tcaggactct actccctcag cagcgtggtg | 1200 |
| actgtgccct ctagcagctt gggcacccag acctacatct gcaacgtgaa tcacaagccc | 1260 |
| agcaacacca aggtggacaa gaaagttgaa cccaaatctt gcgacaaaac tcacacatgc | 1320 |
| ccaccgtgcc cagcacctga actcctgggg ggaccgtcag tcttcctctt ccccccaaaa | 1380 |
| cccaaggaca ccctcatgat ctcccggacc cctgaggtca catgcgtggt ggtggacgtg | 1440 |
| agccacgaag accctgaggt caagttcaac tggtacgtgg acggcgtgga ggtgcataat | 1500 |
| gccaagacaa agccgcggga ggagcagtac aacagcacgt accgtgtggt cagcgtcctc | 1560 |
| accgtcctgc accaggactg gctgaatggc aaggagtaca agtgcaaggt ctccaacaaa | 1620 |
| gccctcccag cccccatcga gaaaaccatc tccaaagcca agggcagccc cgagaaccca | 1680 |
| caggtgtaca ccctgccccc atcccgggat gagctgacca agaaccaggt cagcctgacc | 1740 |
| tgcctggtca aaggcttcta tcccagcgac atcgccgtgg agtgggagag caatgggcag | 1800 |
| ccggagaaca actacaagac cacgcctccc gtgctggact ccgacggctc cttcttcctc | 1860 |
| tacagcaagc tcaccgtgga caagagcagg tggcagcagg ggaacgtctt ctcatgctcc | 1920 |
| gtgatgcatg aggctctgca caaccactac acgcagaaga gcctctccct gtctccgggt | 1980 |
| aaa | 1983 |

<210> SEQ ID NO 39
<211> LENGTH: 1995
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

| | |
|---|---|
| caggtccagc tgagagagag cggcccttca ctggtcaagc catcccagac actgagcctg | 60 |
| acatgcacag caagcgggtt ttcactgagc gacaaggcag tgggatgggt ccgacaggca | 120 |
| ccaggaaaag ccctggaatg gctgggcagc atcgataccg gcgggaacac agggtacaat | 180 |
| cccggactga agagcagact gtccattacc aaggacaact ctaaaagtca ggtgtcactg | 240 |
| agcgtgagct ccgtcaccac agaggatagt gcaacttact attgcacctc tgtgcaccag | 300 |

```
ggcggaagcg gagcaaagct cgccgcactg aaagccaagc tggccgctct gaagggaggc    360
ggtggctcca ccccccttgg ccctgcccga tccctgcccc agagcttcct gctcaagtgc    420
ttagagcaag tgaggaaaat ccaggctgat ggcgccgagc tgcaggagag gctgtgtgcc    480
gcccacaagc tgtgccaccc ggaggagctg atgctgctca ggcactctct gggcatcccc    540
caggctcccc taagcagctg ctccagccag tccctgcagc tgacgagctg cctgaaccaa    600
ctacacggcg gcctctttct ctaccagggc ctcctgcagg ccctggcggg catctcccca    660
gagctggccc ccaccttgga cacactgcag ctggacgtca ctgactttgc cacgaacatc    720
tggctgcaga tggaggacct gggggcggcc ccgctgtgc agcccaccca gggcgccatg    780
ccgaccttca cttcagcctt ccaacgcaga gcaggagggg tcctggttgc ttcccagctg    840
catcgtttcc tggagctggc ataccgtggc ctgcgctacc ttgctgagcc cggcggtggc    900
ggaagcgaac tggccgcact ggaagctgag ctggctgccc tcgaagctgg aggctctgga    960
tggcatgtgg atgtctgggg acagggcctg ctggtgacag tctctagtgc ttccacaact   1020
gcaccaaagg tgtaccccct gtcaagctgc tgtggggaca atcctctag taccgtgaca   1080
ctgggatgcc tggtctcaag ctatatgccc gagcctgtga ctgtcacctg gaactcagga   1140
gccctgaaaa gcggagtgca caccttccca gctgtgctgc agtcctctgg cctgtatagc   1200
ctgagttcaa tggtgacagt ccccggcagt acttcagggc agaccttcac ctgtaatgtg   1260
gcccatcctg ccagctccac caaagtggac aaagcagtgg aacccaaatc ttgcgacaaa   1320
actcacacat gcccaccgtg cccagcacct gaactcctgg ggggaccgtc agtcttcctc   1380
ttccccccaa aacccaagga caccctcatg atctcccgga cccctgaggt cacatgcgtg   1440
gtggtggacg tgagccacga agaccctgag gtcaagttca actggtacgt ggacggcgtg   1500
gaggtgcata atgccaagac aaagccgcgg gaggagcagt acaacagcac gtaccgtgtg   1560
gtcagcgtcc tcaccgtcct gcaccaggac tggctgaatg gcaaggagta caagtgcaag   1620
gtctccaaca agccctccc agcccccatc gagaaaacca tctccaaagc caagggcag   1680
ccccgagaac acaggtgta ccctgccc ccatcccggg atgagctgac caagaaccag   1740
gtcagcctga cctgcctggt caaaggcttc tatcccagcg acatcgccgt ggagtgggag   1800
agcaatgggc agccggagaa caactacaag accacgcctc ccgtgctgga ctccgacggc   1860
tccttcttcc tctacagcaa gctcaccgtg gacaagagca ggtggcagca ggggaacgtc   1920
ttctcatgct ccgtgatgca tgaggctctg cacaaccact acacgcagaa gagcctctcc   1980
ctgtctccgg gtaaa                                                    1995
```

<210> SEQ ID NO 40
<211> LENGTH: 1593
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
gaggtgcagc tggtggagtc tggaggaggc ttggtccagc ctgggggtc cctgagactc     60
tcctgtgcag cctctgggtt caatattaag gacacttaca tccactgggt ccgccaggct    120
ccagggaagg gctggagtg gtcgcacgt atttatccta ccaatggtta cacacgctac    180
gcagactccg tgaagggccg attcaccatc tccgcagaca cttccaagaa cacggcgtat    240
cttcaaatga acagcctgag agccgaggac acggccgtgt attactgttc gagaggcgga    300
```

| | |
|---|---|
| agcggagcaa agctcgccgc actgaaagcc aagctggccg ctctgaagtg cgggggtggc | 360 |
| ggaagcatcg aaggtcgtca cggagaagga acatttacca gcgacctcag caagcagatg | 420 |
| gaggaagagg ccgtgaggct gttcatcgag tggctgaaga acggcggacc ctcctctggc | 480 |
| gctccacccc ctagcggcgg aggtgggagt tgcgaactgg ccgcactgga agctgagctg | 540 |
| gctgccctcg aagctggagg ctctggagac tactggggcc aaggaaccct ggtcaccgtc | 600 |
| tcctcagcct ccaccaaggg cccatcggtc ttccccctgg cacccctcct caagagcacc | 660 |
| tctgggggca gcgcggccct gggctgcctg gtcaaggact acttccccga accggtgacg | 720 |
| gtgtcgtgga actcaggcgc cctgaccagc ggcgtgcaca ccttcccggc tgtcctacag | 780 |
| tcctcaggac tctactccct cagcagcgtg gtgactgtgc cctctagcag cttgggcacc | 840 |
| cagacctaca tctgcaacgt gaatcacaag cccagcaaca ccaaggtgga caagaaagtt | 900 |
| gaacccaaat cttgcgacaa aactcacaca tgcccaccgt gcccagcacc tccagtcgcc | 960 |
| ggaccgtcag tcttcctctt ccctccaaaa cccaaggaca ccctcatgat ctcccggacc | 1020 |
| cctgaggtca catgcgtggt ggtggacgtg agccacgaag accctgaggt caagttcaac | 1080 |
| tggtacgtgg acggcgtgga ggtgcataat gccaagacaa agccgcggga ggagcagtac | 1140 |
| aacagcacgt accgtgtggt cagcgtcctc accgtcctgc accaggactg gctgaatggc | 1200 |
| aaggagtaca agtgcaaggt ctccaacaaa ggcctcccaa gctccatcga gaaaaccatc | 1260 |
| tccaaagcca agggcagccc cgagaaccag gtgtaca ccctgcctcc atcccgggat | 1320 |
| gagctgacca agaaccaggt cagcctgacc tgcctggtca aaggcttcta tcccagcgac | 1380 |
| atcgccgtgg agtgggagag caatgggcag ccggagaaca actacaagac cacgcctccc | 1440 |
| gtgctggact ccgacggctc cttcttcctc tacagcaagc tcaccgtgga caagagcagg | 1500 |
| tggcagcagg ggaacgtctt ctcatgctcc gtgatgcatg aggctctgca caaccactac | 1560 |
| acgcagaaga gcctctccct gtctccgggt aaa | 1593 |

<210> SEQ ID NO 41
<211> LENGTH: 1563
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

| | |
|---|---|
| gaggtgcagc tggtggagtc tggaggaggc ttggtccagc ctggggggtc cctgagactc | 60 |
| tcctgtgcag cctctgggtt caatattaag gacacttaca tccactgggt ccgccaggct | 120 |
| ccagggaagg gctggagtg ggtcgcacgt atttatccta ccaatggtta cacacgctac | 180 |
| gcagactccg tgaagggccg attcaccatc tccgcagaca cttccaagaa cacggcgtat | 240 |
| cttcaaatga acagcctgag agccgaggac acggccgtgt attactgttc gagaggcgga | 300 |
| agcggagcaa agctcgccgc actgaaagcc aagctggccg ctctgaaggg aggcggtggc | 360 |
| tccatcaacg tgaagtgcag cctgccccag cagtgcatca gccctgcaa ggacgccggc | 420 |
| atgcggttcg gcaagtgcat gaacaagaag tgcaggtgct acagcggcgg tggcggaagc | 480 |
| gaactggccg cactggaagc tgagctggct gccctcgaag ctggaggctc tggagactac | 540 |
| tggggccaag gaaccctggt caccgtctcc tcagcctcca ccaagggccc atcggtcttc | 600 |
| cccctggcac ctcctccaa gagcacctct ggggcacag cggccctggg ctgcctggtc | 660 |
| aaggactact tccccgaacc ggtgacggtg tcgtggaact caggcgccct gaccagcggc | 720 |

```
gtgcacacct tcccggctgt cctacagtcc tcaggactct actccctcag cagcgtggtg     780
actgtgccct ctagcagctt gggcacccag acctacatct gcaacgtgaa tcacaagccc     840
agcaacacca aggtggacaa gaaagttgaa cccaaatctt gcgacaaaac tcacacatgc     900
ccaccgtgcc cagcacctga actcctgggg gaccgtcag tcttcctctt ccccccaaaa     960
cccaaggaca ccctcatgat ctcccggacc cctgaggtca catgcgtggt ggtggacgtg    1020
agccacgaag accctgaggt caagttcaac tggtacgtgg acggcgtgga ggtgcataat    1080
gccaagacaa agccgcggga ggagcagtac aacagcacgt accgtgtggt cagcgtcctc    1140
accgtcctgc accaggactg gctgaatggc aaggagtaca agtgcaaggt ctccaacaaa    1200
gccctcccag cccccatcga gaaaaccatc tccaaagcca agggcagcc cgagaaccac    1260 caggtgtaca ccctgccccc atcccgggat gagctgacca gaaccaggt cagcctgacc    1320 tgcctggtca aaggcttcta tcccagcgac atcgccgtgg agtgggagag caatgggcag    1380
ccggagaaca actacaagac cacgcctccc gtgctggact ccgacggctc cttcttcctc    1440
tacagcaagc tcaccgtgga caagagcagg tggcagcagg ggaacgtctt ctcatgctcc    1500
gtgatgcatg aggctctgca caaccactac acgcagaaga gcctctccct gtctccgggt    1560
aaa                                                                  1563

<210> SEQ ID NO 42
<211> LENGTH: 1569
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gaggtgcagc tggtggagtc tggaggaggc ttggtccagc ctggggggtc cctgagactc      60
tcctgtgcag cctctgggtt caatattaag gacacttaca tccactgggt ccgccaggct     120
ccagggaagg ggctggagtg ggtcgcacgt atttatccta ccaatggtta cacacgctac     180
gcagactccg tgaagggccg attcaccatc tccgcagaca cttccaagaa cacggcgtat     240
cttcaaatga acagcctgag agccgaggac acggccgtgt attactgttc gagaggcgga     300
agcggagcaa agctcgccgc actgaaagcc aagctggccg ctctgaaggg aggcggtggc     360
tccgccgctg caatctcctg cgtcggcagc cccgaatgtc ctcccaagtg ccgggctcag     420
ggatgcaaga acggcaagtg tatgaaccgg aagtgcaagt gctactattg cggcggtggc     480
ggaagcgaac tggccgcact ggaagctgag ctggctgccc tcgaagctgg aggctctgga     540
gactactggg gccaaggaac cctggtcacc gtctcctcag cctccaccaa gggcccatcg     600
gtcttccccc tggcaccctc ctccaagagc acctctgggg gcacagcggc cctgggctgc     660
ctggtcaagg actacttccc cgaaccggtg acggtgtcgt ggaactcagg cgccctgacc     720
agcggcgtgc acaccttccc ggctgtccta cagtcctcag actctactc cctcagcagc     780 gtggtgactg tgccctctag cagcttgggc acccagacct acatctgcaa cgtgaatcac     840
aagcccagca acaccaaggt ggacaagaaa gttgaaccca atcttgcga caaaactcac     900 acatgcccac cgtgcccagc acctgaactc ctggggggac cgtcagtctt cctcttcccc     960
ccaaaaccca aggacaccct catgatctcc cggacccctg aggtcacatg cgtggtggtg    1020
gacgtgagcc acgaagaccc tgaggtcaag ttcaactggt acgtgacgg cgtggaggtg    1080 cataatgcca agacaaagcc gcgggaggag cagtacaaca gcacgtaccg tgtggtcagc    1140
```

| | |
|---|---|
| gtcctcaccg tcctgcacca ggactggctg aatggcaagg agtacaagtg caaggtctcc | 1200 |
| aacaaagccc tcccagcccc catcgagaaa accatctcca aagccaaagg cagccccga | 1260 |
| gaaccacagg tgtacaccct gcccccatcc cgggatgagc tgaccaagaa ccaggtcagc | 1320 |
| ctgacctgcc tggtcaaagg cttctatccc agcgacatcg ccgtggagtg ggagagcaat | 1380 |
| gggcagccgg agaacaacta caagaccacg cctcccgtgc tggactccga cggctccttc | 1440 |
| ttcctctaca gcaagctcac cgtggacaag agcaggtggc agcagggaa cgtcttctca | 1500 |
| tgctccgtga tgcatgaggc tctgcacaac cactacacgc agaagagcct ctccctgtct | 1560 |
| ccgggtaaa | 1569 |

<210> SEQ ID NO 43
<211> LENGTH: 1986
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

| | |
|---|---|
| gaggtgcagc tggtggagtc tggaggaggc ttggtccagc ctgggggtc cctgagactc | 60 |
| tcctgtgcag cctctgggtt caatattaag gacacttaca tccactgggt ccgccaggct | 120 |
| ccagggaagg ggctggagtg ggtcgcacgt atttatccta ccaatggtta cacacgctac | 180 |
| gcagactccg tgaagggccg attcaccatc tccgcagaca cttccaagaa cacggcgtat | 240 |
| cttcaaatga acagcctgag agccgaggac acggccgtgt attactgttc gagaggcgga | 300 |
| agcggagcaa agctcgccgc actgaaagcc aagctggccg ctctgaaggg gggtggcgga | 360 |
| agcgccacac ctctgggccc cgcctcctcc ctgcctcaga gctttctgct caaatgtctg | 420 |
| gagcaggtgc ggaagatcca gggcgacggc gccgctctgc aagagaaact ggtcagcgaa | 480 |
| tgcgccacat ataagctgtg tcaccccgag gaactggtcc tcttgggcca cagcctgggc | 540 |
| atcccctggg ccctctcag ctcctgcccc tccaagctc tccaactggc tggatgtctg | 600 |
| tcccaactgc actccggcct cttcctgtac cagggactcc tccaggctct cgaagggatc | 660 |
| agccccgaac tgggcccac actggacacc ttgcaactcg atgtggccga tttcgccaca | 720 |
| accatctggc agcagatgga agaactcgga atggctcctg ctctccagcc cacacaggga | 780 |
| gctatgcctg ctttcgcctc tgcttccag cggagagctg tggtgtgct cgtcgcatcc | 840 |
| cacctccaga gcttcttgga ggtgtcctat cgggtgctcc ggcatctggc ccaacccggc | 900 |
| ggaggtggga gtgaactggc cgcactgaa gctgagctgg ctgccctcga agctggaggc | 960 |
| tctggagact actggggcca aggaaccctg gtcaccgtct cctcagccag cactaaaggt | 1020 |
| ccatctgtgt tccctctggc tccttgcagc cggagcacct ccgagtccac agccgctctg | 1080 |
| ggatgtctgg tgaaagatta cttccccgag cccgtcaccg tgagctggaa tagcggagca | 1140 |
| ctgacctccg gcgtccacac attccccgcc gtgctccaaa gctccggcct gtacagcctc | 1200 |
| tcctccgtgg tcaccgtgcc agcagctct ctgggcacaa agacctatac ctgtaacgtg | 1260 |
| gatcacaagc ctagcaacac caaagtggat aagcgggtgg agagcaagta cggccctccc | 1320 |
| tgtcccccctt gccccgctcc tgaggccgct ggcggaccttc cgtgttcct gtttccccct | 1380 |
| aagcccaagg acaccctcat gattagccgg acccccgaag tgacctgcgt ggtcgtggat | 1440 |
| gtgtcccagg aggaccctga agtgcaattt aactggtacg tggacggcgt cgaggtgcac | 1500 |
| aacgccaaga ccaagcctcg ggaagagcag ttcaacagca cctaccgggt ggtcagcgtg | 1560 |

```
ctgacagtgc tgcaccagga ctggctgaac ggcaaggagt acaagtgcaa ggtgagcaac    1620
aagggcctgc ccagctccat cgagaagacc atcagcaagg ccaagggcca gcccagggaa    1680
ccccaggtgt ataccctgcc ccctagccag gaggaaatga ccaaaaacca ggtgagcctg    1740
acctgcctgg tgaagggctt ctaccccagc gacatcgccg tggagtggga gagcaacggc    1800
cagcccgaga caattacaa gaccacccct cctgtgctgg acagcgacgg ctccttcttt    1860
ctgtatagcc ggctgaccgt ggacaagagc aggtggcagg agggcaacgt gttctcctgt    1920
agcgtgatgc acgaggccct gcacaaccat tacacccaga gagcttgag cctgagcctg    1980 ggcaaa                                                              1986
```

<210> SEQ ID NO 44
<211> LENGTH: 2025
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

```
gaggtgcagc tggtggagtc tggaggaggc ttggtccagc ctggggggtc cctgagactc      60
tcctgtgcag cctctgggtt caatattaag gacacttaca tccactgggt ccgccaggct     120
ccagggaagg ggctggagtg ggtcgcacgt atttatccta ccaatggtta cacacgctac     180
gcagactccg tgaagggccg attcaccatc tccgcagaca cttccaagaa cacggcgtat     240
cttcaaatga acagcctgag agccgaggac acggccgtgt attactgttc gagaggcgga     300
agcggagcaa agctcgccgc actgaaagcc aagctggccg ctctgaaggg gggtggcgga     360
agcttcccaa ccattccctt atccaggctt tttgacaacg ctatgctccg cgcccatcgt     420
ctgcaccagc tggcctttga cacctaccag gagtttgaag aagcctatat cccaaaggaa     480
cagaagtatt cattcctgca gaaccccag acctccctct gtttctcaga gtctattccg     540
acaccctcca acagggagga aacacaacag aaatccaacc tagagctgct ccgcatctcc     600
ctgctgctca tccagtcgtg gctggagccc gtgcagttcc tcaggagtgt cttcgccaac     660
agcctggtgt acggcgcctc tgacagcaac gtctatgacc tcctaaagga cctagaggaa     720
ggcatccaaa cgctgatggg gaggctggaa gatggcagcc ccggactgg gcagatcttc     780 aagcagacct acagcaagtt cgacacaaac tcacacaacg atgacgcact actcaagaac     840
tacgggctgc tctactgctt caggaaggac atggacaagg tcgagacatt cctgcgcatc     900
gtgcagtgcc gctctgtgga gggcagctgt ggcttcggcg aggtggag tgaactggcc     960 gcactggaag ctgagctggc tgccctcgaa gctggaggct ctggagacta ctggggccaa    1020
ggaaccctgg tcaccgtctc ctcagccagc actaaaggtc catctgtgtt ccctctggct    1080
ccttgcagcc ggagcaccct cgagtccaca gccgctctgg gatgtctggt gaaagattac    1140
ttccccgagc ccgtcaccgt gagctggaat agcgagcac tgacctccgg cgtccacaca    1200
ttccccgccg tgctccaaag ctccggcctg tacagcctct cctccgtggt caccgtgccc    1260
agcagctctc tgggcacaaa gacctatacc tgtaacgtgg atcacaagcc tagcaacacc    1320
aaagtggata gcgggtgga gagcaagtac ggccctccct gtcccccttg ccccgctcct    1380
gaggccgctg gcggaccttc cgtgttcctg tttcccccta gcccaagga cacctcatg    1440 attagccgga cacccgaagt gacctgcgtg gtcgtggatg tgtcccagga ggaccctgaa    1500
gtgcaattta actggtacgt ggacggcgtc gaggtgcaca acgccaagac caagcctcgg    1560
```

| | |
|---|---:|
| gaagagcagt tcaacagcac ctaccgggtg gtcagcgtgc tgacagtgct gcaccaggac | 1620 |
| tggctgaacg gcaaggagta caagtgcaag gtgagcaaca agggcctgcc cagctccatc | 1680 |
| gagaagacca tcagcaaggc caagggccag cccagggaac cccaggtgta ccctgccc | 1740 |
| cctagccagg aggaaatgac caaaaaccag gtgagcctga cctgcctggt gaagggcttc | 1800 |
| taccccagcg acatcgccgt ggagtgggag agcaacggcc agcccgagaa caattacaag | 1860 |
| accacccctc ctgtgctgga cagcgacggc tccttctttc tgtatagccg gctgaccgtg | 1920 |
| gacaagagca ggtggcagga gggcaacgtg ttctcctgta gcgtgatgca cgaggccctg | 1980 |
| cacaaccatt acacccagaa gagcttgagc ctgagcctgg gcaaa | 2025 |

<210> SEQ ID NO 45
<211> LENGTH: 2058
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

| | |
|---|---:|
| gaggtgcagc tggtggagtc tggaggaggc ttggtccagc ctggggggtc cctgagactc | 60 |
| tcctgtgcag cctctgggtt caatattaag gacacttaca tccactgggt ccgccaggct | 120 |
| ccagggaagg ggctggagtg ggtcgcacgt atttatcctg gcggaagcgg agcaaagctc | 180 |
| gccgcactga agccaagct ggccgctctg aagggtggtg gcggaagctt cccaaccatt | 240 |
| cccttatcca ggcttttga caacgctatg ctccgcgccc atcgtctgca ccagctggcc | 300 |
| tttgacacct accaggagtt tgaagaagcc tatatcccaa aggaacagaa gtattcattc | 360 |
| ctgcagaacc cccagacctc cctctgtttc tcagagtcta ttccgacacc ctccaacagg | 420 |
| gaggaaacac aacagaaatc caacctagag ctgctccgca tctccctgct gctcatccag | 480 |
| tcgtggctgg agcccgtgca gttcctcagg agtgtcttcg ccaacagcct ggtgtacggc | 540 |
| gcctctgaca gcaacgtcta tgacctccta aaggacctag aggaaggcat ccaaacgctg | 600 |
| atggggaggc tggaagatgg cagccccgg actgggcaga tcttcaagca gacctacagc | 660 |
| aagttcgaca caaactcaca caacgatgac gcactactag agaactacgg gctgctctac | 720 |
| tgcttcagga aggacatgga caaggtcgag acattcctgc gcatcgtgca gtgccgctct | 780 |
| gtggagggca gctgtggctt cggcggaggt gggagtgaac tggccgcact ggaagctgag | 840 |
| ctggctgccc tcgaagctgg aggctctgga ggttacacac gctacgcaga ctccgtgaag | 900 |
| ggccgattca ccatctccgc agacacttcc aagaacacgg cgtatcttca aatgaacagc | 960 |
| ctgagagccg aggacacggc cgtgtattac tgttcgagat ggggcggtga cggcttctat | 1020 |
| gccatggact actggggcca aggaaccctg gtcaccgtct cctcagcctc caccaagggc | 1080 |
| ccatcggtct tccccctggc accctcctcc aagagcacct ctgggggcac agcggccctg | 1140 |
| ggctgcctgg tcaaggacta cttccccgaa ccggtgacgg tgtcgtggaa ctcaggcgcc | 1200 |
| ctgaccagcg gcgtgcacac cttcccggct gtcctacagt cctcaggact ctactccctc | 1260 |
| agcagcgtgg tgactgtgcc ctctagcagc ttgggcaccc agacctacat ctgcaacgtg | 1320 |
| aatcacaagc ccagcaacac caaggtggac aagaaagttg aacccaaatc ttgcgacaaa | 1380 |
| actcacacat gcccaccgtg cccagcacct ccagtcgccg accgtcagt cttcctcttc | 1440 |
| cctccaaaac ccaaggacac cctcatgatc tcccggaccc ctgaggtcac atgcgtggtg | 1500 |
| gtggacgtga gccacgaaga ccctgaggtc aagttcaact ggtacgtgga cggcgtggag | 1560 |

```
gtgcataatg ccaagacaaa gccgcgggag gagcagtaca acagcacgta ccgtgtggtc    1620
agcgtcctca ccgtcctgca ccaggactgg ctgaatggca aggagtacaa gtgcaaggtc    1680
tccaacaaag gcctcccaag ctccatcgag aaaaccatct ccaaagccaa agggcagccc    1740
cgagaaccac aggtgtacac cctgcctcca tcccgggatg agctgaccaa gaaccaggtc    1800
agcctgacct gcctggtcaa aggcttctat cccagcgaca tcgccgtgga gtgggagagc    1860
aatgggcagc cggagaacaa ctacaagacc acgcctcccg tgctggactc cgacggctcc    1920
ttcttcctct acagcaagct caccgtggac aagagcaggt ggcagcaggg gaacgtcttc    1980
tcatgctccg tgatgcatga ggctctgcac aaccactaca cgcagaagag cctctccctg    2040
tctccgggta aatgataa                                                 2058

<210> SEQ ID NO 46
<211> LENGTH: 2028
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga gagcagact gtccattacc aaggacaact ctaaaagtca ggtgtcactg     240
agcgtgagct ccgtcaccac agaggatagt gcaacttact attgcggcgg aagcggagca     300
aagctcgccg cactgaaagc caagctggcc gctctgaagg ggggtggcgg aagcttccca     360
accattccct tatccaggct ttttgacaac gctatgctcc gcgcccatcg tctgcaccag     420
ctggcctttg acacctacca ggagtttgaa gaagcctata tcccaaagga acagaagtat     480
tcattcctgc agaaccccca gacctccctc tgtttctcag agtctattcc gacaccctcc     540 aacaggagg aaacacaaca gaaatccaac ctagagctgc tccgcatctc cctgctgctc     600
atccagtcgt ggctggagcc cgtgcagttc tcaggagtg tcttcgccaa cagcctggtg     660
tacggcgcct ctgacagcaa cgtctatgac ctcctaaagg acctagagga aggcatccaa     720
acgctgatgg ggaggctgga agatggcagc ccccggactg ggcagatctt caagcagacc     780
tacagcaagt tcgacacaaa ctcacacaac gatgacgcac tactcaagaa ctacgggctg     840
ctctactgct tcaggaagga catggacaag gtcgagacat tcctgcgcat cgtgcagtgc     900
cgctctgtgg agggcagctg tggcttcggc gaaggtggga gtgaactggc cgcactggaa     960
gctgagctgc tgccctcga agctggaggc tctggacatg tggatgtctg gggacagggc    1020
ctgctggtga cagtctctag tgcttccaca actgcaccaa ggtgtacccc cctgtcaagc    1080
tgctgtgggg acaaatcctc tagtaccgtg cactgggat gcctggtctc aagctatatg    1140
cccgagcctg tgactgtcac ctggaactca ggagccctga aaagcggagt gcacaccttc    1200
ccagctgtgc tgcagtcctc tggcctgtat agcctgagtt caatggtgac agtccccggc    1260
agtacttcag ggcagacctt cacctgtaat gtggcccatc ctgccagctc caccaaagtg    1320
gacaaagcag tggaacccaa atcttgcgac aaaactcaca catgcccacc gtgcccagca    1380
cctgaactcc tgggggggacc gtcagtcttc ctcttccccc caaaacccaa ggacaccctc    1440
atgatctccc ggaccctga ggtcacatgc gtggtggtgg acgtgagcca cgaagaccct    1500
```

| gaggtcaagt | tcaactggta | cgtggacggc | gtggaggtgc | ataatgccaa | gacaaagccg | 1560 |
| gggaggagc | agtacaacag | cacgtaccgt | gtggtcagcg | tcctcaccgt | cctgcaccag | 1620 |
| gactggctga | atggcaagga | gtacaagtgc | aaggtctcca | acaaagccct | cccagccccc | 1680 |
| atcgagaaaa | ccatctccaa | agccaaaggg | cagccccgag | aaccacaggt | gtacaccctg | 1740 |
| cccccatccc | gggatgagct | gaccaagaac | caggtcagcc | tgacctgcct | ggtcaaaggc | 1800 |
| ttctatccca | gcgacatcgc | cgtggagtgg | gagagcaatg | ggcagccgga | gaacaactac | 1860 |
| aagaccacgc | ctcccgtgct | ggactccgac | ggctccttct | tcctctacag | caagctcacc | 1920 |
| gtggacaaga | gcaggtggca | gcaggggaac | gtcttctcat | gctccgtgat | gcatgaggct | 1980 |
| ctgcacaacc | actacacgca | gaagagcctc | tccctgtctc | cgggtaaa | | 2028 |

<210> SEQ ID NO 47
<211> LENGTH: 1896
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 47

| gaggtgcagc | tggtggagtc | tggaggaggc | ttggtccagc | ctggggggtc | cctgagactc | 60 |
| tcctgtgcag | cctctgggtt | caatattaag | gacacttaca | tccactgggt | ccgccaggct | 120 |
| ccagggaagg | ggctggagtg | ggtcgcacgt | atttatccta | ccaatggtta | cacacgctac | 180 |
| gcagactccg | tgaagggccg | attcaccatc | tccgcagaca | cttccaagaa | cacggcgtat | 240 |
| cttcaaatga | acagcctgag | agccgaggac | acggccgtgt | attactgttc | gagaggcgga | 300 |
| agcggagcaa | agctcgccgc | actgaaagcc | aagctggccg | ctctgaaggg | gggtggcgga | 360 |
| agcgttccaa | ttcaaaaggt | tcaagatgat | accaaaactc | tgattaaaac | tatttgtcacg | 420 |
| cgtataaacg | acatcagcca | tacccagtcg | gttagctcaa | agcaaaaagt | taccggtttg | 480 |
| gactttattc | cgggactgca | cccgatcctg | acccttagta | aaatggacca | gacactggcc | 540 |
| gtctaccagc | aaatcctgac | atcgatgcca | tccagaaatg | tgatacaaat | tagcaacgat | 600 |
| ttggaaaacc | ttcgcgatct | gctgcacgtg | ctggccttca | gtaagtcctg | tcatctgccg | 660 |
| tgggcgtcgg | gactgagac | tcttgactcg | ctgggtggag | tgttagaggc | ctctggctat | 720 |
| tctactgaag | tcgttgcgct | gtcacgcctc | caggggagcc | tgcaggacat | gctgtggcag | 780 |
| ctggacctgt | cacctggctg | cggcggaggt | gggagtgaac | tggccgcact | ggaagctgag | 840 |
| ctggctgccc | tcgaagctgg | aggctctgga | gactactggg | gccaaggaac | cctggtcacc | 900 |
| gtctcctcag | cctccaccaa | gggcccatcg | gtcttccccc | tggcaccctc | ctccaagagc | 960 |
| acctctgggg | gcacagcggc | cctgggctgc | ctggtcaagg | actacttccc | cgaaccggtg | 1020 |
| acggtgtcgt | ggaactcagg | cgccctgacc | agcggcgtgc | acaccttccc | ggctgtccta | 1080 |
| cagtcctcag | gactctactc | cctcagcagc | gtggtgactg | tgccctctag | cagcttgggc | 1140 |
| acccagacct | acatctgcaa | cgtgaatcac | aagcccagca | acaccaaggt | ggacaagaaa | 1200 |
| gttgaaccca | aatcttgcga | caaaactcac | acatgcccac | cgtgcccagc | acctccagtc | 1260 |
| gccgaccgt | cagtcttcct | cttccctcca | aaacccaagg | acaccctcat | gatctcccgg | 1320 |
| acccctgagg | tcacatgcgt | ggtggtggac | gtgagccacg | aagaccctga | ggtcaagttc | 1380 |
| aactggtacg | tggacggcgt | ggaggtgcat | aatgccaaga | caaagccgcg | ggaggagcag | 1440 |
| tacaacagca | cgtaccgtgt | ggtcagcgtc | ctcaccgtcc | tgcaccagga | ctggctgaat | 1500 |

```
ggcaaggagt acaagtgcaa ggtctccaac aaaggcctcc caagctccat cgagaaaacc    1560
atctccaaag ccaaagggca gccccgagaa ccacaggtgt acaccctgcc tccatcccgg    1620
gatgagctga ccaagaacca ggtcagcctg acctgcctgg tcaaaggctt ctatcccagc    1680
gacatcgccg tggagtggga gagcaatggg cagccggaga caactacaa gaccacgcct     1740 cccgtgctgg actccgacgg ctccttcttc ctctacagca agctcaccgt ggacaagagc    1800
aggtggcagc aggggaacgt cttctcatgc tccgtgatgc atgaggctct gcacaaccac    1860
tacacgcaga agagcctctc cctgtctccg ggtaaa                               1896

<210> SEQ ID NO 48
<211> LENGTH: 1911
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gaggtgcagc tggtggagtc tggaggaggc ttggtccagc ctgggggtc cctgagactc       60 tcctgtgcag cctctgggtt caatattaag gacacttaca tccactgggt ccgccaggct    120
ccagggaagg ggctggagtg ggtcgcacgt attggcggaa gcggagcaaa gctcgccgca    180
ctgaaagcca agctggccgc tctgaagggg ggtggcggaa gcgttccaat tcaaaaggtt    240
caagatgata ccaaaactct gattaaaact attgtcacgc gtataaacga catctcacat    300
acccagtcgg ttagctcaaa gcaaaaagtt accggtttgg actttattcc gggactgcac    360
ccgatcctga cccttagtaa aatggaccag acactggccg tctaccagca aatcctgaca    420
tcgatgccat ccagaaatgt gatacaaatt agcaacgatt tggaaaacct tcgcgatctg    480
ctgcacgtgc tggccttcag taagtcctgt catctgccgt gggcgtcggg actggagact    540
cttgactcgc tgggtggagt gttagaggcc tctggctatt ctactgaagt cgttgcgctg    600
tcacgcctcc aggggagcct gcaggacatg ctgtggcagc tggacctgtc acctggctgc    660
ggcggaggtg ggagtgaact ggccgcactg gaagctgagc tggctgccct cgaagctgga    720
ggctctggaa cacgctacgc agactccgtg aagggccgat tcaccatctc cgcagacact    780
tccaagaaca cggcgtatct tcaaatgaac agcctgagag ccgaggacac ggccgtgtat    840
tactgttcga gatggggcgg tgacggcttc tatgccatgg actactgggg ccaaggaacc    900
ctggtcaccg tctcctcagc ctccaccaag ggcccatcgg tcttccccct ggcaccctcc    960
tccaagagca cctctggggg cacagcggcc ctgggctgcc tggtcaagga ctacttcccc    1020
gaaccggtga cggtgtcgtg gaactcaggc gccctgacca gcggcgtgca caccttcccg    1080
gctgtcctac agtcctcagg actctactcc ctcagcagcg tggtgactgt gccctctagc    1140
agcttgggca cccagaccta catctgcaac gtgaatcaca agcccagcaa caccaaggtg    1200
gacaagaaag ttgaacccaa atcttgcgac aaaactcaca catgcccacc gtgcccagca    1260
cctccagtcg ccggaccgtc agtcttcctc ttcccctccaa acccaaggac accctcatg    1320 atctcccgga cccctgaggt cacatgcgtg gtggtggacg tgagccacga agaccctgag    1380
gtcaagttca actggtacgt ggacggcgtg gaggtgcata atgccaagac aaagccgcgg    1440
gaggagcagt acaacagcac gtaccgtgtg gtcagcgtcc tcaccgtcct gcaccaggac    1500
tggctgaatg gcaaggagta caagtgcaag gtctccaaca aaggcctccc aagctccatc    1560
gagaaaacca tctccaaagc caaagggcag ccccgagaac acaggtgta cccctgcct   1620
```

| | |
|---|---|
| ccatcccggg atgagctgac caagaaccag gtcagcctga cctgcctggt caaaggcttc | 1680 |
| tatcccagcg acatcgccgt ggagtgggag agcaatgggc agccggagaa caactacaag | 1740 |
| accacgcctc ccgtgctgga ctccgacggc tccttcttcc tctacagcaa gctcaccgtg | 1800 |
| gacaagagca ggtggcagca ggggaacgtc ttctcatgct ccgtgatgca tgaggctctg | 1860 |
| cacaaccact acacgcagaa gagcctctcc ctgtctccgg gtaaatgata a | 1911 |

<210> SEQ ID NO 49
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

| | |
|---|---|
| gacatccaga tgacccagtc tccatcctcc ctgtctgcat ctgtaggaga cagagtcacc | 60 |
| atcacttgcc gggcaagtca ggatgtgaat accgcgtcg catggtatca gcagaaacca | 120 |
| gggaaagccc ctaagctcct gatctattct gcatccttct tgtatagtgg ggtcccatca | 180 |
| aggttcagtg gcagtagatc tgggacagat ttcactctca ccatcagcag tctgcaacct | 240 |
| gaagattttg caacttacta ctgtcaacag cattacggcg gaagcggagc aaagctcgcc | 300 |
| gcactgaaag ccaagctggc cgctctgaag ggggtggcg gaagcgttcc aattcaaaag | 360 |
| gttcaagatg ataccaaaac tctgattaaa actattgtca cgcgtataaa cgacatctca | 420 |
| catacccagt cggttagctc aaagcaaaaa gttaccggtt tggactttat tccgggactg | 480 |
| cacccgatcc tgacccttag taaaatggac cagacactgg ccgtctacca gcaaatcctg | 540 |
| acatcgatgc catccagaaa tgtgatacaa attagcaacg atttggaaaa ccttcgcgat | 600 |
| ctgctgcacg tgctggcctt cagtaagtcc tgtcatctgc cgtgggcgtc gggactggag | 660 |
| actcttgact cgctgggtgg agtgttagag gcctctggct attctactga agtcgttgcg | 720 |
| ctgtcacgcc tccaggggag cctgcaggac atgctgtggc agctggacct gtcacctggc | 780 |
| tgcggcggag gtgggagtga actggccgca ctggaagctg agctggctgc cctcgaagct | 840 |
| ggaggctctg gaccgacgtt cggccaaggt accaagcttg agatcaaacg aactgtggct | 900 |
| gcaccatctg tcttcatctt cccgccatct gatgagcagt tgaaatctgg aactgcctct | 960 |
| gtcgtgtgcc tgctgaataa cttctatccc agagaggcca agtacagtg gaaggtggat | 1020 |
| aacgccctcc aatcgggtaa ctcccaggag agtgtcacag agcaggacag caaggacagc | 1080 |
| acctacagcc tcagcagcac cctgacgctg agcaaagcag actacgagaa acacaaagtc | 1140 |
| tacgcctgcg aagtcaccca tcagggcctg tcctcgcccg tcacaaagag cttcaacagg | 1200 |
| ggagagtgt | 1209 |

<210> SEQ ID NO 50
<211> LENGTH: 1947
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

| | |
|---|---|
| gaggtgcagc tggtggagtc tggaggaggc ttggtccagc ctgggggtc cctgagactc | 60 |
| tcctgtgcag cctctgggtt caatattaag gacacttaca tccactgggt ccgccaggct | 120 |
| ccagggaagg ggctggagtg ggtcgcacgt atttatccta ccaatggtta cacacgctac | 180 |

```
gcagactccg tgaagggccg attcaccatc tccgcagaca cttccaagaa cacggcgtat    240
cttcaaatga acagcctgag agccgaggac acggccgtgt attactgttc gagaggcgga    300
agcggagcaa agctcgccgc actgaaagcc aagctggccg ctctgaaggg tggtggcgga    360
agctgtgatc tgcctcaaac ccacagcctg ggtagcagga ggaccttgat gctcctggca    420
cagatgagga gaatctctct tttctcctgc ttgaaggaca gacatgactt tggatttccc    480
caggaggagt ttggcaacca gttccaaaag gctgaaacca tccctgtcct ccatgagatg    540
atccagcaga tcttcaatct cttcagcaca aaggactcat ctgctgcttg ggatgagacc    600
ctcctagaca aattctacac tgaactctac cagcagctga atgacctgga agcctgtgtg    660 atacagggg tgggggtgac agagactccc ctgatgaagg aggactccat tctggctgtg    720
aggaaatact tccaaagaat cactctctat ctgaaagaga agaaatacag cccttgtgcc    780
tgggaggttg tcagagcaga aatcatgaga tcttttttctt tgtcaacaaa cttgcaagaa    840
agtttaagaa gtaaggaagg cggaggtggg agtgaactgg ccgcactgga agctgagctg    900
gctgccctcg aagctggagg ctctggagac tactgggcc aaggaaccct ggtcaccgtc    960
tcctcagcca gcactaaagg tccatctgtg ttccctctgg ctccttgcag ccggagcacc   1020
tccgagtcca cagccgctct gggatgtctg gtgaaagatt acttccccga gcccgtcacc   1080
gtgagctgga atagcggagc actgacctcc ggcgtccaca cattccccgc cgtgctccaa   1140
agctccggcc tgtacagcct ctcctccgtg gtcaccgtgc ccagcagctc tctgggcaca   1200
aagacctata cctgtaacgt ggatcacaag cctagcaaca ccaaagtgga taagcgggtg   1260
gagagcaagt acggccctcc ctgtcccct tgccccgctc ctgaggccgc tggcggacct   1320
tccgtgttcc tgtttccccc taagcccaag gacaccctca tgattagccg gacacccgaa   1380
gtgacctgcg tggtcgtgga tgtgtcccag gaggaccctg aagtgcaatt taactggtac   1440
gtggacggcg tcgaggtgca caacgccaag accaagcctc gggaagagca gttcaacagc   1500
acctaccggg tggtcagcgt gctgacagtg ctgcaccagg actggctgaa cggcaaggag   1560
tacaagtgca aggtgagcaa caagggcctc ccagctcca tcgagaagac catcagcaag   1620
gccaagggcc agcccaggga accccaggtg tatacccctgc cccctagcca ggaggaaatg   1680
accaaaaacc aggtgagcct gacctgcctg gtgaagggct tctacccag cgacatcgcc   1740 gtggagtggg agagcaacgg ccagcccgag aacaattaca agaccacccc tcctgtgctg   1800
gacagcgacg gctccttctt tctgtatagc cggctgaccg tggacaagag caggtggcag   1860
gagggcaacg tgttctcctg tagcgtgatg cacgaggccc tgcacaacca ttacacccag   1920
aagagcttga gcctgagcct gggcaaa                                        1947

<210> SEQ ID NO 51
<211> LENGTH: 1962
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gaggtgcagc tggtggagtc tggaggaggc ttggtccagc ctgggggtc cctgagactc     60 tcctgtgcag cctctgggtt caatattaag gacacttaca tccactgggt ccgccaggct   120
ccagggaagg ggctgagtg gtcgcacgt atttatccta ccaatggtta cacacgctac    180
gcagactccg tgaagggccg attcaccatc tccgcagaca cttccaagaa cacggcgtat   240
```

```
cttcaaatga acagcctgag agccgaggac acggccgtgt attactgttc gagaggcgga    300
agcggagcaa agctcgccgc actgaaagcc aagctggccg ctctgaaggg tggtggcgga    360
agcatgagct acaacttgct tggattccta caaagaagca gcaattttca gtgtcagaag    420
ctcctgtggc aattgaatgg gaggcttgaa tactgcctca aggacaggat gaactttgac    480
atccctgagg agattaagca gctgcagcag ttccagaagg aggacgccgc attgaccatc    540
tatgagatgc tccagaacat ctttgctatt ttcagacaag attcatctag cactggctgg    600
aatgagacta ttgttgagaa cctcctggct aatgtctatc atcagataaa ccatctgaag    660
acagtcctgg aagaaaaact ggagaaagaa gatttcacca ggggaaaact catgagcagt    720
ctgcacctga aagatatta tgggaggatt ctgcattacc tgaaggccaa ggagtacagt    780
cactgtgcct ggaccatagt cagagtggaa atcctaagga acttttactt cattaacaga    840
cttacaggtt acctccgaaa cggcggaggt gggagtgaac tggccgcact ggaagctgag    900
ctggctgccc tcgaagctgg aggctctgga gactactggg gccaaggaac cctggtcacc    960
gtctcctcag cctccaccaa gggcccatcg gtcttccccc tggcaccctc ctccaagagc   1020
acctctgggg gcacagcggc cctgggctgc ctggtcaagg actacttccc cgaaccggtg   1080
acggtgtcgt ggaactcagg cgccctgacc agcggcgtgc acaccttccc ggctgtccta   1140
cagtcctcag gactctactc cctcagcagc gtggtgactg tgccctctag cagcttgggc   1200
acccagacct acatctgcaa cgtgaatcac aagcccagca caccaaggt ggacaagaaa   1260 gttgaaccca aatcttgcga caaaactcac acatgcccac cgtgcccagc acctccagtc   1320
gccggaccgt cagtcttcct cttccctcca aaacccaagg acaccctcat gatctcccgg   1380
acccctgagg tcacatgcgt ggtggtggac gtgagccacg aagaccctga ggtcaagttc   1440
aactggtacg tggacggcgt ggaggtgcat aatgccaaga caaagccgcg ggaggagcag   1500
tacaacagca cgtaccgtgt ggtcagcgtc ctcaccgtcc tgcaccagga ctggctgaat   1560
ggcaaggagt acaagtgcaa ggtctccaac aaaggcctcc aagctccat cgagaaaacc   1620 atctccaaag ccaaagggca gccccgagaa ccacaggtgt acaccctgcc tccatcccgg   1680
gatgagctga ccaagaacca ggtcagcctg acctgcctgg tcaaaggctt ctatcccagc   1740
gacatcgccg tggagtggga gagcaatggg cagccggaga acaactacaa gaccacgcct   1800
cccgtgctgg actccgacgg ctccttcttc ctctacagca agctcaccgt ggacaagagc   1860
aggtggcagc aggggaacgt cttctcatgc tccgtgatgc atgaggctct gcacaaccac   1920
tacacgcaga gagcctctc cctgtctccg ggtaaatgat aa                      1962
```

<210> SEQ ID NO 52
<211> LENGTH: 1953
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 52

```
caggtccagc tgagagagag cggcccttca ctggtcaagc catcccagac actgagcctg     60
acatgcacag caagcgggtt ttcactgagc gacaaggcag tgggatgggt ccgacaggca    120
ccaggaaaag ccctggaatg gctgggcagc atcgataccg gcgggaacac agggtacaat    180 cccgactga agagcagact gtccattacc aaggacaact ctaaaagtca ggtgtcactg    240
agcgtgagct ccgtcaccac agaggatagt gcaacttact attgcggcgg aagcggagca    300
```

```
aagctcgccg cactgaaagc caagctggcc gctctgaagg ggggtggcgg aagcatgagc      360
tacaacttgc ttggattcct acaaagaagc agcaattttc agtgtcagaa gctcctgtgg      420
caattgaatg ggaggcttga atactgcctc aaggacagga tgaactttga catccctgag      480
gagattaagc agctgcagca gttccagaag gaggacgccg cattgaccat ctatgagatg      540
ctccagaaca tctttgctat tttcagacaa gattcatcta gcactggctg aatgagact      600 attgttgaga acctcctggc taatgtctat catcagataa accatctgaa gacagtcctg      660
gaagaaaaac tggagaaaga gatttcacc aggggaaaac tcatgagcag tctgcacctg      720
aaaagatatt atgggaggat tctgcattac ctgaaggcca aggagtacag tcactgtgcc      780
tggaccatag tcagagtgga atcctaagg aacttttact tcattaacag acttacaggt      840
tacctccgaa acgcggagg tgggagtgaa ctggccgcac tggaagctga gctggctgcc      900
ctcgaagctg gaggctctgg acatgtggat gtctgggac agggcctgct ggtgacagtc      960
tctagtgctt ccacaactgc accaaaggtg taccccctgt caagctgctg tggggacaaa     1020
tcctctagta ccgtgacact gggatgcctg gtctcaagct atatgcccga gcctgtgact     1080
gtcacctgga actcaggagc cctgaaaagc ggagtgcaca ccttcccagc tgtgctgcag     1140
tcctctggcc tgtatagcct gagttcaatg gtgacagtcc ccggcagtac ttcagggcag     1200
accttcacct gtaatgtggc ccatcctgcc agctccacca agtggacaa agcagtggaa     1260 cccaaatctt gcgacaaaac tcacacatgc ccaccgtgcc cagcacctga actcctgggg     1320
ggaccgtcag tcttcctctt ccccccaaaa cccaaggaca ccctcatgat ctcccggacc     1380
cctgaggtca catgcgtggt ggtggacgtg agccacgaag accctgaggt caagttcaac     1440
tggtacgtgg acggcgtgga ggtgcataat gccaagacaa agccgcggga ggagcagtac     1500
aacagcacgt accgtgtggt cagcgtcctc accgtcctgc accaggactg gctgaatggc     1560
aaggagtaca agtgcaaggt ctccaacaaa gccctcccag cccccatcga gaaaaccatc     1620
tccaaagcca agggcagcc ccgagaacca caggtgtaca ccctgccccc atcccgggat     1680
gagctgacca agaaccaggt cagcctgacc tgcctggtca aaggcttcta tcccagcgac     1740
atcgccgtgg agtgggagag caatgggcag ccggagaaca actacaagac cacgcctccc     1800
gtgctggact ccgacggctc cttcttcctc tacagcaagc tcaccgtgga caagagcagg     1860
tggcagcagg ggaacgtctt ctcatgctcc gtgatgcatg aggctctgca caaccactac     1920
acgcagaaga gcctctccct gtctccgggt aaa                                  1953
```

<210> SEQ ID NO 53
<211> LENGTH: 1566
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
gaggtgcagc tggtggagtc tggaggaggc ttggtccagc ctggggggtc cctgagactc       60
tcctgtgcag cctctgggtt caatattaag gacacttaca tccactgggt ccgccaggct      120
ccagggaagg gctggagtg gtcgcacgt atttatccta ccaatggtta cacacgctac       180
gcagactccg tgaagggccg attcaccatc tccgcagaca cttccaagaa cacggcgtat      240
cttcaaatga acagcctgag agccgaggac acggccgtgt attactgttc gagaggcgga      300
agcggagcaa agctcgccgc actgaaagcc aagctggccg ctctgaagtg cggggggtggc     360
```

```
ggaagcatcg aaggtcgtca cgctgaggga acattcactt ccgatgtgtc ctcctacctg      420
gagggccagg ctgccaaaga gttcatcgct tggctcgtca agggcagggg cggaggtggg      480
agttgcgaac tggccgcact ggaagctgag ctggctgccc tcgaagctgg aggctctgga      540
gactactggg gccaaggaac cctggtcacc gtctcctcag cctccaccaa gggcccatcg      600
gtcttccccc tggcaccctc ctccaagagc acctctgggg gcacagcggc cctgggctgc      660
ctggtcaagg actacttccc cgaaccggtg acggtgtcgt ggaactcagg cgccctgacc      720
agcggcgtgc acaccttccc ggctgtccta cagtcctcag gactctactc cctcagcagc      780
gtggtgactg tgccctctag cagcttgggc acccagacct acatctgcaa cgtgaatcac      840
aagcccagca acaccaaggt ggacaagaaa gttgaaccca aatcttgcga caaaactcac      900
acatgcccac cgtgcccagc acctccagtc gccggaccgt cagtcttcct cttccctcca      960
aaacccaagg acaccctcat gatctcccgg acccctgagg tcacatgcgt ggtggtggac     1020
gtgagccacg aagaccctga ggtcaagttc aactggtacg tggacggcgt ggaggtgcat     1080
aatgccaaga caaagccgcg ggaggagcag tacaacagca cgtaccgtgt ggtcagcgtc     1140
ctcaccgtcc tgcaccagga ctggctgaat ggcaaggagt acaagtgcaa ggtctccaac     1200
aaaggcctcc caagctccat cgagaaaacc atctccaaag ccaaagggca gccccgagaa     1260
ccacaggtgt acaccctgcc tccatcccgg gatgagctga ccaagaacca ggtcagcctg     1320
acctgcctgg tcaaaggctt ctatcccagc gacatcgccg tggagtggga gagcaatggg     1380
cagccggaga acaactacaa gaccacgcct cccgtgctgg actccgacgg ctccttcttc     1440
ctctacagca agctcaccgt ggacaagagc aggtggcagc aggggaacgt cttctcatgc     1500
tccgtgatgc atgaggctct gcacaaccac tacacgcaga agagcctctc cctgtctccg     1560
ggtaaa                                                                1566
```

<210> SEQ ID NO 54
<211> LENGTH: 1629
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 54

```
gaggtgcagc tggtggagtc tggaggaggc ttggtccagc ctggggggtc cctgagactc       60
tcctgtgcag cctctgggtt caatattaag gacacttaca tccactgggt ccgccaggct      120
ccagggaagg ggctggagtg ggtcgcacgt atttatccta ccaatggtta cacacgctac      180
gcagactccg tgaagggccg attcaccatc tccgcagaca cttccaagaa cacggcgtat      240
cttcaaatga acagcctgag agccgaggac acggccgtgt attactgttc gagaggcgga      300
agcggagcaa agctcgccgc actgaaagcc aagctggccg ctctgaaggg gggtggcgga      360
agcgcgcaag agccagtcaa aggtccagtc tccactaagc ctggctcctg ccccattatc      420
ttgatccggt gcgccatgtt gaatcccoct aaccgctgct gaaagatac tgactgccca      480 ggaatcaaga agtgctgtga aggctcttgc gggatggcct gtttcgttcc caggggcgga      540
ggtgggagtg aactggccgc actggaagct gagctggctg ccctcgaagc tggaggctct      600
ggagactact ggggccaagg aaccctggtc accgtctcct cagcctccac caagggccca      660
tcggtcttcc ccctggcacc ctcctccaag agcacctctg gggggcacagc ggccctgggc      720 tgcctggtca aggactactt ccccgaaccg gtgacggtgt cgtggaactc aggcgccctg      780
```

```
accagcggcg tgcacacctt cccggctgtc ctacagtcct caggactcta ctccctcagc    840
agcgtggtga ctgtgccctc tagcagcttg ggcacccaga cctacatctg caacgtgaat    900
cacaagccca gcaacaccaa ggtggacaag aaagttgaac ccaaatcttg cgacaaaact    960
cacacatgcc caccgtgccc agcacctcca gtcgccggac cgtcagtctt cctcttccct    1020
ccaaaaccca aggacaccct catgatctcc cggacccctg aggtcacatg cgtggtggtg    1080
gacgtgagcc acgaagaccc tgaggtcaag ttcaactggt acgtggacgg cgtggaggtg    1140
cataatgcca agacaaagcc gcgggaggag cagtacaaca gcacgtaccg tgtggtcagc    1200
gtcctcaccg tcctgcacca ggactggctg aatggcaagg agtacaagtg caaggtctcc    1260
aacaaaggcc tcccaagctc catcgagaaa accatctcca aagccaaagg gcagcccga    1320 gaaccacagg tgtacaccct gcctccatcc cgggatgagc tgaccaagaa ccaggtcagc    1380
ctgacctgcc tggtcaaagg cttctatccc agcgacatcg ccgtggagtg ggagagcaat    1440
gggcagccgg agaacaacta caagaccacg cctcccgtgc tggactccga cggctccttc    1500
ttcctctaca gcaagctcac cgtggacaag agcaggtggc agcaggggaa cgtcttctca    1560
tgctccgtga tgcatgaggc tctgcacaac cactacacgc agaagagcct ctccctgtct    1620
ccgggtaaa                                                           1629
```

<210> SEQ ID NO 55
<211> LENGTH: 1740
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
gaggtgcagc tggtggagtc tggaggaggc ttggtccagc ctggggggtc cctgagactc    60
tcctgtgcag cctctgggtt caatattaag gacacttaca tccactgggt ccgccaggct    120
ccagggaagg ggctggagtg ggtcgcacgt atttatccta ccaatggtta cacacgctac    180
gcagactccg tgaagggccg attcaccatc tccgcagaca cttccaagaa cacggcgtat    240
cttcaaatga acagcctgag agccgaggac acggccgtgt attactgttc gagaggcgga    300
agcggagcaa agctcgccgc actgaaagcc aagctggccg ctctgaaggg aggtggcggg    360
agcgactctt ggatggaaga agttatcaaa ctgtgcggtc gtgaactggt tcgtgctcag    420
atcgctatct gcggtatgtc tacctggtct aaacgtgagg cagaggacct gcaggtgggg    480
caggtggagc tgggcggggg ccctggtgca ggcagcctgc agcccttggc cctggagggg    540
tccctgcaga agcgtcgtaa aaaacgtcag ctgtactctg ctctggctaa caatgctgc    600 cacgttggtt gcaccaaacg ttctctggct cgtttctgcg gcggaggtgg gagtgaactg    660
gccgcactgg aagctgagct ggctgccctc gaagctggag gctctggaga ctactggggc    720
caaggaaccc tggtcaccgt ctcctcagcc tccaccaagg gcccatcggt cttccccctg    780
gcaccctcct ccaagagcac ctctgggggc acagcggccc tgggctgcct ggtcaaggac    840
tacttccccg aaccggtgac ggtgtcgtgg aactcaggcg ccctgaccag cggcgtgcac    900
accttcccgg ctgtcctaca gtcctcagga ctctactccc tcagcagcgt ggtgactgtg    960
ccctctagca gcttgggcac ccagacctac atctgcaacg tgaatcacaa gcccagcaac    1020
accaaggtgg acaagaaagt tgaacccaaa tcttgcgaca aaactcacac atgcccaccg    1080
tgcccagcac ctccagtcgc cggaccgtca gtcttcctct tccctccaaa acccaaggac    1140
```

```
acctctcatga tctcccggac ccctgaggtc acatgcgtgg tggtggacgt gagccacgaa   1200
gaccctgagg tcaagttcaa ctggtacgtg gacggcgtgg aggtgcataa tgccaagaca   1260
aagccgcggg aggagcagta caacagcacg taccgtgtgg tcagcgtcct caccgtcctg   1320
caccaggact ggctgaatgg caaggagtac aagtgcaagg tctccaacaa aggcctccca   1380
agctccatcg agaaaaccat ctccaaagcc aagggcagc cccgagaacc acaggtgtac   1440
accctgcctc catcccggga tgagctgacc aagaaccagg tcagcctgac ctgcctggtc   1500
aaaggcttct atcccagcga catcgccgtg gagtgggaga gcaatgggca gccggagaac   1560
aactacaaga ccacgcctcc cgtgctggac tccgacggct ccttcttcct ctacagcaag   1620
ctcaccgtgg acaagagcag gtggcagcag gggaacgtct tctcatgctc cgtgatgcat   1680
gaggctctgc acaaccacta cacgcagaag agcctctccc tgtctccggg taaatgataa   1740

<210> SEQ ID NO 56
<211> LENGTH: 1626
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gaagtgcagc tggtggagtc tggaggaggc ttggtccagc ctggggggtc cctgagactc     60
tcctgtgcag cctctgggtt caatattaag gacacttaca tccactgggt ccgccaggct    120
ccagggaagg ggctggagtg ggtcgcacgt atttatccta ccaatggtta cacacgctac    180
gcagactccg tgaagggccg attcaccatc tccgcagaca cttccaagaa cacggcgtat    240
cttcaaatga acagcctgag agccgaggac acggccgtgt attactgttc gggcggaagc    300
ggagcaaagc tcgccgcact gaaagccaag ctggccgctc tgaaggggg tggcggaagc    360 ctgaaatgtt accaacatgg taaagttgtg acttgtcatc gagatatgaa gttttgctat    420
cataacactg gcatgccttt tcgaaatctc aagctcatcc tacagggatg ttcttcttcg    480
tgcagtgaaa cagaaaacaa taagtgttgc tcaacagaca gatgcaacaa aggcggaggt    540
gggagtgaac tggccgcact ggaagctgag ctggctgccc tcgaagctgg aggctctgga    600
tggggccaag gaaccctggt caccgtctcc tcagcctcca ccaagggccc atcggtcttc    660
cccctggcac cctcctccaa gagcacctct gggggcacag cggccctggg ctgcctggtc    720
aaggactact ccccgaacc ggtgacggtg tcgtggaact caggcgccct gaccagcggc    780
gtgcacacct tcccggctgt cctacagtcc tcaggactct actccctcag cagcgtggtg    840
actgtgccct ctagcagctt gggcacccag acctacatct gcaacgtgaa tcacaagccc    900
agcaacacca aggtggacaa gaaagttgaa cccaaatctt gcgacaaaac tcacacatgc    960
ccaccgtgcc cagcacctcc agtcgccgga ccgtcagtct tcctcttccc tccaaaaccc    1020
aaggacaccc tcatgatctc ccggacccct gaggtcacat gcgtggtggt ggacgtgagc    1080
cacgaagacc ctgaggtcaa gttcaactgg tacgtggacg gcgtggaggt gcataatgcc    1140
aagacaaagc cgcgggagga gcagtacaac agcacgtacc gtgtggtcag cgtcctcacc    1200
gtcctgcacc aggactggct gaatggcaag gagtacaagt gcaaggtctc caacaaaggc    1260
ctcccaagct ccatcgagaa aaccatctcc aaagccaaag gcagccccg agaaccacag    1320 gtgtacaccc tgcctccatc ccgggatgag ctgaccaaga accaggtcag cctgacctgc    1380
ctggtcaaag gcttctatcc cagcgacatc gccgtggagt gggagagcaa tgggcagccg    1440
```

```
gagaacaact acaagaccac gcctcccgtg ctggactccg acggctcctt cttcctctac    1500
agcaagctca ccgtggacaa gagcaggtgg cagcagggga acgtcttctc atgctccgtg    1560
atgcatgagg ctctgcacaa ccactacacg cagaagagcc tctccctgtc tccgggtaaa    1620
tgataa                                                               1626
```

<210> SEQ ID NO 57
<211> LENGTH: 1566
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
caggtgaccc tgcgcgagtc cggccctgca ctggtgaagc ccacccagac cctgaccctg      60
acctgcacct ctccggcttc tccctgtcc acctccggca tgtccgtggg ctggatccgg     120
cagcctcccg gcaaggccct ggagtggctg gctgacatct ggtgggacga caagaaggac    180
tacaacccct ccctgaagtc ccgcctgacc atctccaagg acacctccaa gaaccaggtg    240
gtgctgaagg tgaccaacat ggaccccgcc gacaccgcca cctactactg cgcccgctct    300
tctgaaacta gaaaggggg tggcggaagc ctgaaatgtt accaacatgg taaagttgtg    360
acttgtcatc gagatatgaa gttttgctat cataacactg gcatgccttt tcgaaatctc    420
aagctcatcc tacagggatg ttcttcttcg tgcagtgaaa cagaaaacaa taagtgttgc    480
tcaacagaca gatgcaacaa aggcggaggt gggagttaca attatgaata ctttgacgtg    540
tggggagccg gtaccaccgt gaccgtgtct tccgcctcca ccaagggccc atcggtcttc    600
cccctggcac cctcctccaa gagcacctct ggggcacag cggccctggg ctgcctggtc    660
aaggactact ccccgaacc ggtgacggtg tcgtggaact caggcgccct gaccagcggc    720
gtgcacacct tcccggctgt cctacagtcc tcaggactct actccctcag cagcgtggtg    780
actgtgccct ctagcagctt gggcacccag acctacatct gcaacgtgaa tcacaagccc    840
agcaacacca aggtggacaa gaaagttgaa cccaaatctt gcgacaaaac tcacacatgc    900
ccaccgtgcc cagcacctcc agtcgccgga ccgtcagtct tcctcttccc tccaaaaccc    960
aaggacaccc tcatgatctc ccggaccct gaggtcacat gcgtggtggt ggacgtgagc   1020
cacgaagacc ctgaggtcaa gttcaactgg tacgtggacg gcgtggaggt gcataatgcc   1080
aagacaaagc cgcgggagga gcagtacaac agcacgtacc gtgtggtcag cgtcctcacc   1140
gtcctgcacc aggactggct gaatggcaag gagtacaagt gcaaggtctc caacaaaggc   1200
ctcccaagct ccatcgagaa aaccatctcc aaagccaaag gcagccccg agaaccacag   1260 gtgtacaccc tgcctccatc ccgggatgag ctgaccaaga accaggtcag cctgacctgc   1320
ctggtcaaag gcttctatcc cagcgacatc gccgtggagt gggagagcaa tgggcagccg   1380
gagaacaact acaagaccac gcctcccgtg ctggactccg acggctcctt cttcctctac   1440
agcaagctca ccgtggacaa gagcaggtgg cagcagggga acgtcttctc atgctccgtg   1500
atgcatgagg ctctgcacaa ccactacacg cagaagagcc tctccctgtc tccgggtaaa   1560
tgataa                                                              1566
```

<210> SEQ ID NO 58
<211> LENGTH: 1660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
gaggtgcagc tggtggagtc tggaggaggc ttggtccagc ctgggggtc cctgagactc      60
tcctgtgcag cctctgggtt caatattaag gacacttaca tccactgggt ccgccaggct    120
ccagggaagg ggctggagtg ggtcgcacgt atttatccta ccaatggtta cacacgctac    180
gcagactccg tgaagggccg attcaccatc tccgcagaca cttccaagaa cacggcgtat    240
cttcaaatga acagcctgag agccgaggac acggccgtgt attactgttc gagaggcgga    300
agcggagcaa agctcgccgc actgaaagcc aagctggccg ctctgaaggg aggtggcggg    360
agcgactctt ggatggaaga agttatcaaa ctgtgcggtc gtgaactggt tcgtgctcag    420
atcgctatct gcggtatgtc tacctggtct aaacgttctc tgtctcagga aatcgagggc    480
cgtaaaaaac gtcagctgta ctctgctctg gctaacaaat gctgccacgt tggttgcacc    540
aaacgttctc tggctcgttt ctgcggcgga ggtgggagtg aactggccgc actggaagct    600
gagctggctg ccctcgaagc tggaggctct ggagactact ggggccaagg aaccctggtc    660
accgtctcct cagcctccac caaggggcca tcggtcttcc cctggcacc ctcctccaag     720
agcacctctg ggggcacagc ggccctgggc tgcctggtca aggactactt ccccgaaccg    780
gtgacggtgt cgtggaactc aggcgccctg accagcggcg tgcacacctt cccggctgtc    840
ctacagtcct caggactcta ctccctcagc agcgtggtga ctgtgccctc tagcagcttg    900
ggcacccaga cctacatctg caacgtgaat cacaagccca gcaacaccaa ggtggacaag    960
aaagttgaac ccaaatcttg cgacaaaact cacacatgcc caccgtgccc agcacctcca   1020
gtcgccggac cgtcagtctt cctcttccct ccaaaaccca aggacaccct catgatctcc   1080
cggaccctg aggtcacatg cgtggtggtg gacgtgagcc acgaagaccc tgaggtcaag    1140
ttcaactggt acgtggacgg cgtggaggtg cataatgcca agacaaagcc gcgggaggag   1200
cagtacaaca gcacgtaccg tgtggtcagc gtcctcaccg tcctgcacca ggactggctg   1260
aatggcaagg agtacaagtg caaggtctcc aacaaaggcc tcccaagctc catcgagaaa   1320
accatctcca aagccaaagg gcagccccga gaaccacagg tgtacaccct gcctccatcc   1380
cgggatgagc tgaccaagaa ccaggtcagc ctgacctgcc tggtcaaagg cttctatccc   1440
agcgacatcg ccgtggagtg ggagagcaat gggcagccgg agaacaacta caagaccacg   1500
cctcccgtgc tggactccga cggctccttc ttcctctaca gcaagctcac cgtggacaag   1560
agcaggtggc agcaggggaa cgtcttctca tgctccgtga tgcatgaggc tctgcacaac   1620
cactacacgc agaagagcct ctccctgtct ccgggtaaat                         1660
```

<210> SEQ ID NO 59
<211> LENGTH: 1686
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
gaggtgcagc tggtggagtc tggaggaggc ttggtccagc ctgggggtc cctgagactc      60
tcctgtgcag cctctgggtt caatattaag gacacttaca tccactgggt ccgccaggct    120
ccagggaagg ggctggagtg ggtcgcacgt atttatccta ccaatggtta cacacgctac    180
```

| | |
|---|---|
| gcagactccg tgaagggccg attcaccatc tccgcagaca cttccaagaa cacggcgtat | 240 |
| cttcaaatga acagcctgag agccgaggac acggccgtgt attactgttc gagaggcgga | 300 |
| agcggagcaa agctcgccgc actgaaagcc aagctggccg ctctgaaggg aggtggcggg | 360 |
| agcgactctt ggatggaaga agttatcaaa ctgtgcggtc gtgaactggt tcgtgctcag | 420 |
| atcgctatct gcggtatgtc tacctggtct aaacgttctc tgtctcagga agacgctccg | 480 |
| cagaccccgc gtccggttat cgagggccgt aaaaaacgtc agctgtactc tgctctggct | 540 |
| aacaaatgct gccacgttgg ttgcaccaaa cgttctctgg ctcgtttctg cggcggaggt | 600 |
| gggagtgaac tggccgcact ggaagctgag ctggctgccc tcgaagctgg aggctctgga | 660 |
| gactactggg gccaaggaac cctggtcacc gtctcctcag cctccaccaa gggcccatcg | 720 |
| gtcttccccc tggcaccctc ctccaagagc acctctgggg gcacagcggc cctgggctgc | 780 |
| ctggtcaagg actacttccc cgaaccggtg acggtgtcgt ggaactcagg cgccctgacc | 840 |
| agcggcgtgc acaccttccc ggctgtccta cagtcctcag gactctactc cctcagcagc | 900 |
| gtggtgactg tgccctctag cagcttgggc acccagacct acatctgcaa cgtgaatcac | 960 |
| aagcccagca acaccaaggt ggacaagaaa gttgaaccca aatcttgcga caaaactcac | 1020 |
| acatgcccac cgtgcccagc acctccagtc gccgaccgt cagtcttcct cttcccctcca | 1080 |
| aaacccaagg acaccctcat gatctcccgg acccctgagg tcacatgcgt ggtggtggac | 1140 |
| gtgagccacg aagaccctga ggtcaagttc aactggtacg tggacggcgt ggaggtgcat | 1200 |
| aatgccaaga caaagccgcg ggaggagcag tacaacagca cgtaccgtgt ggtcagcgtc | 1260 |
| ctcaccgtcc tgcaccagga ctggctgaat ggcaaggagt acaagtgcaa ggtctccaac | 1320 |
| aaaggcctcc caagctccat cgagaaaacc atctccaaag ccaaagggca gccccgagaa | 1380 |
| ccacaggtgt acaccctgcc tccatcccgg gatgagctga ccaagaacca ggtcagcctg | 1440 |
| acctgcctgg tcaaaggctt ctatcccagc gacatcgccg tggagtggga gagcaatggg | 1500 |
| cagccggaga acaactacaa gaccacgcct cccgtgctgg actccgacgg ctccttcttc | 1560 |
| ctctacagca agctcaccgt ggacaagagc aggtggcagc aggggaacgt cttctcatgc | 1620 |
| tccgtgatgc atgaggctct gcacaaccac tacacgcaga agagcctctc cctgtctccg | 1680 |
| ggtaaa | 1686 |

<210> SEQ ID NO 60
<211> LENGTH: 1593
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

| | |
|---|---|
| gaggtgcagc tggtggagtc tggaggaggc ttggtccagc ctgggggtc cctgagactc | 60 |
| tcctgtgcag cctctgggtt caatattaag gacacttaca tccactgggt ccgccaggct | 120 |
| ccagggaagg gctggagtg gtcgcacgt atttatccta ccaatggtta cacacgctac | 180 |
| gcagactccg tgaagggccg attcaccatc tccgcagaca cttccaagaa cacggcgtat | 240 |
| cttcaaatga acagcctgag agccgaggac acggccgtgt attactgttc gagaggcgga | 300 |
| agcggagcaa agctcgccgc actgaaagcc aagctggccg ctctgaagtg cgggggtggc | 360 |
| ggaagcatcg aaggtcgtca cagccagggc acattcacta gcgattatag taaatatctg | 420 |
| gattccaagg cagcgcacga ttttgtagag tggctcttga acgagggccc ttcctccgga | 480 |

| | |
|---|---|
| gctccacctc cgtccggcgg aggtgggagt tgcgaactgg ccgcactgga agctgagctg | 540 |
| gctgccctcg aagctggagg ctctggagac tactggggcc aaggaaccct ggtcaccgtc | 600 |
| tcctcagcct ccaccaaggg cccatcggtc ttccccctgg caccctcctc caagagcacc | 660 |
| tctggggcca cagcggccct gggctgcctg gtcaaggact acttccccga accggtgacg | 720 |
| gtgtcgtgga actcaggcgc cctgaccagc ggcgtgcaca ccttcccggc tgtcctacag | 780 |
| tcctcaggac tctactccct cagcagcgtg gtgactgtgc cctctagcag cttgggcacc | 840 |
| cagacctaca tctgcaacgt gaatcacaag cccagcaaca ccaaggtgga caagaaagtt | 900 |
| gaacccaaat cttgcgacaa aactcacaca tgcccaccgt gcccagcacc tccagtcgcc | 960 |
| ggaccgtcag tcttcctctt ccctccaaaa cccaaggaca ccctcatgat ctcccggacc | 1020 |
| cctgaggtca catgcgtggt ggtggacgtg agccacgaag accctgaggt caagttcaac | 1080 |
| tggtacgtgg acggcgtgga ggtgcataat gccaagacaa agccgcggga ggagcagtac | 1140 |
| aacagcacgt accgtgtggt cagcgtcctc accgtcctgc accaggactg gctgaatggc | 1200 |
| aaggagtaca agtgcaaggt ctccaacaaa ggcctcccaa gctccatcga gaaaaccatc | 1260 |
| tccaaagcca aagggcagcc cgagaaccca ggtgtaca ccctgcctcc atcccgggat | 1320 |
| gagctgacca agaaccaggt cagcctgacc tgcctggtca aaggcttcta tcccagcgac | 1380 |
| atcgccgtgg agtgggagag caatgggcag ccggagaaca actacaagac cacgcctccc | 1440 |
| gtgctggact ccgacggctc cttcttcctc tacagcaagc tcaccgtgga caagagcagg | 1500 |
| tggcagcagg ggaacgtctt ctcatgctcc gtgatgcatg aggctctgca caaccactac | 1560 |
| acgcagaaga gcctctccct gtctccgggt aaa | 1593 |

<210> SEQ ID NO 61
<211> LENGTH: 1593
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 61

| | |
|---|---|
| gaggtgcagc tggtggagtc tggaggaggc ttggtccagc ctggggggtc cctgagactc | 60 |
| tcctgtgcag cctctgggtt caatattaag gacacttaca tccactgggt ccgccaggct | 120 |
| ccagggaagg ggctggagtg ggtcgcacgt atttatccta ccaatggtta cacacgctac | 180 |
| gcagactccg tgaagggccg attcaccatc tccgcagaca cttccaagaa cacggcgtat | 240 |
| cttcaaatga acagcctgag agccgaggac acggccgtgt attactgttc gagaggcgga | 300 |
| agcggagcaa agctcgccgc actgaaagcc aagctggccg ctctgaagtg cgggggtggc | 360 |
| ggaagcatcg aagtcgtca cggccagggc acattcacta gcgattatag taaatatctg | 420 |
| gattccaagg cagcgcacga ttttgtagag tggctcttga acggaggccc ttcctccgga | 480 |
| gctccacctc cgtccggcgg aggtgggagt tgcgaactgg ccgcactgga agctgagctg | 540 |
| gctgccctcg aagctggagg ctctggagac tactggggcc aaggaaccct ggtcaccgtc | 600 |
| tcctcagcct ccaccaaggg cccatcggtc ttccccctgg caccctcctc caagagcacc | 660 |
| tctggggcca cagcggccct gggctgcctg gtcaaggact acttccccga accggtgacg | 720 |
| gtgtcgtgga actcaggcgc cctgaccagc ggcgtgcaca ccttcccggc tgtcctacag | 780 |
| tcctcaggac tctactccct cagcagcgtg gtgactgtgc cctctagcag cttgggcacc | 840 |
| cagacctaca tctgcaacgt gaatcacaag cccagcaaca ccaaggtgga caagaaagtt | 900 |

```
gaacccaaat cttgcgacaa aactcacaca tgcccaccgt gcccagcacc tccagtcgcc    960
ggaccgtcag tcttcctctt ccctccaaaa cccaaggaca ccctcatgat ctcccggacc   1020
cctgaggtca catgcgtggt ggtggacgtg agccacgaag accctgaggt caagttcaac   1080
tggtacgtgg acggcgtgga ggtgcataat gccaagacaa agccgcggga ggagcagtac   1140
aacagcacgt accgtgtggt cagcgtcctc accgtcctgc accaggactg gctgaatggc   1200
aaggagtaca agtgcaaggt ctccaacaaa ggcctcccaa gctccatcga gaaaaccatc   1260
tccaaagcca aagggcagcc ccgagaacca caggtgtaca ccctgcctcc atcccgggat   1320
gagctgacca agaaccaggt cagcctgacc tgcctggtca aaggcttcta tcccagcgac   1380
atcgccgtgg agtgggagag caatgggcag ccggagaaca actacaagac cacgcctccc   1440
gtgctggact ccgacggctc cttcttcctc tacagcaagc tcaccgtgga caagagcagg   1500
tggcagcagg ggaacgtctt ctcatgctcc gtgatgcatg aggctctgca caaccactac   1560
acgcagaaga gcctctccct gtctccgggt aaa                                1593
```

<210> SEQ ID NO 62
<211> LENGTH: 1950
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

```
gaggtgcagc tggtggagtc tggaggaggc ttggtccagc ctgggggggtc cctgagactc     60 tcctgtgcag cctctgggtt caatattaag gacacttaca tccactgggt ccgccaggct    120
ccagggaagg gctggagtg gtcgcacgt atttatccta ccaatggtta cacacgctac     180
gcagactccg tgaagggccg attcaccatc tccgcagaca cttccaagaa cacggcgtat    240
cttcaaatga acagcctgag agccgaggac acggccgtgt attactgttc gagaggcgga    300
agcggagcaa agctcgccgc actgaaagcc aagctggccg ctctgaaggg gggtggcgga    360
agcgccccac cacgcctcat ctgtgacagc cgagtcctgg agaggtacct cttggaggcc    420
aaggaggccg agaatatcac gacgggctgt gctgaacact gcagcttgaa tgagaatatc    480
actgtcccag acaccaaagt taatttctat gcctggaaga ggatggaggt cgggcagcag    540
gccgtagaag tctggcaggg cctggccctg ctgtcgaagg ctgtcctgcg gggccaggcc    600
ctgttggtca actcttccca gccgtgggag cccctgcagc tgcatgtgga taaagccgtc    660
agtggccttc gcagcctcac cactctgctt cgggctctgg gagcccagaa ggaagccatc    720
tcccctccag atgcggcctc agctgctcca ctccgaacaa tcactgctga cactttccgc    780
aaactcttcc gagtctactc caatttcctc cggggaaagc tgaagctgta cacaggggag    840
gcctgcagga caggggacag aggcggaggt gggagtgaac tggccgcact ggaagctgag    900
ctggctgcca tcgaagctgg aggctctgga gactactggg ccaaggaac cctggtcacc    960 gtctcctcag ccagcactaa aggtccatct gtgttccctc tggctccttg cagccggagc   1020
acctccgagt ccacagccgc tctgggatgt ctggtgaaag attacttccc cgagcccgtc   1080
accgtgagct ggaatagcgg agcactgacc tccggcgtcc acacattccc cgccgtgctc   1140
caaagctccg gcctgtacag cctctcctcc gtggtcaccg tgcccagcag ctctctgggc   1200
acaaagacct atacctgtaa cgtggatcac aagcctagca acaccaaagt ggataagcgg   1260
gtggagagca agtacggccc ctcctgtccc ccttgccccg ctcctgaggc cgctggcgga   1320
```

```
ccttccgtgt tcctgtttcc ccctaagccc aaggacaccc tcatgattag ccggacaccc    1380
gaagtgacct gcgtggtcgt ggatgtgtcc caggaggacc ctgaagtgca atttaactgg    1440
tacgtggacg gcgtcgaggt gcacaacgcc aagaccaagc ctcgggaaga gcagttcaac    1500
agcacctacc gggtggtcag cgtgctgaca gtgctgcacc aggactggct gaacggcaag    1560
gagtacaagt gcaaggtgag caacaagggc ctgcccagct ccatcgagaa gaccatcagc    1620
aaggccaagg gccagcccag ggaacccag gtgtataccc tgcccctag ccaggaggaa    1680 atgaccaaaa accaggtgag cctgacctgc ctggtgaagg gcttctaccc cagcgacatc    1740
gccgtggagt gggagagcaa cggccagccc gagaacaatt acaagaccac ccctcctgtg    1800
ctggacagcg acggctcctt ctttctgtat agccggctga ccgtggacaa gagcaggtgg    1860
caggagggca acgtgttctc ctgtagcgtg atgcacgagg ccctgcacaa ccattacacc    1920
cagaagagct tgagcctgag cctgggcaaa                                     1950
```

<210> SEQ ID NO 63
<211> LENGTH: 1293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
gacatccaga tgacccagtc tccatcctcc ctgtctgcat ctgtaggaga cagagtcacc    60
atcacttgcc gggcaagtca ggatgtgaat accgcggtcg catggtatca gcagaaacca    120
gggaaagccc ctaagctcct gatctattct gcatccttct gtatagtgg ggtcccatca    180 aggttcagtg gcagtagatc tgggacagat ttcactctca ccatcagcag tctgcaacct    240
gaagattttg caacttacta ctgtcaacag cattacggcg gaagcggagc aaagctcgcc    300
gcactgaaag ccaagctggc cgctctgaag ggggtggcg gaagcacacc tctgggcccc    360
gcctcctccc tgcctcagag cttctgctc aaatgtctgg agcaggtgcg gaagatccag    420
ggcgacggcg ccgctctgca agagaaactg tgcgccacat ataagctgtg tcaccccgag    480
gaactggtcc tcttgggcca cagcctgggc atccctggg cccctctcag ctcctgcccc    540
tcccaagctc tccaactggc tggatgtctg tcccaactgc actccggcct cttcctgtac    600
cagggactcc tccaggctct cgaagggatc agccccgaac tgggcccac actggacacc    660 ttgcaactcg atgtggccga tttcgccaca accatctggc agcagatgga agaactcgga    720
atggctcctc ctctccagcc cacacaggga gctatgcctg cttcgcctc tgctttccag    780 cggagagctg gtggtgtgct cgtcgcatcc cacctccaga gcttcttgga ggtgtcctat    840
cgggtgctcc ggcatctggc ccaacccggc ggaggtggga gtgaactggc cgcactggaa    900
gctgagctgg ctgccctcga agctggaggc tctggaccga cgttcggcca aggtaccaag    960
cttgagatca aacgaactgt ggctgcacca tctgtcttca tcttcccgcc atctgatgag    1020
cagttgaaat ctggaactgc ctctgtcgtg tgcctgctga ataacttcta tcccagagag    1080
gccaaagtac agtggaaggt ggataacgcc ctccaatcgg gtaactccca ggagagtgtc    1140
acagagcagg acagcaagga cagcacctac agcctcagca gcaccctgac gctgagcaaa    1200
gcagactacg agaaacacaa agtctacgcc tgcgaagtca cccatcaggg cctgtcctcg    1260
cccgtcacaa agagcttcaa caggggagag tgt                                1293
```

<210> SEQ ID NO 64

<211> LENGTH: 1602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

| gaggtgcagc tggtggagtc tggaggaggc ttggtccagc ctgggggtc cctgagactc | 60 |
|---|---|
| tcctgtgcag cctctgggtt caatattaag gacacttaca tccactgggt ccgccaggct | 120 |
| ccagggaagg ggctggagtg ggtcgcacgt atttatccta ccaatggtta cacacgctac | 180 |
| gcagactccg tgaagggccg attcaccatc tccgcagaca cttccaagaa cacggcgtat | 240 |
| cttcaaatga acagcctgag agccgaggac acggccgtgt attactgttc gagaggcgga | 300 |
| agcggagcaa agctcgccgc actgaaagcc aagctggccg ctctgaaggg gggtggcgga | 360 |
| agcgctgaca acaaatgcga aaactctctg cgtcgtgaaa tcgcttgcgg tcagtgccgt | 420 |
| gacaaagtta aaaccgacgg ttacttctac gaatgctgca cctctgactc taccttcaaa | 480 |
| aaatgccagg acctgctgca cggcggaggt gggagtgaac tggccgcact ggaagctgag | 540 |
| ctggctgccc tcgaagctgg aggctctgga gactactggg gccaaggaac cctggtcacc | 600 |
| gtctcctcag cctccaccaa gggcccatcg gtcttccccc tggcaccctc ctccaagagc | 660 |
| acctctgggg gcacagcggc cctgggctgc ctggtcaagg actacttccc cgaaccggtg | 720 |
| acggtgtcgt ggaactcagg cgccctgacc agcggcgtgc acaccttccc ggctgtccta | 780 |
| cagtcctcag gactctactc cctcagcagc gtggtgactg tgccctctag cagcttgggc | 840 |
| acccagacct acatctgcaa cgtgaatcac aagcccagca caccaaggt ggacaagaaa | 900 |
| gttgaaccca aatcttgcga caaaactcac acatgcccac cgtgcccagc acctccagtc | 960 |
| gccggaccgt cagtcttcct cttccctcca aaacccaagg acaccctcat gatctcccgg | 1020 |
| acccctgagg tcacatgcgt ggtggtggac gtgagccacg aagaccctga ggtcaagttc | 1080 |
| aactggtacg tggacggcgt ggaggtgcat aatgccaaga caaagccgcg ggaggagcag | 1140 |
| tacaacagca cgtaccgtgt ggtcagcgtc ctcaccgtcc tgcaccagga ctggctgaat | 1200 |
| ggcaaggagt acaagtgcaa ggtctccaac aaaggcctcc aagctccat cgagaaaacc | 1260 |
| atctccaaag ccaaagggca gccccgagaa ccacaggtgt acaccctgcc tccatcccgg | 1320 |
| gatgagctga ccaagaacca ggtcagcctg acctgcctgg tcaaaggctt ctatcccagc | 1380 |
| gacatcgccg tggagtggga gagcaatggg cagccggaga caactacaa gaccacgcct | 1440 |
| cccgtgctgg actccgacgg ctccttcttc ctctacagca agctcaccgt ggacaagagc | 1500 |
| aggtggcagc aggggaacgt cttctcatgc tccgtgatgc atgaggctct gcacaaccac | 1560 |
| tacacgcaga agagcctctc cctgtctccg ggtaaatgat aa | 1602 |

<210> SEQ ID NO 65
<211> LENGTH: 1614
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

| gaggtgcagc tggtggagtc tggaggaggc ttggtccagc ctgggggtc cctgagactc | 60 |
|---|---|
| tcctgtgcag cctctgggtt caatattaag gacacttaca tccactgggt ccgccaggct | 120 |
| ccagggaagg ggctggagtg ggtcgcacgt atttatccta ccaatggtta cacacgctac | 180 |

```
gcagactccg tgaagggccg attcaccatc tccgcagaca cttccaagaa cacggcgtat    240
cttcaaatga acagcctgag agccgaggac acggccgtgt attactgttc gagaggcgga    300
agcggagcaa agctcgccgc actgaaagcc aagctggccg ctctgaagtg cgggggtggc    360
ggaagcatcg aaggtcgtca cggcgacggt tcattctctg acgaaatgaa tacaatactc    420
gacaacctcg ccgccaggga ctttatcaat tggctcattc aaactaaaat caccgacgga    480
ggcccttcct ccggagctcc acctccgtcc ggcggaggtg ggagttgcga actgccgca    540 ctggaagctg agctggctgc cctcgaagct ggaggctctg agactactg gggccaagga    600 accctggtca ccgtctcctc agcctccacc aagggcccat cggtcttccc cctggcaccc    660
tcctccaaga gcacctctgg gggcacagcg gccctgggct gcctggtcaa ggactacttc    720
cccgaaccgg tgacggtgtc gtggaactca ggcgccctga ccagcggcgt gcacaccttc    780
ccggctgtcc tacagtcctc aggactctac tccctcagca gcgtggtgac tgtgccctct    840
agcagcttgg gcacccagac ctacatctgc aacgtgaatc acaagcccag caacaccaag    900
gtggacaaga agttgaaccc aaatcttgc gacaaaactc acacatgccc accgtgccca    960
gcacctccag tcgccggacc gtcagtcttc ctcttccctc caaaacccaa ggacaccctc   1020
atgatctccc ggacccctga ggtcacatgc gtggtggtgg acgtgagcca cgaagaccct   1080
gaggtcaagt tcaactggta cgtggacggc gtggaggtgc ataatgccaa gacaaagccg   1140
cgggaggagc agtacaacag cacgtaccgt gtggtcagcg tcctcaccgt cctgcaccag   1200
gactggctga atggcaagga gtacaagtgc aaggtctcca acaaaggcct cccaagctcc   1260
atcgagaaaa ccatctccaa agccaaaggg cagccccgag aaccacaggt gtacaccctg   1320
cctccatccc gggatgagct gaccaagaac caggtcagcc tgacctgcct ggtcaaaggc   1380
ttctatccca gcgacatcgc cgtggagtgg gagagcaatg ggcagccgga gaacaactac   1440
aagaccacgc ctcccgtgct ggactccgac ggctccttct tcctctacag caagctcacc   1500
gtggacaaga gcaggtggca gcaggggaac gtcttctcat gctccgtgat gcatgaggct   1560
ctgcacaacc actacacgca gaagagcctc tccctgtctc cgggtaaatg ataa         1614
```

<210> SEQ ID NO 66
<211> LENGTH: 1989
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
gaggtgcagc tggtggagtc tggaggaggc ttggtccagc ctgggggtc cctgagactc     60 tcctgtgcag cctctgggtt caatattaag gacacttaca tccactgggt ccgccaggct    120
ccagggaagg gctggagtg gtcgcacgt atttatccta ccaatggtta cacacgctac     180
gcagactccg tgaagggccg attcaccatc tccgcagaca cttccaagaa cacggcgtat    240
cttcaaatga acagcctgag agccgaggac acggccgtgt attactgttc gagaggcgga    300
agcggagcaa agctcgccgc actgaaagcc aagctggccg ctctgaaggg aggtggcggg    360
agcgctcctc tgggcggtcc tgaaccagca cagtacgagg aactgacact gttgttccat    420
ggagccttgc agctgggcca ggccctcaac ggcgtgtacc gcgccacaga ggcacgtttg    480
accgaggccg acacagcct gggttttgtac gacagagccc tggagtttct gggtaccgaa    540
gtgcgtcagg gccaggacgc aactcaggag ctgagaacct ccctctctga gatccaggtg    600
```

```
gaggaggacg ccctgcacct gcgcgccgag gcgacagcac gctctttggg agaagttgct      660
cgcgctcagc aggccctgcg tgataccgtg cggagactcc aagttcagct cagaggcgct      720
tggctcggac aggcgcatca ggagttcgag accctgaaag ctcgtgccga caaacagtcc      780
cacctgctgt gggcgctcac cggtcacgtc cagcgccagc aacgcgaaat ggccgagcag      840
cagcaatggc tgcgccaaat ccagcagcgc ctgcataccg cggccctgcc agcgggcgga      900
ggtgggagtg aactggccgc actggaagct gagctggctg ccctcgaagc tggaggctct      960
ggagactact ggggccaagg aaccctggtc accgtctcct cagcctccac caagggccca     1020
tcggtcttcc ccctggcacc ctcctccaag agcacctctg gggcacagc ggccctgggc      1080 tgcctggtca aggactactt ccccgaaccg gtgacggtgt cgtggaactc aggcgccctg     1140
accagcggcg tgcacacctt cccggctgtc ctacagtcct caggactcta ctccctcagc     1200
agcgtggtga ctgtgccctc tagcagcttg gcacccagaa cctacatctg caacgtgaat     1260
cacaagccca gcaacaccaa ggtggacaag aaagttgaac ccaaatcttg cgacaaaact     1320
cacacatgcc caccgtgccc agcacctcca gtcgccggac cgtcagtctt cctcttccct     1380
ccaaaaccca aggacaccct catgatctcc cggacccctg aggtcacatg cgtggtggtg     1440
gacgtgagcc acgaagaccc tgaggtcaag ttcaactggt acgtggacgg cgtggaggtg     1500
cataatgcca agacaaagcc gcgggaggag cagtacaaca gcacgtaccg tgtggtcagc     1560
gtcctcaccg tcctgcacca ggactggctg aatggcaagg agtacaagtg caaggtctcc     1620
aacaaaggcc tcccaagctc catcgagaaa accatctcca aagccaaagg cagccccga     1680 gaaccacagg tgtacaccct gcctccatcc cgggatgagc tgaccaagaa ccaggtcagc     1740
ctgacctgcc tggtcaaagg cttctatccc agcgacatcg ccgtgagtg ggagagcaat     1800 gggcagccgg agaacaacta caagaccacg cctcccgtgc tggactccga cggctccttc     1860
ttcctctaca gcaagctcac cgtggacaag agcaggtggc agcagggaa cgtcttctca     1920 tgctccgtga tgcatgaggc tctgcacaac cactacacgc agaagagcct ctccctgtct     1980
ccgggtaaa                                                              1989
```

<210> SEQ ID NO 67
<211> LENGTH: 900
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
gacatccaga tgacccagtc tccatcctcc ctgtctgcat ctgtaggaga cagagtcacc       60
atcacttgcc gggcaagtca ggatgtgaat accgcggtcg catggtatca gcagaaacca      120
gggaaagccc ctaagctcct gatctattct gcatccttct gtatagtgg ggtcccatca       180 aggttcagtg gcagtagatc tgggacagat ttcactctca ccatcagcag tctgcaacct      240
gaagattttg caacttacta ctgtcaacag ggcggaagcg gagcaaagct cgccgcactg      300
aaagccaagc tggccgctct gaagtgcggg gtggcggaa gcatcgaagg tcgtcacgga      360
gaaggaacat taccagcga cctcagcaag cagatggagg aagaggccgt gaggctgttc      420
atcgagtggc tgaagaacgg cggaccctcc tctgcgctc cacccctag cggcggaggt       480 gggagttgcg aactggccgc actggaagct gagctggctg ccctcgaagc tggaggctct      540
ggaccgacgt tcggccaagg taccaagctt gagatcaaac gaactgtggc tgcaccatct      600
```

-continued

```
gtcttcatct tcccgccatc tgatgagcag ttgaaatctg gaactgcctc tgtcgtgtgc    660
ctgctgaata acttctatcc cagagaggcc aaagtacagt ggaaggtgga taacgccctc    720
caatcgggta actcccagga gagtgtcaca gagcaggaca gcaaggacag cacctacagc    780
ctcagcagca ccctgacgct gagcaaagca gactacgaga acacaaagt ctacgcctgc     840 gaagtcaccc atcagggcct gtcctcgccc gtcacaaaga gcttcaacag gggagagtgt    900
```

<210> SEQ ID NO 68
<211> LENGTH: 423
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Gly Ser Gly Ala
            20                  25                  30

Lys Leu Ala Ala Leu Lys Ala Lys Leu Ala Ala Leu Lys Gly Gly Gly
        35                  40                  45

Gly Ser Ala Pro Pro Arg Leu Ile Cys Asp Ser Arg Val Leu Glu Arg
    50                  55                  60

Tyr Leu Leu Glu Ala Lys Glu Ala Glu Asn Ile Thr Thr Gly Cys Ala
65                  70                  75                  80

Glu His Cys Ser Leu Asn Glu Asn Ile Thr Val Pro Asp Thr Lys Val
                85                  90                  95

Asn Phe Tyr Ala Trp Lys Arg Met Glu Val Gly Gln Gln Ala Val Glu
            100                 105                 110

Val Trp Gln Gly Leu Ala Leu Leu Ser Glu Ala Val Leu Arg Gly Gln
        115                 120                 125

Ala Leu Leu Val Asn Ser Ser Gln Pro Trp Glu Pro Leu Gln Leu His
    130                 135                 140

Val Asp Lys Ala Val Ser Gly Leu Arg Ser Leu Thr Thr Leu Leu Arg
145                 150                 155                 160

Ala Leu Gly Ala Gln Lys Glu Ala Ile Ser Pro Pro Asp Ala Ala Ser
                165                 170                 175

Ala Ala Pro Leu Arg Thr Ile Thr Ala Asp Thr Phe Arg Lys Leu Phe
            180                 185                 190

Arg Val Tyr Ser Asn Phe Leu Arg Gly Lys Leu Lys Leu Tyr Thr Gly
        195                 200                 205

Glu Ala Cys Arg Thr Gly Asp Arg Gly Gly Gly Ser Glu Leu Ala
    210                 215                 220

Ala Leu Glu Ala Glu Leu Ala Ala Leu Glu Ala Gly Gly Ser Gly Thr
225                 230                 235                 240

Ala Val Ala Trp Tyr Gln Gln Lys Pro Gly Lys Ala Pro Lys Leu Leu
                245                 250                 255

Ile Tyr Ser Ala Ser Phe Leu Tyr Ser Gly Val Pro Ser Arg Phe Ser
            260                 265                 270

Gly Ser Arg Ser Gly Thr Asp Phe Thr Leu Thr Ile Ser Ser Leu Gln
        275                 280                 285

Pro Glu Asp Phe Ala Thr Tyr Tyr Cys Gln Gln His Tyr Thr Thr Pro
    290                 295                 300
```

```
Pro Thr Phe Gly Gln Gly Thr Lys Leu Glu Ile Lys Arg Thr Val Ala
305                 310                 315                 320

Ala Pro Ser Val Phe Ile Phe Pro Pro Ser Asp Glu Gln Leu Lys Ser
                325                 330                 335

Gly Thr Ala Ser Val Val Cys Leu Leu Asn Asn Phe Tyr Pro Arg Glu
            340                 345                 350

Ala Lys Val Gln Trp Lys Val Asp Asn Ala Leu Gln Ser Gly Asn Ser
        355                 360                 365

Gln Glu Ser Val Thr Glu Gln Asp Ser Lys Asp Ser Thr Tyr Ser Leu
    370                 375                 380

Ser Ser Thr Leu Thr Leu Ser Lys Ala Asp Tyr Glu Lys His Lys Val
385                 390                 395                 400

Tyr Ala Cys Glu Val Thr His Gln Gly Leu Ser Ser Pro Val Thr Lys
                405                 410                 415

Ser Phe Asn Arg Gly Glu Cys
            420

<210> SEQ ID NO 69
<211> LENGTH: 661
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110

Ala Ala Leu Lys Gly Gly Gly Gly Ser Thr Pro Leu Gly Pro Ala Arg
        115                 120                 125

Ser Leu Pro Gln Ser Phe Leu Leu Lys Cys Leu Glu Gln Val Arg Lys
    130                 135                 140

Ile Gln Ala Asp Gly Ala Glu Leu Gln Glu Arg Leu Cys Ala Ala His
145                 150                 155                 160

Lys Leu Cys His Pro Glu Glu Leu Met Leu Leu Arg His Ser Leu Gly
                165                 170                 175

Ile Pro Gln Ala Pro Leu Ser Ser Cys Ser Ser Gln Ser Leu Gln Leu
            180                 185                 190

Thr Ser Cys Leu Asn Gln Leu His Gly Gly Leu Phe Leu Tyr Gln Gly
        195                 200                 205

Leu Leu Gln Ala Leu Ala Gly Ile Ser Pro Glu Leu Ala Pro Thr Leu
    210                 215                 220

Asp Thr Leu Gln Leu Asp Val Thr Asp Phe Ala Thr Asn Ile Trp Leu
225                 230                 235                 240
```

```
Gln Met Glu Asp Leu Gly Ala Ala Pro Ala Val Gln Pro Thr Gln Gly
                245                 250                 255

Ala Met Pro Thr Phe Thr Ser Ala Phe Gln Arg Arg Ala Gly Gly Val
            260                 265                 270

Leu Val Ala Ser Gln Leu His Arg Phe Leu Glu Leu Ala Tyr Arg Gly
        275                 280                 285

Leu Arg Tyr Leu Ala Glu Pro Gly Gly Gly Ser Glu Leu Ala Ala
    290                 295                 300

Leu Glu Ala Glu Leu Ala Leu Glu Ala Gly Ser Gly Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Lys Val Glu Pro Lys
            420                 425                 430

Ser Cys Asp Lys Thr His Thr Cys Pro Pro Cys Pro Ala Pro Glu Leu
        435                 440                 445

Leu Gly Gly Pro Ser Val Phe Leu Phe Pro Pro Lys Pro Lys Asp Thr
    450                 455                 460

Leu Met Ile Ser Arg Thr Pro Glu Val Thr Cys Val Val Val Asp Val
465                 470                 475                 480

Ser His Glu Asp Pro Glu Val Lys Phe Asn Trp Tyr Val Asp Gly Val
                485                 490                 495

Glu Val His Asn Ala Lys Thr Lys Pro Arg Glu Glu Gln Tyr Asn Ser
            500                 505                 510

Thr Tyr Arg Val Val Ser Val Leu Thr Val Leu His Gln Asp Trp Leu
        515                 520                 525

Asn Gly Lys Glu Tyr Lys Cys Lys Val Ser Asn Lys Ala Leu Pro Ala
    530                 535                 540

Pro Ile Glu Lys Thr Ile Ser Lys Ala Lys Gly Gln Pro Arg Glu Pro
545                 550                 555                 560

Gln Val Tyr Thr Leu Pro Pro Ser Arg Asp Glu Leu Thr Lys Asn Gln
                565                 570                 575

Val Ser Leu Thr Cys Leu Val Lys Gly Phe Tyr Pro Ser Asp Ile Ala
            580                 585                 590

Val Glu Trp Glu Ser Asn Gly Gln Pro Glu Asn Asn Tyr Lys Thr Thr
        595                 600                 605

Pro Pro Val Leu Asp Ser Asp Gly Ser Phe Phe Leu Tyr Ser Lys Leu
    610                 615                 620

Thr Val Asp Lys Ser Arg Trp Gln Gln Gly Asn Val Phe Ser Cys Ser
625                 630                 635                 640

Val Met His Glu Ala Leu His Asn His Tyr Thr Gln Lys Ser Leu Ser
                645                 650                 655
```

Leu Ser Pro Gly Lys
            660

<210> SEQ ID NO 70
<211> LENGTH: 665
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Gly Gly Ser Gly Ala Lys Leu Ala Ala Leu Lys Ala
            100                 105                 110

Lys Leu Ala Ala Leu Lys Gly Gly Gly Gly Ser Thr Pro Leu Gly Pro
        115                 120                 125

Ala Arg Ser Leu Pro Gln Ser Phe Leu Leu Lys Cys Leu Glu Gln Val
    130                 135                 140

Arg Lys Ile Gln Ala Asp Gly Ala Glu Leu Gln Glu Arg Leu Cys Ala
145                 150                 155                 160

Ala His Lys Leu Cys His Pro Glu Glu Leu Met Leu Leu Arg His Ser
                165                 170                 175

Leu Gly Ile Pro Gln Ala Pro Leu Ser Ser Cys Ser Ser Gln Ser Leu
            180                 185                 190

Gln Leu Thr Ser Cys Leu Asn Gln Leu His Gly Gly Leu Phe Leu Tyr
        195                 200                 205

Gln Gly Leu Leu Gln Ala Leu Ala Gly Ile Ser Pro Glu Leu Ala Pro
    210                 215                 220

Thr Leu Asp Thr Leu Gln Leu Asp Val Thr Asp Phe Ala Thr Asn Ile
225                 230                 235                 240

Trp Leu Gln Met Glu Asp Leu Gly Ala Ala Pro Ala Val Gln Pro Thr
                245                 250                 255

Gln Gly Ala Met Pro Thr Phe Thr Ser Ala Phe Gln Arg Arg Ala Gly
            260                 265                 270

Gly Val Leu Val Ala Ser Gln Leu His Arg Phe Leu Glu Leu Ala Tyr
        275                 280                 285

Arg Gly Leu Arg Tyr Leu Ala Glu Pro Gly Gly Gly Ser Glu Leu
    290                 295                 300

Ala Ala Leu Glu Ala Glu Leu Ala Leu Glu Ala Gly Gly Ser Gly
305                 310                 315                 320

Trp His Val Asp Val Trp Gly Gln Gly Leu Leu Val Thr Val Ser Ser
                325                 330                 335

Ala Ser Thr Thr Ala Pro Lys Val Tyr Pro Leu Ser Ser Cys Cys Gly
            340                 345                 350

Asp Lys Ser Ser Ser Thr Val Thr Leu Gly Cys Leu Val Ser Ser Tyr
            355                 360                 365

Met Pro Glu Pro Val Thr Val Thr Trp Asn Ser Gly Ala Leu Lys Ser
    370                 375                 380

Gly Val His Thr Phe Pro Ala Val Leu Gln Ser Ser Gly Leu Tyr Ser
385                 390                 395                 400

Leu Ser Ser Met Val Thr Val Pro Gly Ser Thr Ser Gly Gln Thr Phe
                405                 410                 415

Thr Cys Asn Val Ala His Pro Ala Ser Ser Thr Lys Val Asp Lys Ala
                420                 425                 430

Val Glu Pro Lys Ser Cys Asp Lys Thr His Thr Cys Pro Pro Cys Pro
            435                 440                 445

Ala Pro Glu Leu Leu Gly Gly Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
    515                 520                 525

Gln Asp Trp Leu Asn Gly Lys Glu Tyr Lys Cys Lys Val Ser Asn Lys
530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Asp Glu Leu
                565                 570                 575

Thr Lys Asn Gln Val Ser Leu Thr Cys Leu Val Lys Gly Phe Tyr Pro
            580                 585                 590

Ser Asp Ile Ala Val Glu Trp Glu Ser Asn Gly Gln Pro Glu Asn Asn
    595                 600                 605

Tyr Lys Thr Thr Pro Pro Val Leu Asp Ser Asp Gly Ser Phe Phe Leu
610                 615                 620

Tyr Ser Lys Leu Thr Val Asp Lys Ser Arg Trp Gln Gln Gly Asn Val
                630                 635                 640
625

Phe Ser Cys Ser Val Met His Glu Ala Leu His Asn His Tyr Thr Gln
            645                 650                 655

Lys Ser Leu Ser Leu Ser Pro Gly Lys
            660                 665

<210> SEQ ID NO 71
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val

-continued

```
                35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Gly Gly Ser Gly Ala Lys Leu Ala Ala Leu Lys Ala Lys Leu
                100                 105                 110
Ala Ala Leu Lys Cys Gly Gly Gly Ser Ile Glu Gly Arg His Gly
                115                 120                 125
Glu Gly Thr Phe Thr Ser Asp Leu Ser Lys Gln Met Glu Glu Glu Ala
                130                 135                 140
Val Arg Leu Phe Ile Glu Trp Leu Lys Asn Gly Gly Pro Ser Ser Gly
145                 150                 155                 160
Ala Pro Pro Pro Ser Gly Gly Gly Ser Cys Glu Leu Ala Ala Leu
                165                 170                 175
Glu Ala Glu Leu Ala Ala Leu Glu Ala Gly Gly Ser Gly Asp Tyr Trp
                180                 185                 190
Gly Gln Gly Thr Leu Val Thr Val Ser Ser Ala Ser Thr Lys Gly Pro
                195                 200                 205
Ser Val Phe Pro Leu Ala Pro Ser Ser Lys Ser Thr Ser Gly Gly Thr
                210                 215                 220
Ala Ala Leu Gly Cys Leu Val Lys Asp Tyr Phe Pro Glu Pro Val Thr
225                 230                 235                 240
Val Ser Trp Asn Ser Gly Ala Leu Thr Ser Gly Val His Thr Phe Pro
                245                 250                 255
Ala Val Leu Gln Ser Ser Gly Leu Tyr Ser Leu Ser Ser Val Val Thr
                260                 265                 270
Val Pro Ser Ser Ser Leu Gly Thr Gln Thr Tyr Ile Cys Asn Val Asn
                275                 280                 285
His Lys Pro Ser Asn Thr Lys Val Asp Lys Val Glu Pro Lys Ser
                290                 295                 300
Cys Asp Lys Thr His Thr Cys Pro Pro Cys Pro Ala Pro Pro Val Ala
305                 310                 315                 320
Gly Pro Ser Val Phe Leu Phe Pro Pro Lys Pro Lys Asp Thr Leu Met
                325                 330                 335
Ile Ser Arg Thr Pro Glu Val Thr Cys Val Val Val Asp Val Ser His
                340                 345                 350
Glu Asp Pro Glu Val Lys Phe Asn Trp Tyr Val Asp Gly Val Glu Val
                355                 360                 365
His Asn Ala Lys Thr Lys Pro Arg Glu Glu Gln Tyr Asn Ser Thr Tyr
                370                 375                 380
Arg Val Val Ser Val Leu Thr Val Leu His Gln Asp Trp Leu Asn Gly
385                 390                 395                 400
Lys Glu Tyr Lys Cys Lys Val Ser Asn Lys Gly Leu Pro Ser Ser Ile
                405                 410                 415
Glu Lys Thr Ile Ser Lys Ala Lys Gly Gln Pro Arg Glu Pro Gln Val
                420                 425                 430
Tyr Thr Leu Pro Pro Ser Arg Asp Glu Leu Thr Lys Asn Gln Val Ser
                435                 440                 445
Leu Thr Cys Leu Val Lys Gly Phe Tyr Pro Ser Asp Ile Ala Val Glu
                450                 455                 460
```

Trp Glu Ser Asn Gly Gln Pro Glu Asn Asn Tyr Lys Thr Thr Pro Pro
465                 470                 475                 480

Val Leu Asp Ser Asp Gly Ser Phe Phe Leu Tyr Ser Lys Leu Thr Val
                485                 490                 495

Asp Lys Ser Arg Trp Gln Gln Gly Asn Val Phe Ser Cys Ser Val Met
            500                 505                 510

His Glu Ala Leu His Asn His Tyr Thr Gln Lys Ser Leu Ser Leu Ser
        515                 520                 525

Pro Gly Lys
    530

<210> SEQ ID NO 72
<211> LENGTH: 521
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110

Ala Ala Leu Lys Gly Gly Gly Gly Ser Ile Asn Val Lys Cys Ser Leu
        115                 120                 125

Pro Gln Gln Cys Ile Lys Pro Cys Lys Asp Ala Gly Met Arg Phe Gly
130                 135                 140

Lys Cys Met Asn Lys Lys Cys Arg Cys Tyr Ser Gly Gly Gly Gly Ser
145                 150                 155                 160

Glu Leu Ala Ala Leu Glu Ala Glu Leu Ala Ala Leu Glu Ala Gly Gly
                165                 170                 175

Ser Gly Asp Tyr Trp Gly Gln Gly Thr Leu Val Thr Val Ser Ser Ala
            180                 185                 190

Ser Thr Lys Gly Pro Ser Val Phe Pro Leu Ala Pro Ser Ser Lys Ser
        195                 200                 205

Thr Ser Gly Gly Thr Ala Ala Leu Gly Cys Leu Val Lys Asp Tyr Phe
210                 215                 220

Pro Glu Pro Val Thr Val Ser Trp Asn Ser Gly Ala Leu Thr Ser Gly
225                 230                 235                 240

Val His Thr Phe Pro Ala Val Leu Gln Ser Ser Gly Leu Tyr Ser Leu
                245                 250                 255

Ser Ser Val Val Thr Val Pro Ser Ser Ser Leu Gly Thr Gln Thr Tyr
            260                 265                 270

Ile Cys Asn Val Asn His Lys Pro Ser Asn Thr Lys Val Asp Lys Lys

```
                275                 280                 285
Val Glu Pro Lys Ser Cys Asp Lys Thr His Thr Cys Pro Pro Cys Pro
    290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
            340                 345                 350

Val Asp Gly Val Glu Val His Asn Ala Lys Thr Lys Pro Arg Glu Glu
        355                 360                 365

Gln Tyr Asn Ser Thr Tyr Arg Val Val Ser Val Leu Thr Val Leu His
    370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Asp Glu Leu
            420                 425                 430

Thr Lys Asn Gln Val Ser Leu Thr Cys Leu Val Lys Gly Phe Tyr Pro
        435                 440                 445

Ser Asp Ile Ala Val Glu Trp Glu Ser Asn Gly Gln Pro Glu Asn Asn
    450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val
                485                 490                 495

Phe Ser Cys Ser Val Met His Glu Ala Leu His Asn His Tyr Thr Gln
            500                 505                 510

Lys Ser Leu Ser Leu Ser Pro Gly Lys
        515                 520

<210> SEQ ID NO 73
<211> LENGTH: 523
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110
```

-continued

```
Ala Ala Leu Lys Gly Gly Gly Ser Ala Ala Ile Ser Cys Val
        115             120             125

Gly Ser Pro Glu Cys Pro Pro Lys Cys Arg Ala Gln Gly Cys Lys Asn
130             135                 140

Gly Lys Cys Met Asn Arg Lys Cys Lys Cys Tyr Tyr Cys Gly Gly Gly
145                 150                 155                 160

Gly Ser Glu Leu Ala Ala Leu Glu Ala Glu Leu Ala Ala Leu Glu Ala
                165                 170                 175

Gly Gly Ser Gly Asp Tyr Trp Gly Gln Gly Thr Leu Val Thr Val Ser
            180                 185                 190

Ser Ala Ser Thr Lys Gly Pro Ser Val Phe Pro Leu Ala Pro Ser Ser
        195                 200                 205

Lys Ser Thr Ser Gly Gly Thr Ala Ala Leu Gly Cys Leu Val Lys Asp
    210                 215                 220

Tyr Phe Pro Glu Pro Val Thr Val Ser Trp Asn Ser Gly Ala Leu Thr
225                 230                 235                 240

Ser Gly Val His Thr Phe Pro Ala Val Leu Gln Ser Ser Gly Leu Tyr
                245                 250                 255

Ser Leu Ser Ser Val Val Thr Val Pro Ser Ser Ser Leu Gly Thr Gln
            260                 265                 270

Thr Tyr Ile Cys Asn Val Asn His Lys Pro Ser Asn Thr Lys Val Asp
        275                 280                 285

Lys Lys Val Glu Pro Lys Ser Cys Asp Lys Thr His Thr Cys Pro Pro
    290                 295                 300

Cys Pro Ala Pro Glu Leu Leu Gly Gly Pro Ser Val Phe Leu Phe Pro
305                 310                 315                 320

Pro Lys Pro Lys Asp Thr Leu Met Ile Ser Arg Thr Pro Glu Val Thr
                325                 330                 335

Cys Val Val Val Asp Val Ser His Glu Asp Pro Glu Val Lys Phe Asn
            340                 345                 350

Trp Tyr Val Asp Gly Val Glu Val His Asn Ala Lys Thr Lys Pro Arg
        355                 360                 365

Glu Glu Gln Tyr Asn Ser Thr Tyr Arg Val Val Ser Val Leu Thr Val
    370                 375                 380

Leu His Gln Asp Trp Leu Asn Gly Lys Glu Tyr Lys Cys Lys Val Ser
385                 390                 395                 400

Asn Lys Ala Leu Pro Ala Pro Ile Glu Lys Thr Ile Ser Lys Ala Lys
                405                 410                 415

Gly Gln Pro Arg Glu Pro Gln Val Tyr Thr Leu Pro Pro Ser Arg Asp
            420                 425                 430

Glu Leu Thr Lys Asn Gln Val Ser Leu Thr Cys Leu Val Lys Gly Phe
        435                 440                 445

Tyr Pro Ser Asp Ile Ala Val Glu Trp Glu Ser Asn Gly Gln Pro Glu
    450                 455                 460

Asn Asn Tyr Lys Thr Thr Pro Pro Val Leu Asp Ser Asp Gly Ser Phe
465                 470                 475                 480

Phe Leu Tyr Ser Lys Leu Thr Val Asp Lys Ser Arg Trp Gln Gln Gly
                485                 490                 495

Asn Val Phe Ser Cys Ser Val Met His Glu Ala Leu His Asn His Tyr
            500                 505                 510

Thr Gln Lys Ser Leu Ser Leu Ser Pro Gly Lys
        515                 520
```

<210> SEQ ID NO 74
<211> LENGTH: 662
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110

Ala Ala Leu Lys Gly Gly Gly Ser Ala Thr Pro Leu Gly Pro Ala
        115                 120                 125

Ser Ser Leu Pro Gln Ser Phe Leu Leu Lys Cys Leu Glu Gln Val Arg
    130                 135                 140

Lys Ile Gln Gly Asp Gly Ala Ala Leu Gln Glu Lys Leu Val Ser Glu
145                 150                 155                 160

Cys Ala Thr Tyr Lys Leu Cys His Pro Glu Glu Leu Val Leu Leu Gly
                165                 170                 175

His Ser Leu Gly Ile Pro Trp Ala Pro Leu Ser Ser Cys Pro Ser Gln
            180                 185                 190

Ala Leu Gln Leu Ala Gly Cys Leu Ser Gln Leu His Ser Gly Leu Phe
        195                 200                 205

Leu Tyr Gln Gly Leu Leu Gln Ala Leu Glu Gly Ile Ser Pro Glu Leu
    210                 215                 220

Gly Pro Thr Leu Asp Thr Leu Gln Leu Asp Val Ala Asp Phe Ala Thr
225                 230                 235                 240

Thr Ile Trp Gln Gln Met Glu Glu Leu Gly Met Ala Pro Ala Leu Gln
                245                 250                 255

Pro Thr Gln Gly Ala Met Pro Ala Phe Ala Ser Ala Phe Gln Arg Arg
            260                 265                 270

Ala Gly Gly Val Leu Val Ala Ser His Leu Gln Ser Phe Leu Glu Val
        275                 280                 285

Ser Tyr Arg Val Leu Arg His Leu Ala Gln Pro Gly Gly Gly Gly Ser
    290                 295                 300

Glu Leu Ala Ala Leu Glu Ala Glu Leu Ala Ala Leu Glu Ala Gly Gly
305                 310                 315                 320

Ser Gly Asp Tyr Trp Gly Gln Gly Thr Leu Val Thr Val Ser Ser Ala
                325                 330                 335

Ser Thr Lys Gly Pro Ser Val Phe Pro Leu Ala Pro Cys Ser Arg Ser
            340                 345                 350

Thr Ser Glu Ser Thr Ala Ala Leu Gly Cys Leu Val Lys Asp Tyr Phe
        355                 360                 365
```

Pro Glu Pro Val Thr Val Ser Trp Asn Ser Gly Ala Leu Thr Ser Gly
            370                 375                 380

Val His Thr Phe Pro Ala Val Leu Gln Ser Ser Gly Leu Tyr Ser Leu
385                 390                 395                 400

Ser Ser Val Val Thr Val Pro Ser Ser Ser Leu Gly Thr Lys Thr Tyr
            405                 410                 415

Thr Cys Asn Val Asp His Lys Pro Ser Asn Thr Lys Val Asp Lys Arg
            420                 425                 430

Val Glu Ser Lys Tyr Gly Pro Pro Cys Pro Pro Cys Pro Ala Pro Glu
            435                 440                 445

Ala Ala Gly Gly Pro Ser Val Phe Leu Phe Pro Pro Lys Pro Lys Asp
450                 455                 460

Thr Leu Met Ile Ser Arg Thr Pro Glu Val Thr Cys Val Val Val Asp
465                 470                 475                 480

Val Ser Gln Glu Asp Pro Glu Val Gln Phe Asn Trp Tyr Val Asp Gly
            485                 490                 495

Val Glu Val His Asn Ala Lys Thr Lys Pro Arg Glu Glu Gln Phe Asn
            500                 505                 510

Ser Thr Tyr Arg Val Val Ser Val Leu Thr Val Leu His Gln Asp Trp
            515                 520                 525

Leu Asn Gly Lys Glu Tyr Lys Cys Lys Val Ser Asn Lys Gly Leu Pro
530                 535                 540

Ser Ser Ile Glu Lys Thr Ile Ser Lys Ala Lys Gly Gln Pro Arg Glu
545                 550                 555                 560

Pro Gln Val Tyr Thr Leu Pro Pro Ser Gln Glu Glu Met Thr Lys Asn
            565                 570                 575

Gln Val Ser Leu Thr Cys Leu Val Lys Gly Phe Tyr Pro Ser Asp Ile
            580                 585                 590

Ala Val Glu Trp Glu Ser Asn Gly Gln Pro Glu Asn Asn Tyr Lys Thr
            595                 600                 605

Thr Pro Pro Val Leu Asp Ser Asp Gly Ser Phe Phe Leu Tyr Ser Arg
610                 615                 620

Leu Thr Val Asp Lys Ser Arg Trp Gln Glu Gly Asn Val Phe Ser Cys
625                 630                 635                 640

Ser Val Met His Glu Ala Leu His Asn His Tyr Thr Gln Lys Ser Leu
            645                 650                 655

Ser Leu Ser Leu Gly Lys
            660

<210> SEQ ID NO 75
<211> LENGTH: 675
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Gly Gly Ser Gly Ala Lys Leu Ala Ala Leu Lys Ala Lys Leu
            100                 105                 110

Ala Ala Leu Lys Gly Gly Gly Ser Phe Pro Thr Ile Pro Leu Ser
        115                 120                 125

Arg Leu Phe Asp Asn Ala Met Leu Arg Ala His Arg Leu His Gln Leu
130                 135                 140

Ala Phe Asp Thr Tyr Gln Glu Phe Glu Glu Ala Tyr Ile Pro Lys Glu
145                 150                 155                 160

Gln Lys Tyr Ser Phe Leu Gln Asn Pro Gln Thr Ser Leu Cys Phe Ser
                165                 170                 175

Glu Ser Ile Pro Thr Pro Ser Asn Arg Glu Glu Thr Gln Gln Lys Ser
            180                 185                 190

Asn Leu Glu Leu Leu Arg Ile Ser Leu Leu Leu Ile Gln Ser Trp Leu
        195                 200                 205

Glu Pro Val Gln Phe Leu Arg Ser Val Phe Ala Asn Ser Leu Val Tyr
210                 215                 220

Gly Ala Ser Asp Ser Asn Val Tyr Asp Leu Leu Lys Asp Leu Glu Glu
225                 230                 235                 240

Gly Ile Gln Thr Leu Met Gly Arg Leu Glu Asp Gly Ser Pro Arg Thr
                245                 250                 255

Gly Gln Ile Phe Lys Gln Thr Tyr Ser Lys Phe Asp Thr Asn Ser His
            260                 265                 270

Asn Asp Asp Ala Leu Leu Lys Asn Tyr Gly Leu Leu Tyr Cys Phe Arg
        275                 280                 285

Lys Asp Met Asp Lys Val Glu Thr Phe Leu Arg Ile Val Gln Cys Arg
290                 295                 300

Ser Val Glu Gly Ser Cys Gly Phe Gly Gly Gly Ser Glu Leu Ala
305                 310                 315                 320

Ala Leu Glu Ala Glu Leu Ala Ala Leu Glu Ala Gly Gly Ser Gly Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Cys Ser Arg Ser Thr Ser Glu
        355                 360                 365

Ser Thr Ala Ala Leu Gly Cys Leu Val Lys Asp Tyr Phe Pro Glu Pro
370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Lys Thr Tyr Thr Cys Asn
            420                 425                 430

Val Asp His Lys Pro Ser Asn Thr Lys Val Asp Lys Arg Val Glu Ser
        435                 440                 445

Lys Tyr Gly Pro Pro Cys Pro Pro Cys Pro Ala Pro Glu Ala Ala Gly
450                 455                 460

Gly Pro Ser Val Phe Leu Phe Pro Pro Lys Pro Lys Asp Thr Leu Met
465                 470                 475                 480
```

```
Ile Ser Arg Thr Pro Glu Val Thr Cys Val Val Asp Val Ser Gln
                485                 490                 495

Glu Asp Pro Glu Val Gln Phe Asn Trp Tyr Val Asp Gly Val Glu Val
            500                 505                 510

His Asn Ala Lys Thr Lys Pro Arg Glu Glu Gln Phe Asn Ser Thr Tyr
            515                 520                 525

Arg Val Val Ser Val Leu Thr Val Leu His Gln Asp Trp Leu Asn Gly
    530                 535                 540

Lys Glu Tyr Lys Cys Lys Val Ser Asn Lys Gly Leu Pro Ser Ser Ile
545                 550                 555                 560

Glu Lys Thr Ile Ser Lys Ala Lys Gly Gln Pro Arg Glu Pro Gln Val
                565                 570                 575

Tyr Thr Leu Pro Pro Ser Gln Glu Glu Met Thr Lys Asn Gln Val Ser
            580                 585                 590

Leu Thr Cys Leu Val Lys Gly Phe Tyr Pro Ser Asp Ile Ala Val Glu
            595                 600                 605

Trp Glu Ser Asn Gly Gln Pro Glu Asn Asn Tyr Lys Thr Thr Pro Pro
            610                 615                 620

Val Leu Asp Ser Asp Gly Ser Phe Phe Leu Tyr Ser Arg Leu Thr Val
625                 630                 635                 640

Asp Lys Ser Arg Trp Gln Gln Gly Asn Val Phe Ser Cys Ser Val Met
                645                 650                 655

His Glu Ala Leu His Asn His Tyr Thr Gln Lys Ser Leu Ser Leu Ser
            660                 665                 670

Leu Gly Lys
        675

<210> SEQ ID NO 76
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Gly Gly Ser Gly Ala Lys Leu Ala Ala Leu Lys
50                  55                  60

Ala Lys Leu Ala Ala Leu Lys Gly Gly Gly Ser Phe Pro Thr Ile
65                  70                  75                  80

Pro Leu Ser Arg Leu Phe Asp Asn Ala Met Leu Arg Ala His Arg Leu
                85                  90                  95

His Gln Leu Ala Phe Asp Thr Tyr Gln Glu Phe Glu Glu Ala Tyr Ile
            100                 105                 110

Pro Lys Glu Gln Lys Tyr Ser Phe Leu Gln Asn Pro Gln Thr Ser Leu
        115                 120                 125

Cys Phe Ser Glu Ser Ile Pro Thr Pro Ser Asn Arg Glu Glu Thr Gln
    130                 135                 140

Gln Lys Ser Asn Leu Glu Leu Leu Arg Ile Ser Leu Leu Leu Ile Gln
145                 150                 155                 160
```

-continued

Ser Trp Leu Glu Pro Val Gln Phe Leu Arg Ser Val Phe Ala Asn Ser
             165                 170                 175

Leu Val Tyr Gly Ala Ser Asp Ser Asn Val Tyr Asp Leu Leu Lys Asp
         180                 185                 190

Leu Glu Glu Gly Ile Gln Thr Leu Met Gly Arg Leu Glu Asp Gly Ser
     195                 200                 205

Pro Arg Thr Gly Gln Ile Phe Lys Gln Thr Tyr Ser Lys Phe Asp Thr
 210                 215                 220

Asn Ser His Asn Asp Asp Ala Leu Leu Lys Asn Tyr Gly Leu Leu Tyr
225                 230                 235                 240

Cys Phe Arg Lys Asp Met Asp Lys Val Glu Thr Phe Leu Arg Ile Val
             245                 250                 255

Gln Cys Arg Ser Val Glu Gly Ser Cys Gly Phe Gly Gly Gly Gly Ser
         260                 265                 270

Glu Leu Ala Ala Leu Glu Ala Glu Leu Ala Ala Leu Glu Ala Gly Gly
     275                 280                 285

Ser Gly Gly Tyr Thr Arg Tyr Ala Asp Ser Val Lys Gly Arg Phe Thr
 290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
             325                 330                 335

Asp Gly Phe Tyr Ala Met Asp Tyr Trp Gly Gln Gly Thr Leu Val Thr
         340                 345                 350

Val Ser Ser Ala Ser Thr Lys Gly Pro Ser Val Phe Pro Leu Ala Pro
     355                 360                 365

Ser Ser Lys Ser Thr Ser Gly Gly Thr Ala Ala Leu Gly Cys Leu Val
 370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
             405                 410                 415

Leu Tyr Ser Leu Ser Ser Val Val Thr Val Pro Ser Ser Ser Leu Gly
         420                 425                 430

Thr Gln Thr Tyr Ile Cys Asn Val Asn His Lys Pro Ser Asn Thr Lys
     435                 440                 445

Val Asp Lys Lys Val Glu Pro Lys Ser Cys Asp Lys Thr His Thr Cys
 450                 455                 460

Pro Pro Cys Pro Ala Pro Val Ala Gly Pro Ser Val Phe Leu Phe
465                 470                 475                 480

Pro Pro Lys Pro Lys Asp Thr Leu Met Ile Ser Arg Thr Pro Glu Val
             485                 490                 495

Thr Cys Val Val Val Asp Val Ser His Glu Asp Pro Glu Val Lys Phe
         500                 505                 510

Asn Trp Tyr Val Asp Gly Val Glu Val His Asn Ala Lys Thr Lys Pro
     515                 520                 525

Arg Glu Glu Gln Tyr Asn Ser Thr Tyr Arg Val Val Ser Val Leu Thr
 530                 535                 540

Val Leu His Gln Asp Trp Leu Asn Gly Lys Glu Tyr Lys Cys Lys Val
545                 550                 555                 560

Ser Asn Lys Gly Leu Pro Ser Ser Ile Glu Lys Thr Ile Ser Lys Ala
             565                 570                 575

```
Lys Gly Gln Pro Arg Glu Pro Gln Val Tyr Thr Leu Pro Pro Ser Arg
                580                 585                 590

Asp Glu Leu Thr Lys Asn Gln Val Ser Leu Thr Cys Leu Val Lys Gly
            595                 600                 605

Phe Tyr Pro Ser Asp Ile Ala Val Glu Trp Glu Ser Asn Gly Gln Pro
        610                 615                 620

Glu Asn Asn Tyr Lys Thr Thr Pro Pro Val Leu Asp Ser Asp Gly Ser
625                 630                 635                 640

Phe Phe Leu Tyr Ser Lys Leu Thr Val Asp Lys Ser Arg Trp Gln Gln
                645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Lys
        675                 680

<210> SEQ ID NO 77
<211> LENGTH: 676
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Gly
                85                  90                  95

Gly Ser Gly Ala Lys Leu Ala Ala Leu Lys Ala Lys Leu Ala Ala Leu
            100                 105                 110

Lys Gly Gly Gly Gly Ser Phe Pro Thr Ile Pro Leu Ser Arg Leu Phe
        115                 120                 125

Asp Asn Ala Met Leu Arg Ala His Arg Leu His Gln Leu Ala Phe Asp
    130                 135                 140

Thr Tyr Gln Glu Phe Glu Glu Ala Tyr Ile Pro Lys Glu Gln Lys Tyr
145                 150                 155                 160

Ser Phe Leu Gln Asn Pro Gln Thr Ser Leu Cys Phe Ser Glu Ser Ile
                165                 170                 175

Pro Thr Pro Ser Asn Arg Glu Glu Thr Gln Gln Lys Ser Asn Leu Glu
            180                 185                 190

Leu Leu Arg Ile Ser Leu Leu Leu Ile Gln Ser Trp Leu Glu Pro Val
        195                 200                 205

Gln Phe Leu Arg Ser Val Phe Ala Asn Ser Leu Val Tyr Gly Ala Ser
    210                 215                 220

Asp Ser Asn Val Tyr Asp Leu Leu Lys Asp Leu Glu Glu Gly Ile Gln
225                 230                 235                 240

Thr Leu Met Gly Arg Leu Glu Asp Gly Ser Pro Arg Thr Gly Gln Ile
                245                 250                 255
```

Phe Lys Gln Thr Tyr Ser Lys Phe Asp Thr Asn Ser His Asn Asp Asp
                260                 265                 270

Ala Leu Leu Lys Asn Tyr Gly Leu Leu Tyr Cys Phe Arg Lys Asp Met
                275                 280                 285

Asp Lys Val Glu Thr Phe Leu Arg Ile Val Gln Cys Arg Ser Val Glu
                290                 295                 300

Gly Ser Cys Gly Phe Gly Gly Gly Ser Glu Leu Ala Ala Leu Glu
305                 310                 315                 320

Ala Glu Leu Ala Ala Leu Glu Ala Gly Ser Gly His Val Asp Val
                325                 330                 335

Trp Gly Gln Gly Leu Leu Val Thr Val Ser Ser Ala Ser Thr Thr Ala
                340                 345                 350

Pro Lys Val Tyr Pro Leu Ser Ser Cys Cys Gly Asp Lys Ser Ser Ser
                355                 360                 365

Thr Val Thr Leu Gly Cys Leu Val Ser Ser Tyr Met Pro Glu Pro Val
                370                 375                 380

Thr Val Thr Trp Asn Ser Gly Ala Leu Lys Ser Gly Val His Thr Phe
385                 390                 395                 400

Pro Ala Val Leu Gln Ser Ser Gly Leu Tyr Ser Leu Ser Ser Met Val
                405                 410                 415

Thr Val Pro Gly Ser Thr Ser Gly Gln Thr Phe Thr Cys Asn Val Ala
                420                 425                 430

His Pro Ala Ser Ser Thr Lys Val Asp Lys Ala Val Glu Pro Lys Ser
                435                 440                 445

Cys Asp Lys Thr His Thr Cys Pro Pro Cys Pro Ala Pro Glu Leu Leu
                450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
                500                 505                 510

Val His Asn Ala Lys Thr Lys Pro Arg Glu Glu Gln Tyr Asn Ser Thr
                515                 520                 525

Tyr Arg Val Val Ser Val Leu Thr Val Leu His Gln Asp Trp Leu Asn
                530                 535                 540

Gly Lys Glu Tyr Lys Cys Lys Val Ser Asn Lys Ala Leu Pro Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Ser Arg Asp Glu Leu Thr Lys Asn Gln Val
                580                 585                 590

Ser Leu Thr Cys Leu Val Lys Gly Phe Tyr Pro Ser Asp Ile Ala Val
                595                 600                 605

Glu Trp Glu Ser Asn Gly Gln Pro Glu Asn Asn Tyr Lys Thr Thr Pro
                610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
                660                 665                 670

Ser Pro Gly Lys
        675

<210> SEQ ID NO 78
<211> LENGTH: 632
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110

Ala Ala Leu Lys Gly Gly Gly Gly Ser Val Pro Ile Gln Lys Val Gln
        115                 120                 125

Asp Asp Thr Lys Thr Leu Ile Lys Thr Ile Val Thr Arg Ile Asn Asp
    130                 135                 140

Ile Ser His Thr Gln Ser Val Ser Lys Gln Lys Val Thr Gly Leu
145                 150                 155                 160

Asp Phe Ile Pro Gly Leu His Pro Ile Leu Thr Leu Ser Lys Met Asp
                165                 170                 175

Gln Thr Leu Ala Val Tyr Gln Gln Ile Leu Thr Ser Met Pro Ser Arg
            180                 185                 190

Asn Val Ile Gln Ile Ser Asn Asp Leu Glu Asn Leu Arg Asp Leu Leu
        195                 200                 205

His Val Leu Ala Phe Ser Lys Ser Cys His Leu Pro Trp Ala Ser Gly
    210                 215                 220

Leu Glu Thr Leu Asp Ser Leu Gly Gly Val Leu Glu Ala Ser Gly Tyr
225                 230                 235                 240

Ser Thr Glu Val Val Ala Leu Ser Arg Leu Gln Gly Ser Leu Gln Asp
                245                 250                 255

Met Leu Trp Gln Leu Asp Leu Ser Pro Gly Cys Gly Gly Gly Gly Ser
            260                 265                 270

Glu Leu Ala Ala Leu Glu Ala Glu Leu Ala Ala Leu Glu Ala Gly Gly
        275                 280                 285

Ser Gly Asp Tyr Trp Gly Gln Gly Thr Leu Val Thr Val Ser Ser Ala
    290                 295                 300

Ser Thr Lys Gly Pro Ser Val Phe Pro Leu Ala Pro Ser Ser Lys Ser
305                 310                 315                 320

Thr Ser Gly Gly Thr Ala Ala Leu Gly Cys Leu Val Lys Asp Tyr Phe
                325                 330                 335

Pro Glu Pro Val Thr Val Ser Trp Asn Ser Gly Ala Leu Thr Ser Gly
            340                 345                 350

```
Val His Thr Phe Pro Ala Val Leu Gln Ser Ser Gly Leu Tyr Ser Leu
            355                 360                 365

Ser Ser Val Val Thr Val Pro Ser Ser Leu Gly Thr Gln Thr Tyr
        370                 375                 380

Ile Cys Asn Val Asn His Lys Pro Ser Asn Thr Lys Val Asp Lys Lys
385                 390                 395                 400

Val Glu Pro Lys Ser Cys Asp Lys Thr His Thr Cys Pro Pro Cys Pro
                405                 410                 415

Ala Pro Pro Val Ala Gly Pro Ser Val Phe Leu Phe Pro Pro Lys Pro
            420                 425                 430

Lys Asp Thr Leu Met Ile Ser Arg Thr Pro Glu Val Thr Cys Val Val
            435                 440                 445

Val Asp Val Ser His Glu Asp Pro Glu Val Lys Phe Asn Trp Tyr Val
        450                 455                 460

Asp Gly Val Glu Val His Asn Ala Lys Thr Lys Pro Arg Glu Glu Gln
465                 470                 475                 480

Tyr Asn Ser Thr Tyr Arg Val Val Ser Val Leu Thr Val Leu His Gln
                485                 490                 495

Asp Trp Leu Asn Gly Lys Glu Tyr Lys Cys Lys Val Ser Asn Lys Gly
            500                 505                 510

Leu Pro Ser Ser Ile Glu Lys Thr Ile Ser Lys Ala Lys Gly Gln Pro
            515                 520                 525

Arg Glu Pro Gln Val Tyr Thr Leu Pro Pro Ser Arg Asp Glu Leu Thr
            530                 535                 540

Lys Asn Gln Val Ser Leu Thr Cys Leu Val Lys Gly Phe Tyr Pro Ser
545                 550                 555                 560

Asp Ile Ala Val Glu Trp Glu Ser Asn Gly Gln Pro Glu Asn Asn Tyr
                565                 570                 575

Lys Thr Thr Pro Pro Val Leu Asp Ser Asp Gly Ser Phe Phe Leu Tyr
            580                 585                 590

Ser Lys Leu Thr Val Asp Lys Ser Arg Trp Gln Gln Gly Asn Val Phe
            595                 600                 605

Ser Cys Ser Val Met His Glu Ala Leu His Asn His Tyr Thr Gln Lys
            610                 615                 620

Ser Leu Ser Leu Ser Pro Gly Lys
625                 630

<210> SEQ ID NO 79
<211> LENGTH: 635
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Gly Gly Ser Gly Ala Lys Leu Ala Leu Lys Ala Lys
        50                  55                  60

Leu Ala Ala Leu Lys Gly Gly Gly Gly Ser Val Pro Ile Gln Lys Val
```

-continued

```
            65                  70                  75                  80
Gln Asp Asp Thr Lys Thr Leu Ile Lys Thr Ile Val Thr Arg Ile Asn
                    85                  90                  95
Asp Ile Ser His Thr Gln Ser Val Ser Ser Lys Gln Lys Val Thr Gly
                    100                 105                 110
Leu Asp Phe Ile Pro Gly Leu His Pro Ile Leu Thr Leu Ser Lys Met
                    115                 120                 125
Asp Gln Thr Leu Ala Val Tyr Gln Gln Ile Leu Thr Ser Met Pro Ser
            130                 135                 140
Arg Asn Val Ile Gln Ile Ser Asn Asp Leu Glu Asn Leu Arg Asp Leu
145                 150                 155                 160
Leu His Val Leu Ala Phe Ser Lys Ser Cys His Leu Pro Trp Ala Ser
                    165                 170                 175
Gly Leu Glu Thr Leu Asp Ser Leu Gly Gly Val Leu Glu Ala Ser Gly
                    180                 185                 190
Tyr Ser Thr Glu Val Val Ala Leu Ser Arg Leu Gln Gly Ser Leu Gln
                    195                 200                 205
Asp Met Leu Trp Gln Leu Asp Leu Ser Pro Gly Cys Gly Gly Gly Gly
            210                 215                 220
Ser Glu Leu Ala Ala Leu Glu Ala Glu Leu Ala Ala Leu Glu Ala Gly
225                 230                 235                 240
Gly Ser Gly Thr Arg Tyr Ala Asp Ser Val Lys Gly Arg Phe Thr Ile
                    245                 250                 255
Ser Ala Asp Thr Ser Lys Asn Thr Ala Tyr Leu Gln Met Asn Ser Leu
                    260                 265                 270
Arg Ala Glu Asp Thr Ala Val Tyr Tyr Cys Ser Arg Trp Gly Gly Asp
                    275                 280                 285
Gly Phe Tyr Ala Met Asp Tyr Trp Gly Gln Gly Thr Leu Val Thr Val
            290                 295                 300
Ser Ser Ala Ser Thr Lys Gly Pro Ser Val Phe Pro Leu Ala Pro Ser
305                 310                 315                 320
Ser Lys Ser Thr Ser Gly Gly Thr Ala Ala Leu Gly Cys Leu Val Lys
                    325                 330                 335
Asp Tyr Phe Pro Glu Pro Val Thr Val Ser Trp Asn Ser Gly Ala Leu
                    340                 345                 350
Thr Ser Gly Val His Thr Phe Pro Ala Val Leu Gln Ser Ser Gly Leu
                    355                 360                 365
Tyr Ser Leu Ser Ser Val Val Thr Val Pro Ser Ser Ser Leu Gly Thr
            370                 375                 380
Gln Thr Tyr Ile Cys Asn Val Asn His Lys Pro Ser Asn Thr Lys Val
385                 390                 395                 400
Asp Lys Lys Val Glu Pro Lys Ser Cys Asp Lys Thr His Thr Cys Pro
                    405                 410                 415
Pro Cys Pro Ala Pro Pro Val Ala Gly Pro Ser Val Phe Leu Phe Pro
                    420                 425                 430
Pro Lys Pro Lys Asp Thr Leu Met Ile Ser Arg Thr Pro Glu Val Thr
                    435                 440                 445
Cys Val Val Val Asp Val Ser His Glu Asp Pro Glu Val Lys Phe Asn
            450                 455                 460
Trp Tyr Val Asp Gly Val Glu Val His Asn Ala Lys Thr Lys Pro Arg
465                 470                 475                 480
Glu Glu Gln Tyr Asn Ser Thr Tyr Arg Val Val Ser Val Leu Thr Val
                    485                 490                 495
```

```
Leu His Gln Asp Trp Leu Asn Gly Lys Glu Tyr Lys Cys Lys Val Ser
            500                 505                 510

Asn Lys Gly Leu Pro Ser Ser Ile Glu Lys Thr Ile Ser Lys Ala Lys
            515                 520                 525

Gly Gln Pro Arg Glu Pro Gln Val Tyr Thr Leu Pro Pro Ser Arg Asp
            530                 535                 540

Glu Leu Thr Lys Asn Gln Val Ser Leu Thr Cys Leu Val Lys Gly Phe
545                 550                 555                 560

Tyr Pro Ser Asp Ile Ala Val Glu Trp Glu Ser Asn Gly Gln Pro Glu
            565                 570                 575

Asn Asn Tyr Lys Thr Thr Pro Pro Val Leu Asp Ser Asp Gly Ser Phe
            580                 585                 590

Phe Leu Tyr Ser Lys Leu Thr Val Asp Lys Ser Arg Trp Gln Gln Gly
            595                 600                 605

Asn Val Phe Ser Cys Ser Val Met His Glu Ala Leu His Asn His Tyr
            610                 615                 620

Thr Gln Lys Ser Leu Ser Leu Ser Pro Gly Lys
625                 630                 635

<210> SEQ ID NO 80
<211> LENGTH: 403
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Gln Gln His Tyr Gly Gly Ser Gly
                85                  90                  95

Ala Lys Leu Ala Ala Leu Lys Ala Lys Leu Ala Ala Leu Lys Gly Gly
            100                 105                 110

Gly Gly Ser Val Pro Ile Gln Lys Val Gln Asp Asp Thr Lys Thr Leu
        115                 120                 125

Ile Lys Thr Ile Val Thr Arg Ile Asn Asp Ile Ser His Thr Gln Ser
    130                 135                 140

Val Ser Ser Lys Gln Lys Val Thr Gly Leu Asp Phe Ile Pro Gly Leu
145                 150                 155                 160

His Pro Ile Leu Thr Leu Ser Lys Met Asp Gln Thr Leu Ala Val Tyr
                165                 170                 175

Gln Gln Ile Leu Thr Ser Met Pro Ser Arg Asn Val Ile Gln Ile Ser
            180                 185                 190

Asn Asp Leu Glu Asn Leu Arg Asp Leu Leu His Val Leu Ala Phe Ser
        195                 200                 205

Lys Ser Cys His Leu Pro Trp Ala Ser Gly Leu Glu Thr Leu Asp Ser
```

```
                210                 215                 220
Leu Gly Gly Val Leu Glu Ala Ser Gly Tyr Ser Thr Glu Val Val Ala
225                 230                 235                 240

Leu Ser Arg Leu Gln Gly Ser Leu Gln Asp Met Leu Trp Gln Leu Asp
                245                 250                 255

Leu Ser Pro Gly Cys Gly Gly Gly Ser Glu Leu Ala Ala Leu Glu
            260                 265                 270

Ala Glu Leu Ala Ala Leu Glu Ala Gly Ser Gly Pro Thr Phe Gly
            275                 280                 285

Gln Gly Thr Lys Leu Glu Ile Lys Arg Thr Val Ala Ala Pro Ser Val
            290                 295                 300

Phe Ile Phe Pro Pro Ser Asp Glu Gln Leu Lys Ser Gly Thr Ala Ser
305                 310                 315                 320

Val Val Cys Leu Leu Asn Asn Phe Tyr Pro Arg Glu Ala Lys Val Gln
                325                 330                 335

Trp Lys Val Asp Asn Ala Leu Gln Ser Gly Asn Ser Gln Glu Ser Val
                340                 345                 350

Thr Glu Gln Asp Ser Lys Asp Ser Thr Tyr Ser Leu Ser Ser Thr Leu
                355                 360                 365

Thr Leu Ser Lys Ala Asp Tyr Glu Lys His Lys Val Tyr Ala Cys Glu
            370                 375                 380

Val Thr His Gln Gly Leu Ser Ser Pro Val Thr Lys Ser Phe Asn Arg
385                 390                 395                 400

Gly Glu Cys

<210> SEQ ID NO 81
<211> LENGTH: 649
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110

Ala Ala Leu Lys Gly Gly Gly Gly Ser Cys Asp Leu Pro Gln Thr His
            115                 120                 125

Ser Leu Gly Ser Arg Arg Thr Leu Met Leu Leu Ala Gln Met Arg Arg
            130                 135                 140

Ile Ser Leu Phe Ser Cys Leu Lys Asp Arg His Asp Phe Gly Phe Pro
145                 150                 155                 160

Gln Glu Glu Phe Gly Asn Gln Phe Gln Lys Ala Glu Thr Ile Pro Val
```

```
            165                 170                 175
Leu His Glu Met Ile Gln Gln Ile Phe Asn Leu Phe Ser Thr Lys Asp
                180                 185                 190

Ser Ser Ala Ala Trp Asp Glu Thr Leu Leu Asp Lys Phe Tyr Thr Glu
                195                 200                 205

Leu Tyr Gln Gln Leu Asn Asp Leu Glu Ala Cys Val Ile Gln Gly Val
            210                 215                 220

Gly Val Thr Glu Thr Pro Leu Met Lys Glu Asp Ser Ile Leu Ala Val
225                 230                 235                 240

Arg Lys Tyr Phe Gln Arg Ile Thr Leu Tyr Leu Lys Glu Lys Lys Tyr
                245                 250                 255

Ser Pro Cys Ala Trp Glu Val Val Arg Ala Glu Ile Met Arg Ser Phe
            260                 265                 270

Ser Leu Ser Thr Asn Leu Gln Glu Ser Leu Arg Ser Lys Glu Gly Gly
            275                 280                 285

Gly Gly Ser Glu Leu Ala Ala Leu Glu Ala Glu Leu Ala Ala Leu Glu
        290                 295                 300

Ala Gly Gly Ser Gly Asp Tyr Trp Gly Gln Gly Thr Leu Val Thr Val
305                 310                 315                 320

Ser Ser Ala Ser Thr Lys Gly Pro Ser Val Phe Pro Leu Ala Pro Cys
                325                 330                 335

Ser Arg Ser Thr Ser Glu Ser Thr Ala Ala Leu Gly Cys Leu Val Lys
            340                 345                 350

Asp Tyr Phe Pro Glu Pro Val Thr Val Ser Trp Asn Ser Gly Ala Leu
            355                 360                 365

Thr Ser Gly Val His Thr Phe Pro Ala Val Leu Gln Ser Ser Gly Leu
        370                 375                 380

Tyr Ser Leu Ser Ser Val Val Thr Val Pro Ser Ser Ser Leu Gly Thr
385                 390                 395                 400

Lys Thr Tyr Thr Cys Asn Val Asp His Lys Pro Ser Asn Thr Lys Val
                405                 410                 415

Asp Lys Arg Val Glu Ser Lys Tyr Gly Pro Pro Cys Pro Pro Cys Pro
            420                 425                 430

Ala Pro Glu Ala Ala Gly Gly Pro Ser Val Phe Leu Phe Pro Pro Lys
        435                 440                 445

Pro Lys Asp Thr Leu Met Ile Ser Arg Thr Pro Glu Val Thr Cys Val
        450                 455                 460

Val Val Asp Val Ser Gln Glu Asp Pro Glu Val Gln Phe Asn Trp Tyr
465                 470                 475                 480

Val Asp Gly Val Glu Val His Asn Ala Lys Thr Lys Pro Arg Glu Glu
                485                 490                 495

Gln Phe Asn Ser Thr Tyr Arg Val Val Ser Val Leu Thr Val Leu His
                500                 505                 510

Gln Asp Trp Leu Asn Gly Lys Glu Tyr Lys Cys Lys Val Ser Asn Lys
            515                 520                 525

Gly Leu Pro Ser Ser Ile Glu Lys Thr Ile Ser Lys Ala Lys Gly Gln
        530                 535                 540

Pro Arg Glu Pro Gln Val Tyr Thr Leu Pro Pro Ser Gln Glu Glu Met
545                 550                 555                 560

Thr Lys Asn Gln Val Ser Leu Thr Cys Leu Val Lys Gly Phe Tyr Pro
                565                 570                 575

Ser Asp Ile Ala Val Glu Trp Glu Ser Asn Gly Gln Pro Glu Asn Asn
            580                 585                 590
```

```
Tyr Lys Thr Thr Pro Pro Val Leu Asp Ser Asp Gly Ser Phe Phe Leu
            595                 600                 605

Tyr Ser Arg Leu Thr Val Asp Lys Ser Arg Trp Gln Glu Gly Asn Val
    610                 615                 620

Phe Ser Cys Ser Val Met His Glu Ala Leu His Asn His Tyr Thr Gln
625                 630                 635                 640

Lys Ser Leu Ser Leu Ser Leu Gly Lys
                645
```

<210> SEQ ID NO 82
<211> LENGTH: 652
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 82

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110

Ala Ala Leu Lys Gly Gly Gly Gly Ser Met Ser Tyr Asn Leu Leu Gly
        115                 120                 125

Phe Leu Gln Arg Ser Ser Asn Phe Gln Cys Gln Lys Leu Leu Trp Gln
    130                 135                 140

Leu Asn Gly Arg Leu Glu Tyr Cys Leu Lys Asp Arg Met Asn Phe Asp
145                 150                 155                 160

Ile Pro Glu Glu Ile Lys Gln Leu Gln Gln Phe Gln Lys Glu Asp Ala
                165                 170                 175

Ala Leu Thr Ile Tyr Glu Met Leu Gln Asn Ile Phe Ala Ile Phe Arg
            180                 185                 190

Gln Asp Ser Ser Ser Thr Gly Trp Asn Glu Thr Ile Val Glu Asn Leu
        195                 200                 205

Leu Ala Asn Val Tyr His Gln Ile Asn His Leu Lys Thr Val Leu Glu
    210                 215                 220

Glu Lys Leu Glu Lys Glu Asp Phe Thr Arg Gly Lys Leu Met Ser Ser
225                 230                 235                 240

Leu His Leu Lys Arg Tyr Tyr Gly Arg Ile Leu His Tyr Leu Lys Ala
                245                 250                 255

Lys Glu Tyr Ser His Cys Ala Trp Thr Ile Val Arg Val Glu Ile Leu
            260                 265                 270

Arg Asn Phe Tyr Phe Ile Asn Arg Leu Thr Gly Tyr Leu Arg Asn Gly
        275                 280                 285

Gly Gly Gly Ser Glu Leu Ala Ala Leu Glu Ala Glu Leu Ala Ala Leu
```

```
                    290                 295                 300
Glu Ala Gly Gly Ser Gly Asp Tyr Trp Gly Gln Gly Thr Leu Val Thr
305                 310                 315                 320

Val Ser Ser Ala Ser Thr Lys Gly Pro Ser Val Phe Pro Leu Ala Pro
                325                 330                 335

Ser Ser Lys Ser Thr Ser Gly Gly Thr Ala Ala Leu Gly Cys Leu Val
            340                 345                 350

Lys Asp Tyr Phe Pro Glu Pro Val Thr Val Ser Trp Asn Ser Gly Ala
        355                 360                 365

Leu Thr Ser Gly Val His Thr Phe Pro Ala Val Leu Gln Ser Ser Gly
370                 375                 380

Leu Tyr Ser Leu Ser Ser Val Val Thr Val Pro Ser Ser Ser Leu Gly
385                 390                 395                 400

Thr Gln Thr Tyr Ile Cys Asn Val Asn His Lys Pro Ser Asn Thr Lys
                405                 410                 415

Val Asp Lys Lys Val Glu Pro Lys Ser Cys Asp Lys Thr His Thr Cys
            420                 425                 430

Pro Pro Cys Pro Ala Pro Pro Val Ala Gly Pro Ser Val Phe Leu Phe
        435                 440                 445

Pro Pro Lys Pro Lys Asp Thr Leu Met Ile Ser Arg Thr Pro Glu Val
450                 455                 460

Thr Cys Val Val Val Asp Val Ser His Glu Asp Pro Glu Val Lys Phe
465                 470                 475                 480

Asn Trp Tyr Val Asp Gly Val Glu Val His Asn Ala Lys Thr Lys Pro
                485                 490                 495

Arg Glu Glu Gln Tyr Asn Ser Thr Tyr Arg Val Val Ser Val Leu Thr
            500                 505                 510

Val Leu His Gln Asp Trp Leu Asn Gly Lys Glu Tyr Lys Cys Lys Val
        515                 520                 525

Ser Asn Lys Gly Leu Pro Ser Ser Ile Glu Lys Thr Ile Ser Lys Ala
530                 535                 540

Lys Gly Gln Pro Arg Glu Pro Gln Val Tyr Thr Leu Pro Pro Ser Arg
545                 550                 555                 560

Asp Glu Leu Thr Lys Asn Gln Val Ser Leu Thr Cys Leu Val Lys Gly
                565                 570                 575

Phe Tyr Pro Ser Asp Ile Ala Val Glu Trp Glu Ser Asn Gly Gln Pro
            580                 585                 590

Glu Asn Asn Tyr Lys Thr Thr Pro Pro Val Leu Asp Ser Asp Gly Ser
        595                 600                 605

Phe Phe Leu Tyr Ser Lys Leu Thr Val Asp Lys Ser Arg Trp Gln Gln
610                 615                 620

Gly Asn Val Phe Ser Cys Ser Val Met His Glu Ala Leu His Asn His
625                 630                 635                 640

Tyr Thr Gln Lys Ser Leu Ser Leu Ser Pro Gly Lys
                645                 650

<210> SEQ ID NO 83
<211> LENGTH: 651
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83
```

-continued

```
Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Gly
                85                  90                  95

Gly Ser Gly Ala Lys Leu Ala Ala Leu Lys Ala Lys Leu Ala Ala Leu
            100                 105                 110

Lys Gly Gly Gly Gly Ser Met Ser Tyr Asn Leu Leu Gly Phe Leu Gln
            115                 120                 125

Arg Ser Ser Asn Phe Gln Cys Gln Lys Leu Leu Trp Gln Leu Asn Gly
            130                 135                 140

Arg Leu Glu Tyr Cys Leu Lys Asp Arg Met Asn Phe Asp Ile Pro Glu
145                 150                 155                 160

Glu Ile Lys Gln Leu Gln Gln Phe Gln Lys Glu Asp Ala Ala Leu Thr
                165                 170                 175

Ile Tyr Glu Met Leu Gln Asn Ile Phe Ala Ile Phe Arg Gln Asp Ser
            180                 185                 190

Ser Ser Thr Gly Trp Asn Glu Thr Ile Val Glu Asn Leu Leu Ala Asn
            195                 200                 205

Val Tyr His Gln Ile Asn His Leu Lys Thr Val Leu Glu Glu Lys Leu
        210                 215                 220

Glu Lys Glu Asp Phe Thr Arg Gly Lys Leu Met Ser Ser Leu His Leu
225                 230                 235                 240

Lys Arg Tyr Tyr Gly Arg Ile Leu His Tyr Leu Lys Ala Lys Glu Tyr
                245                 250                 255

Ser His Cys Ala Trp Thr Ile Val Arg Val Glu Ile Leu Arg Asn Phe
            260                 265                 270

Tyr Phe Ile Asn Arg Leu Thr Gly Tyr Leu Arg Asn Gly Gly Gly Gly
        275                 280                 285

Ser Glu Leu Ala Ala Leu Glu Ala Glu Leu Ala Ala Leu Glu Ala Gly
    290                 295                 300

Gly Ser Gly His Val Asp Val Trp Gly Gln Gly Leu Leu Val Thr Val
305                 310                 315                 320

Ser Ser Ala Ser Thr Thr Ala Pro Lys Val Tyr Pro Leu Ser Ser Cys
                325                 330                 335

Cys Gly Asp Lys Ser Ser Ser Thr Val Thr Leu Gly Cys Leu Val Ser
            340                 345                 350

Ser Tyr Met Pro Glu Pro Val Thr Val Thr Trp Asn Ser Gly Ala Leu
        355                 360                 365

Lys Ser Gly Val His Thr Phe Pro Ala Val Leu Gln Ser Ser Gly Leu
    370                 375                 380

Tyr Ser Leu Ser Ser Met Val Thr Val Pro Gly Ser Thr Ser Gly Gln
385                 390                 395                 400

Thr Phe Thr Cys Asn Val Ala His Pro Ala Ser Ser Thr Lys Val Asp
                405                 410                 415

Lys Ala Val Glu Pro Lys Ser Cys Asp Lys Thr His Thr Cys Pro Pro
```

```
            420                 425                 430
Cys Pro Ala Pro Glu Leu Leu Gly Gly Pro Ser Val Phe Leu Phe Pro
            435                 440                 445

Pro Lys Pro Lys Asp Thr Leu Met Ile Ser Arg Thr Pro Glu Val Thr
450                 455                 460

Cys Val Val Val Asp Val Ser His Glu Asp Pro Glu Val Lys Phe Asn
465                 470                 475                 480

Trp Tyr Val Asp Gly Val Glu Val His Asn Ala Lys Thr Lys Pro Arg
                485                 490                 495

Glu Glu Gln Tyr Asn Ser Thr Tyr Arg Val Val Ser Val Leu Thr Val
                500                 505                 510

Leu His Gln Asp Trp Leu Asn Gly Lys Glu Tyr Lys Cys Lys Val Ser
                515                 520                 525

Asn Lys Ala Leu Pro Ala Pro Ile Glu Lys Thr Ile Ser Lys Ala Lys
            530                 535                 540

Gly Gln Pro Arg Glu Pro Gln Val Tyr Thr Leu Pro Pro Ser Arg Asp
545                 550                 555                 560

Glu Leu Thr Lys Asn Gln Val Ser Leu Thr Cys Leu Val Lys Gly Phe
                565                 570                 575

Tyr Pro Ser Asp Ile Ala Val Glu Trp Glu Ser Asn Gly Gln Pro Glu
                580                 585                 590

Asn Asn Tyr Lys Thr Thr Pro Pro Val Leu Asp Ser Asp Gly Ser Phe
                595                 600                 605

Phe Leu Tyr Ser Lys Leu Thr Val Asp Lys Ser Arg Trp Gln Gln Gly
            610                 615                 620

Asn Val Phe Ser Cys Ser Val Met His Glu Ala Leu His Asn His Tyr
625                 630                 635                 640

Thr Gln Lys Ser Leu Ser Leu Ser Pro Gly Lys
                645                 650

<210> SEQ ID NO 84
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
                100                 105                 110

Ala Ala Leu Lys Cys Gly Gly Gly Ser Ile Glu Gly Arg His Ala
            115                 120                 125
```

```
Glu Gly Thr Phe Thr Ser Asp Val Ser Ser Tyr Leu Glu Gly Gln Ala
            130                 135                 140
Ala Lys Glu Phe Ile Ala Trp Leu Val Lys Gly Arg Gly Gly Gly Gly
145                 150                 155                 160
Ser Cys Glu Leu Ala Ala Leu Glu Ala Glu Leu Ala Ala Leu Glu Ala
                165                 170                 175
Gly Gly Ser Gly Asp Tyr Trp Gly Gln Gly Thr Leu Val Thr Val Ser
            180                 185                 190
Ser Ala Ser Thr Lys Gly Pro Ser Val Phe Pro Leu Ala Pro Ser Ser
        195                 200                 205
Lys Ser Thr Ser Gly Gly Thr Ala Ala Leu Gly Cys Leu Val Lys Asp
    210                 215                 220
Tyr Phe Pro Glu Pro Val Thr Val Ser Trp Asn Ser Gly Ala Leu Thr
225                 230                 235                 240
Ser Gly Val His Thr Phe Pro Ala Val Leu Gln Ser Ser Gly Leu Tyr
                245                 250                 255
Ser Leu Ser Ser Val Val Thr Val Pro Ser Ser Ser Leu Gly Thr Gln
            260                 265                 270
Thr Tyr Ile Cys Asn Val Asn His Lys Pro Ser Asn Thr Lys Val Asp
        275                 280                 285
Lys Lys Val Glu Pro Lys Ser Cys Asp Lys Thr His Thr Cys Pro Pro
    290                 295                 300
Cys Pro Ala Pro Pro Val Ala Gly Pro Ser Val Phe Leu Phe Pro Pro
305                 310                 315                 320
Lys Pro Lys Asp Thr Leu Met Ile Ser Arg Thr Pro Glu Val Thr Cys
                325                 330                 335
Val Val Val Asp Val Ser His Glu Asp Pro Glu Val Lys Phe Asn Trp
            340                 345                 350
Tyr Val Asp Gly Val Glu Val His Asn Ala Lys Thr Lys Pro Arg Glu
        355                 360                 365
Glu Gln Tyr Asn Ser Thr Tyr Arg Val Val Ser Val Leu Thr Val Leu
    370                 375                 380
His Gln Asp Trp Leu Asn Gly Lys Glu Tyr Lys Cys Lys Val Ser Asn
385                 390                 395                 400
Lys Gly Leu Pro Ser Ser Ile Glu Lys Thr Ile Ser Lys Ala Lys Gly
                405                 410                 415
Gln Pro Arg Glu Pro Gln Val Tyr Thr Leu Pro Pro Ser Arg Asp Glu
            420                 425                 430
Leu Thr Lys Asn Gln Val Ser Leu Thr Cys Leu Val Lys Gly Phe Tyr
        435                 440                 445
Pro Ser Asp Ile Ala Val Glu Trp Glu Ser Asn Gly Gln Pro Glu Asn
    450                 455                 460
Asn Tyr Lys Thr Thr Pro Pro Val Leu Asp Ser Asp Gly Ser Phe Phe
465                 470                 475                 480
Leu Tyr Ser Lys Leu Thr Val Asp Lys Ser Arg Trp Gln Gln Gly Asn
                485                 490                 495
Val Phe Ser Cys Ser Val Met His Glu Ala Leu His Asn His Tyr Thr
            500                 505                 510
Gln Lys Ser Leu Ser Leu Ser Pro Gly Lys
        515                 520

<210> SEQ ID NO 85
<211> LENGTH: 543
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 85

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110

Ala Ala Leu Lys Gly Gly Gly Ser Ala Gln Glu Pro Val Lys Gly
            115                 120                 125

Pro Val Ser Thr Lys Pro Gly Ser Cys Pro Ile Ile Leu Ile Arg Cys
            130                 135                 140

Ala Met Leu Asn Pro Pro Asn Arg Cys Leu Lys Asp Thr Asp Cys Pro
145                 150                 155                 160

Gly Ile Lys Lys Cys Cys Glu Gly Ser Cys Gly Met Ala Cys Phe Val
                165                 170                 175

Pro Gln Gly Gly Gly Gly Ser Glu Leu Ala Ala Leu Glu Ala Glu Leu
            180                 185                 190

Ala Ala Leu Glu Ala Gly Gly Ser Gly Asp Tyr Trp Gly Gln Gly Thr
            195                 200                 205

Leu Val Thr Val Ser Ser Ala Ser Thr Lys Gly Pro Ser Val Phe Pro
            210                 215                 220

Leu Ala Pro Ser Ser Lys Ser Thr Ser Gly Gly Thr Ala Ala Leu Gly
225                 230                 235                 240

Cys Leu Val Lys Asp Tyr Phe Pro Glu Pro Val Thr Val Ser Trp Asn
                245                 250                 255

Ser Gly Ala Leu Thr Ser Gly Val His Thr Phe Pro Ala Val Leu Gln
            260                 265                 270

Ser Ser Gly Leu Tyr Ser Leu Ser Ser Val Val Thr Val Pro Ser Ser
            275                 280                 285

Ser Leu Gly Thr Gln Thr Tyr Ile Cys Asn Val Asn His Lys Pro Ser
            290                 295                 300

Asn Thr Lys Val Asp Lys Lys Val Glu Pro Lys Ser Cys Asp Lys Thr
305                 310                 315                 320

His Thr Cys Pro Pro Cys Pro Ala Pro Val Ala Gly Pro Ser Val
                325                 330                 335

Phe Leu Phe Pro Pro Lys Pro Lys Asp Thr Leu Met Ile Ser Arg Thr
            340                 345                 350

Pro Glu Val Thr Cys Val Val Val Asp Val Ser His Glu Asp Pro Glu
            355                 360                 365

Val Lys Phe Asn Trp Tyr Val Asp Gly Val Glu Val His Asn Ala Lys
        370                 375                 380
```

-continued

```
Thr Lys Pro Arg Glu Glu Gln Tyr Asn Ser Thr Tyr Arg Val Val Ser
385                 390                 395                 400

Val Leu Thr Val Leu His Gln Asp Trp Leu Asn Gly Lys Glu Tyr Lys
            405                 410                 415

Cys Lys Val Ser Asn Lys Gly Leu Pro Ser Ser Ile Glu Lys Thr Ile
                420                 425                 430

Ser Lys Ala Lys Gly Gln Pro Arg Glu Pro Gln Val Tyr Thr Leu Pro
            435                 440                 445

Pro Ser Arg Asp Glu Leu Thr Lys Asn Gln Val Ser Leu Thr Cys Leu
        450                 455                 460

Val Lys Gly Phe Tyr Pro Ser Asp Ile Ala Val Glu Trp Glu Ser Asn
465                 470                 475                 480

Gly Gln Pro Glu Asn Asn Tyr Lys Thr Thr Pro Pro Val Leu Asp Ser
                485                 490                 495

Asp Gly Ser Phe Phe Leu Tyr Ser Lys Leu Thr Val Asp Lys Ser Arg
            500                 505                 510

Trp Gln Gln Gly Asn Val Phe Ser Cys Ser Val Met His Glu Ala Leu
        515                 520                 525

His Asn His Tyr Thr Gln Lys Ser Leu Ser Leu Ser Pro Gly Lys
    530                 535                 540

<210> SEQ ID NO 86
<211> LENGTH: 578
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Gly Gly Ser Gly Ala Lys Leu Ala Ala Leu Lys Ala Lys Leu
            100                 105                 110

Ala Ala Leu Lys Gly Gly Gly Gly Ser Asp Ser Trp Met Glu Glu Val
        115                 120                 125

Ile Lys Leu Cys Gly Arg Glu Leu Val Arg Ala Gln Ile Ala Ile Cys
    130                 135                 140

Gly Met Ser Thr Trp Ser Lys Arg Glu Ala Glu Asp Leu Gln Val Gly
145                 150                 155                 160

Gln Val Glu Leu Gly Gly Gly Pro Gly Ala Gly Ser Leu Gln Pro Leu
                165                 170                 175

Ala Leu Glu Gly Ser Leu Gln Lys Arg Arg Lys Lys Arg Gln Leu Tyr
            180                 185                 190

Ser Ala Leu Ala Asn Lys Cys Cys His Val Gly Cys Thr Lys Arg Ser
        195                 200                 205
```

Leu Ala Arg Phe Cys Gly Gly Gly Ser Glu Leu Ala Ala Leu Glu
    210                 215                 220

Ala Glu Leu Ala Ala Leu Glu Ala Gly Gly Ser Gly Asp Tyr Trp Gly
225                 230                 235                 240

Gln Gly Thr Leu Val Thr Val Ser Ser Ala Ser Thr Lys Gly Pro Ser
                245                 250                 255

Val Phe Pro Leu Ala Pro Ser Ser Lys Ser Thr Ser Gly Gly Thr Ala
            260                 265                 270

Ala Leu Gly Cys Leu Val Lys Asp Tyr Phe Pro Glu Pro Val Thr Val
        275                 280                 285

Ser Trp Asn Ser Gly Ala Leu Thr Ser Gly Val His Thr Phe Pro Ala
290                 295                 300

Val Leu Gln Ser Ser Gly Leu Tyr Ser Leu Ser Ser Val Val Thr Val
305                 310                 315                 320

Pro Ser Ser Ser Leu Gly Thr Gln Thr Tyr Ile Cys Asn Val Asn His
                325                 330                 335

Lys Pro Ser Asn Thr Lys Val Asp Lys Lys Val Glu Pro Lys Ser Cys
            340                 345                 350

Asp Lys Thr His Thr Cys Pro Pro Cys Pro Ala Pro Pro Val Ala Gly
        355                 360                 365

Pro Ser Val Phe Leu Phe Pro Pro Lys Pro Lys Asp Thr Leu Met Ile
370                 375                 380

Ser Arg Thr Pro Glu Val Thr Cys Val Val Val Asp Val Ser His Glu
385                 390                 395                 400

Asp Pro Glu Val Lys Phe Asn Trp Tyr Val Asp Gly Val Glu Val His
                405                 410                 415

Asn Ala Lys Thr Lys Pro Arg Glu Glu Gln Tyr Asn Ser Thr Tyr Arg
            420                 425                 430

Val Val Ser Val Leu Thr Val Leu His Gln Asp Trp Leu Asn Gly Lys
        435                 440                 445

Glu Tyr Lys Cys Lys Val Ser Asn Lys Gly Leu Pro Ser Ser Ile Glu
450                 455                 460

Lys Thr Ile Ser Lys Ala Lys Gly Gln Pro Arg Glu Pro Gln Val Tyr
465                 470                 475                 480

Thr Leu Pro Pro Ser Arg Asp Glu Leu Thr Lys Asn Gln Val Ser Leu
                485                 490                 495

Thr Cys Leu Val Lys Gly Phe Tyr Pro Ser Asp Ile Ala Val Glu Trp
            500                 505                 510

Glu Ser Asn Gly Gln Pro Glu Asn Asn Tyr Lys Thr Thr Pro Pro Val
        515                 520                 525

Leu Asp Ser Asp Gly Ser Phe Phe Leu Tyr Ser Lys Leu Thr Val Asp
530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly Lys

<210> SEQ ID NO 87
<211> LENGTH: 540
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Gly Gly Ser Gly Ala Lys Leu Ala Ala Leu Lys Ala Lys Leu Ala
            100                 105                 110

Ala Leu Lys Gly Gly Gly Gly Ser Leu Lys Cys Tyr Gln His Gly Lys
        115                 120                 125

Val Val Thr Cys His Arg Asp Met Lys Phe Cys Tyr His Asn Thr Gly
    130                 135                 140

Met Pro Phe Arg Asn Leu Lys Leu Ile Leu Gln Gly Cys Ser Ser Ser
145                 150                 155                 160

Cys Ser Glu Thr Glu Asn Asn Lys Cys Cys Ser Thr Asp Arg Cys Asn
                165                 170                 175

Lys Gly Gly Gly Gly Ser Glu Leu Ala Leu Glu Ala Glu Leu Ala
            180                 185                 190

Ala Leu Glu Ala Gly Gly Ser Gly Trp Gly Gln Gly Thr Leu Val Thr
        195                 200                 205

Val Ser Ser Ala Ser Thr Lys Gly Pro Ser Val Phe Pro Leu Ala Pro
    210                 215                 220

Ser Ser Lys Ser Thr Ser Gly Gly Thr Ala Ala Leu Gly Cys Leu Val
225                 230                 235                 240

Lys Asp Tyr Phe Pro Glu Pro Val Thr Val Ser Trp Asn Ser Gly Ala
                245                 250                 255

Leu Thr Ser Gly Val His Thr Phe Pro Ala Val Leu Gln Ser Ser Gly
            260                 265                 270

Leu Tyr Ser Leu Ser Ser Val Val Thr Val Pro Ser Ser Ser Leu Gly
        275                 280                 285

Thr Gln Thr Tyr Ile Cys Asn Val Asn His Lys Pro Ser Asn Thr Lys
    290                 295                 300

Val Asp Lys Lys Val Glu Pro Lys Ser Cys Asp Lys Thr His Thr Cys
305                 310                 315                 320

Pro Pro Cys Pro Ala Pro Val Ala Gly Pro Ser Val Phe Leu Phe
                325                 330                 335

Pro Pro Lys Pro Lys Asp Thr Leu Met Ile Ser Arg Thr Pro Glu Val
            340                 345                 350

Thr Cys Val Val Val Asp Val Ser His Glu Asp Pro Glu Val Lys Phe
        355                 360                 365

Asn Trp Tyr Val Asp Gly Val Glu Val His Asn Ala Lys Thr Lys Pro
    370                 375                 380

Arg Glu Glu Gln Tyr Asn Ser Thr Tyr Arg Val Val Ser Val Leu Thr
385                 390                 395                 400
```

Val Leu His Gln Asp Trp Leu Asn Gly Lys Glu Tyr Lys Cys Lys Val
                405                 410                 415

Ser Asn Lys Gly Leu Pro Ser Ser Ile Glu Lys Thr Ile Ser Lys Ala
            420                 425                 430

Lys Gly Gln Pro Arg Glu Pro Gln Val Tyr Thr Leu Pro Pro Ser Arg
435                 440                 445

Asp Glu Leu Thr Lys Asn Gln Val Ser Leu Thr Cys Leu Val Lys Gly
    450                 455                 460

Phe Tyr Pro Ser Asp Ile Ala Val Glu Trp Glu Ser Asn Gly Gln Pro
465                 470                 475                 480

Glu Asn Asn Tyr Lys Thr Thr Pro Pro Val Leu Asp Ser Asp Gly Ser
                485                 490                 495

Phe Phe Leu Tyr Ser Lys Leu Thr Val Asp Lys Ser Arg Trp Gln Gln
            500                 505                 510

Gly Asn Val Phe Ser Cys Ser Val Met His Glu Ala Leu His Asn His
        515                 520                 525

Tyr Thr Gln Lys Ser Leu Ser Leu Ser Pro Gly Lys
    530                 535                 540

<210> SEQ ID NO 88
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Gly Ser Gly Ala Lys Leu Ala Ala Leu Lys Ala
            100                 105                 110

Lys Leu Ala Ala Leu Lys Gly Gly Gly Gly Ser Leu Lys Cys Tyr Gln
        115                 120                 125

His Gly Lys Val Val Thr Cys His Arg Asp Met Lys Phe Cys Tyr His
    130                 135                 140

Asn Thr Gly Met Pro Phe Arg Asn Leu Lys Leu Ile Leu Gln Gly Cys
145                 150                 155                 160

Ser Ser Ser Cys Ser Glu Thr Glu Asn Asn Lys Cys Cys Ser Thr Asp
                165                 170                 175

Arg Cys Asn Lys Gly Gly Gly Gly Ser Glu Leu Ala Ala Leu Glu Ala
            180                 185                 190

Glu Leu Ala Ala Leu Glu Ala Gly Gly Ser Gly Tyr Phe Asp Val Trp
        195                 200                 205

Gly Ala Gly Thr Thr Val Thr Val Ser Ser Ala Ser Thr Lys Gly Pro
    210                 215                 220

```
Ser Val Phe Pro Leu Ala Pro Ser Ser Lys Ser Thr Ser Gly Gly Thr
225                 230                 235                 240

Ala Ala Leu Gly Cys Leu Val Lys Asp Tyr Phe Pro Glu Pro Val Thr
            245                 250                 255

Val Ser Trp Asn Ser Gly Ala Leu Thr Ser Gly Val His Thr Phe Pro
        260                 265                 270

Ala Val Leu Gln Ser Ser Gly Leu Tyr Ser Leu Ser Ser Val Val Thr
    275                 280                 285

Val Pro Ser Ser Ser Leu Gly Thr Gln Thr Tyr Ile Cys Asn Val Asn
290                 295                 300

His Lys Pro Ser Asn Thr Lys Val Asp Lys Val Glu Pro Lys Ser
305                 310                 315                 320

Cys Asp Lys Thr His Thr Cys Pro Pro Cys Pro Ala Pro Pro Val Ala
                325                 330                 335

Gly Pro Ser Val Phe Leu Phe Pro Pro Lys Pro Lys Asp Thr Leu Met
            340                 345                 350

Ile Ser Arg Thr Pro Glu Val Thr Cys Val Val Val Asp Val Ser His
        355                 360                 365

Glu Asp Pro Glu Val Lys Phe Asn Trp Tyr Val Asp Gly Val Glu Val
    370                 375                 380

His Asn Ala Lys Thr Lys Pro Arg Glu Glu Gln Tyr Asn Ser Thr Tyr
385                 390                 395                 400

Arg Val Val Ser Val Leu Thr Val Leu His Gln Asp Trp Leu Asn Gly
                405                 410                 415

Lys Glu Tyr Lys Cys Lys Val Ser Asn Lys Gly Leu Pro Ser Ser Ile
            420                 425                 430

Glu Lys Thr Ile Ser Lys Ala Lys Gly Gln Pro Arg Glu Pro Gln Val
        435                 440                 445

Tyr Thr Leu Pro Pro Ser Arg Asp Glu Leu Thr Lys Asn Gln Val Ser
    450                 455                 460

Leu Thr Cys Leu Val Lys Gly Phe Tyr Pro Ser Asp Ile Ala Val Glu
465                 470                 475                 480

Trp Glu Ser Asn Gly Gln Pro Glu Asn Asn Tyr Lys Thr Thr Pro Pro
                485                 490                 495

Val Leu Asp Ser Asp Gly Ser Phe Phe Leu Tyr Ser Lys Leu Thr Val
            500                 505                 510

Asp Lys Ser Arg Trp Gln Gln Gly Asn Val Phe Ser Cys Ser Val Met
        515                 520                 525

His Glu Ala Leu His Asn His Tyr Thr Gln Lys Ser Leu Ser Leu Ser
    530                 535                 540

Pro Gly Lys
545

<210> SEQ ID NO 89
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
```

```
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Gly Gly Ser Gly Ala Lys Leu Ala Ala Leu Lys Ala Lys Leu
            100                 105                 110
Ala Ala Leu Lys Gly Gly Gly Ser Asp Ser Trp Met Glu Glu Val
            115                 120                 125
Ile Lys Leu Cys Gly Arg Glu Leu Val Arg Ala Gln Ile Ala Ile Cys
            130                 135                 140
Gly Met Ser Thr Trp Ser Lys Arg Ser Leu Ser Gln Glu Ile Glu Gly
145                 150                 155                 160
Arg Lys Lys Arg Gln Leu Tyr Ser Ala Leu Ala Asn Lys Cys Cys His
                165                 170                 175
Val Gly Cys Thr Lys Arg Ser Leu Ala Arg Phe Cys Gly Gly Gly
            180                 185                 190
Ser Glu Leu Ala Ala Leu Glu Ala Glu Leu Ala Ala Leu Glu Ala Gly
            195                 200                 205
Gly Ser Gly Asp Tyr Trp Gly Gln Gly Thr Leu Val Thr Val Ser Ser
            210                 215                 220
Ala Ser Thr Lys Gly Pro Ser Val Phe Pro Leu Ala Pro Ser Ser Lys
225                 230                 235                 240
Ser Thr Ser Gly Gly Thr Ala Ala Leu Gly Cys Leu Val Lys Asp Tyr
                245                 250                 255
Phe Pro Glu Pro Val Thr Val Ser Trp Asn Ser Gly Ala Leu Thr Ser
            260                 265                 270
Gly Val His Thr Phe Pro Ala Val Leu Gln Ser Ser Gly Leu Tyr Ser
            275                 280                 285
Leu Ser Ser Val Val Thr Val Pro Ser Ser Ser Leu Gly Thr Gln Thr
            290                 295                 300
Tyr Ile Cys Asn Val Asn His Lys Pro Ser Asn Thr Lys Val Asp Lys
305                 310                 315                 320
Lys Val Glu Pro Lys Ser Cys Asp Lys Thr His Thr Cys Pro Pro Cys
                325                 330                 335
Pro Ala Pro Pro Val Ala Gly Pro Ser Val Phe Leu Phe Pro Pro Lys
            340                 345                 350
Pro Lys Asp Thr Leu Met Ile Ser Arg Thr Pro Glu Val Thr Cys Val
            355                 360                 365
Val Val Asp Val Ser His Glu Asp Pro Glu Val Lys Phe Asn Trp Tyr
            370                 375                 380
Val Asp Gly Val Glu Val His Asn Ala Lys Thr Lys Pro Arg Glu Glu
385                 390                 395                 400
Gln Tyr Asn Ser Thr Tyr Arg Val Val Ser Val Leu Thr Val Leu His
                405                 410                 415
Gln Asp Trp Leu Asn Gly Lys Glu Tyr Lys Cys Lys Val Ser Asn Lys
            420                 425                 430
Gly Leu Pro Ser Ser Ile Glu Lys Thr Ile Ser Lys Ala Lys Gly Gln
            435                 440                 445
```

```
Pro Arg Glu Pro Gln Val Tyr Thr Leu Pro Pro Ser Arg Asp Glu Leu
        450                 455                 460

Thr Lys Asn Gln Val Ser Leu Thr Cys Leu Val Lys Gly Phe Tyr Pro
465                 470                 475                 480

Ser Asp Ile Ala Val Glu Trp Glu Ser Asn Gly Gln Pro Glu Asn Asn
                485                 490                 495

Tyr Lys Thr Thr Pro Pro Val Leu Asp Ser Asp Gly Ser Phe Phe Leu
            500                 505                 510

Tyr Ser Lys Leu Thr Val Asp Lys Ser Arg Trp Gln Gln Gly Asn Val
        515                 520                 525

Phe Ser Cys Ser Val Met His Glu Ala Leu His Asn His Tyr Thr Gln
    530                 535                 540

Lys Ser Leu Ser Leu Ser Pro Gly Lys
545                 550

<210> SEQ ID NO 90
<211> LENGTH: 562
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110

Ala Ala Leu Lys Gly Gly Gly Ser Asp Ser Trp Met Glu Glu Val
        115                 120                 125

Ile Lys Leu Cys Gly Arg Glu Leu Val Arg Ala Gln Ile Ala Ile Cys
    130                 135                 140

Gly Met Ser Thr Trp Ser Lys Arg Ser Leu Ser Gln Glu Asp Ala Pro
145                 150                 155                 160

Gln Thr Pro Arg Pro Val Ile Glu Gly Arg Lys Lys Arg Gln Leu Tyr
                165                 170                 175

Ser Ala Leu Ala Asn Lys Cys Cys His Val Gly Cys Thr Lys Arg Ser
            180                 185                 190

Leu Ala Arg Phe Cys Gly Gly Gly Ser Glu Leu Ala Ala Leu Glu
        195                 200                 205

Ala Glu Leu Ala Ala Leu Glu Ala Gly Gly Ser Gly Asp Tyr Trp Gly
    210                 215                 220

Gln Gly Thr Leu Val Thr Val Ser Ser Ala Ser Thr Lys Gly Pro Ser
225                 230                 235                 240

Val Phe Pro Leu Ala Pro Ser Ser Lys Ser Thr Ser Gly Gly Thr Ala
```

```
                    245                 250                 255

Ala Leu Gly Cys Leu Val Lys Asp Tyr Phe Pro Glu Pro Val Thr Val
                260                 265                 270

Ser Trp Asn Ser Gly Ala Leu Thr Ser Gly Val His Thr Phe Pro Ala
            275                 280                 285

Val Leu Gln Ser Ser Gly Leu Tyr Ser Leu Ser Ser Val Val Thr Val
        290                 295                 300

Pro Ser Ser Ser Leu Gly Thr Gln Thr Tyr Ile Cys Asn Val Asn His
305                 310                 315                 320

Lys Pro Ser Asn Thr Lys Val Asp Lys Val Glu Pro Lys Ser Cys
                325                 330                 335

Asp Lys Thr His Thr Cys Pro Pro Cys Pro Ala Pro Val Ala Gly
            340                 345                 350

Pro Ser Val Phe Leu Phe Pro Pro Lys Pro Lys Asp Thr Leu Met Ile
        355                 360                 365

Ser Arg Thr Pro Glu Val Thr Cys Val Val Val Asp Val Ser His Glu
370                 375                 380

Asp Pro Glu Val Lys Phe Asn Trp Tyr Val Asp Gly Val Glu Val His
385                 390                 395                 400

Asn Ala Lys Thr Lys Pro Arg Glu Glu Gln Tyr Asn Ser Thr Tyr Arg
                405                 410                 415

Val Val Ser Val Leu Thr Val Leu His Gln Asp Trp Leu Asn Gly Lys
            420                 425                 430

Glu Tyr Lys Cys Lys Val Ser Asn Lys Gly Leu Pro Ser Ser Ile Glu
        435                 440                 445

Lys Thr Ile Ser Lys Ala Lys Gly Gln Pro Arg Glu Pro Gln Val Tyr
450                 455                 460

Thr Leu Pro Pro Ser Arg Asp Glu Leu Thr Lys Asn Gln Val Ser Leu
465                 470                 475                 480

Thr Cys Leu Val Lys Gly Phe Tyr Pro Ser Asp Ile Ala Val Glu Trp
                485                 490                 495

Glu Ser Asn Gly Gln Pro Glu Asn Asn Tyr Lys Thr Thr Pro Pro Val
            500                 505                 510

Leu Asp Ser Asp Gly Ser Phe Phe Leu Tyr Ser Lys Leu Thr Val Asp
        515                 520                 525

Lys Ser Arg Trp Gln Gln Gly Asn Val Phe Ser Cys Ser Val Met His
    530                 535                 540

Glu Ala Leu His Asn His Tyr Thr Gln Lys Ser Leu Ser Leu Ser Pro
545                 550                 555                 560

Gly Lys

<210> SEQ ID NO 91
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

```
                  35                  40                  45
Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Gly Gly Ser Gly Ala Lys Leu Ala Ala Leu Lys Ala Lys Leu
                100                 105                 110

Ala Ala Leu Lys Cys Gly Gly Gly Ser Ile Glu Gly Arg His Ser
                115                 120                 125

Gln Gly Thr Phe Thr Ser Asp Tyr Ser Lys Tyr Leu Asp Ser Lys Ala
                130                 135                 140

Ala His Asp Phe Val Glu Trp Leu Leu Asn Gly Gly Pro Ser Ser Gly
145                 150                 155                 160

Ala Pro Pro Ser Gly Gly Gly Ser Cys Glu Leu Ala Ala Leu
                165                 170                 175

Glu Ala Glu Leu Ala Ala Leu Glu Ala Gly Gly Ser Gly Asp Tyr Trp
                180                 185                 190

Gly Gln Gly Thr Leu Val Thr Val Ser Ser Ala Ser Thr Lys Gly Pro
                195                 200                 205

Ser Val Phe Pro Leu Ala Pro Ser Ser Lys Ser Thr Ser Gly Gly Thr
210                 215                 220

Ala Ala Leu Gly Cys Leu Val Lys Asp Tyr Phe Pro Glu Pro Val Thr
225                 230                 235                 240

Val Ser Trp Asn Ser Gly Ala Leu Thr Ser Gly Val His Thr Phe Pro
                245                 250                 255

Ala Val Leu Gln Ser Ser Gly Leu Tyr Ser Leu Ser Ser Val Val Thr
                260                 265                 270

Val Pro Ser Ser Ser Leu Gly Thr Gln Thr Tyr Ile Cys Asn Val Asn
                275                 280                 285

His Lys Pro Ser Asn Thr Lys Val Asp Lys Val Glu Pro Lys Ser
                290                 295                 300

Cys Asp Lys Thr His Thr Cys Pro Pro Cys Pro Ala Pro Pro Val Ala
305                 310                 315                 320

Gly Pro Ser Val Phe Leu Phe Pro Pro Lys Pro Lys Asp Thr Leu Met
                325                 330                 335

Ile Ser Arg Thr Pro Glu Val Thr Cys Val Val Val Asp Val Ser His
                340                 345                 350

Glu Asp Pro Glu Val Lys Phe Asn Trp Tyr Val Asp Gly Val Glu Val
                355                 360                 365

His Asn Ala Lys Thr Lys Pro Arg Glu Glu Gln Tyr Asn Ser Thr Tyr
                370                 375                 380

Arg Val Val Ser Val Leu Thr Val Leu His Gln Asp Trp Leu Asn Gly
385                 390                 395                 400

Lys Glu Tyr Lys Cys Lys Val Ser Asn Lys Gly Leu Pro Ser Ser Ile
                405                 410                 415

Glu Lys Thr Ile Ser Lys Ala Lys Gly Gln Pro Arg Glu Pro Gln Val
                420                 425                 430

Tyr Thr Leu Pro Pro Ser Arg Asp Glu Leu Thr Lys Asn Gln Val Ser
                435                 440                 445

Leu Thr Cys Leu Val Lys Gly Phe Tyr Pro Ser Asp Ile Ala Val Glu
                450                 455                 460
```

```
Trp Glu Ser Asn Gly Gln Pro Glu Asn Asn Tyr Lys Thr Thr Pro Pro
465                 470                 475                 480

Val Leu Asp Ser Asp Gly Ser Phe Phe Leu Tyr Ser Lys Leu Thr Val
                485                 490                 495

Asp Lys Ser Arg Trp Gln Gln Gly Asn Val Phe Ser Cys Ser Val Met
            500                 505                 510

His Glu Ala Leu His Asn His Tyr Thr Gln Lys Ser Leu Ser Leu Ser
        515                 520                 525

Pro Gly Lys
    530

<210> SEQ ID NO 92
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110

Ala Ala Leu Lys Cys Gly Gly Gly Gly Ser Ile Glu Gly Arg His Gly
        115                 120                 125

Gln Gly Thr Phe Thr Ser Asp Tyr Ser Lys Tyr Leu Asp Ser Lys Ala
    130                 135                 140

Ala His Asp Phe Val Glu Trp Leu Leu Asn Gly Gly Pro Ser Ser Gly
145                 150                 155                 160

Ala Pro Pro Pro Ser Gly Gly Gly Gly Ser Cys Glu Leu Ala Ala Leu
                165                 170                 175

Glu Ala Glu Leu Ala Ala Leu Glu Ala Gly Gly Ser Gly Asp Tyr Trp
            180                 185                 190

Gly Gln Gly Thr Leu Val Thr Val Ser Ser Ala Ser Thr Lys Gly Pro
        195                 200                 205

Ser Val Phe Pro Leu Ala Pro Ser Ser Lys Ser Thr Ser Gly Gly Thr
    210                 215                 220

Ala Ala Leu Gly Cys Leu Val Lys Asp Tyr Phe Pro Glu Pro Val Thr
225                 230                 235                 240

Val Ser Trp Asn Ser Gly Ala Leu Thr Ser Gly Val His Thr Phe Pro
                245                 250                 255

Ala Val Leu Gln Ser Ser Gly Leu Tyr Ser Leu Ser Ser Val Val Thr
            260                 265                 270

Val Pro Ser Ser Ser Leu Gly Thr Gln Thr Tyr Ile Cys Asn Val Asn
```

```
                275                 280                 285
His Lys Pro Ser Asn Thr Lys Val Asp Lys Val Glu Pro Lys Ser
    290                 295                 300

Cys Asp Lys Thr His Thr Cys Pro Pro Cys Pro Ala Pro Pro Val Ala
305                 310                 315                 320

Gly Pro Ser Val Phe Leu Phe Pro Pro Lys Pro Lys Asp Thr Leu Met
                325                 330                 335

Ile Ser Arg Thr Pro Glu Val Thr Cys Val Val Val Asp Val Ser His
            340                 345                 350

Glu Asp Pro Glu Val Lys Phe Asn Trp Tyr Val Asp Gly Val Glu Val
                355                 360                 365

His Asn Ala Lys Thr Lys Pro Arg Glu Glu Gln Tyr Asn Ser Thr Tyr
    370                 375                 380

Arg Val Val Ser Val Leu Thr Val Leu His Gln Asp Trp Leu Asn Gly
385                 390                 395                 400

Lys Glu Tyr Lys Cys Lys Val Ser Asn Lys Gly Leu Pro Ser Ser Ile
                405                 410                 415

Glu Lys Thr Ile Ser Lys Ala Lys Gly Gln Pro Arg Glu Pro Gln Val
            420                 425                 430

Tyr Thr Leu Pro Pro Ser Arg Asp Glu Leu Thr Lys Asn Gln Val Ser
                435                 440                 445

Leu Thr Cys Leu Val Lys Gly Phe Tyr Pro Ser Asp Ile Ala Val Glu
    450                 455                 460

Trp Glu Ser Asn Gly Gln Pro Glu Asn Asn Tyr Lys Thr Thr Pro Pro
465                 470                 475                 480

Val Leu Asp Ser Asp Gly Ser Phe Phe Leu Tyr Ser Lys Leu Thr Val
                485                 490                 495

Asp Lys Ser Arg Trp Gln Gln Gly Asn Val Phe Ser Cys Ser Val Met
            500                 505                 510

His Glu Ala Leu His Asn His Tyr Thr Gln Lys Ser Leu Ser Leu Ser
    515                 520                 525

Pro Gly Lys
    530

<210> SEQ ID NO 93
<211> LENGTH: 650
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ser Arg Gly Gly Ser Gly Ala Lys Leu Ala Ala Leu Lys Ala Lys Leu
            100                 105                 110

Ala Ala Leu Lys Gly Gly Gly Ser Ala Pro Pro Arg Leu Ile Cys
        115                 120                 125

Asp Ser Arg Val Leu Glu Arg Tyr Leu Leu Glu Ala Lys Glu Ala Glu
        130                 135                 140

Asn Ile Thr Thr Gly Cys Ala Glu His Cys Ser Leu Asn Glu Asn Ile
145                 150                 155                 160

Thr Val Pro Asp Thr Lys Val Asn Phe Tyr Ala Trp Lys Arg Met Glu
                165                 170                 175

Val Gly Gln Gln Ala Val Glu Val Trp Gln Gly Leu Ala Leu Leu Ser
            180                 185                 190

Glu Ala Val Leu Arg Gly Gln Ala Leu Leu Val Asn Ser Ser Gln Pro
            195                 200                 205

Trp Glu Pro Leu Gln Leu His Val Asp Lys Ala Val Ser Gly Leu Arg
        210                 215                 220

Ser Leu Thr Thr Leu Leu Arg Ala Leu Gly Ala Gln Lys Glu Ala Ile
225                 230                 235                 240

Ser Pro Pro Asp Ala Ala Ser Ala Ala Pro Leu Arg Thr Ile Thr Ala
                245                 250                 255

Asp Thr Phe Arg Lys Leu Phe Arg Val Tyr Ser Asn Phe Leu Arg Gly
            260                 265                 270

Lys Leu Lys Leu Tyr Thr Gly Glu Ala Cys Arg Thr Gly Asp Arg Gly
            275                 280                 285

Gly Gly Gly Ser Glu Leu Ala Ala Leu Glu Ala Glu Leu Ala Ala Leu
        290                 295                 300

Glu Ala Gly Gly Ser Gly Asp Tyr Trp Gly Gln Gly Thr Leu Val Thr
305                 310                 315                 320

Val Ser Ser Ala Ser Thr Lys Gly Pro Ser Val Phe Pro Leu Ala Pro
                325                 330                 335

Cys Ser Arg Ser Thr Ser Glu Ser Thr Ala Ala Leu Gly Cys Leu Val
            340                 345                 350

Lys Asp Tyr Phe Pro Glu Pro Val Thr Val Ser Trp Asn Ser Gly Ala
            355                 360                 365

Leu Thr Ser Gly Val His Thr Phe Pro Ala Val Leu Gln Ser Ser Gly
370                 375                 380

Leu Tyr Ser Leu Ser Ser Val Val Thr Val Pro Ser Ser Ser Leu Gly
385                 390                 395                 400

Thr Lys Thr Tyr Thr Cys Asn Val Asp His Lys Pro Ser Asn Thr Lys
                405                 410                 415

Val Asp Lys Arg Val Glu Ser Lys Tyr Gly Pro Pro Cys Pro Pro Cys
            420                 425                 430

Pro Ala Pro Glu Ala Ala Gly Gly Pro Ser Val Phe Leu Phe Pro Pro
        435                 440                 445

Lys Pro Lys Asp Thr Leu Met Ile Ser Arg Thr Pro Glu Val Thr Cys
450                 455                 460

Val Val Val Asp Val Ser Gln Glu Asp Pro Glu Val Gln Phe Asn Trp
465                 470                 475                 480

Tyr Val Asp Gly Val Glu Val His Asn Ala Lys Thr Lys Pro Arg Glu
                485                 490                 495

Glu Gln Phe Asn Ser Thr Tyr Arg Val Val Ser Val Leu Thr Val Leu
            500                 505                 510

His Gln Asp Trp Leu Asn Gly Lys Glu Tyr Lys Cys Lys Val Ser Asn
```

```
                    515                 520                 525
Lys Gly Leu Pro Ser Ser Ile Glu Lys Thr Ile Ser Lys Ala Lys Gly
            530                 535                 540

Gln Pro Arg Glu Pro Gln Val Tyr Thr Leu Pro Pro Ser Gln Glu Glu
545                 550                 555                 560

Met Thr Lys Asn Gln Val Ser Leu Thr Cys Leu Val Lys Gly Phe Tyr
                565                 570                 575

Pro Ser Asp Ile Ala Val Glu Trp Glu Ser Asn Gly Gln Pro Glu Asn
            580                 585                 590

Asn Tyr Lys Thr Thr Pro Pro Val Leu Asp Ser Asp Gly Ser Phe Phe
        595                 600                 605

Leu Tyr Ser Arg Leu Thr Val Asp Lys Ser Arg Trp Gln Glu Gly Asn
        610                 615                 620

Val Phe Ser Cys Ser Val Met His Glu Ala Leu His Asn His Tyr Thr
625                 630                 635                 640

Gln Lys Ser Leu Ser Leu Ser Leu Gly Lys
                645                 650

<210> SEQ ID NO 94
<211> LENGTH: 431
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Gly Ser Gly
                85                  90                  95

Ala Lys Leu Ala Ala Leu Lys Ala Lys Leu Ala Ala Leu Lys Gly Gly
            100                 105                 110

Gly Gly Ser Thr Pro Leu Gly Pro Ala Ser Ser Leu Pro Gln Ser Phe
        115                 120                 125

Leu Leu Lys Cys Leu Glu Gln Val Arg Lys Ile Gln Gly Asp Gly Ala
    130                 135                 140

Ala Leu Gln Glu Lys Leu Cys Ala Thr Tyr Lys Leu Cys His Pro Glu
145                 150                 155                 160

Glu Leu Val Leu Leu Gly His Ser Leu Gly Ile Pro Trp Ala Pro Leu
                165                 170                 175

Ser Ser Cys Pro Ser Gln Ala Leu Gln Leu Ala Gly Cys Leu Ser Gln
            180                 185                 190

Leu His Ser Gly Leu Phe Leu Tyr Gln Gly Leu Leu Gln Ala Leu Glu
        195                 200                 205

Gly Ile Ser Pro Glu Leu Gly Pro Thr Leu Asp Thr Leu Gln Leu Asp
    210                 215                 220
```

```
Val Ala Asp Phe Ala Thr Thr Ile Trp Gln Gln Met Glu Glu Leu Gly
225                 230                 235                 240

Met Ala Pro Ala Leu Gln Pro Thr Gln Gly Ala Met Pro Ala Phe Ala
                245                 250                 255

Ser Ala Phe Gln Arg Arg Ala Gly Gly Val Leu Val Ala Ser His Leu
            260                 265                 270

Gln Ser Phe Leu Glu Val Ser Tyr Arg Val Leu Arg His Leu Ala Gln
        275                 280                 285

Pro Gly Gly Gly Gly Ser Glu Leu Ala Ala Leu Glu Ala Glu Leu Ala
    290                 295                 300

Ala Leu Glu Ala Gly Gly Ser Gly Pro Thr Phe Gly Gln Gly Thr Lys
305                 310                 315                 320

Leu Glu Ile Lys Arg Thr Val Ala Ala Pro Ser Val Phe Ile Phe Pro
                325                 330                 335

Pro Ser Asp Glu Gln Leu Lys Ser Gly Thr Ala Ser Val Val Cys Leu
            340                 345                 350

Leu Asn Asn Phe Tyr Pro Arg Glu Ala Lys Val Gln Trp Lys Val Asp
        355                 360                 365

Asn Ala Leu Gln Ser Gly Asn Ser Gln Glu Ser Val Thr Glu Gln Asp
370                 375                 380

Ser Lys Asp Ser Thr Tyr Ser Leu Ser Ser Thr Leu Thr Leu Ser Lys
385                 390                 395                 400

Ala Asp Tyr Glu Lys His Lys Val Tyr Ala Cys Glu Val Thr His Gln
                405                 410                 415

Gly Leu Ser Ser Pro Val Thr Lys Ser Phe Asn Arg Gly Glu Cys
            420                 425                 430

<210> SEQ ID NO 95
<211> LENGTH: 532
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110

Ala Ala Leu Lys Gly Gly Gly Ser Ala Asp Asn Lys Cys Glu Asn
        115                 120                 125

Ser Leu Arg Arg Glu Ile Ala Cys Gly Gln Cys Arg Asp Lys Val Lys
    130                 135                 140

Thr Asp Gly Tyr Phe Tyr Glu Cys Cys Thr Ser Asp Ser Thr Phe Lys
145                 150                 155                 160
```

Lys Cys Gln Asp Leu Leu His Gly Gly Gly Ser Glu Leu Ala Ala
                165                 170                 175

Leu Glu Ala Glu Leu Ala Ala Leu Glu Ala Gly Gly Ser Gly Asp Tyr
                180                 185                 190

Trp Gly Gln Gly Thr Leu Val Thr Val Ser Ala Ser Thr Lys Gly
                195                 200                 205

Pro Ser Val Phe Pro Leu Ala Pro Ser Ser Lys Ser Thr Ser Gly Gly
210                 215                 220

Thr Ala Ala Leu Gly Cys Leu Val Lys Asp Tyr Phe Pro Glu Pro Val
225                 230                 235                 240

Thr Val Ser Trp Asn Ser Gly Ala Leu Thr Ser Gly Val His Thr Phe
                245                 250                 255

Pro Ala Val Leu Gln Ser Ser Gly Leu Tyr Ser Leu Ser Ser Val Val
                260                 265                 270

Thr Val Pro Ser Ser Ser Leu Gly Thr Gln Thr Tyr Ile Cys Asn Val
                275                 280                 285

Asn His Lys Pro Ser Asn Thr Lys Val Asp Lys Lys Val Glu Pro Lys
        290                 295                 300

Ser Cys Asp Lys Thr His Thr Cys Pro Pro Cys Pro Ala Pro Pro Val
305                 310                 315                 320

Ala Gly Pro Ser Val Phe Leu Phe Pro Pro Lys Pro Lys Asp Thr Leu
                325                 330                 335

Met Ile Ser Arg Thr Pro Glu Val Thr Cys Val Val Val Asp Val Ser
                340                 345                 350

His Glu Asp Pro Glu Val Lys Phe Asn Trp Tyr Val Asp Gly Val Glu
                355                 360                 365

Val His Asn Ala Lys Thr Lys Pro Arg Glu Glu Gln Tyr Asn Ser Thr
        370                 375                 380

Tyr Arg Val Val Ser Val Leu Thr Val Leu His Gln Asp Trp Leu Asn
385                 390                 395                 400

Gly Lys Glu Tyr Lys Cys Lys Val Ser Asn Lys Gly Leu Pro Ser Ser
                405                 410                 415

Ile Glu Lys Thr Ile Ser Lys Ala Lys Gly Gln Pro Arg Glu Pro Gln
                420                 425                 430

Val Tyr Thr Leu Pro Pro Ser Arg Asp Glu Leu Thr Lys Asn Gln Val
                435                 440                 445

Ser Leu Thr Cys Leu Val Lys Gly Phe Tyr Pro Ser Asp Ile Ala Val
        450                 455                 460

Glu Trp Glu Ser Asn Gly Gln Pro Glu Asn Asn Tyr Lys Thr Thr Pro
465                 470                 475                 480

Pro Val Leu Asp Ser Asp Gly Ser Phe Phe Leu Tyr Ser Lys Leu Thr
                485                 490                 495

Val Asp Lys Ser Arg Trp Gln Gln Gly Asn Val Phe Ser Cys Ser Val
                500                 505                 510

Met His Glu Ala Leu His Asn His Tyr Thr Gln Lys Ser Leu Ser Leu
                515                 520                 525

Ser Pro Gly Lys
        530

<210> SEQ ID NO 96
<211> LENGTH: 536
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110

Ala Ala Leu Lys Cys Gly Gly Gly Gly Ser Ile Glu Gly Arg His Gly
        115                 120                 125

Asp Gly Ser Phe Ser Asp Glu Met Asn Thr Ile Leu Asp Asn Leu Ala
    130                 135                 140

Ala Arg Asp Phe Ile Asn Trp Leu Ile Gln Thr Lys Ile Thr Asp Gly
145                 150                 155                 160

Gly Pro Ser Ser Gly Ala Pro Pro Ser Gly Gly Gly Ser Cys
                165                 170                 175

Glu Leu Ala Ala Leu Glu Ala Glu Leu Ala Ala Leu Glu Ala Gly Gly
            180                 185                 190

Ser Gly Asp Tyr Trp Gly Gln Gly Thr Leu Val Thr Val Ser Ser Ala
        195                 200                 205

Ser Thr Lys Gly Pro Ser Val Phe Pro Leu Ala Pro Ser Ser Lys Ser
    210                 215                 220

Thr Ser Gly Gly Thr Ala Ala Leu Gly Cys Leu Val Lys Asp Tyr Phe
225                 230                 235                 240

Pro Glu Pro Val Thr Val Ser Trp Asn Ser Gly Ala Leu Thr Ser Gly
                245                 250                 255

Val His Thr Phe Pro Ala Val Leu Gln Ser Ser Gly Leu Tyr Ser Leu
            260                 265                 270

Ser Ser Val Val Thr Val Pro Ser Ser Ser Leu Gly Thr Gln Thr Tyr
        275                 280                 285

Ile Cys Asn Val Asn His Lys Pro Ser Asn Thr Lys Val Asp Lys Lys
    290                 295                 300

Val Glu Pro Lys Ser Cys Asp Lys Thr His Thr Cys Pro Pro Cys Pro
305                 310                 315                 320

Ala Pro Pro Val Ala Gly Pro Ser Val Phe Leu Phe Pro Pro Lys Pro
                325                 330                 335

Lys Asp Thr Leu Met Ile Ser Arg Thr Pro Glu Val Thr Cys Val Val
            340                 345                 350

Val Asp Val Ser His Glu Asp Pro Glu Val Lys Phe Asn Trp Tyr Val
        355                 360                 365

Asp Gly Val Glu Val His Asn Ala Lys Thr Lys Pro Arg Glu Glu Gln
    370                 375                 380

Tyr Asn Ser Thr Tyr Arg Val Val Ser Val Leu Thr Val Leu His Gln
385                 390                 395                 400

```
Asp Trp Leu Asn Gly Lys Glu Tyr Lys Cys Lys Val Ser Asn Lys Gly
            405                 410                 415

Leu Pro Ser Ser Ile Glu Lys Thr Ile Ser Lys Ala Lys Gly Gln Pro
        420                 425                 430

Arg Glu Pro Gln Val Tyr Thr Leu Pro Pro Ser Arg Asp Glu Leu Thr
    435                 440                 445

Lys Asn Gln Val Ser Leu Thr Cys Leu Val Lys Gly Phe Tyr Pro Ser
450                 455                 460

Asp Ile Ala Val Glu Trp Glu Ser Asn Gly Gln Pro Glu Asn Asn Tyr
465                 470                 475                 480

Lys Thr Thr Pro Pro Val Leu Asp Ser Asp Gly Ser Phe Phe Leu Tyr
                485                 490                 495

Ser Lys Leu Thr Val Asp Lys Ser Arg Trp Gln Gln Gly Asn Val Phe
            500                 505                 510

Ser Cys Ser Val Met His Glu Ala Leu His Asn His Tyr Thr Gln Lys
        515                 520                 525

Ser Leu Ser Leu Ser Pro Gly Lys
    530                 535

<210> SEQ ID NO 97
<211> LENGTH: 663
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Ser Gly Ala Lys Leu Ala Ala Leu Lys Ala Lys Leu
            100                 105                 110

Ala Ala Leu Lys Gly Gly Gly Gly Ser Ala Pro Leu Gly Gly Pro Glu
        115                 120                 125

Pro Ala Gln Tyr Glu Glu Leu Thr Leu Leu Phe His Gly Ala Leu Gln
    130                 135                 140

Leu Gly Gln Ala Leu Asn Gly Val Tyr Arg Ala Thr Glu Ala Arg Leu
145                 150                 155                 160

Thr Glu Ala Gly His Ser Leu Gly Leu Tyr Asp Arg Ala Leu Glu Phe
                165                 170                 175

Leu Gly Thr Glu Val Arg Gln Gly Gln Asp Ala Thr Gln Glu Leu Arg
            180                 185                 190

Thr Ser Leu Ser Glu Ile Gln Val Glu Asp Ala Leu His Leu Arg
        195                 200                 205

Ala Glu Ala Thr Ala Arg Ser Leu Gly Glu Val Ala Arg Ala Gln Gln
```

-continued

```
            210                 215                 220
Ala Leu Arg Asp Thr Val Arg Arg Leu Gln Val Gln Leu Arg Gly Ala
225                 230                 235                 240

Trp Leu Gly Gln Ala His Gln Glu Phe Glu Thr Leu Lys Ala Arg Ala
                245                 250                 255

Asp Lys Gln Ser His Leu Leu Trp Ala Leu Thr Gly His Val Gln Arg
            260                 265                 270

Gln Gln Arg Glu Met Ala Glu Gln Gln Trp Leu Arg Gln Ile Gln
        275                 280                 285

Gln Arg Leu His Thr Ala Ala Leu Pro Ala Gly Gly Gly Ser Glu
    290                 295                 300

Leu Ala Ala Leu Glu Ala Glu Leu Ala Ala Leu Glu Ala Gly Gly Ser
305                 310                 315                 320

Gly Asp Tyr Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
                340                 345                 350

Ser Gly Gly Thr Ala Ala Leu Gly Cys Leu Val Lys Asp Tyr Phe Pro
            355                 360                 365

Glu Pro Val Thr Val Ser Trp Asn Ser Gly Ala Leu Thr Ser Gly Val
        370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
                405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
        435                 440                 445

Pro Pro Val Ala Gly Pro Ser Val Phe Leu Phe Pro Pro Lys Pro Lys
    450                 455                 460

Asp Thr Leu Met Ile Ser Arg Thr Pro Glu Val Thr Cys Val Val Val
465                 470                 475                 480

Asp Val Ser His Glu Asp Pro Glu Val Lys Phe Asn Trp Tyr Val Asp
                485                 490                 495

Gly Val Glu Val His Asn Ala Lys Thr Lys Pro Arg Glu Glu Gln Tyr
            500                 505                 510

Asn Ser Thr Tyr Arg Val Val Ser Val Leu Thr Val Leu His Gln Asp
        515                 520                 525

Trp Leu Asn Gly Lys Glu Tyr Lys Cys Lys Val Ser Asn Lys Gly Leu
    530                 535                 540

Pro Ser Ser Ile Glu Lys Thr Ile Ser Lys Ala Lys Gly Gln Pro Arg
545                 550                 555                 560

Glu Pro Gln Val Tyr Thr Leu Pro Pro Ser Arg Asp Glu Leu Thr Lys
                565                 570                 575

Asn Gln Val Ser Leu Thr Cys Leu Val Lys Gly Phe Tyr Pro Ser Asp
            580                 585                 590

Ile Ala Val Glu Trp Glu Ser Asn Gly Gln Pro Glu Asn Asn Tyr Lys
        595                 600                 605

Thr Thr Pro Pro Val Leu Asp Ser Asp Gly Ser Phe Phe Leu Tyr Ser
    610                 615                 620

Lys Leu Thr Val Asp Lys Ser Arg Trp Gln Gln Gly Asn Val Phe Ser
625                 630                 635                 640
```

```
Cys Ser Val Met His Glu Ala Leu His Asn His Tyr Thr Gln Lys Ser
            645                 650                 655

Leu Ser Leu Ser Pro Gly Lys
            660

<210> SEQ ID NO 98
<211> LENGTH: 302
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Gly Ser Gly Ala
            20                  25                  30

Lys Leu Ala Ala Leu Lys Ala Lys Leu Ala Ala Leu Lys Cys Gly Gly
        35                  40                  45

Gly Gly Ser Ile Glu Gly Arg His Gly Glu Gly Thr Phe Thr Ser Asp
    50                  55                  60

Leu Ser Lys Gln Met Glu Glu Ala Val Arg Leu Phe Ile Glu Trp
65                  70                  75                  80

Leu Lys Asn Gly Gly Pro Ser Ser Gly Ala Pro Pro Ser Gly Gly
                85                  90                  95

Gly Gly Ser Cys Glu Leu Ala Ala Leu Glu Ala Glu Leu Ala Ala Leu
            100                 105                 110

Glu Ala Gly Gly Ser Gly Thr Ala Val Ala Trp Tyr Gln Gln Lys Pro
        115                 120                 125

Gly Lys Ala Pro Lys Leu Leu Ile Tyr Ser Ala Ser Phe Leu Tyr Ser
    130                 135                 140

Gly Val Pro Ser Arg Phe Ser Gly Ser Arg Ser Gly Thr Asp Phe Thr
145                 150                 155                 160

Leu Thr Ile Ser Ser Leu Gln Pro Glu Asp Phe Ala Thr Tyr Tyr Cys
                165                 170                 175

Gln Gln His Tyr Thr Thr Pro Pro Thr Phe Gly Gln Gly Thr Lys Leu
            180                 185                 190

Glu Ile Lys Arg Thr Val Ala Ala Pro Ser Val Phe Ile Phe Pro Pro
        195                 200                 205

Ser Asp Glu Gln Leu Lys Ser Gly Thr Ala Ser Val Val Cys Leu Leu
    210                 215                 220

Asn Asn Phe Tyr Pro Arg Glu Ala Lys Val Gln Trp Lys Val Asp Asn
225                 230                 235                 240

Ala Leu Gln Ser Gly Asn Ser Gln Glu Ser Val Thr Glu Gln Asp Ser
                245                 250                 255

Lys Asp Ser Thr Tyr Ser Leu Ser Thr Leu Thr Leu Ser Lys Ala
            260                 265                 270

Asp Tyr Glu Lys His Lys Val Tyr Ala Cys Glu Val Thr His Gln Gly
        275                 280                 285

Leu Ser Ser Pro Val Thr Lys Ser Phe Asn Arg Gly Glu Cys
    290                 295                 300

<210> SEQ ID NO 99
<211> LENGTH: 648
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 99

```
Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Gly
                85                  90                  95

Gly Ser Gly Ala Lys Leu Ala Ala Leu Lys Ala Lys Leu Ala Ala Leu
            100                 105                 110

Lys Gly Gly Gly Gly Ser Asp Ser Trp Met Glu Glu Val Ile Lys Leu
        115                 120                 125

Cys Gly Arg Glu Leu Val Arg Ala Gln Ile Ala Ile Cys Gly Met Ser
    130                 135                 140

Thr Trp Ser Ile Glu Gly Arg Ser Leu Ser Gln Glu Asp Ala Pro Gln
145                 150                 155                 160

Thr Pro Arg Pro Val Ala Glu Ile Val Pro Ser Phe Ile Asn Lys Asp
                165                 170                 175

Thr Glu Thr Ile Asn Met Met Ser Glu Phe Val Ala Asn Leu Pro Gln
            180                 185                 190

Glu Leu Lys Leu Thr Leu Ser Glu Met Gln Pro Ala Leu Pro Gln Leu
        195                 200                 205

Gln Gln His Val Pro Val Leu Lys Asp Ser Ser Leu Leu Phe Glu Glu
    210                 215                 220

Phe Lys Lys Leu Ile Arg Asn Arg Gln Ser Glu Ala Ala Asp Ser Ser
225                 230                 235                 240

Pro Ser Glu Leu Lys Tyr Leu Gly Leu Asp Thr His Ser Ile Glu Gly
                245                 250                 255

Arg Gln Leu Tyr Ser Ala Leu Ala Asn Lys Cys Cys His Val Gly Cys
            260                 265                 270

Thr Lys Arg Ser Leu Ala Arg Phe Cys Gly Gly Gly Ser Glu Leu
        275                 280                 285

Ala Ala Leu Glu Ala Glu Leu Ala Ala Leu Glu Ala Gly Gly Ser Gly
    290                 295                 300

His Val Asp Val Trp Gly Gln Gly Leu Leu Val Thr Val Ser Ser Ala
305                 310                 315                 320

Ser Thr Thr Ala Pro Lys Val Tyr Pro Leu Ser Ser Cys Cys Gly Asp
                325                 330                 335

Lys Ser Ser Ser Thr Val Thr Leu Gly Cys Leu Val Ser Ser Tyr Met
            340                 345                 350

Pro Glu Pro Val Thr Val Thr Trp Asn Ser Gly Ala Leu Lys Ser Gly
        355                 360                 365

Val His Thr Phe Pro Ala Val Leu Gln Ser Ser Gly Leu Tyr Ser Leu
    370                 375                 380
```

```
Ser Ser Met Val Thr Val Pro Gly Ser Thr Ser Gly Gln Thr Phe Thr
385                 390                 395                 400

Cys Asn Val Ala His Pro Ala Ser Ser Thr Lys Val Asp Lys Ala Val
            405                 410                 415

Glu Pro Lys Ser Cys Asp Lys Thr His Thr Cys Pro Pro Cys Pro Ala
            420                 425                 430

Pro Glu Leu Leu Gly Gly Pro Ser Val Phe Leu Phe Pro Pro Lys Pro
            435                 440                 445

Lys Asp Thr Leu Met Ile Ser Arg Thr Pro Glu Val Thr Cys Val Val
        450                 455                 460

Val Asp Val Ser His Glu Asp Pro Glu Val Lys Phe Asn Trp Tyr Val
465                 470                 475                 480

Asp Gly Val Glu Val His Asn Ala Lys Thr Lys Pro Arg Glu Glu Gln
            485                 490                 495

Tyr Asn Ser Thr Tyr Arg Val Val Ser Val Leu Thr Val Leu His Gln
            500                 505                 510

Asp Trp Leu Asn Gly Lys Glu Tyr Lys Cys Lys Val Ser Asn Lys Ala
        515                 520                 525

Leu Pro Ala Pro Ile Glu Lys Thr Ile Ser Lys Ala Lys Gly Gln Pro
530                 535                 540

Arg Glu Pro Gln Val Tyr Thr Leu Pro Pro Ser Arg Asp Glu Leu Thr
545                 550                 555                 560

Lys Asn Gln Val Ser Leu Thr Cys Leu Val Lys Gly Phe Tyr Pro Ser
            565                 570                 575

Asp Ile Ala Val Glu Trp Glu Ser Asn Gly Gln Pro Glu Asn Asn Tyr
            580                 585                 590

Lys Thr Thr Pro Pro Val Leu Asp Ser Asp Gly Ser Phe Phe Leu Tyr
        595                 600                 605

Ser Lys Leu Thr Val Asp Lys Ser Arg Trp Gln Gln Gly Asn Val Phe
610                 615                 620

Ser Cys Ser Val Met His Glu Ala Leu His Asn His Tyr Thr Gln Lys
625                 630                 635                 640

Ser Leu Ser Leu Ser Pro Gly Lys
                645

<210> SEQ ID NO 100
<211> LENGTH: 1161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gacatccaga tgacccagtc tccatcctcc ctgtctgcat ctgtaggaga cagagtcacc        60
atcacttgcc gggcaagtca gggggtggc ggaagcgccc caccacgcct catctgtgac       120
agccgagtcc tggagaggta cctcttggag gccaaggagg ccgagaatat cacgacgggc       180
tgtgctgaac actgcagctt gaatgagaat atcactgtcc agacaccaa agttaatttc       240 tatgcctgga agaggatgga ggtcgggcag caggccgtag aagtctggca gggcctggcc       300
ctgctgtcgg aagctgtcct gcggggccag gccctgttgg tcaactcttc ccagccgtgg       360
gagcccctgc agctgcatgt ggataaagcc gtcagtggcc ttcgcagcct caccactctg       420
cttcgggctc tggagcccca gaaggaagcc atctccctc cagatgcggc ctcagctgct       480
ccactccgaa caatcactgc tgacactttc cgcaaactct tccgagtcta ctccaatttc       540
```

```
ctccggggaa agctgaagct gtacacaggg gaggcctgca ggacagggga cagaggcgga      600
ggtgggagta ccgcggtcgc atggtatcag cagaaaccag ggaaagcccc taagctcctg      660
atctattctg catccttctt gtatagtggg gtcccatcaa ggttcagtgg cagtagatct      720
gggacagatt tcactctcac catcagcagt ctgcaacctg aagattttgc aacttactac      780
tgtcaacagc attacactac ccctccgacg ttcggccaag gtaccaagct tgagatcaaa      840
cgaactgtgg ctgcaccatc tgtcttcatc ttcccgccat ctgatgagca gttgaaatct      900
ggaactgcct ctgtcgtgtg cctgctgaat aacttctatc ccagagaggc caaagtacag      960
tggaaggtgg ataacgccct ccaatcgggt aactcccagg agagtgtcac agagcaggac     1020
agcaaggaca gcacctacag cctcagcagc accctgacgc tgagcaaagc agactacgag     1080
aaacacaaag tctacgcctg cgaagtcacc catcagggcc tgtcctcgcc cgtcacaaag     1140
agcttcaaca ggggagagtg t                                               1161

<210> SEQ ID NO 101
<211> LENGTH: 1902
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
gaggtgcagc tggtggagtc tggaggaggc ttggtccagc ctggggggtc cctgagactc       60
tcctgtgcag cctctgggtt caatattaag gacacttaca tccactgggt ccgccaggct      120
ccagggaagg ggctggagtg ggtcgcacgt atttatccta ccaatggtta cacacgctac      180
gcagactccg tgaagggccg attcaccatc tccgcagaca cttccaagaa cacggcgtat      240
cttcaaatga acagcctgag agccgaggac acggccgtgt attactgttc gagatggggc      300
ggtgacggag gcggtggctc caccccccct tggccctgcc catccctgcc ccagagcttc      360
ctgctcaagt gcttagagca agtgaggaaa atccaggctg atggcgccga gctgcaggag      420
aggctgtgtg ccgcccacaa gctgtgccac cggaggagc tgatgctgct caggcactct      480
ctgggcatcc cccaggctcc cctaagcagc tgctccagcc agtccctgca gctgacgagc      540
tgcctgaacc aactcacacgg cggcctctttt ctctaccagg gcctcctgca ggccctggcg      600
ggcatctccc cagagctggc ccccaccttg gacacactgc agctggacgt cactgacttt      660
gccacgaaca tctggctgca gatggaggac ctggggcgg ccccgctgt gcagcccacc      720 cagggcgcca tgccgacctt cacttcagcc ttccaacgca gagcaggagg ggtcctggtt      780
gcttcccagc tgcatcgttt cctggagctg gcataccgtg gcctgcgcta ccttgctgag      840
cccggcggtg gcggaagcgg cttctatgcc atggactact ggggccaagg aaccctggtc      900
accgtctcct cagcctccac caagggccca tcggtcttcc cctggcacc ctcctccaag      960 agcacctctg gggcacagc ggccctgggc tgcctggtca aggactactt ccccgaaccg     1020
gtgacggtgt cgtggaactc aggcgccctg accagcggcg tgcacacctt cccggctgtc     1080
ctacagtcct caggactcta ctccctcagc agcgtggtga ctgtgccctc tagcagcttg     1140
ggcacccaga cctacatctg caacgtgaat cacaagccca gcaacaccaa ggtggacaag     1200
aaagttgaac ccaaatcttg cgacaaaact cacacatgcc caccgtgccc agcacctgaa     1260
ctcctggggg gaccgtcagt cttcctcttc cccccaaaac ccaaggacac cctcatgatc     1320
tcccggaccc ctgaggtcac atgcgtggtg gtggacgtga gccacgaaga ccctgaggtc     1380
```

| | |
|---|---|
| aagttcaact ggtacgtgga cggcgtggag gtgcataatg ccaagacaaa gccgcgggag | 1440 |
| gagcagtaca acagcacgta ccgtgtggtc agcgtcctca ccgtcctgca ccaggactgg | 1500 |
| ctgaatggca aggagtacaa gtgcaaggtc tccaacaaag ccctcccagc ccccatcgag | 1560 |
| aaaaccatct ccaaagccaa agggcagccc cgagaaccac aggtgtacac cctgccccca | 1620 |
| tcccgggatg agctgaccaa gaaccaggtc agcctgacct gcctggtcaa aggcttctat | 1680 |
| cccagcgaca tcgccgtgga gtgggagagc aatgggcagc cggagaacaa ctacaagacc | 1740 |
| acgcctcccg tgctggactc cgacggctcc ttcttcctct acagcaagct caccgtggac | 1800 |
| aagagcaggt ggcagcaggg gaacgtcttc tcatgctccg tgatgcatga ggctctgcac | 1860 |
| aaccactaca cgcagaagag cctctccctg tctccgggta aa | 1902 |

<210> SEQ ID NO 102
<211> LENGTH: 1488
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 102

| | |
|---|---|
| gaggtgcagc tggtggagtc tggaggaggc ttggtccagc ctgggggggtc cctgagactc | 60 |
| tcctgtgcag cctctgggtt caatattaag gacacttaca tccactgggt ccgccaggct | 120 |
| ccagggaagg ggctggagtg ggtcgcacgt atttatccta ccaatggtta cacacgctac | 180 |
| gcagactccg tgaagggccg attcaccatc tccgcagaca cttccaagaa cacggcgtat | 240 |
| cttcaaatga acagcctgag agccgaggac acggccgtgt attactgttc gagatgcggg | 300 |
| ggtggcggaa gcatcgaagg tcgtcacgga aaggaacat ttaccagcga cctcagcaag | 360 |
| cagatggagg aagaggccgt gaggctgttc atcgagtggc tgaagaacgg cggaccctcc | 420 |
| tctggcgctc cacccctag cggcggaggt gggagttgcg actactgggg ccaaggaacc | 480 |
| ctggtcaccg tctcctcagc ctccaccaag ggcccatcgg tcttccccct ggcaccctcc | 540 |
| tccaagagca cctctggggg cacagcggcc ctgggctgcc tggtcaagga ctacttcccc | 600 |
| gaaccggtga cggtgtcgtg gaactcaggc gccctgacca gcggcgtgca caccttcccg | 660 |
| gctgtcctac agtcctcagg actctactcc ctcagcagcg tggtgactgt gccctctagc | 720 |
| agcttgggca cccagaccta catctgcaac gtgaatcaca agcccagcaa caccaaggtg | 780 |
| gacaagaaag ttgaacccaa atcttgcgac aaaactcaca catgcccacc gtgcccagca | 840 |
| cctgaactcc tggggggacc gtcagtcttc ctcttccccc caaaacccaa ggacaccctc | 900 |
| atgatctccc ggacccctga ggtcacatgc gtggtggtgg acgtgagcca cgaagaccct | 960 |
| gaggtcaagt tcaactggta cgtggacggc gtggaggtgc ataatgccaa gacaaagccg | 1020 |
| cgggaggagc agtacaacag cacgtaccgt gtggtcagcg tcctcaccgt cctgcaccag | 1080 |
| gactggctga atggcaagga gtacaagtgc aaggtctcca acaaagccct cccagccccc | 1140 |
| atcgagaaaa ccatctccaa agccaaaggg cagccccgag aaccacaggt gtacaccctg | 1200 |
| cccccatccc gggatgagct gaccaagaac caggtcagcc tgacctgcct ggtcaaaggc | 1260 |
| ttctatccca gcgacatcgc cgtggagtgg gagagcaatg ggcagccgga gaacaactac | 1320 |
| aagaccacgc ctcccgtgct ggactccgac ggctccttct tcctctacag caagctcacc | 1380 |
| gtggacaaga gcaggtggca gcaggggaac gtcttctcat gctccgtgat gcatgaggct | 1440 |
| ctgcacaacc actacacgca gaagagcctc tccctgtctc cgggtaaa | 1488 |

<210> SEQ ID NO 103
<211> LENGTH: 1455
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
gaggtgcagc tggtggagtc tggaggaggc ttggtccagc ctgggggtc cctgagactc        60 tcctgtgcag cctctgggtt caatattaag gacacttaca tccactgggt ccgccaggct       120
ccagggaagg ggctggagtg ggtcgcacgt atttatccta ccaatggtta cacacgctac      180
gcagactccg tgaagggccg attcaccatc tccgcagaca cttccaagaa cacggcgtat       240
cttcaaatga acagcctgag agccgaggac acggccgtgt attactgttc gagaggaggc       300
ggtggctcca tcaacgtgaa gtgcagcctg ccccagcagt gcatcaagcc ctgcaaggac       360
gccggcatgc ggttcggcaa gtgcatgaac aagaagtgca ggtgctacag cggcggtggc       420
ggaagcgact actggggcca aggaaccctg gtcaccgtct cctcagcctc caccaagggc       480
ccatcggtct tccccctggc accctcctcc aagagcacct ctgggggcac agcggccctg       540
ggctgcctgg tcaaggacta cttccccgaa ccggtgacgg tgtcgtggaa ctcaggcgcc       600
ctgaccagcg gcgtgcacac cttcccggct gtcctacagt cctcaggact ctactccctc       660
agcagcgtgg tgactgtgcc ctctagcagc ttgggcaccc agacctacat ctgcaacgtg       720
aatcacaagc ccagcaacac caaggtggac aagaaagttg aacccaaatc ttgcgacaaa       780
actcacacat gcccaccgtg cccagcacct gaactcctgg ggggaccgtc agtcttcctc       840
ttccccccaa aacccaagga caccctcatg atctcccgga cccctgaggt cacatgcgtg       900
gtggtggacg tgagccacga agaccctgag gtcaagttca actggtacgt ggacggcgtg       960
gaggtgcata atgccaagac aaagccgcgg gaggagcagt acaacagcac gtaccgtgtg      1020
gtcagcgtcc tcaccgtcct gcaccaggac tggctgaatg gcaaggagta caagtgcaag      1080
gtctccaaca aagccctccc agcccccatc gagaaaacca tctccaaagc caaagggcag      1140
ccccgagaac cacaggtgta caccctgccc ccatcccggg atgagctgac caagaaccag      1200
gtcagcctga cctgcctggt caaaggcttc tatcccagcg acatcgccgt ggagtgggag      1260
agcaatgggc agccggagaa caactacaag accacgcctc ccgtgctgga ctccgacggc      1320
tccttcttcc tctacagcaa gctcaccgtg gacaagagca ggtggcagca ggggaacgtc      1380
ttctcatgct ccgtgatgca tgaggctctg cacaaccact acacgcagaa gagcctctcc      1440
ctgtctccgg gtaaa                                                       1455
```

<210> SEQ ID NO 104
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
gaggtgcagc tggtggagtc tggaggaggc ttggtccagc ctgggggtc cctgagactc        60 tcctgtgcag cctctgggtt caatattaag gacacttaca tccactgggt ccgccaggct       120
ccagggaagg ggctggagtg ggtcgcacgt atttatccta ccaatggtta cacacgctac      180
```

```
gcagactccg tgaagggccg attcaccatc tccgcagaca cttccaagaa cacggcgtat    240
cttcaaatga acagcctgag agccgaggac acggccgtgt attactgttc gagaggaggc    300
ggtggctccg ccgctgcaat ctcctgcgtc ggcagccccg aatgtcctcc caagtgccgg    360
gctcagggat gcaagaacgg caagtgtatg aaccggaagt gcaagtgcta ctattgcggc    420
ggtggcggaa gcgactactg gggccaagga accctggtca ccgtctcctc agcctccacc    480
aagggcccat cggtcttccc cctggcaccc tcctccaaga gcacctctgg gggcacagcg    540
gccctgggct gcctggtcaa ggactacttc cccgaaccgg tgacggtgtc gtggaactca    600
ggcgccctga ccagcggcgt gcacaccttc ccggctgtcc tacagtcctc aggactctac    660
tccctcagca gcgtggtgac tgtgccctct agcagcttgg gcacccagac ctacatctgc    720
aacgtgaatc acaagcccag caacaccaag gtggacaaga agttgaaccc aaatcttgc     780 gacaaaactc acacatgccc accgtgccca gcacctgaac tcctgggggg accgtcagtc    840
ttcctcttcc ccccaaaacc caaggacacc ctcatgatct cccggacccc tgaggtcaca    900
tgcgtggtgg tggacgtgag ccacgaagac cctgaggtca agttcaactg gtacgtggac    960
ggcgtggagg tgcataatgc caagacaaag ccgcgggagg agcagtacaa cagcacgtac   1020
cgtgtggtca gcgtcctcac cgtcctgcac caggactggc tgaatggcaa ggagtacaag   1080
tgcaaggtct ccaacaaagc cctcccagcc cccatcgaga aaaccatctc caaagccaaa   1140
gggcagcccc gagaaccaca ggtgtacacc ctgcccccat cccgggatga gctgaccaag   1200
aaccaggtca gcctgacctg cctggtcaaa ggcttctatc ccagcgacat cgccgtggag   1260
tgggagagca atgggcagcc ggagaacaac tacaagacca cgcctcccgt gctggactcc   1320
gacggctcct tcttcctcta cagcaagctc accgtggaca gagcaggtg gcagcagggg    1380 aacgtcttct catgctccgt gatgcatgag gctctgcaca accactacac gcagaagagc   1440
ctctccctgt ctccgggtaa a                                              1461
```

<210> SEQ ID NO 105  
<211> LENGTH: 1878  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 105

```
gaggtgcagc tggtggagtc tggaggaggc ttggtccagc ctgggggtc cctgagactc      60 tcctgtgcag cctctgggtt caatattaag gacacttaca tccactgggt ccgccaggct    120
ccagggaagg ggctggagtg ggtcgcacgt atttatccta ccaatggtta cacacgctac    180
gcagactccg tgaagggccg attcaccatc tccgcagaca cttccaagaa cacggcgtat    240
cttcaaatga acagcctgag agccgaggac acggccgtgt attactgttc gagaggggggt   300 ggcggaagcg ccacacctct gggccccgcc tcctccctgc ctcagagctt tctgctcaaa    360
tgtctggagc aggtgcggaa gatccagggc gacggcgccg ctctgcaaga gaaactggtc    420
agcgaatgcg ccacatataa gctgtgtcac cccgaggaac tggtcctctt gggccacagc    480
ctgggcatcc cctgggcccc tctcagctcc tgccctccc aagctctcca actggctgga    540
tgtctgtccc aactgcactc cggcctcttc ctgtaccagg actcctcca ggctctcgaa     600 gggatcagcc ccgaactggg ccccacactg gacaccttgc aactcgatgt ggccgatttc    660
gccacaacca tctggcagca gatggaagaa ctcggaatgg ctcctgctct ccagcccaca    720
```

```
cagggagcta tgcctgcttt cgcctctgct ttccagcgga gagctggtgg tgtgctcgtc    780
gcatcccacc tccagagctt cttggaggtg tcctatcggg tgctccggca tctggcccaa    840
cccggcggag gtgggagtga ctactggggc caaggaaccc tggtcaccgt ctcctcagcc    900
agcactaaag gtccatctgt gttccctctg gctccttgca gccggagcac ctccgagtcc    960
acagccgctc tgggatgtct ggtgaaagat tacttccccg agcccgtcac cgtgagctgg   1020
aatagcggag cactgacctc cggcgtccac acattcccg ccgtgctcca aagctccggc    1080
ctgtacagcc tctcctccgt ggtcaccgtg cccagcagct ctctgggcac aaagacctat   1140
acctgtaacg tggatcacaa gcctagcaac accaaagtgg ataagcgggt ggagagcaag   1200
tacggccctc cctgtccccc ttgccccgct cctgaggccg ctggcggacc ttccgtgttc   1260
ctgtttcccc ctaagcccaa ggacacccta atgattagcc ggacacccga agtgacctgc   1320
gtggtcgtgg atgtgtccca ggaggaccct gaagtgcaat taactggta cgtggacggc    1380 gtcgaggtgc acaacgccaa gaccaagcct cgggaagagc agttcaacag cacctaccgg   1440
gtggtcagcg tgctgacagt gctgcaccag gactggctga acggcaagga gtacaagtgc   1500
aaggtgagca acaagggcct gcccagctcc atcgagaaga ccatcagcaa ggccaagggc   1560
cagcccaggg aaccccaggt gtataccctg cccctagcc aggaggaaat gaccaaaaac    1620
caggtgagcc tgacctgcct ggtgaagggc ttctaccca gcgacatcgc cgtggagtgg   1680
gagagcaacg gccagcccga gaacaattac aagaccaccc ctcctgtgct ggacagcgac   1740
ggctccttct ttctgtatag ccggctgacc gtggacaaga gcaggtggca ggagggcaac   1800
gtgttctcct gtagcgtgat gcacgaggcc ctgcacaacc attaccccca gaagagcttg   1860
agcctgagcc tgggcaaa                                                 1878

<210> SEQ ID NO 106
<211> LENGTH: 1917
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
gaggtgcagc tggtggagtc tgaggaggc ttggtccagc ctgggggtc cctgagactc      60 tcctgtgcag cctctgggtt caatattaag gacacttaca tccactgggt ccgccaggct   120
ccagggaagg ggctggagtg ggtcgcacgt atttatccta ccaatggtta cacacgctac    180
gcagactccg tgaagggccg attcaccatc tccgcagaca cttccaagaa cacggcgtat   240
cttcaaatga acagcctgag agccgaggac acggccgtgt attactgttc gagagggggt   300
ggcggaagct tccaaccat tcccttatcc aggcttttg acaacgctat gctccgcgcc     360
catcgtctgc accagctggc ctttgacacc taccaggagt ttgaagaagc ctatatccca   420
aaggaacaga gtattcatt cctgcagaac ccccagacct cctctgtttt ctcagagtct   480
attccgacac cctccaacag ggaggaaaca caacagaaat ccaacctaga gctgctccgc   540
atctccctgc tgctcatcca gtcgtggctg gagcccgtgc agttcctcag gagtgtcttc   600 gccaacagc tggtgtacgg cgcctctgac agcaacgtct atgacctcct aaaggaccta   660
gaggaaggca tccaaacgct gatggggagg ctggaagatg gcagccccg gactgggcag   720 atcttcaagc agacctacag caagttcgac acaaactcac acaacgatga cgcactactc   780
aagaactacg ggctgctcta ctgcttcagg aaggacatgg acaaggtcga gacattcctg   840
```

| | |
|---|---|
| cgcatcgtgc agtgccgctc tgtggagggc agctgtggct tcggcggagg tgggagtgac | 900 |
| tactggggcc aaggaaccct ggtcaccgtc tcctcagcca gcactaaagg tccatctgtg | 960 |
| ttccctctgg ctccttgcag ccggagcacc tccgagtcca cagccgctct gggatgtctg | 1020 |
| gtgaaagatt acttcccga gcccgtcacc gtgagctgga atagcggagc actgaccctcc | 1080 |
| ggcgtccaca cattccccgc cgtgctccaa agctccggcc tgtacagcct ctcctccgtg | 1140 |
| gtcaccgtgc ccagcagctc tctgggcaca aagacctata cctgtaacgt ggatcacaag | 1200 |
| cctagcaaca ccaaagtgga taagcgggtg gagagcaagt acggccctcc ctgtcccct | 1260 |
| tgccccgctc ctgaggccgc tggcggacct tccgtgttcc tgtttccccc taagcccaag | 1320 |
| gacaccctca tgattagccg gacacccgaa gtgacctgcg tggtcgtgga tgtgtcccag | 1380 |
| gaggaccctg aagtgcaatt taactggtac gtggacggcg tcgaggtgca aacgccaag | 1440 |
| accaagcctc gggaagagca gttcaacagc acctaccggg tggtcagcgt gctgacagtg | 1500 |
| ctgcaccagg actggctgaa cggcaaggag tacaagtgca aggtgagcaa caagggcctg | 1560 |
| cccagctcca tcgagaagac catcagcaag gccaagggca gcccaggga ccccaggtg | 1620 |
| tataccctgc ccctagcca ggaggaaatg accaaaaacc aggtgagcct gacctgcctg | 1680 |
| gtgaagggct tctaccccag cgacatcgcc gtggagtggg agagcaacgg ccagcccgag | 1740 |
| aacaattaca agaccacccc tcctgtgctg gacagcgacg gctccttctt tctgtatagc | 1800 |
| cggctgaccg tggacaagag caggtggcag gagggcaacg tgttctcctg tagcgtgatg | 1860 |
| cacgaggccc tgcacaacca ttacacccag aagagcttga gcctgagcct gggcaaa | 1917 |

<210> SEQ ID NO 107
<211> LENGTH: 1782
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107

| | |
|---|---|
| gaggtgcagc tggtggagtc tggaggaggc ttggtccagc ctgggggtc cctgagactc | 60 |
| tcctgtgcag cctctgggtt caatattaag gacacttaca tccactgggt ccgccaggct | 120 |
| ccagggaagg gctgagtg gtcgcacgt atttatccta ccaatggtta cacacgctac | 180 |
| gcagactccg tgaagggccg attcaccatc tccgcagaca cttccaagaa cacggcgtat | 240 |
| cttcaaatga acagcctgag agccgaggac acggccgtgt attactgttc gagaggtggc | 300 |
| ggaggatctg ttccaattca aaaggttcaa gatgatacca aaactctgat taaaactatt | 360 |
| gtcacgcgta taaacgacat cagccatacc cagtcggtta gctcaaagca aaaagttacc | 420 |
| ggtttggact ttattccggg actgcacccg atcctgaccc ttagtaaaat ggaccagaca | 480 |
| ctggccgtct accagcaaat cctgacatcg atgccatcca gaatgtgat acaaattagc | 540 |
| aacgatttgg aaaaccttcg cgatctgctg cacgtgctgg ccttcagtaa gtcctgtcat | 600 |
| ctgccgtggg cgtcgggact ggagactctt gactcgctgg tggagtgtt agaggcctct | 660 |
| ggctattcta ctgaagtcgt tgcgctgtca cgcctccagg ggagcctgca ggacatgctg | 720 |
| tggcagctga acctgtcacc tggctgcgga ggtggtggtt cagactactg gggccaagga | 780 |
| accctggtca ccgtctcctc agccagcact aaaggtccat ctgtgttccc tctggctcct | 840 |
| tgcagccgga gcacctccga gtccacagcc gctctgggat gtctggtgaa agattacttc | 900 |
| cccgagcccg tcaccgtgag ctggaatagc ggagcactga cctccggcgt ccacacattc | 960 |

| | | |
|---|---|---|
| cccgccgtgc tccaaagctc cggcctgtac agcctctcct ccgtggtcac cgtgcccagc | 1020 | |
| agctctctgg gcacaaagac ctatacctgt aacgtggatc acaagcctag caacaccaaa | 1080 | |
| gtggataagc gggtggagag caagtacggc cctccctgtc ccccttgccc cgctcctgag | 1140 | |
| gccgctggcg gaccttccgt gttcctgttt cccctaagc ccaaggacac cctcatgatt | 1200 | |
| agccggacac ccgaagtgac ctgcgtggtc gtggatgtgt cccaggagga ccctgaagtg | 1260 | |
| caatttaact ggtacgtgga cggcgtcgag gtgcacaacg ccaagaccaa gcctcgggaa | 1320 | |
| gagcagttca acagcaccta ccgggtggtc agcgtgctga cagtgctgca ccaggactgg | 1380 | |
| ctgaacggca aggagtacaa gtgcaaggtg agcaacaagg gcctgcccag ctccatcgag | 1440 | |
| aagaccatca gcaaggccaa gggccagccc agggaacccc aggtgtatac cctgcccct | 1500 | |
| agccaggagg aaatgaccaa aaaccaggtg agcctgacct gcctggtgaa gggcttctac | 1560 | |
| cccagcgaca tcgccgtgga gtgggagagc aacggccagc ccgagaacaa ttacaagacc | 1620 | |
| accccctcctg tgctggacag cgacggctcc ttctttctgt atagccggct gaccgtggac | 1680 | |
| aagagcaggt ggcaggaggg caacgtgttc tcctgtagcg tgatgcacga ggccctgcac | 1740 | |
| aaccattaca cccagaagag cttgagcctg agcctgggca aa | 1782 | |

<210> SEQ ID NO 108
<211> LENGTH: 1839
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108

| | | |
|---|---|---|
| gaggtgcagc tggtggagtc tggaggaggc ttggtccagc ctggggggtc cctgagactc | 60 | |
| tcctgtgcag cctctgggtt caatattaag gacacttaca tccactgggt ccgccaggct | 120 | |
| ccagggaagg gctggagtg gtcgcacgt atttatccta ccaatggtta cacacgctac | 180 | |
| gcagactccg tgaagggccg attcaccatc tccgcagaca cttccaagaa cacggcgtat | 240 | |
| cttcaaatga acagcctgag agccgaggac acggccgtgt attactgttc gagaggtggt | 300 | |
| ggcggaagct gtgatctgcc tcaaacccac agcctgggta gcaggaggac cttgatgctc | 360 | |
| ctggcacaga tgaggagaat ctctcttttc tcctgcttga aggacagaca tgactttgga | 420 | |
| tttccccagg aggagtttgg caaccagttc caaaaggctg aaaccatccc tgtcctccat | 480 | |
| gagatgatcc agcagatctt caatctcttc agcacaaagg actcatctgc tgcttgggat | 540 | |
| gagaccctcc tagacaaatt ctacactgaa ctctaccagc agctgaatga cctggaagcc | 600 | |
| tgtgtgatac aggggtggg ggtgacagag actcccctga tgaaggagga ctccattctg | 660 | |
| gctgtgagga atacttcca agaatcact ctctatctga agagaagaa atacagccct | 720 | |
| tgtgcctggg aggttgtcag agcagaaatc atgagatctt tttctttgtc aacaaacttg | 780 | |
| caagaaagtt taagaagtaa ggaaggcgga ggtgggagtg actactgggg ccaaggaacc | 840 | |
| ctggtcaccg tctcctcagc cagcactaaa ggtccatctg tgttccctct ggctccttgc | 900 | |
| agccggagca cctccgagtc cacagccgct ctgggatgtc tggtgaaaga ttacttcccc | 960 | |
| gagcccgtca ccgtgagctg gaatagcgga gcactgacct ccggcgtcca cacattcccc | 1020 | |
| gccgtgctcc aaagctccgg cctgtacagc ctctcctccg tggtcaccgt gcccagcagc | 1080 | |
| tctctgggca aaagacccta tacctgtaac gtggatcaca agcctagcaa caccaaagtg | 1140 | |
| gataagcggg tggagagcaa gtacggccct cctgtccccc cttgcccgc tcctgaggcc | 1200 | |

```
gctggcggac cttccgtgtt cctgtttccc cctaagccca aggacaccct catgattagc    1260
cggacacccg aagtgacctg cgtggtcgtg gatgtgtccc aggaggaccc tgaagtgcaa    1320
tttaactggt acgtggacgg cgtcgaggtg cacaacgcca agaccaagcc tcgggaagag    1380
cagttcaaca gcacctaccg ggtggtcagc gtgctgacag tgctgcacca ggactggctg    1440
aacggcaagg agtacaagtg caaggtgagc aacaagggcc tgcccagctc catcgagaag    1500
accatcagca aggccaaggg ccagcccagg aaccccaggt gtataccctg ccccctagc    1560 caggaggaaa tgaccaaaaa ccaggtgagc ctgacctgcc tggtgaaggg cttctacccc    1620
agcgacatcg ccgtggagtg ggagagcaac ggccagcccg agaacaatta caagaccacc    1680
cctcctgtgc tggacagcga cggctccttc tttctgtata gccggctgac cgtggacaag    1740
agcaggtggc aggagggcaa cgtgttctcc tgtagcgtga tgcacgaggc cctgcacaac    1800
cattacaccc agaagagctt gagcctgagc ctgggcaaa                           1839

<210> SEQ ID NO 109
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
gaggtgcagc tggtggagtc tgaggaggc ttggtccagc ctggggggtc cctgagactc      60
tcctgtgcag cctctgggtt caatattaag gacacttaca tccactgggt ccgccaggct    120
ccagggaagg ggctggagtg ggtcgcacgt atttatccta ccaatggtta cacacgctac    180
gcagactccg tgaagggccg attcaccatc tccgcagaca cttccaagaa cacggcgtat    240
cttcaaatga acagcctgag agccgaggac acggccgtgt attactgttc gagatgcggg    300
ggtggcggaa gcatcgaagg tcgtcacgct gagggaacat tcacttccga tgtgtcctcc    360
tacctggagg gccaggctgc caaagagttc atcgcttggc tcgtcaaggg caggggcgga    420
ggtgggagtt cgactactg gggccaagga accctggtca ccgtctcctc agcctccacc    480
aagggcccat cggtcttccc cctggcaccc tcctccaaga gcacctctgg gggcacagcg    540
gccctgggct gcctggtcaa ggactacttc cccgaaccgg tgacggtgtc gtggaactca    600
ggcgccctga ccagcggcgt gcacaccttc ccggctgtcc tacagtcctc aggactctac    660
tccctcagca gcgtggtgac tgtgccctct agcagcttgg gcacccagac ctacatctgc    720
aacgtgaatc acaagcccag caacaccaag gtggacaaga agttgaaccc caaatcttgc    780
gacaaaactc acacatgccc accgtgccca gcacctccag tcgccggacc gtcagtcttc    840 ctcttcccctc caaaacccaa ggacaccctc atgatctccc ggacccctga ggtcacatgc    900
gtggtggtgg acgtgagcca cgaagaccct gaggtcaagt tcaactggta cgtggacggc    960
gtggaggtgc ataatgccaa gacaaagccg cggaggagc agtacaacag cacgtaccgt    1020
gtggtcagcg tcctcaccgt cctgcaccag gactggctga atggcaagga gtacaagtgc    1080
aaggtctcca acaaaggcct cccagcctcc atcgagaaaa ccatctccaa agccaagggg    1140
cagccccgag aaccacaggt gtacaccctg cctccatccc gggatgagct gaccaagaac    1200
caggtcagcc tgacctgcct ggtcaaaggc ttctatccca gcgacatcgc cgtggagtgg    1260
gagagcaatg ggcagccgga gaacaactac aagaccacgc ctcccgtgct ggactccgac    1320
ggctccttct tcctctacag caagctcacc gtggacaaga gcaggtggca gcaggggaac    1380
```

| | |
|---|---|
| gtcttctcat gctccgtgat gcatgaggct ctgcacaacc actacacgca aagagcctc | 1440 |
| tccctgtctc cgggtaaa | 1458 |

<210> SEQ ID NO 110
<211> LENGTH: 1521
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110

| | |
|---|---|
| gaggtgcagc tggtggagtc tgaggaggc ttggtccagc ctgggggtc cctgagactc | 60 |
| tcctgtgcag cctctgggtt caatattaag gacacttaca tccactgggt ccgccaggct | 120 |
| ccagggaagg gctggagtg gtcgcacgt atttatccta ccaatggtta cacacgctac | 180 |
| gcagactccg tgaagggccg attcaccatc tccgcagaca cttccaagaa cacggcgtat | 240 |
| cttcaaatga acagcctgag agccgaggac acggccgtgt attactgttc gagaggggt | 300 |
| ggcggaagcg cgcaagagcc agtcaaaggt ccagtctcca ctaagcctgg ctcctgcccc | 360 |
| attatcttga tccggtgcgc catgttgaat ccccctaacc gctgcttgaa agatactgac | 420 |
| tgcccaggaa tcaagaagtg ctgtgaaggc tcttgcggga tggcctgttt cgttccccag | 480 |
| ggcgaggtg ggagtgacta ctggggccaa ggaaccctgg tcaccgtctc ctcagcctcc | 540 |
| accaagggcc catcggtctt ccccctggca ccctcctcca agagcacctc tgggggcaca | 600 |
| gcggccctgg gctgcctggt caaggactac ttccccgaac cggtgacggt gtcgtggaac | 660 |
| tcaggcgccc tgaccagcgg cgtgcacacc ttcccggctg tcctacagtc ctcaggactc | 720 |
| tactccctca gcagcgtggt gactgtgccc tctagcagct gggcaccca gacctacatc | 780 |
| tgcaacgtga atcacaagcc cagcaacacc aaggtggaca agaaagttga acccaaatct | 840 |
| tgcgacaaaa ctcacacatg cccaccgtgc ccagcacctc cagtcgcgg accgtcagtc | 900 |
| ttcctcttcc ctccaaaacc caaggacacc ctcatgatct cccggacccc tgaggtcaca | 960 |
| tgcgtggtgg tggacgtgag ccacgaagac cctgaggtca agttcaactg gtacgtggac | 1020 |
| ggcgtggagg tgcataatgc caagacaaag ccgcgggagg agcagtacaa cagcacgtac | 1080 |
| cgtgtggtca gcgtcctcac cgtcctgcac caggactggc tgaatggcaa ggagtacaag | 1140 |
| tgcaaggtct ccaacaaagg cctcccagc tccatcgaga aaaccatctc caaagccaaa | 1200 |
| gggcagcccc gagaaccaca ggtgtacacc ctgcctccat cccgggatga gctgaccaag | 1260 |
| aaccaggtca gcctgacctg cctggtcaaa ggcttctatc ccagcgacat cgccgtggag | 1320 |
| tgggagagca atgggcagcc ggagaacaac tacaagacca cgcctcccgt gctggactcc | 1380 |
| gacggctcct tcttcctcta cagcaagctc accgtggaca agagcaggtg gcagcagggg | 1440 |
| aacgtcttct catgctccgt gatgcatgag gctctgcaca accactacac gcagaagagc | 1500 |
| ctctcccctgt ctccgggtaa a | 1521 |

<210> SEQ ID NO 111
<211> LENGTH: 1518
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

| | |
|---|---|
| gaagtgcagc tggtggagtc tgaggaggc ttggtccagc ctgggggtc cctgagactc | 60 |

```
tcctgtgcag cctctgggtt caatattaag gacacttaca tccactgggt ccgccaggct    120
ccagggaagg ggctggagtg ggtcgcacgt atttatccta ccaatggtta cacacgctac    180
gcagactccg tgaagggccg attcaccatc tccgcagaca cttccaagaa cacggcgtat    240
cttcaaatga cagcctgag agccgaggac acggccgtgt attactgttc ggggggtggc    300
ggaagcctga aatgttacca acatggtaaa gttgtgactt gtcatcgaga tatgaagttt    360
tgctatcata acactggcat gccttttcga aatctcaagc tcatcctaca gggatgttct    420
tcttcgtgca gtgaaacaga aaacaataag tgttgctcaa cagacagatg caacaaaggc    480
ggaggtggga gttggggcca aggaaccctg gtcaccgtct cctcagcctc caccaagggc    540
ccatcggtct tccccctggc accctcctcc aagagcacct ctgggggcac agcggccctg    600
ggctgcctgg tcaaggacta cttccccgaa ccggtgacgg tgtcgtggaa ctcaggcgcc    660
ctgaccagcg gcgtgcacac cttcccggct gtcctacagt cctcaggact ctactccctc    720
agcagcgtgg tgactgtgcc ctctagcagc ttgggcaccc agacctacat ctgcaacgtg    780
aatcacaagc ccagcaacac caaggtggac aagaaagttg aacccaaatc ttgcgacaaa    840
actcacacat gcccaccgtg cccagcacct ccagtcgccg gaccgtcagt cttcctcttc    900
cctccaaaac ccaaggacac cctcatgatc tcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggagtacaa gtgcaaggtc   1140
tccaacaaag gcctcccaag ctccatcgag aaaaccatct ccaaagccaa agggcagccc   1200
cgagaaccac aggtgtacac cctgcctcca tcccgggatg agctgaccaa gaaccaggtc   1260
agcctgacct gcctggtcaa aggcttctat cccagcgaca tcgccgtgga gtgggagagc   1320
aatgggcagc cggagaacaa ctacaagacc acgcctcccg tgctggactc cgacggctcc   1380
ttcttcctct acagcaagct caccgtggac aagagcaggt ggcagcaggg gaacgtcttc   1440
tcatgctccg tgatgcatga ggctctgcac aaccactaca cgcagaagag cctctccctg   1500
tctccgggta aatgataa                                                  1518
```

<210> SEQ ID NO 112  
<211> LENGTH: 1552  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 112

```
gaggtgcagc tggtggagtc tggaggaggc ttggtccagc ctgggggtc cctgagactc     60 tcctgtgcag cctctgggtt caatattaag gacacttaca tccactgggt ccgccaggct    120
ccagggaagg ggctggagtg ggtcgcacgt atttatccta ccaatggtta cacacgctac    180
gcagactccg tgaagggccg attcaccatc tccgcagaca cttccaagaa cacggcgtat    240
cttcaaatga cagcctgag agccgaggac acggccgtgt attactgttc gagaggaggt    300
ggcgggagcg actcttggat ggaagaagtt atcaaactgt gcggtcgtga actggttcgt    360
gctcagatcg ctatctgcgg tatgtctacc tggtctaaac gttctctgtc tcaggaaatc    420
gagggccgta aaaaacgtca gctgtactct gctctggcta caaatgctg ccacgttggt    480 tgcaccaaac gttctctggc tcgtttctgc ggcggaggtg ggagtgacta ctggggccaa    540
```

```
ggaaccctgg tcaccgtctc ctcagcctcc accagggcc catcggtctt cccctggca      600
ccctcctcca agagcacctc tgggggcaca gcggccctgg gctgcctggt caaggactac    660
ttccccgaac cggtgacggt gtcgtggaac tcaggcgccc tgaccagcgg cgtgcacacc    720
ttccggctg tcctacagtc ctcaggactc tactccctca gcagcgtggt gactgtgccc     780
tctagcagct tgggcaccca gacctacatc tgcaacgtga atcacaagcc cagcaacacc    840
aaggtggaca agaaagttga acccaaatct tgcgacaaaa ctcacacatg cccaccgtgc    900
ccagcacctc cagtcgccgg accgtcagtc ttcctcttcc ctccaaaacc caaggacacc    960
ctcatgatct cccggacccc tgaggtcaca tgcgtggtgg tggacgtgag ccacgaagac   1020
cctgaggtca agttcaactg gtacgtggac ggcgtggagg tgcataatgc caagacaaag   1080
ccgcgggagg agcagtacaa cagcacgtac cgtgtggtca gcgtcctcac cgtcctgcac   1140
caggactggc tgaatggcaa ggagtacaag tgcaaggtct ccaacaaagg cctcccaagc   1200
tccatcgaga aaaccatctc caaagccaaa gggcagcccc gagaaccaca ggtgtacacc   1260
ctgcctccat cccgggatga gctgaccaag aaccaggtca gcctgacctg cctggtcaaa   1320
ggcttctatc ccagcgacat cgccgtggag tgggagagca atgggcagcc ggagaacaac   1380
tacaagacca cgcctcccgt gctggactcc gacggctcct tcttcctcta cagcaagctc   1440
accgtggaca gagcaggtg gcagcagggg aacgtcttct catgctccgt gatgcatgag   1500
gctctgcaca accactacac gcagaagagc ctctccctgt ctccgggtaa at           1552
```

<210> SEQ ID NO 113
<211> LENGTH: 1578
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 113

```
gaggtgcagc tggtggagtc tggaggaggc ttggtccagc ctgggggtc cctgagactc      60
tcctgtgcag cctctgggtt caatattaag gacacttaca tccactgggt ccgccaggct    120
ccagggaagg gctggagtg gtcgcacgt atttatccta ccaatggtta cacacgctac      180
gcagactccg tgaagggccg attccaccatc tccgcagaca cttccaagaa cacggcgtat    240
cttcaaatga acagcctgag agccgaggac acggccgtgt attactgttc gagaggaggt    300
ggcgggagcg actcttggat ggaagaagtt atcaaactgt gcggtcgtga actggttcgt    360
gctcagatcg ctatctgcgg tatgtctacc tggtctaaac gttctctgtc tcaggaagac    420
gctccgcaga cccccgcgtcc ggttatcgag ggccgtaaaa acgtcagct gtactctgct   480
ctggctaaca aatgctgcca cgttggttgc accaaacgtt ctctggctcg tttctgcggc    540
ggaggtggga gtgactactg gggccaagga accctggtca ccgtctcctc agcctccacc    600
aagggcccat cggtcttccc cctggcaccc tcctccaaga gcacctctgg ggcacagcg     660
gccctgggct gcctggtcaa ggactacttc cccgaaccgg tgacggtgtc gtggaactca    720
ggcgccctga ccagcggcgt gcacaccttc cggctgtcc tacagtcctc aggactctac    780
tcctcagca gcgtggtgac tgtgccctct agcagcttgg gcacccagac ctacatctgc    840
aacgtgaatc acaagcccag caacaccaag gtggacaaga agttgaacc caaatcttgc    900
gacaaaactc acacatgccc accgtgccca gcacctccag tcgccggacc gtcagtcttc    960
ctcttccctc caaaacccaa ggacaccctc atgatctccc ggaccctga ggtcacatgc   1020
```

```
gtggtggtgg acgtgagcca cgaagaccct gaggtcaagt tcaactggta cgtggacggc    1080
gtggaggtgc ataatgccaa gacaaagccg cgggaggagc agtacaacag cacgtaccgt    1140
gtggtcagcg tcctcaccgt cctgcaccag gactggctga atggcaagga gtacaagtgc    1200
aaggtctcca acaaaggcct cccaagctcc atcgagaaaa ccatctccaa agccaaaggg    1260
cagccccgag aaccacaggt gtacaccctg cctccatccc gggatgagct gaccaagaac    1320
caggtcagcc tgacctgcct ggtcaaaggc ttctatccca gcgacatcgc cgtggagtgg    1380
gagagcaatg ggcagccgga gaacaactac aagaccacgc ctcccgtgct ggactccgac    1440
ggctccttct tcctctacag caagctcacc gtggacaaga gcaggtggca gcaggggaac    1500
gtcttctcat gctccgtgat gcatgaggct ctgcacaacc actacacgca gaagagcctc    1560
tccctgtctc cgggtaaa                                                  1578

<210> SEQ ID NO 114
<211> LENGTH: 1929
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
gaggtgcagc tggtggagtc tggaggaggc ttggtccagc ctggggggtc cctgagactc      60
tcctgtgcag cctctgggtt caatattaag gacacttaca tccactgggt ccgccaggct     120
ccagggaagg ggctggagtg ggtcgcacgt atttatccta ccaatggtta cacacgctac     180
gcagactccg tgaagggccg attcaccatc tccgcagaca cttccaagaa cacggcgtat     240
cttcaaatga acagcctgag agccgaggac acggccgtgt attactgttc gagaggtggt     300
ggcggaagct tcccaaccat tcccttatcc aggcttttg acaacgctat gctccgcgcc     360
catcgtctgc accagctggc cttgacacc taccaggagt ttgaagaagc ctatatccca     420
aaggaacaga gtattcatt cctgcagaac ccccagacct ccctctgttt ctcagagtct     480
attccgacac cctccaacag ggaggaaaca caacagaaat ccaacctaga gctgctccgc     540
atctccctgc tgctcatcca gtcgtggctg gagcccgtgc agttcctcag gagtgtcttc     600
gccaacagcc tggtgtacgg cgcctctgac agcaacgtct atgacctcct aaaggaccta     660
gaggaaggca tccaaacgct gatggggagg ctggaagatg gcagccccg gactgggcag     720 atcttcaagc agacctacag caagttcgac acaaactcac acaacgatga cgcactactc     780
aagaactacg gcctgctcta ctgcttcagg aaggacatgg acaaggtcga cattcctg       840 cgcatcgtgc agtgccgctc tgtggagggc agctgtggct tcggcggagg tgggagtgac     900
tactggggcc aaggaaccct ggtcaccgtc tcctcagcct ccaccaaggg cccatcggtc     960
ttccccctgg cacctcctc caagagcacc tctgggggca gcggccct gggctgcctg       1020 gtcaaggact acttccccga accggtgacg gtgtcgtgga actcaggcgc cctgaccagc    1080
ggcgtgcaca ccttcccggc tgtcctacag tcctcaggac tctactccct cagcagcgtg    1140
gtgactgtgc cctctagcag cttgggcacc cagacctaca tctgcaacgt gaatcacaag    1200
cccagcaaca ccaaggtgga caagaaagtt gaacccaaat cttgcgacaa aactcacaca    1260
tgcccaccgt gcccagcacc tccagtcgcc ggaccgtcag tcttcctctt ccctccaaaa    1320
cccaaggaca cctcatgat ctcccggacc cctgaggtca catgcgtggt ggtggacgtg    1380
agccacgaag accctgaggt caagttcaac tggtacgtgg acggcgtgga ggtgcataat    1440
```

| | |
|---|---|
| gccaagacaa agccgcggga ggagcagtac aacagcacgt accgtgtggt cagcgtcctc | 1500 |
| accgtcctgc accaggactg gctgaatggc aaggagtaca agtgcaaggt ctccaacaaa | 1560 |
| ggcctcccaa gctccatcga gaaaaccatc tccaaagcca agggcagcc ccgagaacca | 1620 |
| caggtgtaca ccctgcctcc atcccgggat gagctgacca gaaccaggt cagcctgacc | 1680 |
| tgcctggtca aaggcttcta tcccagcgac atcgccgtgg agtgggagag caatgggcag | 1740 |
| ccggagaaca actacaagac cacgcctccc gtgctggact ccgacggctc cttcttcctc | 1800 |
| tacagcaagc tcaccgtgga caagagcagg tggcagcagg ggaacgtctt ctcatgctcc | 1860 |
| gtgatgcatg aggctctgca caaccactac acgcagaaga gcctctccct gtctccgggt | 1920 |
| aaatgataa | 1929 |

<210> SEQ ID NO 115
<211> LENGTH: 1855
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

| | |
|---|---|
| gaggtgcagc tggtggagtc tggaggaggc ttggtccagc ctggggggtc cctgagactc | 60 |
| tcctgtgcag cctctgggtt caatattaag gacacttaca tccactgggt ccgccaggct | 120 |
| ccagggaagg ggctggagtg ggtcgcacgt atttatccta ccaatggtta cacacgctac | 180 |
| gcagactccg tgaagggccg attcaccatc tccgcagaca cttccaagaa cacggcgtat | 240 |
| cttcaaatga acagcctgag agccgaggac acggccgtgt attactgttc gagagggtgg | 300 |
| tggcggaagc atgagctaca acttgcttgg attcctacaa agaagcagca attttcagtg | 360 |
| tcagaagctc ctgtggcaat tgaatgggag gcttgaatac tgcctcaagg acaggatgaa | 420 |
| ctttgacatc cctgaggaga ttaagcagct gcagcagttc cagaaggagg acgccgcatt | 480 |
| gaccatctat gagatgctcc agaacatctt tgctattttc agacaagatt catctagcac | 540 |
| tggctggaat gagactattg ttgagaacct cctggctaat gtctatcatc agataaacca | 600 |
| tctgaagaca gtcctggaag aaaaactgga gaagaagat ttcaccaggg gaaaactcat | 660 |
| gagcagtctg cacctgaaaa gatattatgg gaggattctg cattacctga aggccaagga | 720 |
| gtacagtcac tgtgcctgga ccatagtcag agtggaaatc ctaaggaact tttacttcat | 780 |
| taacagactt acaggttacc tccgaaacgg cggaggtggg agtgactact ggggccaagg | 840 |
| aaccctggtc accgtctcct cagcctccac caagggccca tcggtcttcc ccctggcacc | 900 |
| ctcctccaag agcacctctg ggggcacagc ggccctgggc tgcctggtca aggactactt | 960 |
| ccccgaaccg gtgacggtgt cgtggaactc aggcgccctg accagcggcg tgcacacctt | 1020 |
| cccggctgtc ctacagtcct caggactcta ctccctcagc agcgtggtga ctgtgccctc | 1080 |
| tagcagcttg ggcacccaga cctacatctg caacgtgaat cacaagccca gcaacaccaa | 1140 |
| ggtggacaag aaagttgaac ccaaatcttg cgacaaaact cacacatgcc caccgtgccc | 1200 |
| agcacctcca gtcgccggac cgtcagtctt cctcttcccc ccaaaaccca aggacaccct | 1260 |
| catgatctcc cggacccctg aggtcacatg cgtggtggtg gacgtgagcc acgaagaccc | 1320 |
| tgaggtcaag ttcaactggt acgtggacgg cgtggaggtg cataatgcca agacaaagcc | 1380 |
| gcgggaggag cagtacaaca gcacgtaccg tgtggtcagc gtcctcaccg tcctgcacca | 1440 |
| ggactggctg aatggcaagg agtacaagtg caaggtctcc aacaaaggcc tcccaagctc | 1500 |

```
catcgagaaa accatctcca aagccaaagg gcagccccga gaaccacagg tgtacaccct    1560
gcctccatcc cgggatgagc tgaccaagaa ccaggtcagc ctgacctgcc tggtcaaagg    1620
cttctatccc agcgacatcg ccgtggagtg ggagagcaat gggcagccgg agaacaacta    1680
caagaccacg cctcccgtgc tggactccga cggctccttc ttcctctaca gcaagctcac    1740
cgtggacaag agcaggtggc agcagggaa cgtcttctca tgctccgtga tgcatgaggc    1800
tctgcacaac cactacacgc agaagagcct ctccctgtct ccgggtaaat gataa        1855
```

<210> SEQ ID NO 116
<211> LENGTH: 1539
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 116

```
caggtgaccc tgcgcgagtc cggccctgca ctggtgaagc ccacccagac cctgaccctg     60
acctgcacct tctccggctt ctccctgtcc acctccggca tgtccgtggg ctggatccgg    120
cagcctcccg gcaaggccct ggagtggctg gctgacatct ggtgggacga caagaaggac    180
tacaacccct ccctgaagtc ccgcctgacc atctccaagg acacctccaa gaaccaggtg    240
gtgctgaagg tgaccaacat ggaccccgcc gacaccgcca cctactactg cgcccgctct    300
gggggtggcg gaagcctgaa atgttaccaa catggtaaag ttgtgacttg tcatcgagat    360
atgaagtttt gctatcataa cactggcatg ccttttcgaa atctcaagct catcctacag    420
ggatgttctt cttcgtgcag tgaaacagaa acaataagt gttgctcaac agacagatgc    480
aacaaaggcg gaggtgggag ttactttgac gtgtggggag ccgtaccac cgtgaccgtg    540 tcttccgcct ccaccaaggg cccatcggtc ttccccctgg cacctcctc caagagcacc    600 tctgggggca gcggccct gggctgcctg gtcaaggact acttccccga accggtgacg    660
gtgtcgtgga actcaggcgc cctgaccagc ggcgtgcaca ccttcccggc tgtcctacag    720
tcctcaggac tctactccct cagcagcgtg gtgactgtgc cctctagcag cttgggcacc    780
cagacctaca tctgcaacgt gaatcacaag cccagcaaca ccaaggtgga caagaaagtt    840
gaacccaaat cttgcgacaa aactcacaca tgcccaccgt gccagcacc tccagtcgcc    900 ggaccgtcag tcttcctctt ccctccaaaa cccaaggaca cctcatgat ctcccggacc    960 cctgaggtca catgcgtggt ggtggacgtg agccacgaag accctgaggt caagttcaac    1020
tggtacgtgg acggcgtgga ggtgcataat gccaagacaa agccgcggga ggagcagtac    1080
aacagcacgt accgtgtggt cagcgtcctc accgtcctgc accaggactg gctgaatggc    1140
aaggagtaca agtgcaaggt ctccaacaaa gccctcccaa gctccatcga gaaaaccatc    1200
tccaaagcca aagggcagcc ccgagaacca caggtgtaca ccctgcctcc atcccgggat    1260
gagctgacca agaaccaggt cagcctgacc tgcctggtca aaggcttcta tcccagcgac    1320
atcgccgtgg agtgggagag caatgggcag ccggagaaca actacaagac cacgcctccc    1380
gtgctggact ccgacggctc cttcttcctc tacagcaagc tcaccgtgga caagagcagg    1440
tggcagcagg ggaacgtctt ctcatgctcc gtgatgcatg aggctctgca caaccactac    1500
acgcagaaga gcctctccct gtctccgggt aaatgataa                            1539
```

<210> SEQ ID NO 117
<211> LENGTH: 1911

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 117

```
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga agagcagact gtccattacc aaggacaact ctaaaagtca ggtgtcactg     240
agcgtgagct ccgtcaccac agaggatagt gcaacttact attgcggggg tggcggaagc     300
gggggtggcg gaagcgctcc tctgggcggt cctgaaccag cacagtacga ggaactgaca     360
ctgttgttcc atggagcctt gcagctgggc caggccctca acggcgtgta ccgcgccaca     420
gaggcacgtt tgaccgaggc cggacacagc ctgggtttgt acgacagagc cctggagttt     480
ctgggtaccg aagtgcgtca gggccaggac gcaactcagg agctgagaac ctccctctct     540
gagatccagg tggaggagga cgccctgcac ctgcgcgccg aggcgacagc acgtctcttg     600
ggagaagttg ctcgcgctca gcaggccctg cgtgataccg tgcggagact ccaagttcag     660
ctcagaggcg cttggctcgg acaggcgcat caggagttcg agaccctgaa agctcgtgcc     720
gacaaacagt cccacctgct gtgggcgctc accggtcacg tccagcgcca gaacgcgaa      780
atggccgagc agcagcaatg gctgcgccaa atccagcagc gcctgcatac cgcggccctg     840
ccagcgtaag gcggaggtgg gagtggcgga ggtgggagtc atgtggatgt ctggggacag     900
ggcctgctgg tgacagtctc tagtgcttcc acaactgcac caaaggtgta cccctgtca      960
agctgctgtg gggacaaatc ctctagtacc gtgacactgg gatgcctggt ctcaagctat    1020
atgcccgagc ctgtgactgt cacctggaac tcaggagccc tgaaaagcgg agtgcacacc    1080
ttcccagctg tgctgcagtc ctctggcctg tatagcctga gttcaatggt gacagtcccc    1140
ggcagtactt cagggcagac cttcacctgt aatgtggccc atcctgccag ctccaccaaa    1200
gtggacaaag cagtggaacc caaatcttgc gacaaaactc acacatgccc accgtgccca    1260
gcacctgaac tcctgggggg accgtcagtc ttcctcttcc ccccaaaacc caaggacacc    1320
ctcatgatct cccggacccc tgaggtcaca tgcgtggtgg tggacgtgag ccacgaagac    1380
cctgaggtca agttcaactg gtacgtggac ggcgtggagg tgcataatgc caagacaaag    1440
ccgcgggagg agcagtacaa cagcacgtac cgtgtggtca gcgtcctcac cgtcctgcac    1500
caggactggc tgaatggcaa ggagtacaag tgcaaggtct ccaacaaagc cctcccagcc    1560
cccatcgaga aaaccatctc caaagccaaa gggcagcccc gagaaccaca ggtgtacacc    1620
ctgcccccat cccgggatga gctgaccaag aaccaggtca gcctgacctg cctggtcaaa    1680
ggcttctatc ccagcgacat cgccgtggag tgggagagca atgggcagcc ggagaacaac    1740
tacaagacca cgcctcccgt gctggactcc gacggctcct tcttcctcta cagcaagctc    1800
accgtggaca agagcaggtg gcagcagggg aacgtcttct catgctccgt gatgcatgag    1860
gctctgcaca accactacac gcagaagagc ctctccctgt ctccgggtaa a             1911
```

<210> SEQ ID NO 118
<211> LENGTH: 1881
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 118

```
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga agagcagact gtccattacc aaggacaact ctaaaagtca ggtgtcactg     240
agcgtgagct ccgtcaccac agaggatagt gcaacttact attgcggggg tggcggaagc     300
gctcctctgg gcggtcctga accagcacag tacgaggaac tgacactgtt gttccatgga     360
gccttgcagc tgggccaggc cctcaacggc gtgtaccgcg ccacagaggc acgtttgacc     420
gaggccggac acagcctggg tttgtacgac agagccctgg agtttctggg taccgaagtg     480
cgtcagggcc aggacgcaac tcaggagctg agaacctccc tctctgagat ccaggtggag     540
gaggacgccc tgcacctgcg cgccgaggcg acagcacgct ctttgggaga agttgctcgc     600
gctcagcagg ccctgcgtga taccgtgcgg agactccaag ttcagctcag aggcgcttgg     660
ctcggacagg cgcatcagga gttcgagacc ctgaaagctc gtgccgacaa acagtcccac     720
ctgctgtggg cgctcaccgg tcacgtccag cgccagcaac gcgaaatggc cgagcagcag     780
caatggctgc gccaaatcca gcagcgcctg cataccgcgg ccctgccagc gtaaggcgga     840
ggtgggagtc atgtggatgt ctggggacag ggcctgctgg tgacagtctc tagtgcttcc     900
acaactgcac caaaggtgta ccccctgtca agctgctgtg gggacaaatc ctctagtacc     960
gtgacactgg gatgcctggt ctcaagctat atgcccgagc ctgtgactgt cacctggaac    1020
tcaggagccc tgaaaagcgg agtgcacacc ttcccagctg tgctgcagtc ctctggcctg    1080
tatagcctga gttcaatggt gacagtcccc ggcagtactt cagggcagac cttcacctgt    1140
aatgtggccc atcctgccag ctccaccaaa gtggacaaag cagtggaacc caaatcttgc    1200
gacaaaactc acacatgccc accgtgccca gcacctgaac tcctgggggg accgtcagtc    1260
ttcctcttcc ccccaaaacc caaggacacc ctcatgatct cccggacccc tgaggtcaca    1320
tgcgtggtgg tggacgtgag ccacgaagac cctgaggtca agttcaactg gtacgtggac    1380
ggcgtggagg tgcataatgc caagacaaag ccgcgggagg agcagtacaa cagcacgtac    1440
cgtgtggtca gcgtcctcac cgtcctgcac caggactggc tgaatggcaa ggagtacaag    1500
tgcaaggtct ccaacaaagc cctcccagcc cccatcgaga aaaccatctc aaagccaaaa    1560
gggcagcccc gagaaccaca ggtgtacacc ctgcccccat cccgggatga gctgaccaag    1620
aaccaggtca gcctgacctg cctggtcaaa ggcttctatc ccagcgacat cgccgtggag    1680
tgggagagca atgggcagcc ggagaacaac tacaagacca cgcctcccgt gctggactcc    1740
gacggctcct tcttcctcta cagcaagctc accgtggaca agagcaggtg gcagcagggg    1800
aacgtcttct catgctccgt gatgcatgag gctctgcaca accactacac gcagaagagc    1860
ctctccctgt ctccgggtaa a                                              1881
```

<210> SEQ ID NO 119
<211> LENGTH: 1920
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

```
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga agagcagact gtccattacc aaggacaact ctaaaagtca ggtgtcactg     240
agcgtgagct ccgtcaccac agaggatagt gcaacttact attgcggggg tggcggaagc     300
ttcccaacca ttcccttatc caggcttttt gacaacgcta tgctccgcgc ccatcgtctg     360
caccagctgg cctttgacac ctaccaggag tttgaagaag cctatatccc aaaggaacag     420
aagtattcat cctgcagaa cccccagacc tccctctgtt tctcagagtc tattccgaca      480
ccctccaaca gggaggaaac acaacagaaa tccaacctag agctgctccg catctccctg     540
ctgctcatcc agtcgtggct ggagcccgtg cagttcctca ggagtgtctt cgccaacagc     600
ctggtgtacg gcgcctctga cagcaacgtc tatgacctcc taaggaccct agaggaaggc     660
atccaaacgc tgatggggag gctggaagat ggcagccccc ggactgggca gatcttcaag     720
cagacctaca gcaagttcga cacaaactca cacaacgatg acgcactact caagaactac     780
gggctgctct actgcttcag gaaggacatg gacaaggtcg acattcctgc gcatcgtg      840 cagtgccgct ctgtggaggg cagctgtggc ttcggcggag gtgggagtca tgtggatgtc     900
tggggacagg gcctgctggt gacagtctct agtgcttcca caactgcacc aaaggtgtac     960
cccctgtcaa gctgctgtgg ggacaaatcc tctagtaccg tgacactggg atgcctggtc    1020
tcaagctata tgcccgagcc tgtgactgtc acctggaact caggagccct gaaaagcgga    1080
gtgcacacct tcccagctgt gctgcagtcc tctggcctgt atagcctgag ttcaatggtg    1140
acagtccccg gcagtacttc agggcagacc ttcacctgta atgtggccca tcctgccagc    1200
tccaccaaag tggacaaagc agtggaaccc aaatcttgcg acaaaactca cacatgccca    1260
ccgtgcccag cacctgaact cctgggggga ccgtcagtct tcctcttccc cccaaaaccc    1320
aaggacaccc tcatgatctc ccggacccct gaggtcacat gcgtggtggt ggacgtgagc    1380
cacgaagacc ctgaggtcaa gttcaactgg tacgtggacg gcgtggaggt gcataatgcc    1440
aagacaaagc cgcgggagga gcagtacaac agcacgtacc gtgtggtcag cgtcctcacc    1500
gtcctgcacc aggactggct gaatggcaag gagtacaagt gcaaggtctc caacaaagcc    1560
ctcccagccc ccatcgagaa aaccatctcc aaagccaaag gcagccccg  agaaccacag    1620 gtgtacaccc tgcccccatc ccgggatgag ctgaccaaga accaggtcag cctgacctgc    1680
ctggtcaaag gcttctatcc cagcgacatc gccgtggagt gggagagcaa tgggcagccg    1740
gagaacaact acaagaccac gcctcccgtg ctggactccg acggctcctt cttcctctac    1800
agcaagctca ccgtggacaa gagcaggtgg cagcagggga acgtcttctc atgctccgtg    1860
atgcatgagg ctctgcacaa ccactacacg cagaagagcc tctccctgtc tccgggtaaa    1920
```

<210> SEQ ID NO 120
<211> LENGTH: 1845
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

```
caggtccagc tgagagagag cggcccttca ctggtcaagc catcccagac actgagcctg      60
acatgcacag caagcgggtt ttcactgagc gacaaggcag tgggatgggt ccgacaggca     120
```

```
ccaggaaaag ccctggaatg gctgggcagc atcgataccg gcgggaacac agggtacaat      180
cccggactga agagcagact gtccattacc aaggacaact ctaaaagtca ggtgtcactg      240
agcgtgagct ccgtcaccac agaggatagt gcaacttact attgcggggg tggcggaagc      300
atgagctaca acttgcttgg attcctacaa agaagcagca attttcagtg tcagaagctc      360
ctgtggcaat tgaatgggag gcttgaatac tgcctcaagg acaggatgaa ctttgacatc      420
cctgaggaga ttaagcagct gcagcagttc agaaggagg acgccgcatt gaccatctat       480
gagatgctcc agaacatctt tgctattttc agacaagatt catctagcac tggctggaat      540
gagactattg ttgagaacct cctggctaat gtctatcatc agataaacca tctgaagaca      600
gtcctggaag aaaaactgga gaagaagat ttcaccaggg gaaaactcat gagcagtctg        660
cacctgaaaa gatattatgg gaggattctg cattacctga aggccaagga gtacagtcac      720
tgtgcctgga ccatagtcag agtggaaatc ctaaggaact tttacttcat taacagactt      780
acaggttacc tccgaaacgg cggaggtggg agtcatgtgg atgtctgggg acagggcctg      840
ctggtgacag tctctagtgc ttccacaact gcaccaaagg gtaccccct gtcaagctgc       900 tgtgggggaca atcctctag taccgtgaca ctgggatgcc tggtctcaag ctatatgccc       960
gagcctgtga ctgtcacctg gaactcagga gccctgaaaa gcggagtgca cccttccca     1020 gctgtgctgc agtcctctgg cctgtatagc ctgagttcaa tggtgacagt ccccggcagt     1080
acttcagggc agaccttcac ctgtaatgtg gcccatcctg ccagtccac caaagtggac      1140 aaagcagtgg aacccaaatc ttgcgacaaa actcacacat gcccaccgtg cccagcacct     1200
gaactcctgg gggaccgtc agtcttcctc ttccccccaa acccaagga cacctcatg        1260 atctccccgga ccctgaggt cacatgcgtg gtggtggacg tgagccacga agaccctgag      1320
gtcaagttca actggtacgt ggacggcgtg gaggtgcata atgccaagac aaagccgcgg     1380
gaggagcagt acaacagcac gtaccgtgtg gtcagcgtcc tcaccgtcct gcaccaggac     1440
tggctgaatg gcaaggagta caagtgcaag gtctccaaca aagccctccc agcccccatc     1500
gagaaaacca tctccaaagc caaagggcag ccccgagaac acaggtgta cacccctgccc     1560 ccatcccggg atgagctgac caagaaccag gtcagcctga cctgcctggt caaaggcttc     1620
tatcccagcg acatcgccgt ggagtgggag agcaatgggc agccggagaa caactacaag     1680
accacgcctc ccgtgctgga ctccgacggc tccttcttcc tctacagcaa gctcaccgtg     1740
gacaagagca ggtggcagca ggggaacgtc ttctcatgct ccgtgatgca tgaggctctg     1800
cacaaccact acacgcagaa gagcctctcc ctgtctccgg gtaaa                      1845
```

<210> SEQ ID NO 121
<211> LENGTH: 1944
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121

```
caggtccagc tgagagagag cggcccttca ctggtcaagc catcccagac actgagcctg       60
acatgcacag caagcgggtt ttcactgagc gacaaggcag tgggatgggt ccgacaggca      120
ccaggaaaag ccctggaatg gctgggcagc atcgataccg gcgggaacac agggtacaat      180
cccggactga agagcagact gtccattacc aaggacaact ctaaaagtca ggtgtcactg      240
agcgtgagct ccgtcaccac agaggatagt gcaacttact attgcaccctc tgtgcaccag    300
```

```
ggaggtggcg aagcttccc aaccattccc ttatccaggc tttttgacaa cgctatgctc    360
cgcgcccatc gtctgcacca gctggccttt gacacctacc aggagtttga agaagcctat   420
atcccaaagg aacagaagta ttcattcctg cagaacccc agacctccct ctgtttctca    480
gagtctattc cgacaccctc caacagggag gaaacacaac agaaatccaa cctagagctg   540
ctccgcatct ccctgctgct catccagtcg tggctggagc ccgtgcagtt cctcaggagt   600
gtcttcgcca acagcctggt gtacggcgcc tctgacagca cgtctatga cctcctaaag    660
gacctagagg aaggcatcca aacgctgatg gggaggctgg aagatggcag ccccggact    720
gggcagatct tcaagcagac ctacagcaag ttcgacacaa actcacacaa cgatgacgca   780
ctactcaaga actacgggct gctctactgc ttcaggaagg acatggacaa ggtcgagaca   840
ttcctgcgca tcgtgcagtg ccgctctgtg gagggcagct gtggcttcgg cggaggtggg   900
agttggcatg tggatgtctg gggacagggc ctgctggtga cagtctctag tgcttccaca   960
actgcaccaa aggtgtaccc cctgtcaagc tgctgtgggg acaaatcctc tagtaccgtg  1020
acactgggat gcctggtctc aagctatatg cccgagcctg tgactgtcac ctggaactca  1080
ggagccctga aaagcggagt gcacaccttc ccagctgtgc tgcagtcctc tggcctgtat  1140
agcctgagtt caatggtgac agtccccggc agtacttcag gcagaccttt cacctgtaat  1200
gtggcccatc ctgccagctc caccaaagtg gacaaagcag tggaacccaa atcttgcgac  1260
aaaactcaca catgcccacc gtgcccagca cctgaactcc tggggggacc gtcagtcttc  1320
ctcttccccc caaaacccaa ggacaccctc atgatctccc ggacccctga ggtcacatgc  1380
gtggtggtgg acgtgagcca cgaagaccct gaggtcaagt tcaactggta cgtggacggc  1440
gtggaggtgc ataatgccaa gacaaagccg cgggaggagc agtacaacag cacgtaccgt  1500
gtggtcagcg tcctcaccgt cctgcaccag gactggctga atggcaagga gtacaagtgc  1560
aaggtctcca acaaagccct cccagccccc atcgagaaaa ccatctccaa agccaagggg  1620
cagccccgag aaccacaggt gtacaccctg cccccatccc gggatgagct gaccaagaac  1680
caggtcagcc tgacctgcct ggtcaaaggc ttctatccca gcgacatcgc cgtggagtgg  1740
gagagcaatg ggcagccgga gaacaactac aagaccacgc ctcccgtgct ggactccgac  1800
ggctccttct tcctctacag caagctcacc gtggacaaga gcaggtggca gcaggggaac  1860
gtcttctcat gctccgtgat gcatgaggct ctgcacaacc actacacgca gaagagcctc  1920
tccctgtctc cgggtaaatg ataa                                         1944
```

<210> SEQ ID NO 122
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Gly Gly Gly Ser
            20                  25                  30

Ala Pro Pro Arg Leu Ile Cys Asp Ser Arg Val Leu Glu Arg Tyr Leu
        35                  40                  45

Leu Glu Ala Lys Glu Ala Glu Asn Ile Thr Thr Gly Cys Ala Glu His
    50                  55                  60

```
Cys Ser Leu Asn Glu Asn Ile Thr Val Pro Asp Thr Lys Val Asn Phe
 65                  70                  75                  80

Tyr Ala Trp Lys Arg Met Glu Val Gly Gln Gln Ala Val Glu Val Trp
                 85                  90                  95

Gln Gly Leu Ala Leu Leu Ser Glu Ala Val Leu Arg Gly Gln Ala Leu
            100                 105                 110

Leu Val Asn Ser Ser Gln Pro Trp Glu Pro Leu Gln Leu His Val Asp
        115                 120                 125

Lys Ala Val Ser Gly Leu Arg Ser Leu Thr Thr Leu Leu Arg Ala Leu
130                 135                 140

Gly Ala Gln Lys Glu Ala Ile Ser Pro Pro Asp Ala Ala Ser Ala Ala
145                 150                 155                 160

Pro Leu Arg Thr Ile Thr Ala Asp Thr Phe Arg Lys Leu Phe Arg Val
                165                 170                 175

Tyr Ser Asn Phe Leu Arg Gly Lys Leu Lys Leu Tyr Thr Gly Glu Ala
            180                 185                 190

Cys Arg Thr Gly Asp Arg Gly Gly Gly Ser Thr Ala Val Ala Trp
        195                 200                 205

Tyr Gln Gln Lys Pro Gly Lys Ala Pro Lys Leu Leu Ile Tyr Ser Ala
210                 215                 220

Ser Phe Leu Tyr Ser Gly Val Pro Ser Arg Phe Ser Gly Ser Arg Ser
225                 230                 235                 240

Gly Thr Asp Phe Thr Leu Thr Ile Ser Ser Leu Gln Pro Glu Asp Phe
                245                 250                 255

Ala Thr Tyr Tyr Cys Gln Gln His Tyr Thr Thr Pro Pro Thr Phe Gly
            260                 265                 270

Gln Gly Thr Lys Leu Glu Ile Lys Arg Thr Val Ala Ala Pro Ser Val
        275                 280                 285

Phe Ile Phe Pro Pro Ser Asp Glu Gln Leu Lys Ser Gly Thr Ala Ser
290                 295                 300

Val Val Cys Leu Leu Asn Asn Phe Tyr Pro Arg Glu Ala Lys Val Gln
305                 310                 315                 320

Trp Lys Val Asp Asn Ala Leu Gln Ser Gly Asn Ser Gln Glu Ser Val
                325                 330                 335

Thr Glu Gln Asp Ser Lys Asp Ser Thr Tyr Ser Leu Ser Ser Thr Leu
            340                 345                 350

Thr Leu Ser Lys Ala Asp Tyr Glu Lys His Lys Val Tyr Ala Cys Glu
        355                 360                 365

Val Thr His Gln Gly Leu Ser Ser Pro Val Thr Lys Ser Phe Asn Arg
370                 375                 380

Gly Glu Cys
385

<210> SEQ ID NO 123
<211> LENGTH: 634
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30
```

```
Tyr Ile His Trp Val Arg Gln Ala Pro Gly Lys Gly Leu Glu Trp Val
     35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Gly Gly Ser Thr Pro Leu Gly Pro
                100                 105                 110
Ala Arg Ser Leu Pro Gln Ser Phe Leu Leu Lys Cys Leu Glu Gln Val
                115                 120                 125
Arg Lys Ile Gln Ala Asp Gly Ala Glu Leu Gln Glu Arg Leu Cys Ala
        130                 135                 140
Ala His Lys Leu Cys His Pro Glu Glu Leu Met Leu Leu Arg His Ser
145                 150                 155                 160
Leu Gly Ile Pro Gln Ala Pro Leu Ser Ser Cys Ser Ser Gln Ser Leu
                165                 170                 175
Gln Leu Thr Ser Cys Leu Asn Gln Leu His Gly Gly Leu Phe Leu Tyr
            180                 185                 190
Gln Gly Leu Leu Gln Ala Leu Ala Gly Ile Ser Pro Glu Leu Ala Pro
        195                 200                 205
Thr Leu Asp Thr Leu Gln Leu Asp Val Thr Asp Phe Ala Thr Asn Ile
210                 215                 220
Trp Leu Gln Met Glu Asp Leu Gly Ala Ala Pro Ala Val Gln Pro Thr
225                 230                 235                 240
Gln Gly Ala Met Pro Thr Phe Thr Ser Ala Phe Gln Arg Arg Ala Gly
                245                 250                 255
Gly Val Leu Val Ala Ser Gln Leu His Arg Phe Leu Glu Leu Ala Tyr
            260                 265                 270
Arg Gly Leu Arg Tyr Leu Ala Glu Pro Gly Gly Gly Ser Gly Phe
        275                 280                 285
Tyr Ala Met Asp Tyr Trp Gly Gln Gly Thr Leu Val Thr Val Ser Ser
290                 295                 300
Ala Ser Thr Lys Gly Pro Ser Val Phe Pro Leu Ala Pro Ser Ser Lys
305                 310                 315                 320
Ser Thr Ser Gly Gly Thr Ala Ala Leu Gly Cys Leu Val Lys Asp Tyr
                325                 330                 335
Phe Pro Glu Pro Val Thr Val Ser Trp Asn Ser Gly Ala Leu Thr Ser
            340                 345                 350
Gly Val His Thr Phe Pro Ala Val Leu Gln Ser Ser Gly Leu Tyr Ser
        355                 360                 365
Leu Ser Ser Val Val Thr Val Pro Ser Ser Ser Leu Gly Thr Gln Thr
370                 375                 380
Tyr Ile Cys Asn Val Asn His Lys Pro Ser Asn Thr Lys Val Asp Lys
385                 390                 395                 400
Lys Val Glu Pro Lys Ser Cys Asp Lys Thr His Thr Cys Pro Pro Cys
                405                 410                 415
Pro Ala Pro Glu Leu Leu Gly Gly Pro Ser Val Phe Leu Phe Pro Pro
            420                 425                 430
Lys Pro Lys Asp Thr Leu Met Ile Ser Arg Thr Pro Glu Val Thr Cys
        435                 440                 445
```

```
Val Val Val Asp Val Ser His Glu Asp Pro Glu Val Lys Phe Asn Trp
        450                 455                 460

Tyr Val Asp Gly Val Glu Val His Asn Ala Lys Thr Lys Pro Arg Glu
465                 470                 475                 480

Glu Gln Tyr Asn Ser Thr Tyr Arg Val Val Ser Val Leu Thr Val Leu
                485                 490                 495

His Gln Asp Trp Leu Asn Gly Lys Glu Tyr Lys Cys Lys Val Ser Asn
            500                 505                 510

Lys Ala Leu Pro Ala Pro Ile Glu Lys Thr Ile Ser Lys Ala Lys Gly
        515                 520                 525

Gln Pro Arg Glu Pro Gln Val Tyr Thr Leu Pro Pro Ser Arg Asp Glu
530                 535                 540

Leu Thr Lys Asn Gln Val Ser Leu Thr Cys Leu Val Lys Gly Phe Tyr
545                 550                 555                 560

Pro Ser Asp Ile Ala Val Glu Trp Glu Ser Asn Gly Gln Pro Glu Asn
                565                 570                 575

Asn Tyr Lys Thr Thr Pro Pro Val Leu Asp Ser Asp Gly Ser Phe Phe
            580                 585                 590

Leu Tyr Ser Lys Leu Thr Val Asp Lys Ser Arg Trp Gln Gln Gly Asn
        595                 600                 605

Val Phe Ser Cys Ser Val Met His Glu Ala Leu His Asn His Tyr Thr
610                 615                 620

Gln Lys Ser Leu Ser Leu Ser Pro Gly Lys
625                 630

<210> SEQ ID NO 124
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Cys Gly Gly Gly Gly Ser Ile Glu Gly Arg His Gly Glu Gly
            100                 105                 110

Thr Phe Thr Ser Asp Leu Ser Lys Gln Met Glu Glu Glu Ala Val Arg
        115                 120                 125

Leu Phe Ile Glu Trp Leu Lys Asn Gly Gly Pro Ser Ser Gly Ala Pro
    130                 135                 140

Pro Pro Ser Gly Gly Gly Gly Ser Cys Asp Tyr Trp Gly Gln Gly Thr
145                 150                 155                 160

Leu Val Thr Val Ser Ser Ala Ser Thr Lys Gly Pro Ser Val Phe Pro
                165                 170                 175
```

```
Leu Ala Pro Ser Ser Lys Ser Thr Ser Gly Gly Thr Ala Ala Leu Gly
            180                 185                 190

Cys Leu Val Lys Asp Tyr Phe Pro Glu Pro Val Thr Val Ser Trp Asn
            195                 200                 205

Ser Gly Ala Leu Thr Ser Gly Val His Thr Phe Pro Ala Val Leu Gln
        210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
            245                 250                 255

Asn Thr Lys Val Asp Lys Lys Val Glu Pro Lys Ser Cys Asp Lys Thr
            260                 265                 270

His Thr Cys Pro Pro Cys Pro Ala Pro Glu Leu Leu Gly Gly Pro Ser
            275                 280                 285

Val Phe Leu Phe Pro Pro Lys Pro Lys Asp Thr Leu Met Ile Ser Arg
        290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
            325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
            370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
            405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
            485                 490                 495

<210> SEQ ID NO 125
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

-continued

```
                35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Gly Gly Gly Gly Ser Ile Asn Val Lys Cys Ser Leu Pro Gln
                100                 105                 110
Gln Cys Ile Lys Pro Cys Lys Asp Ala Gly Met Arg Phe Gly Lys Cys
            115                 120                 125
Met Asn Lys Lys Cys Arg Cys Tyr Ser Gly Gly Gly Ser Asp Tyr
        130                 135                 140
Trp Gly Gln Gly Thr Leu Val Thr Val Ser Ser Ala Ser Thr Lys Gly
145                 150                 155                 160
Pro Ser Val Phe Pro Leu Ala Pro Ser Ser Lys Ser Thr Ser Gly Gly
                165                 170                 175
Thr Ala Ala Leu Gly Cys Leu Val Lys Asp Tyr Phe Pro Glu Pro Val
            180                 185                 190
Thr Val Ser Trp Asn Ser Gly Ala Leu Thr Ser Gly Val His Thr Phe
        195                 200                 205
Pro Ala Val Leu Gln Ser Ser Gly Leu Tyr Ser Leu Ser Ser Val Val
    210                 215                 220
Thr Val Pro Ser Ser Ser Leu Gly Thr Gln Thr Tyr Ile Cys Asn Val
225                 230                 235                 240
Asn His Lys Pro Ser Asn Thr Lys Val Asp Lys Lys Val Glu Pro Lys
                245                 250                 255
Ser Cys Asp Lys Thr His Thr Cys Pro Pro Cys Pro Ala Pro Glu Leu
            260                 265                 270
Leu Gly Gly Pro Ser Val Phe Leu Phe Pro Pro Lys Pro Lys Asp Thr
        275                 280                 285
Leu Met Ile Ser Arg Thr Pro Glu Val Thr Cys Val Val Val Asp Val
    290                 295                 300
Ser His Glu Asp Pro Glu Val Lys Phe Asn Trp Tyr Val Asp Gly Val
305                 310                 315                 320
Glu Val His Asn Ala Lys Thr Lys Pro Arg Glu Glu Gln Tyr Asn Ser
                325                 330                 335
Thr Tyr Arg Val Val Ser Val Leu Thr Val Leu His Gln Asp Trp Leu
            340                 345                 350
Asn Gly Lys Glu Tyr Lys Cys Lys Val Ser Asn Lys Ala Leu Pro Ala
        355                 360                 365
Pro Ile Glu Lys Thr Ile Ser Lys Ala Lys Gly Gln Pro Arg Glu Pro
    370                 375                 380
Gln Val Tyr Thr Leu Pro Pro Ser Arg Asp Glu Leu Thr Lys Asn Gln
385                 390                 395                 400
Val Ser Leu Thr Cys Leu Val Lys Gly Phe Tyr Pro Ser Asp Ile Ala
                405                 410                 415
Val Glu Trp Glu Ser Asn Gly Gln Pro Glu Asn Asn Tyr Lys Thr Thr
            420                 425                 430
Pro Pro Val Leu Asp Ser Asp Gly Ser Phe Phe Leu Tyr Ser Lys Leu
        435                 440                 445
Thr Val Asp Lys Ser Arg Trp Gln Gln Gly Asn Val Phe Ser Cys Ser
    450                 455                 460
```

```
Val Met His Glu Ala Leu His Asn His Tyr Thr Gln Lys Ser Leu Ser
465                 470                 475                 480

Leu Ser Pro Gly Lys
                485

<210> SEQ ID NO 126
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Gly Gly Ser Ala Ala Ala Ile Ser Cys Val Gly Ser
            100                 105                 110

Pro Glu Cys Pro Pro Lys Cys Arg Ala Gln Gly Cys Lys Asn Gly Lys
        115                 120                 125

Cys Met Asn Arg Lys Cys Lys Cys Tyr Tyr Cys Gly Gly Gly Gly Ser
130                 135                 140

Asp Tyr Trp Gly Gln Gly Thr Leu Val Thr Val Ser Ser Ala Ser Thr
145                 150                 155                 160

Lys Gly Pro Ser Val Phe Pro Leu Ala Pro Ser Ser Lys Ser Thr Ser
                165                 170                 175

Gly Gly Thr Ala Ala Leu Gly Cys Leu Val Lys Asp Tyr Phe Pro Glu
            180                 185                 190

Pro Val Thr Val Ser Trp Asn Ser Gly Ala Leu Thr Ser Gly Val His
        195                 200                 205

Thr Phe Pro Ala Val Leu Gln Ser Ser Gly Leu Tyr Ser Leu Ser Ser
    210                 215                 220

Val Val Thr Val Pro Ser Ser Ser Leu Gly Thr Gln Thr Tyr Ile Cys
225                 230                 235                 240

Asn Val Asn His Lys Pro Ser Asn Thr Lys Val Asp Lys Lys Val Glu
                245                 250                 255

Pro Lys Ser Cys Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
```

```
                        325                 330                 335
Asn Ser Thr Tyr Arg Val Val Ser Val Leu Thr Val Leu His Gln Asp
                340                 345                 350
Trp Leu Asn Gly Lys Glu Tyr Lys Cys Lys Val Ser Asn Lys Ala Leu
            355                 360                 365
Pro Ala Pro Ile Glu Lys Thr Ile Ser Lys Ala Lys Gly Gln Pro Arg
        370                 375                 380
Glu Pro Gln Val Tyr Thr Leu Pro Pro Ser Arg Asp Glu Leu Thr Lys
385                 390                 395                 400
Asn Gln Val Ser Leu Thr Cys Leu Val Lys Gly Phe Tyr Pro Ser Asp
                405                 410                 415
Ile Ala Val Glu Trp Glu Ser Asn Gly Gln Pro Glu Asn Asn Tyr Lys
            420                 425                 430
Thr Thr Pro Pro Val Leu Asp Ser Asp Gly Ser Phe Phe Leu Tyr Ser
        435                 440                 445
Lys Leu Thr Val Asp Lys Ser Arg Trp Gln Gln Gly Asn Val Phe Ser
450                 455                 460
Cys Ser Val Met His Glu Ala Leu His Asn His Tyr Thr Gln Lys Ser
465                 470                 475                 480
Leu Ser Leu Ser Pro Gly Lys
                485

<210> SEQ ID NO 127
<211> LENGTH: 626
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Gly Gly Gly Gly Ser Ala Thr Pro Leu Gly Pro Ala Ser Ser
            100                 105                 110
Leu Pro Gln Ser Phe Leu Leu Lys Cys Leu Glu Gln Val Arg Lys Ile
        115                 120                 125
Gln Gly Asp Gly Ala Ala Leu Gln Glu Lys Leu Val Ser Glu Cys Ala
    130                 135                 140
Thr Tyr Lys Leu Cys His Pro Glu Glu Leu Val Leu Leu Gly His Ser
145                 150                 155                 160
Leu Gly Ile Pro Trp Ala Pro Leu Ser Ser Cys Pro Ser Gln Ala Leu
                165                 170                 175
Gln Leu Ala Gly Cys Leu Ser Gln Leu His Ser Gly Leu Phe Leu Tyr
            180                 185                 190
```

-continued

Gln Gly Leu Leu Gln Ala Leu Glu Gly Ile Ser Pro Glu Leu Gly Pro
          195                 200                 205

Thr Leu Asp Thr Leu Gln Leu Asp Val Ala Asp Phe Ala Thr Thr Ile
    210                 215                 220

Trp Gln Gln Met Glu Glu Leu Gly Met Ala Pro Ala Leu Gln Pro Thr
225                 230                 235                 240

Gln Gly Ala Met Pro Ala Phe Ala Ser Ala Phe Gln Arg Arg Ala Gly
              245                 250                 255

Gly Val Leu Val Ala Ser His Leu Gln Ser Phe Leu Glu Val Ser Tyr
          260                 265                 270

Arg Val Leu Arg His Leu Ala Gln Pro Gly Gly Gly Ser Asp Tyr
          275                 280                 285

Trp Gly Gln Gly Thr Leu Val Thr Val Ser Ser Ala Ser Thr Lys Gly
    290                 295                 300

Pro Ser Val Phe Pro Leu Ala Pro Cys Ser Arg Ser Thr Ser Glu Ser
305                 310                 315                 320

Thr Ala Ala Leu Gly Cys Leu Val Lys Asp Tyr Phe Pro Glu Pro Val
              325                 330                 335

Thr Val Ser Trp Asn Ser Gly Ala Leu Thr Ser Gly Val His Thr Phe
          340                 345                 350

Pro Ala Val Leu Gln Ser Ser Gly Leu Tyr Ser Leu Ser Ser Val Val
          355                 360                 365

Thr Val Pro Ser Ser Ser Leu Gly Thr Lys Thr Tyr Thr Cys Asn Val
    370                 375                 380

Asp His Lys Pro Ser Asn Thr Lys Val Asp Lys Arg Val Glu Ser Lys
385                 390                 395                 400

Tyr Gly Pro Pro Cys Pro Pro Cys Pro Ala Pro Glu Ala Ala Gly Gly
              405                 410                 415

Pro Ser Val Phe Leu Phe Pro Pro Lys Pro Lys Asp Thr Leu Met Ile
          420                 425                 430

Ser Arg Thr Pro Glu Val Thr Cys Val Val Val Asp Val Ser Gln Glu
    435                 440                 445

Asp Pro Glu Val Gln Phe Asn Trp Tyr Val Asp Gly Val Glu Val His
450                 455                 460

Asn Ala Lys Thr Lys Pro Arg Glu Glu Gln Phe Asn Ser Thr Tyr Arg
465                 470                 475                 480

Val Val Ser Val Leu Thr Val Leu His Gln Asp Trp Leu Asn Gly Lys
              485                 490                 495

Glu Tyr Lys Cys Lys Val Ser Asn Lys Gly Leu Pro Ser Ser Ile Glu
          500                 505                 510

Lys Thr Ile Ser Lys Ala Lys Gly Gln Pro Arg Glu Pro Gln Val Tyr
    515                 520                 525

Thr Leu Pro Pro Ser Gln Glu Glu Met Thr Lys Asn Gln Val Ser Leu
530                 535                 540

Thr Cys Leu Val Lys Gly Phe Tyr Pro Ser Asp Ile Ala Val Glu Trp
545                 550                 555                 560

Glu Ser Asn Gly Gln Pro Glu Asn Asn Tyr Lys Thr Thr Pro Pro Val
              565                 570                 575

Leu Asp Ser Asp Gly Ser Phe Phe Leu Tyr Ser Arg Leu Thr Val Asp
          580                 585                 590

Lys Ser Arg Trp Gln Glu Gly Asn Val Phe Ser Cys Ser Val Met His
    595                 600                 605

Glu Ala Leu His Asn His Tyr Thr Gln Lys Ser Leu Ser Leu Ser Leu 610                 615                 620

Gly Lys
625

<210> SEQ ID NO 128
<211> LENGTH: 639
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Gly Gly Ser Phe Pro Thr Ile Pro Leu Ser Arg Leu
            100                 105                 110

Phe Asp Asn Ala Met Leu Arg Ala His Arg Leu His Gln Leu Ala Phe
        115                 120                 125

Asp Thr Tyr Gln Glu Phe Glu Glu Ala Tyr Ile Pro Lys Glu Gln Lys
    130                 135                 140

Tyr Ser Phe Leu Gln Asn Pro Gln Thr Ser Leu Cys Phe Ser Glu Ser
145                 150                 155                 160

Ile Pro Thr Pro Ser Asn Arg Glu Glu Thr Gln Gln Lys Ser Asn Leu
                165                 170                 175

Glu Leu Leu Arg Ile Ser Leu Leu Leu Ile Gln Ser Trp Leu Glu Pro
            180                 185                 190

Val Gln Phe Leu Arg Ser Val Phe Ala Asn Ser Leu Val Tyr Gly Ala
        195                 200                 205

Ser Asp Ser Asn Val Tyr Asp Leu Leu Lys Asp Leu Glu Glu Gly Ile
    210                 215                 220

Gln Thr Leu Met Gly Arg Leu Glu Asp Gly Ser Pro Arg Thr Gly Gln
225                 230                 235                 240

Ile Phe Lys Gln Thr Tyr Ser Lys Phe Asp Thr Asn Ser His Asn Asp
                245                 250                 255

Asp Ala Leu Leu Lys Asn Tyr Gly Leu Leu Tyr Cys Phe Arg Lys Asp
            260                 265                 270

Met Asp Lys Val Glu Thr Phe Leu Arg Ile Val Gln Cys Arg Ser Val
        275                 280                 285

Glu Gly Ser Cys Gly Phe Gly Gly Gly Ser Asp Tyr Trp Gly Gln
    290                 295                 300

Gly Thr Leu Val Thr Val Ser Ser Ala Ser Thr Lys Gly Pro Ser Val
305                 310                 315                 320

Phe Pro Leu Ala Pro Cys Ser Arg Ser Thr Ser Glu Ser Thr Ala Ala
                325                 330                 335

```
Leu Gly Cys Leu Val Lys Asp Tyr Phe Pro Glu Pro Val Thr Val Ser
            340                 345                 350

Trp Asn Ser Gly Ala Leu Thr Ser Gly Val His Thr Phe Pro Ala Val
            355                 360                 365

Leu Gln Ser Ser Gly Leu Tyr Ser Leu Ser Ser Val Val Thr Val Pro
        370                 375                 380

Ser Ser Ser Leu Gly Thr Lys Thr Tyr Thr Cys Asn Val Asp His Lys
385                 390                 395                 400

Pro Ser Asn Thr Lys Val Asp Lys Arg Val Glu Ser Lys Tyr Gly Pro
                405                 410                 415

Pro Cys Pro Pro Cys Pro Ala Pro Glu Ala Ala Gly Gly Pro Ser Val
            420                 425                 430

Phe Leu Phe Pro Pro Lys Pro Lys Asp Thr Leu Met Ile Ser Arg Thr
        435                 440                 445

Pro Glu Val Thr Cys Val Val Val Asp Val Ser Gln Glu Asp Pro Glu
        450                 455                 460

Val Gln Phe Asn Trp Tyr Val Asp Gly Val Glu Val His Asn Ala Lys
465                 470                 475                 480

Thr Lys Pro Arg Glu Glu Gln Phe Asn Ser Thr Tyr Arg Val Val Ser
                485                 490                 495

Val Leu Thr Val Leu His Gln Asp Trp Leu Asn Gly Lys Glu Tyr Lys
            500                 505                 510

Cys Lys Val Ser Asn Lys Gly Leu Pro Ser Ser Ile Glu Lys Thr Ile
        515                 520                 525

Ser Lys Ala Lys Gly Gln Pro Arg Glu Pro Gln Val Tyr Thr Leu Pro
        530                 535                 540

Pro Ser Gln Glu Glu Met Thr Lys Asn Gln Val Ser Leu Thr Cys Leu
545                 550                 555                 560

Val Lys Gly Phe Tyr Pro Ser Asp Ile Ala Val Glu Trp Glu Ser Asn
                565                 570                 575

Gly Gln Pro Glu Asn Asn Tyr Lys Thr Thr Pro Pro Val Leu Asp Ser
            580                 585                 590

Asp Gly Ser Phe Phe Leu Tyr Ser Arg Leu Thr Val Asp Lys Ser Arg
        595                 600                 605

Trp Gln Glu Gly Asn Val Phe Ser Cys Ser Val Met His Glu Ala Leu
        610                 615                 620

His Asn His Tyr Thr Gln Lys Ser Leu Ser Leu Ser Leu Gly Lys
625                 630                 635

<210> SEQ ID NO 129
<211> LENGTH: 594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Gly Gly Gly Gly Ser Val Pro Ile Gln Lys Val Gln Asp Asp
            100                 105                 110

Thr Lys Thr Leu Ile Lys Thr Ile Val Thr Arg Ile Asn Asp Ile Ser
        115                 120                 125

His Thr Gln Ser Val Ser Ser Lys Gln Lys Val Thr Gly Leu Asp Phe
    130                 135                 140

Ile Pro Gly Leu His Pro Ile Leu Thr Leu Ser Lys Met Asp Gln Thr
145                 150                 155                 160

Leu Ala Val Tyr Gln Gln Ile Leu Thr Ser Met Pro Ser Arg Asn Val
                165                 170                 175

Ile Gln Ile Ser Asn Asp Leu Glu Asn Leu Arg Asp Leu Leu His Val
            180                 185                 190

Leu Ala Phe Ser Lys Ser Cys His Leu Pro Trp Ala Ser Gly Leu Glu
        195                 200                 205

Thr Leu Asp Ser Leu Gly Gly Val Leu Glu Ala Ser Gly Tyr Ser Thr
    210                 215                 220

Glu Val Val Ala Leu Ser Arg Leu Gln Gly Ser Leu Gln Asp Met Leu
225                 230                 235                 240

Trp Gln Leu Asp Leu Ser Pro Gly Cys Gly Gly Gly Ser Asp Tyr
                245                 250                 255

Trp Gly Gln Gly Thr Leu Val Thr Val Ser Ser Ala Ser Thr Lys Gly
            260                 265                 270

Pro Ser Val Phe Pro Leu Ala Pro Cys Ser Arg Ser Thr Ser Glu Ser
        275                 280                 285

Thr Ala Ala Leu Gly Cys Leu Val Lys Asp Tyr Phe Pro Glu Pro Val
    290                 295                 300

Thr Val Ser Trp Asn Ser Gly Ala Leu Thr Ser Gly Val His Thr Phe
305                 310                 315                 320

Pro Ala Val Leu Gln Ser Ser Gly Leu Tyr Ser Leu Ser Ser Val Val
                325                 330                 335

Thr Val Pro Ser Ser Ser Leu Gly Thr Lys Thr Tyr Thr Cys Asn Val
            340                 345                 350

Asp His Lys Pro Ser Asn Thr Lys Val Asp Lys Arg Val Glu Ser Lys
        355                 360                 365

Tyr Gly Pro Pro Cys Pro Pro Cys Pro Ala Pro Glu Ala Ala Gly Gly
    370                 375                 380

Pro Ser Val Phe Leu Phe Pro Pro Lys Pro Lys Asp Thr Leu Met Ile
385                 390                 395                 400

Ser Arg Thr Pro Glu Val Thr Cys Val Val Val Asp Val Ser Gln Glu
                405                 410                 415

Asp Pro Glu Val Gln Phe Asn Trp Tyr Val Asp Gly Val Glu Val His
            420                 425                 430

Asn Ala Lys Thr Lys Pro Arg Glu Glu Gln Phe Asn Ser Thr Tyr Arg
        435                 440                 445

Val Val Ser Val Leu Thr Val Leu His Gln Asp Trp Leu Asn Gly Lys
    450                 455                 460

Glu Tyr Lys Cys Lys Val Ser Asn Lys Gly Leu Pro Ser Ser Ile Glu
465                 470                 475                 480
```

```
Lys Thr Ile Ser Lys Ala Lys Gly Gln Pro Arg Glu Pro Gln Val Tyr
                485                 490                 495

Thr Leu Pro Pro Ser Gln Glu Glu Met Thr Lys Asn Gln Val Ser Leu
            500                 505                 510

Thr Cys Leu Val Lys Gly Phe Tyr Pro Ser Asp Ile Ala Val Glu Trp
        515                 520                 525

Glu Ser Asn Gly Gln Pro Glu Asn Asn Tyr Lys Thr Thr Pro Pro Val
    530                 535                 540

Leu Asp Ser Asp Gly Ser Phe Phe Leu Tyr Ser Arg Leu Thr Val Asp
545                 550                 555                 560

Lys Ser Arg Trp Gln Glu Gly Asn Val Phe Ser Cys Ser Val Met His
                565                 570                 575

Glu Ala Leu His Asn His Tyr Thr Gln Lys Ser Leu Ser Leu Ser Leu
            580                 585                 590

Gly Lys

<210> SEQ ID NO 130
<211> LENGTH: 613
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Gly Gly Ser Cys Asp Leu Pro Gln Thr His Ser Leu
            100                 105                 110

Gly Ser Arg Arg Thr Leu Met Leu Leu Ala Gln Met Arg Arg Ile Ser
        115                 120                 125

Leu Phe Ser Cys Leu Lys Asp Arg His Asp Phe Gly Phe Pro Gln Glu
    130                 135                 140

Glu Phe Gly Asn Gln Phe Gln Lys Ala Glu Thr Ile Pro Val Leu His
145                 150                 155                 160

Glu Met Ile Gln Gln Ile Phe Asn Leu Phe Ser Thr Lys Asp Ser Ser
                165                 170                 175

Ala Ala Trp Asp Glu Thr Leu Leu Asp Lys Phe Tyr Thr Glu Leu Tyr
            180                 185                 190

Gln Gln Leu Asn Asp Leu Glu Ala Cys Val Ile Gln Gly Val Gly Val
        195                 200                 205

Thr Glu Thr Pro Leu Met Lys Glu Asp Ser Ile Leu Ala Val Arg Lys
    210                 215                 220

Tyr Phe Gln Arg Ile Thr Leu Tyr Leu Lys Glu Lys Lys Tyr Ser Pro
225                 230                 235                 240
```

Cys Ala Trp Glu Val Val Arg Ala Glu Ile Met Arg Ser Phe Ser Leu
              245                 250                 255

Ser Thr Asn Leu Gln Glu Ser Leu Arg Ser Lys Glu Gly Gly Gly Gly
            260                 265                 270

Ser Asp Tyr Trp Gly Gln Gly Thr Leu Val Thr Val Ser Ser Ala Ser
        275                 280                 285

Thr Lys Gly Pro Ser Val Phe Pro Leu Ala Pro Cys Ser Arg Ser Thr
    290                 295                 300

Ser Glu Ser Thr Ala Ala Leu Gly Cys Leu Val Lys Asp Tyr Phe Pro
305                 310                 315                 320

Glu Pro Val Thr Val Ser Trp Asn Ser Gly Ala Leu Thr Ser Gly Val
                325                 330                 335

His Thr Phe Pro Ala Val Leu Gln Ser Ser Gly Leu Tyr Ser Leu Ser
            340                 345                 350

Ser Val Val Thr Val Pro Ser Ser Ser Leu Gly Thr Lys Thr Tyr Thr
        355                 360                 365

Cys Asn Val Asp His Lys Pro Ser Asn Thr Lys Val Asp Lys Arg Val
    370                 375                 380

Glu Ser Lys Tyr Gly Pro Pro Cys Pro Pro Cys Pro Ala Pro Glu Ala
385                 390                 395                 400

Ala Gly Gly Pro Ser Val Phe Leu Phe Pro Pro Lys Pro Lys Asp Thr
                405                 410                 415

Leu Met Ile Ser Arg Thr Pro Glu Val Thr Cys Val Val Val Asp Val
            420                 425                 430

Ser Gln Glu Asp Pro Glu Val Gln Phe Asn Trp Tyr Val Asp Gly Val
        435                 440                 445

Glu Val His Asn Ala Lys Thr Lys Pro Arg Glu Glu Gln Phe Asn Ser
    450                 455                 460

Thr Tyr Arg Val Val Ser Val Leu Thr Val Leu His Gln Asp Trp Leu
465                 470                 475                 480

Asn Gly Lys Glu Tyr Lys Cys Lys Val Ser Asn Lys Gly Leu Pro Ser
                485                 490                 495

Ser Ile Glu Lys Thr Ile Ser Lys Ala Lys Gly Gln Pro Arg Glu Pro
            500                 505                 510

Gln Val Tyr Thr Leu Pro Pro Ser Gln Glu Glu Met Thr Lys Asn Gln
        515                 520                 525

Val Ser Leu Thr Cys Leu Val Lys Gly Phe Tyr Pro Ser Asp Ile Ala
    530                 535                 540

Val Glu Trp Glu Ser Asn Gly Gln Pro Glu Asn Asn Tyr Lys Thr Thr
545                 550                 555                 560

Pro Pro Val Leu Asp Ser Asp Gly Ser Phe Phe Leu Tyr Ser Arg Leu
                565                 570                 575

Thr Val Asp Lys Ser Arg Trp Gln Glu Gly Asn Val Phe Ser Cys Ser
            580                 585                 590

Val Met His Glu Ala Leu His Asn His Tyr Thr Gln Lys Ser Leu Ser
    595                 600                 605

Leu Ser Leu Gly Lys
    610

<210> SEQ ID NO 131
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Cys Gly Gly Gly Ser Ile Glu Gly Arg His Ala Glu Gly
            100                 105                 110

Thr Phe Thr Ser Asp Val Ser Ser Tyr Leu Glu Gly Gln Ala Ala Lys
        115                 120                 125

Glu Phe Ile Ala Trp Leu Val Lys Gly Arg Gly Gly Gly Ser Cys
130                 135                 140

Asp Tyr Trp Gly Gln Gly Thr Leu Val Thr Val Ser Ser Ala Ser Thr
145                 150                 155                 160

Lys Gly Pro Ser Val Phe Pro Leu Ala Pro Ser Ser Lys Ser Thr Ser
                165                 170                 175

Gly Gly Thr Ala Ala Leu Gly Cys Leu Val Lys Asp Tyr Phe Pro Glu
            180                 185                 190

Pro Val Thr Val Ser Trp Asn Ser Gly Ala Leu Thr Ser Gly Val His
        195                 200                 205

Thr Phe Pro Ala Val Leu Gln Ser Ser Gly Leu Tyr Ser Leu Ser Ser
    210                 215                 220

Val Val Thr Val Pro Ser Ser Ser Leu Gly Thr Gln Thr Tyr Ile Cys
225                 230                 235                 240

Asn Val Asn His Lys Pro Ser Asn Thr Lys Val Asp Lys Lys Val Glu
                245                 250                 255

Pro Lys Ser Cys Asp Lys Thr His Thr Cys Pro Pro Cys Pro Ala Pro
            260                 265                 270

Pro Val Ala Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Gly Leu Pro
        355                 360                 365

Ser Ser Ile Glu Lys Thr Ile Ser Lys Ala Lys Gly Gln Pro Arg Glu
    370                 375                 380

Pro Gln Val Tyr Thr Leu Pro Pro Ser Arg Asp Glu Leu Thr Lys Asn
385                 390                 395                 400
```

Gln Val Ser Leu Thr Cys Leu Val Lys Gly Phe Tyr Pro Ser Asp Ile
            405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
            435                 440                 445

Leu Thr Val Asp Lys Ser Arg Trp Gln Gln Gly Asn Val Phe Ser Cys
450                 455                 460

Ser Val Met His Glu Ala Leu His Asn His Tyr Thr Gln Lys Ser Leu
465                 470                 475                 480

Ser Leu Ser Pro Gly Lys
            485

<210> SEQ ID NO 132
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Gly Gly Ser Ala Gln Glu Pro Val Lys Gly Pro Val
            100                 105                 110

Ser Thr Lys Pro Gly Ser Cys Pro Ile Ile Leu Ile Arg Cys Ala Met
        115                 120                 125

Leu Asn Pro Pro Asn Arg Cys Leu Lys Asp Thr Asp Cys Pro Gly Ile
    130                 135                 140

Lys Lys Cys Cys Glu Gly Ser Cys Gly Met Ala Cys Phe Val Pro Gln
145                 150                 155                 160

Gly Gly Gly Gly Ser Asp Tyr Trp Gly Gln Gly Thr Leu Val Thr Val
                165                 170                 175

Ser Ser Ala Ser Thr Lys Gly Pro Ser Val Phe Pro Leu Ala Pro Ser
            180                 185                 190

Ser Lys Ser Thr Ser Gly Gly Thr Ala Ala Leu Gly Cys Leu Val Lys
        195                 200                 205

Asp Tyr Phe Pro Glu Pro Val Thr Val Ser Trp Asn Ser Gly Ala Leu
    210                 215                 220

Thr Ser Gly Val His Thr Phe Pro Ala Val Leu Gln Ser Ser Gly Leu
225                 230                 235                 240

Tyr Ser Leu Ser Ser Val Val Thr Val Pro Ser Ser Ser Leu Gly Thr
                245                 250                 255

Gln Thr Tyr Ile Cys Asn Val Asn His Lys Pro Ser Asn Thr Lys Val
            260                 265                 270

Asp Lys Lys Val Glu Pro Lys Ser Cys Asp Lys Thr His Thr Cys Pro
                275                 280                 285

Pro Cys Pro Ala Pro Pro Val Ala Gly Pro Ser Val Phe Leu Phe Pro
        290                 295                 300

Pro Lys Pro Lys Asp Thr Leu Met Ile Ser Arg Thr Pro Glu Val Thr
305                 310                 315                 320

Cys Val Val Val Asp Val Ser His Glu Asp Pro Glu Val Lys Phe Asn
                325                 330                 335

Trp Tyr Val Asp Gly Val Glu Val His Asn Ala Lys Thr Lys Pro Arg
            340                 345                 350

Glu Glu Gln Tyr Asn Ser Thr Tyr Arg Val Val Ser Val Leu Thr Val
                355                 360                 365

Leu His Gln Asp Trp Leu Asn Gly Lys Glu Tyr Lys Cys Lys Val Ser
        370                 375                 380

Asn Lys Gly Leu Pro Ser Ser Ile Glu Lys Thr Ile Ser Lys Ala Lys
385                 390                 395                 400

Gly Gln Pro Arg Glu Pro Gln Val Tyr Thr Leu Pro Pro Ser Arg Asp
                405                 410                 415

Glu Leu Thr Lys Asn Gln Val Ser Leu Thr Cys Leu Val Lys Gly Phe
            420                 425                 430

Tyr Pro Ser Asp Ile Ala Val Glu Trp Glu Ser Asn Gly Gln Pro Glu
        435                 440                 445

Asn Asn Tyr Lys Thr Thr Pro Pro Val Leu Asp Ser Asp Gly Ser Phe
450                 455                 460

Phe Leu Tyr Ser Lys Leu Thr Val Asp Lys Ser Arg Trp Gln Gln Gly
465                 470                 475                 480

Asn Val Phe Ser Cys Ser Val Met His Glu Ala Leu His Asn His Tyr
                485                 490                 495

Thr Gln Lys Ser Leu Ser Leu Ser Pro Gly Lys
            500                 505

<210> SEQ ID NO 133
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Gly Gly Gly Gly Ser Leu Lys Cys Tyr Gln His Gly Lys Val Val
            100                 105                 110

Thr Cys His Arg Asp Met Lys Phe Cys Tyr His Asn Thr Gly Met Pro

```
            115                 120                 125
Phe Arg Asn Leu Lys Leu Ile Leu Gln Gly Cys Ser Ser Cys Ser
130                 135                 140

Glu Thr Glu Asn Asn Lys Cys Cys Ser Thr Asp Arg Cys Asn Lys Gly
145                 150                 155                 160

Gly Gly Gly Ser Trp Gly Gln Gly Thr Leu Val Thr Val Ser Ser Ala
                165                 170                 175

Ser Thr Lys Gly Pro Ser Val Phe Pro Leu Ala Pro Ser Ser Lys Ser
            180                 185                 190

Thr Ser Gly Gly Thr Ala Ala Leu Gly Cys Leu Val Lys Asp Tyr Phe
        195                 200                 205

Pro Glu Pro Val Thr Val Ser Trp Asn Ser Gly Ala Leu Thr Ser Gly
    210                 215                 220

Val His Thr Phe Pro Ala Val Leu Gln Ser Ser Gly Leu Tyr Ser Leu
225                 230                 235                 240

Ser Ser Val Val Thr Val Pro Ser Ser Ser Leu Gly Thr Gln Thr Tyr
                245                 250                 255

Ile Cys Asn Val Asn His Lys Pro Ser Asn Thr Lys Val Asp Lys Lys
            260                 265                 270

Val Glu Pro Lys Ser Cys Asp Lys Thr His Thr Cys Pro Pro Cys Pro
        275                 280                 285

Ala Pro Pro Val Ala Gly Pro Ser Val Phe Leu Phe Pro Pro Lys Pro
290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Gly
370                 375                 380

Leu Pro Ser Ser Ile Glu Lys Thr Ile Ser Lys Ala Lys Gly Gln Pro
385                 390                 395                 400

Arg Glu Pro Gln Val Tyr Thr Leu Pro Pro Ser Arg Asp Glu Leu Thr
                405                 410                 415

Lys Asn Gln Val Ser Leu Thr Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
    450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500

<210> SEQ ID NO 134
<211> LENGTH: 517
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Gly Gly Ser Asp Ser Trp Met Glu Glu Val Ile Lys
            100                 105                 110

Leu Cys Gly Arg Glu Leu Val Arg Ala Gln Ile Ala Ile Cys Gly Met
        115                 120                 125

Ser Thr Trp Ser Lys Arg Ser Leu Ser Gln Glu Ile Glu Gly Arg Lys
130                 135                 140

Lys Arg Gln Leu Tyr Ser Ala Leu Ala Asn Lys Cys Cys His Val Gly
145                 150                 155                 160

Cys Thr Lys Arg Ser Leu Ala Arg Phe Cys Gly Gly Gly Gly Ser Asp
                165                 170                 175

Tyr Trp Gly Gln Gly Thr Leu Val Thr Val Ser Ser Ala Ser Thr Lys
            180                 185                 190

Gly Pro Ser Val Phe Pro Leu Ala Pro Ser Ser Lys Ser Thr Ser Gly
        195                 200                 205

Gly Thr Ala Ala Leu Gly Cys Leu Val Lys Asp Tyr Phe Pro Glu Pro
    210                 215                 220

Val Thr Val Ser Trp Asn Ser Gly Ala Leu Thr Ser Gly Val His Thr
225                 230                 235                 240

Phe Pro Ala Val Leu Gln Ser Ser Gly Leu Tyr Ser Leu Ser Ser Val
                245                 250                 255

Val Thr Val Pro Ser Ser Ser Leu Gly Thr Gln Thr Tyr Ile Cys Asn
            260                 265                 270

Val Asn His Lys Pro Ser Asn Thr Lys Val Asp Lys Lys Val Glu Pro
        275                 280                 285

Lys Ser Cys Asp Lys Thr His Thr Cys Pro Pro Cys Pro Ala Pro Pro
    290                 295                 300

Val Ala Gly Pro Ser Val Phe Leu Phe Pro Pro Lys Pro Lys Asp Thr
305                 310                 315                 320

Leu Met Ile Ser Arg Thr Pro Glu Val Thr Cys Val Val Val Asp Val
                325                 330                 335

Ser His Glu Asp Pro Glu Val Lys Phe Asn Trp Tyr Val Asp Gly Val
            340                 345                 350

Glu Val His Asn Ala Lys Thr Lys Pro Arg Glu Glu Gln Tyr Asn Ser
        355                 360                 365

Thr Tyr Arg Val Val Ser Val Leu Thr Val Leu His Gln Asp Trp Leu
    370                 375                 380

Asn Gly Lys Glu Tyr Lys Cys Lys Val Ser Asn Lys Gly Leu Pro Ser

```
                385                 390                 395                 400
Ser Ile Glu Lys Thr Ile Ser Lys Ala Lys Gly Gln Pro Arg Glu Pro
                405                 410                 415

Gln Val Tyr Thr Leu Pro Pro Ser Arg Asp Glu Leu Thr Lys Asn Gln
            420                 425                 430

Val Ser Leu Thr Cys Leu Val Lys Gly Phe Tyr Pro Ser Asp Ile Ala
            435                 440                 445

Val Glu Trp Glu Ser Asn Gly Gln Pro Glu Asn Asn Tyr Lys Thr Thr
        450                 455                 460

Pro Pro Val Leu Asp Ser Asp Gly Ser Phe Phe Leu Tyr Ser Lys Leu
465                 470                 475                 480

Thr Val Asp Lys Ser Arg Trp Gln Gln Gly Asn Val Phe Ser Cys Ser
                485                 490                 495

Val Met His Glu Ala Leu His Asn His Tyr Thr Gln Lys Ser Leu Ser
            500                 505                 510

Leu Ser Pro Gly Lys
        515

<210> SEQ ID NO 135
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gly Gly Gly Ser Asp Ser Trp Met Glu Glu Val Ile Lys
            100                 105                 110

Leu Cys Gly Arg Glu Leu Val Arg Ala Gln Ile Ala Ile Cys Gly Met
        115                 120                 125

Ser Thr Trp Ser Lys Arg Ser Leu Ser Gln Glu Asp Ala Pro Gln Thr
    130                 135                 140

Pro Arg Pro Val Ile Glu Gly Arg Lys Arg Gln Leu Tyr Ser Ala
145                 150                 155                 160

Leu Ala Asn Lys Cys Cys His Val Gly Cys Thr Lys Arg Ser Leu Ala
                165                 170                 175

Arg Phe Cys Gly Gly Gly Gly Ser Asp Tyr Trp Gly Gln Gly Thr Leu
            180                 185                 190

Val Thr Val Ser Ser Ala Ser Thr Lys Gly Pro Ser Val Phe Pro Leu
        195                 200                 205

Ala Pro Ser Ser Lys Ser Thr Ser Gly Gly Thr Ala Ala Leu Gly Cys
    210                 215                 220
```

-continued

```
Leu Val Lys Asp Tyr Phe Pro Glu Pro Val Thr Val Ser Trp Asn Ser
225                 230                 235                 240

Gly Ala Leu Thr Ser Gly Val His Thr Phe Pro Ala Val Leu Gln Ser
            245                 250                 255

Ser Gly Leu Tyr Ser Leu Ser Ser Val Val Thr Val Pro Ser Ser Ser
        260                 265                 270

Leu Gly Thr Gln Thr Tyr Ile Cys Asn Val Asn His Lys Pro Ser Asn
    275                 280                 285

Thr Lys Val Asp Lys Lys Val Glu Pro Lys Ser Cys Asp Lys Thr His
290                 295                 300

Thr Cys Pro Pro Cys Pro Ala Pro Pro Val Ala Gly Pro Ser Val Phe
305                 310                 315                 320

Leu Phe Pro Pro Lys Pro Lys Asp Thr Leu Met Ile Ser Arg Thr Pro
            325                 330                 335

Glu Val Thr Cys Val Val Val Asp Val Ser His Glu Asp Pro Glu Val
        340                 345                 350

Lys Phe Asn Trp Tyr Val Asp Gly Val Glu Val His Asn Ala Lys Thr
    355                 360                 365

Lys Pro Arg Glu Glu Gln Tyr Asn Ser Thr Tyr Arg Val Val Ser Val
370                 375                 380

Leu Thr Val Leu His Gln Asp Trp Leu Asn Gly Lys Glu Tyr Lys Cys
385                 390                 395                 400

Lys Val Ser Asn Lys Gly Leu Pro Ser Ser Ile Glu Lys Thr Ile Ser
            405                 410                 415

Lys Ala Lys Gly Gln Pro Arg Glu Pro Gln Val Tyr Thr Leu Pro Pro
        420                 425                 430

Ser Arg Asp Glu Leu Thr Lys Asn Gln Val Ser Leu Thr Cys Leu Val
    435                 440                 445

Lys Gly Phe Tyr Pro Ser Asp Ile Ala Val Glu Trp Glu Ser Asn Gly
450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
            485                 490                 495

Gln Gln Gly Asn Val Phe Ser Cys Ser Val Met His Glu Ala Leu His
        500                 505                 510

Asn His Tyr Thr Gln Lys Ser Leu Ser Leu Ser Pro Gly Lys
    515                 520                 525

<210> SEQ ID NO 136
<211> LENGTH: 641
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

-continued

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Gly Gly Gly Gly Ser Phe Pro Thr Ile Pro Leu Ser Arg Leu
            100                 105                 110

Phe Asp Asn Ala Met Leu Arg Ala His Arg Leu His Gln Leu Ala Phe
        115                 120                 125

Asp Thr Tyr Gln Glu Phe Glu Glu Ala Tyr Ile Pro Lys Glu Gln Lys
    130                 135                 140

Tyr Ser Phe Leu Gln Asn Pro Gln Thr Ser Leu Cys Phe Ser Glu Ser
145                 150                 155                 160

Ile Pro Thr Pro Ser Asn Arg Glu Glu Thr Gln Gln Lys Ser Asn Leu
                165                 170                 175

Glu Leu Leu Arg Ile Ser Leu Leu Leu Ile Gln Ser Trp Leu Glu Pro
            180                 185                 190

Val Gln Phe Leu Arg Ser Val Phe Ala Asn Ser Leu Val Tyr Gly Ala
        195                 200                 205

Ser Asp Ser Asn Val Tyr Asp Leu Leu Lys Asp Leu Glu Glu Gly Ile
210                 215                 220

Gln Thr Leu Met Gly Arg Leu Glu Asp Gly Ser Pro Arg Thr Gly Gln
225                 230                 235                 240

Ile Phe Lys Gln Thr Tyr Ser Lys Phe Asp Thr Asn Ser His Asn Asp
                245                 250                 255

Asp Ala Leu Leu Lys Asn Tyr Gly Leu Leu Tyr Cys Phe Arg Lys Asp
            260                 265                 270

Met Asp Lys Val Glu Thr Phe Leu Arg Ile Val Gln Cys Arg Ser Val
        275                 280                 285

Glu Gly Ser Cys Gly Phe Gly Gly Gly Ser Asp Tyr Trp Gly Gln
290                 295                 300

Gly Thr Leu Val Thr Val Ser Ser Ala Ser Thr Lys Gly Pro Ser Val
305                 310                 315                 320

Phe Pro Leu Ala Pro Ser Ser Lys Ser Thr Ser Gly Thr Ala Ala
                325                 330                 335

Leu Gly Cys Leu Val Lys Asp Tyr Phe Pro Glu Pro Val Thr Val Ser
            340                 345                 350

Trp Asn Ser Gly Ala Leu Thr Ser Gly Val His Thr Phe Pro Ala Val
        355                 360                 365

Leu Gln Ser Ser Gly Leu Tyr Ser Leu Ser Ser Val Val Thr Val Pro
    370                 375                 380

Ser Ser Ser Leu Gly Thr Gln Thr Tyr Ile Cys Asn Val Asn His Lys
385                 390                 395                 400

Pro Ser Asn Thr Lys Val Asp Lys Lys Val Glu Pro Lys Ser Cys Asp
                405                 410                 415

Lys Thr His Thr Cys Pro Pro Cys Pro Ala Pro Pro Val Ala Gly Pro
            420                 425                 430

Ser Val Phe Leu Phe Pro Pro Lys Pro Lys Asp Thr Leu Met Ile Ser
        435                 440                 445

Arg Thr Pro Glu Val Thr Cys Val Val Val Asp Val Ser His Glu Asp
    450                 455                 460

Pro Glu Val Lys Phe Asn Trp Tyr Val Asp Gly Val Glu Val His Asn
465                 470                 475                 480
```

Ala Lys Thr Lys Pro Arg Glu Glu Gln Tyr Asn Ser Thr Tyr Arg Val
            485                 490                 495
Val Ser Val Leu Thr Val Leu His Gln Asp Trp Leu Asn Gly Lys Glu
        500                 505                 510
Tyr Lys Cys Lys Val Ser Asn Lys Gly Leu Pro Ser Ser Ile Glu Lys
    515                 520                 525
Thr Ile Ser Lys Ala Lys Gly Gln Pro Arg Glu Pro Gln Val Tyr Thr
530                 535                 540
Leu Pro Pro Ser Arg Asp Glu Leu Thr Lys Asn Gln Val Ser Leu Thr
545                 550                 555                 560
Cys Leu Val Lys Gly Phe Tyr Pro Ser Asp Ile Ala Val Glu Trp Glu
                565                 570                 575
Ser Asn Gly Gln Pro Glu Asn Asn Tyr Lys Thr Thr Pro Pro Val Leu
            580                 585                 590
Asp Ser Asp Gly Ser Phe Phe Leu Tyr Ser Lys Leu Thr Val Asp Lys
        595                 600                 605
Ser Arg Trp Gln Gln Gly Asn Val Phe Ser Cys Ser Val Met His Glu
    610                 615                 620
Ala Leu His Asn His Tyr Thr Gln Lys Ser Leu Ser Leu Ser Pro Gly
625                 630                 635                 640
Lys

```
<210> SEQ ID NO 137
<211> LENGTH: 616
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 137

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Gly Gly Gly Gly Ser Met Ser Tyr Asn Leu Leu Gly Phe Leu
            100                 105                 110
Gln Arg Ser Ser Asn Phe Gln Cys Gln Lys Leu Leu Trp Gln Leu Asn
        115                 120                 125
Gly Arg Leu Glu Tyr Cys Leu Lys Asp Arg Met Asn Phe Asp Ile Pro
    130                 135                 140
Glu Glu Ile Lys Gln Leu Gln Gln Phe Gln Lys Glu Asp Ala Ala Leu
145                 150                 155                 160
Thr Ile Tyr Glu Met Leu Gln Asn Ile Phe Ala Ile Phe Arg Gln Asp
                165                 170                 175
Ser Ser Ser Thr Gly Trp Asn Glu Thr Ile Val Glu Asn Leu Leu Ala
            180                 185                 190

```
Asn Val Tyr His Gln Ile Asn His Leu Lys Thr Val Leu Glu Glu Lys
            195                 200                 205

Leu Glu Lys Glu Asp Phe Thr Arg Gly Lys Leu Met Ser Ser Leu His
            210                 215                 220

Leu Lys Arg Tyr Tyr Gly Arg Ile Leu His Tyr Leu Lys Ala Lys Glu
225                 230                 235                 240

Tyr Ser His Cys Ala Trp Thr Ile Val Arg Val Glu Ile Leu Arg Asn
                245                 250                 255

Phe Tyr Phe Ile Asn Arg Leu Thr Gly Tyr Leu Arg Asn Gly Gly Gly
                260                 265                 270

Gly Ser Asp Tyr Trp Gly Gln Gly Thr Leu Val Thr Val Ser Ser Ala
            275                 280                 285

Ser Thr Lys Gly Pro Ser Val Phe Pro Leu Ala Pro Ser Ser Lys Ser
            290                 295                 300

Thr Ser Gly Gly Thr Ala Ala Leu Gly Cys Leu Val Lys Asp Tyr Phe
305                 310                 315                 320

Pro Glu Pro Val Thr Val Ser Trp Asn Ser Gly Ala Leu Thr Ser Gly
                325                 330                 335

Val His Thr Phe Pro Ala Val Leu Gln Ser Ser Gly Leu Tyr Ser Leu
                340                 345                 350

Ser Ser Val Val Thr Val Pro Ser Ser Ser Leu Gly Thr Gln Thr Tyr
            355                 360                 365

Ile Cys Asn Val Asn His Lys Pro Ser Asn Thr Lys Val Asp Lys Lys
            370                 375                 380

Val Glu Pro Lys Ser Cys Asp Lys Thr His Thr Cys Pro Pro Cys Pro
385                 390                 395                 400

Ala Pro Pro Val Ala Gly Pro Ser Val Phe Leu Phe Pro Pro Lys Pro
                405                 410                 415

Lys Asp Thr Leu Met Ile Ser Arg Thr Pro Glu Val Thr Cys Val Val
                420                 425                 430

Val Asp Val Ser His Glu Asp Pro Glu Val Lys Phe Asn Trp Tyr Val
            435                 440                 445

Asp Gly Val Glu Val His Asn Ala Lys Thr Lys Pro Arg Glu Glu Gln
            450                 455                 460

Tyr Asn Ser Thr Tyr Arg Val Val Ser Val Leu Thr Val Leu His Gln
465                 470                 475                 480

Asp Trp Leu Asn Gly Lys Glu Tyr Lys Cys Lys Val Ser Asn Lys Gly
                485                 490                 495

Leu Pro Ser Ser Ile Glu Lys Thr Ile Ser Lys Ala Lys Gly Gln Pro
                500                 505                 510

Arg Glu Pro Gln Val Tyr Thr Leu Pro Pro Ser Arg Asp Glu Leu Thr
            515                 520                 525

Lys Asn Gln Val Ser Leu Thr Cys Leu Val Lys Gly Phe Tyr Pro Ser
            530                 535                 540

Asp Ile Ala Val Glu Trp Glu Ser Asn Gly Gln Pro Glu Asn Asn Tyr
545                 550                 555                 560

Lys Thr Thr Pro Pro Val Leu Asp Ser Asp Gly Ser Phe Phe Leu Tyr
                565                 570                 575

Ser Lys Leu Thr Val Asp Lys Ser Arg Trp Gln Gln Gly Asn Val Phe
                580                 585                 590

Ser Cys Ser Val Met His Glu Ala Leu His Asn His Tyr Thr Gln Lys
            595                 600                 605

Ser Leu Ser Leu Ser Pro Gly Lys
```

<210> SEQ ID NO 138
<211> LENGTH: 511
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 138

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Gly Gly Gly Ser Leu Lys Cys Tyr Gln His Gly
            100                 105                 110

Lys Val Val Thr Cys His Arg Asp Met Lys Phe Cys Tyr His Asn Thr
            115                 120                 125

Gly Met Pro Phe Arg Asn Leu Lys Leu Ile Leu Gln Gly Cys Ser Ser
        130                 135                 140

Ser Cys Ser Glu Thr Glu Asn Asn Lys Cys Cys Ser Thr Asp Arg Cys
145                 150                 155                 160

Asn Lys Gly Gly Gly Gly Ser Tyr Phe Asp Val Trp Gly Ala Gly Thr
                165                 170                 175

Thr Val Thr Val Ser Ser Ala Ser Thr Lys Gly Pro Ser Val Phe Pro
            180                 185                 190

Leu Ala Pro Ser Ser Lys Ser Thr Ser Gly Gly Thr Ala Ala Leu Gly
        195                 200                 205

Cys Leu Val Lys Asp Tyr Phe Pro Glu Pro Val Thr Val Ser Trp Asn
    210                 215                 220

Ser Gly Ala Leu Thr Ser Gly Val His Thr Phe Pro Ala Val Leu Gln
225                 230                 235                 240

Ser Ser Gly Leu Tyr Ser Leu Ser Ser Val Val Thr Val Pro Ser Ser
                245                 250                 255

Ser Leu Gly Thr Gln Thr Tyr Ile Cys Asn Val Asn His Lys Pro Ser
            260                 265                 270

Asn Thr Lys Val Asp Lys Lys Val Glu Pro Lys Ser Cys Asp Lys Thr
        275                 280                 285

His Thr Cys Pro Pro Cys Pro Ala Pro Pro Val Ala Gly Pro Ser Val
    290                 295                 300

Phe Leu Phe Pro Pro Lys Pro Lys Asp Thr Leu Met Ile Ser Arg Thr
305                 310                 315                 320

Pro Glu Val Thr Cys Val Val Asp Val Ser His Glu Asp Pro Glu
                325                 330                 335

Val Lys Phe Asn Trp Tyr Val Asp Gly Val Glu Val His Asn Ala Lys
            340                 345                 350

```
Thr Lys Pro Arg Glu Glu Gln Tyr Asn Ser Thr Tyr Arg Val Val Ser
            355                 360                 365

Val Leu Thr Val Leu His Gln Asp Trp Leu Asn Gly Lys Glu Tyr Lys
        370                 375                 380

Cys Lys Val Ser Asn Lys Gly Leu Pro Ser Ser Ile Glu Lys Thr Ile
385                 390                 395                 400

Ser Lys Ala Lys Gly Gln Pro Arg Glu Pro Gln Val Tyr Thr Leu Pro
                405                 410                 415

Pro Ser Arg Asp Glu Leu Thr Lys Asn Gln Val Ser Leu Thr Cys Leu
            420                 425                 430

Val Lys Gly Phe Tyr Pro Ser Asp Ile Ala Val Glu Trp Glu Ser Asn
        435                 440                 445

Gly Gln Pro Glu Asn Asn Tyr Lys Thr Thr Pro Pro Val Leu Asp Ser
    450                 455                 460

Asp Gly Ser Phe Phe Leu Tyr Ser Lys Leu Thr Val Asp Lys Ser Arg
465                 470                 475                 480

Trp Gln Gln Gly Asn Val Phe Ser Cys Ser Val Met His Glu Ala Leu
                485                 490                 495

His Asn His Tyr Thr Gln Lys Ser Leu Ser Leu Ser Pro Gly Lys
            500                 505                 510

<210> SEQ ID NO 139
<211> LENGTH: 642
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Gly Gly Gly Ser Gly Gly Gly Ser Ala Pro
            100                 105                 110

Leu Gly Gly Pro Glu Pro Ala Gln Tyr Glu Glu Leu Thr Leu Leu Phe
            115                 120                 125

His Gly Ala Leu Gln Leu Gly Gln Ala Leu Asn Gly Val Tyr Arg Ala
        130                 135                 140

Thr Glu Ala Arg Leu Thr Glu Ala Gly His Ser Leu Gly Leu Tyr Asp
145                 150                 155                 160

Arg Ala Leu Glu Phe Leu Gly Thr Glu Val Arg Gln Gly Gln Asp Ala
                165                 170                 175

Thr Gln Glu Leu Arg Thr Ser Leu Ser Glu Ile Gln Val Glu Asp
            180                 185                 190

Ala Leu His Leu Arg Ala Glu Ala Thr Ala Arg Ser Leu Gly Glu Val
        195                 200                 205
```

```
Ala Arg Ala Gln Gln Ala Leu Arg Asp Thr Val Arg Leu Gln Val
    210                 215                 220

Gln Leu Arg Gly Ala Trp Leu Gly Gln Ala His Gln Glu Phe Glu Thr
225                 230                 235                 240

Leu Lys Ala Arg Ala Asp Lys Gln Ser His Leu Leu Trp Ala Leu Thr
                245                 250                 255

Gly His Val Gln Arg Gln Gln Arg Glu Met Ala Glu Gln Gln Gln Trp
            260                 265                 270

Leu Arg Gln Ile Gln Gln Arg Leu His Thr Ala Ala Leu Pro Ala Gly
        275                 280                 285

Gly Gly Gly Ser Gly Gly Gly Ser Trp His Val Asp Val Trp Gly
290                 295                 300

Gln Gly Leu Leu Val Thr Val Ser Ser Ala Ser Thr Thr Ala Pro Lys
305                 310                 315                 320

Val Tyr Pro Leu Ser Ser Cys Cys Gly Asp Lys Ser Ser Thr Val
                325                 330                 335

Thr Leu Gly Cys Leu Val Ser Ser Tyr Met Pro Glu Pro Val Thr Val
                340                 345                 350

Thr Trp Asn Ser Gly Ala Leu Lys Ser Gly Val His Thr Phe Pro Ala
            355                 360                 365

Val Leu Gln Ser Ser Gly Leu Tyr Ser Leu Ser Ser Met Val Thr Val
370                 375                 380

Pro Gly Ser Thr Ser Gly Gln Thr Phe Thr Cys Asn Val Ala His Pro
385                 390                 395                 400

Ala Ser Ser Thr Lys Val Asp Lys Ala Val Glu Pro Lys Ser Cys Asp
                405                 410                 415

Lys Thr His Thr Cys Pro Pro Cys Pro Ala Pro Glu Leu Leu Gly Gly
                420                 425                 430

Pro Ser Val Phe Leu Phe Pro Pro Lys Pro Lys Asp Thr Leu Met Ile
            435                 440                 445

Ser Arg Thr Pro Glu Val Thr Cys Val Val Val Asp Val Ser His Glu
450                 455                 460

Asp Pro Glu Val Lys Phe Asn Trp Tyr Val Asp Gly Val Glu Val His
465                 470                 475                 480

Asn Ala Lys Thr Lys Pro Arg Glu Glu Gln Tyr Asn Ser Thr Tyr Arg
                485                 490                 495

Val Val Ser Val Leu Thr Val Leu His Gln Asp Trp Leu Asn Gly Lys
            500                 505                 510

Glu Tyr Lys Cys Lys Val Ser Asn Lys Ala Leu Pro Ala Pro Ile Glu
        515                 520                 525

Lys Thr Ile Ser Lys Ala Lys Gly Gln Pro Arg Glu Pro Gln Val Tyr
    530                 535                 540

Thr Leu Pro Pro Ser Arg Asp Glu Leu Thr Lys Asn Gln Val Ser Leu
545                 550                 555                 560

Thr Cys Leu Val Lys Gly Phe Tyr Pro Ser Asp Ile Ala Val Glu Trp
                565                 570                 575

Glu Ser Asn Gly Gln Pro Glu Asn Asn Tyr Lys Thr Thr Pro Pro Val
            580                 585                 590

Leu Asp Ser Asp Gly Ser Phe Phe Leu Tyr Ser Lys Leu Thr Val Asp
        595                 600                 605

Lys Ser Arg Trp Gln Gln Gly Asn Val Phe Ser Cys Ser Val Met His
    610                 615                 620
```

```
Glu Ala Leu His Asn His Tyr Thr Gln Lys Ser Leu Ser Leu Ser Pro
625                 630                 635                 640

Gly Lys

<210> SEQ ID NO 140
<211> LENGTH: 632
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Gly Gly Gly Ser Ala Pro Leu Gly Gly Pro Glu
            100                 105                 110

Pro Ala Gln Tyr Glu Glu Leu Thr Leu Leu Phe His Gly Ala Leu Gln
        115                 120                 125

Leu Gly Gln Ala Leu Asn Gly Val Tyr Arg Ala Thr Glu Ala Arg Leu
    130                 135                 140

Thr Glu Ala Gly His Ser Leu Gly Leu Tyr Asp Arg Ala Leu Glu Phe
145                 150                 155                 160

Leu Gly Thr Glu Val Arg Gln Gly Gln Asp Ala Thr Gln Glu Leu Arg
                165                 170                 175

Thr Ser Leu Ser Glu Ile Gln Val Glu Glu Asp Ala Leu His Leu Arg
            180                 185                 190

Ala Glu Ala Thr Ala Arg Ser Leu Gly Glu Val Ala Arg Ala Gln Gln
        195                 200                 205

Ala Leu Arg Asp Thr Val Arg Arg Leu Gln Val Gln Leu Arg Gly Ala
    210                 215                 220

Trp Leu Gly Gln Ala His Gln Glu Phe Glu Thr Leu Lys Ala Arg Ala
225                 230                 235                 240

Asp Lys Gln Ser His Leu Leu Trp Ala Leu Thr Gly His Val Gln Arg
                245                 250                 255

Gln Gln Arg Glu Met Ala Glu Gln Gln Gln Trp Leu Arg Gln Ile Gln
            260                 265                 270

Gln Arg Leu His Thr Ala Ala Leu Pro Ala Gly Gly Gly Gly Ser Trp
        275                 280                 285

His Val Asp Val Trp Gly Gln Gly Leu Leu Val Thr Val Ser Ser Ala
    290                 295                 300

Ser Thr Thr Ala Pro Lys Val Tyr Pro Leu Ser Ser Cys Cys Gly Asp
305                 310                 315                 320

Lys Ser Ser Ser Thr Val Thr Leu Gly Cys Leu Val Ser Ser Tyr Met
                325                 330                 335
```

```
Pro Glu Pro Val Thr Val Thr Trp Asn Ser Gly Ala Leu Lys Ser Gly
                340                 345                 350

Val His Thr Phe Pro Ala Val Leu Gln Ser Ser Gly Leu Tyr Ser Leu
            355                 360                 365

Ser Ser Met Val Thr Val Pro Gly Ser Thr Ser Gly Gln Thr Phe Thr
370                 375                 380

Cys Asn Val Ala His Pro Ala Ser Ser Thr Lys Val Asp Lys Ala Val
385                 390                 395                 400

Glu Pro Lys Ser Cys Asp Lys Thr His Thr Cys Pro Pro Cys Pro Ala
                405                 410                 415

Pro Glu Leu Leu Gly Gly Pro Ser Val Phe Leu Phe Pro Pro Lys Pro
            420                 425                 430

Lys Asp Thr Leu Met Ile Ser Arg Thr Pro Glu Val Thr Cys Val Val
        435                 440                 445

Val Asp Val Ser His Glu Asp Pro Glu Val Lys Phe Asn Trp Tyr Val
450                 455                 460

Asp Gly Val Glu Val His Asn Ala Lys Thr Lys Pro Arg Glu Glu Gln
465                 470                 475                 480

Tyr Asn Ser Thr Tyr Arg Val Val Ser Val Leu Thr Val Leu His Gln
                485                 490                 495

Asp Trp Leu Asn Gly Lys Glu Tyr Lys Cys Lys Val Ser Asn Lys Ala
            500                 505                 510

Leu Pro Ala Pro Ile Glu Lys Thr Ile Ser Lys Ala Lys Gly Gln Pro
        515                 520                 525

Arg Glu Pro Gln Val Tyr Thr Leu Pro Pro Ser Arg Asp Glu Leu Thr
530                 535                 540

Lys Asn Gln Val Ser Leu Thr Cys Leu Val Lys Gly Phe Tyr Pro Ser
545                 550                 555                 560

Asp Ile Ala Val Glu Trp Glu Ser Asn Gly Gln Pro Glu Asn Asn Tyr
                565                 570                 575

Lys Thr Thr Pro Pro Val Leu Asp Ser Asp Gly Ser Phe Phe Leu Tyr
            580                 585                 590

Ser Lys Leu Thr Val Asp Lys Ser Arg Trp Gln Gln Gly Asn Val Phe
        595                 600                 605

Ser Cys Ser Val Met His Glu Ala Leu His Asn His Tyr Thr Gln Lys
610                 615                 620

Ser Leu Ser Leu Ser Pro Gly Lys
625                 630

<210> SEQ ID NO 141
<211> LENGTH: 646
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60
```

```
Ser Arg Leu Ser Ile Thr Lys Asp Asn Ser Lys Ser Gln Val Ser Leu
 65                  70                  75                  80

Ser Val Ser Ser Val Thr Thr Glu Asp Ser Ala Thr Tyr Tyr Cys Thr
                 85                  90                  95

Ser Val His Gln Gly Gly Gly Ser Phe Pro Thr Ile Pro Leu Ser
            100                 105                 110

Arg Leu Phe Asp Asn Ala Met Leu Arg Ala His Arg Leu His Gln Leu
        115                 120                 125

Ala Phe Asp Thr Tyr Gln Glu Phe Glu Glu Ala Tyr Ile Pro Lys Glu
130                 135                 140

Gln Lys Tyr Ser Phe Leu Gln Asn Pro Gln Thr Ser Leu Cys Phe Ser
145                 150                 155                 160

Glu Ser Ile Pro Thr Pro Ser Asn Arg Glu Glu Thr Gln Gln Lys Ser
                165                 170                 175

Asn Leu Glu Leu Leu Arg Ile Ser Leu Leu Leu Ile Gln Ser Trp Leu
            180                 185                 190

Glu Pro Val Gln Phe Leu Arg Ser Val Phe Ala Asn Ser Leu Val Tyr
            195                 200                 205

Gly Ala Ser Asp Ser Asn Val Tyr Asp Leu Leu Lys Asp Leu Glu Glu
210                 215                 220

Gly Ile Gln Thr Leu Met Gly Arg Leu Glu Asp Gly Ser Pro Arg Thr
225                 230                 235                 240

Gly Gln Ile Phe Lys Gln Thr Tyr Ser Lys Phe Asp Thr Asn Ser His
                245                 250                 255

Asn Asp Asp Ala Leu Leu Lys Asn Tyr Gly Leu Leu Tyr Cys Phe Arg
            260                 265                 270

Lys Asp Met Asp Lys Val Glu Thr Phe Leu Arg Ile Val Gln Cys Arg
            275                 280                 285

Ser Val Glu Gly Ser Cys Gly Phe Gly Gly Gly Ser Trp His Val
290                 295                 300

Asp Val Trp Gly Gln Gly Leu Leu Val Thr Val Ser Ser Ala Ser Thr
305                 310                 315                 320

Thr Ala Pro Lys Val Tyr Pro Leu Ser Ser Cys Cys Gly Asp Lys Ser
                325                 330                 335

Ser Ser Thr Val Thr Leu Gly Cys Leu Val Ser Ser Tyr Met Pro Glu
            340                 345                 350

Pro Val Thr Val Thr Trp Asn Ser Gly Ala Leu Lys Ser Gly Val His
            355                 360                 365

Thr Phe Pro Ala Val Leu Gln Ser Ser Gly Leu Tyr Ser Leu Ser Ser
        370                 375                 380

Met Val Thr Val Pro Gly Ser Thr Ser Gly Gln Thr Phe Thr Cys Asn
385                 390                 395                 400

Val Ala His Pro Ala Ser Ser Thr Lys Val Asp Lys Ala Val Glu Pro
                405                 410                 415

Lys Ser Cys Asp Lys Thr His Thr Cys Pro Pro Cys Pro Ala Pro Glu
            420                 425                 430

Leu Leu Gly Gly Pro Ser Val Phe Leu Phe Pro Pro Lys Pro Lys Asp
            435                 440                 445

Thr Leu Met Ile Ser Arg Thr Pro Glu Val Thr Cys Val Val Val Asp
        450                 455                 460

Val Ser His Glu Asp Pro Glu Val Lys Phe Asn Trp Tyr Val Asp Gly
465                 470                 475                 480
```

-continued

```
Val Glu Val His Asn Ala Lys Thr Lys Pro Arg Glu Glu Gln Tyr Asn
            485                 490                 495
Ser Thr Tyr Arg Val Val Ser Val Leu Thr Val Leu His Gln Asp Trp
        500                 505                 510
Leu Asn Gly Lys Glu Tyr Lys Cys Lys Val Ser Asn Lys Ala Leu Pro
    515                 520                 525
Ala Pro Ile Glu Lys Thr Ile Ser Lys Ala Lys Gly Gln Pro Arg Glu
530                 535                 540
Pro Gln Val Tyr Thr Leu Pro Pro Ser Arg Asp Glu Leu Thr Lys Asn
545                 550                 555                 560
Gln Val Ser Leu Thr Cys Leu Val Lys Gly Phe Tyr Pro Ser Asp Ile
                565                 570                 575
Ala Val Glu Trp Glu Ser Asn Gly Gln Pro Glu Asn Asn Tyr Lys Thr
            580                 585                 590
Thr Pro Pro Val Leu Asp Ser Asp Gly Ser Phe Phe Leu Tyr Ser Lys
        595                 600                 605
Leu Thr Val Asp Lys Ser Arg Trp Gln Gln Gly Asn Val Phe Ser Cys
    610                 615                 620
Ser Val Met His Glu Ala Leu His Asn His Tyr Thr Gln Lys Ser Leu
625                 630                 635                 640
Ser Leu Ser Pro Gly Lys
                645

<210> SEQ ID NO 142
<211> LENGTH: 621
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Val Gln Leu Arg Glu Ser Gly Pro Ser Leu Val Lys Pro Ser Gln
1               5                   10                  15
Thr Leu Ser Leu Thr Cys Thr Ala Ser Gly Phe Ser Leu Ser Asp Lys
            20                  25                  30
Ala Val Gly Trp Val Arg Gln Ala Pro Gly Lys Ala Leu Glu Trp Leu
        35                  40                  45
Gly Ser Ile Asp Thr Gly Gly Asn Thr Gly Tyr Asn Pro Gly Leu Lys
    50                  55                  60
Ser Arg Leu Ser Ile Thr Lys Asp Asn Ser Lys Ser Gln Val Ser Leu
65                  70                  75                  80
Ser Val Ser Ser Val Thr Thr Glu Asp Ser Ala Thr Tyr Tyr Cys Thr
                85                  90                  95
Ser Val His Gln Gly Gly Gly Ser Met Ser Tyr Asn Leu Leu Gly
            100                 105                 110
Phe Leu Gln Arg Ser Ser Asn Phe Gln Cys Gln Lys Leu Leu Trp Gln
        115                 120                 125
Leu Asn Gly Arg Leu Glu Tyr Cys Leu Lys Asp Arg Met Asn Phe Asp
    130                 135                 140
Ile Pro Glu Glu Ile Lys Gln Leu Gln Gln Phe Gln Lys Glu Asp Ala
145                 150                 155                 160
Ala Leu Thr Ile Tyr Glu Met Leu Gln Asn Ile Phe Ala Ile Phe Arg
                165                 170                 175
Gln Asp Ser Ser Ser Thr Gly Trp Asn Glu Thr Ile Val Glu Asn Leu
            180                 185                 190
```

-continued

```
Leu Ala Asn Val Tyr His Gln Ile Asn His Leu Lys Thr Val Leu Glu
            195                 200                 205

Glu Lys Leu Glu Lys Glu Asp Phe Thr Arg Gly Lys Leu Met Ser Ser
210                 215                 220

Leu His Leu Lys Arg Tyr Tyr Gly Arg Ile Leu His Tyr Leu Lys Ala
225                 230                 235                 240

Lys Glu Tyr Ser His Cys Ala Trp Thr Ile Val Arg Val Glu Ile Leu
                245                 250                 255

Arg Asn Phe Tyr Phe Ile Asn Arg Leu Thr Gly Tyr Leu Arg Asn Gly
                260                 265                 270

Gly Gly Gly Ser Trp His Val Asp Val Trp Gln Gly Leu Leu Val
                275                 280                 285

Thr Val Ser Ser Ala Ser Thr Thr Ala Pro Lys Val Tyr Pro Leu Ser
    290                 295                 300

Ser Cys Cys Gly Asp Lys Ser Ser Thr Val Thr Leu Gly Cys Leu
305                 310                 315                 320

Val Ser Ser Tyr Met Pro Glu Pro Val Thr Val Thr Trp Asn Ser Gly
                325                 330                 335

Ala Leu Lys Ser Gly Val His Thr Phe Pro Ala Val Leu Gln Ser Ser
                340                 345                 350

Gly Leu Tyr Ser Leu Ser Ser Met Val Thr Val Pro Gly Ser Thr Ser
            355                 360                 365

Gly Gln Thr Phe Thr Cys Asn Val Ala His Pro Ala Ser Ser Thr Lys
    370                 375                 380

Val Asp Lys Ala Val Glu Pro Lys Ser Cys Asp Lys Thr His Thr Cys
385                 390                 395                 400

Pro Pro Cys Pro Ala Pro Glu Leu Leu Gly Gly Pro Ser Val Phe Leu
                405                 410                 415

Phe Pro Pro Lys Pro Lys Asp Thr Leu Met Ile Ser Arg Thr Pro Glu
                420                 425                 430

Val Thr Cys Val Val Val Asp Val Ser His Glu Asp Pro Glu Val Lys
            435                 440                 445

Phe Asn Trp Tyr Val Asp Gly Val Glu Val His Asn Ala Lys Thr Lys
    450                 455                 460

Pro Arg Glu Glu Gln Tyr Asn Ser Thr Tyr Arg Val Val Ser Val Leu
465                 470                 475                 480

Thr Val Leu His Gln Asp Trp Leu Asn Gly Lys Glu Tyr Lys Cys Lys
                485                 490                 495

Val Ser Asn Lys Ala Leu Pro Ala Pro Ile Glu Lys Thr Ile Ser Lys
                500                 505                 510

Ala Lys Gly Gln Pro Arg Glu Pro Gln Val Tyr Thr Leu Pro Pro Ser
            515                 520                 525

Arg Asp Glu Leu Thr Lys Asn Gln Val Ser Leu Thr Cys Leu Val Lys
    530                 535                 540

Gly Phe Tyr Pro Ser Asp Ile Ala Val Glu Trp Glu Ser Asn Gly Gln
545                 550                 555                 560

Pro Glu Asn Asn Tyr Lys Thr Thr Pro Pro Val Leu Asp Ser Asp Gly
                565                 570                 575

Ser Phe Phe Leu Tyr Ser Lys Leu Thr Val Asp Lys Ser Arg Trp Gln
                580                 585                 590

Gln Gly Asn Val Phe Ser Cys Ser Val Met His Glu Ala Leu His Asn
            595                 600                 605
```

His Tyr Thr Gln Lys Ser Ser Leu Ser Pro Gly Lys
    610                 615                 620

<210> SEQ ID NO 143
<211> LENGTH: 646
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Gly Gly Gly Ser Phe Pro Thr Ile Pro Leu Ser
            100                 105                 110

Arg Leu Phe Asp Asn Ala Met Leu Arg Ala His Arg Leu His Gln Leu
        115                 120                 125

Ala Phe Asp Thr Tyr Gln Glu Phe Glu Glu Ala Tyr Ile Pro Lys Glu
    130                 135                 140

Gln Lys Tyr Ser Phe Leu Gln Asn Pro Gln Thr Ser Leu Cys Phe Ser
145                 150                 155                 160

Glu Ser Ile Pro Thr Pro Ser Asn Arg Glu Glu Thr Gln Gln Lys Ser
                165                 170                 175

Asn Leu Glu Leu Leu Arg Ile Ser Leu Leu Leu Ile Gln Ser Trp Leu
            180                 185                 190

Glu Pro Val Gln Phe Leu Arg Ser Val Phe Ala Asn Ser Leu Val Tyr
        195                 200                 205

Gly Ala Ser Asp Ser Asn Val Tyr Asp Leu Leu Lys Asp Leu Glu Glu
    210                 215                 220

Gly Ile Gln Thr Leu Met Gly Arg Leu Glu Asp Gly Ser Pro Arg Thr
225                 230                 235                 240

Gly Gln Ile Phe Lys Gln Thr Tyr Ser Lys Phe Asp Thr Asn Ser His
                245                 250                 255

Asn Asp Asp Ala Leu Leu Lys Asn Tyr Gly Leu Leu Tyr Cys Phe Arg
            260                 265                 270

Lys Asp Met Asp Lys Val Glu Thr Phe Leu Arg Ile Val Gln Cys Arg
        275                 280                 285

Ser Val Glu Gly Ser Cys Gly Phe Gly Gly Gly Ser Trp His Val
    290                 295                 300

Asp Val Trp Gly Gln Gly Leu Leu Val Thr Val Ser Ser Ala Ser Thr
305                 310                 315                 320

Thr Ala Pro Lys Val Tyr Pro Leu Ser Ser Cys Cys Gly Asp Lys Ser
                325                 330                 335

Ser Ser Thr Val Thr Leu Gly Cys Leu Val Ser Ser Tyr Met Pro Glu
            340                 345                 350

Pro Val Thr Val Thr Trp Asn Ser Gly Ala Leu Lys Ser Gly Val His
            355                 360                 365

Thr Phe Pro Ala Val Leu Gln Ser Ser Gly Leu Tyr Ser Leu Ser Ser
        370                 375                 380

Met Val Thr Val Pro Gly Ser Thr Ser Gly Gln Thr Phe Thr Cys Asn
385                 390                 395                 400

Val Ala His Pro Ala Ser Ser Thr Lys Val Asp Lys Ala Val Glu Pro
                405                 410                 415

Lys Ser Cys Asp Lys Thr His Thr Cys Pro Pro Cys Pro Ala Pro Glu
            420                 425                 430

Leu Leu Gly Gly Pro Ser Val Phe Leu Phe Pro Pro Lys Pro Lys Asp
            435                 440                 445

Thr Leu Met Ile Ser Arg Thr Pro Glu Val Thr Cys Val Val Val Asp
        450                 455                 460

Val Ser His Glu Asp Pro Glu Val Lys Phe Asn Trp Tyr Val Asp Gly
465                 470                 475                 480

Val Glu Val His Asn Ala Lys Thr Lys Pro Arg Glu Glu Gln Tyr Asn
                485                 490                 495

Ser Thr Tyr Arg Val Val Ser Val Leu Thr Val Leu His Gln Asp Trp
            500                 505                 510

Leu Asn Gly Lys Glu Tyr Lys Cys Lys Val Ser Asn Lys Ala Leu Pro
            515                 520                 525

Ala Pro Ile Glu Lys Thr Ile Ser Lys Ala Lys Gly Gln Pro Arg Glu
        530                 535                 540

Pro Gln Val Tyr Thr Leu Pro Pro Ser Arg Asp Glu Leu Thr Lys Asn
545                 550                 555                 560

Gln Val Ser Leu Thr Cys Leu Val Lys Gly Phe Tyr Pro Ser Asp Ile
                565                 570                 575

Ala Val Glu Trp Glu Ser Asn Gly Gln Pro Glu Asn Asn Tyr Lys Thr
            580                 585                 590

Thr Pro Pro Val Leu Asp Ser Asp Gly Ser Phe Phe Leu Tyr Ser Lys
            595                 600                 605

Leu Thr Val Asp Lys Ser Arg Trp Gln Gln Gly Asn Val Phe Ser Cys
        610                 615                 620

Ser Val Met His Glu Ala Leu His Asn His Tyr Thr Gln Lys Ser Leu
625                 630                 635                 640

Ser Leu Ser Pro Gly Lys
                645

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(14)
<223> OTHER INFORMATION: Any positively charged or hydrophobic amino
      acid
<220> FEATURE:
<223> OTHER INFORMATION: See specification as filed for detailed
      description of substitutions and preferred embodiments

<400> SEQUENCE: 144

Xaa Xaa Xaa Xaa Xaa Xaa Xaa Xaa Xaa Xaa Xaa Xaa Xaa Xaa
1               5                   10

```
<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: Any positively charged or hydrophobic amino
      acid
<220> FEATURE:
<223> OTHER INFORMATION: See specification as filed for detailed
      description of substitutions and preferred embodiments

<400> SEQUENCE: 145

Xaa Xaa Xaa Xaa Xaa Xaa Xaa
1               5

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any hydrophobic amino acid
<220> FEATURE:
<221> NAME/KEY: MOD_RES
<222> LOCATION: (3)..(3)
<223> OTHER INFORMATION: Any polar, uncharged amino acid
<220> FEATURE:
<221> NAME/KEY: MOD_RES
<222> LOCATION: (4)..(4)
<223> OTHER INFORMATION: Any hydrophobic amino acid
<220> FEATURE:
<221> NAME/KEY: MOD_RES
<222> LOCATION: (5)..(11)
<223> OTHER INFORMATION: Any positively charged or hydrophobic amino
      acid
<220> FEATURE:
<223> OTHER INFORMATION: See specification as filed for detailed
      description of substitutions and preferred embodiments

<400> SEQUENCE: 146

Xaa Xaa Xaa Xaa Xaa Xaa Xaa Xaa Xaa Xaa Xaa
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any hydrophobic amino acid
<220> FEATURE:
<221> NAME/KEY: MOD_RES
<222> LOCATION: (3)..(3)
<223> OTHER INFORMATION: Any polar, uncharged amino acid
<220> FEATURE:
<221> NAME/KEY: MOD_RES
<222> LOCATION: (4)..(4)
<223> OTHER INFORMATION: Any hydrophobic amino acid
<220> FEATURE:
<223> OTHER INFORMATION: See specification as filed for detailed
```

```
      description of substitutions and preferred embodiments

<400> SEQUENCE: 147

Xaa Xaa Xaa Xaa Ala Lys Leu Ala Ala Leu Lys
1               5                   10

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 148

Ala Lys Leu Ala Ala Leu Lys
1               5

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 149

Gly Gly Ser Gly Ala Lys Leu Ala Ala Leu Lys
1               5                   10

<210> SEQ ID NO 150
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 150

Ala Lys Leu Ala Ala Leu Lys Ala Lys Leu Ala Ala Leu Lys
1               5                   10

<210> SEQ ID NO 151
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Gly Ser Gly Ala Lys Leu Ala Ala Leu Lys Ala Lys Leu Ala Ala
1               5                   10                  15

Leu Lys

<210> SEQ ID NO 152
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 152

Cys Ala Ala Leu Lys Ser Lys Val Ser Ala Leu Lys Ser Lys Val Ala
1               5                   10                  15

Ser Leu Lys Ser Lys Val Ala Ala Leu
            20                  25

<210> SEQ ID NO 153
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Leu Lys Lys Glu Leu Gln Ala Asn Lys Lys Glu Leu Ala Gln Leu
1               5                   10                  15

Lys Lys Glu Leu Gln Ala Leu Lys Lys Glu Leu Ala Gln
            20                  25

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(14)
<223> OTHER INFORMATION: Any negatively charged or hydrophobic amino
      acid
<220> FEATURE:
<223> OTHER INFORMATION: See specification as filed for detailed
      description of substitutions and preferred embodiments

<400> SEQUENCE: 154

Xaa Xaa Xaa Xaa Xaa Xaa Xaa Xaa Xaa Xaa Xaa Xaa Xaa Xaa
1               5                   10

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: Any positively charged or hydrophobic amino
      acid
<220> FEATURE:
<223> OTHER INFORMATION: See specification as filed for detailed
      description of substitutions and preferred embodiments

<400> SEQUENCE: 155

Xaa Xaa Xaa Xaa Xaa Xaa Xaa
1               5

<210> SEQ ID NO 156
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: Any positively charged or hydrophobic amino
      acid
<220> FEATURE:
<221> NAME/KEY: MOD_RES
<222> LOCATION: (8)..(9)
<223> OTHER INFORMATION: Any hydrophobic amino acid
<220> FEATURE:
<221> NAME/KEY: MOD_RES
<222> LOCATION: (10)..(10)
<223> OTHER INFORMATION: Any polar, uncharged amino acid
<220> FEATURE:
<221> NAME/KEY: MOD_RES
<222> LOCATION: (11)..(11)
<223> OTHER INFORMATION: Any hydrophobic amino acid
<220> FEATURE:
<223> OTHER INFORMATION: See specification as filed for detailed
      description of substitutions and preferred embodiments

<400> SEQUENCE: 156

Xaa Xaa Xaa Xaa Xaa Xaa Xaa Xaa Xaa Xaa Xaa
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Any hydrophobic amino acid
<220> FEATURE:
<221> NAME/KEY: MOD_RES
<222> LOCATION: (10)..(10)
<223> OTHER INFORMATION: Any polar, uncharged amino acid
<220> FEATURE:
<221> NAME/KEY: MOD_RES
<222> LOCATION: (11)..(11)
<223> OTHER INFORMATION: Any hydrophobic amino acid
<220> FEATURE:
<223> OTHER INFORMATION: See specification as filed for detailed
      description of substitutions and preferred embodiments

<400> SEQUENCE: 157

Glu Leu Ala Ala Leu Glu Ala Xaa Xaa Xaa Xaa
1               5                   10

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 158

Glu Leu Ala Ala Leu Glu Ala
1               5

<210> SEQ ID NO 159
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 159

Glu Leu Ala Ala Leu Glu Ala Asn Gly Gly Ser Gly
1               5                   10

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Glu Leu Ala Ala Leu Glu Ala Glu Leu Ala Ala Leu Glu Ala
1               5                   10

<210> SEQ ID NO 161
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Glu Leu Ala Ala Leu Glu Ala Glu Leu Ala Ala Leu Glu Ala Gly Gly
1               5                   10                  15

Ser Gly

<210> SEQ ID NO 162
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Leu Ala Ala Val Glu Ser Glu Leu Ser Ala Val Glu Ser Glu Leu Ala
1               5                   10                  15

Ser Val Glu Ser Glu Leu Ala Ala Cys
            20                  25

<210> SEQ ID NO 163
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gln Leu Glu Lys Lys Leu Gln Ala Leu Glu Lys Lys Leu Ala Gln Leu
1               5                   10                  15

Glu Lys Lys Asn Gln Ala Leu Glu Lys Lys Leu Ala Gln
            20                  25

<210> SEQ ID NO 164
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Cys Ala Ala Leu Lys Ser Lys Val Ser Ala Leu Lys Ser Lys Val Ala
1               5                   10                  15

Ser Leu Lys Ser Lys Val Ala Ala Leu
            20                  25

<210> SEQ ID NO 165
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Leu Ala Ala Val Glu Ser Glu Leu Ser Ala Val Glu Ser Glu Leu Ala
1               5                   10                  15

Ser Val Glu Ser Glu Leu Ala Ala Cys
            20                  25

<210> SEQ ID NO 166
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Leu Lys Lys Glu Leu Gln Ala Asn Lys Lys Glu Leu Ala Gln Leu
1               5                   10                  15

Lys Lys Glu Leu Gln Ala Leu Lys Lys Glu Leu Ala Gln
            20                  25

<210> SEQ ID NO 167
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gln Leu Glu Lys Lys Leu Gln Ala Leu Glu Lys Lys Leu Ala Gln Leu
1               5                   10                  15

Glu Lys Lys Asn Gln Ala Leu Glu Lys Lys Leu Ala Gln
            20                  25

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Leu Lys Leu Glu Leu Gln Leu Ile Lys Gln Tyr Arg Glu Ala Leu
1               5                   10                  15
```

```
<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Leu Ala Lys Ile Leu Glu Asp Glu Glu Lys His Ile Glu Trp Leu
1               5                   10                  15

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Leu Ser Asp Leu His Arg Gln Val Ser Arg Leu Val
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Leu Gln Asp Ala Lys Val Leu Leu Glu Ala Ala Leu
1               5                   10

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Leu Gln Gln Lys Ile His Glu Leu Glu Gly Leu Ile Ala Gln His
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Ala Gln Ile Arg Asp Gln Leu His Gln Leu Arg Glu Leu Phe
1               5                   10                  15

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 174

Glu Leu Ala Arg Leu Ile Arg Leu Tyr Phe Ala Leu
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gln Glu Ser Leu Tyr Val Asp Leu Phe Asp Lys Phe
1               5                   10

<210> SEQ ID NO 176
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any hydrophobic amino acid
<220> FEATURE:
<221> NAME/KEY: MOD_RES
<222> LOCATION: (4)..(4)
<223> OTHER INFORMATION: Any polar, uncharged amino acid
<220> FEATURE:
<223> OTHER INFORMATION: See specification as filed for detailed
      description of substitutions and preferred embodiments

<400> SEQUENCE: 176

Xaa Xaa Xaa Xaa
1

<210> SEQ ID NO 177
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any hydrophobic amino acid
<220> FEATURE:
<221> NAME/KEY: MOD_RES
<222> LOCATION: (5)..(5)
<223> OTHER INFORMATION: Any polar, uncharged amino acid
<220> FEATURE:
<223> OTHER INFORMATION: See specification as filed for detailed
      description of substitutions and preferred embodiments

<400> SEQUENCE: 177

Cys Xaa Xaa Xaa Xaa
1               5

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(3)
<223> OTHER INFORMATION: Any hydrophobic amino acid
<220> FEATURE:
<221> NAME/KEY: MOD_RES
<222> LOCATION: (4)..(4)
<223> OTHER INFORMATION: Any polar, uncharged amino acid
<220> FEATURE:
<223> OTHER INFORMATION: See specification as filed for detailed
      description of substitutions and preferred embodiments

<400> SEQUENCE: 178

Xaa Xaa Xaa Xaa Cys
1               5

<210> SEQ ID NO 179
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Gly Gly Gly Ser
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Gly Gly Ser Gly Gly Gly Gly Ser
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Gly Gly Gly Ser Gly Gly Gly Ser
1               5

<210> SEQ ID NO 182
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
atcgaaggtc gt                                                        12

<210> SEQ ID NO 183
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 183

Ile Glu Gly Arg
1

<210> SEQ ID NO 184
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cgtaaaaaac gt                                                         12

<210> SEQ ID NO 185
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Arg Lys Lys Arg
1

<210> SEQ ID NO 186
<211> LENGTH: 522
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186 acccccttg gccctgcccg atccctgccc cagagcttcc tgctcaagtg cttagagcaa      60
gtgaggaaaa tccaggctga tgcgccgag ctgcaggaga ggctgtgtgc cgcccacaag     120
ctgtgccacc cggaggagct gatgctgctc aggcactctc tgggcatccc ccaggctccc    180
ctaagcagct gctccagcca gtccctgcag ctgacgagct gcctgaacca actacacggc    240
ggcctctttc tctaccaggg cctcctgcag gccctggcgg gcatctcccc agagctggcc    300
cccaccttgg acacactgca gctggacgtc actgactttg ccacgaacat ctggctgcag    360
atggaggacc tgggggcggc ccccgctgtg cagcccaccc agggcgccat gccgaccttc    420
acttcagcct ccaacgcag agcaggaggg gtcctggttg cttcccagct gcatcgtttc      480
ctggagctgg cataccgtgg cctgcgctac cttgctgagc cc                       522

<210> SEQ ID NO 187
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
gccacacctc tgggccccgc ctcctccctg cctcagagct ttctgctcaa atgtctggag     60
caggtgcgga agatccaggg cgacggcgcc gctctgcaag agaaactggt cagcgaatgc    120
gccacatata agctgtgtca ccccgaggaa ctggtcctct tgggccacag cctgggcatc    180
ccctgggccc ctctcagctc ctgcccctcc caagctctcc aactggctgg atgtctgtcc    240

```
caactgcact ccggcctctt cctgtaccag ggactcctcc aggctctcga agggatcagc    300
cccgaactgg gccccacact ggacaccttg caactcgatg tggccgattt cgccacaacc    360
atctggcagc agatggaaga actcggaatg gctcctgctc tccagcccac acaggagct    420 atgcctgctt tcgcctctgc tttccagcgg agagctggtg gtgtgctcgt cgcatcccac    480
ctccagagct tcttggaggt gtcctatcgg gtgctccggc atctggccca accc          534
```

<210> SEQ ID NO 188
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188

```
cacggagaag gaacatttac cagcgacctc agcaagcaga tggaggaaga ggccgtgagg    60
ctgttcatcg agtggctgaa gaacggcgga ccctcctctg gcgctccacc ccctagc      117
```

<210> SEQ ID NO 189
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 189

```
atcaacgtga agtgcagcct gccccagcag tgcatcaagc cctgcaagga cgccggcatg    60
cggttcggca agtgcatgaa caagaagtgc aggtgctaca gc                      102
```

<210> SEQ ID NO 190
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190

```
gccgctgcaa tctcctgcgt cggcagcccc gaatgtcctc ccaagtgccg ggctcaggga    60
tgcaagaacg gcaagtgtat gaaccggaag tgcaagtgct actattgc                108
```

<210> SEQ ID NO 191
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191

```
catgcggaag gcacctttac cagcgatgtg agcagctatc tggaaggcca ggcggcgaaa    60
gaatttattg cgtggctggt gaaaggccgc                                     90
```

<210> SEQ ID NO 192
<211> LENGTH: 498
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192

```
gccccaccac gcctcatctg tgacagccga gtcctggaga ggtacctctt ggaggccaag      60
gaggccgaga atatcacgac gggctgtgct gaacactgca gcttgaatga aatatcact     120
gtcccagaca ccaaagttaa tttctatgcc tggaagagga tggaggtcgg gcagcaggcc    180
gtagaagtct ggcagggcct ggccctgctg tcggaagctg tcctgcgggg ccaggccctg    240
ttggtcaact cttcccagcc gtgggagccc ctgcagctgc atgtggataa agccgtcagt    300
ggccttcgca gcctcaccac tctgcttcgg gctctgggag cccagaagga agccatctcc    360
cctccagatg cggcctcagc tgctccactc cgaacaatca ctgctgacac tttccgcaaa    420
ctcttccgag tctactccaa tttcctccgg ggaaagctga agctgtacac aggggaggcc    480
tgcaggacag gggacaga                                                  498
```

<210> SEQ ID NO 193
<211> LENGTH: 543
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 193

```
catccgattc cggatagcag cccgctgctg cagtttggcg gccaggtgcg ccagcgctat     60
ctgtataccg atgatgcgca gcagaccgaa gcgcatctgg aaattcgcga agatggcacc    120
gtgggcggcg cggcggatca gagcccggaa agcctgctgc agctgaaagc gctgaaaccg    180
ggcgtgattc agattctggg cgtgaaaacc agccgctttc tgtgccagcg cccggatggc    240
gcgctgtatg cagcctgca ttttgatccg gaagcgtgca gctttcgcga actgctgctg    300
gaagatggct ataacgtgta tcagagcgaa gcgcatggcc tgccgctgca tctgccgggc    360
aacaaaagcc gcatcgcga tccggcgccg cgcggcccgg cgcgctttct gccgctgccg    420
ggcctgccgc cggcgccgcc ggaaccgccg ggcattctgg cgccgcagcc gccggatgtg    480
ggcagcagcg atccgctgag catggtgggc ccgagccagg gccgcagccc gagctatgcg    540
agc                                                                  543
```

<210> SEQ ID NO 194
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 194

```
gcgccggcgc gcagcccgag cccgagcacc cagccgtggg aacatgtgaa cgcgattcag     60
gaagcgcgcc gcctgctgaa cctgagccgc gataccgcgg cggaaatgaa cgaaaccgtg    120
gaagtgatta gcgaaatgtt tgatctgcag gaaccgacct gcctgcagac cgcctggaa    180
ctgtataaac agggcctgcg cggcagcctg accaaactga aggcccgct gaccatgatg    240
gcgagccatt ataaacagca ttgcccgccg acccgaaa ccagctgcgc gacccagatt    300
attacctttg aaagctttaa agaaaacctg aaagattttc tgctggtgat tccgtttgat    360
tgctgggaac cggtgcagga a                                              381
```

<210> SEQ ID NO 195

<211> LENGTH: 498
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195

```
atgagctata acctgctggg ctttctgcag cgcagcagca actttcagtg ccagaaactg      60
ctgtggcagc tgaacggccg cctggaatat tgcctgaaag atcgcatgaa ctttgatatt     120
ccggaagaaa ttaaacagct gcagcagttt cagaaagaag atgcggcgct gaccatttat     180
gaaatgctgc agaacatttt tgcgattttt cgccaggata gcagcagcac cggctggaac     240
gaaaccattg tggaaaacct gctggcgaac gtgtatcatc agattaacca tctgaaaacc     300
gtgctggaag aaaaactgga aaagaagat tttacccgcg gcaaactgat gagcagcctg     360
catctgaaac gctattatgg ccgcattctg cattatctga agcgaaaga atatagccat     420
tgcgcgtgga ccattgtgcg cgtggaaatt ctgcgcaact tttattttat taaccgcctg     480
accggctatc tgcgcaac                                                   498
```

<210> SEQ ID NO 196
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196

```
cactctcagg gtaccttcac ctctgactac tctaaatacc tggactctcg tcgtgctcag      60
gacttcgttc agtggctgat gaacaccaaa cgtaaccgta caacatcgc t               111
```

<210> SEQ ID NO 197
<211> LENGTH: 438
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197

```
gttccaattc aaaaggttca agatgatacc aaaactctga ttaaaactat tgtcacgcgt      60
ataaacgaca tcagccatac ccagtcggtt agctcaaagc aaaaagttac cggtttggac     120
tttattccgg gactgcaccc gatcctgacc cttagtaaaa tggaccagac actggccgtc     180
taccagcaaa tcctgacatc gatgccatcc agaaatgtga tacaaattag caacgatttg     240
gaaaaccttc gcgatctgct gcacgtgctg gccttcagta agtcctgtca tctgccgtgg     300
gcgtcgggac tggagactct tgactcgctg gtggagtgt tagaggcctc tggctattct     360
actgaagtcg ttgcgctgtc acgcctccag gggagcctgc aggacatgct gtggcagctg     420
gacctgtcac ctggctgc                                                   438
```

<210> SEQ ID NO 198
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198

| | |
|---|---|
| gctcctctgg gcggtcctga accagcacag tacgaggaac tgacactgtt gttccatgga | 60 |
| gccttgcagc tgggccaggc cctcaacggc gtgtaccgcg ccacagaggc acgtttgacc | 120 |
| gaggccggac acagcctggg tttgtacgac agagccctgg agtttctggg taccgaagtg | 180 |
| cgtcagggcc aggacgcaac tcaggagctg agaacctccc tctctgagat ccaggtggag | 240 |
| gaggacgccc tgcacctgcg cgccgaggcg acagcacgct ctttgggaga agttgctcgc | 300 |
| gctcagcagg ccctgcgtga taccgtgcgg agactccaag ttcagctcag aggcgcttgg | 360 |
| ctcggacagg cgcatcagga gttcgagacc ctgaaagctc gtgccgacaa acagtcccac | 420 |
| ctgctgtggg cgctcaccgg tcacgtccag cgccagcaac gcgaaatggc cgagcagcag | 480 |
| caatggctgc gccaaatcca gcagcgcctg cataccgcgg ccctgccagc gtaa | 534 |

<210> SEQ ID NO 199
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 199

| | |
|---|---|
| aacctgggtc tggactgcga cgaacactct tctgaatctc gttgctgccg ttacccgctg | 60 |
| accgttgact tcgaggcgtt cggttgggac tggatcatcg ctccgaaacg ttacaaagct | 120 |
| aactactgct ctggtcagtg cgaatacatg ttcatgcaga ataccagcca caccacctg | 180 |
| gttcagcagg ctaacccgcg tggttctgct ggtccgtgct gcaccccgac caaaatgtct | 240 |
| ccgatcaaca tgctgtactt caacgacaaa cagcagatca tctacggtaa aatcccgggt | 300 |
| atggttgttg accgttgcgg ttgctcttaa | 330 |

<210> SEQ ID NO 200
<211> LENGTH: 1162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200

| | |
|---|---|
| ggatccggtg gtttcaccat caaactgctg ctgttcatcg ttccgctggt tatctcttct | 60 |
| cgtatcgacc aggacaactc ttctttcgac tctctgtctc cggaaccgaa atctcgtttc | 120 |
| gctatgctga cgacgttaa aatcctggct aacggtctgc tgcagctggg tcacggtctg | 180 |
| aaagacttcg ttcacaaaac caaaggtcag atcaacgaca tcttccagaa actgaacatc | 240 |
| ttcgaccagt ctttctacga cctgtctctg cagacctctg aaatcaaaga agaagaaaaa | 300 |
| gaactgcgtc gtaccaccta caaactgcag gttaaaaacg aagaagttaa aacatgtct | 360 |
| ctggaactga actctaaact ggaatctctg ctggaagaaa aaatcctgct gcagcagaaa | 420 |
| gttaaatacc tggaagaaca gctgaccaac ctgatccaga ccagccggaa accccggaa | 480 |
| cacccggaag ttacctctct gaaaaccttc gttgaaaaac aggacaactc tatcaaagac | 540 |
| ctgctgcaga ccgttgaaga ccagtacaaa cagctgaacc agcagcactc tcagatcaaa | 600 |
| gaaatcgaaa accagctgcg tcgtacctct atccaggaac cgaccgaaat ctctctgtct | 660 |
| tctaaaccgc gtgctccgcg taccaccccg ttcctgcagc tgaacgaaat ccgtaacgtt | 720 |
| aaacacgacg gtatcccggc tgaatgcacc accatctaca ccgtggtga acacacctct | 780 |

-continued

```
ggtatgtacg ctatccgtcc gtctaactct caggttttcc acgtttactg cgacgttatc      840
tctggttctc cgtggaccct gatccagcac cgtatcgacg gttctcagaa cttcaacgaa      900
acctgggaaa actacaaata cggtttcggt cgtctggacg gtgaattctg gctgggtctg      960
gaaaaaatct actctatcgt taaacagtct aactacgttc tgcgtatcga actggaagac     1020
tggaaagaca acaaacacta catcgaatac tctttctacc tgggtaacca cgaaaccaac     1080
tacaccctgc acctggttgc tatcaccggt aacgttccga cgctatccc gaagaagaag      1140 aagaaaaaaa agaagaagaa at                                              1162
```

<210> SEQ ID NO 201
<211> LENGTH: 573
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 201

```
ttcccaacca ttcccttatc caggcttttt gacaacgcta tgctccgcgc ccatcgtctg       60
caccagctgg cctttgacac ctaccaggag tttgaagaag cctatatccc aaaggaacag      120
aagtattcat tcctgcagaa ccccagacc tccctctgtt tctcagagtc tattccgaca      180
ccctccaaca gggaggaaac acaacagaaa tccaacctag agctgctccg catctccctg     240
ctgctcatcc agtcgtggct ggagcccgtg cagttcctca ggagtgtctt cgccaacagc     300
ctggtgtacg gcgcctctga cagcaacgtc tatgacctcc taaggaccct agaggaaggc     360
atccaaacgc tgatggggag gctggaagat ggcagccccc ggactgggca gatcttcaag     420
cagacctaca gcaagttcga cacaaactca cacaacgatg acgcactact caagaactac     480
gggctgctct actgcttcag gaaggacatg gacaaggtcg agacattcct gcgcatcgtg     540
cagtgccgct ctgtggaggg cagctgtggc ttc                                  573
```

<210> SEQ ID NO 202
<211> LENGTH: 495
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 202

```
tgtgatctgc ctcaaaccca cagcctgggt agcaggagga ccttgatgct cctggcacag       60
atgaggagaa tctctctttt ctcctgcttg aaggacagac atgactttgg atttccccag      120
gaggagtttg gcaaccagtt ccaaaaggct gaaaccatcc ctgtcctcca tgagatgatc      180
cagcagatct tcaatctctt cagcacaaag gactcatctg ctgcttggga tgagaccctc     240
ctagacaaat tctacactga actctaccag cagctgaatg acctggaagc ctgtgtgata     300 caggggggtgg gggtgacaga gactcccctg atgaaggagg actccattct ggctgtgagg     360
aaatacttcc aaagaatcac tctctatctg aaagagaaga aatacagccc ttgtgcctgg      420
gaggttgtca gagcagaaat catgagatct ttttctttgt caacaaactt gcaagaaagt      480
ttaagaagta aggaa                                                       495
```

<210> SEQ ID NO 203
<211> LENGTH: 170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
ctgaaatgtt accaacatgg taaagttgtg acttgtcatc gagatatgaa gttttgctat      60
cataacactg gcatgccttt tcgaaatctc aagctcatcc tacagggatg ttcttcttcg    120
tgcagtgaaa cagaaaacaa taagtgttgc tcaacagaca gatgcaacaa               170

<210> SEQ ID NO 204
<211> LENGTH: 252
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
tctgtgagtg aaatacagct tatgcataac ctgggaaaac atctgaactc gatggagaga      60
gtagaatggc tgcgtaagaa gctgcaggat gtgcacaatt ttgttgccct tggagctcct    120
ctagctccca gagatgctgg ttcccagagg ccccgaaaaa aggaagacaa tgtcttggtt    180
gagagccatg aaaaaagtct tggagaggca gacaaagctg atgtgaatgt attaactaaa    240
gctaaatccc ag                                                        252

<210> SEQ ID NO 205
<211> LENGTH: 597
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
atgaactgcg tgtgccgcct ggtgctggtg gtgctgagcc tgtggccgga taccgcggtg      60
gcgccgggcc cgccgccggg cccgccgcgc gtgagcccgg atccgcgcgc ggaactggat    120
agcaccgtgc tgctgacccg cagcctgctg gcggatavcc gccagctggc ggcgcagctg    180
cgcgataaat ttccggcgga tggcgatcat aacctggata gcctgccgac cctggcgatg    240
agcgcgggcg cgctgggcgc gctgcagctg ccgggcgtgc tgacccgcct gcgcgcggat    300
ctgctgagct atctgcgcca tgtgcagtgg ctgcgccgcg cgggcggcag cagcctgaaa    360
accctggaac cggaactggg caccctgcag gcgcgcctgg atcgcctgct gcgccgcctg    420
cagctgctga tgagccgcct ggcgctgccg cagccgccgc cggatccgcc ggcgccgccg    480
ctggcgccgc cgagcagcgc gtggggcggc attcgcgcgg cgctggcgat tctgggcggc    540
ctgcatctga ccctggattg gcggtgcgc ggcctgctgc tgctgaaaac ccgcctg        597

<210> SEQ ID NO 206
<211> LENGTH: 183
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206
gactcttgga tggaagaagt tatcaaactg tgcggtcgtg aactggttcg tgctcagatc      60
gctatctgcg gtatgtctac ctggtctggt ggcggtcgtg gcggtcgtca gctgtactct    120

```
gctctggcta acaaatgctg ccacgttggt tgcaccaaac gttctctggc tcgtttctgc    180
taa                                                                   183
```

<210> SEQ ID NO 207
<211> LENGTH: 489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207

```
gatagctgga tggaagaagt gattaaactg tgcggccgcg aactggtgcg cgcgcagatt     60
gcgatttgcg gcatgagcac ctggagcatt gaaggccgca gcctgagcca ggaagatgcg    120
ccgcagaccc cgcgcccggt ggcggaaatt gtgccgagct ttattaacaa agataccgaa    180
accattaaca tgatgagcga atttgtggcg aacctgccgc aggaactgaa actgaccctg    240
agcgaaatgc agccggcgct gccgcagctg cagcagcatg tgccggtgct gaaagatagc    300
agcctgctgt ttgaagaatt taaaaaactg attcgcaacc gccagagcga agcggcggat    360
agcagcccga gcgaactgaa atatctgggc ctggataccc atagcattga aggccgccag    420
ctgtatagcg cgctggcgaa caaatgctgc catgtgggct gcaccaaacg cagcctggcg    480
cgcttttgc                                                            489
```

<210> SEQ ID NO 208
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208

```
agcctgagcc aggaagatgc gccgcagacc ccgcgcccgg tggcggaaat tgtgccgagc     60
tttattaaca aagataccga aaccattaac atgatgagcg aatttgtggc gaacctgccg    120
caggaactga aactgaccct gagcgaaatg cagccggcgc tgccgcagct gcagcagcat    180
gtgccggtgc tgaaagatag cagcctgctg tttgaagaat ttaaaaaact gattcgcaac    240
cgccagagcg aagcggcgga tagcagcccg agcgaactga atatctgggc cctggatacc    300
catagc                                                              306
```

<210> SEQ ID NO 209
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209

```
gactcttgga tggaagaagt tatcaaactg tgcggtcgtg aactggttcg tgctcagatc     60
gctatctgcg gtatgtctac ctggtctaaa cgttctctgt ctcaggaaga cgctccgcag    120
accccgcgtc cggtt                                                     135
```

<210> SEQ ID NO 210
<211> LENGTH: 72
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 210
cagctgtact ctgctctggc taacaaatgc tgccacgttg gttgcaccaa acgttctctg    60
gctcgtttct gc                                                        72

<210> SEQ ID NO 211
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211
ccgcgcagcg cgaaagaact gcgctgccag tgcattaaaa cctatagcaa accgtttcat    60
ccgaaattta ttaaagaact gcgcgtgatt gaaagcggcc cgcattgcgc gaacaccgaa   120
attattgtga aactgagcga tggccgcgaa ctgtgcctgg atccgaaaga aaactgggtg   180
cagcgcgtgg tggaaaaatt tctgaaacgc gcggaaaaca gc                      222

<210> SEQ ID NO 212
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tgcaaaggca aggcgcgaa atgcagccgc ctgatgtatg attgctgcac cggcagctgc     60
cgcagcggca aatgc                                                    75

<210> SEQ ID NO 213
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
gcgggctgca aaaacttttt ttggaaaacc tttaccagct gcggc                    45

<210> SEQ ID NO 214
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214
atgtgcatgc cgtgctttac caccgatcat cagatggcgc gcaaatgcga tgattgctgc    60
ggcggcaaag gccgcggcaa atgctatggc ccgcagtgcc tg                     102

<210> SEQ ID NO 215
<211> LENGTH: 204
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 215

```
aaaccggtga gcctgagcta tcgctgcccg tgccgctttt ttgaaagcca tgtggcgcgc    60
gcgaacgtga acatctgaa aattctgaac accccgaact gcgcgctgca gattgtggcg   120
cgcctgaaaa acaacaaccg ccaggtgtgc attgatccga aactgaaatg gattcaggaa   180
tatctggaaa aagcgctgaa caaa                                         204
```

<210> SEQ ID NO 216
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 216

```
cagggccagg atcgccatat gattcgcatg cgccagctga ttgatattgt ggatcagctg    60
aaaaactatg tgaacgatct ggtgccggaa tttctgccgg cgccggaaga tgtggaaacc   120
aactgcgaat ggagcgcgtt tagctgcttt cagaaagcgc agctgaaaag cgcgaacacc   180
ggcaacaacg aacgcattat taacgtgagc attaaaaaac tgaaacgcaa accgccgagc   240
accaacgcgg ccgccgcca gaaacatcgc ctgacctgcc cgagctgcga tagctatgaa   300
aaaaaaccgc cgaaagaatt tctggaacgc tttaaaagcc tgctgcagaa aatgattcat   360
cagcatctga gcagccgcac ccatggcagc gaagatagc                          399
```

<210> SEQ ID NO 217
<211> LENGTH: 171
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 217

```
gcgcaagagc cagtcaaagg tccagtctcc actaagcctg gctcctgccc cattatcttg    60
atccggtgcg ccatgttgaa tcccctaac cgctgcttga aagatactga ctgcccagga   120
atcaagaagt gctgtgaagg ctcttgcggg atggcctgtt tcgttcccca g            171
```

<210> SEQ ID NO 218
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 218

```
atgtgtaccg caagcatacc accccaatgc tac                                33
```

<210> SEQ ID NO 219
<211> LENGTH: 117
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 219

```
cacagccagg gcacattcac tagcgattat agtaaatatc tggattccaa ggcagcgcac    60
```

```
gattttgtag agtggctctt gaacggaggc ccttcctccg gagctccacc tccgtcc      117
```

<210> SEQ ID NO 220
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 220

```
cacggccagg gcacattcac tagcgattat agtaaatatc tggattccaa ggcagcgcac   60
gattttgtag agtggctctt gaacggaggc ccttcctccg gagctccacc tccgtcc      117
```

<210> SEQ ID NO 221
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221

```
gctgacaaca aatgcgaaaa ctctctgcgt cgtgaaatcg cttgcggtca gtgccgtgac   60
aaagttaaaa ccgacggtta cttctacgaa tgctgcacct ctgactctac cttcaaaaaa  120
tgccaggacc tgctgcac                                                138
```

<210> SEQ ID NO 222
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222

```
cacggcgacg gttcattctc tgacgaaatg aatacaatac tcgacaacct cgccgccagg   60
gactttatca attggctcat tcaaactaaa atcaccgacg gaggcccttc ctccggagct  120
ccacctccgt cc                                                      132
```

<210> SEQ ID NO 223
<211> LENGTH: 555
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223

```
gactcttgga tggaagaagt tatcaaactg tgcggtcgtg aactggttcg tgctcagatc   60
gctatctgcg gtatgtctac ctggtctaaa cgtggaggtg gcgggagcgg cacttctgag  120
tctgctactc cagaaagcgg cccaggttct gaaccagcaa cttctggctc tgagactcca  180
ggcacttctg agtccgcaac gcctgaatcc ggtcctggtt ctgaaccagc tacttccggc  240
agcgaaaccc caggtaccgg aggtggcggg agccaccatc accaccacca cggaggtggc  300
gggagctctg agtctgcgac tccagagtct ggtcctggta cttccactga gcctagcgag  360
ggttccgcac caggttctcc ggctggtagc ccgaccagca cggaggaggg tacgtctgaa  420
tctgcaacgc cggaatcggg cccaggttcg gaggaggag gtggcgggag ccgtaaaaaa  480
cgtcagctgt actctgctct ggctaacaaa tgctgccacg ttggttgcac caaacgttct  540
```

```
ctggctcgtt tctgc                                                  555
```

<210> SEQ ID NO 224
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224

```
gactcttgga tggaagaagt tatcaaactg tgcggtcgtg aactggttcg tgctcagatc    60
gctatctgcg gtatgtctac ctggtctaaa cgtggaggtg gcgggagctc tggcagcgaa   120
accccgggta cctccgaatc tgctacaccg gaaagcggtg gaggtggcgg gagccaccat   180
caccaccacc acggaggtgg cgggagccct ggcagccctg gtccgggcac tagcaccgag   240
ccatcggagg gctccgcacc aggaggtggc gggagccgta aaaaacgtca gctgtactct   300
gctctggcta caaatgctg ccacgttggt tgcaccaaac gttctctggc tcgttctgc    360
```

<210> SEQ ID NO 225
<211> LENGTH: 276
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225

```
gactcttgga tggaagaagt tatcaaactg tgcggtcgtg aactggttcg tgctcagatc    60
gctatctgcg gtatgtctac ctggtctaaa cgtgaggcag aggacctgca ggtggggcag   120
gtggagctgg gcgggggccc tggtgcaggc agcctgcagc ccttggccct ggaggggtcc   180
ctgcagaagc gtcgtaaaaa acgtcagctg tactctgctc tggctaacaa atgctgccac   240
gttggttgca ccaaacgttc tctggctcgt ttctgc                             276
```

<210> SEQ ID NO 226
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226

```
gactcttgga tggaagaagt tatcaaactg tgcggtcgtg aactggttcg tgctcagatc    60
gctatctgcg gtatgtcttct ggcagcgaaa ccccgggtac ctccgaatct             120
gctacaccgg aaagcggtcc tggcagccct cagctgtact ctgctctggc taacaaatgc   180
tgccacgttg gttgcaccaa acgttctctg gctcgtttct gc                      222
```

<210> SEQ ID NO 227
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Thr Pro Leu Gly Pro Ala Arg Ser Leu Pro Gln Ser Phe Leu Leu Lys
1               5                   10                  15

Cys Leu Glu Gln Val Arg Lys Ile Gln Ala Asp Gly Ala Glu Leu Gln
            20                  25                  30

Glu Arg Leu Cys Ala Ala His Lys Leu Cys His Pro Glu Glu Leu Met
        35                  40                  45

Leu Leu Arg His Ser Leu Gly Ile Pro Gln Ala Pro Leu Ser Ser Cys
    50                  55                  60

Ser Ser Gln Ser Leu Gln Leu Thr Ser Cys Leu Asn Gln Leu His Gly
65                  70                  75                  80

Gly Leu Phe Leu Tyr Gln Gly Leu Leu Gln Ala Leu Ala Gly Ile Ser
                85                  90                  95

Pro Glu Leu Ala Pro Thr Leu Asp Thr Leu Gln Leu Asp Val Thr Asp
            100                 105                 110

Phe Ala Thr Asn Ile Trp Leu Gln Met Glu Asp Leu Gly Ala Ala Pro
            115                 120                 125

Ala Val Gln Pro Thr Gln Gly Ala Met Pro Thr Phe Thr Ser Ala Phe
        130                 135                 140

Gln Arg Arg Ala Gly Gly Val Leu Val Ala Ser Gln Leu His Arg Phe
145                 150                 155                 160

Leu Glu Leu Ala Tyr Arg Gly Leu Arg Tyr Leu Ala Glu Pro
                165                 170

<210> SEQ ID NO 228
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 229
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Ile Asn Val Lys Cys Ser Leu Pro Gln Gln Cys Ile Lys Pro Cys Lys
1               5                   10                  15

Asp Ala Gly Met Arg Phe Gly Lys Cys Met Asn Lys Lys Cys Arg Cys
            20                  25                  30

Tyr Ser

<210> SEQ ID NO 230
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 230

Ala Ala Ala Ile Ser Cys Val Gly Ser Pro Glu Cys Pro Pro Lys Cys
1               5                   10                  15

Arg Ala Gln Gly Cys Lys Asn Gly Lys Cys Met Asn Arg Lys Cys Lys
            20                  25                  30

Cys Tyr Tyr Cys
        35

<210> SEQ ID NO 231
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Ala Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Val Ser Glu Cys Ala Thr Tyr Lys Leu Cys His Pro
        35                  40                  45

Glu Glu Leu Val Leu Leu Gly His Ser Leu Gly Ile Pro Trp Ala Pro
    50                  55                  60

Leu Ser Ser Cys Pro Ser Gln Ala Leu Gln Leu Ala Gly Cys Leu Ser
65                  70                  75                  80

Gln Leu His Ser Gly Leu Phe Leu Tyr Gln Gly Leu Leu Gln Ala Leu
                85                  90                  95

Glu Gly Ile Ser Pro Glu Leu Gly Pro Thr Leu Asp Thr Leu Gln Leu
            100                 105                 110

Asp Val Ala Asp Phe Ala Thr Thr Ile Trp Gln Gln Met Glu Glu Leu
        115                 120                 125

Gly Met Ala Pro Ala Leu Gln Pro Thr Gln Gly Ala Met Pro Ala Phe
    130                 135                 140

Ala Ser Ala Phe Gln Arg Arg Ala Gly Gly Val Leu Val Ala Ser His
145                 150                 155                 160

Leu Gln Ser Phe Leu Glu Val Ser Tyr Arg Val Leu Arg His Leu Ala
                165                 170                 175

Gln Pro

<210> SEQ ID NO 232
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 233
<211> LENGTH: 165
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 233

Pro Pro Arg Leu Ile Cys Asp Ser Arg Val Leu Glu Arg Tyr Leu Leu
1               5                   10                  15

Glu Ala Lys Glu Ala Glu Asn Ile Thr Thr Gly Cys Ala Glu His Cys
            20                  25                  30

Ser Leu Asn Glu Asn Ile Thr Val Pro Asp Thr Lys Val Asn Phe Tyr
        35                  40                  45

Ala Trp Lys Arg Met Glu Val Gly Gln Gln Ala Val Glu Val Trp Gln
    50                  55                  60

Gly Leu Ala Leu Leu Ser Glu Ala Val Leu Arg Gly Gln Ala Leu Leu
65                  70                  75                  80

Val Asn Ser Ser Gln Pro Trp Glu Pro Leu Gln Leu His Val Asp Lys
                85                  90                  95

Ala Val Ser Gly Leu Arg Ser Leu Thr Thr Leu Leu Arg Ala Leu Gly
            100                 105                 110

Ala Gln Lys Glu Ala Ile Ser Pro Pro Asp Ala Ala Ser Ala Ala Pro
        115                 120                 125

Leu Arg Thr Ile Thr Ala Asp Thr Phe Arg Lys Leu Phe Arg Val Tyr
    130                 135                 140

Ser Asn Phe Leu Arg Gly Lys Leu Lys Leu Tyr Thr Gly Glu Ala Cys
145                 150                 155                 160

Arg Thr Gly Asp Arg
                165

<210> SEQ ID NO 234
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160
```

```
Gly Ser Ser Asp Pro Leu Ser Met Val Gly Pro Ser Gln Gly Arg Ser
            165                 170                 175

Pro Ser Tyr Ala Ser
            180

<210> SEQ ID NO 235
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 236
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140
```

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 237
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
                20                  25                  30

Arg Asn Asn Ile Ala
            35

<210> SEQ ID NO 238
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 239
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Ala Pro Leu Gly Gly Pro Glu Pro Ala Gln Tyr Glu Glu Leu Thr Leu
1               5                   10                  15

Leu Phe His Gly Ala Leu Gln Leu Gly Gln Ala Leu Asn Gly Val Tyr
            20                  25                  30

Arg Ala Thr Glu Ala Arg Leu Thr Glu Ala Gly His Ser Leu Gly Leu
        35                  40                  45

Tyr Asp Arg Ala Leu Glu Phe Leu Gly Thr Glu Val Arg Gln Gly Gln
    50                  55                  60

Asp Ala Thr Gln Glu Leu Arg Thr Ser Leu Glu Ile Gln Val Glu
65                  70                  75                  80

Glu Asp Ala Leu His Leu Arg Ala Glu Ala Thr Ala Arg Ser Leu Gly
                85                  90                  95

Glu Val Ala Arg Ala Gln Gln Ala Leu Arg Asp Thr Val Arg Arg Leu
            100                 105                 110

Gln Val Gln Leu Arg Gly Ala Trp Leu Gly Gln Ala His Gln Glu Phe
        115                 120                 125

Glu Thr Leu Lys Ala Arg Ala Asp Lys Gln Ser His Leu Leu Trp Ala
    130                 135                 140

Leu Thr Gly His Val Gln Arg Gln Arg Glu Met Ala Glu Gln Gln
145                 150                 155                 160

Gln Trp Leu Arg Gln Ile Gln Gln Arg Leu His Thr Ala Ala Leu Pro
                165                 170                 175

Ala

<210> SEQ ID NO 240
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 241
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gly Ser Gly Gly Phe Thr Ile Lys Leu Leu Leu Phe Ile Val Pro Leu

```
            1               5               10              15
            Val Ile Ser Ser Arg Ile Asp Gln Asp Asn Ser Ser Phe Asp Ser Leu
                           20                  25              30
            Ser Pro Glu Pro Lys Ser Arg Phe Ala Met Leu Asp Asp Val Lys Ile
                           35                  40              45
            Leu Ala Asn Gly Leu Leu Gln Leu Gly His Gly Leu Lys Asp Phe Val
            50                             55                  60
            His Lys Thr Lys Gly Gln Ile Asn Asp Ile Phe Gln Lys Leu Asn Ile
            65                             70              75                  80
            Phe Asp Gln Ser Phe Tyr Asp Leu Ser Leu Gln Thr Ser Glu Ile Lys
                                   85                  90                  95
            Glu Glu Glu Lys Glu Leu Arg Arg Thr Thr Tyr Lys Leu Gln Val Lys
                               100                 105                 110
            Asn Glu Glu Val Lys Asn Met Ser Leu Glu Leu Asn Ser Lys Leu Glu
                               115                 120                 125
            Ser Leu Leu Glu Glu Lys Ile Leu Leu Gln Gln Lys Val Lys Tyr Leu
                           130                 135                 140
            Glu Glu Gln Leu Thr Asn Leu Ile Gln Asn Gln Pro Glu Thr Pro Glu
            145                 150                 155                 160
            His Pro Glu Val Thr Ser Leu Lys Thr Phe Val Glu Lys Gln Asp Asn
                               165                 170                 175
            Ser Ile Lys Asp Leu Leu Gln Thr Val Glu Asp Gln Tyr Lys Gln Leu
                           180                 185                 190
            Asn Gln Gln His Ser Gln Ile Lys Glu Ile Glu Asn Gln Leu Arg Arg
                           195                 200                 205
            Thr Ser Ile Gln Glu Pro Thr Glu Ile Ser Leu Ser Ser Lys Pro Arg
            210                 215                 220
            Ala Pro Arg Thr Thr Pro Phe Leu Gln Leu Asn Glu Ile Arg Asn Val
            225                 230                 235                 240
            Lys His Asp Gly Ile Pro Ala Glu Cys Thr Thr Ile Tyr Asn Arg Gly
                           245                 250                 255
            Glu His Thr Ser Gly Met Tyr Ala Ile Arg Pro Ser Asn Ser Gln Val
                           260                 265                 270
            Phe His Val Tyr Cys Asp Val Ile Ser Gly Ser Pro Trp Thr Leu Ile
                           275                 280                 285
            Gln His Arg Ile Asp Gly Ser Gln Asn Phe Asn Glu Thr Trp Glu Asn
                           290                 295                 300
            Tyr Lys Tyr Gly Phe Gly Arg Leu Asp Gly Glu Phe Trp Leu Gly Leu
            305                 310                 315                 320
            Glu Lys Ile Tyr Ser Ile Val Lys Gln Ser Asn Tyr Val Leu Arg Ile
                           325                 330                 335
            Glu Leu Glu Asp Trp Lys Asp Asn Lys His Tyr Ile Glu Tyr Ser Phe
                           340                 345                 350
            Tyr Leu Gly Asn His Glu Thr Asn Tyr Thr Leu His Leu Val Ala Ile
                           355                 360                 365
            Thr Gly Asn Val Pro Asn Ala Ile Pro Lys Lys Lys Lys Lys Lys Lys
                           370                 375                 380
            Lys Lys Lys
            385

<210> SEQ ID NO 242
<211> LENGTH: 191
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 242

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 243
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140
```

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 244
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Leu Lys Cys Tyr Gln His Gly Lys Val Val Thr Cys His Arg Asp Met
1               5                   10                  15

Lys Phe Cys Tyr His Asn Thr Gly Met Pro Phe Arg Asn Leu Lys Leu
            20                  25                  30

Ile Leu Gln Gly Cys Ser Ser Cys Ser Glu Thr Glu Asn Asn Lys
        35                  40                  45

Cys Cys Ser Thr Asp Arg Cys Asn
    50                  55

<210> SEQ ID NO 245
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 246
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Met Asn Cys Val Cys Arg Leu Val Leu Val Val Leu Ser Leu Trp Pro
1               5                   10                  15

Asp Thr Ala Val Ala Pro Gly Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe

```
                50                  55                  60
Pro Ala Asp Gly Asp His Asn Leu Asp Ser Leu Pro Thr Leu Ala Met
 65                  70                  75                  80

Ser Ala Gly Ala Leu Gly Ala Leu Gln Leu Pro Gly Val Leu Thr Arg
                 85                  90                  95

Leu Arg Ala Asp Leu Leu Ser Tyr Leu Arg His Val Gln Trp Leu Arg
                100                 105                 110

Arg Ala Gly Gly Ser Ser Leu Lys Thr Leu Glu Pro Glu Leu Gly Thr
                115                 120                 125

Leu Gln Ala Arg Leu Asp Arg Leu Leu Arg Arg Leu Gln Leu Leu Met
            130                 135                 140

Ser Arg Leu Ala Leu Pro Gln Pro Pro Pro Asp Pro Pro Ala Pro Pro
145                 150                 155                 160

Leu Ala Pro Pro Ser Ser Ala Trp Gly Gly Ile Arg Ala Ala Leu Ala
                165                 170                 175

Ile Leu Gly Gly Leu His Leu Thr Leu Asp Trp Ala Val Arg Gly Leu
                180                 185                 190

Leu Leu Leu Lys Thr Arg Leu
            195

<210> SEQ ID NO 247
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Asp Ser Trp Met Glu Glu Val Ile Lys Leu Cys Gly Arg Glu Leu Val
  1               5                  10                  15

Arg Ala Gln Ile Ala Ile Cys Gly Met Ser Thr Trp Ser Gly Gly Gly
                 20                  25                  30

Arg Gly Gly Arg Gln Leu Tyr Ser Ala Leu Ala Asn Lys Cys Cys His
             35                  40                  45

Val Gly Cys Thr Lys Arg Ser Leu Ala Arg Phe Cys
         50                  55                  60

<210> SEQ ID NO 248
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Asp Ser Trp Met Glu Glu Val Ile Lys Leu Cys Gly Arg Glu Leu Val
  1               5                  10                  15

Arg Ala Gln Ile Ala Ile Cys Gly Met Ser Thr Trp Ser Ile Glu Gly
                 20                  25                  30

Arg Ser Leu Ser Gln Glu Asp Ala Pro Gln Thr Pro Arg Pro Val Ala
             35                  40                  45

Glu Ile Val Pro Ser Phe Ile Asn Lys Asp Thr Glu Thr Ile Asn Met
         50                  55                  60

Met Ser Glu Phe Val Ala Asn Leu Pro Gln Glu Leu Lys Leu Thr Leu
 65                  70                  75                  80

Ser Glu Met Gln Pro Ala Leu Pro Gln Leu Gln Gln His Val Pro Val
```

85                  90                  95

Leu Lys Asp Ser Ser Leu Leu Phe Glu Glu Phe Lys Lys Leu Ile Arg
            100                 105                 110

Asn Arg Gln Ser Glu Ala Ala Asp Ser Ser Pro Ser Glu Leu Lys Tyr
        115                 120                 125

Leu Gly Leu Asp Thr His Ser Ile Glu Gly Arg Gln Leu Tyr Ser Ala
    130                 135                 140

Leu Ala Asn Lys Cys Cys His Val Gly Cys Thr Lys Arg Ser Leu Ala
145                 150                 155                 160

Arg Phe Cys

<210> SEQ ID NO 249
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Ser Leu Ser Gln Glu Asp Ala Pro Gln Thr Pro Arg Pro Val Ala Glu
1               5                   10                  15

Ile Val Pro Ser Phe Ile Asn Lys Asp Thr Glu Thr Ile Asn Met Met
            20                  25                  30

Ser Glu Phe Val Ala Asn Leu Pro Gln Glu Leu Lys Leu Thr Leu Ser
        35                  40                  45

Glu Met Gln Pro Ala Leu Pro Gln Leu Gln Gln His Val Pro Val Leu
    50                  55                  60

Lys Asp Ser Ser Leu Leu Phe Glu Glu Phe Lys Lys Leu Ile Arg Asn
65                  70                  75                  80

Arg Gln Ser Glu Ala Ala Asp Ser Ser Pro Ser Glu Leu Lys Tyr Leu
                85                  90                  95

Gly Leu Asp Thr His Ser
            100

<210> SEQ ID NO 250
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 251
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 252
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Pro Arg Ser Ala Lys Glu Leu Arg Cys Gln Cys Ile Lys Thr Tyr Ser
1               5                   10                  15

Lys Pro Phe His Pro Lys Phe Ile Lys Glu Leu Arg Val Ile Glu Ser
            20                  25                  30

Gly Pro His Cys Ala Asn Thr Glu Ile Ile Val Lys Leu Ser Asp Gly
        35                  40                  45

Arg Glu Leu Cys Leu Asp Pro Lys Glu Asn Trp Val Gln Arg Val Val
    50                  55                  60

Glu Lys Phe Leu Lys Arg Ala Glu Asn Ser
65                  70

<210> SEQ ID NO 253
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25

<210> SEQ ID NO 254
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ala Gly Cys Lys Asn Phe Phe Trp Lys Thr Phe Thr Ser Cys Gly
1               5                   10                  15

<210> SEQ ID NO 255
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu

```
<210> SEQ ID NO 256
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 257
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 258
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Ala Gln Glu Pro Val Lys Gly Pro Val Ser Thr Lys Pro Gly Ser Cys
1               5                   10                  15

Pro Ile Ile Leu Ile Arg Cys Ala Met Leu Asn Pro Pro Asn Arg Cys
```

```
                  20                  25                  30

Leu Lys Asp Thr Asp Cys Pro Gly Ile Lys Lys Cys Cys Glu Gly Ser
            35                  40                  45

Cys Gly Met Ala Cys Phe Val Pro Gln
        50                  55

<210> SEQ ID NO 259
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Met Cys Thr Ala Ser Ile Pro Pro Gln Cys Tyr
1               5                   10

<210> SEQ ID NO 260
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Ile Glu Gly Arg His Ser Gln Gly Thr Phe Thr Ser Asp Tyr Ser Lys
1               5                   10                  15

Tyr Leu Asp Ser Lys Ala Ala His Asp Phe Val Glu Trp Leu Leu Asn
            20                  25                  30

Gly Gly Pro Ser Ser Gly Ala Pro Pro Pro Ser
        35                  40

<210> SEQ ID NO 261
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Ile Glu Gly Arg His Gly Gln Gly Thr Phe Thr Ser Asp Tyr Ser Lys
1               5                   10                  15

Tyr Leu Asp Ser Lys Ala Ala His Asp Phe Val Glu Trp Leu Leu Asn
            20                  25                  30

Gly Gly Pro Ser Ser Gly Ala Pro Pro Pro Ser
        35                  40

<210> SEQ ID NO 262
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Ala Asp Asn Lys Cys Glu Asn Ser Leu Arg Arg Glu Ile Ala Cys Gly
1               5                   10                  15

Gln Cys Arg Asp Lys Val Lys Thr Asp Gly Tyr Phe Tyr Glu Cys Cys
            20                  25                  30
```

```
Thr Ser Asp Ser Thr Phe Lys Lys Cys Gln Asp Leu Leu His
            35                  40                  45
```

<210> SEQ ID NO 263
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

```
Ile Glu Gly Arg His Gly Asp Gly Ser Phe Ser Asp Glu Met Asn Thr
1               5                   10                  15

Ile Leu Asp Asn Leu Ala Ala Arg Asp Phe Ile Asn Trp Leu Ile Gln
                20                  25                  30

Thr Lys Ile Thr Asp Gly Gly Pro Ser Ser Gly Ala Pro Pro Pro Ser
            35                  40                  45
```

<210> SEQ ID NO 264
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

```
Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Lys Arg Gly
                20                  25                  30

Gly Gly Gly Ser Gly Thr Ser Glu Ser Ala Thr Pro Glu Ser Gly Pro
            35                  40                  45

Gly Ser Glu Pro Ala Thr Ser Gly Ser Glu Thr Pro Gly Thr Ser Glu
        50                  55                  60

Ser Ala Thr Pro Glu Ser Gly Pro Gly Ser Glu Pro Ala Thr Ser Gly
65                  70                  75                  80

Ser Glu Thr Pro Gly Thr Gly Gly Gly Ser His His His His His His
                85                  90                  95

His Gly Gly Gly Ser Ser Glu Ser Ala Thr Pro Glu Ser Gly Pro
            100                 105                 110

Gly Thr Ser Thr Glu Pro Ser Glu Gly Ser Ala Pro Gly Ser Pro Ala
        115                 120                 125

Gly Ser Pro Thr Ser Thr Glu Glu Gly Thr Ser Glu Ser Ala Thr Pro
    130                 135                 140

Glu Ser Gly Pro Gly Ser Glu Gly Gly Gly Gly Ser Arg Lys Lys
145                 150                 155                 160

Arg Gln Leu Tyr Ser Ala Leu Ala Asn Lys Cys Cys His Val Gly Cys
                165                 170                 175

Thr Lys Arg Ser Leu Ala Arg Phe Cys
            180                 185
```

<210> SEQ ID NO 265
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Lys Arg Gly
            20                  25                  30

Gly Gly Gly Ser Ser Gly Ser Glu Thr Pro Gly Thr Ser Glu Ser Ala
        35                  40                  45

Thr Pro Glu Ser Gly Gly Gly Gly Ser His His His His His
50                  55                  60

Gly Gly Gly Gly Ser Pro Gly Ser Pro Gly Pro Gly Thr Ser Thr Glu
65                  70                  75                  80

Pro Ser Glu Gly Ser Ala Pro Gly Gly Gly Ser Arg Lys Lys Arg
                85                  90                  95

Gln Leu Tyr Ser Ala Leu Ala Asn Lys Cys Cys His Val Gly Cys Thr
            100                 105                 110

Lys Arg Ser Leu Ala Arg Phe Cys
            115                 120

<210> SEQ ID NO 266
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Lys Arg Glu
            20                  25                  30

Ala Glu Asp Leu Gln Val Gly Gln Val Glu Leu Gly Gly Gly Pro Gly
        35                  40                  45

Ala Gly Ser Leu Gln Pro Leu Ala Leu Glu Gly Ser Leu Gln Lys Arg
50                  55                  60

Arg Lys Lys Arg Gln Leu Tyr Ser Ala Leu Ala Asn Lys Cys Cys His
65                  70                  75                  80

Val Gly Cys Thr Lys Arg Ser Leu Ala Arg Phe Cys
                85                  90

<210> SEQ ID NO 267
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Ser Gly Ser
            20                  25                  30

Glu Thr Pro Gly Thr Ser Glu Ser Ala Thr Pro Glu Ser Gly Pro Gly
        35                  40                  45

Ser Pro Gln Leu Tyr Ser Ala Leu Ala Asn Lys Cys Cys His Val Gly
50                  55                  60

Cys Thr Lys Arg Ser Leu Ala Arg Phe Cys
                65                  70

<210> SEQ ID NO 268
<211> LENGTH: 840
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 268

```
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg cgggaacac agggtacaat      180
cccggactga agagcagact gtccattacc aaggacaact ctaaaagtca ggtgtcactg     240
agcgtgagct ccgtcaccac agaggatagt gcaacttact attgcacctc tgtgcaccag     300
gaaactaaga ataccagag ctgtcctgac ggctatcggg agagatctga ttgcagtaat      360
aggccagctt gtggcacatc cgactgctgt cgcgtgtctg tcttcgggaa ctgcctgact     420
accctgcctg tgtcctactc ttatacctac aattatgaat ggcatgtgga tgtctgggga    480
cagggcctgc tggtgacagt ctctagtgct tccacaactg caccaaaggt gtacccctg     540
tcaagctgct gtggggacaa atcctctagt accgtgacac tgggatgcct ggtctcaagc   600
tatatgcccg agcctgtgac tgtcacctgg aactcaggag ccctgaaaag cggagtgcac   660
accttcccag ctgtgctgca gtcctctggc ctgtatagcc tgagttcaat ggtgacagtc    720
cccggcagta cttcagggca gaccttcacc tgtaatgtgg cccatcctgc cagctccacc   780
aaagtggaca agcagtgga acccaaatct gcgacggca gccatcacca tcatcatcac    840
```

<210> SEQ ID NO 269
<211> LENGTH: 825
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 269

```
caggtccagc tgagagagag cgggccttca ctggtccagc cttcacagac actgagcctg     60
acttgtactg cctccgggtt ttcactgtct gacaaggctg tgggatgggt ccgacaggca    120
ccagggaaag ctctggagtg gctgggaagt atcgataccg cgggtcaac agggtacaac     180
cctggactga agtccagact gtctattact aaggacaatt ctaaaagtca ggtgtcactg    240
agcgtgagct ccgtcaccac agaggattct gcaacatact attgcactac cgtgcaccag   300
gaaacaagga aaacttgtag tgacggctat atcgcagtgg atagctgcgg acgaggacag   360
tccgacggat gcgtgaacga ttgcaatagc tgttactatg gatggcgaaa ctgccggaga    420
cagccagcaa ttcattcata cgagtttcat gtggatgctt ggggcgggg gctgctggtc    480
accgtctcct cagcttccac aactgcacca aaggtgtacc cctgtcaag ctgctgtggg    540
gacaaatcct ctagtaccgt gacactggga tgcctggtct caagctatat gcccgagcct   600
gtgactgtca cctggaactc aggagccctg aaaagcggag tgcacacctt cccagctgtg   660
ctgcagtcct ctggcctgta tagcctgagt tcaatggtga cagtccccgg cagtacttca    720
gggcagacct tcacctgtaa tgtggcccat cctgccagct ccaccaaagt ggacaaagca    780
gtggaaccca atcttgcga cggcagccat caccatcatc atcac                    825
```

```
<210> SEQ ID NO 270
<211> LENGTH: 828
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 270
caggtccagc tgagggaatc cggcccatca ctggtcaagc cttcacagac actgagcctg     60
acatgtactg caagcgggtt ttcactgagt gacaaggcag tgggatgggt ccggagagca    120
ccaggaaaag ccctggagtg gctgggaacc acagatactg gaggatccgc cgcttacaac    180
cctggcctga gtcccggct gtctatcacc aaggacaact ctaaaagtca ggtgtcactg    240
agcgtgtcca atgtcgctac agaagattct gcaacttact attgtagctc cgtgactcag    300
aggacccacg tctctcgcag ttgtccagac gggtgcagtg acggagatgg ctgcgtggat    360
ggatgctgtt gctcagctta ccgatgttat acacccgggg tcagagacct gagctgcacc    420
tcatatagca ttacatacac ttacgaatgg aatgtggatg cttggggaca gggactgctg    480
gtgaccgtct cttcagcttc cacaactgca ccaaggtgt accccctgtc aagctgctgt    540
ggggacaaat cctctagtac cgtgacactg gatgcctgg tctcaagcta tgcccgag      600 cctgtgactg tcacctggaa ctcaggagcc ctgaaaagcg gagtgcacac cttcccagct    660
gtgctgcagt cctctggcct gtatagcctg agttcaatgg tgacagtccc cggcagtact    720
tcagggcaga ccttcacctg taatgtggcc catcctgcca gctccaccaa agtggacaaa    780
gcagtggaac ccaaatcttg cgacggcagc catcaccatc atcatcac                828

<210> SEQ ID NO 271
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Cys Pro Asp Gly Tyr
            100                 105                 110

Arg Glu Arg Ser Asp Cys Ser Asn Arg Pro Ala Cys Gly Thr Ser Asp
        115                 120                 125

Cys Cys Arg Val Ser Val Phe Gly Asn Cys Leu Thr Thr Leu Pro Val
    130                 135                 140

Ser Tyr Ser Tyr Thr Tyr Asn Tyr Glu Trp His Val Asp Val Trp Gly
```

```
            145                 150                 155                 160
Gln Gly Leu Leu Val Thr Val Ser Ser Ala Ser Thr Thr Ala Pro Lys
                165                 170                 175

Val Tyr Pro Leu Ser Ser Cys Cys Gly Asp Lys Ser Ser Ser Thr Val
                180                 185                 190

Thr Leu Gly Cys Leu Val Ser Ser Tyr Met Pro Glu Pro Val Thr Val
                195                 200                 205

Thr Trp Asn Ser Gly Ala Leu Lys Ser Gly Val His Thr Phe Pro Ala
            210                 215                 220

Val Leu Gln Ser Ser Gly Leu Tyr Ser Leu Ser Ser Met Val Thr Val
225                 230                 235                 240

Pro Gly Ser Thr Ser Gly Gln Thr Phe Thr Cys Asn Val Ala His Pro
                245                 250                 255

Ala Ser Ser Thr Lys Val Asp Lys Ala Val Glu Pro Lys Ser Cys Asp
                260                 265                 270

Gly Ser His His His His His His
            275                 280

<210> SEQ ID NO 272
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Gln Val Gln Leu Arg Glu Ser Gly Pro Ser Leu Val Gln Pro Ser Gln
1               5                   10                  15

Thr Leu Ser Leu Thr Cys Thr Ala Ser Gly Phe Ser Leu Ser Asp Lys
                20                  25                  30

Ala Val Gly Trp Val Arg Gln Ala Pro Gly Lys Ala Leu Glu Trp Leu
            35                  40                  45

Gly Ser Ile Asp Thr Gly Gly Ser Thr Gly Tyr Asn Pro Gly Leu Lys
        50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Thr Val His Gln Glu Thr Arg Lys Thr Cys Ser Asp Gly Tyr Ile Ala
                100                 105                 110

Val Asp Ser Cys Gly Arg Gly Gln Ser Asp Gly Cys Val Asn Asp Cys
            115                 120                 125

Asn Ser Cys Tyr Tyr Gly Trp Arg Asn Cys Arg Arg Gln Pro Ala Ile
        130                 135                 140

His Ser Tyr Glu Phe His Val Asp Ala Trp Gly Arg Gly Leu Leu Val
145                 150                 155                 160

Thr Val Ser Ser Ala Ser Thr Thr Ala Pro Lys Val Tyr Pro Leu Ser
                165                 170                 175

Ser Cys Cys Gly Asp Lys Ser Ser Ser Thr Val Thr Leu Gly Cys Leu
                180                 185                 190

Val Ser Ser Tyr Met Pro Glu Pro Val Thr Val Thr Trp Asn Ser Gly
            195                 200                 205

Ala Leu Lys Ser Gly Val His Thr Phe Pro Ala Val Leu Gln Ser Ser
        210                 215                 220
```

Gly Leu Tyr Ser Leu Ser Ser Met Val Thr Val Pro Gly Ser Thr Ser
225                 230                 235                 240

Gly Gln Thr Phe Thr Cys Asn Val Ala His Pro Ala Ser Ser Thr Lys
                245                 250                 255

Val Asp Lys Ala Val Glu Pro Lys Ser Cys Asp Gly Ser His His His
            260                 265                 270

His His His
        275

<210> SEQ ID NO 273
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Arg Ala Pro Gly Lys Ala Leu Glu Trp Leu
        35                  40                  45

Gly Thr Thr Asp Thr Gly Gly Ser Ala Ala Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Asn Val Ala Thr Glu Asp Ser Ala Thr Tyr Tyr Cys Ser
                85                  90                  95

Ser Val Thr Gln Arg Thr His Val Ser Arg Ser Cys Pro Asp Gly Cys
            100                 105                 110

Ser Asp Gly Asp Gly Cys Val Asp Gly Cys Cys Ser Ala Tyr Arg
        115                 120                 125

Cys Tyr Thr Pro Gly Val Arg Asp Leu Ser Cys Thr Ser Tyr Ser Ile
    130                 135                 140

Thr Tyr Thr Tyr Glu Trp Asn Val Asp Ala Trp Gly Gln Gly Leu Leu
145                 150                 155                 160

Val Thr Val Ser Ser Ala Ser Thr Thr Ala Pro Lys Val Tyr Pro Leu
                165                 170                 175

Ser Ser Cys Cys Gly Asp Lys Ser Ser Ser Thr Val Thr Leu Gly Cys
            180                 185                 190

Leu Val Ser Ser Tyr Met Pro Glu Pro Val Thr Val Thr Trp Asn Ser
        195                 200                 205

Gly Ala Leu Lys Ser Gly Val His Thr Phe Pro Ala Val Leu Gln Ser
    210                 215                 220

Ser Gly Leu Tyr Ser Leu Ser Ser Met Val Thr Val Pro Gly Ser Thr
225                 230                 235                 240

Ser Gly Gln Thr Phe Thr Cys Asn Val Ala His Pro Ala Ser Ser Thr
                245                 250                 255

Lys Val Asp Lys Ala Val Glu Pro Lys Ser Cys Asp Gly Ser His His
            260                 265                 270

His His His His
        275

<210> SEQ ID NO 274

```
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 274

His His His His His His
1               5

<210> SEQ ID NO 275
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(100)
<223> OTHER INFORMATION: This sequence may encompass 1-20 'Gly Gly Gly
      Gly Ser' repeating units, wherein some positions may be absent
<220> FEATURE:
<223> OTHER INFORMATION: See specification as filed for detailed
      description of substitutions and preferred embodiments

<400> SEQUENCE: 275

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100

<210> SEQ ID NO 276
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Cys Gly Gly Gly Gly Ser
1               5

<210> SEQ ID NO 277
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Gly Gly Gly Gly Ser Cys
1               5
```

```
<210> SEQ ID NO 278
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ile Glu Gly Arg Lys Lys Arg
1               5

<210> SEQ ID NO 279
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Gly Ser Gly
1
```

COILED COIL IMMUNOGLOBULIN FUSION PROTEINS AND COMPOSITIONS THEREOF

CROSS-REFERENCE TO RELATED APPLICATIONS

This application is a U.S. National Stage entry of International Application No. PCT/US2014/046419, filed Jul. 11, 2014; which claims the benefit of priority from U.S. Provisional Application No. 61/845,280 filed Jul. 11, 2013; U.S. Provisional Application No. 61/845,287 filed Jul. 11, 2013; U.S. Provisional Application No. 61/925,904 filed Jan. 10, 2014; and U.S. Provisional Application No. 62/017,713 filed Jun. 26, 2014, all of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Aug. 12, 2014, is named 41135-712-831-SEQUENCE.txt and is 565,158 bytes in size.

BACKGROUND OF THE INVENTION

Antibodies are natural proteins that the vertebrate immune system forms in response to foreign substances (antigens), primarily for defense against infection. For over a century, antibodies have been induced in animals under artificial conditions and harvested for use in therapy or diagnosis of disease conditions, or for biological research. Each individual antibody producing cell produces a single type of antibody with a chemically defined composition, however, antibodies obtained directly from animal serum in response to antigen inoculation actually comprise an ensemble of non-identical molecules (e.g., polyclonal antibodies) made from an ensemble of individual antibody producing cells.

Antibody fusion constructs can be used to improve the delivery of drugs or other agents to target cells, tissues and tumors. Antibody fusion constructs may comprise a chemical linker to attach a drug or other agent to antibody. Exemplary antibody fusion constructs and methods of producing antibody fusion constructs are disclosed in US patent application numbers 2006/0182751, 2007/0160617 and U.S. Pat. No. 7,736,652.

Disclosed herein are novel immunoglobulin fusion proteins and methods of producing such immunoglobulin fusion proteins. Further disclosed herein are uses of the immunoglobulin fusion proteins for the treatment of various diseases and conditions. Methods of extending the half-life of a therapeutic agent are also disclosed herein.

SUMMARY OF THE INVENTION

In one aspect of the disclosure, provided herein is an immunoglobulin fusion protein comprising a first antibody region, a first therapeutic agent, and a first connecting peptide; wherein the first therapeutic agent is attached to the first antibody region by the connecting peptide; and wherein the connecting peptide does not comprise a region having beta strand secondary structure.

In one embodiment, the connecting peptide comprises a first extender peptide. The first extender peptide may comprise one or more regions having alpha helical secondary structure. In one instance, the first extender peptide does not comprise more than 7 consecutive amino acids that are based on or derived from a bovine ultralong CDR3 amino acid sequence.

In one embodiment, the connecting peptide comprises a first linking peptide. The first linking peptide may not comprise alpha helical or beta strand secondary structure. The first linking peptide may comprise from about 0 to about 50 amino acids.

In one embodiment, the connecting peptide comprises from about 0 to about 50 amino acids. The connecting peptide may comprise from about 4 to about 100 amino acids.

In one embodiment, the first connecting peptide is attached to a CDR of the first antibody region. In one embodiment, the first therapeutic peptide replaces one or more regions of the first antibody region. In another embodiment, the first connecting peptide replaces one or more regions of the first antibody region.

In one embodiment, the immunoglobulin fusion protein further comprises a second connecting peptide. In one embodiment, the second connecting peptide does not comprise a region having beta strand secondary structure. The second connecting peptide may comprise a second extender peptide. The second extender peptide may comprise one or more regions having alpha helical secondary structure. The second peptide may comprise a second linking peptide. The second linking peptide may not comprise alpha helical or beta strand secondary structure.

In one embodiment, the immunoglobulin fusion protein further comprises a second therapeutic agent.

In one embodiment, the first antibody region comprises an amino acid sequence that is based on or derived from any one of SEQ ID NOs: 19-36 and 271-273. In one embodiment, the first antibody region comprises an amino acid sequence that is at least about 50% identical and/or homologous to an amino acid sequence of any one of SEQ ID NOs: 19-36 and 271-273. In one embodiment, the first antibody region comprises an amino acid sequence that is at least about 80% identical and/or homologous to an amino acid sequence of any one of SEQ ID NOs: 19-36 and 271-273.

In one embodiment, the first antibody region comprises an amino acid sequence that is based on or derived from a trastuzumab immunoglobulin. In one embodiment, the first antibody region comprises an amino acid sequence that is at least about 50% identical and/or homologous to an amino acid sequence of trastuzumab immunoglobulin. In one embodiment, the first antibody region comprises an amino acid sequence that is at least about 80% identical and/or homologous to an amino acid sequence of trastuzumab immunoglobulin.

In one embodiment, the first antibody region comprises an amino acid sequence that is based on or derived from a palivizumab immunoglobulin. In one embodiment, the first antibody region comprises an amino acid sequence that is at least about 50% identical and/or homologous to an amino acid sequence of palivizumab immunoglobulin. In one embodiment, the first antibody region comprises an amino acid sequence that is at least about 80% identical and/or homologous to an amino acid sequence of palivizumab immunoglobulin.

In one embodiment, the immunoglobulin fusion protein further comprises a second antibody region. In one instance, the first antibody region comprises a region of an antibody light chain and the second antibody region comprises a region of an antibody heavy chain. In one instance, the first antibody region comprises a region of an antibody heavy chain and the second antibody region comprises a region of an antibody light chain. In one instance, the first antibody region comprises a first region of an antibody light chain and the second antibody region comprises a second region of an antibody light chain. In one instance, the first antibody region comprises a first region of an antibody heavy chain and the second antibody region comprises a second region of an antibody heavy chain. In one embodiment, the second antibody region comprises an amino acid sequence that is based on or derived from any one of SEQ ID NOs: 19-36 and 271-273. In one embodiment, the second antibody region comprises an amino acid sequence that is at least about 50% identical and/or homologous to an amino acid sequence of any one of SEQ ID NOs: 19-36 and 271-273. In one embodiment, the second antibody region comprises an amino acid sequence that is at least about 80% identical and/or homologous to an amino acid sequence of any one of SEQ ID NOs: 19-36 and 271-273.

In one embodiment, the second antibody region comprises an amino acid sequence that is based on or derived from a trastuzumab immunoglobulin. In one embodiment, the second antibody region comprises an amino acid sequence that is at least about 50% identical and/or homologous to an amino acid sequence of trastuzumab immunoglobulin. In one embodiment, the second antibody region comprises an amino acid sequence that is at least about 80% identical and/or homologous to an amino acid sequence of trastuzumab immunoglobulin. In one embodiment, the second antibody region comprises an amino acid sequence that is based on or derived from a palivizumab immunoglobulin. In one embodiment, the second antibody region comprises an amino acid sequence that is at least about 50% identical and/or homologous to an amino acid sequence of palivizumab immunoglobulin. In one embodiment, the second antibody region comprises an amino acid sequence that is at least about 80% identical and/or homologous to an amino acid sequence of palivizumab immunoglobulin.

In one embodiment, the first connecting peptide comprises an amino acid sequence that is based on or derived from any one of SEQ ID NOs: 144-176, 179-185 and 275-277. In one embodiment, the first connecting peptide comprises an amino acid sequence that is at least about 50% identical and/or homologous to an amino acid sequence of any of one of SEQ ID NOs: 144-176, 179-185 and 275-277. In one embodiment, the first connecting peptide comprises an amino acid sequence that is at least about 80% identical and/or homologous to an amino acid sequence of any of one of SEQ ID NOs: 144-176, 179-185 and 275-277.

In one embodiment, the second connecting peptide comprises an amino acid sequence that is based on or derived from any one of SEQ ID NOs: 144-176, 179-185 and 275-277. In one embodiment, the second connecting peptide comprises an amino acid sequence that is at least about 50% identical and/or homologous to an amino acid sequence of any one of SEQ ID NOs: 144-176, 179-185 and 275-277. In one embodiment, the second connecting peptide comprises an amino acid sequence that is at least about 80% identical and/or homologous to an amino acid sequence of any of one of SEQ ID NOs: 144-176, 179-185 and 275-277.

In one embodiment, the first connecting peptide comprises a protease cleavage site. In one embodiment, the second connecting peptide comprises a protease cleavage site. In one instance, the first therapeutic agent comprises an amino acid sequence configured for recognition by a protease. In one instance, the second therapeutic agent comprises an amino acid sequence configured for recognition by a protease.

In one embodiment, the first connecting peptide comprises one or more extender peptides and one or more linker peptides. In one embodiment, the first connecting peptide comprises one or more extender peptides, one or more linker peptides, and one or more protease cleavage sites. In one embodiment, the first connecting peptide comprises one or more extender peptides and one or more protease cleavage sites. In one embodiment, the first connecting peptide comprises one or more linker peptides and one or more protease cleavage sites.

In one embodiment, the second connecting peptide comprises one or more extender peptides and one or more linker peptides. In one embodiment, the second connecting peptide comprises one or more extender peptides, one or more linker peptides, and one or more protease cleavage sites. In one embodiment, the second connecting peptide comprises one or more extender peptides and one or more protease cleavage sites. In one embodiment, the second connecting peptide comprises one or more linker peptides and one or more protease cleavage sites.

In one embodiment, the first therapeutic agent comprises an amino acid sequence that is based on or derived from any one of SEQ ID NOs: 227-267. In one embodiment, the first therapeutic agent comprises an amino acid sequence that is at least about 50% identical and/or homologous to an amino acid sequence of any of one of SEQ ID NOs: 227-267. In one embodiment, the first therapeutic agent comprises an amino acid sequence that is at least about 80% identical and/or homologous to an amino acid sequence of any of one of SEQ ID NOs: 227-267. In one embodiment, the first therapeutic agent comprises from about 5 to about 1,000 amino acids comprising from about 5 to about 350 amino acids identical and/or homologous to any one of SEQ ID NOs: 227-267.

In one embodiment, the immunoglobulin fusion protein comprises an amino acid sequence that is based on or derived from any one of SEQ ID NOs: 68-99. In one embodiment, the immunoglobulin fusion protein comprises an amino acid sequence that is at least about 50% identical and/or homologous to an amino acid sequence of any of one of SEQ ID NOs: 68-99. In one embodiment, the immunoglobulin fusion protein comprises an amino acid sequence that is at least about 80% identical and/or homologous to an amino acid sequence of any of one of SEQ ID NOs: 68-99. In one embodiment, the immunoglobulin fusion protein comprises from about 5 to about 3,000 amino acids comprising from about 50 to about 700 amino acids identical and/or homologous to any one of SEQ ID NOs: 68-99.

In another aspect, provided herein is a first genetic construct comprising nucleic acids encoding the immunoglobulin fusion protein of any of SEQ ID NOs: 68-99. In one embodiment, a first genetic construct comprises nucleic acids derived from any one of SEQ ID NOs: 37-67. In one embodiment, a first genetic construct comprises a nucleic acid sequence that is at least about 50% identical and/or homologous to a nucleic acid sequence of any one of SEQ ID NOs: 37-67. In one embodiment, a first genetic construct comprises a nucleic acid sequence that is at least about 80% identical and/or homologous to a nucleic acid sequence of any one of SEQ ID NOs: 37-67.

In another aspect, provided herein is a first expression vector comprising a first genetic construct comprising nucleic acids encoding the immunoglobulin fusion protein of any of SEQ ID NOs: 68-99. In one embodiment, provided herein is a first expression vector comprising a first genetic construct comprising nucleic acids derived from any one of SEQ ID NOs: 37-67. In one embodiment, provided herein is a first expression vector comprising a first genetic construct comprising a nucleic acid sequence that is at least about 50% identical and/or homologous to a nucleic acid sequence of any one of SEQ ID NOs: 37-67. In one embodiment, provided herein is a first expression vector comprising a first genetic construct comprising a nucleic acid sequence that is at least about 80% identical and/or homologous to a nucleic acid sequence of any one of SEQ ID NOs: 37-67. In one instance, provided herein is a mammalian expression host comprising a first expression vector. In one embodiment, provided herein is a method of producing an immunoglobulin fusion protein comprising (a) transfecting a first expression vector transiently in a mammalian cell culture, (b) growing the cell culture in an expression medium at a controlled temperature and percentage $CO_2$, (c) and harvesting the secreted immunoglobulin fusion protein. In one embodiment, the method of producing an immunoglobulin fusion protein further comprises purifying the immunoglobulin fusion protein.

In another aspect, provided herein is a method of treating a disease or condition in a subject in need thereof, the method comprising administering to the subject a therapeutically effective amount an immunoglobulin fusion protein comprising an amino acid sequence derived from any one of SEQ ID NOs 68-99. In another aspect, provided herein is a method of treating a disease or condition in a subject in need thereof, the method comprising administering to the subject a therapeutically effective amount an immunoglobulin fusion protein comprising an amino acid sequence that is at least about 50% identical and/or homologous to any one of SEQ ID NOs 68-99. In another aspect, provided herein is a method of treating a disease or condition in a subject in need thereof, the method comprising administering to the subject a therapeutically effective amount an immunoglobulin fusion protein comprising an amino acid sequence that is at least about 80% identical and/or homologous to any one of SEQ ID NOs 68-99.

In another aspect, provided herein is a pharmaceutical composition comprising an immunoglobulin fusion protein derived from any one of SEQ ID NOs: 68-99. In another aspect, provided herein is a pharmaceutical composition comprising an immunoglobulin fusion protein comprising an amino acid sequence that is at least about 50% identical and/or homologous to any one of SEQ ID NOs: 68-99. In another aspect, provided herein is a pharmaceutical composition comprising an immunoglobulin fusion protein comprising an amino acid sequence that is at least about 80% identical and/or homologous to any one of SEQ ID NOs: 68-99. In one embodiment, the pharmaceutical composition further comprises a pharmaceutically acceptable excipient.

In one embodiment, the immunoglobulin fusion protein comprises an amino acid sequence that is based on or derived from any one of SEQ ID NOs: 122-143. In one embodiment, the immunoglobulin fusion protein comprises an amino acid sequence that is at least about 50% identical and/or homologous to an amino acid sequence of any of one of SEQ ID NOs: 122-143. In one embodiment, the immunoglobulin fusion protein comprises an amino acid sequence that is at least about 80% identical and/or homologous to an amino acid sequence of any of one of SEQ ID NOs: 122-143. In one embodiment, the first immunoglobulin fusion protein comprises from about 5 to about 3,000 amino acids comprising from about 50 to about 700 amino acids identical and/or homologous to any one of SEQ ID NOs: 122-143.

In another aspect, provided herein is a first genetic construct comprising nucleic acids encoding the immunoglobulin fusion protein of any of SEQ ID NOs: 122-143. In one embodiment, a first genetic construct comprises nucleic acids derived from any one of SEQ ID NOs: 100-121. In one embodiment, a first genetic construct comprises a nucleic acid sequence that is at least about 50% identical and/or homologous to a nucleic acid sequence of any one of SEQ ID NOs: 100-121. In one embodiment, a first genetic construct comprises a nucleic acid sequence that is at least about 80% identical and/or homologous to a nucleic acid sequence of any one of SEQ ID NOs: 100-121.

In another aspect, provided herein is a first expression vector comprising a first genetic construct comprising nucleic acids encoding the immunoglobulin fusion protein of any of SEQ ID NOs: 122-143. In one embodiment, provided herein is a first expression vector comprising a first genetic construct comprising nucleic acids derived from any one of SEQ ID NOs: 100-121. In one embodiment, provided herein is a first expression vector comprising a first genetic construct comprising a nucleic acid sequence that is at least about 50% identical and/or homologous to a nucleic acid sequence of any one of SEQ ID NOs: 100-121. In one embodiment, provided herein is a first expression vector comprising a first genetic construct comprising a nucleic acid sequence that is at least about 80% identical and/or homologous to a nucleic acid sequence of any one of SEQ ID NOs: 100-121. In one instance, provided herein is a mammalian expression host comprising a first expression vector. In one embodiment, provided herein is a method of producing an immunoglobulin fusion protein comprising (a) transfecting a first expression vector transiently in a mammalian cell culture, (b) growing the cell culture in an expression medium at a controlled temperature and percentage $CO_2$, (c) and harvesting the secreted immunoglobulin fusion protein. In one embodiment, the method of producing an immunoglobulin fusion protein further comprises purifying the immunoglobulin fusion protein.

In another aspect, provided herein is a method of treating a disease or condition in a subject in need thereof, the method comprising administering to the subject a therapeutically effective amount an immunoglobulin fusion protein comprising an amino acid sequence derived from any one of SEQ ID NOs: 122-143. In another aspect, provided herein is a method of treating a disease or condition in a subject in need thereof, the method comprising administering to the subject a therapeutically effective amount an immunoglobulin fusion protein comprising an amino acid sequence that is at least about 50% identical and/or homologous to any one of SEQ ID NOs: 122-143. In another aspect, provided herein is a method of treating a disease or condition in a subject in need thereof, the method comprising administering to the subject a therapeutically effective amount an immunoglobulin fusion protein comprising an amino acid sequence that is at least about 80% identical and/or homologous to any one of SEQ ID NOs: 122-143.

In another aspect, provided herein is a pharmaceutical composition comprising an immunoglobulin fusion protein derived from any one of SEQ ID NOs: 122-143. In another aspect, provided herein is a pharmaceutical composition comprising an immunoglobulin fusion protein comprising an amino acid sequence that is at least about 50% identical and/or homologous to any one of SEQ ID NOs: 122-143. In another aspect, provided herein is a pharmaceutical composition comprising an immunoglobulin fusion protein comprising an amino acid sequence that is at least about 80% identical and/or homologous to any one of SEQ ID NOs:

122-143. In one embodiment, the pharmaceutical composition further comprises a pharmaceutically acceptable excipient.

In one embodiment, the first therapeutic peptide is configured to treat neutropenia and/or a neutropenia related disease. In one embodiment, the first therapeutic peptide is configured to treat diabetes and/or a diabetes related disease. In one embodiment, the first therapeutic peptide is configured to treat obesity and/or an obesity related disease. In one embodiment, the first therapeutic peptide is configured to treat an autoimmune disease and/or an autoimmune related disease. In one embodiment, the first therapeutic peptide is configured to treat anemia and/or an anemia related disease. In one embodiment, the first therapeutic peptide is configured to treat growth hormone deficiency and/or a growth hormone related disease. In one embodiment, the first therapeutic peptide is configured to treat chronic obstructive pulmonary disease (COPD) and/or a COPD related disease. In one embodiment, the first therapeutic peptide is configured to treat pain. In one embodiment, the first therapeutic peptide is configured to treat irritable bowel syndrome (IBS) and/or an IBS related disease. In one embodiment, the first therapeutic peptide is configured to treat Crohn's disease and/or a Crohn's disease related illness. In one embodiment, the first therapeutic peptide is configured to treat neutropenia and/or a neutropenia related disease. In one embodiment, the first therapeutic peptide is configured to treat a metabolic disorder and/or a disease resulting from said metabolic disorder. In one embodiment, the metabolic disorder includes lipodystrophy, diabetes, and hypertriglyceridemia. In one embodiment, the first therapeutic peptide is configured to treat short bowel syndrome and/or a short bowel syndrome related disease. In one embodiment, the first therapeutic peptide is configured to treat a patient with heart failure. In one embodiment, the first therapeutic peptide is configured to treat fibrosis and/or a fibrosis related disease.

In one embodiment, the immunoglobulin fusion protein is configured to treat neutropenia and/or a neutropenia related disease. In one embodiment, the immunoglobulin fusion protein is configured to treat diabetes and/or a diabetes related disease. In one embodiment, the immunoglobulin fusion protein is configured to treat obesity and/or an obesity related disease. In one embodiment, the immunoglobulin fusion protein is configured to treat an autoimmune disease and/or an autoimmune related disease. In one embodiment, the immunoglobulin fusion protein is configured to treat anemia and/or an anemia related disease. In one embodiment, the immunoglobulin fusion protein is configured to treat growth hormone deficiency and/or a growth hormone related disease. In one embodiment, the immunoglobulin fusion protein is configured to treat chronic obstructive pulmonary disease (COPD) and/or a COPD related disease. In one embodiment, the immunoglobulin fusion protein is configured to treat pain. In one embodiment, the immunoglobulin fusion protein is configured to treat irritable bowel syndrome (IBS) and/or an IBS related disease. In one embodiment, the immunoglobulin fusion protein is configured to treat Crohn's disease and/or a Crohn's disease related illness. In one embodiment, the immunoglobulin fusion protein is configured to treat neutropenia and/or a neutropenia related disease. In one embodiment, the immunoglobulin fusion protein is configured to treat a metabolic disorder and/or a disease resulting from said metabolic disorder. In one embodiment, the metabolic disorder includes lipodystrophy, diabetes, and hypertriglyceridemia. In one embodiment, the immunoglobulin fusion protein is configured to treat short bowel syndrome and/or a short bowel syndrome related disease. In one embodiment, the immunoglobulin fusion protein is configured to treat a patient with heart failure. In one embodiment, the immunoglobulin fusion protein is configured to treat fibrosis and/or a fibrosis related disease. In one embodiment, the first therapeutic peptide is configured to treat pulmonary arterial hypertension, ventilator-induced injury of the immature lung and/or lung transplant rejection.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown. It is emphasized that, according to common practice, the various features of the drawings are not to-scale. On the contrary, the dimensions of the various features are arbitrarily expanded or reduced for clarity.

In some figures, trastuzumab is referred to as Herceptin. It is to be understood that trastuzumab and Herceptin may be used interchangeably throughout this disclosure. In some figures, an immunoglobulin fusion protein is described in the following order: antibody, coil or direct, therapeutic agent, and antibody region to which the therapeutic agent is attached; for example, trastuzumab-coil hEPO (CDRH3). The immunoglobulin fusion protein may be described in any other manner, for example, trastuzumab-CDRH3-coil-hEPO is the same fusion as trastuzumab-coil hEPO (CDRH3). In some instances, an antibody is abbreviated in the figures, for example, bAb and BLVH12 are abbreviations for a bovine antibody. PBS is an abbreviation of phosphate buffered saline. In some instances, hAb is an abbreviation for Herceptin or trastuzumab antibody. In some instances, H2 is an abbreviation of CDRH2, H3 is an abbreviation of CDRH3, and L3 is an abbreviation of CDRL3. In some instances, CDRH3 and CDR3H indicate a complementary determining region 3 of a heavy chain, CDRH2 and CDR2H indicate a complementary determining region 2 of a heavy chain, and CDRL3 and CDR3L indicate a complementary determining region 3 of a light chain.

Figure 1:
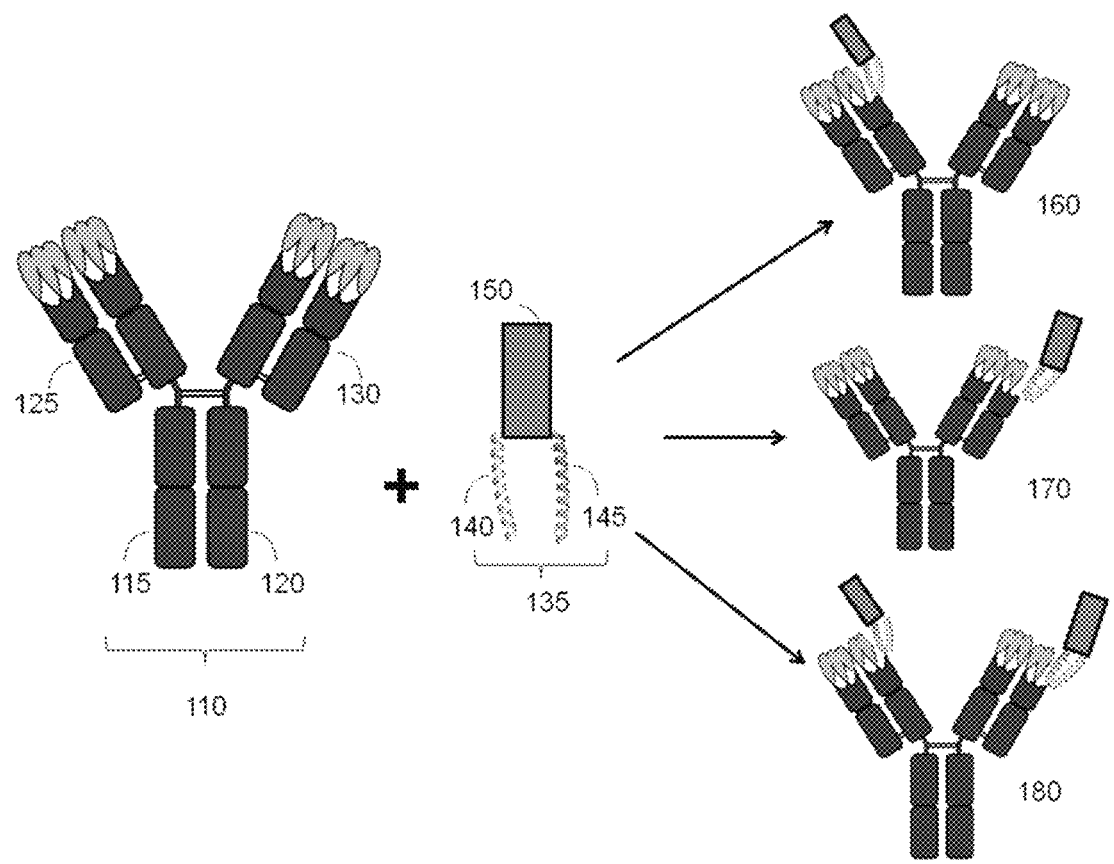

Provided herein are immunoglobulin fusion proteins comprising the term coil, wherein in some instances, these immunoglobulin fusion proteins comprising at least one extender peptide comprising amino acids having an alpha helical secondary structure. Provided herein are immunoglobulin fusion proteins comprising the term direct, wherein in some instances, these immunoglobulin fusion proteins do not comprise an extender peptide.

Included in the drawings are the following figures.

FIG. 1 depicts a schematic of various immunoglobulin fusion proteins with an extender peptide comprising an alpha helix (e.g., coil) structure.

Figure 2A:
Figure 2B:
Figure 2C:
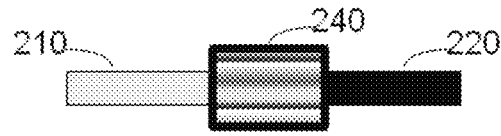
Figure 2D:
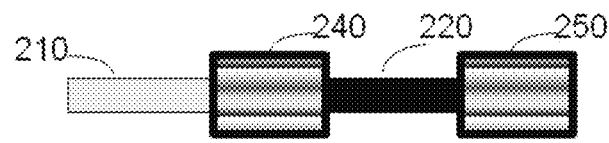
Figure 2E:
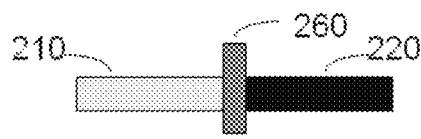
Figure 2F:
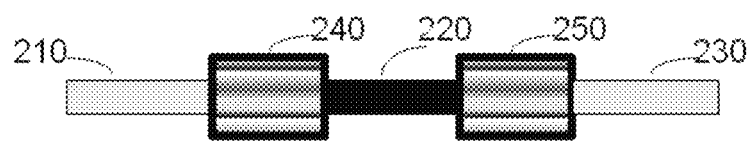

FIG. 2A-FIG. 2G depict schematics of various non-antibody regions. FIG. 2A depicts a schematic of a non-antibody region. FIG. 2B depicts a schematic of a non-antibody region. FIG. 2C depicts a schematic of a non-antibody region. FIG. 2D depicts a schematic of a non-antibody region. FIG. 2E depicts a schematic of a non-antibody region. FIG. 2F depicts a schematic of a non-antibody region.

Figure 2G:
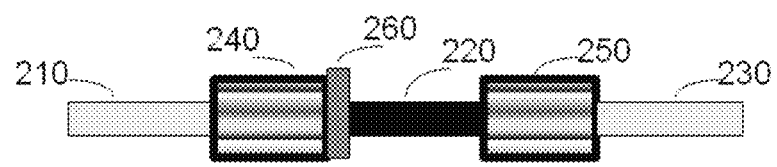

FIG. 2G depicts a schematic of a non-antibody region.

Figure 3:
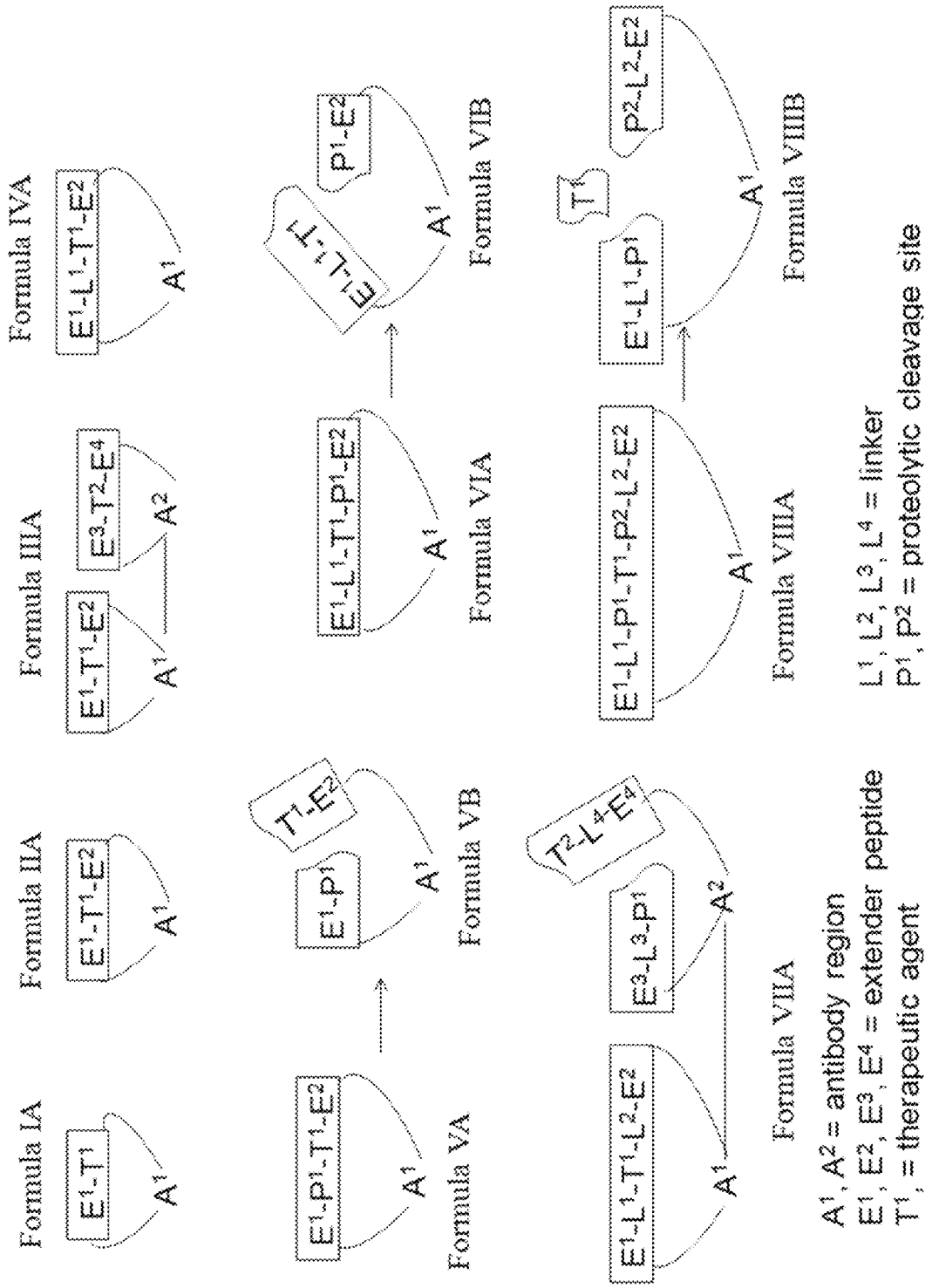

FIG. 3 depicts a schematic of various immunoglobulin fusion proteins with extender peptides.

Figure 4:
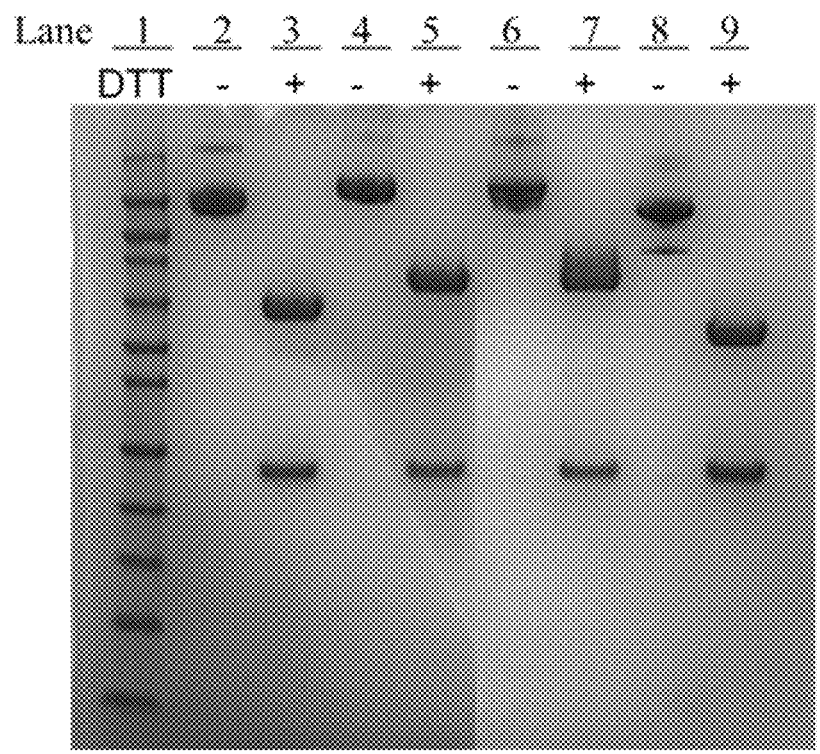

FIG. 4 depicts an SDS-PAGE gel of bovine-coil IgG, bovine-coil bGCSF IgG, trastuzumab IgG, and trastuzumab-coil bGCSF IgG.

Figure 5:
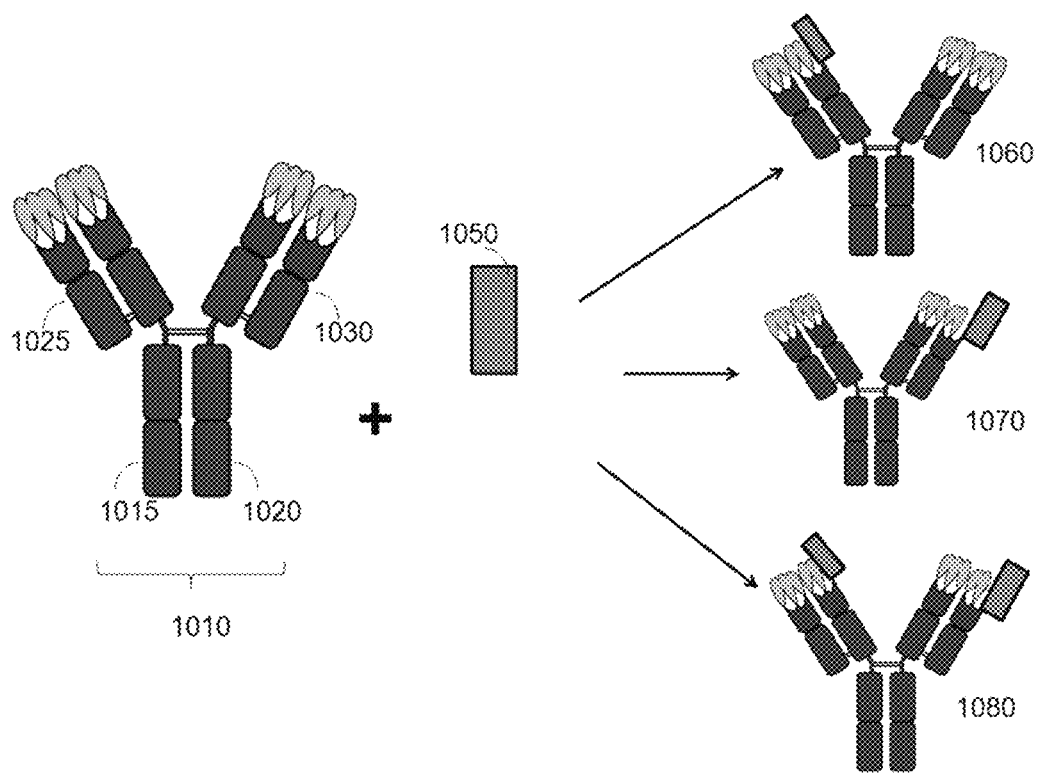

FIG. 5 depicts a schematic of various immunoglobulin fusion proteins with a therapeutic peptide directly inserted into an antibody region.

Figure 6:
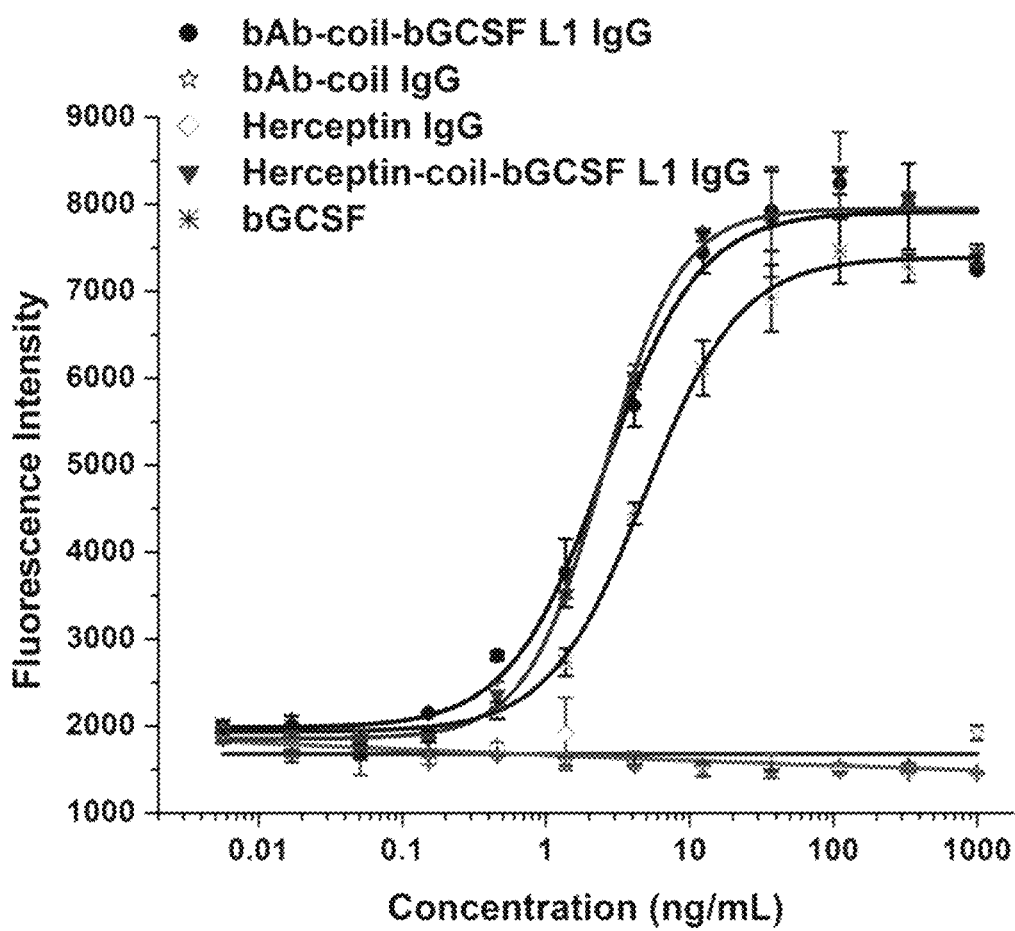

FIG. 6 depicts a graph of the in vitro activity of bovine-coil IgG, bovine-coil bGCSF IgG, trastuzumab IgG, and trastuzumab-coil bGCSF IgG in mouse NFS-60 cells.

Figure 7:
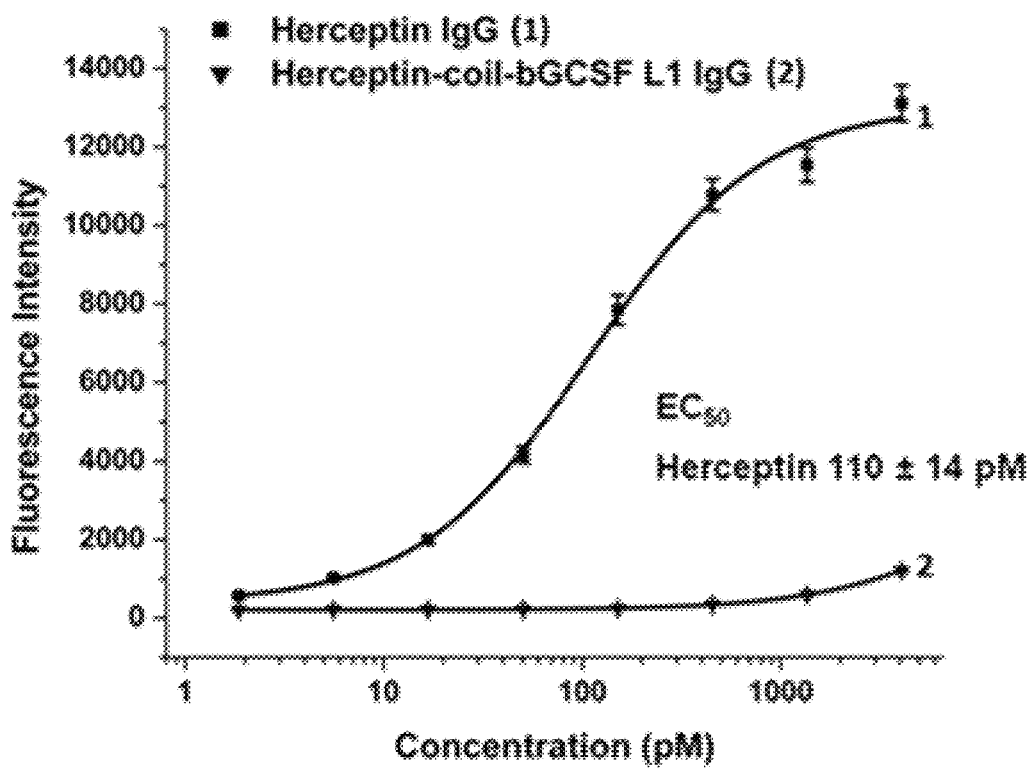

FIG. 7 depicts a graph of the binding affinity of a trastuzumab-coil bGCSF IgG to a Her2 receptor.

Figure 8:
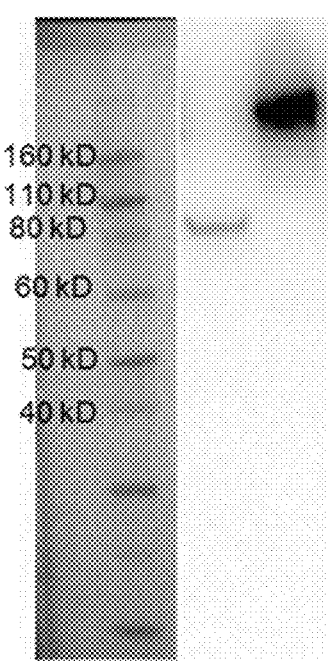

FIG. 8 depicts a Western blot of BLVIH12-coil betatrophin IgG, with and without DTT.

Figure 9:
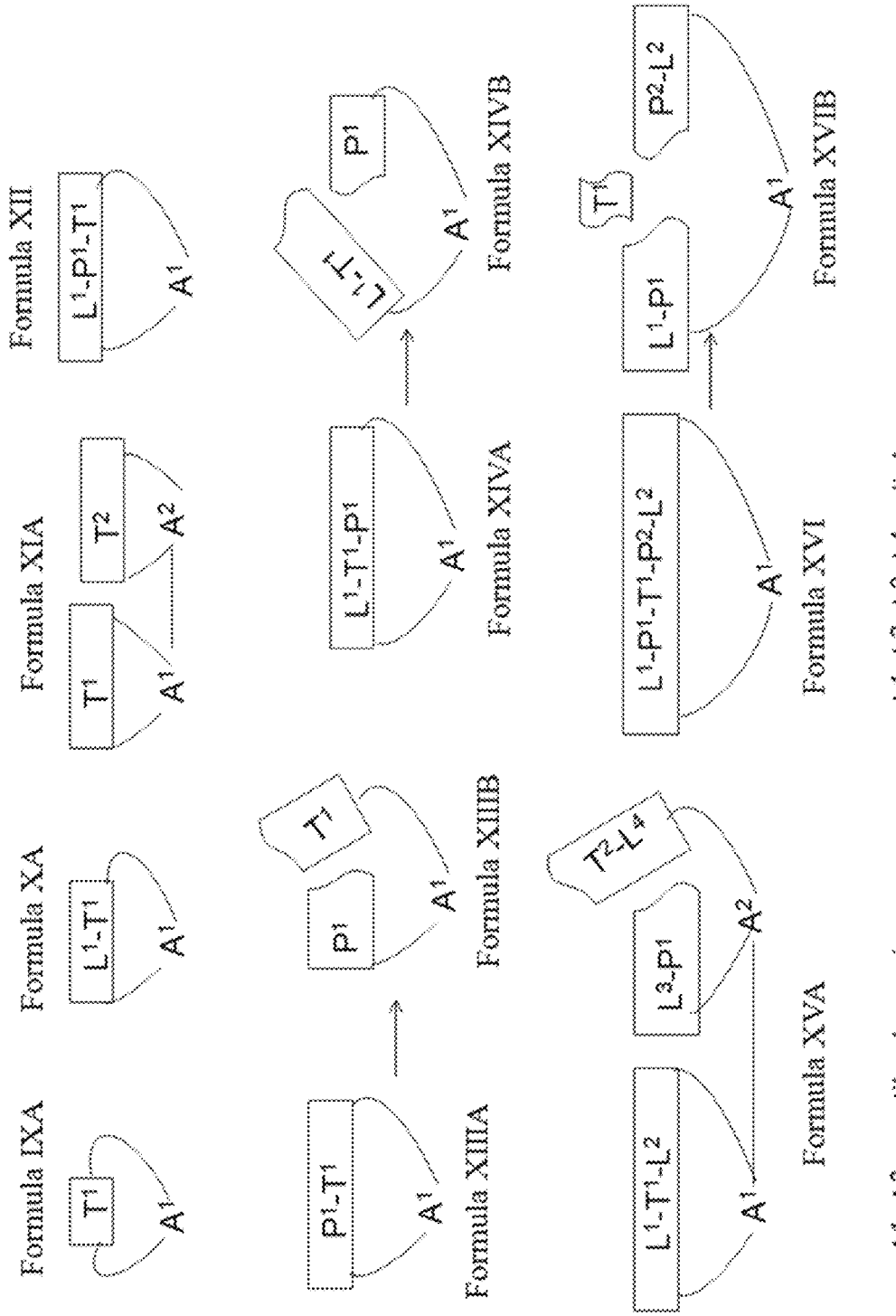

FIG. 9 depicts a schematic of various immunoglobulin fusion proteins without extender peptides.

Figure 10:
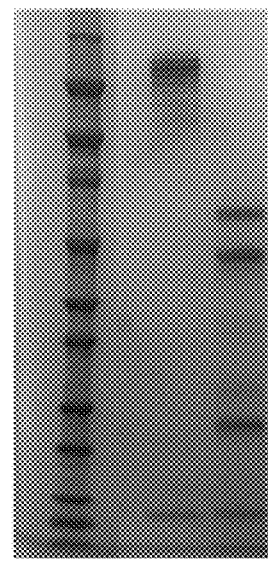

FIG. 10 depicts an SDS-PAGE of trastuzumab-direct bGCSF fusion proteins, with and without DTT.

Figure 11:
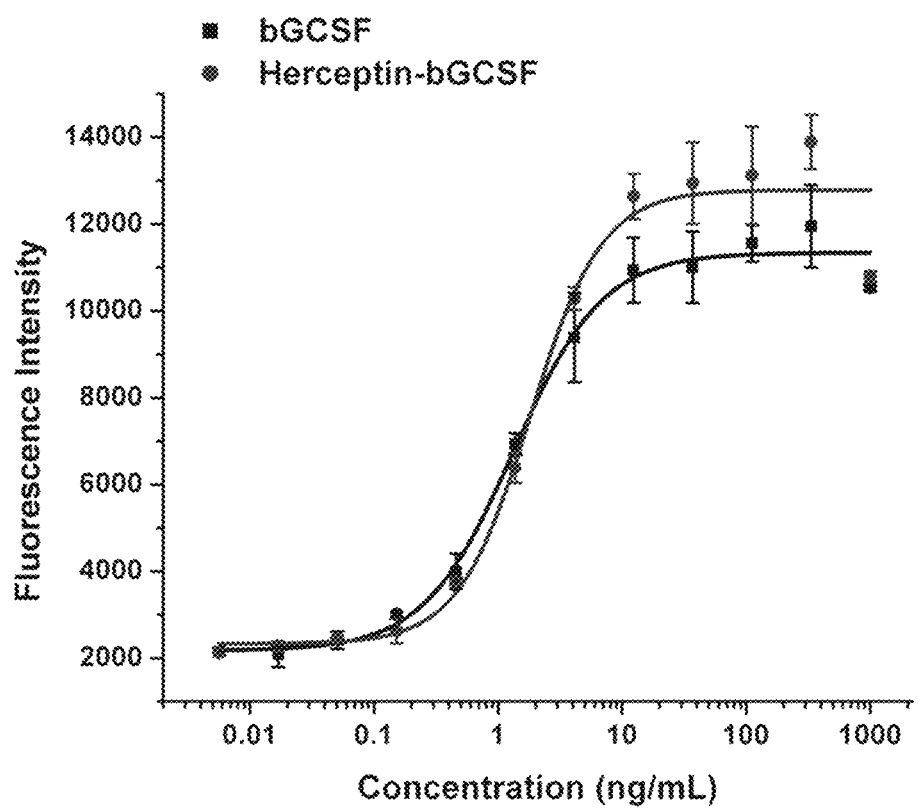

FIG. 11 depicts a graph of the in vitro activity of trastuzumab-direct bGCSF fusion protein and bGCSF in proliferating mouse NFS-60 cells.

Figure 12:
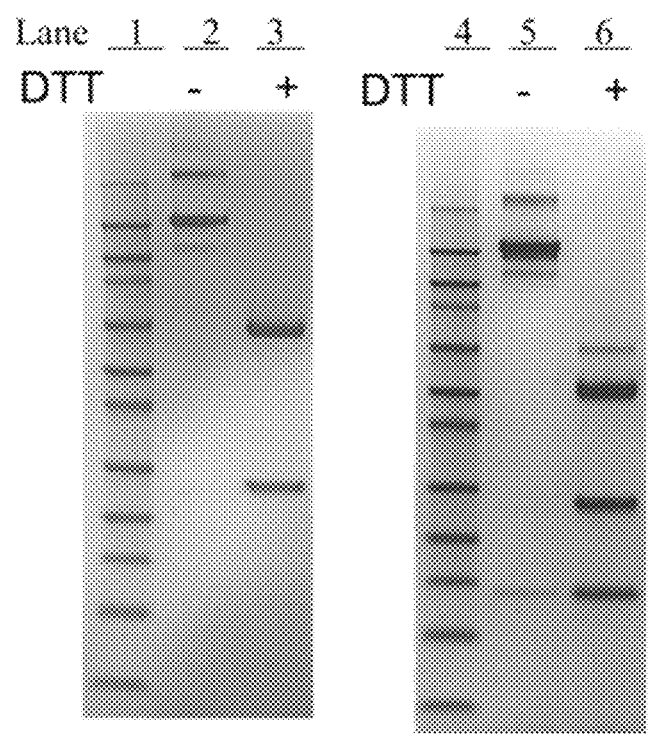

FIG. 12 depicts an SDS-PAGE gel of trastuzumab-coil exendin-4 (CDRH3) fusion protein and trastuzumab-coil exendin-4 fusion protein cleaved with Factor Xa to generate trastuzumab-coil exendin-4 RN.

Figure 13:
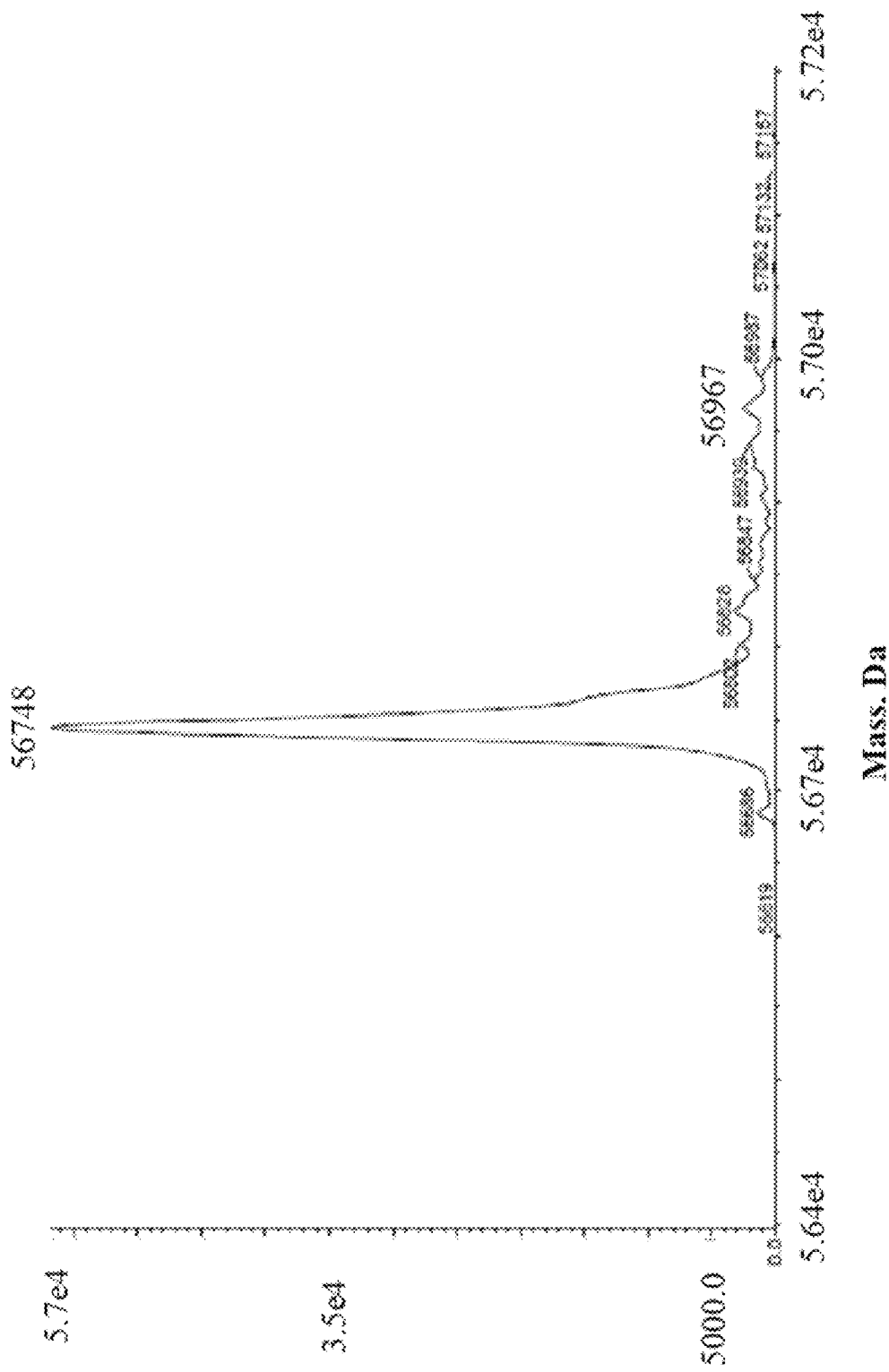

FIG. 13 depicts a chromatograph of an electrospray ionization mass spectrometry (ESI-MS) of trastuzumab-coil exendin-4 (CDRH3) fusion protein treated with peptide N-glycosidase and DTT.

Figure 14B:
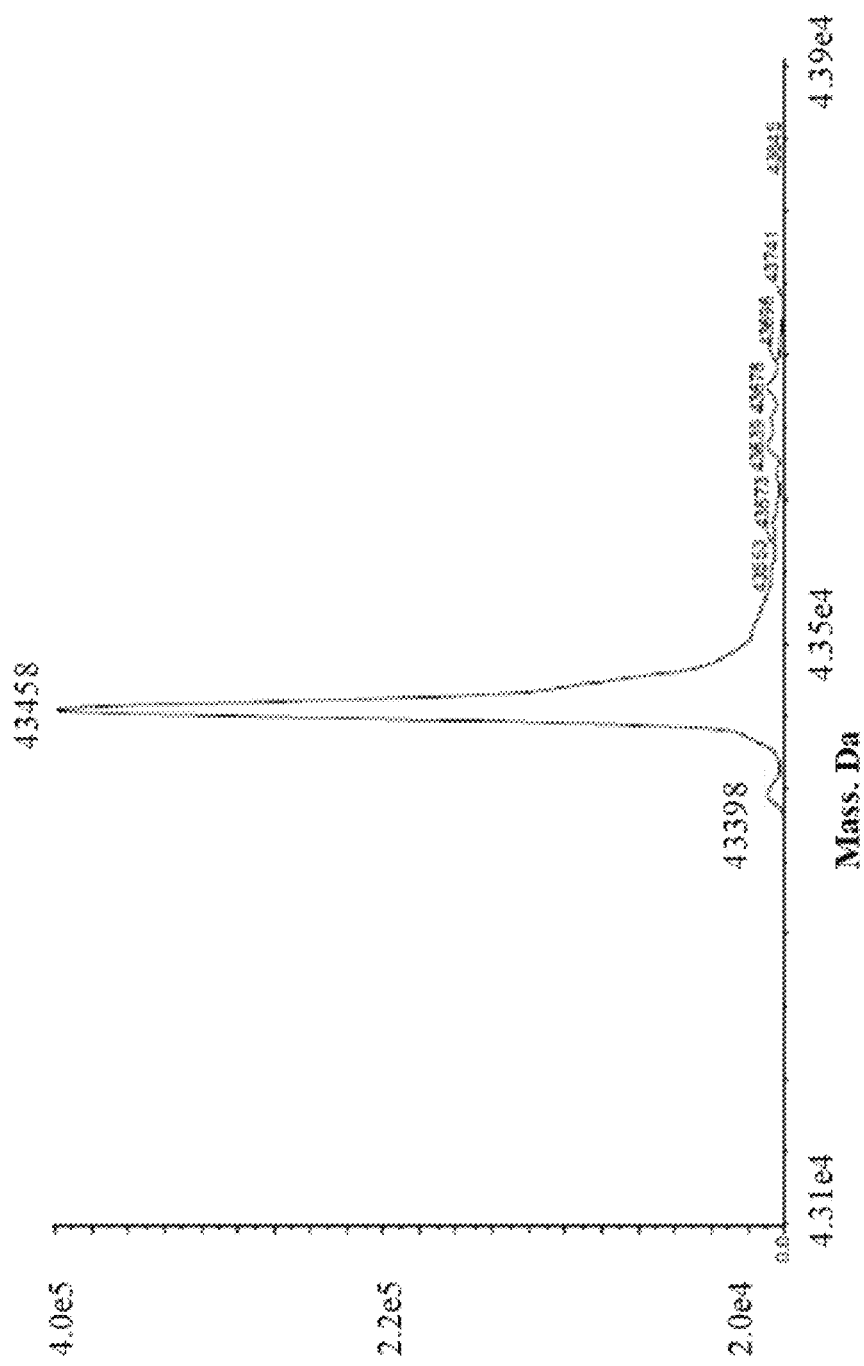

FIG. 14A-FIG. 14B depicts a chromatograph of an ESI-MS of trastuzumab-coil exendin-4 RN (CDRH3) fusion protein treated with peptide N-glycosidase and DTT, (FIG. 14A) N-terminal fragment, (FIG. 14B) C-terminal fragment.

Figure 15:
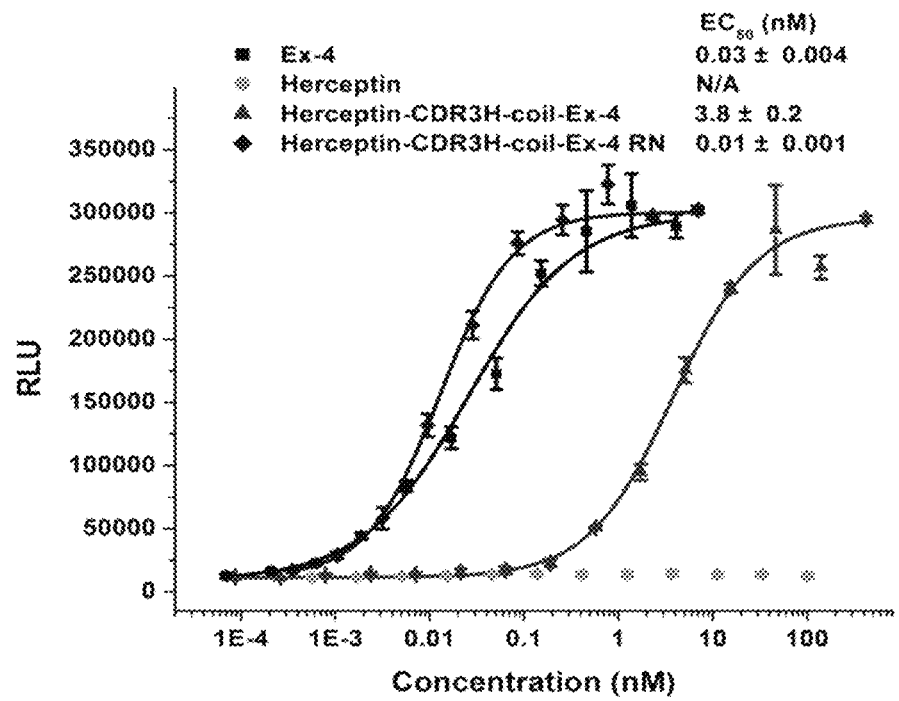

FIG. 15 depicts a graph of the in vitro activities of exendin-4 (Ex-4), trastuzumab, trastuzumab-coil exendin-4 (CDRH3), and trastuzumab-coil exendin-4 (CDRH3) RN in HEK 293 cells overexpressing GLP-1R receptor and cAMP responsive element (CRE)-luciferase (Luc) reporter.

Figure 16:
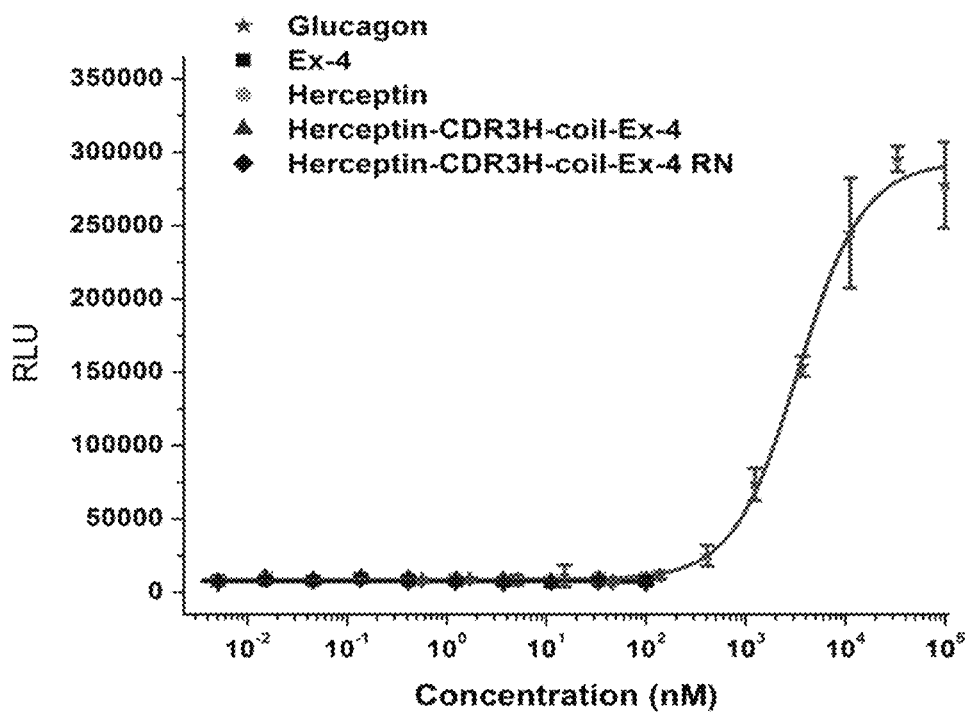

FIG. 16 depicts a graph of the in vitro activities of glucagon, Ex-4, trastuzumab, trastuzumab-coil exendin-4 (CDRH3), and trastuzumab-coil exendin-4 (CDRH3) RN in HEK 293 cells overexpressing glucagon receptor (GCGR) and CRE-Luc reporter.

Figure 17A:
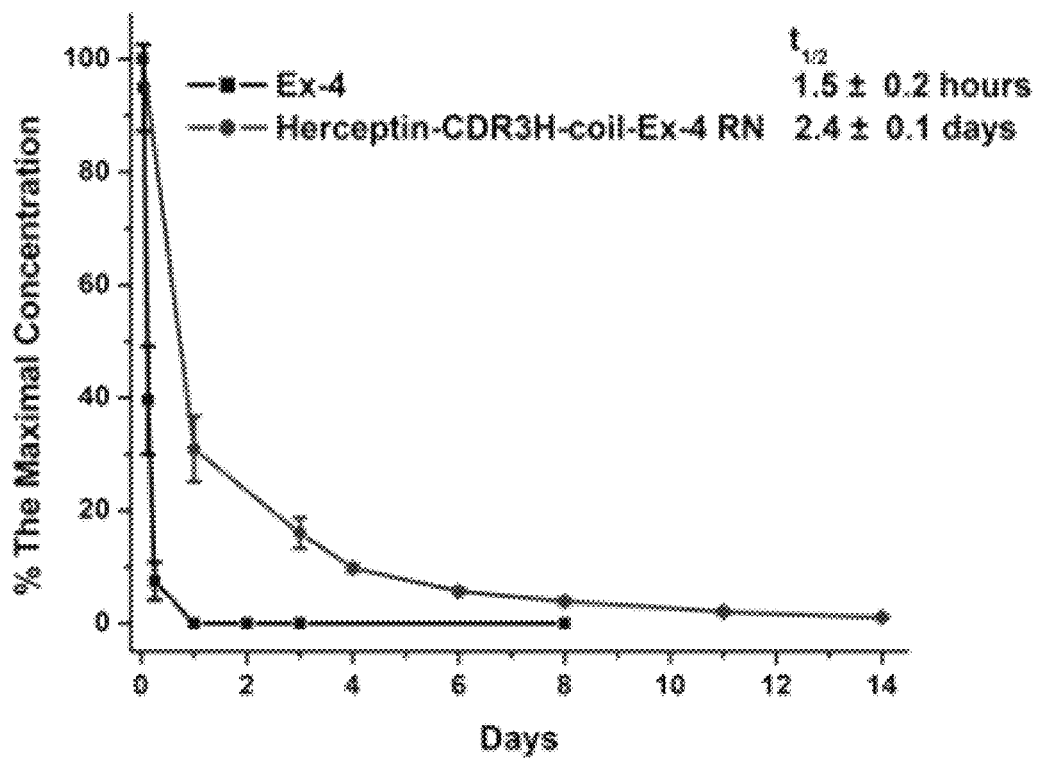
Figure 17B:
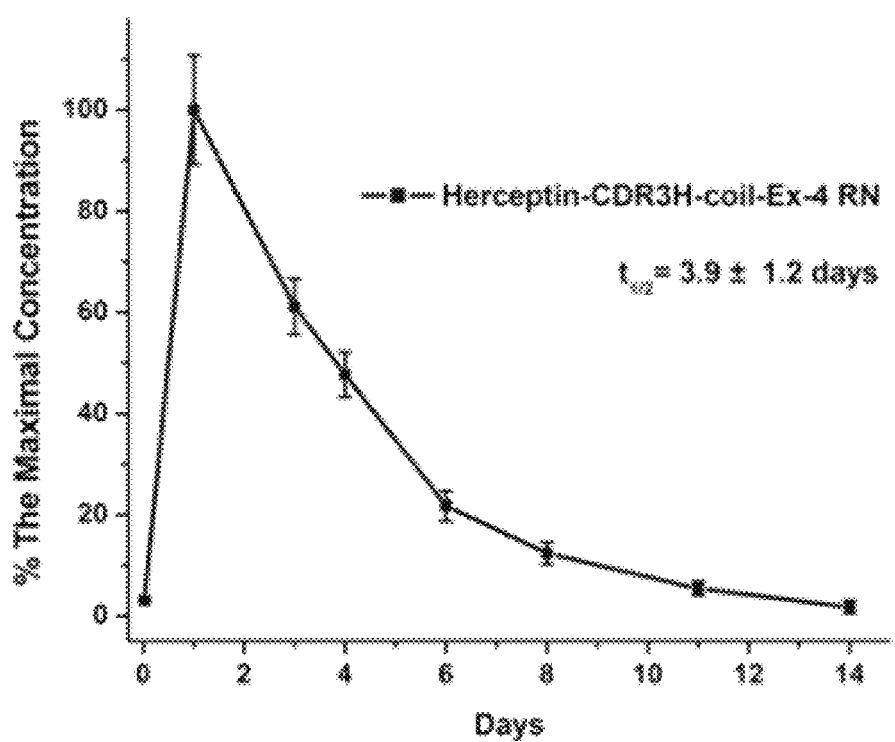

FIG. 17A-FIG. 17B depict a graph of the pharmacokinetics of trastuzumab-coil exendin-4 (CDRH3) IgG with (FIG. 17A) intravenous injection and (FIG. 17B) subcutaneous injection in mice.

Figure 18A:
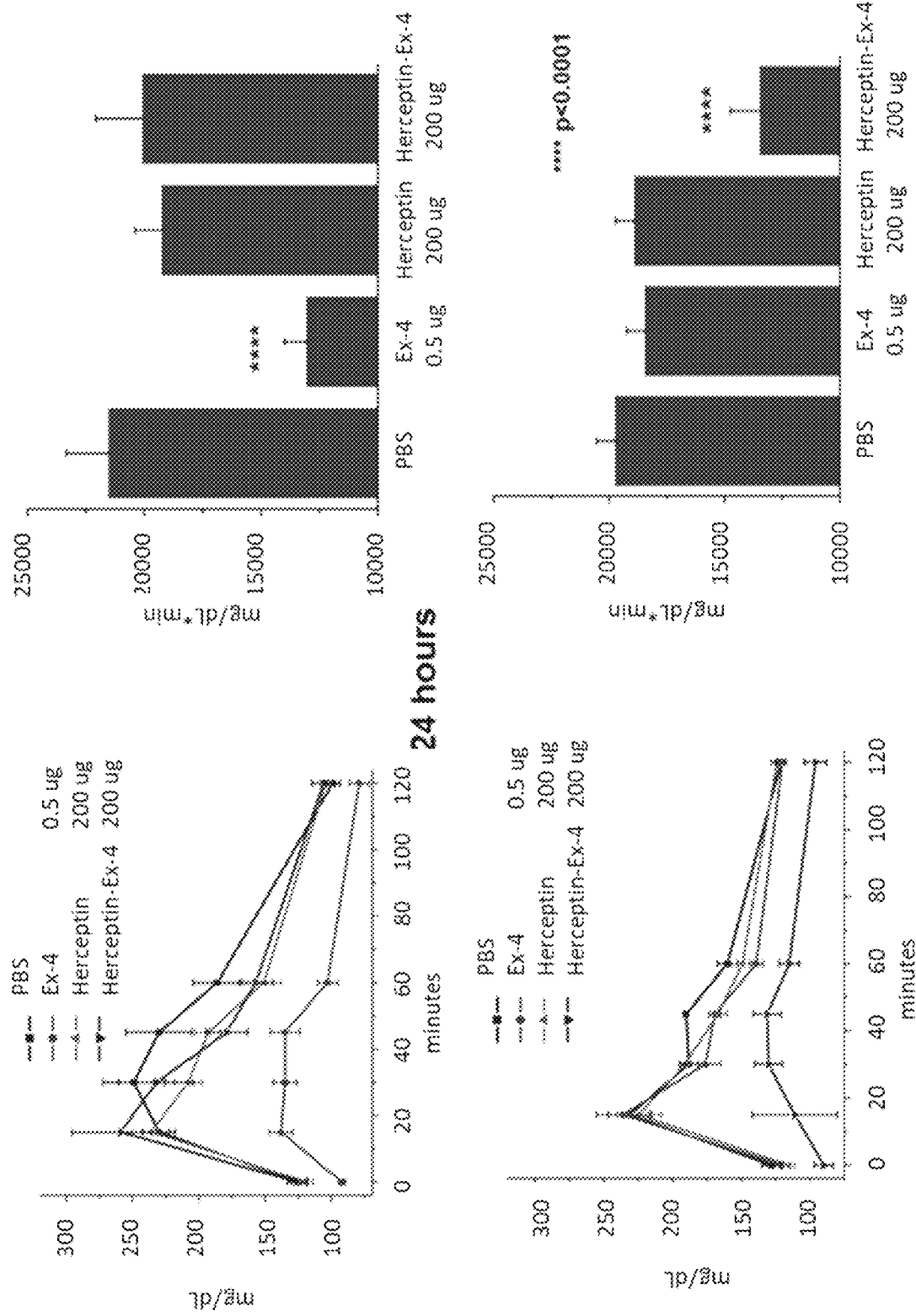
Figure 18:
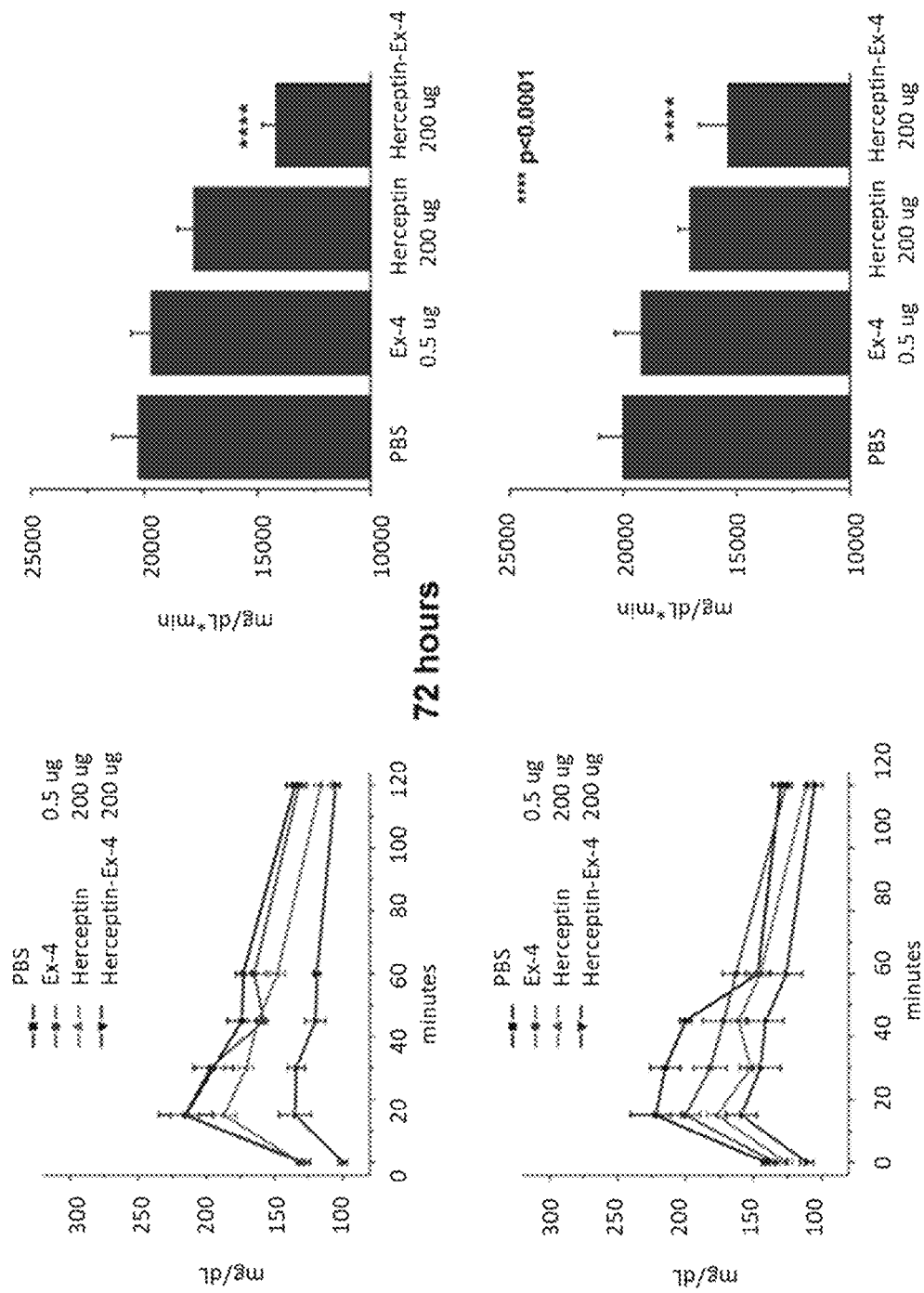
Figure 18:
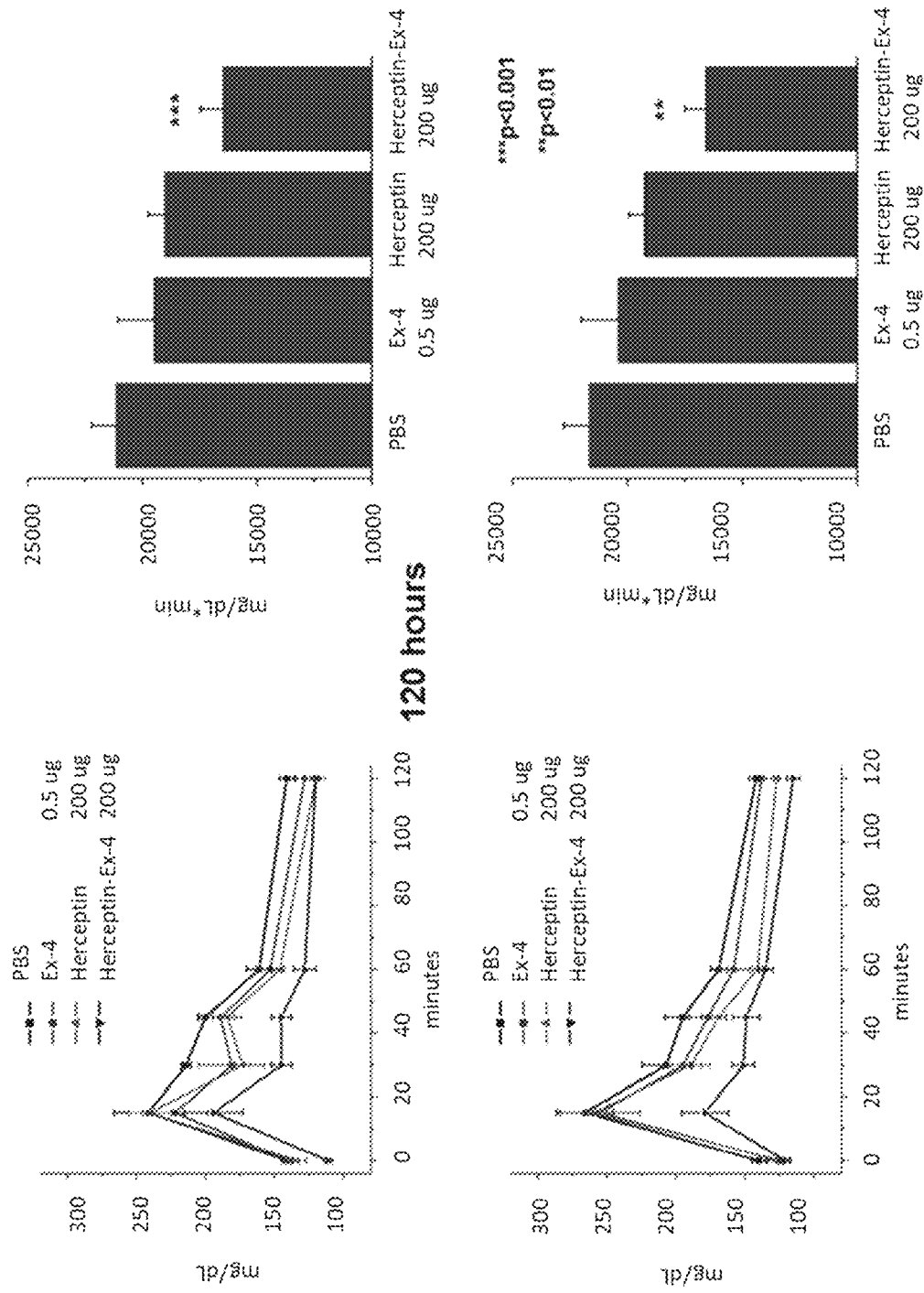
Figure 18D:
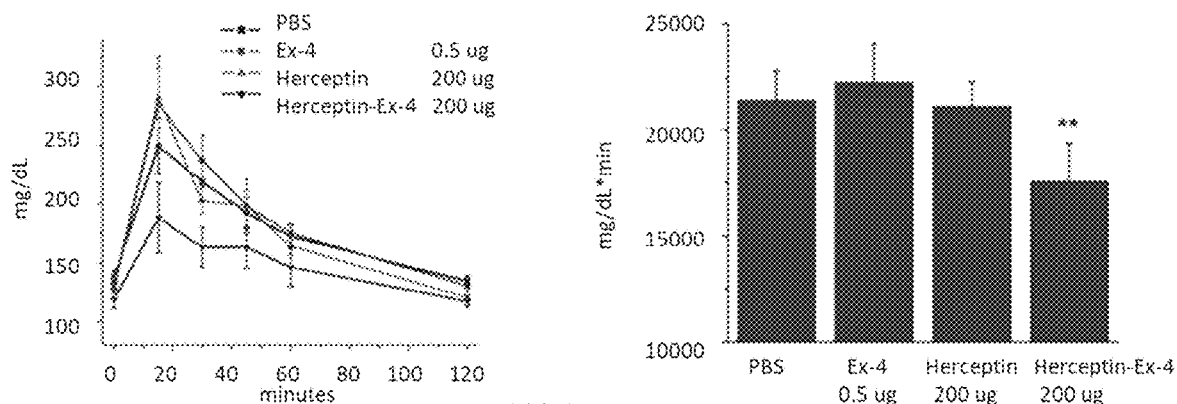
Figure 18D:
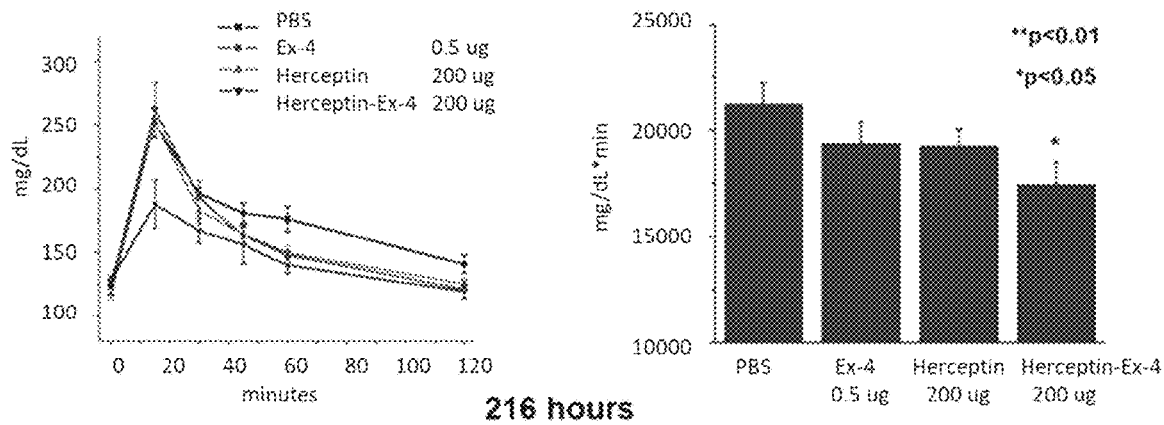
Figure 18D:
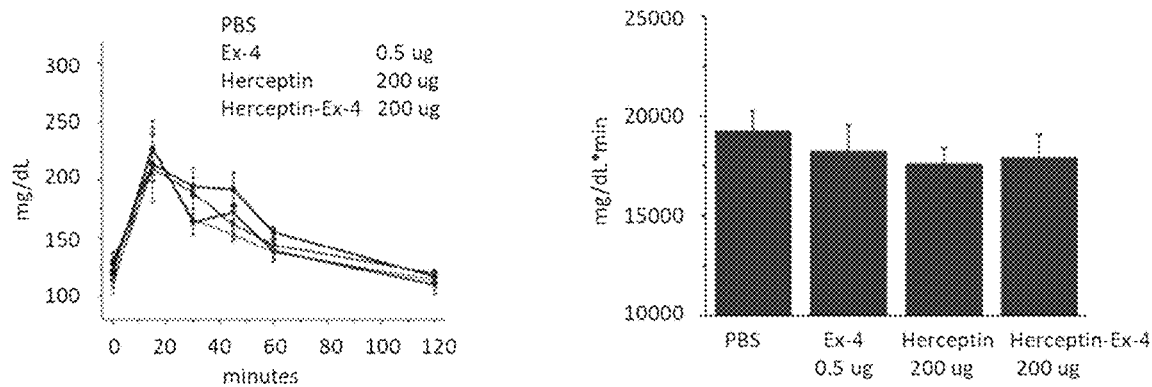

FIG. 18A-FIG. 18D depict the pharmacodynamics of trastuzumab-coil exendin-4 (CDRH3) IgG in mice at different time points: 30 minutes (FIG. 18A), 24 hours (FIG. 18A), 48 hours (FIG. 18B), 72 hours (FIG. 18B), 96 hours (FIG. 18C), 120 hours (FIG. 18C), 144 hours (FIG. 18D), 168 hours (FIG. 18D), and 216 hours (FIG. 18D).

Figure 19A:
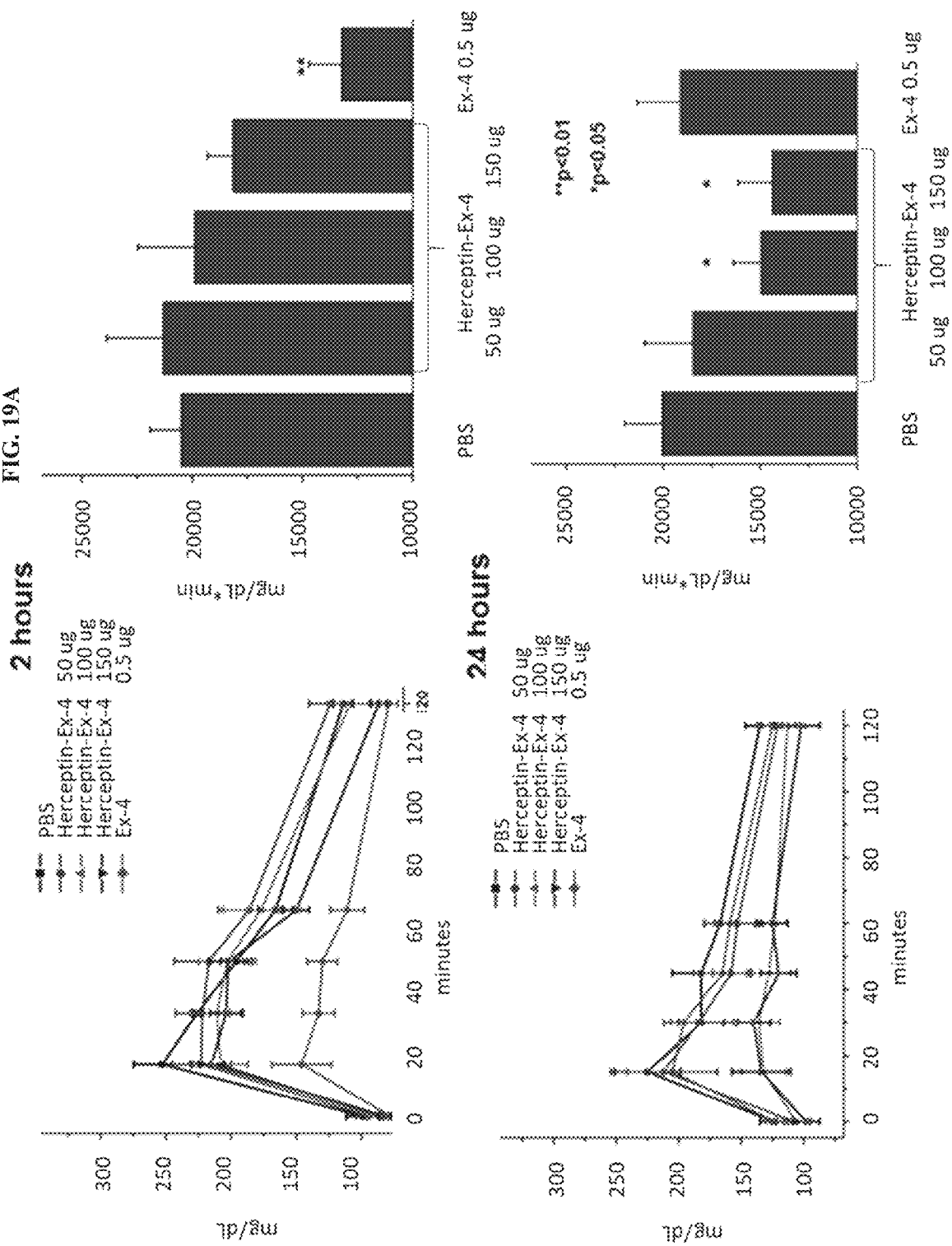
Figure 19C:
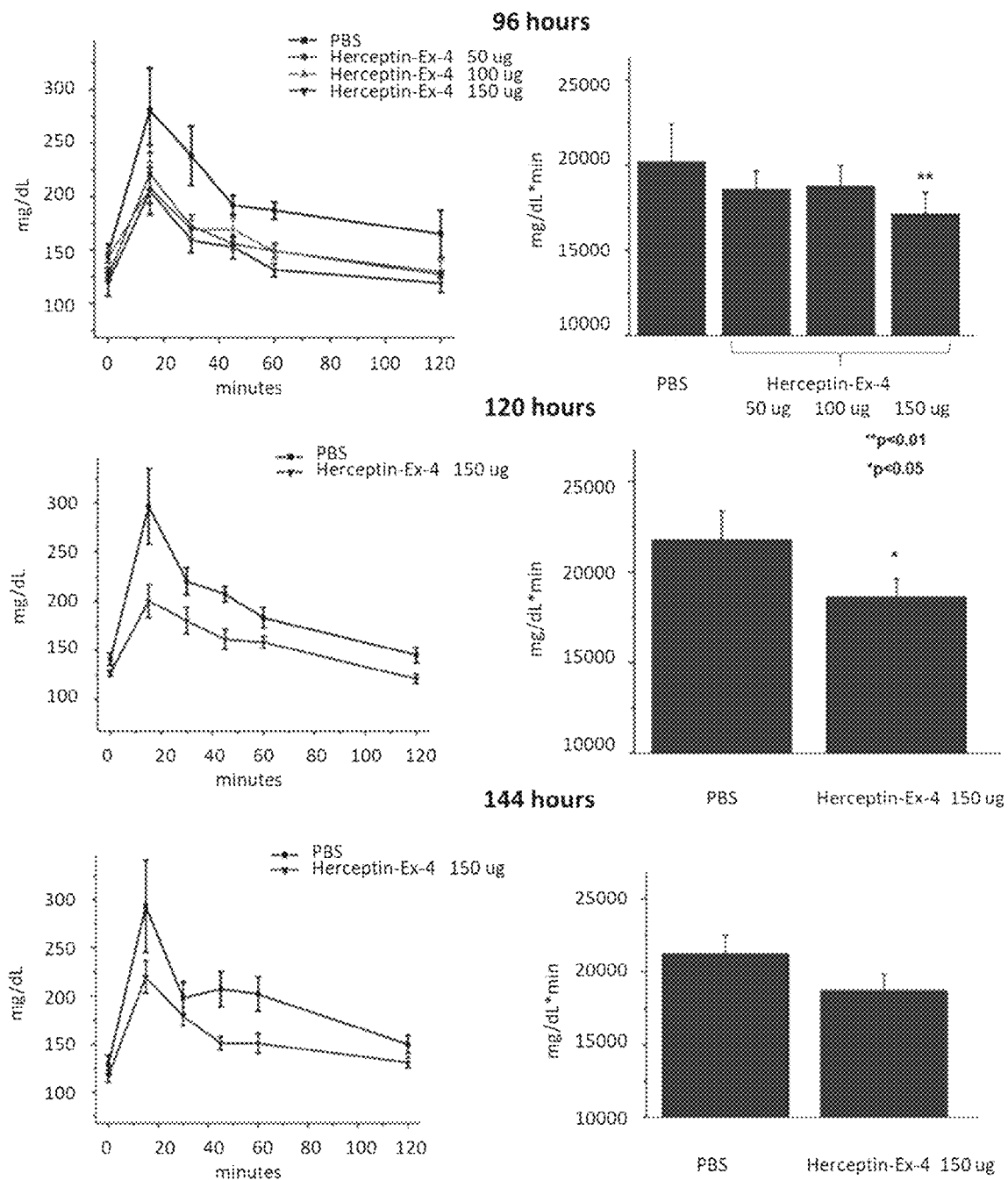

FIG. 19A-FIG. 19C depict the pharmacodynamics of various concentrations of trastuzumab-coil exendin-4 (CDRH3) IgG in mice at different time points: 2 hours (FIG. 19A), 24 hours (FIG. 19A), 48 hours (FIG. 19B), 72 hours (FIG. 19B), 144 hours (FIG. 19C), 168 hours (FIG. 19C), and 216 hours (FIG. 19C).

Figure 20:
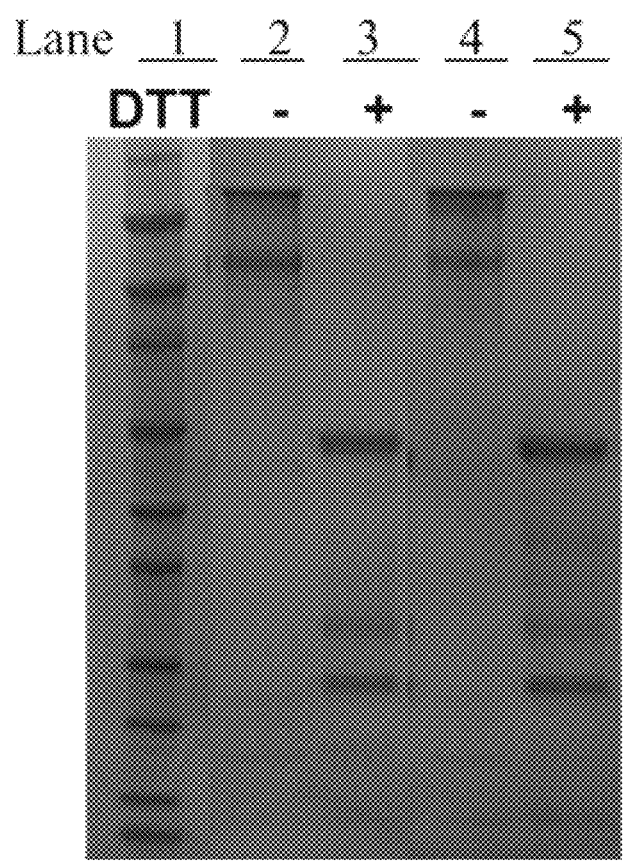

FIG. 20 depicts an SDS-PAGE gel of trastuzumab-coil Moka IgG and trastuzumab-coil Vm24 IgG, with and without DTT.

Figures 21, 22:
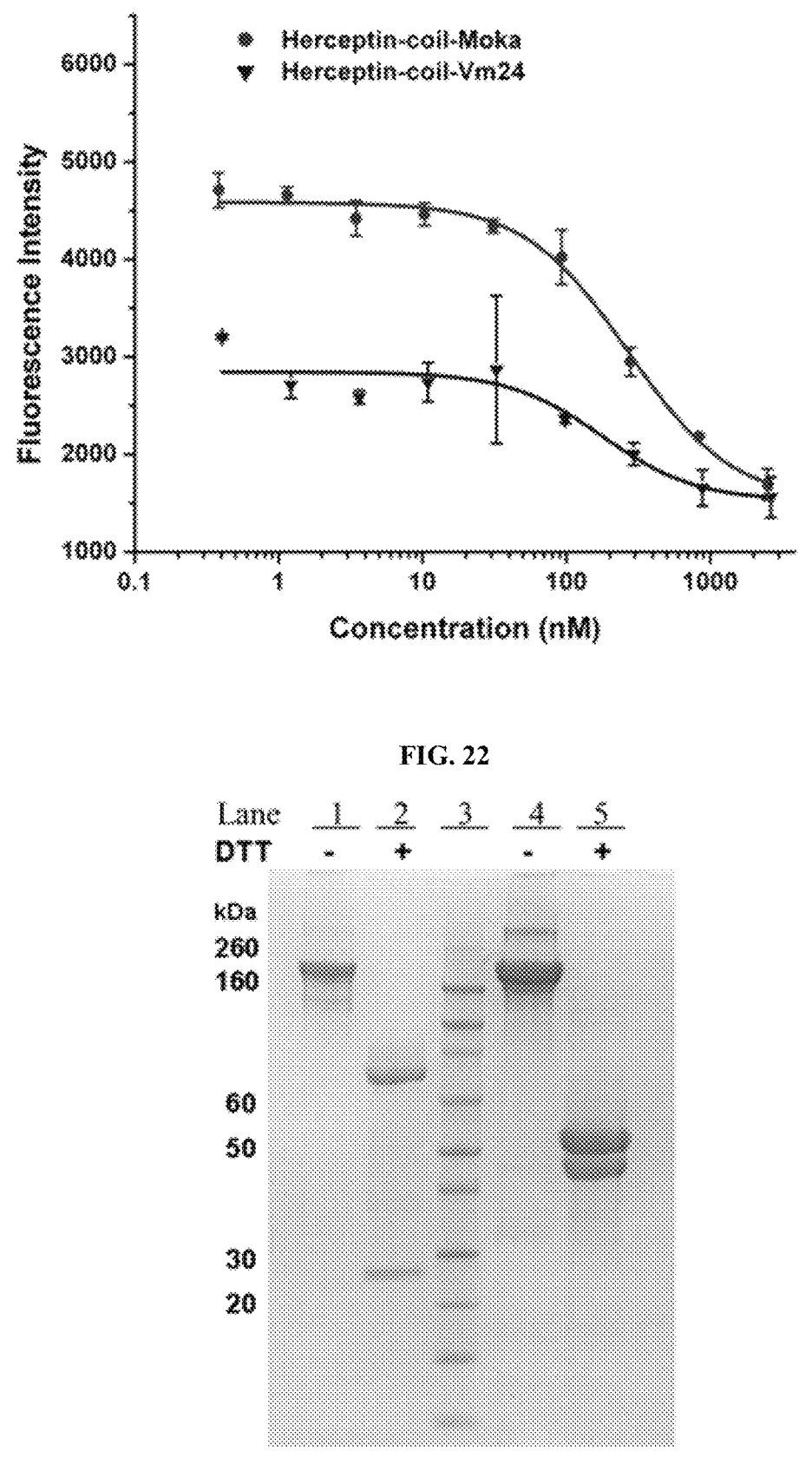

FIG. 21 depicts a graph of the in vitro activities of trastuzumab-coil Moka IgG and trastuzumab-coil Vm24 IgG on T-cell activation in human peripheral blood mononucleated cells (PBMCs).

FIG. 22 depicts an SDS-PAGE of trastuzumab-coil hGCSF (CDRH2) and trastuzumab-coil hGCSF (CDRL3), with and without DTT.

Figure 23A:
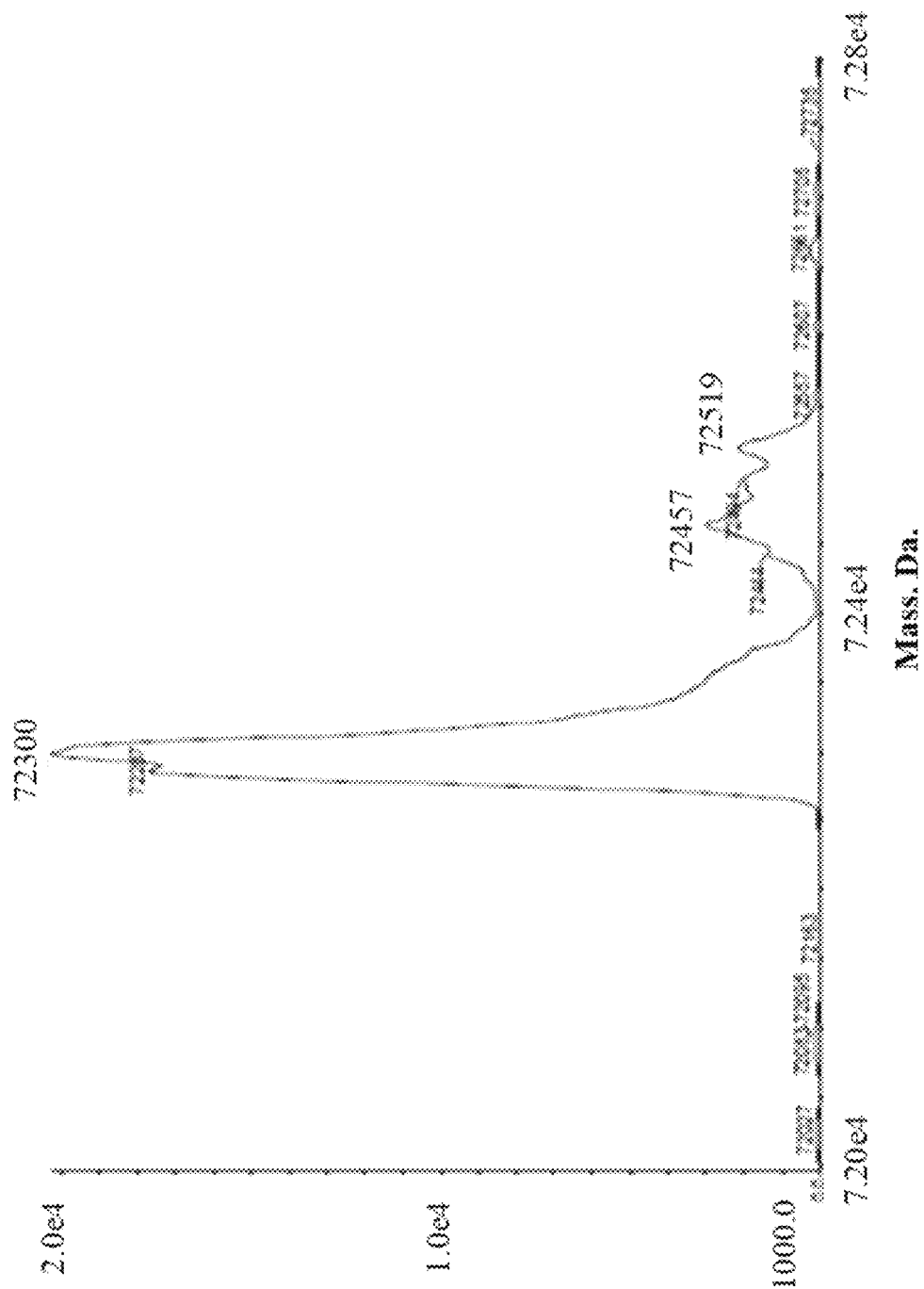
Figure 23B:
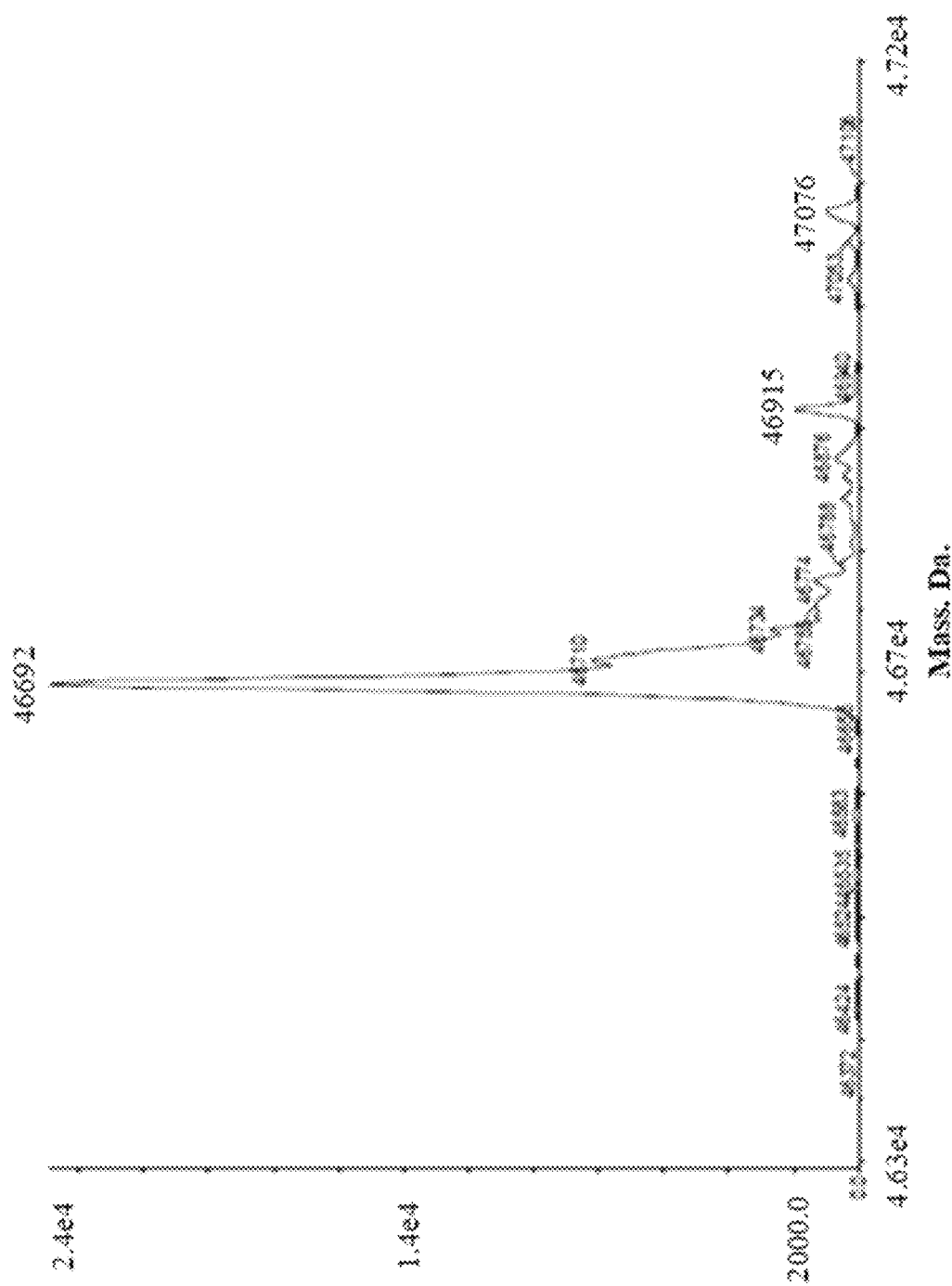

FIG. 23A-FIG. 23B depict an ESI-MS of (FIG. 23A) trastuzumab-coil hGCSF (CDRH2) treated with peptide N-glycosidase and DTT, and (FIG. 23B) trastuzumab-coil hGCSF (CDRL3) treated with peptide N-glycosidase and DTT.

Figure 24:
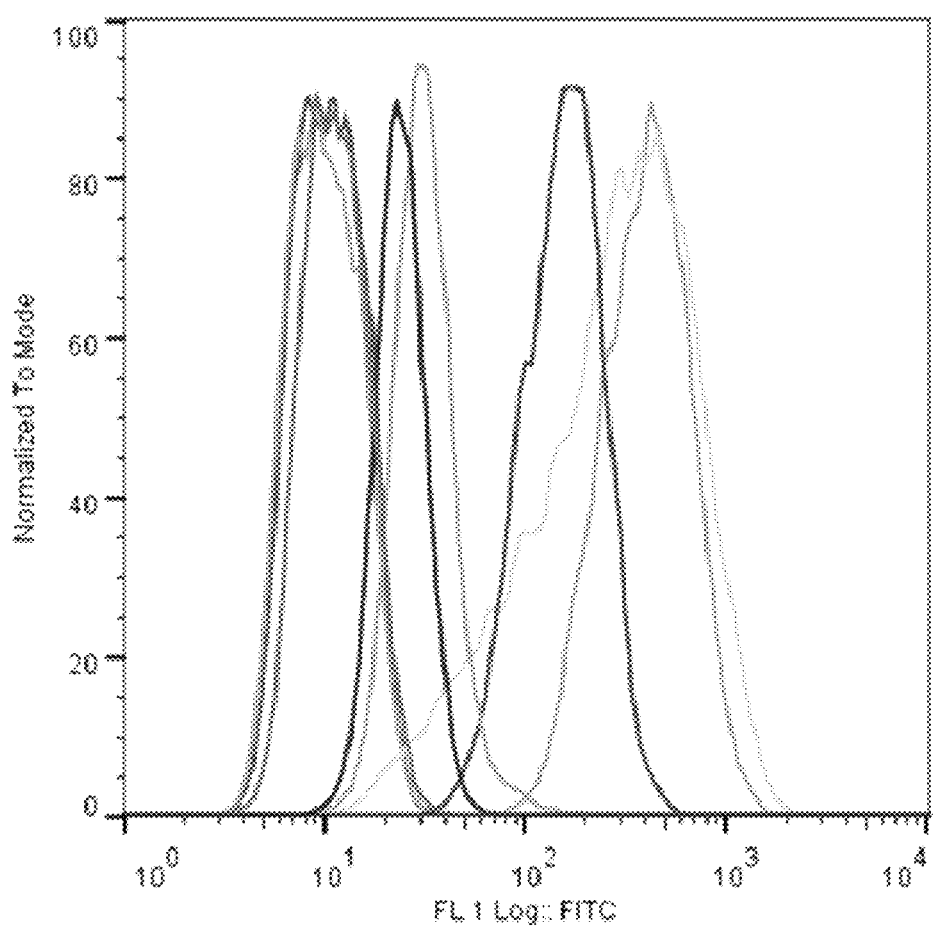

FIG. 24 depicts a histogram of trastuzumab-coil hGCSF (CDRH2) and trastuzumab-coil hGCSF (CDRL3) binding to HER2 receptor.

Figure 25:
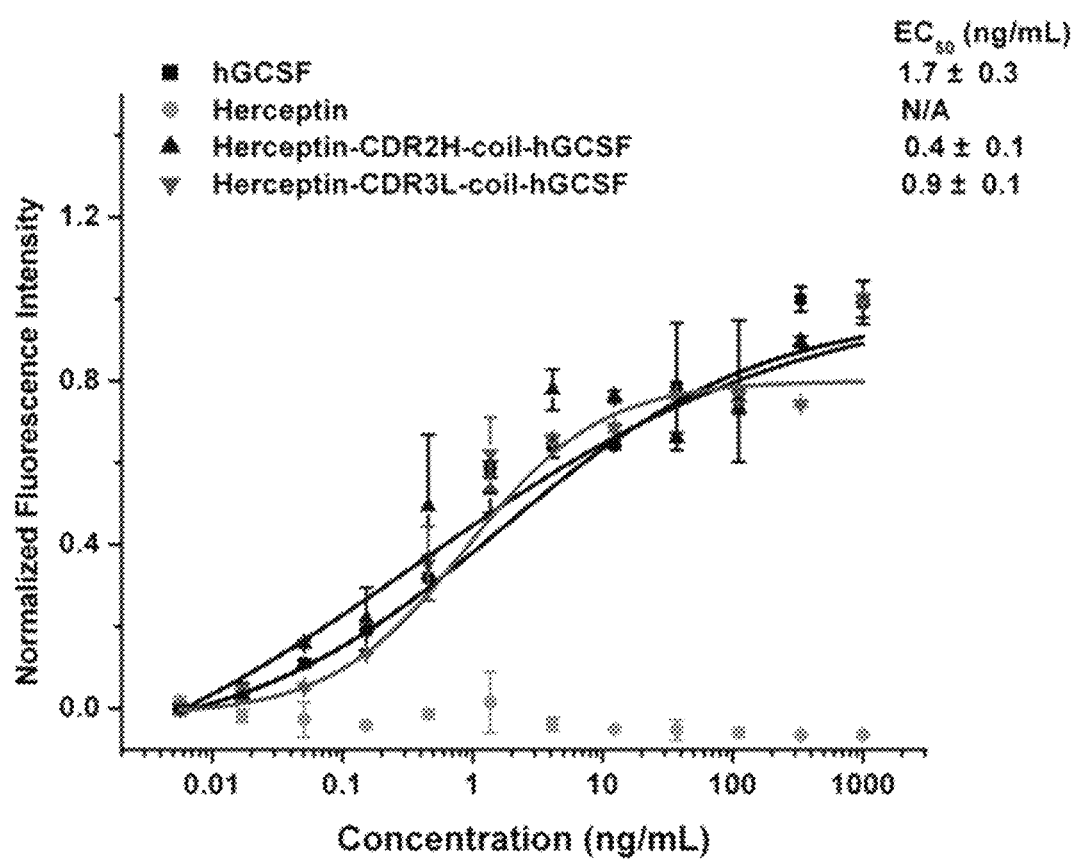

FIG. 25 depicts a graph of the in vitro activity of trastuzumab-coil hGCSF (CDRH2) and trastuzumab-coil hGCSF (CDRL3) in proliferating mouse NFS-60 cells.

Figure 26:
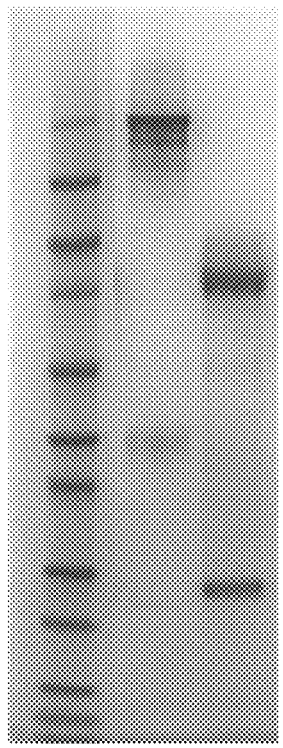

FIG. 26 depicts an SDS-PAGE gel of trastuzumab-coil hEPO (CDRH3), with and without DTT.

Figure 27:
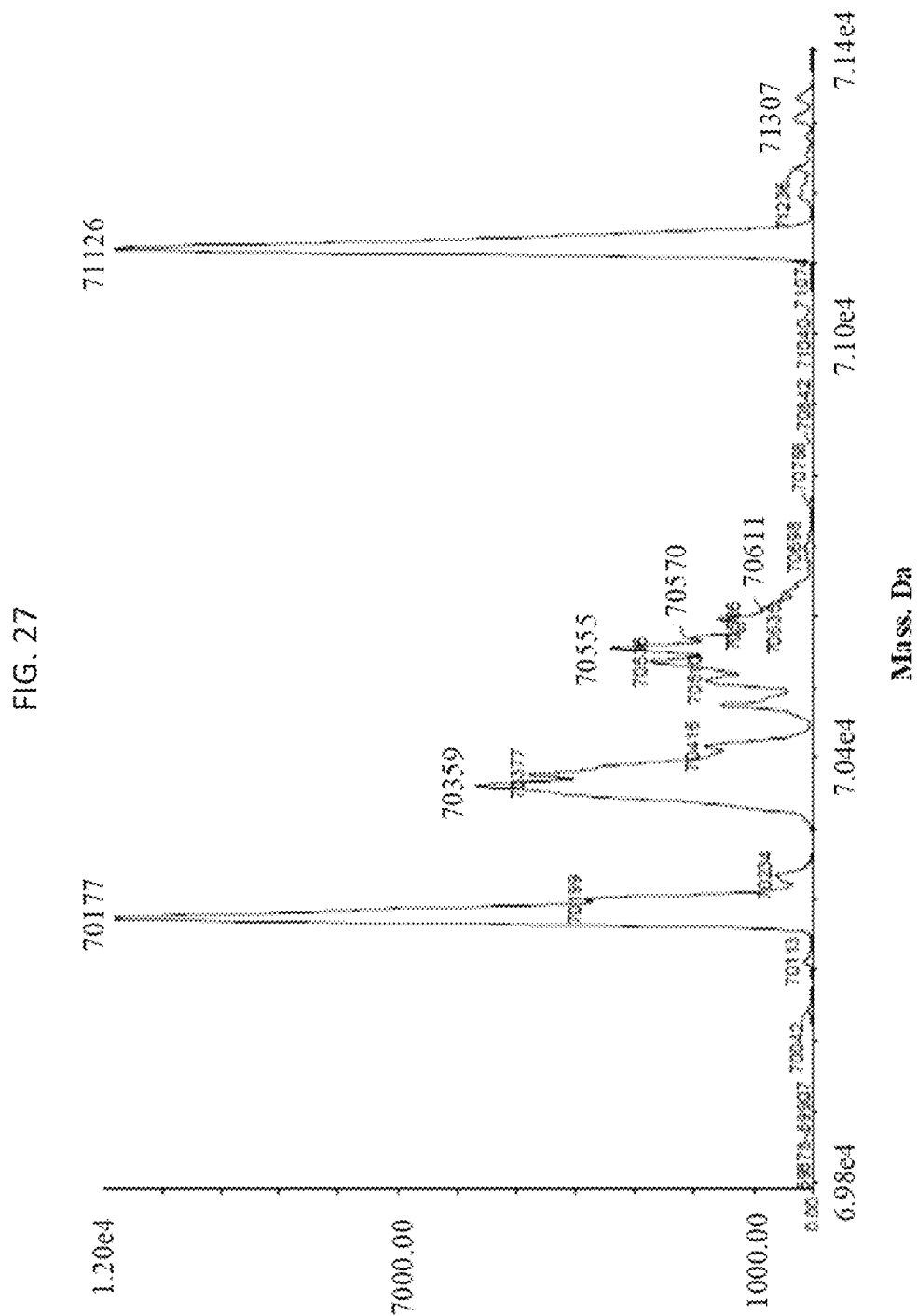

FIG. 27 depicts an ESI-MS of trastuzumab-coil hEPO (CDRH3) IgG treated with peptide N-glycosidase and DTT.

Figure 28:
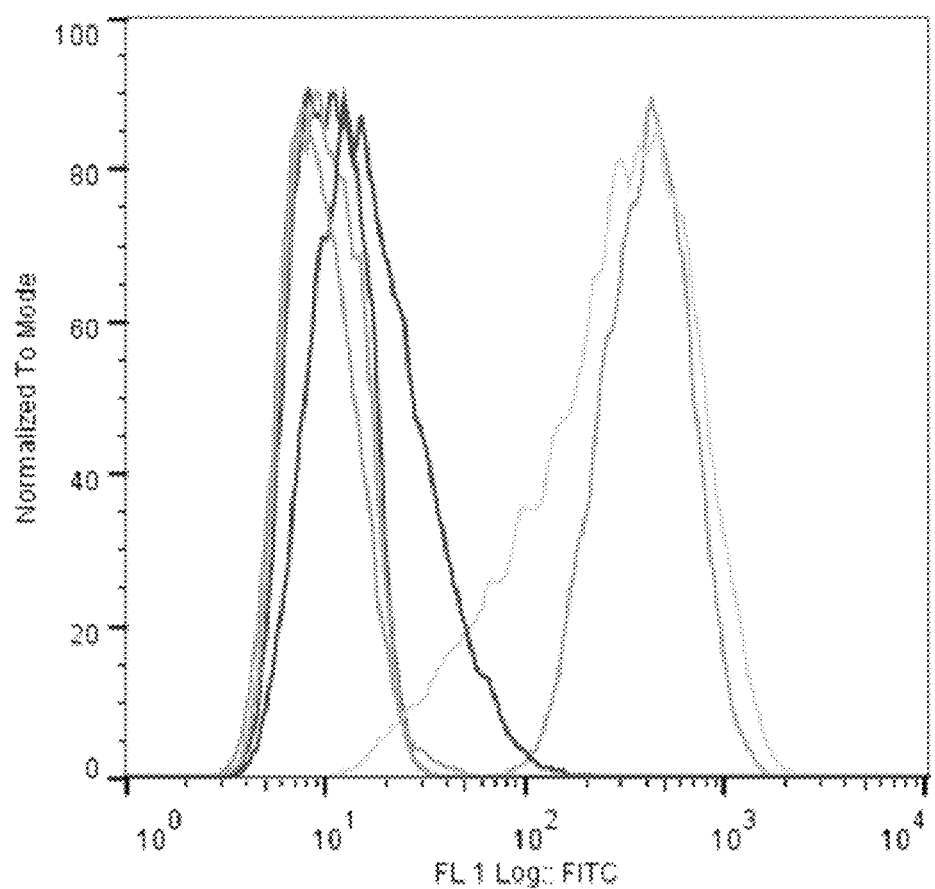

FIG. 28 depicts a histogram of trastuzumab-coil hEPO (CDRH3) binding to HER2 receptor.

Figures 29, 30:
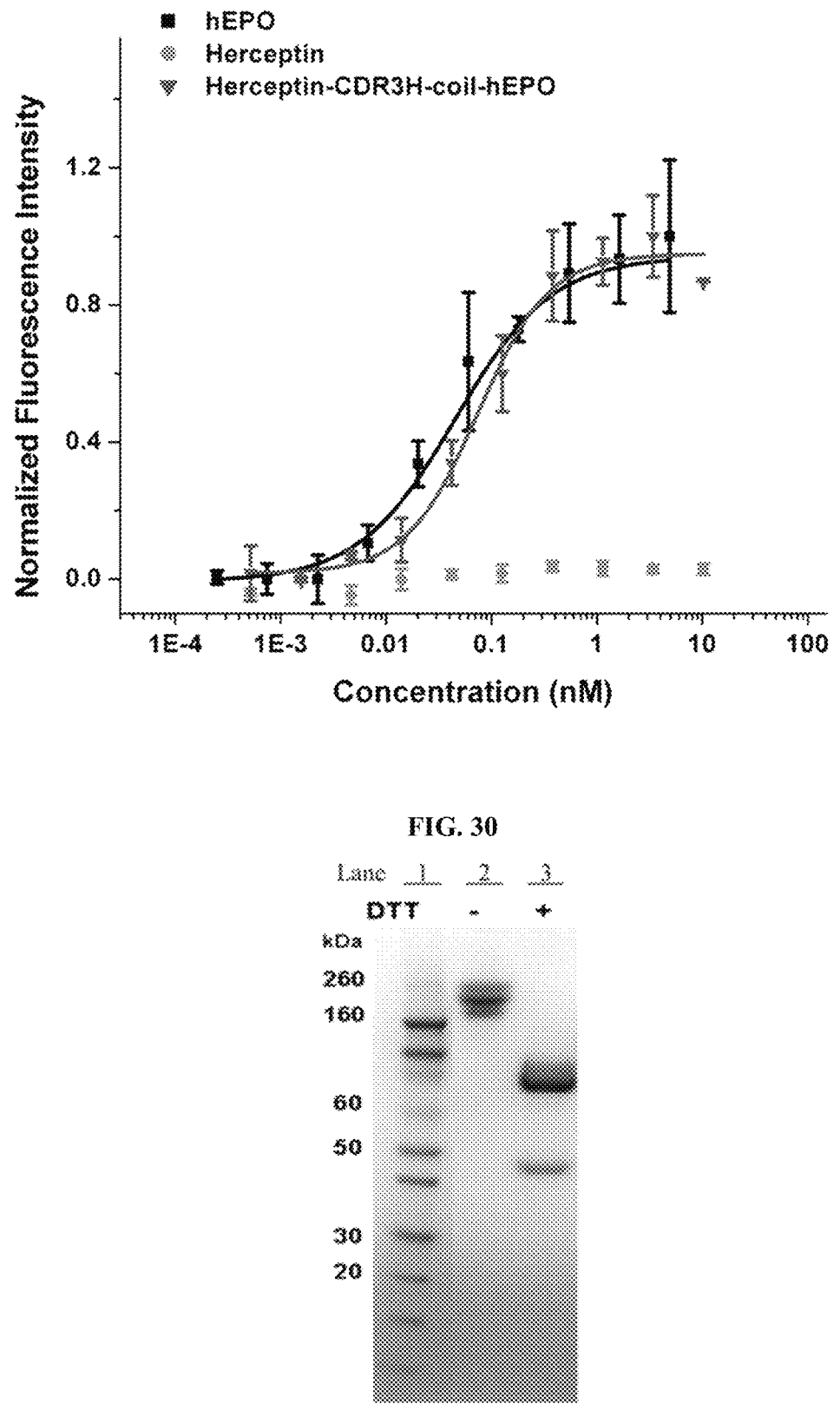

FIG. 29 depicts a graph of the in vitro activity of trastuzumab-coil hEPO (CDRH3) IgG in proliferating human TF-1 cells.

FIG. 30 depicts an SDS-PAGE gel of dual fusion trastuzumab-coil hEPO (CDRH3)-trastuzumab-coil hGCSF (CDRL3) IgG, with and without DTT.

Figure 31A:
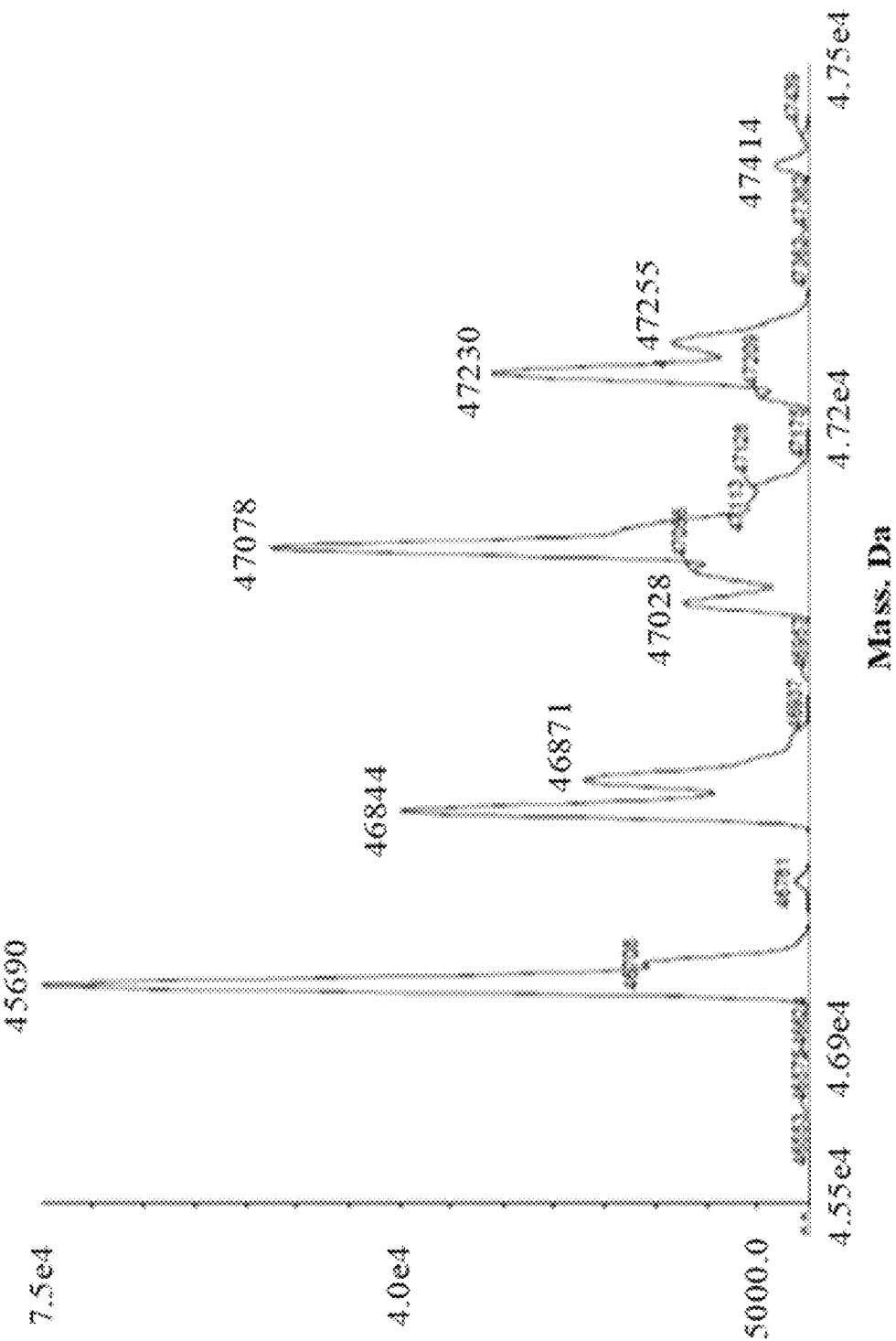
Figure 31B:
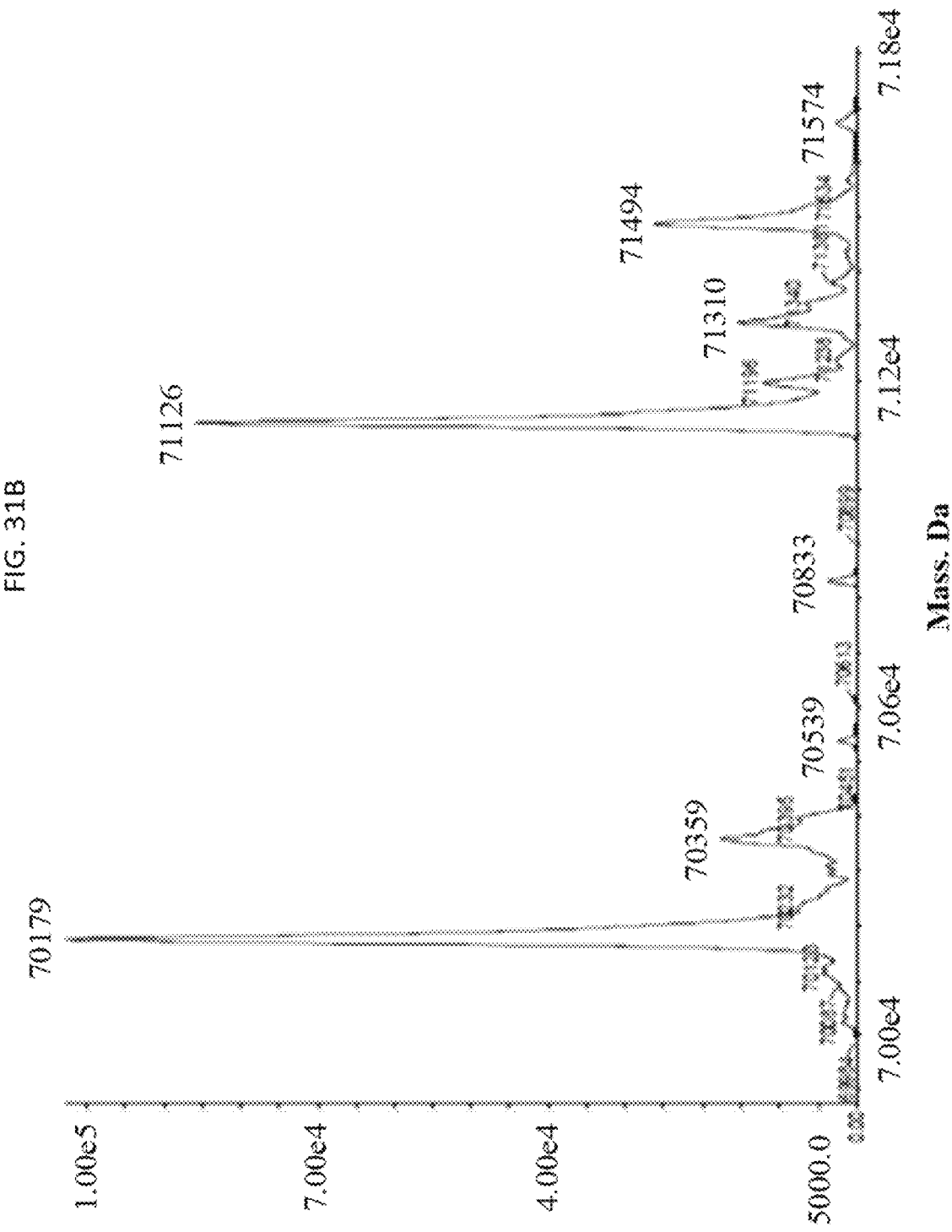

FIG. 31A-FIG. 31B depict an ESI-MS of the light (FIG. 31A) and heavy (FIG. 31B) chains of dual fusion trastuzumab-coil hEPO (CDRH3)-trastuzumab-coil hGCSF (CDRL3) IgG treated with peptide N-glycosidase and DTT.

Figure 32:
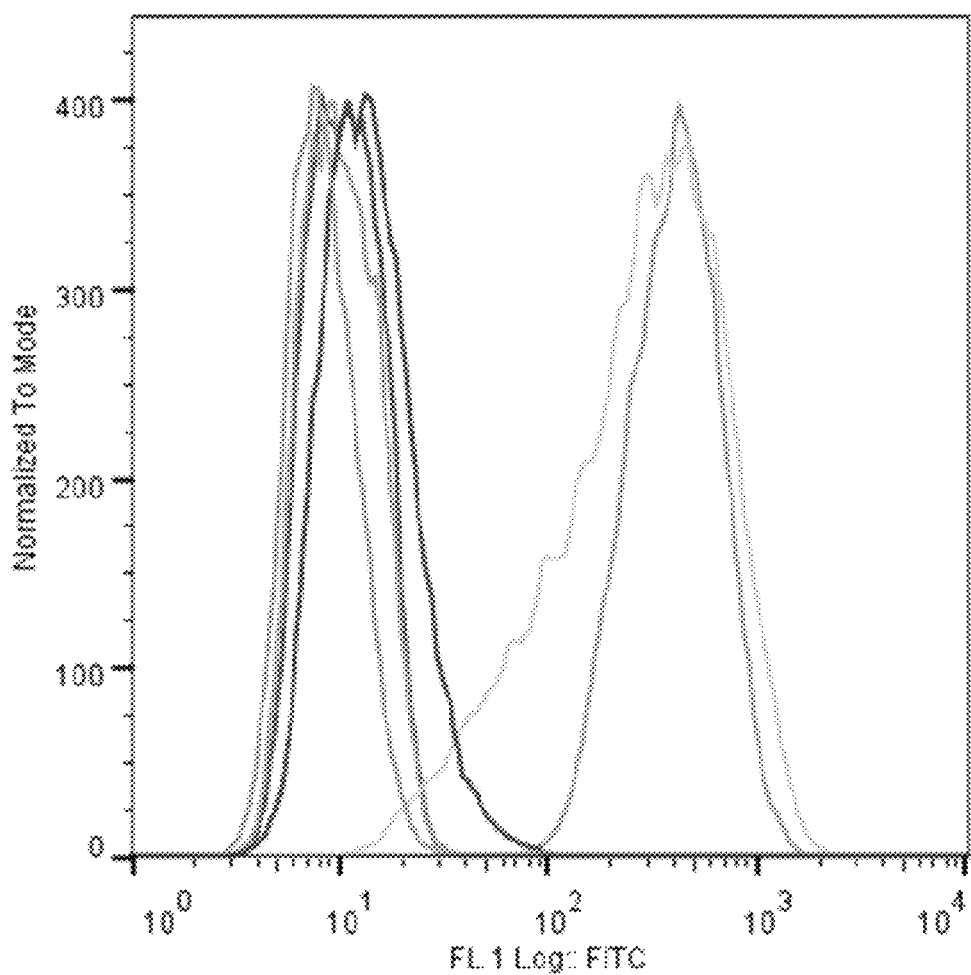

FIG. 32 depicts a histogram of dual fusion trastuzumab-coil hEPO (CDRH3)-trastuzumab-coil hGCSF (CDRL3) IgG binding to HER2 receptor.

Figure 33:
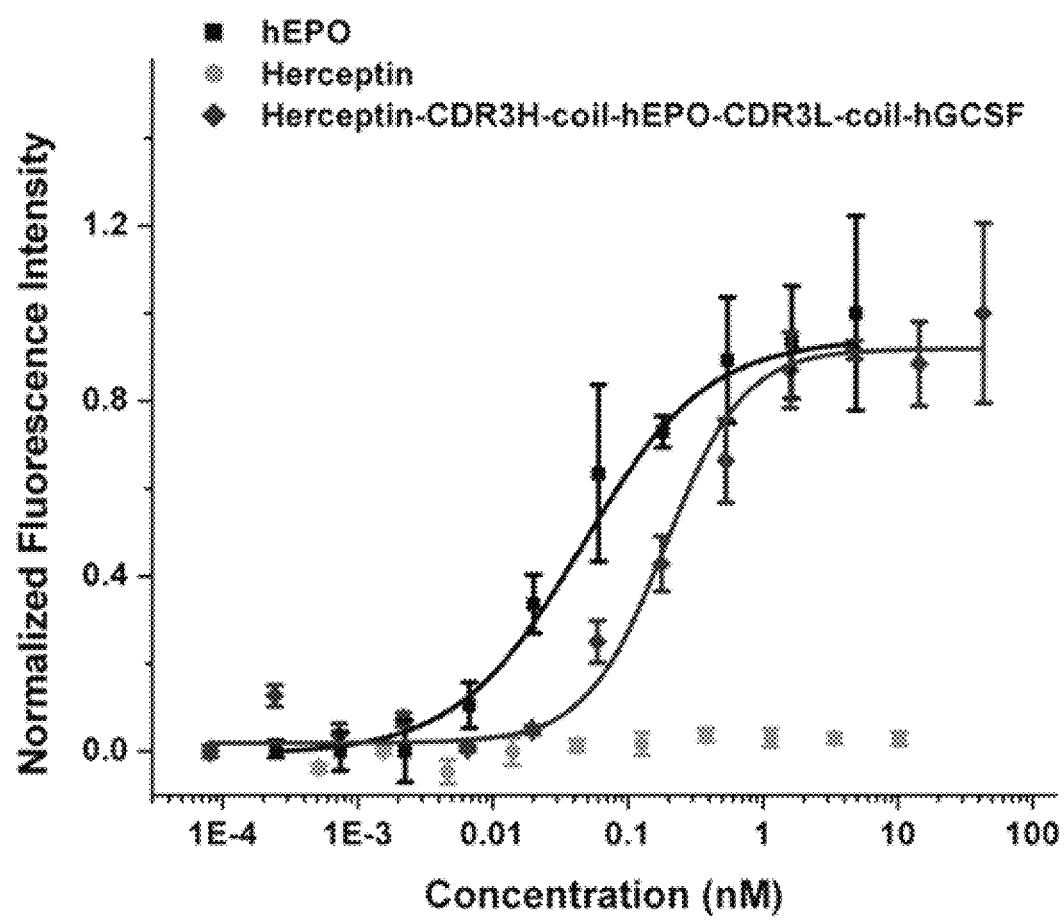

FIG. 33 depicts a graph of the in vitro activity of dual fusion trastuzumab-coil hEPO (CDRH3)-trastuzumab-coil hGCSF (CDRL3) IgG in proliferating human TF-1 cells.

Figure 34:
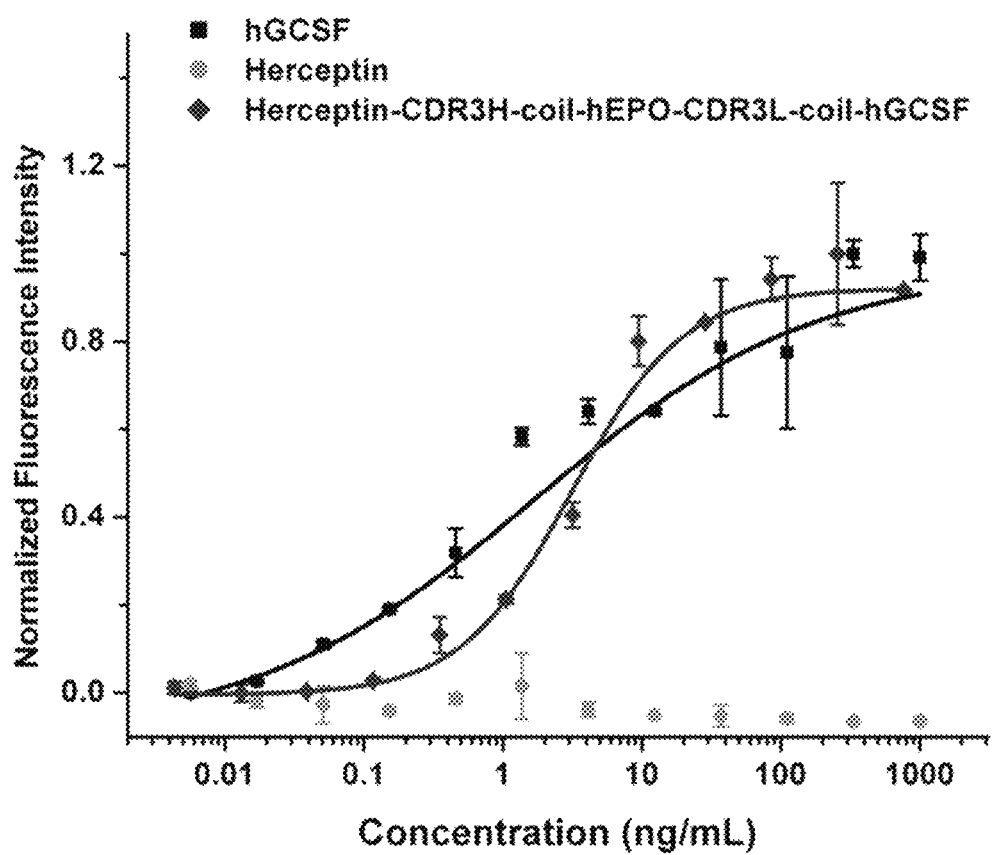

FIG. 34 depicts a graph of the in vitro activity of dual fusion trastuzumab-coil hEPO (CDRH3)-trastuzumab-coil hGCSF (CDRL3) IgG in proliferating mouse NFS-60 cells.

Figure 35:
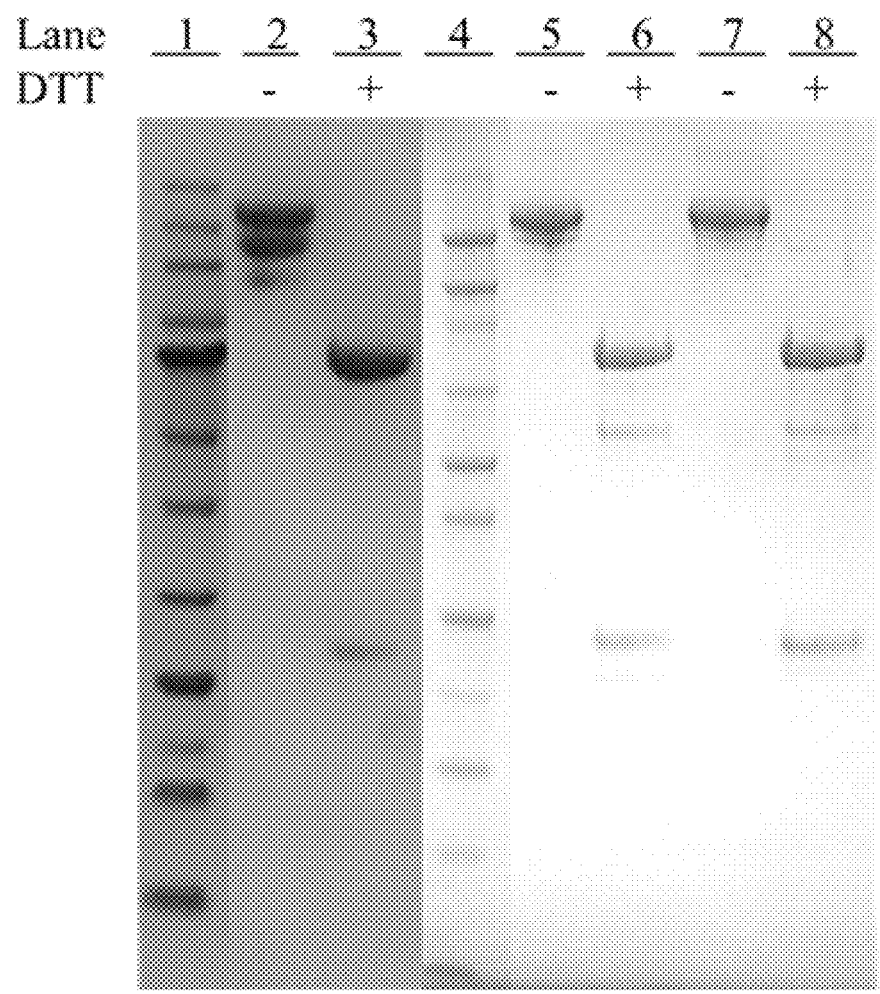

FIG. 35 depicts an SDS-PAGE gel of trastuzumab-coil hGH (CDRH3) IgG after purification, trastuzumab-direct fusion hGH (CDRH2) and trastuzumab-coil hGH (CDRH2) IgGs, with and without DTT.

Figure 36A:
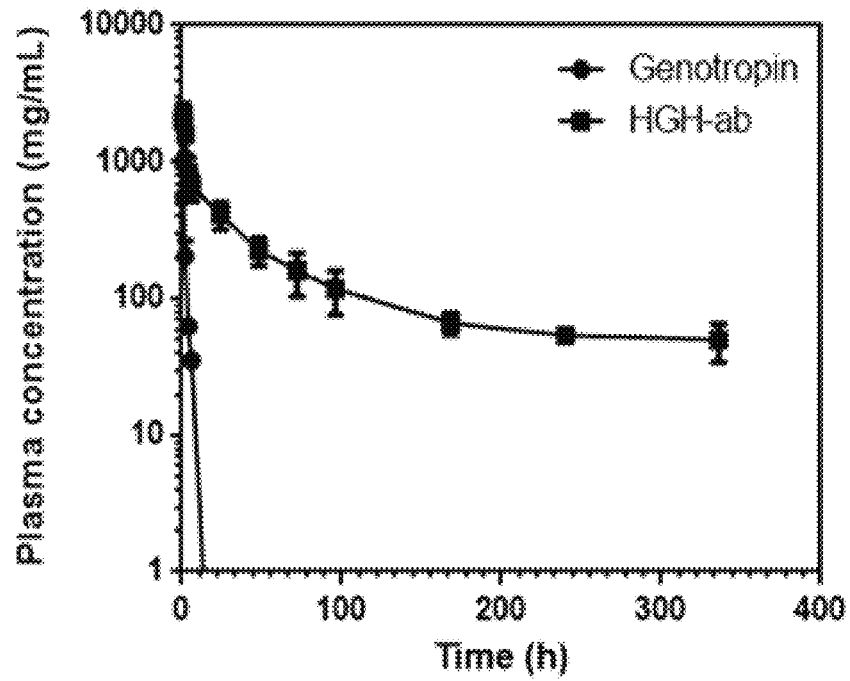
Figure 36B:
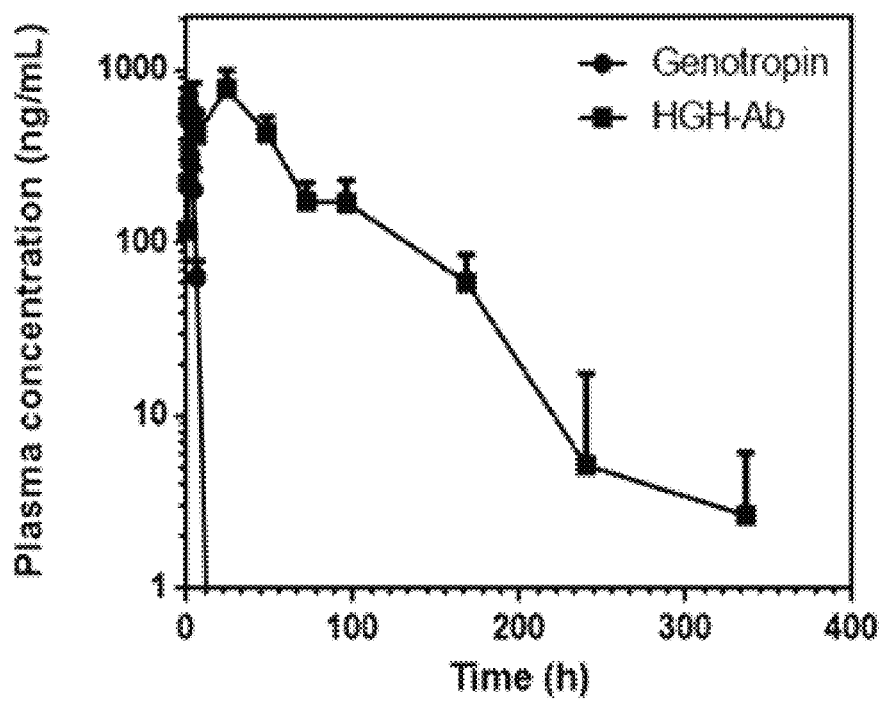

FIG. 36A-FIG. 36B depict the pharmacokinetics of trastuzumab-coil hGH (CDRH3) IgG in rat by (FIG. 36A) intravenous injection and (FIG. 36B) subcutaneous injection.

Figure 37:
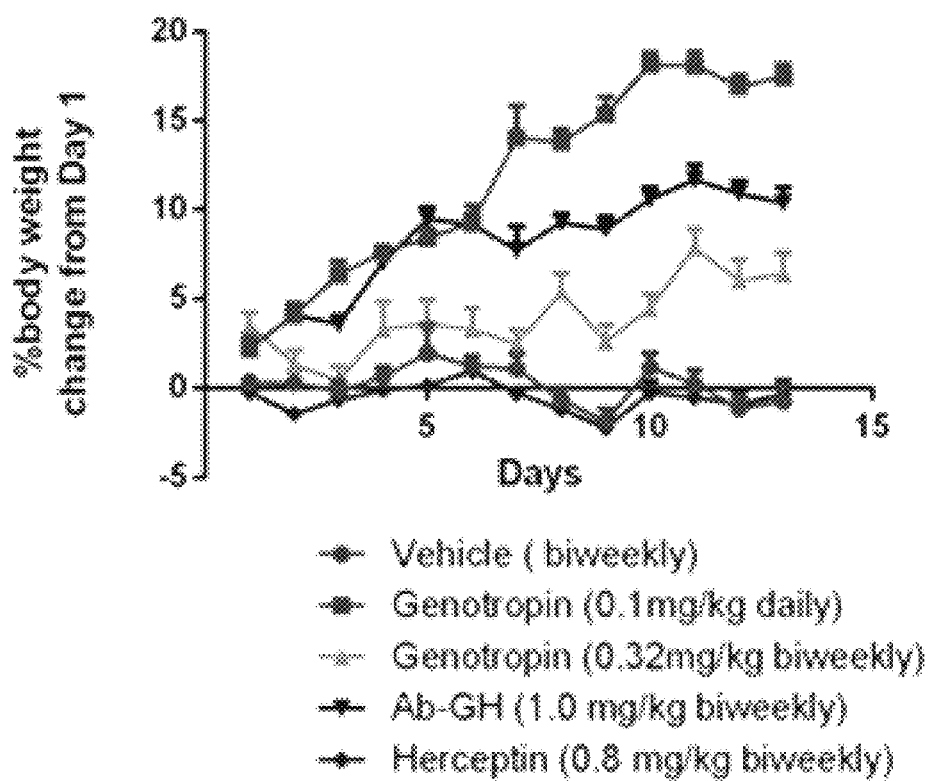

FIG. 37 depicts a graph indicating the percentage of body weight change in rats injected with a vehicle, genotropin, trastuzumab, and trastuzumab-coil hGH (CDRH3) IgG (denoted in the figure as Ab-GH).

Figure 38:
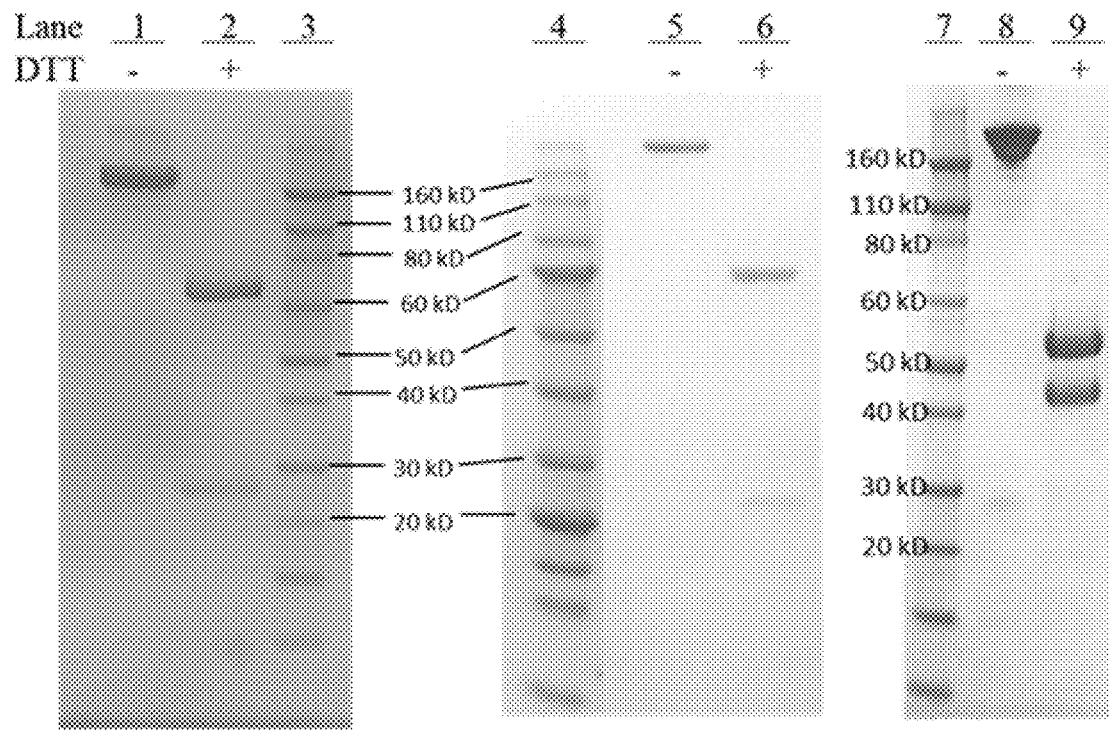

FIG. 38 depicts an SDS-PAGE gel of trastuzumab-coil hLeptin (CDRH2), trastuzumab-coil hLeptin (CDRH3), and trastuzumab-coil hLeptin (CDRL3), with and without DTT.

Figure 39A:
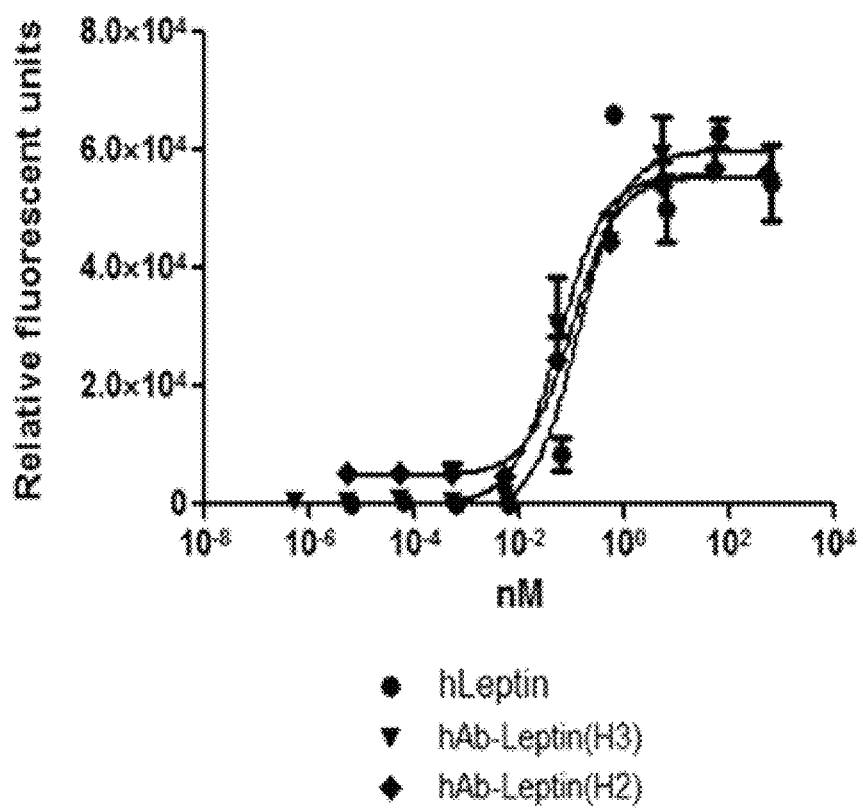

FIG. 39A-FIG. 39B depict graphs of the in vitro activity of (FIG. 39A) hLeptin, trastuzumab-coil hLeptin (CDRH2), trastuzumab-coil hLeptin (CDRH3), and (FIG. 39B) hLeptin, trastuzumab-coil hLeptin (CDRL3) in activating human leptin receptor (LepR).

Figure 40A:
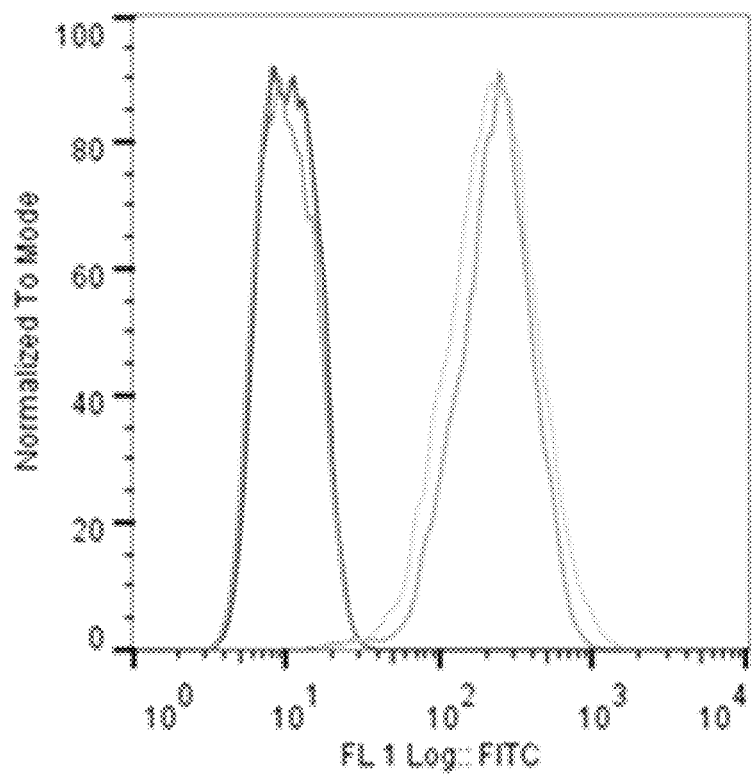
Figure 40B:
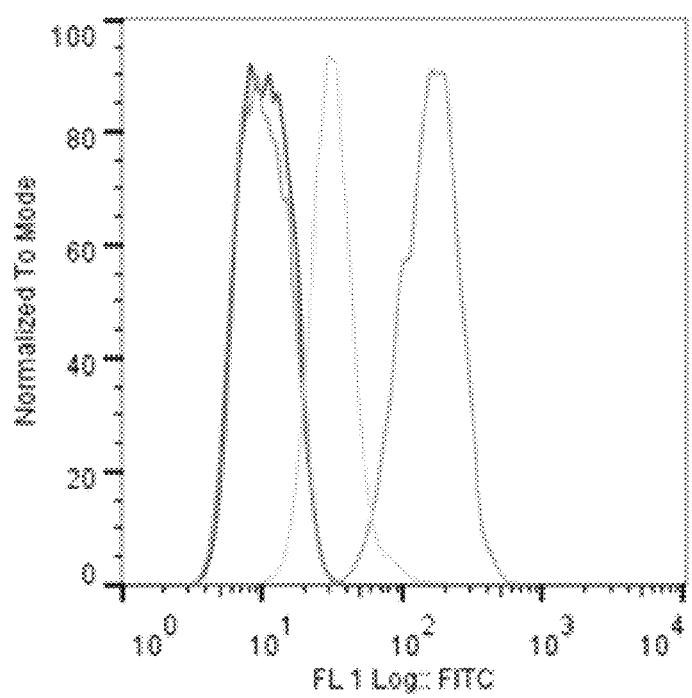
Figure 40C:
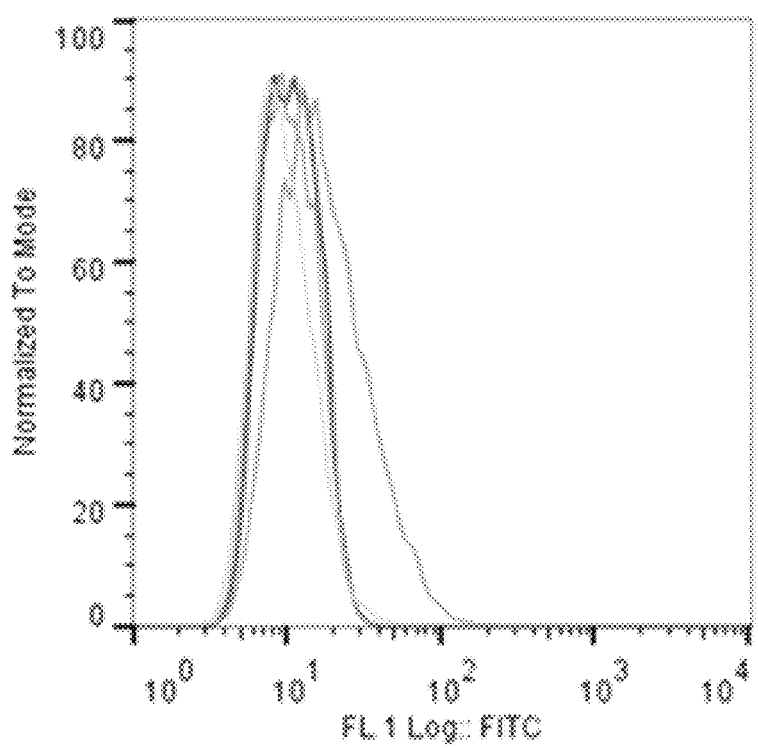

FIG. 40A-FIG. 40C depict histograms of SKBR3 cell binding with (FIG. 40A) wild-type (wt) trastuzumab, (FIG. 40B) trastuzumab-coil hLeptin (CDRH2), and (FIG. 40C) trastuzumab-coil hLeptin (CDRH3).

Figure 41:
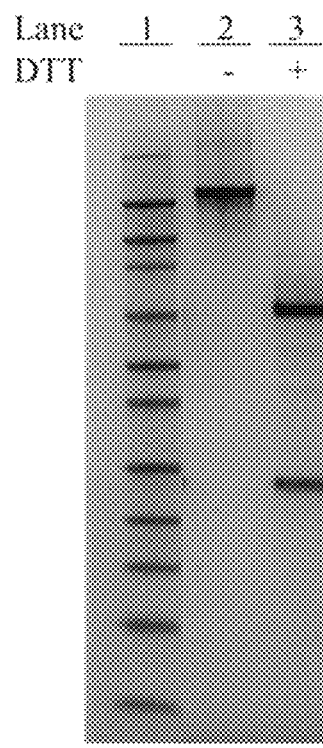

FIG. 41 depicts an SDS-PAGE gel of trastuzumab-coil elafin (CDRH3), with and without DTT.

Figure 42A:
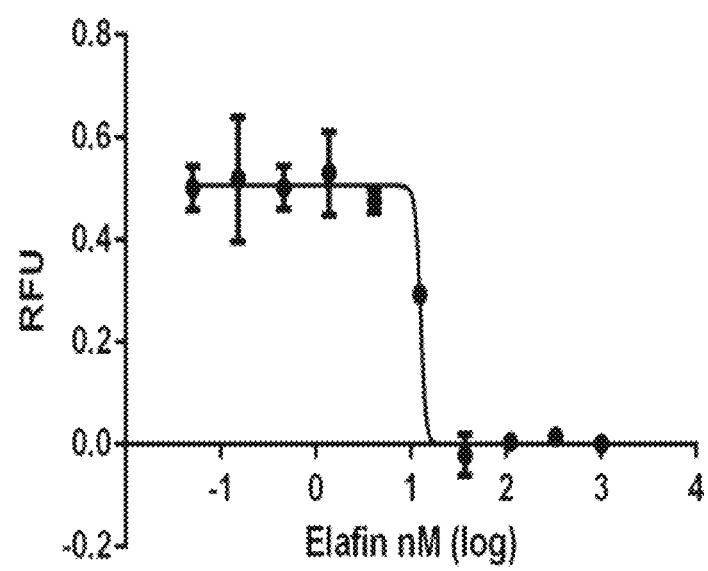
Figure 42B:
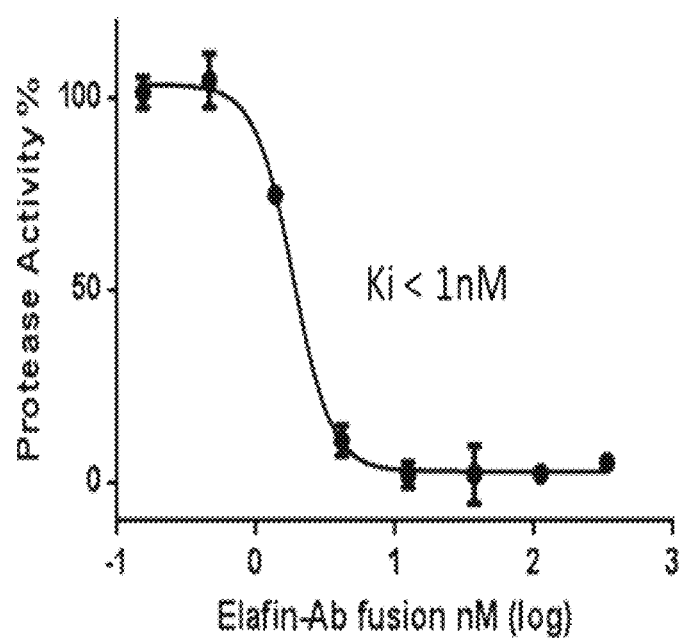

FIG. 42A-FIG. 42B depict graphs of the in vitro inhibition activity of (FIG. 42A) elafin and (FIG. 42B) trastuzumab-coil elafin (CDRH3).

Figure 43:
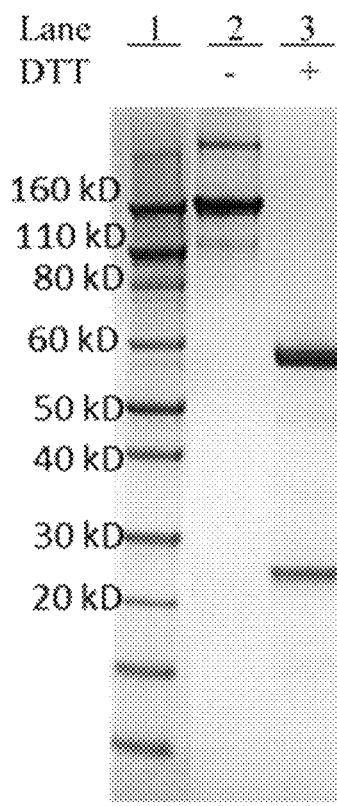

FIG. 43 depicts an SDS-PAGE gel of trastuzumab-coil GLP2 (CDRH3), with and without DTT.

Figure 44:
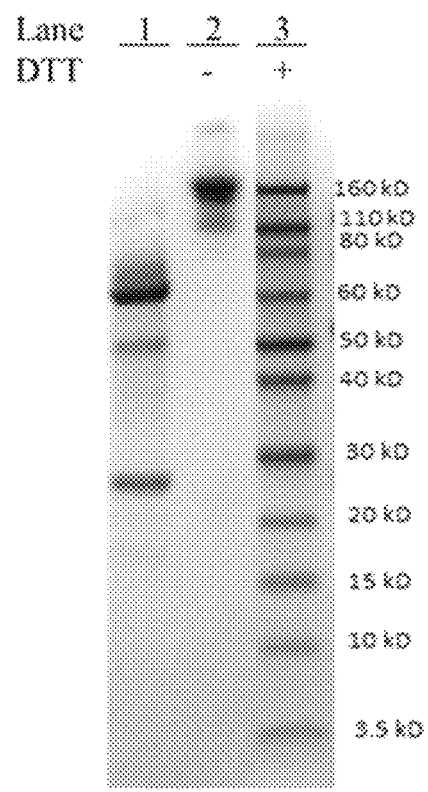

FIG. 44 depicts an SDS-PAGE gel of trastuzumab-coil relaxin (insulin c-peptide) (CDRH3), with and without DTT.

Figure 45:
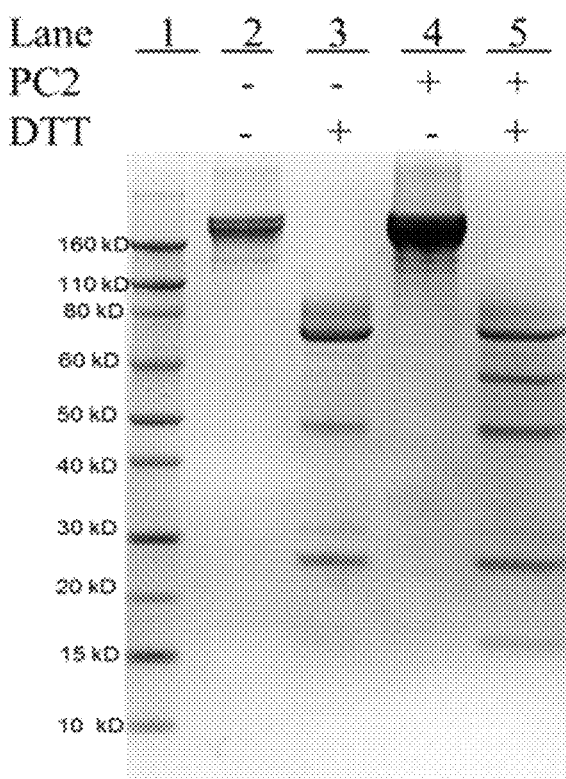

FIG. 45 depicts an SDS-PAGE gel of trastuzumab-coil relaxin (CDRH3) co-transfected with the cleavage enzyme prohormone convertase 2 (PC2), with and without DTT.

Figure 46:
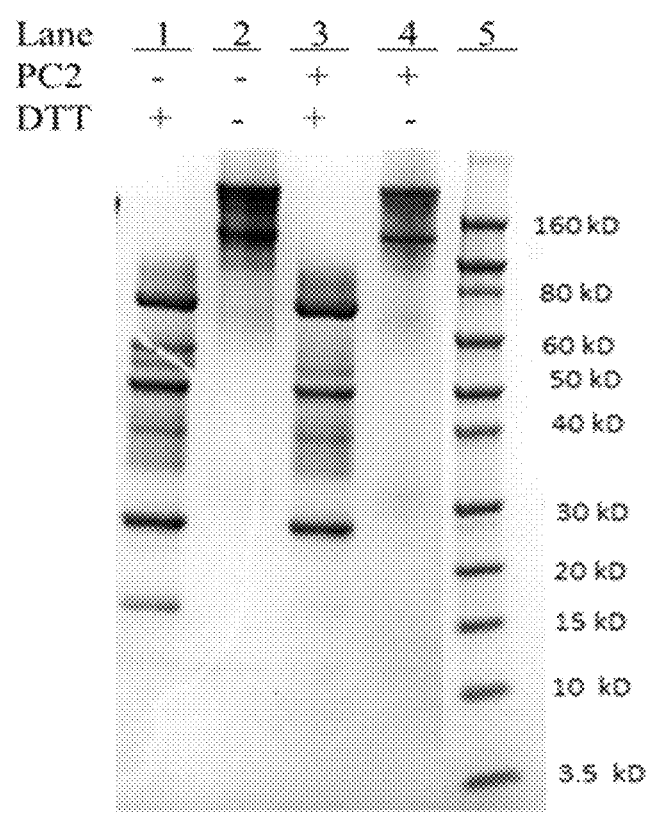

FIG. 46 depicts an SDS-PAGE gel of trastuzumab-coil relaxin (XTEN35) with 6×HIS (SEQ ID NO: 274) (CDRH3) IgG co-transfected with PC2, with and without DTT.

DETAILED DESCRIPTION OF THE INVENTION

Disclosed herein are immunoglobulin fusion proteins and methods of producing such immunoglobulin fusion proteins. Disclosed herein are immunoglobulin fusion proteins comprising an antibody region and a non-antibody region, wherein the non-antibody region comprises: (a) a first extender peptide comprising at least one secondary structure; and (b) a therapeutic agent. The secondary structure may be an alpha helix. In some embodiments, the alpha helix is configured to form a coiled coil. The therapeutic agent may be a therapeutic peptide. The non-antibody region may further comprise a linker. The linker may be a peptide linker. The peptide linker may have no regular secondary structure. The non-antibody region may further comprise a proteolytic cleavage site. In some embodiments, the non-antibody region replaces at least a portion of the antibody region. In some embodiments, the extender peptide connects the therapeutic agent to the antibody region. In some instances, the non-antibody region is connected to a CDR of an antibody. The CDR may be CDR1, CDR2, or CDR3. The CDR may be part of a light chain or a heavy chain. In an exemplary embodiment, the first extender peptide is a connecting peptide or a portion of a connecting peptide. In some embodiments, the peptide linker is a connecting peptide or a portion of a connecting peptide. In some embodiments, the protease cleavage site is a connecting peptide or a portion of a connecting peptide.

Further disclosed herein are immunoglobulin fusion proteins comprising an antibody region and an extender fusion region, wherein the extender fusion region comprises: (a) a first extender peptide, wherein the first extender peptide comprises an amino acid sequence comprising an alpha helix or coiled coil secondary structure, and (b) a therapeutic agent. The therapeutic agent may be a therapeutic peptide. The extender fusion region may further comprise a linker. The linker may be a peptide linker. The peptide linker may have no regular secondary structure. The extender fusion region may further comprise a proteolytic cleavage site. In some embodiments, the extender fusion region replaces at least a portion of the antibody region. In some embodiments, the extender peptide connects the therapeutic agent to the antibody region. In some instances, the extender fusion region is connected to a CDR of an antibody. The CDR may be CDR1, CDR2, or CDR3. The CDR may be part of a light chain or a heavy chain. In an exemplary embodiment, the first extender peptide is a connecting peptide or a portion of a connecting peptide. In some embodiments, the peptide linker is a connecting peptide or a portion of a connecting peptide. In some embodiments, the protease cleavage site is a connecting peptide or a portion of a connecting peptide.

Further disclosed herein are immunoglobulin fusion proteins comprising an antibody region directly attached to a non-antibody region, wherein the non-antibody region comprises a therapeutic agent. These immunoglobulin fusion proteins, in some instances, may be referred to as direct immunoglobulin fusion proteins. In some instances, the therapeutic agent is a therapeutic peptide. In some embodiments, the therapeutic agent is attached to the antibody region without the use of a peptide comprising a secondary structure. In some embodiments, the therapeutic agent replaces at least a portion of the antibody region to which the therapeutic agent is attached. In some embodiments, the therapeutic peptide is attached to the antibody region by one or more linkers comprising no regular secondary structure (e.g., no alpha helices or beta strands). In some embodiments, the linker is a peptide linker. In some embodiments, the immunoglobulin fusion protein further comprises one or more protease cleavage sites. In some embodiments, the therapeutic agent is attached to a CDR of an antibody. The CDR may be CDR1, CDR2, or CDR3. The CDR may be part of a light chain or a heavy chain. In an exemplary embodiment, the peptide linker is a connecting peptide or a portion of a connecting peptide. In some embodiments, the protease cleavage site is a connecting peptide or a portion of a connecting peptide.

Further disclosed herein are immunoglobulin fusion proteins comprising an antibody region directly attached to an extender fusion region, wherein the extender fusion region comprises a therapeutic agent. These immunoglobulin fusion proteins, in some instances, may be referred to as direct immunoglobulin fusion proteins. In some instances, the therapeutic agent is a therapeutic peptide. In some embodiments, the therapeutic agent is attached to the antibody region without the use of a peptide comprising a secondary structure. In some embodiments, the therapeutic agent replaces at least a portion of the antibody region to which the therapeutic agent is attached. In some embodiments, the therapeutic agent is attached to the antibody region by one or more linkers comprising no regular secondary structure (e.g., no alpha helices or beta strands). In some embodiments, the linker is a peptide linker. In some embodiments, the immunoglobulin fusion protein further comprises one or more protease cleavage sites. In some embodiments, the therapeutic agent is attached to a CDR of an antibody. The CDR may be CDR1, CDR2, or CDR3. The CDR may be part of a light chain or a heavy chain. In an exemplary embodiment, the peptide linker is a connecting peptide or a portion of a connecting peptide. In some embodiments, the protease cleavage site is a connecting peptide or a portion of a connecting peptide.

Further disclosed herein are immunoglobulin fusion proteins comprising a first antibody region, a first therapeutic agent, and a first connecting peptide; wherein the first therapeutic agent is attached to the first antibody region by the connecting peptide; and wherein the connecting peptide does not comprise a region having beta strand secondary structure. In an exemplary embodiment, the first therapeutic agent and the first connecting peptide are components of a non-antibody region. In an exemplary embodiment, the first therapeutic agent and the first connecting peptide are components of an extender fusion region. In some embodiments, the connecting peptide comprises one or more extender peptides. In some embodiments, the connecting peptide comprises one or more linking peptides. In some embodiments, the connecting peptide comprises one or more protease cleavage sites. In some embodiments, the first connecting peptide comprises one or more extender peptides and one or more linker peptides. In some embodiments, the first connecting peptide comprises one or more extender peptides, one or more linker peptides, and one or more protease cleavage sites. In some embodiments, the first connecting peptide comprises one or more extender peptides and one or more protease cleavage sites. In some embodiments, the first connecting peptide comprises one or more linker peptides and one or more protease cleavage sites.

Further disclosed herein are immunoglobulin fusion proteins comprising (a) a non-antibody region; and (b) an antibody region, wherein the non-antibody region replaces at least a portion of an antibody from which the antibody region is based on or derived from. The non-antibody region may replace at least a portion of a complementarity determining region. The non-antibody region may replace at least a portion of a variable domain. The non-antibody region may replace at least a portion of a constant domain. The non-antibody region may replace at least a portion of a heavy chain. The non-antibody region may replace at least a portion of a light chain. The non-antibody region may comprise a therapeutic peptide. The non-antibody region may comprise a connecting peptide.

Further disclosed herein are immunoglobulin fusion proteins comprising (a) an extender fusion region; and (b) an antibody region, wherein the extender fusion region replaces at least a portion of an antibody from which the antibody region is based on or derived from. The extender fusion region may replace at least a portion of a complementarity determining region. The extender fusion region may replace at least a portion of a variable domain. The extender fusion region may replace at least a portion of a constant domain. The extender fusion region may replace at least a portion of a heavy chain. The extender fusion region may replace at least a portion of a light chain. The extender fusion may comprise a therapeutic peptide. The extender fusion region may comprise a connecting peptide.

Further disclosed herein are dual fusion proteins comprising two or more therapeutic agents attached to one or more antibody regions or fragments thereof. At least one therapeutic agent may be inserted into or attached to the antibody or fragment thereof. Two or more therapeutic agents may be inserted into or attached to the antibody or fragment thereof. The therapeutic agents may replace at least a portion of the antibody or fragment thereof. In some instances, a dual fusion protein comprises two therapeutic agents attached to a heavy chain. In some instances, a dual fusion protein comprises two therapeutic agents attached to a light chain. In some instances, a dual fusion protein comprises one therapeutic agent attached to a heavy chain and another therapeutic agent attached to a light chain.

In some embodiments, the non-antibody region is an extender fusion region. In some instances, the extender fusion region comprises (a) a first extender peptide comprising at least one secondary structure, and (b) a therapeutic agent. The secondary structure may be an alpha helix. The secondary structure may be configured to form a coiled coil. The therapeutic agent may be a therapeutic peptide. In some embodiments, the non-antibody region comprises a linker. The linker may have no regular secondary structure. In some embodiments, the non-antibody region comprises a protease cleavage site.

In some embodiments, an immunoglobulin fusion protein comprising an extender peptide, wherein the extender peptide forms an alpha helix and may be configured to form a coiled coil, is referred to as a coiled coil immunoglobulin fusion protein. In some embodiments, an immunoglobulin fusion protein which does not comprise an extender peptide having secondary structure is referred to as a direct immunoglobulin fusion protein.

The extender peptide may be based on or derived from an ultralong CDR3. The extender peptide may comprise 7 or fewer amino acids from an ultralong CDR3 sequence. Alternatively, or additionally, the extender peptide does not comprise an amino acid sequence based on or derived from an ultralong CDR3. The extender peptide may comprise one or more secondary structures. The one or more secondary structures may be an alpha helix.

Exemplary immunoglobulin fusion proteins comprising two extender peptides comprising a coiled coil structure (e.g., each extender peptide has an alpha helix secondary structure) are depicted in FIG. 1. As shown in FIG. 1, an antibody region (110) comprising two immunoglobulin heavy chains (115, 120) and two immunoglobulin light chains (125, 130) is attached to a non-antibody region (135) comprising two extender peptides (140, 145) and a therapeutic agent (150) to produce immunoglobulin fusion proteins (160, 170, 180). As shown in FIG. 1, the immunoglobulin fusion protein (160) comprises a non-antibody region attached to one of the immunoglobulin heavy chains of the antibody region. As shown in FIG. 1, the immunoglobulin fusion protein (170) comprises a non-antibody region attached to one of the immunoglobulin light chains of the antibody region. Also shown in FIG. 1, the immunoglobulin fusion protein (180) comprises two non-antibody regions attached two immunoglobulin chains of the antibody region. The two extender peptides may form a coiled coil. The two extender peptides may form anti-parallel coiled coil.

Exemplary direct immunoglobulin fusion proteins in which the non-antibody region/extender fusion region (e.g., therapeutic agent) is directly inserted into the antibody without the aid of an extender peptide having secondary structure are depicted in FIG. 5. As shown in FIG. 5, an antibody region (1010) comprising two immunoglobulin heavy chains (1015, 1020) and two immunoglobulin light chains (1025, 1030) is attached to a non-antibody region (1050) to produce immunoglobulin fusion proteins (1060, 1070, 1080). As shown in FIG. 5, the immunoglobulin fusion protein (1060) comprises a non-antibody region attached to one of the immunoglobulin heavy chains of the antibody region. As shown in FIG. 5, the immunoglobulin fusion protein (1070) comprises a non-antibody region attached to one of the immunoglobulin light chains of the antibody region. Also shown in FIG. 5, the immunoglobulin fusion protein (1080) comprises two non-antibody regions attached two immunoglobulin chains of the antibody region.

Additional exemplary coiled coil immunoglobulin fusion proteins are depicted in FIG. 3. Formula IA of FIG. 3 depicts an immunoglobulin fusion protein comprising an antibody region ($A^1$) attached to an extender fusion region comprising an extender peptide ($E^1$) attached to a therapeutic agent ($T^1$).

Formula IIA of FIG. 3 depicts an immunoglobulin fusion protein comprising an antibody region ($A^1$) attached to an extender fusion region comprising two extender peptides ($E^1$ and $E^2$) attached to a therapeutic agent ($T^1$).

Formula IIIA of FIG. 3 depicts an immunoglobulin dual fusion protein comprising two antibody regions ($A^1$ and $A^2$) attached to each other. The immunoglobulin dual fusion protein may comprise (a) a first antibody region ($A^1$) attached to a first extender fusion region comprising two extender peptides ($E^1$ and $E^2$) attached to a first therapeutic agent ($T^1$); and (b) a second antibody region ($A^2$) attached to a second extender fusion region comprising two extender peptides ($E^3$ and $E^4$) attached to a second therapeutic agent ($T^2$).

Formula IVA of FIG. 3 depicts an immunoglobulin fusion protein comprising an antibody region ($A^1$) attached to an extender fusion region comprising a linker ($L^1$) attached to a therapeutic agent ($T^1$), with the linker and therapeutic agent located between two extender peptides ($E^1$ and $E^2$).

Formula VA of FIG. 3 depicts an immunoglobulin fusion protein comprising an antibody region ($A^1$) attached to an extender fusion region comprising a proteolytic cleavage site ($P^1$) attached to a therapeutic agent ($T^1$), with the proteolytic cleavage site and therapeutic agent located between two extender peptides ($E^1$ and $E^2$). Formula VB of FIG. 3 depicts the clipped version of Formula VA, wherein the proteolytic cleavage site is cleaved by a protease, which results in release of one end of the therapeutic agent. An immunoglobulin fusion protein which may be cleaved to release the amino-terminus of a therapeutic agent is referred to as RN, for released N-terminus. For example, trastuzumab-coil hGH RN indicates that upon proteolytic cleavage, the N-terminus of hGH is released.

Formula VIA of FIG. 3 depicts an immunoglobulin fusion protein comprising an antibody region ($A^1$) attached to an extender fusion region comprising a therapeutic agent ($T^1$) attached to a linker ($L^1$) and a proteolytic cleavage site ($P^1$), which the therapeutic agent, linker and proteolytic cleavage site located between two extender peptides ($E^1$ and $E^2$). Formula VIB of FIG. 3 depicts the clipped version of Formula VIA, wherein the proteolytic cleavage site is cleaved by a protease, which results in release of one end of the therapeutic agent. An immunoglobulin fusion protein which may be cleaved to release the carboxyl-terminus of a therapeutic agent is referred to as RC, for released C-terminus. For example, trastuzumab-coil hGH RC indicates that upon proteolytic cleavage, the C-terminus of hGH is released.

Formula VIIA of FIG. 3 depicts an immunoglobulin dual fusion protein comprising two antibody regions ($A^1$ and $A^2$). The first antibody region ($A^1$) is attached to a first extender fusion region comprising a therapeutic agent ($T^1$) with two linkers ($L^1$ and $L^2$) on each end, with the therapeutic agent and linkers located between two extender peptides ($E^1$ and $E^2$). The second antibody region ($A^2$) is attached to a second extender fusion region comprising a therapeutic agent ($T^2$) attached to a proteolytic cleavage site ($P^1$). The therapeutic agent and proteolytic cleavage site in the second extender fusion region are flanked by two linkers ($L^3$ and $L^4$). The therapeutic agent, proteolytic cleavage site and the two linkers of the second extender region are flanked by two extender peptides ($E^1$ and $E^2$).

Formula VIIIA of FIG. 3 depicts an immunoglobulin fusion protein comprising an antibody region ($A^1$) attached to an extender fusion region comprising two extender peptides ($E^1$ and $E^2$), two linkers ($L^1$ and $L^2$), two proteolytic cleavage sites ($P^1$ and $P^2$) and a therapeutic agent ($T^1$). Formula VIIIB of FIG. 3 depicts the clipped version of Formula VIIIA, wherein the proteolytic cleavage sites located on the N- and C-termini of the therapeutic agent are cleaved by a protease, which results in release of the therapeutic agent from the immunoglobulin fusion protein.

Additional exemplary immunoglobulin fusion proteins without extender peptides (direct immunoglobulin fusion proteins) are depicted in FIG. 9. Formula IXA of FIG. 9 depicts an immunoglobulin fusion protein comprising an antibody region ($A^1$) attached to a non-antibody region comprising a therapeutic agent ($T^1$).

Formula XA of FIG. 9 depicts an immunoglobulin fusion protein comprising an antibody region ($A^1$) attached to a non-antibody region comprising a linker ($L^1$) attached to a therapeutic agent ($T^1$). Formula XIA of FIG. 9 depicts an immunoglobulin dual fusion protein comprising two antibody regions ($A^1$ and $A^2$) attached to each other. The immunoglobulin dual fusion protein may comprise (a) a first antibody region ($A^1$) attached to a first non-antibody region comprising a first therapeutic agent ($T^1$); and (b) a second antibody region ($A^2$) attached to a second non-antibody region comprising a second therapeutic agent ($T^2$).

Formula XIIA of FIG. 9 depicts an immunoglobulin fusion protein comprising an antibody region ($A^1$) attached to a non-antibody region comprising a linker ($L^1$), a proteolytic cleavage site ($P^1$) and a therapeutic agent ($T^1$), wherein the proteolytic cleavage site is located between the linker and the therapeutic agent. The proteolytic cleavage site in the second non-antibody region has been cleaved by a protease, resulting in release of one end of the second therapeutic agent.

Formula XIIIA of FIG. 9 depicts an immunoglobulin fusion protein comprising an antibody region ($A^1$) attached to a non-antibody region comprising a proteolytic cleavage site ($P^1$) attached to a therapeutic agent ($T^1$). Formula XIIIB of FIG. 9 depicts the clipped version of Formula XIIIA, wherein the proteolytic cleavage site is cleaved by a protease, which results in release of one end of the therapeutic agent.

Formula XIVA of FIG. 9 depicts an immunoglobulin fusion protein comprising an antibody region ($A^1$) attached to a non-antibody region comprising a linker ($L^1$), a therapeutic agent ($T^1$), and a proteolytic cleavage site ($P^1$), wherein the therapeutic agent is located between the linker and the proteolytic cleavage site. Formula XIVB of FIG. 9 depicts the clipped version of Formula XIVA, wherein the proteolytic cleavage site is cleaved by a protease, which results in release of one end of the therapeutic agent.

Formula XVA of FIG. 9 depicts an immunoglobulin dual fusion protein comprising two antibody regions ($A^1$ and $A^2$). The first antibody region ($A^1$) is attached to a first non-antibody region comprising a therapeutic agent ($T^1$) with two linkers ($L^1$ and $L^2$) on each end. The second antibody region ($A^2$) is attached to a second non-antibody region comprising a second therapeutic agent ($T^2$) attached to a proteolytic cleavage site ($P^1$). The therapeutic agent and proteolytic cleavage site in the second non-antibody region are flanked by two linkers ($L^3$ and $L^4$). The proteolytic cleavage site in the second non-antibody region has been cleaved by a protease, resulting in release of one end of the second therapeutic agent.

Formula XVIA of FIG. 9 depicts an immunoglobulin fusion protein comprising an antibody region ($A^1$) attached to a non-antibody region comprising two linkers ($L^1$ and $L^2$), two proteolytic cleavage sites ($P^1$ and $P^2$) and a therapeutic agent ($T^1$). Formula XVIB of FIG. 9 depicts the clipped version of Formula XVIA, wherein the proteolytic cleavage sites located on the N- and C-termini of the therapeutic agent are cleaved by a protease, which results in release of the therapeutic agent from the immunoglobulin fusion protein Further disclosed herein are methods of treating a disease or condition in a subject in need thereof. The method may comprise administering to the subject an immunoglobulin fusion protein comprising an antibody region attached to an extender fusion region, wherein the extender fusion region comprises (a) an extender peptide and (b) a therapeutic agent, and wherein the extender peptide does not have secondary structure comprising a beta strand. The method may comprise administering to the subject an immunoglobulin fusion protein comprising an antibody region attached to non-immunoglobulin region, wherein the non-immunoglobulin region comprises (a) an extender peptide and (b) a therapeutic agent, and wherein the extender peptide does not have secondary structure comprising a beta strand. The method may comprise administering to the subject a direct immunoglobulin fusion protein comprising an antibody region attached to an extender fusion region, wherein the extender fusion region comprises a therapeutic agent, and wherein the therapeutic agent is attached to the antibody region without using an extender peptide or linking peptide having secondary structure. The method may comprise administering to the subject an immunoglobulin fusion protein comprising an antibody region attached to non-immunoglobulin region, wherein the non-immunoglobulin region comprises a therapeutic agent, and wherein the therapeutic agent is attached to the antibody region without using an extender peptide or linking peptide having secondary structure. The method may comprise administering to the subject an immunoglobulin fusion protein comprising an antibody region attached to a therapeutic peptide via a connecting peptide.

Further disclosed herein are methods of extending the half-life of a therapeutic agent. The method may comprise attaching a therapeutic agent to an antibody region. The method may comprise attaching a therapeutic agent to an antibody region using one or more linker peptides having no regular secondary structure. The method may comprise attaching a therapeutic agent to an antibody region using one or more protease cleavage sites. The method may comprise attaching a therapeutic agent to an extender fusion peptide. The method may comprise attaching a therapeutic agent to an antibody region using an extender fusion peptide. The method may comprise attaching a therapeutic agent to a connecting peptide. The method may comprise attaching a therapeutic agent to an antibody region using a connecting peptide.

Further disclosed herein are methods of extending the half-life of a therapeutic agent. The method may comprise attaching an antibody region to the therapeutic agent to produce an immunoglobulin fusion protein. The method may further comprise attaching one or more linkers or proteolytic cleavage sites to the immunoglobulin fusion protein. The one or more linkers may be attached to an N- and/or C-terminus of the therapeutic agent. The one or more proteolytic cleavage sites may be attached to an N- and/or C-terminus of the therapeutic agent. The one or more proteolytic cleavage sites may be inserted into the therapeutic agent.

Further disclosed herein are methods of improving the delivery of a therapeutic agent. The method may comprise attaching an extender peptide to a therapeutic agent. The method may further comprise attaching an antibody region to the extender peptide, therapeutic agent, or extender fusion peptide. The method may comprise attaching a therapeutic peptide directly to an antibody region. The method may comprise attaching a connecting peptide to a therapeutic agent. The method may further comprise attaching an antibody region to the connecting peptide and therapeutic agent.

Further disclosed herein are methods of improving the delivery of a therapeutic agent. The method may comprise attaching an antibody region to a therapeutic agent to produce an immunoglobulin fusion protein. The method may further comprise attaching one or more linkers or proteolytic cleavage sites to the immunoglobulin fusion protein. The one or more linkers may be attached to an N- and/or C-terminus of the therapeutic agent. The one or more proteolytic cleavage sites may be attached to an N- and/or C-terminus of the therapeutic agent. The one or more proteolytic cleavage sites may be inserted into the therapeutic agent.

Before the present methods and compositions are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims. Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The terms "homologous," "homology," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

As used herein, an amino acid sequence that is based on another amino acid sequence comprises one or more consecutive amino acid portions of the another amino acid sequence. Consecutive amino acid portions include any number of amino acids in the another amino acid sequence. Consecutive amino acids may be 1-10%, 1-20%, 10-20%, 10-30%, 20-30%, 20-40%, 30-40%, 40-50%, 50-60%, 50-100%, 60-70%, 60-100%, 70-100%, 80-100%, 80-90%, 90-95%, 90-100%, or 1-100% identical to any consecutive amino acid region in the another amino acid sequence.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Immunoglobulin Fusion Proteins

The immunoglobulin fusion proteins disclosed herein may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. The mammalian antibody may be a murine antibody. The mammalian antibody may be a non-human primate antibody.

The immunoglobulin fusion proteins disclosed herein may comprise a therapeutic agent, wherein the therapeutic agent is a functional peptide. The immunoglobulin fusion protein may comprise a functional peptide grafted into an antibody scaffold. The functional peptide may be a linear peptide. The functional peptide may be a modified cyclic peptide. The functional peptide may comprise a peptide modified to comprise a β-hairpin structure. The β-hairpin structure may be locked into a β-hairpin conformation by one or more bonds between two or more amino acid residues of the β-hairpin structure. The N terminus and/or the C terminus of the functional peptide may be grafted to the extender fusion region of the immunoglobulin fusion protein. The N terminus of the functional peptide may be grafted to a first extender peptide of the extender fusion region and the C terminus of the functional peptide may be grafted to a second extender peptide of the extender fusion region. The functional peptide may comprise a peptide modified to comprise a conformationally constrained peptide. A conformationally constrained peptide may have a greatly improved binding affinity and/or specificity to a target relative to an endogenous or naturally-occurring binding partner of the target. An endogenous or naturally-occurring binding partner of the target may be a ligand or substrate of the target. By non-limiting example, the conformationally constrained peptide may be a peptide comprising a β-hairpin structure. The conformationally constrained peptide may comprise a region that binds to a binding site of a target. The target may be a receptor. The target may be an enzyme. The binding site of the target may be a deep pocket of a ligand binding domain or substrate binding domain. The functional peptide or portion thereof may bind the deep pocket of a ligand binding domain or substrate binding domain such that it blocks a target ligand and/or substrate from binding. The functional peptide or portion thereof may bind the deep pocket of a ligand binding domain or substrate binding domain such that it partially blocks the target ligand and/or substrate from binding. The functional peptide or portion thereof may bind the deep pocket of a ligand binding domain or substrate binding domain such that it completely blocks the target ligand or substrate from binding. The functional peptide or portion thereof may bind the surface of the ligand binding domain or substrate binding domain. The functional peptide may be an agonist. The functional peptide may be an antagonist. The functional peptide may be an inhibitor. The functional peptide may be a ligand. The functional peptide may be a substrate.

The immunoglobulin fusion protein may comprise an amino acid sequence that is based on or derived from any one of SEQ ID NOs: 68-99, and 122-143. The immunoglobulin fusion protein may comprise an amino acid sequence that is at least about 50% homologous to any one of SEQ ID NOs: 68-99, and 122-143. The immunoglobulin fusion protein may comprise an amino acid sequence that is at least about 60%, 65%, 70%, 75%, 80%, 85%, 90%, 95%, or 97% homologous to any one of SEQ ID NOs: 68-99, and 122-143. The immunoglobulin fusion protein may comprise an amino acid sequence that is at least about 70% homologous to any one of SEQ ID NOs: 68-99, and 122-143. The immunoglobulin fusion protein may comprise an amino acid sequence that is at least about 80% homologous to any one of SEQ ID NOs: 68-99, and 122-143.

The immunoglobulin fusion protein may comprise an amino acid sequence comprising 10, 20, 30, 40, 50, 60, 70, 80, 90, 100 or more amino acids based on or derived from any one of SEQ ID NOs: 68-99, and 122-143. The immunoglobulin fusion protein may comprise an amino acid sequence comprising 125, 150, 175, 200, 225, 250, 275, 300, 325, 350, 375, 400, 425, 450, 475, 450, 500 or more amino acids based on or derived from any one of SEQ ID NOs: 68-99, and 122-143. The immunoglobulin fusion protein may comprise an amino acid sequence comprising 10 or more amino acids based on or derived from any one of SEQ ID NOs: 68-99, and 122-143. The immunoglobulin fusion protein may comprise an amino acid sequence comprising 50 or more amino acids based on or derived from any one of SEQ ID NOs: 68-99, and 122-143. The immunoglobulin fusion protein may comprise an amino acid sequence comprising 100 or more amino acids based on or derived from any one of SEQ ID NOs: 68-99, and 122-143. The immunoglobulin fusion protein may comprise an amino acid sequence comprising 200 or more amino acids based on or derived from any one of SEQ ID NOs: 68-99, and 122-143.

The amino acids may be consecutive. Alternatively, or additionally, the amino acids are nonconsecutive.

The immunoglobulin fusion protein may be encoded by a nucleotide sequence that is based on or derived from any one of SEQ ID NOs: 37-67, and 100-121. The immunoglobulin fusion protein may be encoded by a nucleotide sequence that is at least about 50% homologous to any one of SEQ ID NOs: 37-67, and 100-121. The immunoglobulin fusion protein may be encoded by a nucleotide sequence that is at least about 60%, 65%, 70%, 75%, 80%, 85%, 90%, 95%, or 97% homologous to any one of SEQ ID NOs: 37-67, and 100-121. The immunoglobulin fusion protein may be encoded by a nucleotide sequence that is at least about 70% homologous to any one of SEQ ID NOs: 37-67, and 100-121. The immunoglobulin fusion protein may be encoded by a nucleotide sequence that is at least about 80% homologous to any one of SEQ ID NOs: 37-67, and 100-121.

The immunoglobulin fusion protein may be encoded by a nucleotide sequence comprising 10, 20, 30, 40, 50, 60, 70, 80, 90, 100 or more nucleotides based on or derived from any one of SEQ ID NOs: 37-67, and 100-121. The immunoglobulin fusion protein may be encoded by a nucleotide sequence comprising 125, 150, 175, 200, 225, 250, 275, 300, 325, 350, 375, 400, 425, 450, 475, 450, 500 or more nucleotides based on or derived from any one of SEQ ID NOs: 37-67, and 100-121. The immunoglobulin fusion protein may be encoded by a nucleotide sequence comprising 600, 650, 700, 750, 800, 850, 900, 950, 1000 or more nucleotides based on or derived from any one of SEQ ID NOs: 37-67, and 100-121. The immunoglobulin fusion protein may be encoded by a nucleotide sequence comprising 1100, 1200, 1300, 1400, 1500 or more nucleotides based on or derived from any one of SEQ ID NOs: 37-67, and 100-121. The immunoglobulin fusion protein may be encoded by a nucleotide sequence comprising 100 or more nucleotides based on or derived from any one of SEQ ID NOs: 37-67, and 100-121. The immunoglobulin fusion protein may be encoded by a nucleotide sequence comprising 500 or more nucleotides based on or derived from any one of SEQ ID NOs: 37-67, and 100-121. The immunoglobulin fusion protein may be encoded by a nucleotide sequence comprising 1000 or more nucleotides based on or derived from any one of SEQ ID NOs: 37-67, and 100-121. The immunoglobulin fusion protein may be encoded by a nucleotide sequence comprising 1300 or more nucleotides based on or derived from any one of SEQ ID NOs: 37-67, and 100-121. The nucleotides may be consecutive. Alternatively, or additionally, the nucleotides are nonconsecutive.

The immunoglobulin fusion protein may further comprise one or more immunoglobulin light chains. The immunoglobulin fusion protein may comprise at least two immunoglobulin light chains. The immunoglobulin light chain may comprise one or more portions of an immunoglobulin light chain. The immunoglobulin light chain may be an immunoglobulin fusion light chain. The immunoglobulin fusion light chain comprises an antibody region derived from an immunoglobulin light chain and a therapeutic agent. The therapeutic agent may be attached to the antibody region by one or more connecting peptides. The immunoglobulin light chain may comprise an amino acid sequence that is based on or derived from any one of SEQ ID NOs: 19-21, 28, 36, 68, 80, 94, 98, and 122. The immunoglobulin light chain may comprise an amino acid sequence that is at least about 50% homologous to any one of SEQ ID NOs: 19-21, 28, 36, 68, 80, 94, 98, and 122. The immunoglobulin light chain may comprise an amino acid sequence that is at least about 60%, 65%, 70%, 75%, 80%, 85%, 90%, 95%, or 97% homologous to any one of SEQ ID NOs: 19-21, 28, 36, 68, 80, 94, 98, and 122. The immunoglobulin light chain may comprise an amino acid sequence that is at least about 70% homologous to any one of SEQ ID NOs: 19-21, 28, 36, 68, 80, 94, 98, and 122. The immunoglobulin light chain may comprise an amino acid sequence that is at least about 80% homologous to any one of SEQ ID NOs: 19-21, 28, 36, 68, 80, 94, 98, and 122.

The immunoglobulin light chain may comprise an amino acid sequence comprising 10, 20, 30, 40, 50, 60, 70, 80, 90, 100 or more amino acids based on or derived from any one of SEQ ID NOs: 19-21, 28, 36, 68, 80, 94, 98, and 122. The immunoglobulin light chain may comprise an amino acid sequence comprising 125, 150, 175, 200, 225, 250, 275, 300, 325, 350, 375, 400, 425, 450, 475, 450, 500 or more amino acids based on or derived from any one of SEQ ID NOs: 19-21, 28, 36, 68, 80, 94, 98, and 122. The immunoglobulin light chain may comprise an amino acid sequence comprising 10 or more amino acids based on or derived from any one of SEQ ID NOs: 19-21, 28, 36, 68, 80, 94, 98, and 122. The immunoglobulin light chain may comprise an amino acid sequence comprising 50 or more amino acids based on or derived from any one of SEQ ID NOs: 19-21, 28, 36, 68, 80, 94, 98, and 122. The immunoglobulin light chain may comprise an amino acid sequence comprising 100 or more amino acids based on or derived from any one of SEQ ID NOs: 19-21, 28, 36, 68, 80, 94, 98, and 122. The immunoglobulin light chain may comprise an amino acid sequence comprising 200 or more amino acids based on or derived from any one of SEQ ID NOs: 19-21, 28, 36, 68, 80, 94, 98, and 122. The amino acids may be consecutive. Alternatively, or additionally, the amino acids are nonconsecutive.

The immunoglobulin light chain may be encoded by a nucleotide sequence that is based on or derived from any one of SEQ ID NOs: 1-3, 10, 18, 37, 49, 63, 67, and 100. The immunoglobulin light chain may be encoded by a nucleotide sequence that is at least about 50% homologous to any one of SEQ ID NOs: 1-3, 10, 18, 37, 49, 63, 67, and 100. The immunoglobulin light chain may be encoded by a nucleotide sequence that is at least about 60%, 65%, 70%, 75%, 80%, 85%, 90%, 95%, or 97% homologous to any one of SEQ ID NOs: 1-3, 10, 18, 37, 49, 63, 67, and 100. The immunoglobulin light chain may be encoded by a nucleotide sequence that is at least about 70% homologous to any one of SEQ ID NOs: 1-3, 10, 18, 37, 49, 63, 67, and 100. The immunoglobulin light chain may be encoded by a nucleotide sequence that is at least about 80% homologous to any one of SEQ ID NOs: 1-3, 10, 18, 37, 49, 63, 67, and 100.

The immunoglobulin light chain may be encoded by a nucleotide sequence comprising 10, 20, 30, 40, 50, 60, 70, 80, 90, 100 or more nucleotides based on or derived from any one of SEQ ID NOs: 1-3, 10, 18, 37, 49, 63, 67, and 100. The immunoglobulin light chain may be encoded by a nucleotide sequence comprising 125, 150, 175, 200, 225, 250, 275, 300, 325, 350, 375, 400, 425, 450, 475, 450, 500 or more nucleotides based on or derived from any one of SEQ ID NOs: 1-3, 10, 18, 37, 49, 63, 67, and 100. The immunoglobulin light chain may be encoded by a nucleotide sequence comprising 600, 650, 700, 750, 800, 850, 900, 950, 1000 or more nucleotides based on or derived from any one of SEQ ID NOs: 1-3, 10, 18, 37, 49, 63, 67, and 100. The immunoglobulin light chain may be encoded by a nucleotide sequence comprising 1100, 1200, 1300, 1400, 1500 or more nucleotides based on or derived from any one of SEQ ID NOs: 1-3, 10, 18, 37, 49, 63, 67, and 100. The immunoglobulin light chain may be encoded by a nucleotide sequence comprising 100 or more nucleotides based on or derived from any one of SEQ ID NOs: 1-3, 10, 18, 37, 49, 63, 67, and 100. The immunoglobulin light chain may be encoded by a nucleotide sequence comprising 500 or more nucleotides based on or derived from any one of SEQ ID NOs: 1-3, 10, 18, 37, 49, 63, 67, and 100. The immunoglobulin light chain may be encoded by a nucleotide sequence comprising 1000 or more nucleotides based on or derived from any one of SEQ ID NOs: 1-3, 10, 18, 37, 49, 63, 67, and 100. The immunoglobulin light chain may be encoded by a nucleotide sequence comprising 1300 or more nucleotides based on or derived from any one of SEQ ID NOs: 1-3, 10, 18, 37, 49, 63, 67, and 100. The nucleotides may be consecutive. Alternatively, or additionally, the nucleotides are nonconsecutive.

The immunoglobulin fusion protein may further comprise one or more immunoglobulin heavy chains. The immunoglobulin fusion protein may comprise at least two immunoglobulin heavy chains. The immunoglobulin heavy chain may comprise one or more portions of an immunoglobulin heavy chain. The immunoglobulin heavy chain may be an immunoglobulin fusion heavy chain. The immunoglobulin fusion heavy chain comprises an antibody region derived from an immunoglobulin heavy chain and a therapeutic agent. The therapeutic agent may be attached to the antibody region by one or more connecting peptides. The immunoglobulin heavy chain may comprise an amino acid sequence that is based on or derived from any one of SEQ ID NOs: 22-27, 29-35, 69-79, 81-93, 95-97, 99, and 123-143. The immunoglobulin heavy chain may comprise an amino acid sequence that is at least about 50% homologous to any one of SEQ ID NOs: 22-27, 29-35, 69-79, 81-93, 95-97, 99, and 123-143. The immunoglobulin heavy chain may comprise an amino acid sequence that is at least about 60%, 65%, 70%, 75%, 80%, 85%, 90%, 95%, or 97% homologous to any one of SEQ ID NOs: 22-27, 29-35, 69-79, 81-93, 95-97, 99, and 123-143. The immunoglobulin heavy chain may comprise an amino acid sequence that is at least about 70% homologous to any one of SEQ ID NOs: 22-27, 29-35, 69-79, 81-93, 95-97, 99, and 123-143. The immunoglobulin heavy chain may comprise an amino acid sequence that is at least about 80% homologous to any one of SEQ ID NOs: 22-27, 29-35, 69-79, 81-93, 95-97, 99, and 123-143.

The immunoglobulin heavy chain may comprise an amino acid sequence comprising 10, 20, 30, 40, 50, 60, 70, 80, 90, 100 or more amino acids based on or derived from any one of SEQ ID NOs: 22-27, 29-35, 69-79, 81-93, 95-97, 99, and 123-143. The immunoglobulin heavy chain may comprise an amino acid sequence comprising 125, 150, 175, 200, 225, 250, 275, 300, 325, 350, 375, 400, 425, 450, 475, 450, 500 or more amino acids based on or derived from any one of SEQ ID NOs: 22-27, 29-35, 69-79, 81-93, 95-97, 99, and 123-143. The immunoglobulin heavy chain may comprise an amino acid sequence comprising 10 or more amino acids based on or derived from any one of SEQ ID NOs: 22-27, 29-35, 69-79, 81-93, 95-97, 99, and 123-143. The immunoglobulin heavy chain may comprise an amino acid sequence comprising 50 or more amino acids based on or derived from any one of SEQ ID NOs: 22-27, 29-35, 69-79, 81-93, 95-97, 99, and 123-143. The immunoglobulin heavy chain may comprise an amino acid sequence comprising 100 or more amino acids based on or derived from any one of SEQ ID NOs: 22-27, 29-35, 69-79, 81-93, 95-97, 99, and 123-143. The immunoglobulin heavy chain may comprise an amino acid sequence comprising 200 or more amino acids based on or derived from any one of SEQ ID NOs: 22-27, 29-35, 69-79, 81-93, 95-97, 99, and 123-143. The amino acids may be consecutive. Alternatively, or additionally, the amino acids are nonconsecutive.

The immunoglobulin heavy chain may be encoded by a nucleotide sequence that is based on or derived from any one of SEQ ID NOs: 4-9, 11-17, 38-48, 50-62, 64-66, and 101-121. The immunoglobulin heavy chain may be encoded by a nucleotide sequence that is at least about 50% homologous to any one of SEQ ID NOs: 4-9, 11-17, 38-48, 50-62, 64-66, and 101-121. The immunoglobulin heavy chain may be encoded by a nucleotide sequence that is at least about 60%, 65%, 70%, 75%, 80%, 85%, 90%, 95%, or 97% homologous to any one of SEQ ID NOs: 4-9, 11-17, 38-48, 50-62, 64-66, and 101-121. The immunoglobulin heavy chain may be encoded by a nucleotide sequence that is at least about 70% homologous to any one of SEQ ID NOs: 4-9, 11-17, 38-48, 50-62, 64-66, and 101-121. The immunoglobulin heavy chain may be encoded by a nucleotide sequence that is at least about 80% homologous to any one of SEQ ID NOs: 4-9, 11-17, 38-48, 50-62, 64-66, and 101-121.

The immunoglobulin heavy chain may be encoded by a nucleotide sequence comprising 10, 20, 30, 40, 50, 60, 70, 80, 90, 100 or more nucleotides based on or derived from any one of SEQ ID NOs: 4-9, 11-17, 38-48, 50-62, 64-66, and 101-121. The immunoglobulin heavy chain may be encoded by a nucleotide sequence comprising 125, 150, 175, 200, 225, 250, 275, 300, 325, 350, 375, 400, 425, 450, 475, 450, 500 or more nucleotides based on or derived from any one of SEQ ID NOs: 4-9, 11-17, 38-48, 50-62, 64-66, and 101-121. The immunoglobulin heavy chain may be encoded by a nucleotide sequence comprising 600, 650, 700, 750, 800, 850, 900, 950, 1000 or more nucleotides based on or derived from any one of SEQ ID NOs: 4-9, 11-17, 38-48, 50-62, 64-66, and 101-121. The immunoglobulin heavy chain may be encoded by a nucleotide sequence comprising 1100, 1200, 1300, 1400, 1500 or more nucleotides based on or derived from any one of SEQ ID NOs: 4-9, 11-17, 38-48, 50-62, 64-66, and 101-121. The immunoglobulin heavy chain may be encoded by a nucleotide sequence comprising 100 or more nucleotides based on or derived from any one of SEQ ID NOs: 4-9, 11-17, 38-48, 50-62, 64-66, and 101-121. The immunoglobulin heavy chain may be encoded by a nucleotide sequence comprising 500 or more nucleotides based on or derived from any one of SEQ ID NOs: 4-9, 11-17, 38-48, 50-62, 64-66, and 101-121. The immunoglobulin heavy chain may be encoded by a nucleotide sequence comprising 1000 or more nucleotides based on or derived from any one of SEQ ID NOs: 4-9, 11-17, 38-48, 50-62, 64-66, and 101-121. The immunoglobulin heavy chain may be encoded by a nucleotide sequence comprising 1300 or more nucleotides based on or derived from any one of SEQ ID NOs: 4-9, 11-17, 38-48, 50-62, 64-66, and 101-121. The nucleotides may be consecutive. Alternatively, or additionally, the nucleotides are nonconsecutive.

The immunoglobulin fusion protein may comprise (a) a first immunoglobulin fusion heavy chain comprising an amino acid sequence that is based on or derived from SEQ ID NOs: 69-79, 81-93, 95-97, 99, and 123-143; and (b) a first immunoglobulin light chain comprising an amino acid sequence that is based on or derived from SEQ ID NOs: 19-21, 28, and 36. The immunoglobulin fusion protein may comprise (a) a first immunoglobulin fusion heavy chain comprising an amino acid sequence that is at least about 50% identical to SEQ ID NOs: 69-79, 81-93, 95-97, 99, and 123-143; and (b) a first immunoglobulin light chain comprising an amino acid sequence that is at least about 50% identical to SEQ ID NOs: 19-21, 28, and 36. The first immunoglobulin fusion heavy chain may comprise an amino acid sequence that is at least about 60%, 70%, 75%, 80%, 90%, 95%, or 97% identical to SEQ ID NOs: 69-79, 81-93, 95-97, 99, and 123-143. The first immunoglobulin light chain comprising an amino acid sequence that is at least about 60%, 70%, 75%, 80%, 90%, 95%, or 97% identical to SEQ ID NOs: 19-21, 28, and 36.

The immunoglobulin fusion protein may comprise (a) a first immunoglobulin fusion heavy chain encoded by a nucleotide sequence of SEQ ID NOs: 38-48, 50-62, 64-66, and 101-121; and (b) a first immunoglobulin light chain encoded by a nucleotide sequence of SEQ ID NOs: 1-3, 10 and 18. The immunoglobulin fusion protein may comprise (a) a first immunoglobulin fusion heavy chain encoded by a nucleotide sequence that is at least 50% or more homologous to a nucleotide sequence of SEQ ID NOs: 38-48, 50-62, 64-66, and 101-121; and (b) a first immunoglobulin light chain encoded by a nucleotide sequence that is at least 50% or more homologous to a nucleotide sequence of SEQ ID NOs: 1-3, 10 and 18. The first immunoglobulin fusion heavy chain encoded by a nucleotide sequence that is at least 60%, 70%, 75%, 80%, 90%, 95%, or 97% or more homologous to a nucleotide sequence of SEQ ID NOs: 38-48, 50-62, 64-66, and 101-121. The first immunoglobulin light chain encoded by a nucleotide sequence that is at least 60%, 70%, 75%, 80%, 90%, 95%, or 97% or more homologous to a nucleotide sequence of SEQ ID NOs: 1-3, 10 and 18.

The immunoglobulin fusion protein may comprise (a) a first immunoglobulin heavy chain comprising an amino acid sequence that is based on or derived from SEQ ID NOs: 22-27, and 29-35; and (b) a first immunoglobulin fusion light chain comprising an amino acid sequence that is based on or derived from SEQ ID NOs: 68, 80, 94, 98, and 122. The immunoglobulin fusion protein may comprise (a) a first immunoglobulin heavy chain comprising an amino acid sequence that is at least about 50% identical to SEQ ID NOs: 22-27, and 29-35; and (b) a first immunoglobulin fusion light chain comprising an amino acid sequence that is at least about 50% identical to SEQ ID NOs: 68, 80, 94, 98, and 122. The first immunoglobulin heavy chain may comprise an amino acid sequence that is at least about 60%, 70%, 75%, 80%, 90%, 95%, or 97% identical to SEQ ID NOs: 22-27, and 29-35. The first immunoglobulin fusion light chain comprising an amino acid sequence that is at least about 60%, 70%, 75%, 80%, 90%, 95%, or 97% identical to SEQ ID NOs: 68, 80, 94, 98, and 122.

The immunoglobulin fusion protein may comprise (a) a first immunoglobulin heavy chain encoded by a nucleotide sequence of SEQ ID NOs: 4-9 and 11-17; and (b) a first immunoglobulin fusion light chain encoded by a nucleotide sequence of SEQ ID NOs: 37, 49, 63, 67, and 100. The immunoglobulin fusion protein may comprise (a) a first immunoglobulin heavy chain encoded by a nucleotide sequence that is at least 50% or more homologous to a nucleotide sequence of SEQ ID NOs: 4-9 and 11-17; and (b) a first immunoglobulin fusion light chain encoded by a nucleotide sequence that is at least 50% or more homologous to a nucleotide sequence of SEQ ID NOs: 37, 49, 63, 67, and 100. The first immunoglobulin heavy chain encoded by a nucleotide sequence that is at least 60%, 70%, 75%, 80%, 90%, 95%, or 97% or more homologous to a nucleotide sequence of SEQ ID NOs: 4-9 and 11-17. The first immunoglobulin fusion light chain encoded by a nucleotide sequence that is at least 60%, 70%, 75%, 80%, 90%, 95%, or 97% or more homologous to a nucleotide sequence of SEQ ID NOs: 37, 49, 63, 67, and 100.

The immunoglobulin fusion protein may comprise (a) a first immunoglobulin fusion heavy chain comprising an amino acid sequence that is based on or derived from SEQ ID NOs: 69-79, 81-93, 95-97, 99, and 123-143; and (b) a first immunoglobulin fusion light chain comprising an amino acid sequence that is based on or derived from SEQ ID NOs: 68, 80, 94, 98, and 122. The immunoglobulin fusion protein may comprise (a) a first immunoglobulin fusion heavy chain comprising an amino acid sequence that is at least about 50% identical to SEQ ID NOs: 69-79, 81-93, 95-97, 99, and 123-143; and (b) a first immunoglobulin fusion light chain comprising an amino acid sequence that is at least about 50% identical to SEQ ID NOs: 68, 80, 94, 98, and 122. The first immunoglobulin fusion heavy chain may comprise an amino acid sequence that is at least about 60%, 70%, 75%, 80%, 90%, 95%, or 97% identical to SEQ ID NOs: 69-79, 81-93, 95-97, 99, and 123-143. The first immunoglobulin fusion light chain comprising an amino acid sequence that is at least about 60%, 70%, 75%, 80%, 90%, 95%, or 97% identical to SEQ ID NOs: 68, 80, 94, 98, and 122.

The immunoglobulin fusion protein may comprise (a) a first immunoglobulin fusion heavy chain encoded by a nucleotide sequence of SEQ ID NOs: 38-48, 50-62, 64-66, and 101-121; and (b) a first immunoglobulin fusion light chain encoded by a nucleotide sequence of SEQ ID NOs: 37, 49, 63, 67, and 100. The immunoglobulin fusion protein may comprise (a) a first immunoglobulin fusion heavy chain encoded by a nucleotide sequence that is at least 50% or more homologous to a nucleotide sequence of SEQ ID NOs: 38-48, 50-62, 64-66, and 101-121; and (b) a first immunoglobulin fusion light chain encoded by a nucleotide sequence that is at least 50% or more homologous to a nucleotide sequence of SEQ ID NOs: 37, 49, 63, 67, and 100. The first immunoglobulin fusion heavy chain encoded by a nucleotide sequence that is at least 60%, 70%, 75%, 80%, 90%, 95%, or 97% or more homologous to a nucleotide sequence of SEQ ID NOs: 38-48, 50-62, 64-66, and 101-121. The first immunoglobulin fusion light chain encoded by a nucleotide sequence that is at least 60%, 70%, 75%, 80%, 90%, 95%, or 97% or more homologous to a nucleotide sequence of SEQ ID NOs: 37, 49, 63, 67, and 100.

Further disclosed herein are immunoglobulin dual fusion proteins comprising (a) an antibody region attached to a non-antibody region, wherein the non-antibody region comprises (i) a first extender peptide, wherein the first extender peptide comprises an amino acid sequence comprising an alpha helix secondary structure and wherein the first extender peptide does not comprise an ultralong CDR3, and (ii) a first therapeutic agent; and (b) a second therapeutic agent. Attachment of the antibody region to the non-antibody region may comprise insertion of the non-antibody region into the antibody region. The first therapeutic agent and the second therapeutic agent may be the same. The first therapeutic agent and the second therapeutic agent may be different. The dual fusion protein may further comprise a second antibody region. The first and second therapeutic agent may be attached to a first antibody region. The first and second therapeutic agent may be each attached to a first antibody region and a second antibody region. The first and second antibody regions may be connected. The first and second antibody regions may be connected by one or more disulfide bonds. The first and second antibody regions may be part of one immunoglobulin light or heavy chain. The immunoglobulin dual fusion protein may further comprise one or more additional extender peptides. The immunoglobulin dual fusion protein may further comprise one or more linker peptides. The immunoglobulin dual fusion protein may further comprise one or more protease cleavage sites.

Alternatively, the immunoglobulin dual fusion protein comprises (a) an antibody region attached to a non-antibody region, wherein the non-antibody region comprises (i) a first extender peptide, wherein the first extender peptide comprises an amino acid sequence comprising an alpha helix secondary structure and wherein the extender peptide comprises 7 or fewer amino acids based on or derived from an ultralong CDR3; and (ii) a first therapeutic agent; and (b) a second therapeutic agent. Attachment of the antibody region to the non-antibody region may comprise insertion of the non-antibody region into the antibody region. The first therapeutic agent and the second therapeutic agent may be the same. The first therapeutic agent and the second therapeutic agent may be different. The dual fusion protein may further comprise a second antibody region. The first and second therapeutic agent may be attached to a first antibody region. The first and second therapeutic agent may be each attached to a first antibody region and a second antibody region. The first and second antibody regions may be connected. The first and second antibody regions may be connected by one or more disulfide bonds. The first and second antibody regions may be part of one immunoglobulin light or heavy chain. The immunoglobulin dual fusion protein may further comprise one or more additional extender peptides. The immunoglobulin dual fusion protein may further comprise one or more linker peptides. The immunoglobulin dual fusion protein may further comprise one or more protease cleavage sites.

Alternatively, the immunoglobulin dual fusion protein comprises (a) an antibody region attached to an extender fusion region, wherein the extender fusion region comprises (i) a first extender peptide, wherein the first extender peptide comprises an amino acid sequence comprising an alpha helix secondary structure and wherein the first extender peptide does not comprise an ultralong CDR3, and (ii) a first therapeutic agent; and (b) a second therapeutic agent. Attachment of the antibody region to the extender fusion region may comprise insertion of the extender fusion region into the antibody region. The first therapeutic agent and the second therapeutic agent may be the same. The first therapeutic agent and the second therapeutic agent may be different. The dual fusion protein may further comprise a second antibody region. The first and second therapeutic agent may be attached to a first antibody region. The first and second therapeutic agent may be each attached to a first antibody region and a second antibody region. The first and second antibody regions may be connected. The first and second antibody regions may be connected by one or more disulfide bonds. The first and second antibody regions may be part of one immunoglobulin light or heavy chain. The immunoglobulin dual fusion protein may further comprise one or more additional extender peptides. The immunoglobulin dual fusion protein may further comprise one or more linker peptides. The immunoglobulin dual fusion protein may further comprise one or more protease cleavage sites.

Alternatively, the immunoglobulin dual fusion protein comprises (a) an antibody region attached to an extender fusion region, wherein the extender fusion region comprises (i) a first extender peptide, wherein the first extender peptide comprises an amino acid sequence comprising an alpha helix secondary structure and wherein the extender peptide comprises 7 or fewer amino acids based on or derived from an ultralong CDR3; and (ii) a first therapeutic agent; and (b) a second therapeutic agent. Attachment of the antibody region to the extender fusion region may comprise insertion of the extender fusion region into the antibody region. The first therapeutic agent and the second therapeutic agent may be the same. The first therapeutic agent and the second therapeutic agent may be different. The dual fusion protein may further comprise a second antibody region. The first and second therapeutic agent may be attached to a first antibody region. The first and second therapeutic agent may be each attached to a first antibody region and a second antibody region. The first and second antibody regions may be connected. The first and second antibody regions may be connected by one or more disulfide bonds. The first and second antibody regions may be part of one immunoglobulin light or heavy chain. The immunoglobulin dual fusion protein may further comprise one or more additional extender peptides. The immunoglobulin dual fusion protein may further comprise one or more linker peptides. The immunoglobulin dual fusion protein may further comprise one or more protease cleavage sites.

Alternatively, the immunoglobulin dual fusion protein comprises (a) an antibody region attached to a non-antibody region, wherein the non-antibody region comprises (i) a first linking peptide, wherein the first linking peptide does not comprise an amino acid sequence comprising an alpha helix or beta strand secondary structure, and (ii) a first therapeutic agent; and (b) a second therapeutic agent. Attachment of the antibody region to the non-antibody region may comprise insertion of the non-antibody region into the antibody region. The first therapeutic agent and the second therapeutic agent may be the same. The first therapeutic agent and the second therapeutic agent may be different. The dual fusion protein may further comprise a second antibody region. The first and second therapeutic agent may be attached to a first antibody region. The first and second therapeutic agent may be each attached to a first antibody region and a second antibody region. The first and second antibody regions may be connected. The first and second antibody regions may be connected by one or more disulfide bonds. The first and second antibody regions may be part of one immunoglobulin light or heavy chain. The immunoglobulin dual fusion protein may further comprise one or more additional linker peptides. The immunoglobulin dual fusion protein may further comprise one or more protease cleavage sites.

Alternatively, the immunoglobulin dual fusion protein comprises (a) an antibody region attached to an extender fusion region, wherein the extender fusion region comprises (i) a first linking peptide, wherein the first linking peptide does not comprise an amino acid sequence comprising an alpha helix or beta strand secondary structure; and (ii) a first therapeutic agent; and (b) a second therapeutic agent. Attachment of the antibody region to the extender fusion region may comprise insertion of the extender fusion region into the antibody region. The first therapeutic agent and the second therapeutic agent may be the same. The first therapeutic agent and the second therapeutic agent may be different. The dual fusion protein may further comprise a second antibody region. The first and second therapeutic agent may be attached to a first antibody region. The first and second therapeutic agent may be each attached to a first antibody region and a second antibody region. The first and second antibody regions may be connected. The first and second antibody regions may be connected by one or more disulfide bonds. The first and second antibody regions may be part of one immunoglobulin light or heavy chain. The immunoglobulin dual fusion protein may further comprise one or more additional linker peptides. The immunoglobulin dual fusion protein may further comprise one or more protease cleavage sites.

The dual fusion antibody may comprise (a) a first immunoglobulin fusion protein comprising a first antibody region attached to a first non-antibody region, wherein the first non-antibody region comprises (i) a first extender peptide, wherein the first extender peptide comprises an amino acid sequence comprising an alpha helix secondary structure and (ii) a first therapeutic agent; and (b) a second immunoglobulin fusion protein comprising a second antibody region attached to a second non-antibody region, wherein the second non-antibody region comprises (i) a second extender peptide comprising at least one secondary structure and (ii) a second therapeutic agent. In some embodiments, the first extender peptide is a connecting peptide or is a part of a connecting peptide. In some embodiments, the second extender peptide is a connecting peptide or is a part of a connecting peptide. In some embodiments, the first extender peptide does not comprise amino acids having a beta strand secondary structure. In some embodiments, the second extender peptide does not comprise amino acids having a beta strand secondary structure. The dual fusion antibody may further comprise one or more peptide linkers. The dual fusion antibody may further comprise one or more protease cleavage sites.

The dual fusion antibody may comprise (a) a first immunoglobulin fusion protein comprising a first antibody region attached to a first non-antibody region, wherein the first non-antibody region comprises (i) a first extender peptide, wherein the first extender peptide comprises an amino acid sequence comprising an alpha helix secondary structure and (ii) a first therapeutic agent; and (b) a second immunoglobulin fusion protein comprising a second antibody region attached to an extender fusion region, wherein the extender fusion region comprises (i) a second extender peptide comprising at least one secondary structure and (ii) a second therapeutic agent. In some embodiments, the first extender peptide is a connecting peptide or is a part of a connecting peptide. In some embodiments, the second extender peptide is a connecting peptide or is a part of a connecting peptide. The dual fusion antibody may further comprise one or more peptide linkers. The dual fusion antibody may further comprise one or more protease cleavage sites. In some embodiments, the first extender peptide does not comprise amino acids having a beta strand secondary structure. In some embodiments, the second extender peptide does not comprise amino acids having a beta strand secondary structure.

The dual fusion antibody may comprise (a) a first immunoglobulin fusion protein comprising a first antibody region attached to a first extender fusion region, wherein the first extender fusion region comprises (i) a first extender peptide, wherein the first extender peptide comprises an amino acid sequence comprising an alpha helix secondary structure and (ii) a first therapeutic agent; and (b) a second immunoglobulin fusion protein comprising a second antibody region attached to a non-antibody region, wherein the non-antibody region comprises (i) a second extender peptide comprising at least one secondary structure and (ii) a second therapeutic agent. In some embodiments, the first extender peptide is a connecting peptide or is a part of a connecting peptide. In some embodiments, the second extender peptide is a connecting peptide or is a part of a connecting peptide. The dual fusion antibody may further comprise one or more peptide linkers. The dual fusion antibody may further comprise one or more protease cleavage sites. In some embodiments, the first extender peptide does not comprise amino acids having a beta strand secondary structure. In some embodiments, the second extender peptide does not comprise amino acids having a beta strand secondary structure.

The dual fusion antibody may comprise (a) a first immunoglobulin fusion protein comprising a first antibody region attached to a first extender fusion region, wherein the first extender fusion region comprises (i) a first extender peptide, wherein the first extender peptide comprises an amino acid sequence comprising an alpha helix secondary structure and (ii) a first therapeutic agent; and (b) a second immunoglobulin fusion protein comprising a second antibody region attached to a second extender fusion region, wherein the extender fusion region comprises (i) a second extender peptide comprising at least one secondary structure and (ii) a second therapeutic agent. In some embodiments, the first extender peptide is a connecting peptide or is a part of a connecting peptide. In some embodiments, the second extender peptide is a connecting peptide or is a part of a connecting peptide. The dual fusion antibody may further comprise one or more peptide linkers. The dual fusion antibody may further comprise one or more protease cleavage sites. In some embodiments, the first extender peptide does not comprise amino acids having a beta strand secondary structure. In some embodiments, the second extender peptide does not comprise amino acids having a beta strand secondary structure.

The dual fusion antibody may comprise (a) a first immunoglobulin fusion protein comprising a first antibody region attached to a first non-antibody region, wherein the first non-antibody region comprises (i) a first peptide linker, wherein the first peptide linker does not comprise an amino acid sequence comprising an alpha helix or beta strand secondary structure and (ii) a first therapeutic agent; and (b) a second immunoglobulin fusion protein comprising a second antibody region attached to a second non-antibody region, wherein the second non-antibody region comprises (i) a second peptide linker, wherein the second peptide linker does not comprise an amino acid sequence comprising an alpha helix or beta strand secondary structure and (ii) a second therapeutic agent. In some embodiments, the first linker peptide is a connecting peptide or is a part of a connecting peptide. In some embodiments, the second linker peptide is a connecting peptide or is a part of a connecting peptide. The dual fusion antibody may further comprise one or more protease cleavage sites.

The dual fusion antibody may comprise (a) a first immunoglobulin fusion protein comprising a first antibody region attached to a first non-antibody region, wherein the first non-antibody region comprises (i) a first peptide linker, wherein the first peptide linker does not comprise an amino acid sequence comprising an alpha helix or beta strand secondary structure and (ii) a first therapeutic agent; and (b) a second immunoglobulin fusion protein comprising a second antibody region attached to an extender fusion region, wherein the extender fusion region comprises (i) a second peptide linker, wherein the second peptide linker does not comprise an amino acid sequence comprising an alpha helix or beta strand secondary structure and (ii) a second therapeutic agent. In some embodiments, the first linker peptide is a connecting peptide or is a part of a connecting peptide. In some embodiments, the second linker peptide is a connecting peptide or is a part of a connecting peptide. The dual fusion antibody may further comprise one or more protease cleavage sites.

The dual fusion antibody may comprise (a) a first immunoglobulin fusion protein comprising a first antibody region attached to a first extender fusion region, wherein the first extender fusion region comprises (i) a first peptide linker, wherein the first peptide linker does not comprise an amino acid sequence comprising an alpha helix or beta strand secondary structure and (ii) a first therapeutic agent; and (b) a second immunoglobulin fusion protein comprising a second antibody region attached to a non-antibody region, wherein the non-antibody region comprises (i) a second peptide linker, wherein the second peptide linker does not comprise an amino acid sequence comprising an alpha helix or beta strand secondary structure and (ii) a second therapeutic agent. In some embodiments, the first linker peptide is a connecting peptide or is a part of a connecting peptide. In some embodiments, the second linker peptide is a connecting peptide or is a part of a connecting peptide. The dual fusion antibody may further comprise one or more protease cleavage sites.

The dual fusion antibody may comprise (a) a first immunoglobulin fusion protein comprising a first antibody region attached to a first extender fusion region, wherein the first extender fusion region comprises (i) a first peptide linker, wherein the first peptide linker does not comprise an amino acid sequence comprising an alpha helix or beta strand secondary structure and (ii) a first therapeutic agent; and (b) a second immunoglobulin fusion protein comprising a second antibody region attached to a second extender fusion region, wherein the extender fusion region comprises (i) a second peptide linker, wherein the second peptide linker does not comprise an amino acid sequence comprising an alpha helix or beta strand secondary structure and (ii) a second therapeutic agent. In some embodiments, the first linker peptide is a connecting peptide or is a part of a connecting peptide. In some embodiments, the second linker peptide is a connecting peptide or is a part of a connecting peptide. The dual fusion antibody may further comprise one or more protease cleavage sites.

The dual fusion antibody may comprise (a) a first immunoglobulin fusion protein comprising a first antibody region attached to a first non-antibody region, wherein the first non-antibody region comprises (i) a first peptide linker, wherein the first peptide linker does not comprise an amino acid sequence comprising an alpha helix or beta strand secondary structure and (ii) a first therapeutic agent; and (b) a second immunoglobulin fusion protein comprising a second antibody region attached to a second non-antibody region, wherein the second non-antibody region comprises (i) an extender peptide comprising at least one secondary structure and (ii) a second therapeutic agent. In some embodiments, the extender peptide comprises amino acids having an alpha helix secondary structure. In some embodiments, the extender peptide does not comprise amino acids having a beta strand secondary structure. In some embodiments, the extender peptide is a connecting peptide or is a part of a connecting peptide. In some embodiments, the peptide linker is a connecting peptide or is a part of a connecting peptide. The dual fusion antibody may further comprise one or more protease cleavage sites. The dual fusion antibody may further comprise one or more additional linkers. The second non-antibody region of the second immunoglobulin fusion protein may further comprise one or more additional extender peptides.

The dual fusion antibody may comprise (a) a first immunoglobulin fusion protein comprising a first antibody region attached to a first non-antibody region, wherein the first non-antibody region comprises (i) a first peptide linker, wherein the first peptide linker does not comprise an amino acid sequence comprising an alpha helix or beta strand secondary structure and (ii) a first therapeutic agent; and (b) a second immunoglobulin fusion protein comprising a second antibody region attached to an extender fusion region, wherein the extender fusion region comprises (i) an extender peptide comprising at least one secondary structure and (ii) a second therapeutic agent. In some embodiments, the extender peptide comprises amino acids having an alpha helix secondary structure. In some embodiments, the extender peptide does not comprise amino acids having a beta strand secondary structure. In some embodiments, the extender peptide is a connecting peptide or is a part of a connecting peptide. In some embodiments, the peptide linker is a connecting peptide or is a part of a connecting peptide. The dual fusion antibody may further comprise one or more protease cleavage sites. The dual fusion antibody may further comprise one or more additional linkers. The extender fusion region of the second immunoglobulin fusion protein may further comprise one or more additional extender peptides.

The dual fusion antibody may comprise (a) a first immunoglobulin fusion protein comprising a first antibody region attached to a first extender fusion region, wherein the first extender fusion region comprises (i) a first peptide linker, wherein the first peptide linker does not comprise an amino acid sequence comprising an alpha helix or beta strand secondary structure and (ii) a first therapeutic agent; and (b) a second immunoglobulin fusion protein comprising a second antibody region attached to a non-antibody region, wherein the non-antibody region comprises (i) an extender peptide comprising at least one secondary structure and (ii) a second therapeutic agent. In some embodiments, the extender peptide comprises amino acids having an alpha helix secondary structure. In some embodiments, the extender peptide does not comprise amino acids having a beta strand secondary structure. In some embodiments, the extender peptide is a connecting peptide or is a part of a connecting peptide. In some embodiments, the peptide linker is a connecting peptide or is a part of a connecting peptide. The dual fusion antibody may further comprise one or more protease cleavage sites. The dual fusion antibody may further comprise one or more additional linkers. The non-antibody region of the second immunoglobulin fusion protein may further comprise one or more additional extender peptides.

The dual fusion antibody may comprise (a) a first immunoglobulin fusion protein comprising a first antibody region attached to a first extender fusion region, wherein the first extender fusion region comprises (i) a first peptide linker, wherein the first peptide linker does not comprise an amino acid sequence comprising an alpha helix or beta strand secondary structure and (ii) a first therapeutic agent; and (b) a second immunoglobulin fusion protein comprising a second antibody region attached to a second extender fusion region, wherein the extender fusion region comprises (i) a second extender peptide comprising at least one secondary structure and (ii) a second therapeutic agent. In some embodiments, the extender peptide comprises amino acids having an alpha helix secondary structure. In some embodiments, the extender peptide does not comprise amino acids having a beta strand secondary structure. In some embodiments, the extender peptide is a connecting peptide or is a part of a connecting peptide. In some embodiments, the peptide linker is a connecting peptide or is a part of a connecting peptide. The dual fusion antibody may further comprise one or more protease cleavage sites. The dual fusion antibody may further comprise one or more additional linkers. The second extender fusion region of the second immunoglobulin fusion protein may further comprise one or more additional extender peptides.

The dual fusion antibody may comprise (a) a first immunoglobulin fusion protein comprising a first antibody region attached to a first non-antibody region, wherein the first non-antibody region comprises (i) a first extender peptide, wherein the first extender peptide comprises an amino acid sequence comprising an alpha helix secondary structure and (ii) a first therapeutic agent; and (b) a second immunoglobulin fusion protein comprising a second antibody region attached to a second non-antibody region, wherein the second non-antibody region comprises (i) a peptide linker, wherein the peptide linker does not comprise an amino acid sequence comprising an alpha helix or beta strand secondary structure and (ii) a second therapeutic agent. In some embodiments, the extender peptide does not comprise amino acids having a beta strand secondary structure. In some embodiments, the extender peptide is a connecting peptide or is a part of a connecting peptide. In some embodiments, the peptide linker is a connecting peptide or is a part of a connecting peptide. The dual fusion antibody may further comprise one or more protease cleavage sites. The dual fusion antibody may further comprise one or more additional linkers. The first non-antibody region of the first immunoglobulin fusion protein may further comprise one or more additional extender peptides.

The dual fusion antibody may comprise (a) a first immunoglobulin fusion protein comprising a first antibody region attached to a first non-antibody region, wherein the first non-antibody region comprises (i) a first extender peptide, wherein the first extender peptide comprises an amino acid sequence comprising an alpha helix secondary structure and (ii) a first therapeutic agent; and (b) a second immunoglobulin fusion protein comprising a second antibody region attached to an extender fusion region, wherein the extender fusion region comprises (i) a peptide linker, wherein the second peptide linker does not comprise an amino acid sequence comprising an alpha helix or beta strand secondary structure and (ii) a second therapeutic agent. In some embodiments, the extender peptide does not comprise amino acids having a beta strand secondary structure. In some embodiments, the extender peptide is a connecting peptide or is a part of a connecting peptide. In some embodiments, the peptide linker is a connecting peptide or is a part of a connecting peptide. The dual fusion antibody may further comprise one or more protease cleavage sites. The dual fusion antibody may further comprise one or more additional linkers. The first non-antibody region of the first immunoglobulin fusion protein may further comprise one or more additional extender peptides.

The dual fusion antibody may comprise (a) a first immunoglobulin fusion protein comprising a first antibody region attached to a first extender fusion region, wherein the first extender fusion region comprises (i) a first extender peptide, wherein the first extender peptide comprises an amino acid sequence comprising an alpha helix secondary structure and (ii) a first therapeutic agent; and (b) a second immunoglobulin fusion protein comprising a second antibody region attached to a non-antibody region, wherein the non-antibody region comprises (i) a peptide linker, wherein the peptide linker does not comprise an amino acid sequence comprising an alpha helix or beta strand secondary structure and (ii) a second therapeutic agent. In some embodiments, the extender peptide does not comprise amino acids having a beta strand secondary structure. In some embodiments, the extender peptide is a connecting peptide or is a part of a connecting peptide. In some embodiments, the peptide linker is a connecting peptide or is a part of a connecting peptide. The dual fusion antibody may further comprise one or more protease cleavage sites. The dual fusion antibody may further comprise one or more additional linkers. The first extender fusion region of the first immunoglobulin fusion protein may further comprise one or more additional extender peptides.

The dual fusion antibody may comprise (a) a first immunoglobulin fusion protein comprising a first antibody region attached to a first extender fusion region, wherein the first extender fusion region comprises (i) a first extender peptide, wherein the first extender peptide comprises an amino acid sequence comprising an alpha helix secondary structure and (ii) a first therapeutic agent; and (b) a second immunoglobulin fusion protein comprising a second antibody region attached to a second extender fusion region, wherein the extender fusion region comprises (i) a peptide linker, wherein the peptide linker does not comprise an amino acid sequence comprising an alpha helix or beta strand secondary structure and (ii) a second therapeutic agent. In some embodiments, the extender peptide does not comprise amino acids having a beta strand secondary structure. In some embodiments, the extender peptide is a connecting peptide or is a part of a connecting peptide. In some embodiments, the peptide linker is a connecting peptide or is a part of a connecting peptide. The dual fusion antibody may further comprise one or more protease cleavage sites. The dual fusion antibody may further comprise one or more additional linkers. The first extender fusion region of the first immunoglobulin fusion protein may further comprise one or more additional extender peptides.

The first therapeutic agent and the second therapeutic agent may be the same. The first therapeutic agent and the second therapeutic agent may be different. The immunoglobulin dual fusion protein may further comprise one or more additional therapeutic agents. The two or more therapeutic agents may be the same. Alternatively, or additionally, the two or more therapeutic agents may be different. The first therapeutic agent may be a therapeutic peptide. The second therapeutic agent may be a therapeutic peptide. One or more of the additional therapeutic agents may be a therapeutic peptide. The first therapeutic agent may comprise a therapeutic peptide. The second therapeutic agent may comprise a therapeutic peptide. One or more of the additional therapeutic agents may comprise one or more therapeutic peptides. A therapeutic agent may comprise one or more therapeutic peptides or regions of therapeutic peptides. A therapeutic agent may comprise, for example, a first therapeutic peptide or portion thereof, an internal peptide, and a second therapeutic peptide or portion thereof. The internal peptide may include, for example, a protease cleavage site or an affinity tag, such as a histidine tag (6×HIS) (SEQ ID NO: 274). The internal peptide may include, for example, another therapeutic peptide or portion thereof. For example, a therapeutic agent may comprise, a first portion of a first therapeutic peptide, a first portion of a second therapeutic peptide, and a second portion of a first therapeutic peptide.

The first antibody region and the second antibody region may be the same. For example, the first antibody region and the second antibody region comprise an immunoglobulin heavy chain. Alternatively, the first antibody region and the second antibody region may comprise an immunoglobulin light chain. The first antibody region and the second antibody region may be different. For example, the first antibody region comprises an immunoglobulin heavy chain and the second antibody region comprises an immunoglobulin light chain or vice versa. The immunoglobulin dual fusion protein may further comprise one or more additional antibody regions. The two or more antibody regions may be the same. Alternatively, or additionally, the two or more antibody regions may be different.

The immunoglobulin dual fusion protein may further comprise one or more extender peptides. The one or more extender peptides may be the same. Alternatively, or additionally, the one or more extender peptides are different. In some embodiments, the extender peptide comprises 7 or fewer amino acids based on or derived from an ultralong CDR3.

The immunoglobulin dual fusion protein may further comprise one or more additional antibody regions. The two or more antibody regions may be the same. Alternatively, or additionally, the two or more antibody regions are different.

The immunoglobulin dual fusion protein may further comprise one or more linkers. The immunoglobulin dual fusion protein may further comprise two or more linkers. The two or more linkers may be the same. Alternatively, or additionally, the two or more linkers are different.

The immunoglobulin dual fusion protein may further comprise one or more proteolytic cleavage sites. The immunoglobulin dual fusion protein may further comprise two or more proteolytic cleavage sites. The two or more proteolytic cleavage sites may be the same. Alternatively, or additionally, the two or more proteolytic cleavage sites are different.

The immunoglobulin dual fusion protein may further comprise one or more therapeutic agents comprising internal peptides. An internal peptide may comprise an affinity tag or label, such as a HHHHHH (6×) Histidine tag (SEQ ID NO: 274). An internal peptide may comprise a portion of a therapeutic peptide.

Exemplary immunoglobulin dual fusion proteins are depicted in FIG. 3, Formula IIIA and Formula VIIA. As shown in Formula IIIA of FIG. 8, the immunoglobulin dual fusion protein may comprise (a) a first antibody region ($A^1$) attached to a first extender fusion region comprising a first therapeutic agent ($T^1$) attached to two extender peptides ($E^1$, $E^2$); and (b) a second antibody region ($A^2$) attached to a second extender fusion region comprising a second therapeutic agent ($T^2$) attached to two extender peptides ($E^3$, $E^4$). The immunoglobulin dual fusion proteins may further comprise one or more linkers and one or more proteolytic cleavage sites. The one or more proteolytic cleavage sites may be attached to the N- and/or C-terminus of a therapeutic agent. Proteolytic cleavage of the proteolytic cleavage site may release the N- and/or C-terminus of the therapeutic agent from the immunoglobulin fusion protein. Formula VIIA of FIG. 3 depicts an exemplary immunoglobulin dual fusion protein in which the N-terminus of the second therapeutic agent ($T^2$) has been released.

Antibody Region

The immunoglobulin fusion proteins disclosed herein comprise one or more antibody regions. The antibody region may comprise an immunoglobulin or a fragment thereof. The antibody region may comprise at least a portion of an immunoglobulin heavy chain, immunoglobulin light chain, or a combination thereof. The antibody region may comprise two or more immunoglobulin chains or portions thereof. The antibody region may comprise three or more immunoglobulin chains or portions thereof. The antibody region may comprise four or more immunoglobulin chains or portions thereof. The antibody region may comprise five or more immunoglobulin chains or portions thereof. The antibody region may comprise two immunoglobulin heavy chains and two immunoglobulin light chains.

The antibody region may comprise an entire immunoglobulin molecule or any polypeptide comprising fragment of an immunoglobulin including, but not limited to, heavy chain, light chain, variable domain, constant domain, complementarity determining region (CDR), framework region, fragment antigen binding (Fab) region, Fab', F(ab')2, F(ab')3, Fab', fragment crystallizable (Fc) region, single chain variable fragment (scFV), di-scFv, single domain immunoglobulin, trifunctional immunoglobulin, chemically linked F(ab')2, and any combination thereof. The immunoglobulin region may comprise one or more mutations. The Fc region may be a mutated Fc region. The mutated Fc region may comprise one or more mutations that eliminate an antibody-dependent cellular cytotoxicity (ADCC) effect of an Fc region. The mutated Fc region may comprise about 1, about 2, about 3, about 4, about 5, about 6, about 7, about 8, about 9, about 10, about 1 to about 10, about 1 to about 20, or about 1 to about 30 mutations.

In some embodiments, an immunoglobulin heavy chain may comprise an entire heavy chain or a portion of a heavy chain. For example, a variable domain or region thereof derived from a heavy chain may be referred to as a heavy chain or a region of a heavy chain. In some embodiments, an immunoglobulin light chain may comprise an entire light chain or a portion of a light chain. For example, a variable domain or region thereof derived from a light chain may be referred to as a light chain or a region of a light chain. A single domain immunoglobulin includes, but is not limited to, a single monomeric variable immunoglobulin domain, for example, a shark variable new antigen receptor immunoglobulin fragment (VNAR).

The immunoglobulin may be derived from any type known to one of skill in the art including, but not limited to, IgA, IgD, IgE, IgG, IgM, IgY, IgW. The antibody region may comprise one or more units, including but not limited to, 1, 2, 3, 4, and 5 units. Functional units may include, but are not limited to, non-antibody regions, heavy chain, light chain, variable domain, constant domain, complementarity determining region (CDR), framework region, fragment antigen binding (Fab) region, Fab', F(ab')2, F(ab')3, Fab', fragment crystallizable (Fc) region, single chain variable fragment (scFV), di-scFv, single domain immunoglobulin, trifunctional immunoglobulin, chemically linked F(ab')2, and any combination or fragments thereof. Non-antibody regions include, but are not limited to, carbohydrates, lipids, small molecules and therapeutic peptides. The antibody region may comprise one or more units connected by one or more disulfide bonds. The antibody region may comprise one or more units connected by a peptide linker, for example, a scFv immunoglobulin. The immunoglobulin may be a recombinant immunoglobulin including immunoglobulins with amino acid mutations, substitutions, and/or deletions. The immunoglobulin may be a recombinant immunoglobulin comprising chemical modifications. The immunoglobulin may comprise a whole or part of an immunoglobulin-drug conjugate.

The antibody region may comprise at least a portion of an immunoglobulin heavy chain. The antibody region may comprise one or more immunoglobulin heavy chains or a portion thereof. The antibody region may comprise two or more immunoglobulin heavy chains or a portion thereof. The antibody region may comprise an amino acid sequence that is at least about 50% homologous to an immunoglobulin heavy chain. The antibody region may comprise an amino acid sequence that is at least about 60%, 65%, 70%, 75%, 80%, 85%, 90%, 92%, 95%, or 97% or more homologous to an immunoglobulin heavy chain. The antibody region may comprise an amino acid sequence that is at least about 70% homologous to an immunoglobulin heavy chain. The antibody region may comprise an amino acid sequence that is at least about 80% homologous to an immunoglobulin heavy chain. The antibody region may comprise an amino acid sequence that is at least about 90% homologous to an immunoglobulin heavy chain. The immunoglobulin heavy chain may comprise amino acids based on or derived from any one of SEQ ID NOs: 22-27, and 29-35. In some embodiments, the antibody region comprises an amino acid sequence that is at least about 50%, 55%, 60%, 65%, 70%, 75%, 80%, 85%, 90%, 95%, or 97% homologous to an amino acid sequence of any one of SEQ ID NOs: 22-27, and 29-35. In some embodiments, the antibody region comprises an amino acid sequence that is at least about 50%, 55%, 60%, 65%, 70%, 75%, 80%, 85%, 90%, 95%, or 97% identical to an amino acid sequence of any one of SEQ ID NOs: 22-27, and 29-35.

The antibody region may comprise an amino acid sequence comprising 5, 10, 15, 20, 25, 30, 35, 40, 45, 50, 60, 70, 80, 90 or more amino acids of an immunoglobulin heavy chain. The antibody region may comprise an amino acid sequence comprising 100, 150, 200, 250, 300, 350, 400, 450, 500, 600, 700, 800, 900 or more amino acids of an immunoglobulin heavy chain. The amino acids may be consecutive. Alternatively, or additionally, the amino acids are non-consecutive.

The immunoglobulin heavy chain may be encoded by a nucleotide sequence based on or derived from SEQ ID NOs: 4-9, and 11-17. The immunoglobulin heavy chain may be encoded by a nucleotide sequence that is at least about 50% homologous to SEQ ID NOs: 4-9, and 11-17. The immunoglobulin heavy chain may be encoded by a nucleotide sequence that is at least about 60%, 65%, 70%, 75%, 80%, 85%, 90%, 92%, 95%, or 97% or more homologous to SEQ ID NOs: 4-9, and 11-17. The immunoglobulin heavy chain may be encoded by a nucleotide sequence that is at least about 75% homologous to SEQ ID NOs: 4-9, and 11-17. The immunoglobulin heavy chain may be encoded by a nucleotide sequence that is at least about 85% homologous to SEQ ID NOs: 4-9, and 11-17. In some embodiments, the antibody region is encoded by a nucleotide sequence that is at least about 50%, 55%, 60%, 65%, 70%, 75%, 80%, 85%, 90%, 95%, or 97% homologous to a nucleotide sequence of any one of SEQ ID NOs: 4-9, and 11-17. In some embodiments, the antibody region is encoded by a nucleotide sequence that is at least about 50%, 55%, 60%, 65%, 70%, 75%, 80%, 85%, 90%, 95%, or 97% identical to a nucleotide sequence of any one of SEQ ID NOs: 4-9, and 11-17.

The antibody region may comprise at least a portion of an immunoglobulin light chain. The antibody region may comprise one or more immunoglobulin light chains or a portion thereof. The antibody region may comprise two or more immunoglobulin light chains or a portion thereof. The antibody region may comprise an amino acid sequence that is at least about 50% homologous to an immunoglobulin light chain. The antibody region may comprise an amino acid sequence that is at least about 60%, 65%, 70%, 75%, 80%, 85%, 90%, 92%, 95%, or 97% or more homologous to an immunoglobulin light chain. The antibody region may comprise an amino acid sequence that is at least about 70% homologous to an immunoglobulin light chain. The antibody region may comprise an amino acid sequence that is at least about 80% homologous to an immunoglobulin light chain. The antibody region may comprise an amino acid sequence that is at least about 90% homologous to an immunoglobulin light chain. The immunoglobulin light chain may comprise amino acids based on or derived from any one of SEQ ID NOs: 19-21, 28, and 36. In some embodiments, the antibody region comprises an amino acid sequence that is at least about 50%, 55%, 60%, 65%, 70%, 75%, 80%, 85%, 90%, 95%, or 97% homologous to an amino acid sequence of any one of SEQ ID NOs: 19-21, 28, and 36. In some embodiments, the antibody region comprises an amino acid sequence that is at least about 50%, 55%, 60%, 65%, 70%, 75%, 80%, 85%, 90%, 95%, or 97% identical to an amino acid sequence of any one of SEQ ID NOs: 19-21, 28, and 36.

The antibody region may comprise an amino acid sequence comprising 5, 10, 15, 20, 25, 30, 35, 40, 45, 50, 60, 70, 80, 90 or more amino acids of an immunoglobulin light chain. The antibody region may comprise an amino acid sequence comprising 100, 150, 200, 250, 300, 350, 400, 450, 500, 600, 700, 800, 900 or more amino acids of an immunoglobulin light chain. The amino acids may be consecutive. Alternatively, or additionally, the amino acids are non-consecutive.

The immunoglobulin light chain may be encoded by a nucleotide sequence based on or derived from SEQ ID NOs: 1-3, 10, and 18. The immunoglobulin light chain may be encoded by a nucleotide sequence that is at least about 50% homologous to SEQ ID NOs: 1-3, 10, and 18. The immunoglobulin light chain may be encoded by a nucleotide sequence that is at least about 60%, 65%, 70%, 75%, 80%, 85%, 90%, 92%, 95%, or 97% or more homologous to SEQ ID NOs: 1-3, 10, and 18. The immunoglobulin light chain may be encoded by a nucleotide sequence that is at least about 75% homologous to SEQ ID NOs: 1-3, 10, and 18. The immunoglobulin light chain may be encoded by a nucleotide sequence that is at least about 85% homologous to SEQ ID NOs: 1-3, 10, and 18. In some embodiments, the antibody region is encoded by a nucleotide sequence that is at least about 50%, 55%, 60%, 65%, 70%, 75%, 80%, 85%, 90%, 95%, or 97% homologous to a nucleotide sequence of any one of SEQ ID NOs: 1-3, 10, and 18. In some embodiments, the antibody region is encoded by a nucleotide sequence that is at least about 50%, 55%, 60%, 65%, 70%, 75%, 80%, 85%, 90%, 95%, or 97% identical to a nucleotide sequence of any one of SEQ ID NOs: 1-3, 10, and 18.

The antibody region may comprise at least a portion of a variable domain. The antibody region may comprise one or more variable domains or portions thereof. The antibody region may comprise 2, 3, 4, 5 or more variable domains or portions thereof. The antibody region may comprise an amino acid sequence comprising 10, 20, 30, 40, 50, 60, 70, 80, 90, 100, 120, 140, 160, 180, 200, 225, 250, 275, 300, 350, 400, 500 or more amino acids based on or derived from an amino acid sequence of one or more variable domains. The amino acids may be consecutive. The amino acids may be non-consecutive.

The antibody region may comprise at least a portion of a constant domain. The antibody region may comprise one or more constant domains or portions thereof. The antibody region may comprise 2, 3, 4, 5, 6, 7, 8, 9, 10 or more constant domains or portions thereof. The antibody region may comprise an amino acid sequence comprising 10, 20, 30, 40, 50, 60, 70, 80, 90, 100, 120, 140, 160, 180, 200, 225, 250, 275, 300, 350, 400, 500, 600, 700, 800, 900, 1000, 1200, 1400 or more amino acids based on or derived from an amino acid sequence of one or more constant domains. The amino acids may be consecutive. The amino acids may be non-consecutive.

The antibody region may comprise at least a portion of a complementarity-determining region (CDR). The antibody region may comprise one or more complementarity-determining regions (CDRs) or portions thereof. The antibody region may comprise 2, 3, 4, 5 or more complementarity-determining regions (CDRs) or portions thereof. The antibody region may comprise 6, 7, 8 or more complementarity-determining regions (CDRs) or portions thereof. The antibody region may comprise four or more complementarity-determining regions (CDRs) or portions thereof. The antibody region may comprise 9, 10, 11 or more complementarity-determining regions (CDRs) or portions thereof. The one or more CDRs may be CDR1, CDR2, CDR3 or a combination thereof. The one or more CDRs may be CDR1. The one or more CDRs may be CDR2. The one or more CDRs may be CDR3. The CDR may be a heavy chain CDR. The one or more CDRs may be a light chain CDR.

The antibody region may comprise an amino acid sequence comprising 1, 2, 3, 4, 5, 6, 7, 8, 9, 10 or more amino acids based on or derived from an amino acid sequence of a CDR. The antibody region may comprise an amino acid sequence comprising 3 or more amino acids based on or derived from an amino acid sequence of a CDR. The antibody region may comprise an amino acid sequence comprising 5 or more amino acids based on or derived from an amino acid sequence of a CDR. The antibody region may comprise an amino acid sequence comprising 10 or more amino acids based on or derived from an amino acid sequence of a CDR. The amino acids may be consecutive. The amino acids may be non-consecutive.

The antibody region may be based on or derived from at least a portion of an anti-T cell receptor immunoglobulin. The antibody region may be based on or derived from at least a portion of an anti-B cell receptor immunoglobulin.

The antibody region may be based on or derived from at least a portion of an anti-T cell co-receptor immunoglobulin. The antibody region may be based on or derived from at least a portion of an anti-CD3 immunoglobulin. The antibody region may be based on or derived from an anti-CD3 immunoglobulin. The anti-CD3 immunoglobulin may be UCHT1. The antibody region may be based on or derived from at least a portion of a Fab fragment of an anti-CD3 immunoglobulin. The antibody region may be based on or derived from an immunoglobulin fragment of an anti-CD3 immunoglobulin.

The antibody region may be based on or derived from an immunoglobulin or immunoglobulin fragment that binds to at least a portion of a receptor on a cell. The antibody region may be based on or derived from an immunoglobulin or immunoglobulin fragment that binds to at least a portion of a co-receptor on a cell. The antibody region may be based on or derived from an immunoglobulin or immunoglobulin fragment that binds to at least a portion of an antigen or cell surface marker on a cell. The cell may be a hematopoietic cell. The hematopoietic cell may be a myeloid cell. The myeloid cell may be an erythrocyte, thrombocyte, neutrophil, monocyte, macrophage, eosinophil, basophil, or mast cell. The hematopoietic cell may be a lymphoid cell. The lymphoid cell may be a B-cell, T-cell, or NK-cell. The hematopoietic cell may be a leukocyte. The hematopoietic cell may be a lymphocyte.

The antibody region may be based on or derived from an immunoglobulin or immunoglobulin fragment that binds to at least a portion of a receptor on a T-cell. The receptor may be a T-cell receptor (TCR). The TCR may comprise TCR alpha, TCR beta, TCR gamma and/or TCR delta. The receptor may be a T-cell receptor zeta.

The antibody region may be based on or derived from an immunoglobulin or immunoglobulin fragment that binds to at least a portion of a receptor on a lymphocyte, B-cell, macrophage, monocytes, neutrophils and/or NK cells. The receptor may be an Fc receptor. The Fc receptor may be an Fc-gamma receptor, Fc-alpha receptor and/or Fc-epsilon receptor. Fc-gamma receptors include, but are not limited to, FcγRI (CD64), FcγRIIA (CD32), FcγRIIB (CD32), FcγRIIIA (CD16a) and FcγRIIIB (CD16b). Fc-alpha receptors include, but are not limited to, FcαRI. Fc-epsilon receptors include, but are not limited to, FcεRI and FcεRII. The receptor may be CD89 (Fc fragment of IgA receptor or FCAR).

The antibody region may be based on or derived from an immunoglobulin or immunoglobulin fragment that binds at least a portion of a co-receptor on a T-cell. The co-receptor may be a CD3, CD4, and/or CD8. The antibody region may be based on or derived from an immunoglobulin fragment that binds to a CD3 co-receptor. The CD3 co-receptor may comprise CD3-gamma, CD3-delta and/or CD3-epsilon. CD8 may comprise CD8-alpha and/or CD8-beta chains.

In some embodiments, the antibody region is not specific for a mammalian target. In some embodiments, the immunoglobulin is an anti-viral immunoglobulin. In some embodiments, the immunoglobulin is an anti-bacterial immunoglobulin. In some embodiments, the immunoglobulin is an anti-parasitic immunoglobulin. In some embodiments, the immunoglobulin is an anti-fungal immunoglobulin. In some embodiments, the antibody region is derived from an immunoglobulin vaccine.

In some embodiments, the antibody region is based on or derived from immunoglobulins including, but not limited to, actoxumab, bezlotoxumab, CR6261, edobacomab, efungumab, exbivirumab, felvizumab, foravirumab, ibalizumab (TMB-355, TNX-355), libivirumab, motavizumab, nebacumab, pagibaximab, palivizumab, panobacumab, rafivirumab, raxibacumab, regavirumab, sevirumab (MSL-109), suvizumab, tefibazumab, tuvirumab, and urtoxazumab.

In some embodiments, the antibody region is based on or derived from immunoglobulins targeting *Clostridium difficile*, Orthomyxoviruses (Influenzavirus A, Influenzavirus B, Influenzavirus C, Isavirus, Thogotovirus), *Escherichia coli*, *Candida*, Rabies, Human Immunodeficiency Virus, Hepatitis, *Staphylococcus*, Respiratory Syncytial Virus, *Pseudomonas aeruginosa*, *Bacillus anthracis*, Cytomegalovirus, or *Staphylococcus aureus*.

The antibody region may be based on or derived from an anti-viral immunoglobulin. The anti-viral immunoglobulin may be directed against an epitope of a viral protein. The anti-bacterial immunoglobulin may target one or more viruses including, but not limited to, Adenoviruses, Herpesviruses, Poxviruses, Parvoviruses, Reoviruses, Picornaviruses, Togaviruses, Orthomyxoviruses, Rhabdoviruses, Retroviruses and Hepadnaviruses. The viral protein may be from a respiratory syncytial virus. The viral protein may be an F protein of the respiratory syncytiral virus. The epitope may be in the A antigenic site of the F protein. The anti-viral immunoglobulin may be based on or derived from palivizumab. The immunoglobulin may be based on or derived from an anti-viral vaccine. The anti-viral immunoglobulin may be based on or derived from exbivirumab, foravirumab, libivirumab, rafivirumab, regavirumab, sevirumab, tuvirumab, felvizumab, motavizumab, palivizumab, and/or suvizumab.

The antibody region may be based on or derived from an anti-viral immunoglobulin G. The antibody region may comprise at least a portion of an anti-viral immunoglobulin G. The antibody region may comprise an amino acid sequence that is at least about 50% homologous to at least a portion of an anti-viral immunoglobulin G. The antibody region may comprise an amino acid sequence that is at least about 60%, 65%, 70%, 75%, 80%, 85%, 90%, 92%, 95%, or 97% or more homologous to at least a portion of an anti-viral immunoglobulin G. The antibody region may comprise an amino acid sequence that is at least about 70% homologous to at least a portion of an anti-viral immunoglobulin G. The antibody region may comprise an amino acid sequence that is at least about 80% homologous to at least a portion of an anti-viral immunoglobulin G. In some embodiments the antibody region comprises an amino acid sequence based on or derived from an anti-viral immunoglobulin M.

The antibody region may comprise an amino acid sequence that comprises 10, 20, 30, 40, 50, 60, 70, 80, 90 or more amino acids of an anti-viral immunoglobulin G sequence. The antibody region may comprise an amino acid sequence that comprises 100, 200, 300, 400, 500, 600, 700, 800, 900 or more amino acids of an anti-viral immunoglobulin G sequence. The antibody region may comprise an amino acid sequence that comprises 50 or more amino acids of an anti-viral immunoglobulin G sequence. The antibody region may comprise an amino acid sequence that comprises 100 or more amino acids of an anti-viral immunoglobulin G sequence. The antibody region may comprise an amino acid sequence that comprises 200 or more amino acids of an anti-viral immunoglobulin G sequence.

The antibody region may be based on or derived from a palivizumab immunoglobulin. The antibody region may comprise at least a portion of a palivizumab immunoglobulin. The antibody region may comprise an amino acid sequence that is at least about 50% homologous to at least a portion of a palivizumab immunoglobulin. The antibody region may comprise an amino acid sequence that is at least about 60%, 65%, 70%, 75%, 80%, 85%, 90%, 92%, 95%, or 97% or more homologous to at least a portion of a palivizumab immunoglobulin. The antibody region may comprise an amino acid sequence that is at least about 70% homologous to at least a portion of a palivizumab immunoglobulin. The antibody region may comprise an amino acid sequence that is at least about 80% homologous to at least a portion of a palivizumab immunoglobulin.

The antibody region may comprise an amino acid sequence that comprises 10, 20, 30, 40, 50, 60, 70, 80, 90 or more amino acids of a palivizumab immunoglobulin sequence. The antibody region may comprise an amino acid sequence that comprises 100, 200, 300, 400, 500, 600, 700, 800, 900 or more amino acids of a palivizumab immunoglobulin sequence. The antibody region may comprise an amino acid sequence that comprises 50 or more amino acids of a palivizumab immunoglobulin sequence. The antibody region may comprise an amino acid sequence that comprises 100 or more amino acids of a palivizumab immunoglobulin sequence. The antibody region may comprise an amino acid sequence that comprises 200 or more amino acids of a palivizumab immunoglobulin sequence.

The antibody region may be based on or derived from an exbivirumab, foravirumab, libivirumab, rafivirumab, regavirumab, sevirumab, tuvirumab, felvizumab, motavizumab, palivizumab, and/or suvizumab immunoglobulin. The antibody region may comprise at least a portion of an exbivirumab, foravirumab, libivirumab, rafivirumab, regavirumab, sevirumab, tuvirumab, felvizumab, motavizumab, palivizumab, and/or suvizumab immunoglobulin. The antibody region may comprise an amino acid sequence that is at least about 50% homologous to at least a portion of an exbivirumab, foravirumab, libivirumab, rafivirumab, regavirumab, sevirumab, tuvirumab, felvizumab, motavizumab, palivizumab, and/or suvizumab immunoglobulin. The antibody region may comprise an amino acid sequence that is at least about 60%, 65%, 70%, 75%, 80%, 85%, 90%, 92%, 95%, or 97% or more homologous to at least a portion of an exbivirumab, foravirumab, libivirumab, rafivirumab, regavirumab, sevirumab, tuvirumab, felvizumab, motavizumab, palivizumab, and/or suvizumab immunoglobulin. The antibody region may comprise an amino acid sequence that is at least about 70% homologous to at least a portion of an exbivirumab, foravirumab, libivirumab, rafivirumab, regavirumab, sevirumab, tuvirumab, felvizumab, motavizumab, palivizumab, and/or suvizumab immunoglobulin. The antibody region may comprise an amino acid sequence that is at least about 80% homologous to at least a portion of an exbivirumab, foravirumab, libivirumab, rafivirumab, regavirumab, sevirumab, tuvirumab, felvizumab, motavizumab, palivizumab, and/or suvizumab immunoglobulin.

The antibody region may comprise an amino acid sequence that comprises 10, 20, 30, 40, 50, 60, 70, 80, 90 or more amino acids of an exbivirumab, foravirumab, libivirumab, rafivirumab, regavirumab, sevirumab, tuvirumab, felvizumab, motavizumab, palivizumab, and/or suvizumab immunoglobulin sequence. The antibody region may comprise an amino acid sequence that comprises 100, 200, 300, 400, 500, 600, 700, 800, 900 or more amino acids of an exbivirumab, foravirumab, libivirumab, rafivirumab, regavirumab, sevirumab, tuvirumab, felvizumab, motavizumab, palivizumab, and/or suvizumab immunoglobulin sequence. The antibody region may comprise an amino acid sequence that comprises 50 or more amino acids of an exbivirumab, foravirumab, libivirumab, rafivirumab, regavirumab, sevirumab, tuvirumab, felvizumab, motavizumab, palivizumab, and/or suvizumab immunoglobulin sequence. The antibody region may comprise an amino acid sequence that comprises 100 or more amino acids of an exbivirumab, foravirumab, libivirumab, rafivirumab, regavirumab, sevirumab, tuvirumab, felvizumab, motavizumab, palivizumab, and/or suvizumab immunoglobulin sequence. The antibody region may comprise an amino acid sequence that comprises 200 or more amino acids of an exbivirumab, foravirumab, libivirumab, rafivirumab, regavirumab, sevirumab, tuvirumab, felvizumab, motavizumab, palivizumab, and/or suvizumab immunoglobulin sequence.

The antibody region may be based on or derived from an anti-bacterial immunoglobulin. The anti-bacterial immunoglobulin may be directed against an epitope of a bacterial protein. The anti-bacterial immunoglobulin may target bacteria including, but not limited to, *Acetobacter aurantius, Agrobacterium radiobacter, Anaplasma phagocytophilum, Azorhizobium caulinodans, Bacillus anthracis, Bacillus brevis, Bacillus cereus, Bacillus subtilis, Bacteroides fragilis, Bacteroides gingivalis, Bacteroides melaninogenicus, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae, Chlamydophila psittaci, Clostridium botulinum, Clostridium difficile, Corynebacterium diphtheriae, Corynebacterium fusiforme, Coxiella burnetii, Enterobacter cloacae, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus influenzae, Haemophilus parainfluenzae,*

*Haemophilus pertussis, Haemophilus vaginalis, Helicobacter pylori, Klebsiella pneumoniae, Lactobacillus acidophilus, Lactococcus lactis, Legionella pneumophila, Listeria monocytogenes, Methanobacterium extroquens, Microbacterium multiforme, Micrococcus luteus, Moraxella catarrhalis, Mycobacterium phlei, Mycobacterium smegmatis, Mycobacterium tuberculosis, Mycoplasma genitalium, Mycoplasma hominis, Mycoplasma pneumonie, Neisseria gonorrhoeae, Neisseria meningitidis, Pasteurella multocida, Pasteurella tularensis, Peptostreptococcus, Porphyromonas gingivalis, Prevotella melaninogenica, Pseudomonas aeruginosa, Rhizobium radiobacter, Rickettsia rickettsii, Rothia dentocariosa, Salmonella enteritidis, Salmonella typhi, Salmonella typhimurium, Shigella dysenteriae, Staphylococcus aureus, Staphylococcus epidermidis, Stenotrophomonas maltophilia, Streptococcus pneumoniae, Streptococcus pyogenes, Treponema pallidum, Treponema denticola, Vibrio cholerae, Vibrio comma, Vibrio parahaemolyticus, Vibrio vulnificus, Yersinia enterocolitica* and *Yersinia pseudotuberculosis*. The immunoglobulin may be based on or derived from a bacterial vaccine. The anti-viral immunoglobulin may be based on or derived from nebacumab, panobacumab, raxibacumab, edobacomab, pagibaximab, and/or tefibazumab.

The antibody region may be based on or derived from an anti-bacterial immunoglobulin G. The antibody region may comprise at least a portion of an anti-bacterial immunoglobulin G. The antibody region may comprise an amino acid sequence that is at least about 50% homologous to at least a portion of an anti-bacterial immunoglobulin G. The antibody region may comprise an amino acid sequence that is at least about 60%, 65%, 70%, 75%, 80%, 85%, 90%, 92%, 95%, or 97% or more homologous to at least a portion of an anti-bacterial immunoglobulin G. The antibody region may comprise an amino acid sequence that is at least about 70% homologous to at least a portion of an anti-bacterial immunoglobulin G. The antibody region may comprise an amino acid sequence that is at least about 80% homologous to at least a portion of an anti-bacterial immunoglobulin G. In some embodiments the antibody region comprises an amino acid sequence based on or derived from an anti-viral immunoglobulin M.

The antibody region may comprise an amino acid sequence that comprises 10, 20, 30, 40, 50, 60, 70, 80, 90 or more amino acids of an anti-bacterial immunoglobulin G sequence. The antibody region may comprise an amino acid sequence that comprises 100, 200, 300, 400, 500, 600, 700, 800, 900 or more amino acids of an anti-bacterial immunoglobulin G sequence. The antibody region may comprise an amino acid sequence that comprises 50 or more amino acids of an anti-bacterial immunoglobulin G sequence. The antibody region may comprise an amino acid sequence that comprises 100 or more amino acids of an anti-bacterial immunoglobulin G sequence. The antibody region may comprise an amino acid sequence that comprises 200 or more amino acids of an anti-bacterial immunoglobulin G sequence.

The antibody region may be based on or derived from a Nebacumab, Panobacumab, Raxibacumab, Edobacomab, Pagibaximab, and/or Tefibazumab immunoglobulin. The antibody region may comprise at least a portion of a nebacumab, panobacumab, raxibacumab, edobacomab, pagibaximab, and/or tefibazumab immunoglobulin. The antibody region may comprise an amino acid sequence that is at least about 50% homologous to at least a portion of a nebacumab, panobacumab, raxibacumab, edobacomab, pagibaximab, and/or tefibazumab immunoglobulin. The antibody region may comprise an amino acid sequence that is at least about 60%, 65%, 70%, 75%, 80%, 85%, 90%, 92%, 95%, or 97% or more homologous to at least a portion of a nebacumab, panobacumab, raxibacumab, edobacomab, pagibaximab, and/or tefibazumab immunoglobulin. The antibody region may comprise an amino acid sequence that is at least about 70% homologous to at least a portion of a nebacumab, panobacumab, raxibacumab, edobacomab, pagibaximab, and/or tefibazumab immunoglobulin. The antibody region may comprise an amino acid sequence that is at least about 80% homologous to at least a portion of a nebacumab, panobacumab, raxibacumab, edobacomab, pagibaximab, and/or tefibazumab immunoglobulin.

The antibody region may comprise an amino acid sequence that comprises 10, 20, 30, 40, 50, 60, 70, 80, 90 or more amino acids of a nebacumab, panobacumab, raxibacumab, edobacomab, pagibaximab, and/or tefibazumab immunoglobulin sequence. The antibody region may comprise an amino acid sequence that comprises 100, 200, 300, 400, 500, 600, 700, 800, 900 or more amino acids of a nebacumab, panobacumab, raxibacumab, edobacomab, pagibaximab, and/or tefibazumab immunoglobulin sequence. The antibody region may comprise an amino acid sequence that comprises 50 or more amino acids of a nebacumab, panobacumab, raxibacumab, edobacomab, pagibaximab, and/or tefibazumab immunoglobulin sequence. The antibody region may comprise an amino acid sequence that comprises 100 or more amino acids of a nebacumab, panobacumab, raxibacumab, edobacomab, pagibaximab, and/or tefibazumab immunoglobulin sequence. The antibody region may comprise an amino acid sequence that comprises 200 or more amino acids of a nebacumab, panobacumab, raxibacumab, edobacomab, pagibaximab, and/or tefibazumab immunoglobulin sequence.

The antibody region may be based on or derived from an anti-parasitic immunoglobulin. The anti-parasitic immunoglobulin may be directed against an epitope of a parasite protein. The anti-parasitic immunoglobulin may target parasites or parasite proteins including, but not limited to parasites *Acanthamoeba, Balamuthia mandrillaris, Babesia (B. divergens, B. bigemina, B. equi, B. microfti, B. duncani), Balantidium coli, Blastocystis, Cryptosporidium, Dientamoeba fragilis, Entamoeba histolytica, Giardia lamblia, Isospora belli, Leishmania, Naegleria fowleri, Plasmodium falciparum, Plasmodium vivax, Plasmodium ovale curtisi, Plasmodium ovale* wallikeri, *Plasmodium malariae, Plasmodium knowlesi, Rhinosporidium seeberi, Sarcocystis bovihominis, Sarcocystis suihominis, Toxoplasma gondii, Trichomonas vaginalis, Trypanosoma brucei, Trypanosoma cruzi, Cestoda, Taenia multiceps, Diphyllobothrium latum, Echinococcus granulosus, Echinococcus multilocularis, Echinococcus vogeli, Echinococcus oligarthrus, Hymenolepis nana, Hymenolepis diminuta, Taenia saginata, Taenia solium, Bertiella mucronata, Bertiella studeri, Spirometra erinaceieuropaei, Clonorchis sinensis; Clonorchis viverrini, Dicrocoelium dendriticum, Fasciola hepatica, Fasciola gigantica, Fasciolopsis buski, Gnathostoma spinigerum, Gnathostoma hispidum, Metagonimus yokogawai, Opisthorchis viverrini, Opisthorchis felineus, Clonorchis sinensis, Paragonimus westermani; Paragonimus africanus; Paragonimus caliensis; Paragonimus kellicotti; Paragonimus skrjabini; Paragonimus uterobilateralis, Schistosoma* sp., *Schistosoma mansoni, Schistosoma haematobium, Schistosoma japonicum, Schistosoma mekongi, Echinostoma echinatum, Trichobilharzia regenti,* Schistosomatidae, *Ancylostoma duodenale, Necator americanus, Angiostrongylus costaricensis, Anisakis, Ascaris* sp. *Ascaris lumbricoides,*

*Baylisascaris procyonis, Brugia malayi, Brugia timori, Dioctophyme renale, Dracunculus medinensis, Enterobius vermicularis, Enterobius gregorii, Halicephalobus gingivalis, Loa* filaria, *Mansonella streptocerca, Onchocerca volvulus, Strongyloides stercoralis, Thelazia californiensis, Thelazia callipaeda, Toxocara canis, Toxocara cati, Trichinella spiralis, Trichinella britovi, Trichinella nelsoni, Trichinella nativa, Trichuris trichiura, Trichuris vulpis, Wuchereria bancrofti*, Archiacanthocephala, *Moniliformis moniliformis, Linguatula serrata*, Oestroidea, Calliphoridae, Sarcophagidae, *Tunga penetrans, Dermatobia hominis*, Ixodidae, Argasidae, *Cimex lectularius, Pediculus humanus, Pediculus humanus* corporis, *Pthirus pubis, Demodex folliculorum/brevis/canis, Sarcoptes scabiei, Cochliomyia hominivorax*, and *Pulex irritans*.

The antibody region may be based on or derived from an anti-parasitic immunoglobulin G. The antibody region may comprise at least a portion of an anti-parasitic immunoglobulin G. The antibody region may comprise an amino acid sequence that is at least about 50% homologous to at least a portion of an anti-parasitic immunoglobulin G. The antibody region may comprise an amino acid sequence that is at least about 60%, 65%, 70%, 75%, 80%, 85%, 90%, 92%, 95%, or 97% or more homologous to at least a portion of an anti-parasitic immunoglobulin G. The antibody region may comprise an amino acid sequence that is at least about 70% homologous to at least a portion of an anti-parasitic immunoglobulin G. The antibody region may comprise an amino acid sequence that is at least about 80% homologous to at least a portion of an anti-parasitic immunoglobulin G. In some embodiments the antibody region comprises an amino acid sequence based on or derived from an anti-parasitic immunoglobulin M.

The antibody region may comprise an amino acid sequence that comprises 10, 20, 30, 40, 50, 60, 70, 80, 90 or more amino acids of an anti-parasitic immunoglobulin G sequence. The antibody region may comprise an amino acid sequence that comprises 100, 200, 300, 400, 500, 600, 700, 800, 900 or more amino acids of an anti-parasitic immunoglobulin G sequence. The antibody region may comprise an amino acid sequence that comprises 50 or more amino acids of an anti-parasitic immunoglobulin G sequence. The antibody region may comprise an amino acid sequence that comprises 100 or more amino acids of an anti-parasitic immunoglobulin G sequence. The antibody region may comprise an amino acid sequence that comprises 200 or more amino acids of an anti-parasitic immunoglobulin G sequence.

The antibody region may be based on or derived from an anti-fungal immunoglobulin. The anti-bacterial immunoglobulin may be directed against an epitope of a fungal protein. The anti-fungal immunoglobulin may target fungi or fungal proteins including, but not limited to *Cryptococcus neoformans, Cryptococcus gattii, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Schizosaccharomyces pombe, Saccharomyces cerevisiae, Brettanomyces bruxellensis, Candida stellata, Schizosaccharomyces pombe, Torulaspora delbrueckii, Zygosaccharomyces bailii, Yarrowia lipolytica, Saccharomyces exiguus* and *Pichia pastoris*. The anti-fungal immunoglobulin may be based on or derived from efungumab.

The antibody region may be based on or derived from an anti-fungal immunoglobulin G. The antibody region may comprise at least a portion of an anti-fungal immunoglobulin G. The antibody region may comprise an amino acid sequence that is at least about 50% homologous to at least a portion of an anti-fungal immunoglobulin G. The antibody region may comprise an amino acid sequence that is at least about 60%, 65%, 70%, 75%, 80%, 85%, 90%, 92%, 95%, or 97% or more homologous to at least a portion of an anti-fungal immunoglobulin G. The antibody region may comprise an amino acid sequence that is at least about 70% homologous to at least a portion of an anti-fungal immunoglobulin G. The antibody region may comprise an amino acid sequence that is at least about 80% homologous to at least a portion of an anti-fungal immunoglobulin G. In some embodiments the antibody region comprises an amino acid sequence based on or derived from an anti-fungal immunoglobulin M.

The antibody region may comprise an amino acid sequence that comprises 10, 20, 30, 40, 50, 60, 70, 80, 90 or more amino acids of an anti-fungal immunoglobulin G sequence. The antibody region may comprise an amino acid sequence that comprises 100, 200, 300, 400, 500, 600, 700, 800, 900 or more amino acids of an anti-fungal immunoglobulin G sequence. The antibody region may comprise an amino acid sequence that comprises 50 or more amino acids of an anti-fungal immunoglobulin G sequence. The antibody region may comprise an amino acid sequence that comprises 100 or more amino acids of an anti-fungal immunoglobulin G sequence. The antibody region may comprise an amino acid sequence that comprises 200 or more amino acids of an anti-fungal immunoglobulin G sequence.

The antibody region may be based on or derived from an efungumab immunoglobulin. The antibody region may comprise at least a portion of an efungumab immunoglobulin. The antibody region may comprise an amino acid sequence that is at least about 50% homologous to at least a portion of an efungumab immunoglobulin. The antibody region may comprise an amino acid sequence that is at least about 60%, 65%, 70%, 75%, 80%, 85%, 90%, 92%, 95%, or 97% or more homologous to at least a portion of an efungumab immunoglobulin. The antibody region may comprise an amino acid sequence that is at least about 70% homologous to at least a portion of an efungumab immunoglobulin. The antibody region may comprise an amino acid sequence that is at least about 80% homologous to at least a portion of an efungumab immunoglobulin.

The antibody region may comprise an amino acid sequence that comprises 10, 20, 30, 40, 50, 60, 70, 80, 90 or more amino acids of an efungumab immunoglobulin sequence. The antibody region may comprise an amino acid sequence that comprises 100, 200, 300, 400, 500, 600, 700, 800, 900 or more amino acids of an efungumab immunoglobulin sequence. The antibody region may comprise an amino acid sequence that comprises 50 or more amino acids of an efungumab immunoglobulin sequence. The antibody region may comprise an amino acid sequence that comprises 100 or more amino acids of an efungumab immunoglobulin sequence. The antibody region may comprise an amino acid sequence that comprises 200 or more amino acids of an efungumab immunoglobulin sequence.

The antibody region may be based on or derived from a trastuzumab immunoglobulin G immunoglobulin. The antibody region may comprise at least a portion of a trastuzumab immunoglobulin G immunoglobulin. The antibody region may comprise an amino acid sequence that is at least about 50% homologous to at least a portion of a trastuzumab immunoglobulin G immunoglobulin. The antibody region may comprise an amino acid sequence that is at least about 60%, 65%, 70%, 75%, 80%, 85%, 90%, 92%, 95%, or 97% or more homologous to at least a portion of a trastuzumab immunoglobulin G immunoglobulin. The antibody region may comprise an amino acid sequence that is at least about 70% homologous to at least a portion of a trastuzumab immunoglobulin G immunoglobulin. The antibody region may comprise an amino acid sequence that is at least about 80% homologous to at least a portion of a trastuzumab immunoglobulin G immunoglobulin. The antibody region may comprise a mutated trastuzumab antibody. The antibody region may comprise a trastuzumab antibody that comprises a heptad mutation in the IgG1 heavy chain. The antibody region may comprise a trastuzumab antibody that comprises a triple mutation in the IgG4 heavy chain.

The antibody region may comprise an amino acid sequence that comprises 10, 20, 30, 40, 50, 60, 70, 80, 90 or more amino acids of a trastuzumab immunoglobulin G immunoglobulin sequence. The antibody region may comprise an amino acid sequence that comprises 100, 200, 300, 400, 500, 600, 700, 800, 900 or more amino acids of a trastuzumab immunoglobulin G immunoglobulin sequence. The antibody region may comprise an amino acid sequence that comprises 50 or more amino acids of a trastuzumab immunoglobulin G immunoglobulin sequence. The antibody region may comprise an amino acid sequence that comprises 100 or more amino acids of a trastuzumab immunoglobulin G immunoglobulin sequence. The antibody region may comprise an amino acid sequence that comprises 200 or more amino acids of a trastuzumab immunoglobulin G immunoglobulin sequence.

The antibody region may be based on or derived from an anti-Her2 immunoglobulin. The antibody region may comprise at least a portion of an anti-Her2 immunoglobulin. The antibody region may comprise an amino acid sequence that is at least about 50% homologous to at least a portion of an anti-Her2 immunoglobulin. The antibody region may comprise an amino acid sequence that is at least about 60%, 65%, 70%, 75%, 80%, 85%, 90%, 92%, 95%, or 97% or more homologous to at least a portion of an anti-Her2 immunoglobulin. The antibody region may comprise an amino acid sequence that is at least about 70% homologous to at least a portion of an anti-Her2 immunoglobulin. The antibody region may comprise an amino acid sequence that is at least about 80% homologous to at least a portion of an anti-Her2 immunoglobulin.

The antibody region may comprise an amino acid sequence that comprises 10, 20, 30, 40, 50, 60, 70, 80, 90 or more amino acids of an anti-Her2 immunoglobulin sequence. The antibody region may comprise an amino acid sequence that comprises 100, 200, 300, 400, 500, 600, 700, 800, 900 or more amino acids of an anti-Her2 immunoglobulin sequence. The antibody region may comprise an amino acid sequence that comprises 50 or more amino acids of an anti-Her2 immunoglobulin sequence. The antibody region may comprise an amino acid sequence that comprises 100 or more amino acids of an anti-Her2 immunoglobulin sequence. The antibody region may comprise an amino acid sequence that comprises 200 or more amino acids of an anti-Her2 immunoglobulin sequence.

The antibody region may be based on or derived from an anti-CD47 immunoglobulin. The antibody region may comprise at least a portion of an anti-CD47 immunoglobulin. The antibody region may comprise an amino acid sequence that is at least about 50% homologous to at least a portion of an anti-CD47 immunoglobulin. The antibody region may comprise an amino acid sequence that is at least about 60%, 65%, 70%, 75%, 80%, 85%, 90%, 92%, 95%, or 97% or more homologous to at least a portion of an anti-CD47 immunoglobulin. The antibody region may comprise an amino acid sequence that is at least about 70% homologous to at least a portion of an anti-CD47 immunoglobulin. The antibody region may comprise an amino acid sequence that is at least about 80% homologous to at least a portion of an anti-CD47 immunoglobulin.

The antibody region may comprise an amino acid sequence that comprises 10, 20, 30, 40, 50, 60, 70, 80, 90 or more amino acids of an anti-CD47 immunoglobulin sequence. The antibody region may comprise an amino acid sequence that comprises 100, 200, 300, 400, 500, 600, 700, 800, 900 or more amino acids of an anti-CD47 immunoglobulin sequence. The antibody region may comprise an amino acid sequence that comprises 50 or more amino acids of an anti-CD47 immunoglobulin sequence. The antibody region may comprise an amino acid sequence that comprises 100 or more amino acids of an anti-CD47 immunoglobulin sequence. The antibody region may comprise an amino acid sequence that comprises 200 or more amino acids of an anti-CD47 immunoglobulin sequence.

The antibody region may be based on or derived from an anti-cancer immunoglobulin. Examples of anti-cancer immunoglobulin include, but are not limited to, abciximab, adalimumab, alemtuzumab, basiliximab, belimumab, bevacizumab, brentuximab, canakinumab, certolizumab, cetuximab, daclizumab, denosumab, eculizumab, efalizumab, gemtuzumab, golimumab, ibritumomab, infliximab, ipilimumab, muromonab-cd3, natalizumab, ofatumumab, omalizumab, palivizumab, panitumumab, ranibizumab, rituximab, tocilizumab, tositumomab, trastuzumab.

The antibody region may comprise at least a portion of a human immunoglobulin. The antibody region may comprise at least a portion of a humanized immunoglobulin. The antibody region may comprise at least a portion of a chimeric immunoglobulin. The antibody region may be based on or derived from a human immunoglobulin. The antibody region may be based on or derived from a humanized immunoglobulin. The antibody region may be based on or derived from a chimeric immunoglobulin. The antibody region may be based on or derived from a monoclonal immunoglobulin. The antibody region may be based on or derived from a polyclonal immunoglobulin. The antibody region may comprise at least a portion of an immunoglobulin from a mammal, avian, reptile, amphibian, or a combination thereof. The mammal may be a human. The mammal may be a non-human primate. The mammal may be a dog, cat, sheep, goat, cow, rabbit, or mouse.

The antibody region may comprise a sequence based on or derived from one or more immunoglobulin and/or immunoglobulin fragment sequences. The antibody region may comprise a sequence that is at least about 50%, 55%, 60%, 65%, 70%, 75%, 80%, 85%, 90%, 92%, 95%, 97%, 98%, 99% or more homologous to a sequence based on or derived from one or more immunoglobulin and/or immunoglobulin fragments. The antibody region may comprise a sequence that is at least about 70% homologous to a sequence based on or derived from one or more immunoglobulin and/or immunoglobulin fragments. The antibody region may comprise a sequence that is at least about 80% homologous to a sequence based on or derived from one or more immunoglobulin and/or immunoglobulin fragments. The antibody region may comprise a sequence that is at least about 90% homologous to a sequence based on or derived from one or more immunoglobulin and/or immunoglobulin fragments. The antibody region may comprise a sequence that is at least about 95% homologous to a sequence based on or derived from one or more immunoglobulin and/or immunoglobulin fragments. The sequence may be a peptide sequence. The sequence may be a nucleotide sequence.

The antibody region may comprise a peptide sequence that differs from a peptide sequence based on or derived from one or more immunoglobulin and/or immunoglobulin fragments by less than or equal to about 200, 150, 100, 90, 80, 70, 60, 50, 40, 30, 20, 17, 15, 12, 10, 8, 6, 5, 4 fewer amino acids. The antibody region may comprise a peptide sequence that differs from a peptide sequence based on or derived from one or more immunoglobulin and/or immunoglobulin fragments by less than or equal to about 4 or fewer amino acids. The antibody region may comprise a peptide sequence that differs from a peptide sequence based on or derived from one or more immunoglobulin and/or immunoglobulin fragments by less than or equal to about 3 or fewer amino acids. The antibody region may comprise a peptide sequence that differs from a peptide sequence based on or derived from one or more immunoglobulin and/or immunoglobulin fragments by less than or equal to about 2 or fewer amino acids. The antibody region may comprise a peptide sequence that differs from a peptide sequence based on or derived from one or more immunoglobulin and/or immunoglobulin fragments by less than or equal to about 1 or fewer amino acids. The amino acids may be consecutive, nonconsecutive, or a combination thereof. For example, the antibody region may comprise a peptide sequence that differs from a peptide sequence based on or derived from one or more immunoglobulin and/or immunoglobulin fragments by less than about 3 consecutive amino acids. Alternatively, or additionally, the antibody region may comprise a peptide sequence that differs from a peptide sequence based on or derived from one or more immunoglobulin and/or immunoglobulin fragments by less than about 2 non-consecutive amino acids. In another example, the antibody region may comprise a peptide sequence that differs from a peptide sequence based on or derived from one or more immunoglobulin and/or immunoglobulin fragments by less than about 5 amino acids, wherein 2 of the amino acids are consecutive and 2 of the amino acids are non-consecutive.

The antibody region may comprise a nucleotide sequence that differs from a nucleotide sequence based on or derived from one or more antibodies and/or immunoglobulin fragments by less than or equal to about 500, 400, 300, 200, 100, 90, 80, 70, 60, 50, 40, 30, 25, 20, 19, 18, 17, 16, 15, 14, 13, 12, 11, 10, 9, 8, 7, 6, 5, 4 or fewer nucleotides or base pairs. The antibody region may comprise a nucleotide sequence that differs from a nucleotide sequence based on or derived from one or more immunoglobulin and/or immunoglobulin fragments by less than or equal to about 15 or fewer nucleotides or base pairs. The antibody region may comprise a nucleotide sequence that differs from a nucleotide sequence based on or derived from one or more immunoglobulin and/or immunoglobulin fragments by less than or equal to about 12 or fewer nucleotides or base pairs. The antibody region may comprise a nucleotide sequence that differs from a nucleotide sequence based on or derived from one or more immunoglobulin and/or immunoglobulin fragments by less than or equal to about 9 or fewer nucleotides or base pairs. The antibody region may comprise a nucleotide sequence that differs from a nucleotide sequence based on or derived from one or more immunoglobulin and/or immunoglobulin fragments by less than or equal to about 6 or fewer nucleotides or base pairs. The antibody region may comprise a nucleotide sequence that differs from a nucleotide sequence based on or derived from one or more immunoglobulin and/or immunoglobulin fragments by less than or equal to about 4 or fewer nucleotides or base pairs. The antibody region may comprise a nucleotide sequence that differs from a nucleotide sequence based on or derived from one or more immunoglobulin and/or immunoglobulin fragments by less than or equal to about 3 or fewer nucleotides or base pairs. The antibody region may comprise a nucleotide sequence that differs from a nucleotide sequence based on or derived from one or more immunoglobulin and/or immunoglobulin fragments by less than or equal to about 2 or fewer nucleotides or base pairs. The antibody region may comprise a nucleotide sequence that differs from a nucleotide sequence based on or derived from one or more immunoglobulin and/or immunoglobulin fragments by less than or equal to about 1 or fewer nucleotides or base pairs. The nucleotides or base pairs may be consecutive, nonconsecutive, or a combination thereof. For example, the antibody region may comprise a nucleotide sequence that differs from a nucleotide sequence based on or derived from one or more immunoglobulin and/or immunoglobulin fragments by less than about 3 consecutive nucleotides or base pairs. Alternatively, or additionally, the antibody region may comprise a nucleotide sequence that differs from a nucleotide sequence based on or derived from one or more immunoglobulin and/or immunoglobulin fragments by less than about 2 non-consecutive nucleotides or base pairs. In another example, the antibody region may comprise a nucleotide sequence that differs from a nucleotide sequence based on or derived from one or more immunoglobulin and/or immunoglobulin fragments by less than about 5 nucleotides or base pairs, wherein 2 of the nucleotides or base pairs are consecutive and 2 of the nucleotides or base pairs are non-consecutive.

The peptide sequence of the antibody region may differ from the peptide sequence of the immunoglobulin or immunoglobulin fragment that it is based on and/or derived from by one or more amino acid substitutions. The peptide sequence of the antibody region may differ from the peptide sequence of the immunoglobulin or immunoglobulin fragment that it is based on and/or derived from by two or more amino acid substitutions. The peptide sequence of the antibody region may differ from the peptide sequence of the immunoglobulin or immunoglobulin fragment that it is based on and/or derived from by three or more amino acid substitutions. The peptide sequence of the antibody region may differ from the peptide sequence of the immunoglobulin or immunoglobulin fragment that it is based on and/or derived from by four or more amino acid substitutions. The peptide sequence of the antibody region may differ from the peptide sequence of the immunoglobulin or immunoglobulin fragment that it is based on and/or derived from by five or more amino acid substitutions. The peptide sequence of the antibody region may differ from the peptide sequence of the immunoglobulin or immunoglobulin fragment that it is based on and/or derived from by six or more amino acid substitutions. The peptide sequence of the antibody region may differ from the peptide sequence of the immunoglobulin or immunoglobulin fragment that it is based on and/or derived from by 1, 2, 3, 4, 5, 6, 7, 8, 9, 10, 12, 14, 15, 17, 20, 25 or more amino acid substitutions. The peptide sequence of the antibody region may differ from the peptide sequence of the immunoglobulin or immunoglobulin fragment that it is based on and/or derived from by about 20-30, 30-40, 40-50, 50-60, 60-70, 80-90, 90-100, 100-150, 150-200, 200-300 or more amino acid substitutions.

The nucleotide sequence of the antibody region may differ from the nucleotide sequence of the immunoglobulin or immunoglobulin fragment that it is based on and/or derived from by one or more nucleotide and/or base pair substitutions. The nucleotide sequence of the antibody region may differ from the nucleotide sequence of the immunoglobulin or immunoglobulin fragment that it is based on and/or derived from by two or more nucleotide and/or base pair substitutions. The nucleotide sequence of the antibody region may differ from the nucleotide sequence of the immunoglobulin or immunoglobulin fragment that it is based on and/or derived from by three or more nucleotide and/or base pair substitutions. The nucleotide sequence of the antibody region may differ from the nucleotide sequence of the immunoglobulin or immunoglobulin fragment that it is based on and/or derived from by four or more nucleotide and/or base pair substitutions. The nucleotide sequence of the antibody region may differ from the nucleotide sequence of the immunoglobulin or immunoglobulin fragment that it is based on and/or derived from by five or more nucleotide and/or base pair substitutions. The nucleotide sequence of the antibody region may differ from the nucleotide sequence of the immunoglobulin or immunoglobulin fragment that it is based on and/or derived from by six or more nucleotide and/or base pair substitutions. The nucleotide sequence of the antibody region may differ from the nucleotide sequence of the immunoglobulin or immunoglobulin fragment that it is based on and/or derived from by nine or more nucleotide and/or base pair substitutions. The nucleotide sequence of the antibody region may differ from the nucleotide sequence of the immunoglobulin or immunoglobulin fragment that it is based on and/or derived from by twelve or more nucleotide and/or base pair substitutions. The nucleotide sequence of the antibody region may differ from the nucleotide sequence of the immunoglobulin or immunoglobulin fragment that it is based on and/or derived from by fifteen or more nucleotide and/or base pair substitutions. The nucleotide sequence of the antibody region may differ from the nucleotide sequence of the immunoglobulin or immunoglobulin fragment that it is based on and/or derived from by eighteen or more nucleotide and/or base pair substitutions. The nucleotide sequence of the antibody region may differ from the nucleotide sequence of the immunoglobulin or immunoglobulin fragment that it is based on and/or derived from by 20, 22, 24, 25, 27, 30 or more nucleotide and/or base pair substitutions. The nucleotide sequence of the antibody region may differ from the nucleotide sequence of the immunoglobulin or immunoglobulin fragment that it is based on and/or derived from by about 30-40, 40-50, 50-60, 60-70, 70-80, 80-90, 90-100, 100-200, 200-300, 300-400 or more nucleotide and/or base pair substitutions.

The antibody region may comprise at least about 10, 20, 30, 40, 50, 60, 70, 80, 90, 100 or more amino acids. The antibody region may comprise at least about 125, 150, 175, 200, 225, 250, 275, 300, 325, 350, 375, 400, 425, 450, 475, 500, 525, 550, 575, 600, 625, 650, 675, 700 or more amino acids. The antibody region may comprise at least about 100 amino acids. The antibody region may comprise at least about 200 amino acids. The antibody region may comprise at least about 400 amino acids. The antibody region may comprise at least about 500 amino acids. The antibody region may comprise at least about 600 amino acids.

The antibody region may comprise less than about 2000, 1900, 1800, 1700, 1600, 1500, 1400, 1300, 1200 or 1100 amino acids. The antibody region may comprise less than about 1000, 950, 900, 850, 800, 750, or 700 amino acids. The antibody region may comprise less than about 1500 amino acids. The antibody region may comprise less than about 1000 amino acids. The antibody region may comprise less than about 800 amino acids. The antibody region may comprise less than about 700 amino acids.

The immunoglobulin fusion protein may further comprise an antibody region comprising 30 or fewer consecutive amino acids of a complementarity determining region 3 (CDR3). The antibody region may comprise 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 or fewer consecutive amino acids of a CDR3. The antibody region may comprise 15 or fewer consecutive amino acids of a CDR3. The antibody region may comprise 14 or fewer consecutive amino acids of a CDR3. The antibody region may comprise 13 or fewer consecutive amino acids of a CDR3. The antibody region may comprise 12 or fewer consecutive amino acids of a CDR3. The antibody region may comprise 11 or fewer consecutive amino acids of a CDR3. The antibody region may comprise 10 or fewer consecutive amino acids of a CDR3. The antibody region may comprise 9 or fewer consecutive amino acids of a CDR3. The antibody region may comprise 8 or fewer consecutive amino acids of a CDR3. The antibody region may comprise 7 or fewer consecutive amino acids of a CDR3. The antibody region may comprise 6 or fewer consecutive amino acids of a CDR3. The antibody region may comprise 5 or fewer consecutive amino acids of a CDR3. The antibody region may comprise 4 or fewer consecutive amino acids of a CDR3. The antibody region may comprise 3 or fewer consecutive amino acids of a CDR3. The antibody region may comprise 2 or fewer consecutive amino acids of a CDR3. The antibody region may comprise 1 or fewer consecutive amino acids of a CDR3. In some instances, the antibody region does not contain a CDR3.

The immunoglobulin fusion protein may comprise a first antibody region comprising 6 or fewer consecutive amino acids of a complementarity determining region 3 (CDR3). The first antibody region may comprise 5 or fewer consecutive amino acids of a CDR3. The first antibody region may comprise 4 or fewer consecutive amino acids of a CDR3. The first antibody region may comprise 3 or fewer consecutive amino acids of a CDR3. The first antibody region may comprise 2 or fewer consecutive amino acids of a CDR3. The first antibody region may comprise 1 or fewer consecutive amino acids of a CDR3. In some instances, the first antibody region does not contain a CDR3.

The immunoglobulin fusion protein may further comprise a second antibody region comprising 30 or fewer consecutive amino acids of a complementarity determining region 3 (CDR3). The second antibody region may comprise 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 or fewer consecutive amino acids of a CDR3. The second antibody region may comprise 15 or fewer consecutive amino acids of a CDR3. The second antibody region may comprise 14 or fewer consecutive amino acids of a CDR3. The second antibody region may comprise 13 or fewer consecutive amino acids of a CDR3. The second antibody region may comprise 12 or fewer consecutive amino acids of a CDR3. The second antibody region may comprise 11 or fewer consecutive amino acids of a CDR3. The second antibody region may comprise 10 or fewer consecutive amino acids of a CDR3. The second antibody region may comprise 9 or fewer consecutive amino acids of a CDR3. The second antibody region may comprise 8 or fewer consecutive amino acids of a CDR3. The second antibody region may comprise 7 or fewer consecutive amino acids of a CDR3. The second antibody region may comprise 6 or fewer consecutive amino acids of a CDR3. The second antibody region may comprise 5 or fewer consecutive amino acids of a CDR3. The second antibody region may comprise 4 or fewer consecutive amino acids of a CDR3. The second antibody region may comprise 3 or fewer consecutive amino acids of a CDR3. The second antibody region may comprise 2 or fewer consecutive amino acids of a CDR3. The second antibody region may comprise 1 or fewer consecutive amino acids of a CDR3. In some instances, the second antibody region does not contain a CDR3.

The antibody region may comprise an amino acid sequence that is based on or derived from any one of SEQ ID NOs: 19-36 and 271-273. The antibody region may comprise an amino acid sequence that is at least about 50% homologous to any one of SEQ ID NOs: 19-36 and 271-273. The antibody region may comprise an amino acid sequence that is at least about 60%, 65%, 70%, 75%, 80%, 85%, 90%, 95%, or 97% homologous to any one of SEQ ID NOs 19-36 and 271-273. The antibody region may comprise an amino acid sequence that is at least about 70% homologous to any one of SEQ ID NOs: 19-36 and 271-273. The antibody region may comprise an amino acid sequence that is at least about 80% homologous to any one of SEQ ID NOs: 19-36 and 271-273. The antibody region may comprise an amino acid sequence that is at least about 50% identical to any one of SEQ ID NOs: 19-36 and 271-273. The antibody region may comprise an amino acid sequence that is at least about 60%, 65%, 70%, 75%, 80%, 85%, 90%, 95%, or 97% identical to any one of SEQ ID NOs 19-36 and 271-273. The antibody region may comprise an amino acid sequence that is at least about 70% identical to any one of SEQ ID NOs: 19-36 and 271-273. The antibody region may comprise an amino acid sequence that is at least about 80% identical to any one of SEQ ID NOs: 19-36 and 271-273. The antibody region may comprise an amino acid sequence that is 100% identical to any one of SEQ ID NOs: 19-36 and 271-273. In some embodiments, the antibody region comprises an amino acid sequence that is at least about 50%, 55%, 60%, 65%, 70%, 75%, 80%, 85%, 90%, 95%, or 97% homologous to an amino acid sequence of any one of SEQ ID NOs: 19-36 and 271-273. In some embodiments, the antibody region comprises an amino acid sequence that is at least about 50%, 55%, 60%, 65%, 70%, 75%, 80%, 85%, 90%, 95%, or 97% identical to an amino acid sequence of any one of SEQ ID NOs: 19-36 and 271-273.

The antibody region may comprise an amino acid sequence comprising 10, 20, 30, 40, 50, 60, 70, 80, 90, 100 or more amino acids based on or derived from any one of SEQ ID NOs: 19-36 and 271-273. The antibody region may comprise an amino acid sequence comprising 125, 150, 175, 200, 225, 250, 275, 300, 325, 350, 375, 400, 425, 450, 475, 450, 500 or more amino acids based on or derived from any one of SEQ ID NOs: 19-36 and 271-273. The antibody region may comprise an amino acid sequence comprising 10 or more amino acids based on or derived from any one of SEQ ID NOs: 19-36 and 271-273. The antibody region may comprise an amino acid sequence comprising 50 or more amino acids based on or derived from any one of SEQ ID NOs: 19-36 and 271-273. The antibody region may comprise an amino acid sequence comprising 100 or more amino acids based on or derived from any one of SEQ ID NOs: 19-36 and 271-273. The antibody region may comprise an amino acid sequence comprising 200 or more amino acids based on or derived from any one of SEQ ID NOs: 19-36 and 271-273. The amino acids may be consecutive. Alternatively, or additionally, the amino acids are nonconsecutive. In some embodiments, the antibody region may comprise amino acids derived from any one of SEQ ID NOs: 19-36 and 271-273 and amino acids not derived from any one of SEQ ID NOs: 19-36 and 271-273. In some embodiments, the antibody region may comprise amino acids derived from one or more of SEQ ID NOs: 19-36 and 271-273 and amino acids not derived from any one of SEQ ID NOs: 19-36 and 271-273. In some embodiments, the antibody region comprises amino acids derived from 1, 2, 3, 4, 5, 6, 7, 8, 9, 10 or more of SEQ ID NOs: 19-36 and 271-273.

The antibody region may be encoded by a nucleotide sequence that is based on or derived from any one of SEQ ID NOs: 1-18 and 268-270. The antibody region may be encoded by a nucleotide sequence that is at least about 50% homologous to any one of SEQ ID NOs: 1-18 and 268-270. The antibody region may be encoded by a nucleotide sequence that is at least about 60%, 65%, 70%, 75%, 80%, 85%, 90%, 95%, or 97% homologous to any one of SEQ ID NOs: 1-18 and 268-270. The antibody region may be encoded by a nucleotide sequence that is at least about 70% homologous to any one of SEQ ID NOs: 1-18 and 268-270. The antibody region may be encoded by a nucleotide sequence that is at least about 80% homologous to any one of SEQ ID NOs: 1-18 and 268-270. The antibody region may be encoded by a nucleotide sequence that is at least about 50% identical to any one of SEQ ID NOs: 1-18 and 268-270. The antibody region may be encoded by a nucleotide sequence that is at least about 60%, 65%, 70%, 75%, 80%, 85%, 90%, 95%, or 97% identical to any one of SEQ ID NOs: 1-18 and 268-270. The antibody region may be encoded by a nucleotide sequence that is at least about 70% identical to any one of SEQ ID NOs: 1-18 and 268-270. The antibody region may be encoded by a nucleotide sequence that is at least about 80% identical to any one of SEQ ID NOs: 1-18 and 268-270. The antibody region may be encoded by a nucleotide sequence that is 100% identical to any one of SEQ ID NOs: 1-18 and 268-270.

The antibody region may be encoded by a nucleotide sequence comprising 10, 20, 30, 40, 50, 60, 70, 80, 90, 100 or more nucleotides based on or derived from any one of SEQ ID NOs: 1-18 and 268-270. The antibody region may be encoded by a nucleotide sequence comprising 125, 150, 175, 200, 225, 250, 275, 300, 325, 350, 375, 400, 425, 450, 475, 450, 500 or more nucleotides based on or derived from any one of SEQ ID NOs: 1-18 and 268-270. The antibody region may be encoded by a nucleotide sequence comprising 600, 650, 700, 750, 800, 850, 900, 950, 1000 or more nucleotides based on or derived from any one of SEQ ID NOs: 1-18 and 268-270. The antibody region may be encoded by a nucleotide sequence comprising 1100, 1200, 1300, 1400, 1500 or more nucleotides based on or derived from any one of SEQ ID NOs: 1-18 and 268-270. The antibody region may be encoded by a nucleotide sequence comprising 100 or more nucleotides based on or derived from any one of SEQ ID NOs: 1-18 and 268-270. The antibody region may be encoded by a nucleotide sequence comprising 500 or more nucleotides based on or derived from any one of SEQ ID NOs: 1-18 and 268-270. The antibody region may be encoded by a nucleotide sequence comprising 1000 or more nucleotides based on or derived from any one of SEQ ID NOs: 1-18 and 268-270. The antibody region may be encoded by a nucleotide sequence comprising 1300 or more nucleotides based on or derived from any one of SEQ ID NOs: 1-18 and 268-270. The nucleotides may be consecutive. In some embodiments, the antibody region is encoded by a nucleotide sequence comprising nucleotides derived from any one of SEQ ID NOs: 1-18 and 268-270 and nucleotides not derived from any one of SEQ ID NOs: 1-18 and 268-270. In some embodiments, the antibody region is encoded by a nucleotide sequence comprising nucleotides derived from one or more of SEQ ID NOs: 1-18 and 268-270 and nucleotides not derived from any one of SEQ ID NOs: 1-18 and 268-270. In some embodiments, the antibody region is encoded by a nucleotide sequence derived from 1, 2, 3, 4, 5, 6, 7, 8, 9, 10 or more of SEQ ID NOs: 1-18 and 268-270.

Non-Antibody Region

The immunoglobulin fusion proteins disclosed herein may comprise one or more non-antibody regions. The immunoglobulin fusion proteins disclosed herein may comprise two or more non-antibody regions. The immunoglobulin fusion proteins disclosed herein may comprise 3, 4, 5, 6, 7, 8, 9, 10 or more non-antibody regions.

The two or more non-antibody regions may be attached to one or more antibody regions. The two or more non-antibody regions may be attached to two or more antibody regions. The two or more non-antibody regions may be attached to one or more immunoglobulin chains. The two or more non-antibody regions may be attached to two or more immunoglobulin chains. The two or more non-antibody regions may be attached to one or more subunits within the one or more antibody regions. The two or more non-antibody regions may be attached to two or more subunits within the one or more antibody regions.

The non-antibody regions may comprise one or more therapeutic agents. The non-antibody regions may comprise two or more therapeutic agents. The non-antibody regions may comprise 3, 4, 5, 6, 7 or more therapeutic agents. The therapeutic agents may be different. The therapeutic agents may be the same.

The non-antibody regions may comprise one or more extender peptides. The non-antibody regions may comprise two or more extender peptides. The non-antibody regions may comprise 3, 4, 5, 6, 7 or more extender peptides. The extender peptides may be different. The extender peptides may be the same. In some embodiments, the extender peptide comprises an amino acid sequence having an alpha helical secondary structure. In some embodiments, the extender peptide does not comprise amino acids having a beta strand secondary structure. In some embodiments, the extender fusion region comprises two extender peptides, wherein the two extender peptides are configured to form a coiled coil. In some instances, the non-antibody region does not comprise an extender peptide. The extender peptide may directly connect a therapeutic peptide to an antibody region.

The non-antibody regions may comprise one or more linkers. The non-antibody regions may comprise two or more linkers. The non-antibody regions may comprise 3, 4, 5, 6, 7 or more linkers. The linkers may be different. The linkers may be the same. The linker may directly connect the therapeutic agent to the antibody region. The linker may connect the therapeutic peptide to an extender peptide. In some instances, the non-antibody region does not comprise a linker. In some embodiments, the linker peptide does not comprise amino acids having alpha helical or beta strand secondary structure.

The non-antibody regions may comprise one or more protease cleavage sites. The non-antibody regions may comprise two or more protease cleavage sites. The cleavage sites may be different. The cleavage sites may be the same. The cleavage site may be directly connect the therapeutic agent to the antibody region. The cleavage site may connect the therapeutic agent to a linker peptide. The cleavage site may connect the therapeutic agent to an extender peptide. In some embodiments, the therapeutic agent comprises a protease cleavage site. In some instances, the non-antibody region does not comprise a protease cleavage site.

The extender fusion regions may comprise one or more connecting peptides. A connecting peptide may comprise an extender peptide. A connecting peptide may comprise a linker peptide. A connecting peptide may comprise a protease cleavage site. A connecting peptide may comprise any sequence of amino acids which are configured for connecting a therapeutic agent to an antibody region.

The non-antibody region may be inserted into the antibody region. Insertion of the non-antibody region into the antibody region may comprise removal or deletion of a portion of the antibody from which the antibody region is based on or derived from. The non-antibody region may replace at least a portion of a heavy chain. The non-antibody region may replace at least a portion of a light chain. The non-antibody region may replace at least a portion of a V region. The non-antibody region may replace at least a portion of a D region. The non-antibody region may replace at least a portion of a J region. The non-antibody region may replace at least a portion of a variable region. The non-antibody region may replace at least a portion of a constant region. The non-antibody region may replace at least a portion of a complementarity determining region (CDR). The non-antibody region may replace at least a portion of a CDR1. The non-antibody region may replace at least a portion of a CDR2. The non-antibody region may replace at least a portion of a CDR3. The non-antibody region may replace at least about 5%, 10%, 15%, 20%, 25%, 30%, 35%, 40%, 45%, 50%, 55%, 60%, 65%, 70%, 75%, 80%, 85%, 90%, 95%, or more of the antibody or portion thereof. For example, the non-antibody region may replace at least about 50% of a CDR. The non-antibody region may replace at least about 70% of a CDR. The non-antibody region may replace at least about 80% of a CDR. The non-antibody region may replace at least about 90% of a CDR. The non-antibody region may replace at least about 95% of a CDR.

Non-antibody regions may comprise (a) one or more extender peptides; (b) one or more therapeutic agents; (c) optionally, one or more linkers; and (d) optionally, one or more proteolytic cleavage sites. In some embodiments, the one or more extender peptides comprise amino acid sequences having alpha helical secondary structures. In some instances, an immunoglobulin fusion protein comprising an antibody region and a non-antibody region, wherein the non-antibody region comprises one or more extender peptides comprising amino acids having alpha helical secondary structures, is referred to as a coil immunoglobulin fusion protein.

Non-antibody regions may comprise (a) one or more linker peptides; (b) one or more therapeutic agents; and (c) optionally, one or more proteolytic cleavage sites. In some embodiments, the one or more linker peptides do not comprise amino acid sequences having alpha helical or beta strand secondary structures. In some instances, an immunoglobulin fusion protein comprising an antibody region and a non-antibody region, wherein the one or more linker peptides do not comprise amino acid sequences having alpha helical or beta strand secondary structure, is referred to as a direct immunoglobulin fusion protein.

In some embodiments, a non-antibody region is an extender fusion region.

Extender Fusion Region

The immunoglobulin fusion proteins disclosed herein may comprise one or more extender fusion regions. The immunoglobulin fusion proteins may comprise two or more extender fusion regions. The immunoglobulin fusion proteins may comprise 3, 4, 5, 6, 7, 8, 9, 10 or more extender fusion regions.

The two or more extender fusion regions may be attached to one or more antibody regions. The two or more extender fusion regions may be attached to two or more antibody regions. The two or more extender fusion regions may be attached to one or more immunoglobulin chains. The two or more extender fusion regions may be attached to two or more immunoglobulin chains. The two or more extender fusion regions may be attached to one or more subunits within the one or more antibody regions. The two or more extender fusion regions may be attached to two or more subunits within the one or more antibody regions.

The extender fusion regions may comprise one or more extender peptides. The extender fusion regions may comprise two or more extender peptides. The extender fusion regions may comprise 3, 4, 5, 6 or more extender peptides. The extender peptides may be different. The extender peptides may be the same. In some embodiments, the extender peptide comprises an amino acid sequence having an alpha helical secondary structure. In some embodiments, the extender peptide does not comprise amino acids having a beta strand secondary structure. In some embodiments, the extender fusion region comprises two extender peptides, wherein the two extender peptides are configured to form a coiled coil. In some instances, the extender fusion region does not comprise an extender peptide. In some embodiments, the extender peptide directly connects a therapeutic agent to an antibody region.

The extender fusion regions may comprise one or more therapeutic agents. The extender fusion regions may comprise two or more therapeutic agents. The extender fusion regions may comprise 3, 4, 5, 6, 7 or more therapeutic agents. The therapeutic agents may be different. The therapeutic agents may be the same.

The extender fusion regions may comprise one or more linkers. The extender fusion regions may comprise two or more linkers. The extender fusion regions may comprise 3, 4, 5, 6, 7 or more linkers. The linkers may be different. The linkers may be the same. The linker may connect a therapeutic agent to a an extender peptide. The linker may connect a therapeutic agent directly to an antibody region. In some instances, the extender fusion region does not comprise a linker. In some embodiments, the linker peptide does not comprise amino acids having alpha helical or beta strand secondary structure.

The extender fusion regions may comprise one or more protease cleavage sites. The extender fusion regions may comprise two or more protease cleavage sites. The cleavage sites may be different. The cleavage sites may be the same. The cleavage site may be directly connect the therapeutic agent to the antibody region. The cleavage site may connect a therapeutic agent to an extender peptide. The cleavage site may connect a therapeutic agent to a linker peptide. In some instances, the extender fusion region does not comprise a protease cleavage site.

The extender fusion regions may comprise one or more connecting peptides. A connecting peptide may comprise an extender peptide. A connecting peptide may comprise a linker peptide. A connecting peptide may comprise a protease cleavage site. A connecting peptide may comprise any sequence of amino acids which are configured for connecting a therapeutic agent to an antibody region.

The immunoglobulin fusion proteins disclosed herein may comprise an antibody region attached to an extender fusion region. The extender fusion region may be attached to the N-terminus, C-terminus, or N- and C-terminus of the antibody region. The antibody region may be directly attached to the extender fusion region. Alternatively, or additionally, the antibody region may be indirectly attached to the non-antibody sequence. Attachment of the extender fusion region to the antibody region may comprise covalent attachment. Attachment may comprise fusion of the extender fusion region to the antibody region. Attachment may comprise chemical conjugation.

Alternatively, or additionally, attachment comprises insertion of the extender fusion region into the antibody region. The extender fusion region may be inserted into a heavy chain of the antibody region. The extender fusion region may be inserted into a light chain of the antibody region. The extender fusion region may be inserted into a variable domain of the antibody region. The extender fusion region may be inserted into a constant domain of the antibody region. The extender fusion region may be inserted into a complementarity-determining region (CDR) of the antibody region.

The extender fusion region may replace at least a portion of an antibody from which the antibody region is based on or derived. The extender fusion region may replace at least a portion of a heavy chain of an antibody from which the antibody region may be based on or derived. The extender fusion region may replace at least a portion a light chain of an antibody from which the antibody region may be based on or derived. The extender fusion region may replace at least a portion of a variable domain of an antibody from which the antibody region may be based on or derived. The extender fusion region may replace at least a portion of a variable domain of an antibody from which the antibody region may be based on or derived. The extender fusion region may replace at least a portion of a complementarity-determining region (CDR) of an antibody from which the antibody region may be based on or derived. The extender fusion region may replace at least a portion of a CDR1, CDR2, CDR3, or a combination thereof of an antibody from which the antibody or fragment thereof may be based on or derived. The extender fusion region may replace at least a portion of a CDR3 of an antibody from which the antibody region may be based on or derived.

The extender fusion region may replace at least about 1, 2, 3, 4, 5, 6, 7, 8, 9 or more amino acids of an antibody from which the antibody region is based on or derived. The extender fusion region may replace at least about 1 or more amino acids of an antibody from which the antibody region is based on or derived. The extender fusion region may replace at least about 3 or more amino acids of an antibody from which the antibody region is based on or derived. The extender fusion region may replace at least about 5 or more amino acids of an antibody from which the antibody region is based on or derived.

The extender fusion region may comprise at least about 5, 10, 15, 20, 25, 30, 35, 40, 45, 50, 55, 60, 65, 70, 75, 80, 85, 90, 95, 100 or more amino acids. The extender fusion region may comprise at least about 150, 200, 250, 300, 350, 400, 450, 500, 600, 700, 800, 900, 1000, 1500, 2000 or more amino acids. The extender fusion region may comprise at least about 10 or more amino acids. The extender fusion region may comprise at least about 25 or more amino acids. The extender fusion region may comprise at least about 50 or more amino acids. The extender fusion region may comprise at least about 75 or more amino acids. The extender fusion region may comprise at least about 100 or more amino acids.

The extender fusion region may comprise less than about 2000, 1500, 1000, 900, 800, 700, 600, or 500 amino acids. The extender fusion region may comprise less than about 450, 400, 350, 300, 275, 250, 225, 200, 175, 150, 125, 100, 90, 80, 70, 60, 50 amino acids. The extender fusion region may comprise less than about 400 amino acids. The extender fusion region may comprise less than about 300 amino acids. The extender fusion region may comprise less than about 250 amino acids.

The extender fusion region may comprise between about 10 to about 1000 amino acids. The extender fusion region may comprise between about 10 to about 500 amino acids. The extender fusion region may comprise between about 10 to about 400 amino acids. The extender fusion region may comprise between about 10 to about 300 amino acids. The extender fusion region may comprise between about 10 to about 250 amino acids. The extender fusion region may comprise between about 20 to about 500 amino acids. The extender fusion region may comprise between about 20 to about 400 amino acids. The extender fusion region may comprise between about 20 to about 300 amino acids.

Extender fusion regions may comprise (a) one or more extender peptides; (b) one or more therapeutic agents; (c) optionally, one or more linkers; and (d) optionally, one or more proteolytic cleavage sites. Exemplary extender fusion regions are depicted in FIG. 2A-FIG. 2G. For example, as shown in FIG. 2A, an extender fusion region comprises an extender peptide (210) and a therapeutic agent (220). As shown in FIG. 2B, an extender fusion region comprises two extender peptides (210, 230) and a therapeutic agent (220). As shown in FIG. 2C, an extender fusion region comprises an extender peptide (210) and a therapeutic agent (220) connected by a linker (240). As shown in FIG. 2D, an extender fusion region comprises an extender peptide (210), and therapeutic agent (220) flanked by two linkers (240, 250). As shown in FIG. 2E, an extender fusion region comprises an extender peptide (210), a therapeutic agent (220) and a proteolytic cleavage site (260), wherein the proteolytic cleavage site (260) is inserted between the extender peptide and therapeutic agent. As shown on FIG. 2F, an extender fusion region comprises two extender peptides (210, 230), two linkers (240, 250) and a therapeutic agent (220). As shown on FIG. 2G, an extender fusion region comprises two extender peptides (210, 230), two linkers (240, 250), a proteolytic cleavage site (260) and a therapeutic agent (220).

The extender fusion regions may comprise (a) a first extender peptide, wherein the first extender peptide comprises (i) an amino acid sequence comprising an alpha helix secondary structure; and (ii) 7 or fewer amino acids based on or derived from an ultralong CDR3; and (b) a therapeutic agent. The extender fusion regions may further comprise one or more additional extender peptides comprising at least one secondary structure. The extender fusion regions may further comprise one or more linkers. The extender fusion regions may further comprise one or more proteolytic cleavage sites.

The extender fusion regions may comprise (a) a first extender peptide, wherein the first extender peptide comprises (i) an amino acid sequence comprising an alpha helix secondary structure; and (ii) an amino acid sequence that does not comprise an ultralong CDR3; and (b) a first therapeutic agent. The extender fusion regions may further comprise one or more additional extender peptides comprising at least one secondary structure. The extender fusion regions may further comprise one or more linkers. The extender fusion regions may further comprise one or more proteolytic cleavage sites.

Extender fusion regions may comprise (a) one or more extender peptides; (b) one or more therapeutic agents; (c) optionally, one or more linkers; and (d) optionally, one or more proteolytic cleavage sites. In some embodiments, the one or more extender peptides comprise amino acid sequences having alpha helical secondary structures. In some instances, an immunoglobulin fusion protein comprising an antibody region and an extender fusion region, wherein the extender fusion region comprises one or more extender peptides comprising amino acids having alpha helical secondary structures, is referred to as a coil immunoglobulin fusion protein.

Extender fusion regions may comprise (a) one or more linker peptides; (b) one or more therapeutic agents; and (c) optionally, one or more proteolytic cleavage sites. In some embodiments, the one or more linker peptides do not comprise amino acid sequences having alpha helical or beta strand secondary structures. In some instances, an immunoglobulin fusion protein comprising an antibody region and an extender fusion region, wherein the one or more linker peptides do not comprise amino acid sequences having alpha helical or beta strand secondary structure, is referred to as a direct immunoglobulin fusion protein.

In some embodiments, an extender fusion region does not comprise amino acids based on or derived from an antibody. In some instances, an extender fusion region is a non-antibody region.

Extender Peptide

The immunoglobulin fusion proteins disclosed herein may comprise one or more extender peptides. The immunoglobulin fusion proteins disclosed herein may comprise two or more extender peptides. The one or more extender peptides may be attached to the N-terminus, C-terminus, or N- and C-terminus of a therapeutic agent. The one or more extender peptides may be attached to each end of a therapeutic agent. The one or more extender peptides may be attached to different ends of a therapeutic agent.

The extender fusion region of the immunoglobulin fusion proteins disclosed herein may comprise one or more extender peptides. The extender fusion region may comprise 2 or more extender peptides. The extender fusion region may comprise 3 or more extender peptides. The extender fusion region may comprise 4 or more extender peptides. The extender fusion region may comprise 5 or more extender peptides. The extender fusion region may comprise a first extender peptide and a second extender peptide.

The extender peptide may comprise one or more secondary structures. The extender peptide may comprise two or more secondary structures. The extender peptide may comprise 3, 4, 5, 6, 7 or more secondary structures. The two or more extender peptide may comprise one or more secondary structures. The two or more extender peptides may comprise two or more secondary structures. The two or more extender peptides may comprise 3, 4, 5, 6, 7 or more secondary structures. Each extender peptide may comprise at least one secondary structure. The secondary structures of the two or more extender peptides may be the same. Alternatively, the secondary structures of the two or more extender peptides may be different.

Alternatively, or additionally, the one or more secondary structures may comprise one or more alpha helices. The extender peptides may comprise two or more alpha helices. For example, the first extender peptide comprises a first alpha helix and the second extender peptide comprises a second alpha helix. The extender peptides may comprise 3, 4, 5, 6, 7 or more alpha helices. The two or more alpha helices may be anti-parallel. The two or more alpha helices may be parallel. The two or more alpha helices may form one or more coiled coil domains.

The one or more extender peptides may comprise at least about 1, 2, 3, 4, 5, 6, 7, 8, 9, 10 or more amino acids. The one or more extender peptides may comprise at least about 10, 11, 12, 13, 14, 15, 16, 17, 18, 19, 20, 21, 22, 23, 24, 25, 26, 27, 28, 29, or 30 or more amino acids. The one or more extender peptides may comprise at least about 35, 40, 45, 50, 60, 70, 80, 90, 100 or more amino acids.

The one or more extender peptides may comprise less than about 100 amino acids. The one or more extender peptides may comprise less than about 95, 90, 85, 80, 75, 70, 65, 60, 55, or 50 amino acids. The one or more extender peptides may comprise less than about 90 amino acids. The one or more extender peptides may comprise less than about 80 amino acids. The one or more extender peptides may comprise less than about 70 amino acids.

The two or more extender peptides may be the same length. For example, the first extender peptide and the second extender peptide are the same length. Alternatively, the two or more extender peptides are different lengths. In another example, the first extender peptide and the second extender peptide are different lengths. The two or more extender peptides may differ in length by at least about 1, 2, 3, 4, 5, 6, 7, 8, 9, 10, 11, 12, 13, 14, 15, 16, 17, 18, 19, 20 or more amino acids. The two or more extender peptides may differ in length by at least about 1 or more amino acids. The two or more extender peptides may differ in length by at least about 3 or more amino acids. The two or more extender peptides may differ in length by at least about 5 or more amino acids.

The extender peptide may be adjacent to an antibody region. The extender peptide may be attached to the N-terminus, C-terminus, or N- and C-terminus of the antibody region. The extender peptide may be adjacent to a non-antibody region. The extender peptide may be attached to the N-terminus, C-terminus, or N- and C-terminus of the non-antibody region. The extender peptide may be adjacent to a therapeutic agent. The extender peptide may be attached to the N-terminus, C-terminus, or N- and C-terminus of the therapeutic agent. The extender peptide may be adjacent to a linker. The extender peptide may be attached to the N-terminus, C-terminus, or N- and C-terminus of the linker. The extender peptide may be adjacent to a proteolytic cleavage site. The extender peptide may be attached to the N-terminus, C-terminus, or N- and C-terminus of the proteolytic cleavage site.

The extender peptide may connect the therapeutic agent to the antibody region. The extender peptide may be between the antibody region and the therapeutic agent, linker, and/or proteolytic cleavage site. The extender peptide may be between two or more antibody regions, therapeutic agents, linkers, proteolytic cleavage sites or a combination thereof. The extender peptide may be N-terminal to the antibody region, therapeutic agent, the linker, the proteolytic cleavage site, or a combination thereof. The extender peptide may be C-terminal to the antibody region, therapeutic agent, the linker, the proteolytic cleavage site, or a combination thereof.

The extender peptide may comprise an amino acid sequence that is based on or derived from any one of SEQ ID NOs: 144-175. The extender peptide may comprise an amino acid sequence that is at least about 50% homologous to an amino acid sequence based on or derived from any one of SEQ ID NOs: 144-175. The extender peptide may comprise an amino acid sequence that is at least about 60%, 65%, 70%, 75%, 80%, 85%, 90%, 95%, 97% or more homologous to an amino acid sequence based on or derived from any one of SEQ ID NOs: 144-175. The extender peptide may comprise an amino acid sequence that is at least about 70% homologous to an amino acid sequence based on or derived from any one of SEQ ID NOs: 144-175. The extender peptide may comprise an amino acid sequence that is at least about 80% homologous to an amino acid sequence based on or derived from any one of SEQ ID NOs: 144-175. The extender peptide may comprise an amino acid sequence that is at least about 85% homologous to an amino acid sequence based on or derived from any one of SEQ ID NOs: 144-175.

The first extender peptide may comprise an amino acid sequence that is based on or derived from any one of SEQ ID NOs: 144-175. The first extender peptide may comprise an amino acid sequence that is at least about 50% homologous to an amino acid sequence based on or derived from any one of SEQ ID NOs: 144-175. The first extender peptide may comprise an amino acid sequence that is at least about 60%, 65%, 70%, 75%, 80%, 85%, 90%, 95%, 97% or more homologous to an amino acid sequence based on or derived from any one of SEQ ID NOs: 144-175. The first extender peptide may comprise an amino acid sequence that is at least about 75% homologous to an amino acid sequence based on or derived from any one of SEQ ID NOs: 144-175. The first extender peptide may comprise an amino acid sequence that is at least about 80% homologous to an amino acid sequence based on or derived from any one of SEQ ID NOs: 144-175.

The first extender peptide may comprise an amino acid sequence that is based on or derived from any one of SEQ ID NOs: 144-153. The first extender peptide may comprise an amino acid sequence that is at least about 50% homologous to an amino acid sequence based on or derived from any one of SEQ ID NOs: 144-153. The first extender peptide may comprise an amino acid sequence that is at least about 60%, 65%, 70%, 75%, 80%, 85%, 90%, 95%, 97% or more homologous to an amino acid sequence based on or derived from any one of SEQ ID NOs: 144-153. The first extender peptide may comprise an amino acid sequence that is at least about 75% homologous to an amino acid sequence based on or derived from any one of SEQ ID NOs: 144-153. The first extender peptide may comprise an amino acid sequence that is at least about 80% homologous to an amino acid sequence based on or derived from any one of SEQ ID NOs: 144-153.

The second extender peptide may comprise an amino acid sequence that is based on or derived from any one of SEQ ID NOs: 144-175. The second extender peptide may comprise an amino acid sequence that is at least about 50% homologous to an amino acid sequence based on or derived from any one of SEQ ID NOs: 144-175. The second extender peptide may comprise an amino acid sequence that is at least about 60%, 65%, 70%, 75%, 80%, 85%, 90%, 95%, 97% or more homologous to an amino acid sequence based on or derived from any one of SEQ ID NOs: 144-175. The second extender peptide may comprise an amino acid sequence that is at least about 70% homologous to an amino acid sequence based on or derived from any one of SEQ ID NOs: 144-175. The second extender peptide may comprise an amino acid sequence that is at least about 80% homologous to an amino acid sequence based on or derived from any one of SEQ ID NOs: 144-175.

The second extender peptide may comprise an amino acid sequence that is based on or derived from any one of SEQ ID NOs: 154-163. The second extender peptide may comprise an amino acid sequence that is at least about 50% homologous to an amino acid sequence based on or derived from any one of SEQ ID NOs: 154-163. The second extender peptide may comprise an amino acid sequence that is at least about 60%, 65%, 70%, 75%, 80%, 85%, 90%, 95%, 97% or more homologous to an amino acid sequence based on or derived from any one of SEQ ID NOs: 154-163. The second extender peptide may comprise an amino acid sequence that is at least about 70% homologous to an amino acid sequence based on or derived from any one of SEQ ID NOs: 154-163. The second extender peptide may comprise an amino acid sequence that is at least about 80% homologous to an amino acid sequence based on or derived from any one of SEQ ID NOs: 154-163.

The extender peptides disclosed herein may be based on or derived from a CDR3. The CDR3 may be an ultralong CDR3. An "ultralong CDR3" or an "ultralong CDR3 sequence", used interchangeably herein, may comprise a CDR3 that is not derived from a human antibody sequence. An ultralong CDR3 may be 35 amino acids in length or longer, for example, 40 amino acids in length or longer, 45 amino acids in length or longer, 50 amino acids in length or longer, 55 amino acids in length or longer, or 60 amino acids in length or longer. The ultralong CDR3 may be a heavy chain CDR3 (CDR-H3 or CDRH3). The ultralong CDR3 may comprise a sequence derived from or based on a ruminant (e.g., bovine) sequence. An ultralong CDR3 may comprise one or more cysteine motifs. An ultralong CDR3 may comprise at least 3 or more cysteine residues, for example, 4 or more cysteine residues, 6 or more cysteine residues, or 8 or more cysteine residues. Additional details on ultralong CDR3 sequences can be found in Saini S S, et al. (Exceptionally long CDR3H region with multiple cysteine residues in functional bovine IgM antibodies, *European Journal of Immunology*, 1999), Zhang Y, et al. (Functional antibody CDR3 fusion proteins with enhanced pharmacological properties, *Angew Chem Int Ed Engl*, 2013), Wang F, et al. (Reshaping antibody diversity, Cell, 2013) and U.S. Pat. No. 6,740,747.

The extender peptides may comprise 7 or fewer amino acids based on or derived from a CDR. The extender peptides may comprise 6, 5, 4, 3, 2, 1 or fewer amino acids based on or derived from a CDR. The amino acids may be consecutive. The amino acids may be non-consecutive. The CDR may be CDR1. The CDR may be CDR2. The CDR may be CDR3. The CDR may be an ultralong CDR.

The extender peptides may be based on or derived from a CDR, wherein the CDR is not an ultralong CDR3. The extender peptides may comprise 10 or fewer amino acids based on or derived from a CDR3. The extender peptides may comprise 9, 8, 7, 6, 5, 4, 3, 2, 1 or fewer amino acids based on or derived from a CDR3. The extender peptides may comprise 8 or fewer amino acids based on or derived from a CDR3. The extender peptides may comprise 7 or fewer amino acids based on or derived from a CDR3. The extender peptides may comprise 5 or fewer amino acids based on or derived from a CDR3.

The extender peptides may comprise an amino acid sequence that is less than about 50% identical to an amino acid sequence comprising an ultralong CDR3. The extender peptides may comprise an amino acid sequence that is less than about 45%, 40%, 35%, 30%, 25%, 20%, 25%, or 10% identical to an amino acid sequence comprising an ultralong CDR3. The extender peptides may comprise an amino acid sequence that is less than about 30% identical to an amino acid sequence comprising an ultralong CDR3. The extender peptides may comprise an amino acid sequence that is less than about 25% identical to an amino acid sequence comprising an ultralong CDR3. The extender peptides may comprise an amino acid sequence that is less than about 20% identical to an amino acid sequence comprising an ultralong CDR3.

The extender peptide may comprise 1, 2, 3, 4, 5, 6, 7, 8, 9, 10, 11, 12, 13, 14, 15 or more amino acids attached to or inserted into an ultralong CDR3-based portion of the extender peptide. The extender peptide may comprise 1 or more amino acids attached to or inserted into an ultralong CDR3-based portion of the extender peptide. The extender peptide may comprise 3 or more amino acids attached to or inserted into an ultralong CDR3-based portion of the extender peptide. The extender peptide may comprise 5 or more amino acids attached to or inserted into an ultralong CDR3-based portion of the extender peptide. The two or more amino acids attached to or inserted into the ultralong CDR3 may be contiguous. Alternatively, or additionally, the two or more amino acids attached to or inserted into the ultralong CDR3 are not contiguous.

The extender peptide may comprise 30, 25, 20, 19, 18, 17, 16, 15, 14, 13, 12, 11, 10 or fewer amino acids attached to or inserted into an ultralong CDR3-based portion of the extender peptide. The extender peptide may comprise 20 or fewer amino acids attached to or inserted into an ultralong CDR3-based portion of the extender peptide. The extender peptide may comprise 15 or fewer amino acids attached to or inserted into an ultralong CDR3-based portion of the extender peptide. The extender peptide may comprise 10 or fewer amino acids attached to or inserted into an ultralong CDR3-based portion of the extender peptide. The amino acids attached to or inserted into the ultralong CDR3 may be contiguous. Alternatively, or additionally, the amino acids attached to or inserted into the ultralong CDR3 are not contiguous.

The extender peptide may comprise the sequence $X^1X^2X^3X^4X^5X^6X^7X^8X^9X^{10}X^{11}X^{12}X^{13}X^{14}$ (SEQ ID NO: 144). In some embodiments, a first extender peptide comprises the sequence $X^1X^2X^3X^4X^5X^6X^7X^8X^9X^{10}X^{11}X^{12}X^{13}X^{14}$ (SEQ ID NO: 144). A first extender peptide, in some instances, is located between the amino terminus of a therapeutic agent and an antibody region. $X^1$-$X^{14}$ may be independently selected from a positively charged amino acid or a hydrophobic amino acid. $X^1$-$X^{14}$ may be independently selected from the group comprising alanine (A), asparagine (N), isoleucine (I) leucine (L), valine (V), glutamine (Q), glutamic acid (E) and lysine (K). $X^1$-$X^{14}$ may be independently selected from the group comprising alanine (A), leucine (L) and lysine (K). Alanine may comprise at least about 30% of the total amino acid composition. Alanine may comprise less than about 70% of the total amino acid composition. Leucine may comprise at least about 20% of the total amino acid composition. Leucine may comprise less than about 50% of the total amino acid composition. Lysine may comprise at least about 20% of the total amino acid composition. Lysine may comprise less than about 50% of the total amino acid composition. The hydrophobic amino acids may comprise at least about 50% of the total amino acid composition. The hydrophobic amino acids may comprise at least about 60% of the total amino acid composition. The hydrophobic amino acids may comprise at least about 70% of the total amino acid composition. The hydrophobic amino acids may comprise less than about 90% of the total amino acid composition.

The extender peptide may comprises the sequence $(X^1X^2X^3X^4X^5X^6X^7)_n$ (SEQ ID NO. 145). In some embodiments, a first extender peptide comprises the sequence $(X^1X^2X^3X^4X^5X^6X^7)$ (SEQ ID NO. 145). A first extender peptide, in some instances, is located between the amino terminus of a therapeutic agent and an antibody region. In some embodiments, n is between about 1 and about 10. In some embodiments, n is between about 1 and about 5. In some embodiments, n is 1, 2, 3, 4, 5, 6, 7, 8, 9, 10, or more. N may be from about 1 to about 3. $X^1$-$X^7$ may be independently selected from a positively charged amino acid or a hydrophobic amino acid. $X^1$-$X^7$ may be independently selected from the group comprising alanine (A), asparagine (N), isoleucine, (I), leucine (L), valine (V), glutamine (Q), glutamic acid (E) and lysine (K). Alanine (A) may comprise at least about 30% of the total amino acid composition. Alanine (A) may comprise less than about 70% of the total amino acid composition. Leucine may comprise at least about 20% of the total amino acid composition. Leucine may comprise less than about 50% of the total amino acid composition. Lysine may comprise at least about 20% of the total amino acid composition. Lysine may comprise less than about 50% of the total amino acid composition. Asparagine may comprise about 50% of the total amino acid composition. Isoleucine may comprise about 50% of the total amino acid composition. Valine may comprise about 50% of the total amino acid composition. Glutamine may comprise about 50% of the total amino acid composition. Glutamic acid may comprise about 50% of the total amino acid composition. The hydrophobic amino acids may comprise at least about 50% of the total amino acid composition. The hydrophobic amino acids may comprise at least about 60% of the total amino acid composition. The hydrophobic amino acids may comprise at least about 70% of the total amino acid composition. The hydrophobic amino acids may comprise less than about 90% of the total amino acid composition.

The extender peptide may comprise the sequence $X^aX^bX^cX^d(X^1X^2X^3X^4X^5X^6X^7)_n$ (SEQ ID NO: 146). In some embodiments, a first extender peptide comprises the sequence $X^aX^bX^cX^d(X^1X^2X^3X^4X^5X^6X^7)_n$ (SEQ ID NO: 146). A first extender peptide, in some instances, is located between the amino terminus of a therapeutic agent and an antibody region. In some embodiments, n is between about 1 and about 10. In some embodiments, n is between about 1 and about 5. In some embodiments, n is 1, 2, 3, 4, 5, 6, 7, 8, 9, 10, or more. N may be from about 1 to about 3. $X^a$, $X^b$ and $X^d$ may be independently selected from a hydrophobic amino acid. $X^c$ may be a polar, uncharged amino acid. $X^a$, $X^b$ and $X^d$ may be the same amino acid. $X^a$, $X^b$ and $X^d$ may be different amino acids. $X^1$-$X^7$ may be independently selected from a positively charged amino acid or a hydrophobic amino acid. $X^1$-$X^7$ may be independently selected from the group comprising alanine (A), asparagine (N), isoleucine, (I), leucine (L), valine (V), glutamine (Q), glutamic acid (E) and lysine (K). $X^1$-$X^7$ may be independently selected from the group comprising A, L and K. A may comprise at least about 30% of the total amino acid composition. A may comprise less than about 70% of the total amino acid composition. L may comprise at least about 20% of the total amino acid composition. L may comprise less than about 50% of the total amino acid composition. K may comprise at least about 20% of the total amino acid composition. K may comprise less than about 50% of the total amino acid composition. The hydrophobic amino acids may comprise at least about 50% of the total amino acid composition. The hydrophobic amino acids may comprise at least about 60% of the total amino acid composition. The hydrophobic amino acids may comprise at least about 70% of the total amino acid composition. The hydrophobic amino acids may comprise less than about 90% of the total amino acid composition. In some embodiments, $X^a$ is glycine (G). In some embodiments, $X^b$ is G. In some embodiments, $X^d$ is glycine. $X^a$, $X^b$ and $X^d$ may be glycine (G). $X^c$ may be serine (S).

The extender peptide may comprise the sequence $X^aX^bX^cX^d(AKLAALK)_n$ (SEQ ID NO. 147). In some embodiments, a first extender peptide comprises the sequence $X^aX^bX^cX^d(AKLAALK)_n$ (SEQ ID NO. 147). A first extender peptide, in some instances, is located between the amino terminus of a therapeutic agent and an antibody region. In some embodiments, n is between about 1 and about 10. In some embodiments, n is between about 1 and about 5. In some embodiments, n is 1, 2, 3, 4, 5, 6, 7, 8, 9, 10, or more. N may be from about 1 to about 3. $X^a$, $X^b$ and $X^d$ may be independently selected from a hydrophobic amino acid. $X^c$ may be a polar, uncharged amino acid. $X^a$, $X^b$ and $X^d$ may be the same amino acid. $X^a$, $X^b$ and $X^d$ may be different amino acids. In some embodiments, $X^a$ is glycine (G). In some embodiments, $X^b$ is glycine. In some embodiments, $X^d$ is glycine. $X^a$, $X^b$ and $X^d$ may be glycine (G). X may be serine (S).

The extender peptide may comprise the sequence $(AKLAALK)_n$ (SEQ ID NO. 148). In some embodiments, a first extender peptide comprises the sequence (AKLAALK) (SEQ ID NO. 148). A first extender peptide, in some instances, is located between the amino terminus of a therapeutic agent and an antibody region. In some embodiments, n is between about 1 and about 10. In some embodiments, n is between about 1 and about 5. In some embodiments, n is 1, 2, 3, 4, 5, 6, 7, 8, 9, 10, or more. N may be from about 1 to about 3.

The extender peptide may comprise the sequence GGSG$(AKLAALK)_n$ (SEQ ID NO: 149). In some embodiments, a first extender peptide comprises the sequence GGSG(AKLAALK)$_n$ (SEQ ID NO: 149). A first extender peptide, in some instances, is located between the amino terminus of a therapeutic agent and an antibody region. In some embodiments, n is between about 1 and about 10. In some embodiments, n is between about 1 and about 5. In some embodiments, n is 1, 2, 3, 4, 5, 6, 7, 8, 9, 10, or more. N may be from about 1 to about 3.

The extender peptide may comprise the sequence $X^1X^2X^3X^4X^5X^6X^7X^8X^9X^{10}X^{11}X^{12}X^{13}X^{14}$ (SEQ ID NO: 154); wherein in $X^1$-$X^{14}$ are independently selected from a negatively charged amino acid or a hydrophobic amino acid. In some embodiments, a second extender peptide comprises the sequence $X^1X^2X^3X^4X^5X^6X^7X^8X^9X^{10}X^{11}X^{12}X^{13}X^{14}$ (SEQ ID NO: 154); wherein in $X^1$-$X^{14}$ are independently selected from a negatively charged amino acid or a hydrophobic amino acid. A second extender peptide, in some instances, is located between the carboxyl terminus of a therapeutic agent and an antibody region. In some embodiments, n is between about 1 and about 10. In some embodiments, n is between about 1 and about 5. In some embodiments, n is 1, 2, 3, 4, 5, 6, 7, 8, 9, 10, or more. N may be from about 1 to about 3. In some embodiments, $X^1$-$X^{14}$ are independently selected from the group comprising alanine (A), leucine (L) and glutamic acid (E). In one embodiment, A comprises at least about 30% of the total amino acid composition. In one embodiment, A comprises less than about 70% of the total amino acid composition. In one embodiment, L comprises at least about 20% of the total amino acid composition. In one embodiment, L comprises less than about 50% of the total amino acid composition. In one embodiment, E comprises at least about 20% of the total amino acid composition. In one embodiment, E comprises less than about 50% of the total amino acid composition. In one embodiment, the hydrophobic amino acids comprises at least about 50% of the total amino acid composition. In one embodiment, the hydrophobic amino acids comprises at least about 60% of the total amino acid composition. In one embodiment, the hydrophobic amino acids comprises at least about 70% of the total amino acid composition. In one embodiment, the hydrophobic amino acids comprises less than about 90% of the total amino acid composition.

The second extender peptide may comprise the sequence $(X^1X^2X^3X^4X^5X^6X^7)_n$ (SEQ ID NO: 155). In some embodiments, a second extender peptide comprises the sequence $(X^1X^2X^3X^4X^5X^6X^7)_n$(SEQ ID NO: 155). A second extender peptide, in some instances, is located between the carboxyl terminus of a therapeutic agent and an antibody region. In some embodiments, n is between about 1 and about 10. In some embodiments, n is between about 1 and about 5. In some embodiments, n is 1, 2, 3, 4, 5, 6, 7, 8, 9, 10, or more. N may be from about 1 to about 3. $X^1$-$X^7$ may be independently selected from a positively charged amino acid or a hydrophobic amino acid. $X^1$-$X^7$ may be independently selected from the group comprising alanine (A), asparagine (N), isoleucine, (I), leucine (L), valine (V), glutamine (Q), glutamic acid (E) and lysine (K). Alanine (A) may comprise at least about 30% of the total amino acid composition. Alanine (A) may comprise less than about 70% of the total amino acid composition. Leucine may comprise at least about 20% of the total amino acid composition. Leucine may comprise less than about 50% of the total amino acid composition. Lysine may comprise at least about 20% of the total amino acid composition. Lysine may comprise less than about 50% of the total amino acid composition. Asparagine may comprise about 50% of the total amino acid composition. Isoleucine may comprise about 50% of the total amino acid composition. Valine may comprise about 50% of the total amino acid composition. Glutamine may comprise about 50% of the total amino acid composition. Glutamic acid may comprise about 50% of the total amino acid composition. The hydrophobic amino acids may comprise at least about 50% of the total amino acid composition. The hydrophobic amino acids may comprise at least about 60% of the total amino acid composition. The hydrophobic amino acids may comprise at least about 70% of the total amino acid composition. The hydrophobic amino acids may comprise less than about 90% of the total amino acid composition.

The extender peptide may comprise the sequence $(X^1X^2X^3X^4X^5X^6X^7)_n$ $X^aX^bX^cX^d$ (SEQ ID NO: 156). In some embodiments, a second extender peptide comprises the sequence $(X^1X^2X^3X^4X^5X^6X^7)_n X^aX^bX^cX^d$ (SEQ ID NO: 156). A second extender peptide, in some instances, is located between the carboxyl terminus of a therapeutic agent and an antibody region. In some embodiments, n is between about 1 and about 10. In some embodiments, n is between about 1 and about 5. In some embodiments, n is 1, 2, 3, 4, 5, 6, 7, 8, 9, 10, or more. N may be from about 1 to about 3. $X^1$-$X^7$ may be independently selected from a positively charged amino acid or a hydrophobic amino acid. $X^1$-$X^7$ may be independently selected from the group comprising alanine (A), leucine (L) and lysine (K). A may comprise at least about 30% of the total amino acid composition. A may comprise less than about 70% of the total amino acid composition. L may comprise at least about 20% of the total amino acid composition. L may comprise less than about 50% of the total amino acid composition. K may comprise at least about 20% of the total amino acid composition. K may comprise less than about 50% of the total amino acid composition. The hydrophobic amino acids may comprise at least about 50% of the total amino acid composition. The hydrophobic amino acids may comprise at least about 60% of the total amino acid composition. The hydrophobic amino acids may comprise at least about 70% of the total amino acid composition. The hydrophobic amino acids may comprise less than about 90% of the total amino acid composition. $X^a$, $X^b$ and $X^d$ may be independently selected from a hydrophobic amino acid. $X^c$ may be a polar, uncharged amino acid. $X^a$, $X^b$ and $X^d$ may be the same amino acid. $X^a$, $X^b$ and $X^d$ may different amino acids. In some embodiments, $X^a$ is glycine (G). In some embodiments, $X^b$ is glycine. In some embodiments, $X^d$ is glycine. $X^a$, $X^b$ and $X^d$ may be glycine (G). $X^c$ may be serine (S).

The extender peptide may comprise the sequence (ELAALEA)$_n$ $X^aX^bX^cX^d$ (SEQ ID NO: 157). In some embodiments, a second extender peptide comprises the sequence (ELAALEA)$_n$ $X^aX^bX^cX^d$ (SEQ ID NO: 157). A second extender peptide, in some instances, is located between the carboxyl terminus of a therapeutic agent and an antibody region. In some embodiments, n is between about 1 and about 10. In some embodiments, n is between about 1 and about 5. In some embodiments, n is 1, 2, 3, 4, 5, 6, 7, 8, 9, 10, or more. N may be from about 1 to about 3. $X^a$, $X^b$ and $X^d$ may be independently selected from a hydrophobic amino acid. $X^c$ may be a polar, uncharged amino acid. $X^a$, $X^b$ and $X^d$ may be the same amino acid. $X^a$, $X^b$ and $X^d$ may be different amino acids. In some embodiments, $X^a$ is glycine (G). In some embodiments, $X^b$ is glycine. In some embodiments, $X^d$ is glycine. $X^a$, $X^b$ and $X^d$ may be glycine (G). $X^c$ may be serine (S).

The extender peptide may comprise the sequence (ELAALEA)$_n$(SEQ ID NO: 158). In some embodiments, a second extender peptide comprises the sequence (ELAALEA)$_n$(SEQ ID NO: 158). A second extender peptide, in some instances, is located between the carboxyl terminus of a therapeutic agent and an antibody region. In some embodiments, n is between about 1 and about 10. In some embodiments, n is between about 1 and about 5. In some embodiments, n is 1, 2, 3, 4, 5, 6, 7, 8, 9, 10, or more. N may be from about 1 to about 3.

The extender peptide may comprise the sequence (ELAALEA)$_n$GGSG (SEQ ID NO: 159). In some embodiments, a second extender peptide comprises the sequence (ELAALEA)$_n$GGSG (SEQ ID NO: 159). A second extender peptide, in some instances, is located between the carboxyl terminus of a therapeutic agent and an antibody region. In some embodiments, n is between about 1 and about 10. In some embodiments, n is between about 1 and about 5. In some embodiments, n is 1, 2, 3, 4, 5, 6, 7, 8, 9, 10, or more. N may be from about 1 to about 3.

The immunoglobulin fusion protein may comprise (a) a first extender peptide comprising an amino acid sequence based on or derived from SEQ ID NO: 151; and (b) a second extender peptide comprising an amino acid sequence based on or derived from SEQ ID NO: 161. The immunoglobulin fusion protein may comprise (a) a first extender peptide comprising an amino acid sequence that is at least about 50% homologous to an amino acid sequence of SEQ ID NO: 151; and (b) a second extender peptide comprising an amino acid sequence that is at least about 50% homologous to an amino acid sequence of SEQ ID NO: 161. The first extender peptide may comprise an amino acid sequence that is at least about 60%, 65%, 70%, 75%, 80%, 85%, 90%, 95% or more homologous to an amino acid sequence of SEQ ID NO: 151. The second extender peptide may comprise an amino acid sequence that is at least about 60%, 65%, 70%, 75%, 80%, 85%, 90%, 95% or more homologous to an amino acid sequence of SEQ ID NO: 161. The first extender peptide may comprise an amino acid sequencing comprising 3, 4, 5, 6, 7 or more amino acids based on or derived from an amino acid sequence of SEQ ID NO: 151. The first extender peptide may comprise an amino acid sequencing comprising 5 or more amino acids based on or derived from an amino acid sequence of SEQ ID NO: 151. The second extender peptide may comprise an amino acid sequencing comprising 3, 4, 5, 6, 7 or more amino acids based on or derived from an amino acid sequence of SEQ ID NO: 161. The second extender peptide may comprise an amino acid sequencing comprising 5 or more amino acids based on or derived from an amino acid sequence of SEQ ID NO: 161.

The aliphatic amino acids may comprise at least about 20% of the total amino acids of the extender peptides. The aliphatic amino acids may comprise at least about 22%, 25%, 27%, 30%, 32%, 35%, 37%, 40%, 42%, 45% or more of the total amino acids of the extender peptides. The aliphatic amino acids may comprise at least about 22% of the total amino acids of the extender peptides. The aliphatic amino acids may comprise at least about 27% of the total amino acids of the extender peptides.

The aliphatic amino acids may comprise less than about 50% of the total amino acids of the extender peptides. The aliphatic amino acids may comprise less than about 47%, 45%, 43%, 40%, 38%, 35%, 33% or 30% of the total amino acids of the extender peptides.

The aliphatic amino acids may comprise between about 20% to about 45% of the total amino acids of the extender peptides. The aliphatic amino acids may comprise between about 23% to about 45% of the total amino acids of the extender peptides. The aliphatic amino acids may comprise between about 23% to about 40% of the total amino acids of the extender peptides.

The aromatic amino acids may comprise less than about 20% of the total amino acids of the extender peptides. The aromatic amino acids may comprise less than about 19%, 18%, 17%, 16%, 15%, 14%, 13%, 12%, 11% or 10% of the total amino acids of the extender peptides. The aromatic amino acids may comprise between 0% to about 20% of the total amino acids of the extender peptides.

The non-polar amino acids may comprise at least about 30% of the total amino acids of the extender peptides. The non-polar amino acids may comprise at least about 31%, 32%, 33%, 34%, 35%, 36%, 37%, 38%, 39%, or 40% of the total amino acids of the extender peptides. The non-polar amino acids may comprise at least about 32% of the total amino acids of the extender peptides.

The non-polar amino acids may comprise less than about 80% of the total amino acids of the extender peptides. The non-polar amino acids may comprise less than about 77%, 75%, 72%, 70%, 69%, or 68% of the total amino acids of the extender peptides.

The non-polar amino acids may comprise between about 35% to about 80% of the total amino acids of the extender peptides. The non-polar amino acids may comprise between about 38% to about 80% of the total amino acids of the extender peptides. The non-polar amino acids may comprise between about 38% to about 75% of the total amino acids of the extender peptides. The non-polar amino acids may comprise between about 35% to about 70% of the total amino acids of the extender peptides.

The polar amino acids may comprise at least about 20% of the total amino acids of the extender peptides. The polar amino acids may comprise at least about 22%, 23%, 24%, 25%, 26%, 27%, 28%, 29%, 30%, 35% or more of the total amino acids of the extender peptides. The polar amino acids may comprise at least about 23% of the total amino acids of the extender peptides.

The polar amino acids may comprise less than about 80% of the total amino acids of the extender peptides. The polar amino acids may comprise less than about 77%, 75%, 72%, 70%, 69%, or 68% of the total amino acids of the extender peptides. The polar amino acids may comprise less than about 77% of the total amino acids of the extender peptides. The polar amino acids may comprise less than about 75% of the total amino acids of the extender peptides. The polar amino acids may comprise less than about 72% of the total amino acids of the extender peptides.

The polar amino acids may comprise between about 25% to about 70% of the total amino acids of the extender peptides. The polar amino acids may comprise between about 27% to about 70% of the total amino acids of the extender peptides. The polar amino acids may comprise between about 30% to about 70% of the total amino acids of the extender peptides.

Alternatively, the immunoglobulin fusion proteins disclosed herein do not comprise an extender peptide.

Therapeutic Agent

The immunoglobulin fusion proteins disclosed herein may comprise one or more therapeutic agents. The therapeutic agent may be a peptide. The therapeutic agent may be a small molecule. The immunoglobulin fusion proteins disclosed herein may comprise two or more therapeutic agents. The immunoglobulin fusion proteins disclosed herein may comprise 3, 4, 5, 6 or more therapeutic agents. The two or more therapeutic agents may be the same. The two or more therapeutic agents may be different.

The therapeutic agent may comprise any secondary structure, for example alpha helix or beta strand or comprise no regular secondary structure. The therapeutic agent may comprise amino acids with one or more modifications including, but not limited to, myristoylation, palmitoylation, isoprenylation, glypiation, lipoylation, acylation, acetylation, aklylation, methylation, glycosylation, malonylation, hydroxylation, iodination, nucleotide addition, oxidation, phosphorylation, adenylylation, propionylation, succinylation, sulfation, selenoylation, biotinylation, pegylation, deimination, deamidation, eliminylation, and carbamylation. The therapeutic agent may comprise one or more amino acids conjugated to one or more small molecules, for example a drug. In some embodiments, the therapeutic agent comprises one or more non-natural amino acids. In some embodiments, the therapeutic agent comprises 1, 2, 3, 4, 5, 6, 7, 8, 9, 10, 11, 12, 13, 14, 15, 16, 17, 18, 19, 20, 30, 40, 50 or more non-natural amino acids. In some embodiments, the therapeutic agent comprises one or more amino acids substitutions. In some embodiments, the therapeutic agent comprises 1, 2, 3, 4, 5, 6, 7, 8, 9, 10, 11, 12, 13, 14, 15, 16, 17, 18, 19, 20, 30, 40, 50 or more amino acid substitutions.

The therapeutic agent may be inserted into the immunoglobulin region. Insertion of the therapeutic agent into the immunoglobulin region may comprise removal or deletion of a portion of the immunoglobulin from which the immunoglobulin region is based on or derived from. The therapeutic agent may replace at least a portion of a heavy chain. The therapeutic agent may replace at least a portion of a light chain. The therapeutic agent may replace at least a portion of a variable domain. The therapeutic agent may replace at least a portion of a constant domain. The therapeutic agent may replace at least a portion of a complementarity determining region (CDR). The therapeutic agent may replace at least a portion of a CDR1. The therapeutic agent may replace at least a portion of a CDR2. The therapeutic agent may replace at least a portion of a CDR3. The therapeutic agent may replace at least about 5%, 10%, 15%, 20%, 25%, 30%, 35%, 40%, 45%, 50%, 55%, 60%, 65%, 70%, 75%, 80%, 85%, 90%, 95%, or more of the immunoglobulin or a portion thereof.

The one or more therapeutic agents may be based on or derived from a protein. The protein may be a growth factor, cytokine, hormone or toxin. The growth factor may be GCSF, GMCSF, GDF11 or FGF21. The GCSF may be a bovine GCSF. The GCSF may be a human GCSF. The GMCSF may be a bovine GMCSF or a human GMCSF. The FGF21 may be a bovine FGF21. The FGF21 may be a human FGF21. The protein may be elafin. The protein may be a peptidase inhibitor. The protein may be a skin-derived antileukoprotease (SKALP).

The cytokine may be an interferon or interleukin. The cytokine may be stromal cell-derived factor 1 (SDF-1). The interferon may be interferon-beta. The interferon may be interferon-alpha. The interleukin may be interleukin 11 (IL-11). The interleukin may be interleukin 8 (IL-8) or interleukin 21 (IL-21).

The hormone may be exendin-4, GLP-1, relaxin, oxyntomodulin, hLeptin, betatrophin, bovine growth hormone (bGH), human growth hormone (hGH), erythropoietin (EPO), or parathyroid hormone. The hormone may be somatostatin. The parathyroid hormone may be a human parathyroid hormone. The erythropoietin may be a human erythropoietin.

The toxin may be Moka1, VM24 or Mamba1. The toxin may be ziconotide or chlorotoxin. In one embodiment, the toxin is mu-SLPTX-Ssm6a (Ssam6).

The protein may be angiopoeitin-like 3 (ANGPTL3). The angiopoeitin-like 3 may be a human angiopoeitin-like 3.

The therapeutic agent may be glucagon-like peptide 2 (GLP2).

In some embodiments, the therapeutic agent is a glucagon analog.

In some embodiments, the therapeutic agent is a dual agonist.

In some embodiments, one or more regions of the therapeutic agent is configured to treat diabetes and/or diabetes related conditions. In some embodiments, 2, 3, 4, 5 or more regions of the therapeutic agent are configured to treat diabetes and/or diabetes related conditions. Diabetes may include, type 1 diabetes, type 2 diabetes, gestational diabetes, and prediabetes. In some embodiments, one or more regions of the therapeutic agent is configured to treat obesity and/or obesity related conditions. In some embodiments, 2, 3, 4, 5 or more regions of the therapeutic agent are configured to treat obesity and/or obesity related conditions. Conditions may include complications and diseases. Examples of diabetes related conditions include, but are not limited to, diabetic retinopathy, diabetic nephropathy, diabetic heart disease, diabetic foot disorders, diabetic neuropathy, macrovascular disease, diabetic cardiomyopathy, infection and diabetic ketoacidosis. Diabetic neuropathy may include, but is not limited to symmetric polyneuropathy, autonomic neuropathy, radiculopathy, cranial neuropathy, and mononeuropathy. Obesity related conditions include, but are not limited to, heart disease, stroke, high blood pressure, diabetes, osteoarthritis, gout, sleep apnea, asthma, gallbladder disease, gallstones, abnormal blood fats (e.g., abnormal levels of LDL and HDL cholesterol), obesity hypoventilation syndrome, reproductive problems, hepatic steatosis, and mental health conditions.

In some embodiments, one or more regions of the therapeutic agent is a glucagon-like protein-1 (GLP-1) receptor agonist or formulation thereof. In some embodiments, one or more regions of the therapeutic agent is an incretin mimetic. In some embodiments, one or more regions of the therapeutic agent comprises an amino acid sequence based on or derived from an amino acid sequence of exendin-4, exenatide, or synthetic thereof. In some embodiments, one or more regions of the therapeutic agent is a glucagon analog or formulation thereof. In some embodiments, one or more regions of the therapeutic agent comprises an amino acid sequence based on or derived from an amino acid sequence of insulin. In some embodiments, one or more regions of the therapeutic agent is dual-specific. In some embodiments, the therapeutic agent has specificity for a GLP-1 receptor and a glucagon receptor. In some embodiments, one or more regions of the therapeutic agent comprises an amino acid sequence based on or derived from an amino acid sequence of oxyntomodulin.

In some embodiments, one or more regions of the therapeutic agent is configured to treat short bowel syndrome and/or short bowel syndrome related conditions. In some embodiments, 2, 3, 4, 5 or more regions of the therapeutic agent are configured to treat short bowel syndrome and/or short bowel syndrome related conditions. Short bowel syndrome related conditions may include, but are not limited to, bacterial overgrowth in the small intestine, metabolic acidosis, gallstones, kidney stones, malnutrition, osteomalacia, intestinal failure, and weight loss. In some embodiments, one or more regions of the therapeutic agent is configured to treat inflammatory bowel disease and/or an inflammatory bowel related conditions. In some embodiments, 2, 3, 4, 5 or more regions of the therapeutic agent are configured to treat inflammatory bowel disease and/or an inflammatory bowel related conditions. Inflammatory bowel disease and/or inflammatory bowel disease related conditions may include, but are not limited to, ulcerative colitis, Crohn's disease, collagenous colitis, lymphocytic colitis, ischaemic colitis, diversion colitis, Behcet's disease, intermediate colitis, anemia, arthritis, pyoderma gangrenosum, primary sclerosing cholangitis, non-thyroidal illness syndrome; and abdominal pain, vomiting, diarrhea, rectal bleeding, internal cramps or muscle spasms, and weight loss in individual with an inflammatory bowel disease.

In some embodiments, one or more regions of the therapeutic agent comprises an amino acid sequence based on or derived from an amino acid sequence of glucagon, glucagon analog, glucagon like peptide, and/or a glucagon like peptide analog. In some embodiments, one or more regions of the therapeutic agent comprises an amino acid sequence based on or derived from an amino acid sequence of a glucagon like peptide-2 (GLP2).

In some embodiments, one or more regions of the therapeutic agent is configured to treat an autoimmune disease and/or autoimmune disease related conditions. In some embodiments, 2, 3, 4, 5 or more regions of the therapeutic agent are configured to treat autoimmune disease and/or autoimmune disease related conditions. Autoimmune disease and/or autoimmune disease related conditions may include, but are not limited to, acute disseminated encephalomyelitis, alopecia areata, antiphospholipid syndrome, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendrocrine syndrome, autoimmune progesterone dermatitis, autoimmune thrombocytopenic purpura, autoimmune urticaria, autoimmune uveitis, Behcet's disease, Celiac disease, cold agglutinin disease, Crohn's disease, dermatomyositis, diabetes mellitus type 1, eosinophilic fasciitis, gastrointestinal pemphigoid, Goodpasture's syndrome, Grave's disease, Guillain-Barre syndrome, Hashimoto's encephalopathy, Hashimoto's thyroiditis, idiopathic thrombocytopenic purpura, lupus erythematosus, Miller-Fisher syndrome, mixed connective tissue disease, multiple sclerosis, myasthenia gravis, narcolepsy, pemphigus vulgaris, pernicious anemia, polymyositis, primary biliary cirrhosis, psoriasis, psoriatic arthritis, relapsing polychondritis, rheumatoid arthritis, rheumatic fever, Sjogren's syndrome, temporal arteritis, transverse myelitis, ulcerative colitis, undifferentiated connective tissue disease, vasculitis, and Wegener's granulomatosis.

In some embodiments, one or more regions of the therapeutic agent comprises an amino acid sequence based on or derived from an amino acid sequence which binds to potassium channels. In some embodiments, one or more regions of the therapeutic agent comprises an amino acid sequence based on or derived from an amino acid sequence of a Mokatoxin-1 (Moka).

In some embodiments, one or more regions of the therapeutic agent is configured to treat pain. In some embodiments, 2, 3, 4, 5 or more regions of the therapeutic agent are configured to treat pain.

In some embodiments, one or more regions of the therapeutic agent comprises an amino acid sequence based on or derived from an amino acid sequence which is a neurotoxin. In some embodiments, one or more regions of the therapeutic agent comprises an amino acid sequence based on or derived from an amino acid sequence of a neurotoxin mu-SLPTX-Ssm6a (Ssam6). In some embodiments, one or more regions of the therapeutic agent comprises an amino acid sequence based on or derived from an amino acid sequence of mambalign-1.

In some embodiments, one or more regions of the therapeutic agent is configured to treat heart failure and/or fibrosis. In some embodiments, one or more regions of the therapeutic agent is configured to treat heart failure and/or fibrosis related conditions. In some embodiments, 2, 3, 4, 5 or more regions of the therapeutic agent are configured to treat heart failure and/or fibrosis. In some embodiments, 2, 3, 4, 5 or more regions of the therapeutic agent are configured to treat heart failure and/or fibrosis related conditions. Heart failure related conditions may include coronary heart disease, high blood pressure, diabetes, cardiomyopathy, heart valve disease, arrhythmias, congenital heart defects, obstructive sleep apnea, myocarditis, hyperthyroidism, hypothyroidism, emphysema, hemochromatosis, and amyloidosis. Heart failure may be left-sided heart failure, right-sided heart failure, systolic heart failure, and diastolic heart failure. Fibrosis may include, but is not limited to, pulmonary fibrosis, idiopathic pulmonary fibrosis, cystic fibrosis, cirrhosis, endomyocardial fibrosis, myocardial infarction, atrial fibrosis, mediastinal fibrosis, myelofibrosis, retroperitoneal fibrosis, progressive massive fibrosis, nephrogenic systemic fibrosis, Crohn's disease, keloid, scleroderma/systemic sclerosis, arthrofibrosis, Peyronie's disease, Dupuytren's contracture, and adhesive capsulitis.

In some embodiments, one or more regions of the therapeutic agent comprises an amino acid sequence based on or derived from an amino acid sequence which belongs to the insulin superfamily. In some embodiments, one or more regions of the therapeutic agent comprises an amino acid sequence based on or derived from an amino acid sequence of insulin.

In some embodiments, amino acids of the therapeutic agent, in whole or in part, are based on or derived from any one of SEQ ID NOs: 227-267. The therapeutic agent may comprise an amino acid sequence that is at least about 50% homologous to any one of SEQ ID NOs: 227-267. The therapeutic agent may comprise an amino acid sequence that is at least about 60%, 65%, 70%, 75%, 80%, 85%, 90%, 95%, or 97% homologous to any one of SEQ ID NOs: 227-267. The therapeutic agent may comprise an amino acid sequence that is at least about 70% homologous to any one of SEQ ID NOs: 227-267. The therapeutic agent may comprise an amino acid sequence that is at least about 80% homologous to any one of SEQ ID NOs: 227-267. The therapeutic agent may comprise an amino acid sequence that is at least about 50% identical to any one of SEQ ID NOs: 227-267. The therapeutic agent may comprise an amino acid sequence that is at least about 60%, 65%, 70%, 75%, 80%, 85%, 90%, 95%, or 97% identical to any one of SEQ ID NOs: 227-267. The therapeutic agent may comprise an amino acid sequence that is at least about 70% identical to any one of SEQ ID NOs: 227-267. The therapeutic agent may comprise an amino acid sequence that is at least about 80% identical to any one of SEQ ID NOs: 227-267. The therapeutic agent may comprise an amino acid sequence that is 100% identical to any one of SEQ ID NOs: 227-267. In some embodiments, the therapeutic agent comprises an amino acid sequence that is at least about 50%, 55%, 60%, 65%, 70%, 75%, 80%, 85%, 90%, 95%, or 97% homologous to an amino acid sequence of any one of SEQ ID NOs: 227-267. In some embodiments, the therapeutic agent comprises an amino acid sequence that is at least about 50%, 55%, 60%, 65%, 70%, 75%, 80%, 85%, 90%, 95%, or 97% identical to an amino acid sequence of any one of SEQ ID NOs: 227-267. In some embodiments, the therapeutic agent comprises an amino acid sequence that is 100% identical to an amino acid sequence of any one of SEQ ID NOs: 227-267.

The therapeutic agent may comprise an amino acid sequence comprising 10, 20, 30, 40, 50, 60, 70, 80, 90, 100 or more amino acids based on or derived from any one of SEQ ID NOs: 227-267. The therapeutic agent may comprise an amino acid sequence comprising 125, 150, 175, 200, 225, 250, 275, 300, 325, 350, 375, 400, 425, 450, 475, 450, 500 or more amino acids based on or derived from any one of SEQ ID NOs: 227-267. The therapeutic agent may comprise an amino acid sequence comprising 10 or more amino acids based on or derived from any one of SEQ ID NOs: 227-267. The therapeutic agent may comprise an amino acid sequence comprising 50 or more amino acids based on or derived from any one of SEQ ID NOs: 227-267. The therapeutic agent may comprise an amino acid sequence comprising 100 or more amino acids based on or derived from any one of SEQ ID NOs: 227-267. The therapeutic agent may comprise an amino acid sequence comprising 200 or more amino acids based on or derived from any one of SEQ ID NOs: 227-267. The amino acids may be consecutive. Alternatively, or additionally, the amino acids are nonconsecutive. In some embodiments, the therapeutic agent may comprise amino acids derived from any one of SEQ ID NOs: 227-267 and amino acids not derived from any one of SEQ ID NOs: 227-267. In some embodiments, the therapeutic agent may comprise amino acids derived from one or more of SEQ ID NOs: 227-267 and amino acids not derived from any one of SEQ ID NOs: 227-267. In some embodiments, the therapeutic agent comprises amino acids derived from 1, 2, 3, or 4 of SEQ ID NOs: 227-267.

The therapeutic agent may be encoded by a nucleic acid sequence based on or derived from any one of SEQ ID NOs: 186-226. The therapeutic agent may be encoded by a nucleic acid sequence that may be at least about 50% homologous to any one of SEQ ID NOs: 186-226. The therapeutic agent may be encoded by a nucleic acid sequence that may be at least about 60%, 65%, 70%, 75%, 80%, 85%, 90%, 95% or more homologous to any one of SEQ ID NOs: 186-226. The therapeutic agent may be encoded by a nucleic acid sequence that may be at least about 70% homologous to any one of SEQ ID NOs: 186-226. The therapeutic agent may be encoded by a nucleic acid sequence that may be at least about 80% homologous to any one of SEQ ID NOs: 186-226.

The therapeutic agent may comprise a protease cleavage site. The protease cleavage site may be inserted within the therapeutic agent. In some embodiments, the therapeutic agent comprises a first therapeutic agent region and a second therapeutic agent region. In some embodiments, the therapeutic agent comprises a protease cleavage site disposed between the first therapeutic agent region and the second therapeutic agent region. In some embodiments, the first therapeutic agent region and the second therapeutic agent region are derived from the same protein or set of amino acid sequences. In some embodiments, the first therapeutic agent region and the second therapeutic agent regions are derived from different proteins or sets of amino acid sequences. The one or more protease cleavage sites may be attached to the N-terminus, C-terminus or both the N- and C-termini of a region of a therapeutic agent.

The therapeutic agent may comprise one or more internal linker peptides. The therapeutic agent may comprise two or more internal linker peptides. The therapeutic agent may comprise 3, 4, 5, 6, 7 or more internal linker peptides. The linker peptides may be different. The linker peptides may be the same. The linker peptide may be inserted within the therapeutic agent. In some embodiments, the therapeutic agent comprises a first therapeutic region, a second therapeutic region, an one or more linker peptides positioned between the first therapeutic region and the second therapeutic region. The one or more linker peptides may be attached to the N-terminus, C-terminus or both the N- and C-termini of a region of a therapeutic agent. In some embodiments, the linker peptide is a protease cleavage site. In some embodiments, the linker peptide is a tag, such as an affinity tag. An example of an affinity tag is a 6×(HHHHHH) histidine tag (SEQ ID NO: 274). In some embodiments, the internal linker comprises amino acids having repeating sequences. In some embodiments, the internal linker has 2, 3, 4, 5, 6, 7, 8, 9, 10 or more repeating sequences. In some embodiments, the internal linker is low immunogenic. In some embodiments, the internal linker is biodegradable.

The therapeutic agents may be inserted into the antibody region. Insertion of the therapeutic agent into the antibody region may comprise removal or deletion of one or more amino acids from the antibody region.

In some embodiments, an immunoglobulin fusion protein comprises one or more extender peptides. The one or more extender peptides may be attached to the N-terminus, C-terminus or both the N- and C-termini of a therapeutic agent.

In some embodiments, an immunoglobulin fusion protein comprises one or more linker peptides. The one or more linkers may be attached to the N-terminus, C-terminus or both the N- and C-termini of a therapeutic agent.

In some embodiments, an immunoglobulin fusion protein comprises one or more proteolytic cleavage sites. The one or more proteolytic cleavage sites may be attached to the N-terminus, C-terminus or both the N- and C-termini of a therapeutic agent.

In some embodiments, the therapeutic agent may be connected to the antibody region without the aid of an extender peptide. The therapeutic agent may be connected to the antibody via one or more linkers.

Linkers

The immunoglobulin fusion proteins, antibody regions, non-antibody regions and/or extender fusion regions may further comprise one or more linkers. The immunoglobulin fusion proteins, antibody regions, non-antibody regions and/or extender fusion region may further comprise 2, 3, 4, 5, 6, 7, 8, 9, 10 or more linkers. The extender fusion region may further comprise one or more linkers. The extender fusion region may further comprise 2, 3, 4, 5, 6, 7, 8, 9, 10 or more linkers.

The one or more linkers are attached to the N-terminus, C-terminus or both N- and C-termini of a therapeutic agent. The one or more linkers are attached to the N-terminus, C-terminus or both N- and C-termini of the extender peptide. The one or more linkers are attached to the N-terminus, C-terminus or both N- and C-termini of a proteolytic cleavage site. The one or more linkers may be attached to a therapeutic agent, extender peptide, proteolytic cleavage site, extender fusion region, antibody region, or a combination thereof.

In some embodiments, the linker peptide is a connecting peptide or part of a connecting peptide.

The one or more linkers may comprise the sequence $(X^e X^f X^g X^h)_n$ (SEQ ID NO: 176). In one embodiment, n is between about 1 and about 20. In one embodiment n is any one of 1, 2, 3, 4, 5, 6, 7, 8, 9, 10, 11, 12, 13, 14, 15, 16, 17, 18, 19, or 20. In one embodiment, n is between about 1 and about 10. In one embodiment, n is between about 1 and about 5. In one embodiment, n is between about 1 and about 3. In one embodiment, $X^e$, $X^f$ and $X^g$ are independently selected from a hydrophobic amino acid. $X^h$ may be a polar, uncharged amino acid. The linker sequence may further comprise one or more cysteine (C) residues. The one or more cysteine residues are at the N-terminus, C-terminus, or a combination thereof. The linker peptide may comprise the sequence $CX^e X^f X^g X^h$ (SEQ ID NO: 177). In one embodiment, $X^e$, $X^f$ and $X^g$ are independently selected from a hydrophobic amino acid. $X^h$ may be a polar, uncharged amino acid. The linker peptide may comprise the sequence $X^e X^f X^g X^h C$ (SEQ ID NO: 178). In one embodiment, $X^e$, $X^f$ and $X^g$ are independently selected from a hydrophobic amino acid. $X^h$ may be a polar, uncharged amino acid.

The one or more linkers may comprise the sequence $(GGGGS)_n$ (SEQ ID NO: 275). In one embodiment, n is between about 1 and about 20. In one embodiment n is any one of 1, 2, 3, 4, 5, 6, 7, 8, 9, 10, 11, 12, 13, 14, 15, 16, 17, 18, 19, or 20. In one embodiment, n is between about 1 and about 10. In one embodiment, n is between about 1 and about 5. In one embodiment, n is between about 1 and about 3.

The one or more linkers may comprise an amino acid sequence selected from any one of SEQ ID NOs: 176, 179-181 and 275-277. The one or more linkers may comprise an amino acid sequence that is at least about 50% homologous to any one of SEQ ID NOs: 176, 179-181 and 275-277. The one or more linkers may comprise an amino acid sequence that is at least about 60%, 65%, 70%, 75%, 80%, 85%, 90%, 95% or more homologous to any one of SEQ ID NOs: 176, 179-181 and 275-277. The one or more linkers may comprise an amino acid sequence that is at least about 70% homologous to any one of SEQ ID NOs: 176, 179-181 and 275-277. The one or more linkers may comprise an amino acid sequence that is at least about 80% homologous to any one of SEQ ID NOs: 176, 179-181 and 275-277.

Proteolytic Cleavage Site

The immunoglobulin fusion proteins disclosed herein may further comprise one or more proteolytic cleavage sites. The immunoglobulin fusion proteins disclosed herein may further comprise 2 or more proteolytic cleavage sites. The immunoglobulin fusion proteins disclosed herein may further comprise 3 or more proteolytic cleavage sites. The immunoglobulin fusion proteins disclosed herein may further comprise 4, 5, 6, 7 or more proteolytic cleavage sites. The therapeutic agents disclosed herein may further comprise one or more proteolytic cleavage sites.

The immunoglobulin fusion proteins may comprise a sequence with one or more cleavage sites between the antibody region and the non-antibody region. The immunoglobulin fusion proteins may comprise a sequence with one or more cleavage sites between the antibody region and the extender fusion region. In some embodiments, the proteolytic cleavage site is a connecting peptide or is part of a connecting peptide.

The one or more proteolytic cleavage sites may be attached to the N-terminus, C-terminus or both N- and C-termini of a therapeutic peptide. The one or more proteolytic cleavage sites may attached to the N-terminus, C-terminus or both N- and C-termini of an extender peptide. The one or more proteolytic cleavage sites may attached to the N-terminus, C-terminus or both N- and C-termini of a linker peptide. The one or more proteolytic cleavage sites may be attached to a therapeutic peptide, extender peptide, linker, extender fusion region, immunoglobulin region, non-immunoglobulin region or a combination thereof.

Digestion of the proteolytic cleavage site may result in release of the N- or C-terminus of the therapeutic agent from the immunoglobulin fusion protein. The proteolytic cleavage site may be on the N- and C-termini of the therapeutic agent. Digestion of the proteolytic cleavage site may result in release of the therapeutic agent from the immunoglobulin fusion protein.

Alternatively, or additionally, the proteolytic cleavage site is located within the amino acid sequence of the therapeutic agent, extender peptide, antibody region, or a combination thereof. The therapeutic agent may comprise one or more proteolytic cleavage sites within its amino acid sequence. For example, SEQ ID NO: 89 discloses a relaxin protein comprising two internal proteolytic cleavage sites. Digestion of the proteolytic cleavage sites within the relaxin protein may result in release of an internal fragment of the relaxin protein.

Two or more proteolytic cleavage sites may surround a therapeutic agent, extender peptide, linker, antibody region, or combination thereof. Digestion of the proteolytic cleavage site may result in release of a peptide fragment located between the two or more proteolytic cleavage sites. For example, the proteolytic cleavage sites may flank a therapeutic agent-linker peptide. Digestion of the proteolytic cleavage sites may result in release of the therapeutic agent-linker.

The proteolytic cleavage site may be recognized by one or more proteases. The one or more proteases may be a serine protease, threonine protease, cysteine protease, aspartate protease, glutamic protease, metalloprotease, exopeptidases, endopeptidases, or a combination thereof. The proteases may be selected from the group comprising Factor VII or Factor Xa. Additional examples of proteases include, but are not limited to, aminopeptidases, carboxypeptidases, trypsin, chymotrypsin, pepsin, papain, and elastase. The protease may be prohormone convertase 2 (PC2).

The one or more proteolytic cleavage sites may comprise an amino acid sequence selected from any one of SEQ ID NOs: 182-185. The one or more proteolytic cleavage sites may comprise an amino acid sequence that is at least about 50% homologous to any one of SEQ ID NOs: 182-185. The one or more proteolytic cleavage sites may comprise an amino acid sequence that is at least about 60%, 65%, 70%, 75%, 80%, 85%, 90%, 95% or more homologous to any one of SEQ ID NOs: 182-185. The one or more proteolytic cleavage sites may comprise an amino acid sequence that is at least about 70% homologous to any one of SEQ ID NOs: 182-185. The one or more proteolytic cleavage sites may comprise an amino acid sequence that is at least about 80% homologous to any one of SEQ ID NOs: 182-185.

Vectors, Host Cells and Recombinant Methods

Immunoglobulin fusion proteins, as disclosed herein, may be expressed by recombinant methods. Generally, a nucleic acid encoding an immunoglobulin fusion protein may be isolated and inserted into a replicable vector for further cloning (amplification of the DNA) or for expression. DNA encoding the immunoglobulin fusion protein may be prepared by PCR amplification and sequenced using conventional procedures (e.g., by using oligonucleotide probes that are capable of binding specifically to nucleotides encoding immunoglobulin fusion proteins). In an exemplary embodiment, nucleic acid encoding an immunoglobulin fusion protein is PCR amplified, restriction enzyme digested and gel purified. The digested nucleic acid may be inserted into a replicable vector. The replicable vector containing the digested immunoglobulin fusion protein insertion may be transformed or transduced into a host cell for further cloning (amplification of the DNA) or for expression. Host cells may be prokaryotic or eukaryotic cells.

Polynucleotide sequences encoding polypeptide components (e.g., antibody region, extender peptide, therapeutic agent) of the immunoglobulin fusion proteins may be obtained by PCR amplification. Polynucleotide sequences may be isolated and sequenced from cells containing nucleic acids encoding the polypeptide components. Alternatively, or additionally, polynucleotides may be synthesized using nucleotide synthesizer or PCR techniques. Once obtained, sequences encoding the polypeptide components may be inserted into a recombinant vector capable of replicating and expressing heterologous polynucleotides in prokaryotic and/or eukaryotic hosts.

In addition, phage vectors containing replicon and control sequences that are compatible with the host microorganism may be used as transforming vectors in connection with these hosts. For example, bacteriophage such as λGEM™-11 may be utilized in making a recombinant vector which may be used to transform susceptible host cells such as *E. coli* LE392.

Immunoglobulin fusion proteins may be expressed intracellularly (e.g., cytoplasm) or extracellularly (e.g., secretion). For extracellular expression, the vector may comprise a secretion signal which enables translocation of the immunoglobulin fusion proteins to the outside of the cell.

Suitable host cells for cloning or expression of immunoglobulin fusion proteins-encoding vectors include prokaryotic or eukaryotic cells. The host cell may be a eukaryotic. Examples of eukaryotic cells include, but are not limited to, Human Embryonic Kidney (HEK) cells, Chinese Hamster Ovary (CHO) cells, fungi, yeasts, invertebrate cells (e.g., plant cells and insect cells), lymphoid cells (e.g., YO, NSO, Sp20 cells). Other examples of suitable mammalian host cell lines are monkey kidney CV line transformed by SV40 (COS-7); baby hamster kidney cells (BHK); mouse sertoli cells; monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells; MRC 5 cells; and FS4 cells. The host cell may be a prokaryotic cell (e.g., E. coli).

Host cells may be transformed with vectors containing nucleotides encoding an immunoglobulin fusion proteins. Transformed host cells may be cultured in media. The media may be supplemented with one or more agents for inducing promoters, selecting transformants, or amplifying or expressing the genes encoding the desired sequences. Methods for transforming host cells are known in the art and may include electroporation, calcium chloride, or polyethylene glycol/DMSO.

Alternatively, host cells may be transfected or transduced with vectors containing nucleotides encoding immunoglobulin fusion proteins. Transfected or transduced host cells may be cultured in media. The media may be supplemented with one or more agents for inducing promoters, selecting transfected or transduced cells, or expressing genes encoding the desired sequences.

Host cells may be transfected or transduced with vectors comprising nucleotides encoding one or more proteases. The protease comprising vectors may be co-transfected with vectors encoding any immunoglobulin fusion protein disclosed herein. Proteases include Factor Xa and PC2.

The expressed immunoglobulin fusion proteins may be secreted into and recovered from the periplasm of the host cells or transported into the culture media. Protein recovery from the periplasm may involve disrupting the host cell. Disruption of the host cell may comprise osmotic shock, sonication or lysis. Centrifugation or filtration may be used to remove cell debris or whole cells. The immunoglobulin fusion proteins may be further purified, for example, by affinity resin chromatography.

Alternatively, immunoglobulin fusion proteins that are secreted into the culture media may be isolated therein. Cells may be removed from the culture and the culture supernatant being filtered and concentrated for further purification of the proteins produced. The expressed polypeptides may be further isolated and identified using commonly known methods such as polyacrylamide gel electrophoresis (PAGE) and Western blot assay.

Immunoglobulin fusion proteins production may be conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (a preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described herein. Cells may be grown for shorter periods prior to induction. Cells are usually induced for about 12-50 hours, although longer or shorter induction time may be used.

To improve the production yield and quality of the immunoglobulin fusion proteins disclosed herein, various fermentation conditions may be modified. For example, to improve the proper assembly and folding of the secreted immunoglobulin fusion proteins polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) may be used to co-transform the host prokaryotic cells. The chaperone proteins have been demonstrated to facilitate the proper folding and solubility of heterologous proteins produced in bacterial host cells.

To minimize proteolysis of expressed heterologous proteins (especially those that are proteolytically sensitive), certain host strains deficient for proteolytic enzymes may be used for the present disclosure. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available.

Standard protein purification methods known in the art may be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, hydroxylapatite chromatography, gel electrophoresis, dialysis, and affinity chromatography and gel filtration using, for example, Sephadex G-75.

Immunoglobulin fusion proteins may be concentrated using a commercially available protein concentration filter, for example, an Amicon or Millipore Pellicon® ultrafiltration unit.

Protease inhibitors or protease inhibitor cocktails may be included in any of the foregoing steps to inhibit proteolysis of the immunoglobulin fusion proteins.

In some cases, an immunoglobulin fusion protein may not be biologically active upon isolation. Various methods for "refolding" or converting a polypeptide to its tertiary structure and generating disulfide linkages, may be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol(DTT)/dithiane DTT, and 2-mercaptoethanol(bME)/di-thio-b(ME). In many instances, a cosolvent may be used to increase the efficiency of the refolding, and common reagents used for this purpose include glycerol, polyethylene glycol of various molecular weights, arginine and the like.

Compositions

Disclosed herein are compositions comprising an immunoglobulin fusion protein and/or component of an immunoglobulin fusion protein disclosed herein. The compositions may comprise 1, 2, 3, 4, 5, 6, 7, 8, 9, 10 or more immunoglobulin fusion proteins. The immunoglobulin fusion proteins may be different. Alternatively, the immunoglobulin fusion proteins may be the same or similar. The immunoglobulin fusion proteins may comprise different antibody regions, extender fusion regions, extender peptides, therapeutic agents or a combination thereof.

The compositions may further comprise one or more pharmaceutically acceptable salts, excipients or vehicles. Pharmaceutically acceptable salts, excipients, or vehicles for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer may be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; the MONAQUAT™ series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Compositions described herein may be formulated for controlled or sustained delivery in a manner that provides local concentration of the product (e.g., bolus, depot effect) and/or increased stability or half-life in a particular local environment. The compositions may comprise the formulation of immunoglobulin fusion proteins, polypeptides, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then may be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents. See, for example, the description of controlled release porous polymeric microparticles for the delivery of pharmaceutical compositions in WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which may be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This may be determined by routine screening in animal models of the target disorder or, if such models are unavailable, in normal animals.

The immunoglobulin fusion proteins disclosed herein may be microencapsulated.

A pharmaceutical composition disclosed herein can be administered to a subject by any suitable administration route, including but not limited to, parenteral (intravenous, subcutaneous, intraperitoneal, intramuscular, intravascular, intrathecal, intravitreal, infusion, or local), topical, oral, or nasal administration.

Formulations suitable for intramuscular, subcutaneous, peritumoral, or intravenous injection can include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent can be optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. The pharmaceutical composition described herein can be in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

Alternatively or additionally, the compositions may be administered locally via implantation into the affected area of a membrane, sponge, or other appropriate material on to which an immunoglobulin fusion protein disclosed herein has been absorbed or encapsulated. Where an implantation device is used, the device may be implanted into any suitable tissue or organ, and delivery of an immunoglobulin fusion protein, nucleic acid, or vector disclosed herein may be directly through the device via bolus, or via continuous administration, or via catheter using continuous infusion.

A pharmaceutical composition comprising an immunoglobulin fusion protein disclosed herein may be formulated for inhalation, such as for example, as a dry powder. Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 μm to 5 μm; however, larger particles may be used, for example, if each particle is fairly porous.

Certain formulations comprising an immunoglobulin fusion protein disclosed herein may be administered orally. Formulations administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also may be employed.

Another preparation may involve an effective quantity of an immunoglobulin fusion protein in a mixture with non-toxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size.

Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

The compositions disclosed herein may be useful for providing prognostic or providing diagnostic information.

"Pharmaceutically acceptable" may refer to approved or approvable by a regulatory agency of the Federal or a state government or listed in the U.S. Pharmacopeia or other generally recognized pharmacopeia for use in animals, including humans.

"Pharmaceutically acceptable salt" may refer to a salt of a compound that is pharmaceutically acceptable and that possesses the desired pharmacological activity of the parent compound.

"Pharmaceutically acceptable excipient, carrier or adjuvant" may refer to an excipient, carrier or adjuvant that may be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" may refer to a diluent, adjuvant, excipient, or carrier with which at least one antibody of the present disclosure is administered.

Kits

Further disclosed herein are kits which comprise one or more immunoglobulin fusion proteins or components thereof. The immunoglobulin fusion proteins may be packaged in a manner which facilitates their use to practice methods of the present disclosure. For example, a kit comprises an immunoglobulin fusion protein described herein packaged in a container with a label affixed to the container or a package insert that describes use of the immunoglobulin fusion protein in practicing the method. Suitable containers include, for example, bottles, vials, syringes, etc. The containers may be formed from a variety of materials such as glass or plastic. The container may have a sterile access port (for example the container may be an intravenous solution bag or a vial having a stopper pierceable by a hypodermic injection needle). The kit may comprise a container with an immunoglobulin fusion protein contained therein. The kit may comprise a container with (a) an antibody region of an immunoglobulin fusion protein; (b) an extender fusion region of an immunoglobulin fusion protein; (c) an extender peptide of the extender fusion region; (d) a therapeutic agent of the extender fusion region; or (e) a combination of a-d. The kit may further comprise a package insert indicating that the first and second compositions may be used to treat a particular condition. Alternatively, or additionally, the kit may further comprise a second (or third) container comprising a pharmaceutically-acceptable buffer (e.g., bacteriostatic water for injection (BWFI), phosphate-buffered saline, Ringer's solution and dextrose solution). It may further comprise other materials desirable from a commercial and user standpoint, including, but not limited to, other buffers, diluents, filters, needles, and syringes. The immunoglobulin fusion protein may be packaged in a unit dosage form. The kit may further comprise a device suitable for administering the immunoglobulin fusion protein according to a specific route of administration or for practicing a screening assay. The kit may contain a label that describes use of the immunoglobulin fusion protein composition.

The composition comprising the immunoglobulin fusion protein may be formulated in accordance with routine procedures as a pharmaceutical composition adapted for intravenous administration to mammals, such as humans, bovines, felines, canines, and murines. Typically, compositions for intravenous administration comprise solutions in sterile isotonic aqueous buffer. Where necessary, the composition may also include a solubilizing agent and/or a local anaesthetic such as lignocaine to ease pain at the site of the injection. Generally, the ingredients may be supplied either separately or mixed together in unit dosage form. For example, the immunoglobulin fusion protein may be supplied as a dry lyophilized powder or water free concentrate in a hermetically sealed container such as an ampoule or sachette indicating the quantity of the immunoglobulin fusion protein. Where the composition is to be administered by infusion, it may be dispensed with an infusion bottle containing sterile pharmaceutical grade water or saline. Where the composition is administered by injection, an ampoule of sterile water for injection or saline may be provided so that the ingredients may be mixed prior to administration.

The amount of the composition described herein which will be effective in the treatment, inhibition and/or prevention of a disease or disorder associated with aberrant expression and/or activity of a therapeutic agent may be determined by standard clinical techniques. In addition, in vitro assays may optionally be employed to help identify optimal dosage ranges. The precise dose to be employed in the formulation may also depend on the route of administration, and the seriousness of the disease or disorder, and should be decided according to the judgment of the practitioner and each patient's circumstances. Effective doses may be extrapolated from dose-response curves derived from in vitro, animal model test systems or clinical trials.

Therapeutic Use

Further disclosed herein are immunoglobulin fusion proteins for and methods of treating, alleviating, inhibiting and/or preventing one or more diseases and/or conditions. The method may comprise administering to a subject in need thereof a composition comprising one or more immunoglobulin fusion proteins disclosed herein. The immunoglobulin fusion protein may comprise an antibody region attached to a non-antibody region. In some instances, the immunoglobulin fusion protein comprises an antibody region attached to an extender fusion region. The non-antibody region comprises one or more therapeutic agents. The extender fusion region comprises one or more therapeutic agents. In some embodiments, the non-immunoglobulin region comprises one or more extender peptides. In some embodiments, the extender fusion region comprises one or more extender peptides. In one embodiment, the extender peptide comprises an amino acid sequence having an alpha helix secondary structure. In one embodiment, the extender peptide does not comprise an amino acid sequence having a beta strand secondary structure. In some embodiments, the non-immunoglobulin region comprises one or more linker peptides. In some embodiments, the extender fusion region comprises one or more linker peptides. In one embodiment, the linker peptide does not comprise an amino acid sequencing having an alpha helix or beta strand secondary structure.

The composition may further comprise a pharmaceutically acceptable carrier. The subject may be a mammal. The mammal may be a human. Alternatively, the mammal is a bovine. The therapeutic agent may be a peptide or derivative or variant thereof. Alternatively, therapeutic agent is a small molecule. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The therapeutic agent may be GCSF, bovine GCSF, human GCSF, Moka1, Vm24, Mamba1, human GLP-1, exendin-4, human EPO, human FGF21, human GMCSF, human interferon-beta, human interferon-alpha, relaxin, oxyntomodulin, hLeptin, betatrophin, growth differentiation factor 11 (GDF11), parathyroid hormone, angiopoietin-like 3 (ANGPTL3), IL-11, human growth hormone (hGH), elafin or derivative or variant thereof. Alternatively, or additionally, therapeutic agent is interleukin 8 (IL-8), IL-21, ziconotide, somatostatin, chlorotoxin, SDF1 alpha or derivative or variation thereof. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The disease or condition may be an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain. The therapeutic agent may be hGCSF and the disease or condition may be neutropenia. The therapeutic agent may be hLeptin and the disease or condition may be diabetes. The therapeutic agent may be hGH and the disease or condition may be a growth disorder. The therapeutic agent may be IFN-alpha and the disease or condition may be a viral infection. The therapeutic agent may be Mamba1 and the disease or condition may be pain. The therapeutic agent may be elafin and the disease or condition may be inflammation. The therapeutic agent may be IFN-alpha and the disease or condition may be an elastase inhibitor peptide and the disease or condition may be chronic obstructive pulmonary disease (COPD).

The disease and/or condition may be a chronic disease or condition. Alternatively, the disease and/or condition is an acute disease or condition. The disease or condition may be recurrent, refractory, accelerated, or in remission. The disease or condition may affect one or more cell types. The one or more diseases and/or conditions may be an autoimmune disease, inflammatory disease, cardiovascular disease, metabolic disorder, pregnancy, and cell proliferative disorder.

The disease or condition may be an autoimmune disease. In some cases, the autoimmune disease may be scleroderma, diffuse scleroderma or systemic scleroderma.

The disease or condition may be an inflammatory disease. In some cases, the inflammatory disease may be hepatitis, fibromyalgia or psoriasis.

The disease or condition may be a rheumatic disease. In some cases, the rheumatic disease may be Ankylosing spondylitis, back pain, bursitis, tendinitis, shoulder pain, wrist pain, bicep pain, leg pain, knee pain, ankle pain, hip pain, Achilles pain, Capsulitis, neck pain, osteoarthritis, systemic lupus, erythematosus, rheumatoid arthritis, juvenile arthritis, Sjogren syndrome, Polymyositis, Behcet's disease, Reiter's syndrome, or Psoriatic arthritis. The rheumatic disease may be chronic. Alternatively, the rheumatic disease is acute.

The disease or condition may be a cardiovascular disease. In some cases, the cardiovascular disease may be acute heart failure, congestive heart failure, compensated heart failure, decompensated heart failure, hypercholesterolemia, atherosclerosis, coronary heart disease or ischemic stroke. The cardiovascular disease may be cardiac hypertrophy.

The disease or condition may be a metabolic disorder. In some cases, the metabolic disorder may be hypercholesterolemia, hypobetalipoproteinemia, hypertriglyceridemia, hyperlipidemia, dyslipidemia, ketosis, hypolipidemia, refractory anemia, appetite control, gastric emptying, non-alcoholic fatty liver disease, obesity, type I diabetes mellitus, type II diabetes mellitus, gestational diabetes mellitus, metabolic syndrome. The metabolic disorder may be type I diabetes. The metabolic disorder may be type II diabetes.

The disease or condition may be pregnancy. The immunoglobulin fusion proteins may be used to treat preeclampsia or induce labor.

The disease or condition may be a cell proliferative disorder. The cell proliferative disorder may be a leukemia, lymphoma, carcinoma, sarcoma, or a combination thereof. The cell proliferative disorder may be a myelogenous leukemia, lymphoblastic leukemia, myeloid leukemia, myelomonocytic leukemia, neutrophilic leukemia, myelodysplastic syndrome, B-cell lymphoma, burkitt lymphoma, large cell lymphoma, mixed cell lymphoma, follicular lymphoma, mantle cell lymphoma, hodgkin lymphoma, recurrent small lymphocytic lymphoma, hairy cell leukemia, multiple myeloma, basophilic leukemia, eosinophilic leukemia, megakaryoblastic leukemia, monoblastic leukemia, monocytic leukemia, erythroleukemia, erythroid leukemia, hepatocellular carcinoma, solid tumors, lymphoma, leukemias, liposarcoma (advanced/metastatic), myeloid malignancy, breast cancer, lung cancer, ovarian cancer, uterine cancer, kidney cancer, pancreatic cancer, and malignant glioma of brain.

Disclosed herein are methods of treating a disease or condition in a subject in need thereof, the method comprising administering to the subject a composition comprising an immunoglobulin fusion protein disclosed herein. The immunoglobulin fusion protein may comprise an antibody region attached to a non-antibody region comprising a therapeutic agent. In some instances, the immunoglobulin fusion protein comprises an antibody region attached to an extender fusion region comprising a therapeutic agent. In one embodiment, the therapeutic agent is oxyntomodulin. The disease or condition may be a metabolic disorder. The metabolic disorder may be diabetes. Diabetes may be type II diabetes mellitus. Diabetes may be type I diabetes. The metabolic disorder may be obesity. Additional metabolic disorders include, but are not limited to, metabolic syndrome, appetite control or gastric emptying.

Disclosed herein are methods of treating a disease or condition in a subject in need thereof, the method comprising administering to the subject a composition comprising an immunoglobulin fusion protein disclosed herein. The immunoglobulin fusion protein may comprise an antibody region attached to a non-antibody region comprising a therapeutic agent. In some instances, the immunoglobulin fusion protein comprises an antibody region attached to an extender fusion region comprising a therapeutic agent. In one embodiment, the therapeutic agent is relaxin. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition is pregnancy. The immunoglobulin fusion protein may be used to treat preeclampsia or induce labor.

Disclosed herein are methods of treating a disease or condition in a subject in need thereof, the method comprising administering to the subject a composition comprising an immunoglobulin fusion protein disclosed herein. The immunoglobulin fusion protein may comprise an antibody region attached to a non-antibody region comprising a therapeutic agent. In some instances, the immunoglobulin fusion protein comprises an antibody region attached to an extender fusion region comprising a therapeutic agent. In one embodiment, the therapeutic agent is beta-trophin. The disease or condition may be a metabolic disorder. The metabolic disorder may be obesity. Alternatively, the metabolic disorder is diabetes. Diabetes may be type I diabetes mellitus or type II diabetes mellitus.

Disclosed herein are methods of treating a disease or condition in a subject in need thereof, the method comprising administering to the subject a composition comprising an immunoglobulin fusion protein disclosed herein. The immunoglobulin fusion protein may comprise an antibody region attached to a non-antibody region comprising a therapeutic agent. In some instances, the immunoglobulin fusion protein comprises an antibody region attached to an extender fusion region comprising a therapeutic agent. In one embodiment, the therapeutic agent is FGF 21. The disease or condition may be a metabolic disorder. The metabolic disorder may be obesity. The metabolic disorder may be diabetes. Diabetes may be type 2 diabetes mellitus, type I diabetes mellitus or gestational diabetes mellitus. Additional metabolic disorders include, but are not limited to, appetite control and non-alcoholic fatty liver disease. The disease or condition may be a cell proliferative disorder. The cell proliferative disorder may be breast cancer.

Disclosed herein are methods of treating a disease or condition in a subject in need thereof, the method comprising administering to the subject a composition comprising an immunoglobulin fusion protein disclosed herein. The immunoglobulin fusion protein may comprise an antibody region attached to a non-antibody region comprising a therapeutic agent. In some instances, the immunoglobulin fusion protein comprises an antibody region attached to an extender fusion region comprising a therapeutic agent. In one embodiment, the therapeutic agent is GDF11. The disease or condition may be a cell proliferative disorder. The cell proliferative disorder may be acute, chronic, recurrent, refractory, accelerated, in remission, stage I, stage II, stage III, stage IV, juvenile or adult. The cell proliferative disorder may be a myelogenous leukemia, lymphoblastic leukemia, myeloid leukemia, myelomonocytic leukemia, neutrophilic leukemia, myelodysplastic syndrome, B-cell lymphoma, burkitt lymphoma, large cell lymphoma, mixed cell lymphoma, follicular lymphoma, mantle cell lymphoma, hodgkin lymphoma, recurrent small lymphocytic lymphoma, hairy cell leukemia, multiple myeloma, basophilic leukemia, eosinophilic leukemia, megakaryoblastic leukemia, monoblastic leukemia, monocytic leukemia, erythroleukemia, erythroid leukemia, hepatocellular carcinoma, solid tumors, lymphoma, leukemias, liposarcoma (advanced/metastatic), myeloid malignancy, breast cancer, lung cancer, ovarian cancer, uterine cancer, kidney cancer, pancreatic cancer, and malignant glioma of brain. The disease or condition may be a cardiovascular disease. The cardiovascular disease may be age-related cardiac disease. The disease or condition may be cardiac hypertrophy.

Disclosed herein are methods of treating a disease or condition in a subject in need thereof, the method comprising administering to the subject a composition comprising an immunoglobulin fusion protein disclosed herein. The immunoglobulin fusion protein may comprise an antibody region attached to a non-antibody region comprising a therapeutic agent. In some instances, the immunoglobulin fusion protein comprises an antibody region attached to an extender fusion region comprising a therapeutic agent. In one embodiment, the therapeutic agent is angiopoietin-like 3. The metabolic disorder may be hypercholesterolemia, hypobetalipoproteinemia, hypertriglyceridemia, hyperlipidemia, dyslipidemia, hypolipidemia or ketosis. The disease or condition may be a cardiovascular disease. The cardiovascular disease may be atherosclerosis, coronary heart disease or ischemic stroke. The disease or condition may be a rheumatic disease. The rheumatic disease may be ankylosing spondylitis, back pain, bursitis, tendinitis, shoulder pain, wrist pain, bicep pain, leg pain, knee (patellar) pain, ankle pain, hip pain, Achilles pain, Capsulitis, Neck pain, osteoarthritis, systemic lupus, erythematosus, rheumatoid arthritis, juvenile arthritis, Sjögren syndrome, scleroderma, Polymyositis, Behcet's disease, Reiter's syndrome, Psoriatic arthritis. In some cases, the disease or condition may be a cell proliferative disorder. The cell proliferative disorder may be hepatocellular carcinoma or ovarian cancer. The disease or condition may be an inflammatory disease. The inflammatory disease may be hepatitis.

Disclosed herein are methods of preventing or treating a disease or condition in a subject in need thereof comprising administering to the subject a composition comprising one or more immunoglobulin fusion proteins disclosed herein. The immunoglobulin fusion protein may comprise one or more immunoglobulin heavy chains, light chains, or a combination thereof.

The immunoglobulin fusion protein may comprise a sequence which shares 50%, 60%, 70%, 80%, 85%, 90%, 95%, 97%, 99%, or more amino acid sequence identity to an amino acid sequence of any of SEQ ID NOs: 68-99, and 122-143. The nucleotide sequence encoding the immunoglobulin fusion protein may comprise a sequence which shares 50%, 60%, 70%, 80%, 85%, 90%, 95%, 97%, 99%, or more nucleotide sequence identity to a nucleotide sequence of any of SEQ ID NOs: 37-67, and 100-121.

The immunoglobulin fusion protein may comprise a sequence which shares 50%, 60%, 70%, 80%, 85%, 90%, 95%, 97%, 99%, or more amino acid sequence identity to a heavy chain sequence provided by SEQ ID NOs: 69-79, 81-93, 95-97, 99, and 123-143. The antibody region may comprise an immunoglobulin heavy chain. The immunoglobulin heavy chain polypeptide may comprise a sequence which shares 50%, 60%, 70%, 80%, 85%, 90%, 95%, 97%, 99%, or more amino acid sequence identity to a heavy chain sequence provided by SEQ ID NOs: 22-27 and 29-35. The antibody region may comprise an immunoglobulin light chain.

The immunoglobulin fusion protein may comprise a sequence which shares 50%, 60%, 70%, 80%, 85%, 90%, 95%, 97%, 99%, or more amino acid sequence identity to a light chain sequence provided by SEQ ID NOs: 68, 80, 94, 98, and 122. The antibody region may comprise an immunoglobulin light chain. The immunoglobulin light chain polypeptide may comprise a sequence which shares 50%, 60%, 70%, 80%, 85%, 90%, 95%, 97%, 99%, or more amino acid sequence identity to a light chain sequence provided by SEQ ID NOs: 19-21, 28, and 36. The antibody region may comprise an immunoglobulin heavy chain.

The immunoglobulin fusion protein may be encoded by a nucleotide sequence that is at least about 50%, 60%, 70%, 80%, 85%, 90%, 95%, 97%, 99% or more homologous to a nucleotide sequence of any one of SEQ ID NOs: 68-99, and 122-143. The immunoglobulin heavy chain may be encoded by a nucleotide sequence that is at least about 50%, 60%, 70%, 80%, 85%, 90%, 95%, 97%, 99%, or more homologous to SEQ ID NOs: 22-27, 29-35, 69-79, 81-93, 95-97, 99, and 123-143. The immunoglobulin light chain may be encoded by a nucleotide sequence that is at least about 50%, 60%, 70%, 80%, 85%, 90%, 95%, 97%, 99%, or more homologous to SEQ ID NOs: 19-21, 28, 36, 68, 80, 94, 98, and 122.

The immunoglobulin fusion protein may comprise one or more extender peptides. The immunoglobulin fusion protein may comprise one or more linkers. The immunoglobulin fusion protein may comprise one or more proteolytic cleavage sites. The disease or condition may be an autoimmune disease, heteroimmune disease or condition, inflammatory disease, pathogenic infection, thromboembolic disorder, respiratory disease or condition, metabolic disease, central nervous system (CNS) disorder, bone disease or cancer. The disease or condition may be a blood disorder. In some instances, the disease or condition may be obesity, diabetes, osteoporosis, anemia, or pain.

Disclosed herein is a method of preventing or treating an autoimmune disease in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The composition may further comprise a pharmaceutically acceptable carrier. The subject may be a mammal. The mammal may be a human. Alternatively, the mammal may be a bovine. The therapeutic agent may be Moka1 or a derivative or variant thereof. The therapeutic agent may be VM24 or a derivative or variant thereof. The therapeutic agent may be beta-interferon or a derivative or variant thereof. The immunoglobulin fusion protein or antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. The mammalian antibody may be a murine antibody. The antibody, antibody region or extender fusion region may further comprise a linker. The linker may attach Moka1, VM24, beta-interferon, or a derivative or variant thereof to the extender peptide. The linker may attach the antibody region to the extender fusion region. The linker may attach a proteolytic cleavage site to the antibody region, extender fusion region, extender peptide, or therapeutic agent. The autoimmune disease may be a T-cell mediated autoimmune disease. T-cell mediated autoimmune diseases include, but are not limited to, multiple sclerosis, type-1 diabetes, and psoriasis. In other instances, the autoimmune disease lupus, Sjogren's syndrome, scleroderma, rheumatoid arthritis, dermatomyositis, Hasmimoto's thyroiditis, Addison's disease, celiac disease, Crohn's disease, pernicious anemia, pemphigus vulgaris, vitiligo, autoimmune hemolytic anemia, idiopathic thrombocytopenic purpura, myasthenia gravis, Ord's thyroiditis, Graves' disease, Guillain-Barre syndrome, acute disseminated encephalomyelitis, opsoclonus-myoclonus syndrome, ankylosing spondylitisis, antiphospholipid antibody syndrome, aplastic anemia, autoimmune hepatitis, Goodpasture's syndrome, Reiter's syndrome, Takayasu's arteritis, temporal arteritis, Wegener's granulomatosis, alopecia universalis, Behcet's disease, chronic fatigue, dysautonomia, endometriosis, interstitial cystitis, neuromyotonia, scleroderma, and vulvodynia. Lupus can include, but may be not limited to, acute cutaneous lupus erythematosus, subacute cutaneous lupus erythematosus, chronic cutaneous lupus erythematosus, discoid lupus erythematosus, childhood discoid lupus erythematosus, generalized discoid lupus erythematosus, localized discoid lupus erythematosus, chilblain lupus erythematosus (hutchinson), lupus erythematosus-lichen planus overlap syndrome, lupus erythematosus panniculitis (lupus erythematosus profundus), tumid lupus erythematosus, verrucous lupus erythematosus (hypertrophic lupus erythematosus), complement deficiency syndromes, drug-induced lupus erythematosus, neonatal lupus erythematosus, and systemic lupus erythematosus. The disease or condition may be multiple sclerosis. The disease or condition may be diabetes.

Further disclosed herein is a method of preventing or treating a disease or condition which would benefit from the modulation of a potassium voltage-gated channel in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The composition may further comprise a pharmaceutically acceptable carrier. The potassium voltage-gated channel may be a KCNA3 or $K_v1.3$ channel. The subject may be a mammal. The mammal may be a human. Alternatively, the mammal may be a bovine. The therapeutic agent may be Moka1 or a derivative or variant thereof. The therapeutic agent may be VM24 or a derivative or variant thereof. The immunoglobulin fusion protein or antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be from a mammalian antibody. Alternatively, the immunoglobulin domain may be from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody may be a murine antibody. The immunoglobulin fusion protein, antibody region, and/or extender fusion region may further comprise one or more linkers. The linker may attach Moka1, VM24, or a derivative or variant thereof to the extender peptide. The linker may attach the antibody region to the extender fusion region. The linker may attach a proteolytic cleavage site to the antibody region, extender fusion region, extender peptide, or therapeutic agent. The disease or condition may be an autoimmune disease. The autoimmune disease may be a T-cell mediated autoimmune disease. The disease or condition may be episodic ataxia, seizure, or neuromyotonia. Modulating a potassium voltage-gated channel may comprise inhibiting or blocking a potassium voltage-gated channel. Modulating a potassium voltage-gated channel may comprise activating a potassium voltage-gated channel.

Provided herein is a method of preventing or treating a metabolic disease or condition in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The composition may further comprise a pharmaceutically acceptable carrier. The subject may be a mammal. The mammal may be a human. Alternatively, the mammal may be a bovine. The therapeutic agent may be GLP-1, exendin-4, FGF21 or a derivative or variant thereof. The GLP-1 may be a human GLP-1. The FGF21 may be a human FGF21. The antibody or antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be from a mammalian antibody. Alternatively, the immunoglobulin domain may be from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody may be a murine antibody. The immunoglobulin fusion protein, antibody region, and/or extender fusion region may further comprise one or more linkers. The linker may attach GLP-1, exendin-4, FGF21, or a derivative or variant thereof to the extender peptide. The linker may attach the antibody region to the extender fusion region. The linker may attach a proteolytic cleavage site to the antibody region, extender fusion region, extender peptide, or therapeutic agent. Metabolic diseases and/or conditions may include disorders of carbohydrate metabolism, amino acid metabolism, organic acid metabolism (organic acidurias), fatty acid oxidation and mitochondrial metabolism, porphyrin metabolism, purine or pyrimidine metabolism, steroid metabolism, mitochondrial function, peroxisomal function, urea cycle disorder, urea cycle defects or lysosomal storage disorders. The metabolic disease or condition may be diabetes. In other instances, the metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating a central nervous system (CNS) disorder in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The composition may further comprise a pharmaceutically acceptable carrier. The subject may be a mammal. The mammal may be a human. Alternatively, the mammal may be a bovine. The therapeutic agent may be GLP-1, exendin-4 or a derivative or variant thereof. The GLP-1 may be a human GLP-1. The antibody may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be from a mammalian antibody. Alternatively, the immunoglobulin domain may be from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody may be a murine antibody. The immunoglobulin fusion protein, antibody region, and/or extender fusion region may further comprise one or more linkers. The linker may attach GLP-1, exendin-4, or a derivative or variant thereof to the immunoglobulin domain or fragment thereof. The linker may attach the antibody region to the extender fusion region. The linker may attach a proteolytic cleavage site to the antibody region, extender fusion region, extender peptide, or therapeutic agent. The CNS disorder may be Alzheimer's disease (AD). Additional CNS disorders include, but are not limited to, encephalitis, meningitis, tropical spastic paraparesis, arachnoid cysts, Huntington's disease, locked-in syndrome, Parkinson's disease, Tourette's, and multiple sclerosis.

Provided herein is a method of preventing or treating a disease or condition which benefits from a GLP-1R and/or glucagon receptor (GCGR) agonist in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The composition may further comprise a pharmaceutically acceptable carrier. The subject may be a mammal. The mammal may be a human. Alternatively, the mammal may be a bovine. The therapeutic agent may be GLP-1, exendin-4 or a derivative or variant thereof. The GLP-1 may be a human GLP-1. The immunoglobulin fusion protein or antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be from a mammalian antibody. Alternatively, the immunoglobulin domain may be from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody may be a murine antibody. The immunoglobulin fusion protein, antibody region, and/or extender fusion region may further comprise one or more linkers. The linker may attach GLP-1, exendin-4, or a derivative or variant thereof to the extender peptide. In other instances, the linker attaches the extender fusion region to the antibody region. The disease or condition may be a metabolic disease or disorder. The disease or condition may be diabetes. In other instances, the disease or condition may be obesity. Additional diseases and/or conditions which benefit from a GLP-1R and/or GCGR agonist include, but are not limited to, dyslipidemia, cardiovascular and fatty liver diseases.

Provided herein is a method of preventing or treating a blood disorder in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The composition may further comprise a pharmaceutically acceptable carrier. The subject may be a mammal. The mammal may be a human. Alternatively, the mammal may be a bovine. The therapeutic agent may be erythropoietin, GMCSF or a derivative or variant thereof. The erythropoietin may be a human erythropoietin. The GMCSF may be a human GMCSF. The antibody may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be from a mammalian antibody. Alternatively, the immunoglobulin domain may be from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody may be a murine antibody. The immunoglobulin fusion protein, antibody region, and/or extender fusion region may further comprise one or more linkers. The linker may attach erythropoietin, GMCSF, or a derivative or variant thereof to the extender peptide. The linker may attach the antibody region to the extender fusion region. The linker may attach a proteolytic cleavage site to the antibody region, extender fusion region, extender peptide, or therapeutic agent. The blood disorder may be anemia. Examples of anemia include, but are not limited to, hereditary xerocytosis, congenital dyserythropoietic anemia, Rh null disease, infectious mononucleosis related anemia, drugs-related anemia, aplastic anemia, microcytic anemia, macrocytic anemia, normocytic anemia, hemolytic anemia, poikilocytic anemia, spherocytic anemia, drepanocytic anemia, normochromic anemia, hyperchromic anemia, hypochromic anemia, macrocytic-normochromic anemia, microcytic-hypochromic anemia, normocytic-normochromic anemia, iron-deficiency anemia, pernicious anemia, folate-deficiency anemia, thalassemia, sideroblastic anemia, posthemorrhagic anemia, sickle cell anemia, chronic anemia, achrestic anemia, autoimmune haemolytic anemia, Cooley's anemia, drug-induced immune haemolytic anemia, erythroblastic anemia, hypoplastic anemia, Diamond-Blackfan anemia, Pearson's anemia, transient anemia, Fanconi's anemia, Lederer's anemia, myelpathic anemia, nutritional anemia, spur-cell anemia, Von Jaksh's anemia, sideroblatic anemia, sideropenic anemia, alpha thalassemia, beta thalassemia, hemoglobin h disease, acute acquired hemolytic anemia, warm autoimmune hemolytic anemia, cold autoimmune hemolytic anemia, primary cold autoimmune hemolytic anemia, secondary cold autoimmune hemolytic anemia, secondary autoimmune hemolytic anemia, primary autoimmune hemolytic anemia, x-linked sideroblastic anemia, pyridoxine-responsive anemia, nutritional sideroblastic anemia, pyridoxine deficiency-induced sideroblastic anemia, copper deficiency-induced sideroblastic anemia, cycloserine-induced sideroblastic anemia, chloramphenicol-induced sideroblastic anemia, ethanol-induced sideroblastic anemia, isoniazid-induced sideroblastic anemia, drug-induced sideroblastic anemia, toxin-induced sideroblastic anemia, microcytic hyperchromic anemia, macrocytic hyperchromic anemia, megalocytic-normochromic anemia, drug-induced immune hemolytic anemia, non-hereditary spherocytic anemia, inherited spherocytic anemia, and congenital spherocytic anemia. In other instances, the blood disorder may be malaria. Alternatively, the blood disorder may be lymphoma, leukemia, multiple myeloma, or myelodysplastic syndrome. The blood disorder may be neutropenia, Shwachmann-Daimond syndrome, Kostmann syndrome, chronic granulomatous disease, leukocyte adhesion deficiency, meyloperoxidase deficiency, or Chediak Higashi syndrome.

Provided herein is a method of preventing or treating a disease or disorder which benefits from stimulating or increasing white blood cell production in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The composition may further comprise a pharmaceutically acceptable carrier. The subject may be a mammal. The mammal may be a human. Alternatively, the mammal may be a bovine. The therapeutic agent may be GMCSF or a derivative or variant thereof. The GMCSF may be a human GMCSF. The immunoglobulin fusion protein or antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be from a mammalian antibody. Alternatively, the immunoglobulin domain may be from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody may be a murine antibody. The immunoglobulin fusion protein, antibody region, and/or extender fusion region may further comprise one or more linkers. The linker may attach the antibody region to the extender fusion region. The linker may attach a proteolytic cleavage site to the antibody region, extender fusion region, extender peptide, or therapeutic agent. The disease or disorder may be neutropenia, Shwachmann-Daimond syndrome, Kostmann syndrome, chronic granulomatous disease, leukocyte adhesion deficiency, meyloperoxidase deficiency, or Chediak Higashi syndrome.

Provided herein is a method of preventing or treating a disease or disorder which benefits from stimulating or increasing red blood cell production in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The composition may further comprise a pharmaceutically acceptable carrier. The subject may be a mammal. The mammal may be a human. Alternatively, the mammal may be a bovine. The therapeutic agent may be erythropoietin or a derivative or variant thereof. The erythropoietin may be a human erythropoietin. The antibody may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be from a mammalian antibody. Alternatively, the immunoglobulin domain may be from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody may be a murine antibody. The immunoglobulin fusion protein, antibody region, and/or extender fusion region may further comprise one or more linkers. The linker may attach erythropoietin, or a derivative or variant thereof to the extender peptide. The linker may attach the antibody region to the extender fusion region. The linker may attach a proteolytic cleavage site to the antibody region, extender fusion region, extender peptide, or therapeutic agent. The disease or disorder may be anemia.

Provided herein is a method of preventing or treating obesity in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The composition may further comprise a pharmaceutically acceptable carrier. The subject may be a mammal. The mammal may be a human. Alternatively, the mammal may be a bovine. The therapeutic agent may be GLP-1 or a derivative or variant thereof. The GLP-1 may be a human GLP-1. The therapeutic agent may be FGF21 or a derivative or variant thereof. The FGF21 may be a human FGF21. The therapeutic agent may be exendin-4 or a derivative or variant thereof. The antibody may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be from a mammalian antibody. Alternatively, the immunoglobulin domain may be from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody may be a murine antibody. The immunoglobulin fusion protein, antibody region, and/or extender fusion region may further comprise one or more linkers. The linker may attach GLP-1, exendin-4, FGF21, or a derivative or variant thereof to the extender peptide. The linker may attach the extender fusion region to the antibody region. The linker may attach a proteolytic cleavage site to the antibody region, extender fusion region, extender peptide, or therapeutic agent.

Provided herein is a method of preventing or treating a pain in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The subject may be a mammal. In certain instances, the mammal may be a human. Alternatively, the mammal may be a bovine. The therapeutic agent may be a Mamba1 or a derivative or variant thereof. The immunoglobulin fusion proteins, antibody regions, and/or extender fusion regions may further comprise one or more linkers. The linker may attach the Mamba1 or a derivative or variant thereof to the extender peptide. The linker may attach the extender fusion region to the antibody region. The linker may attach a proteolytic cleavage site to the antibody region, extender fusion region, extender peptide, or therapeutic agent.

Provided herein is a method of preventing or treating a disease or condition which benefits from modulating a sodium ion channel in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The subject may be a mammal. In certain instances, the mammal may be a human. Alternatively, the mammal may be a bovine. The one or more antibodies, antibody fragments, or immunoglobulin constructs further comprise a linker. The linker may attach the extender fusion region to the antibody region. The linker may attach a proteolytic cleavage site to the antibody region, extender fusion region, extender peptide, or therapeutic agent.

Provided herein is a method of preventing or treating a disease or condition which benefits from modulating an acid sensing ion channel (ASIC) in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The subject may be a mammal. In certain instances, the mammal may be a human. Alternatively, the mammal may be a bovine. The therapeutic agent may be Mamba 1 or a derivative or variant thereof. The therapeutic agent may be neutrophil elastase inhibitor or a derivative or variant thereof. The one or more antibodies, antibody fragments, or immunoglobulin constructs further comprise a linker. The linker may attach the extender fusion region to the antibody region. The linker may attach a proteolytic cleavage site to the antibody region, extender fusion region, extender peptide, or therapeutic agent. Modulating an ASIC may comprise inhibiting or blocking the ASIC. Modulating an ASIC may comprise activating the ASIC. The disease or condition may be a central nervous system disorder. In other instances, the disease or condition is pain.

Provided herein is a method of preventing or treating a pathogenic infection in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The composition may further comprise a pharmaceutically acceptable carrier. The subject may be a mammal. The mammal may be a human. Alternatively, the mammal may be a bovine. The therapeutic agent may be alpha-interferon or a derivative or variant thereof. The therapeutic agent may be beta-interferon or a derivative or variant thereof. The antibody may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be from a mammalian antibody. Alternatively, the immunoglobulin domain may be from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody may be a murine antibody. The immunoglobulin fusion protein, antibody region, and/or extender fusion region may further comprise one or more linkers. The linker may attach alpha-interferon, beta-interferon, or a derivative or variant thereof to the extender peptide. The linker may attach the extender fusion region to the antibody region. The linker may attach a proteolytic cleavage site to the antibody region, extender fusion region, extender peptide, or therapeutic agent. The pathogenic infection may be a bacterial infection. The pathogenic infection may be a fungal infection. The pathogenic infection may be a parasitic infection. The pathogenic infection may be a viral infection. The viral infection may be a herpes virus.

Provided herein is a method of preventing or treating a cancer in a subject in need thereof comprising administering to the subject a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The composition may further comprise a pharmaceutically acceptable carrier. The subject may be a mammal. The mammal may be a human. Alternatively, the mammal may be a bovine. The therapeutic agent may be beta-interferon or a derivative or variant thereof. The antibody may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be from a mammalian antibody. Alternatively, the immunoglobulin domain may be from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody may be a murine antibody. The immunoglobulin fusion protein, antibody region, and/or extender fusion region may further comprise one or more linkers. The linker may attach a therapeutic agent to the extender peptide. The linker may attach the extender fusion region to the antibody region. The linker may attach a proteolytic cleavage site to the antibody region, extender fusion region, extender peptide, or therapeutic agent. The cancer may be a hematological malignancy. The hematological malignancy may be a leukemia or lymphoma. The hematological malignancy may be a B-cell lymphoma, T-cell lymphoma, follicular lymphoma, marginal zone lymphoma, hairy cell leukemia, chronic myeloid leukemia, mantle cell lymphoma, nodular lymphoma, Burkitt's lymphoma, cutaneous T-cell lymphoma, chronic lymphocytic leukemia, or small lymphocytic leukemia.

Provided herein is a method of preventing or treating a disease or condition which would benefit from modulation of a receptor in a subject in need thereof comprising administering to the subject a composition disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises one or more immunoglobulin fusion proteins comprising an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The subject may be a mammal. In certain instances, the mammal may be a human. Alternatively, the mammal may be a bovine. The therapeutic agent may be hGCSF or a derivative or variant thereof and the receptor may be GCSFR. The therapeutic agent may be erythropoietin or a derivative or variant thereof and the receptor may be EPOR. The therapeutic agent may be exendin-4 or a derivative or variant thereof and the receptor may be GLP1R. The therapeutic agent may be GLP-1 or a derivative or variant thereof and the receptor may be GLP1R. The therapeutic agent may be hLeptin or a derivative or variant thereof and the receptor may be LepR. The therapeutic agent may be hGH or a derivative or variant thereof and the receptor may be GHR. The therapeutic agent may be interferon-alpha or a derivative or variant thereof and the receptor may be IFNR. The therapeutic agent may be interferon-beta or a derivative or variant thereof and the receptor may be IFNR. The therapeutic agent may be relaxin or a derivative or variant thereof and the receptor may be LGR7. The therapeutic agent may be GMCSF or a derivative or variant thereof and the receptor may be GMCSFR. The one or more antibodies, antibody fragments, or immunoglobulin constructs further comprise a linker. The linker may attach the extender fusion region to the antibody region. The linker may attach a proteolytic cleavage site to the antibody region, extender fusion region, extender peptide, or therapeutic agent. The disease or condition may be an autoimmune disease. The autoimmune disease may be a T-cell mediated autoimmune disease. The disease or condition may be a metabolic disorder. The metabolic disorder may be diabetes. The disease or condition may be an inflammatory disorder. The inflammatory disorder may be multiple sclerosis. The disease or condition may be a cell proliferative disorder. The disease or condition may be a blood disorder. The blood disorder may be neutropenia. The blood disorder may be anemia. The disease or condition may be a pathogenic infection. The pathogenic infection may be a viral infection. The disease or condition may be a growth disorder. The disease or condition may be a cardiovascular condition. The cardiovascular condition may be acute heart failure. Modulating the receptor may comprise inhibiting or blocking the receptor. Modulating the receptor may comprise activating the receptor. The therapeutic agent may act as a receptor agonist. The therapeutic agent may act as a receptor antagonist.

Provided herein is a method of preventing or treating a disease in a mammal in need thereof comprising administering a pharmaceutical composition described herein to said mammal. In some embodiments, the disease may be an infectious disease. In certain embodiments, the infectious disease may be mastitis. In some embodiments, the infectious disease may be a respiratory disease. In certain embodiments, the respiratory disease may be bovine respiratory disease of shipping fever. In certain embodiments, the mammal in need may be a dairy animal selected from a list comprising cow, camel, donkey, goat, horse, reindeer, sheep, water buffalo, moose and yak. In some embodiments, the mammal in need may be bovine.

Provided may be a method of preventing or treating mastitis in a dairy animal, comprising providing to said dairy animal an effective amount of a composition comprising one or more immunoglobulin fusion proteins disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. In some instances, the immunoglobulin fusion protein comprises an antibody region attached to an extender fusion region, wherein the extender fusion region comprises (a) an extender peptide comprising an amino acid sequence comprising an alpha helix and (i) an amino acid sequence comprising 7 or fewer amino acids based on or derived from an ultralong CDR3 or (ii) an amino acid sequence that does not comprise an ultralong CDR3; and (b) a therapeutic agent. The therapeutic agent may be GCSF. The GCSF may be a bovine GCSF. The GCSF may be a human GCSF. In some embodiments, the dairy animal may be a cow or a water buffalo.

Provided are methods of treatment, inhibition and prevention of a disease or condition in a subject in need thereof by administration to the subject of an effective amount of an immunoglobulin fusion protein or pharmaceutical composition described herein. The immunoglobulin fusion protein may be substantially purified (e.g., substantially free from substances that limit its effect or produce undesired side-effects). The subject may be an animal, including but not limited to animals such as cows, pigs, sheep, goats, rabbits, horses, chickens, cats, dogs, mice, etc. The subject may be a mammal. The subject may be a human. The subject may be a non-human primate. Alternatively, the subject may be a bovine. The subject may be an avian, reptile or amphibian.

Additional Uses

Further disclosed herein are uses of an immunoglobulin fusion protein (IFP) in the manufacture of a medicament for the treatment of a disease or condition. The IFP may be any of the IFPs disclosed herein. Disclosed herein is the use of an immunoglobulin fusion protein in the manufacture of a medicament for the treatment of a disease or condition, the immunoglobulin fusion protein comprising an antibody region attached to a non-antibody region. Further disclosed herein is the use of an immunoglobulin fusion protein in the manufacture of a medicament for the treatment of a disease or condition, the IFP comprising an antibody region attached to an extender fusion region, wherein the extender fusion region comprises a therapeutic agent. The non-antibody region may comprise an extender peptide. The non-antibody region may comprise a linker peptide. The non-antibody region may comprise a proteolytic cleavage site. The extender fusion region may comprise an extender peptide. The extender fusion region may comprise a linker peptide. The extender fusion region may comprise a proteolytic cleavage site. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The non-antibody region may be inserted within the antibody region. The non-antibody region may be inserted within an immunoglobulin heavy chain of the antibody region. The non-antibody region may be inserted within an immunoglobulin light chain of the antibody region. The non-antibody region may be conjugated to the antibody region. The non-antibody may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may comprise GCSF. The GCSF may be a human GCSF. The therapeutic agent may be Moka1. The therapeutic agent may be VM24. The therapeutic agent may be exendin-4. The therapeutic agent may be erythropoietin. The erythropoietin may be a human erythropoietin. The therapeutic agent may be hLeptin. The therapeutic agent may be a growth hormone (GH). The growth hormone may be a human growth hormone (hGH). The therapeutic agent may be interferon-alpha. The therapeutic agent may be interferon-beta. The therapeutic agent may be GLP-1. The therapeutic agent may be neutrophil elastase inhibitor. The therapeutic agent may be relaxin. The therapeutic agent may be Mamba1. The therapeutic agent may be elafin. The therapeutic agent may be betatrophin. The therapeutic agent may be GDF11. The therapeutic agent may be GMCSF. The disease or condition may be an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain. The disease or condition may be a growth disorder.

Disclosed herein is the use of an immunoglobulin fusion protein in the manufacture of a medicament for the treatment of a cell proliferative disorder. The IFP may be any of the IFPs disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The cell proliferative disorder may be cancer. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The non-antibody region may be inserted within the antibody region. The non-antibody region may be inserted within an immunoglobulin heavy chain of the antibody region. The non-antibody region may be inserted within an immunoglobulin light chain of the antibody region. The non-antibody region may be conjugated to the antibody region. The non-antibody region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule.

Disclosed herein is the use of an immunoglobulin fusion protein in the manufacture of a medicament for the treatment of a metabolic disorder. The metabolic disorder may be diabetes. Diabetes may be type I diabetes. Diabetes may be type II diabetes. The IFP may be any of the IFPs disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be exendin-4. The therapeutic agent may be GLP-1. The therapeutic agent may be hLeptin. The therapeutic agent may be betatrophin.

Disclosed herein is the use of an immunoglobulin fusion protein in the manufacture of a medicament for the treatment of an autoimmune disease or condition. The IFP may be any of the IFPs disclosed herein. The IFP may be any of the IFPs disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be Moka1. The therapeutic agent may be VM24.

Disclosed herein is the use of an immunoglobulin fusion protein in the manufacture of a medicament for the treatment of an inflammatory disease or condition. The inflammatory disease or condition may be multiple sclerosis. The IFP may be any of the IFPs disclosed herein. The IFP may be any of the IFPs disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be elafin. The therapeutic agent may be interferon-beta.

Disclosed herein is the use of an immunoglobulin fusion protein in the manufacture of a medicament for the treatment of a disease or condition of the central nervous system. The IFP may be any of the IFPs disclosed herein. The disease or condition of the central nervous system may be pain. The IFP may be any of the IFPs disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be Mamba1.

Disclosed herein is the use of an immunoglobulin fusion protein in the manufacture of a medicament for the treatment of a cardiovascular disease or condition. The IFP may be any of the IFPs disclosed herein. The cardiovascular disease or condition may be acute heart failure. The cardiovascular disease or condition may be cardiac hypertrophy. The IFP may be any of the IFPs disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be relaxin. The therapeutic agent may be GDF11.

Disclosed herein is the use of an immunoglobulin fusion protein in the manufacture of a medicament for the treatment of a hematological disease or condition. The IFP may be any of the IFPs disclosed herein. The hematological disease or condition may be anemia. The hematological disease or condition may be neutropenia. The IFP may be any of the IFPs disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be GCSF. The GCSF may be a human GCSF. The therapeutic agent may be erythropoietin. The erythropoietin may be a human erythropoietin. The therapeutic agent may be GMCSF.

Disclosed herein is the use of an immunoglobulin fusion protein in the manufacture of a medicament for the treatment of a pathogenic infection. The IFP may be any of the IFPs disclosed herein. The pathogenic infection may be a viral infection. The IFP may be any of the IFPs disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody.

The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be interferon-alpha.

Disclosed herein is the use of an immunoglobulin fusion protein in the manufacture of a medicament for the treatment of a growth disorder. The IFP may be any of the IFPs disclosed herein. Examples of growth disorders included, but are not limited to, achondroplasia, achondroplasia in children, acromegaly, adiposogenital dystrophy, dwarfism, gigantism, Brooke Greenberg, hemihypertrophy, hypochondroplasia, Jansen's metaphyseal chondrodysplasia, Kowarski syndrome, Léri-Weill dyschondrosteosis, local gigantism, macrodystrophia lipomatosa, Majewski's polydactyly syndrome, microcephalic osteodysplastic primordial dwarfism type II, midget, overgrowth syndrome, parastremmatic dwarfism, primordial dwarfism, pseudoachondroplasia, psychosocial short stature, Seckel syndrome, short rib—polydactyly syndrome and Silver-Russell syndrome. The IFP may be any of the IFPs disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be a growth hormone. The growth hormone may be a human growth hormone (hGH).

Further disclosed herein are uses of an immunoglobulin fusion protein for the treatment of a disease or condition. The IFP may be any of the IFPs disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may comprise GCSF. The GCSF may be a human GCSF. The therapeutic agent may be Moka1. The therapeutic agent may be VM24. The therapeutic agent may be exendin-4. The therapeutic agent may be erythropoietin. The erythropoietin may be a human erythropoietin. The therapeutic agent may be hLeptin. The therapeutic agent may be a growth hormone (GH). The growth hormone may be a human growth hormone (hGH). The therapeutic agent may be interferon-alpha. The therapeutic agent may be interferon-beta. The therapeutic agent may be GLP-1. The therapeutic agent may be relaxin. The therapeutic agent may be neutrophil elastase inhibitor. The therapeutic agent may be Mamba1. The therapeutic agent may be elafin. The therapeutic agent may be betatrophin. The therapeutic agent may be GDF11. The therapeutic agent may be GMCSF. The disease or condition may be an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain. The disease or condition may be a growth disorder.

Disclosed herein is the use of an immunoglobulin fusion protein for the treatment of a cell proliferative disorder in a subject in need thereof. The IFP may be any of the IFPs disclosed herein. The cell proliferative disorder may be cancer. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule.

Disclosed herein is the use of an immunoglobulin fusion protein for the treatment of a metabolic disorder in a subject in need thereof. The IFP may be any of the IFPs disclosed herein. The metabolic disorder may be diabetes. Diabetes may be type I diabetes. Diabetes may be type II diabetes. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be exendin-4. The therapeutic agent may be GLP-1. The therapeutic agent may be hLeptin. The therapeutic agent may be betatrophin.

Disclosed herein is the use of an immunoglobulin fusion protein for the treatment of an autoimmune disease or condition in a subject in need thereof. The IFP may be any of the IFPs disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be Moka1. The therapeutic agent may be VM24.

Disclosed herein is the use of an immunoglobulin fusion protein for the treatment of an inflammatory disease or condition in a subject in need thereof. The IFP may be any of the IFPs disclosed herein. The inflammatory disease or condition may be multiple sclerosis. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be elafin. The therapeutic agent may be interferon-beta.

Disclosed herein is the use of an immunoglobulin fusion protein for the treatment of a disease or condition of the central nervous system in a subject in need thereof. The IFP may be any of the IFPs disclosed herein. The disease or condition of the central nervous system may be pain. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be Mamba1.

Disclosed herein is the use of an immunoglobulin fusion protein for the treatment of a cardiovascular disease or condition in a subject in need thereof. The IFP may be any of the IFPs disclosed herein. The cardiovascular disease or condition may be acute heart failure. The cardiovascular disease or condition may be cardiac hypertrophy. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be relaxin. The therapeutic agent may be GDF11.

Disclosed herein is the use of an immunoglobulin fusion protein for the treatment of a hematological disease or condition in a subject in need thereof. The IFP may be any of the IFPs disclosed herein. The hematological disease or condition may be anemia. The hematological disease or condition may be neutropenia. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be GCSF. The GCSF may be a human GCSF. The therapeutic agent may be erythropoietin. The erythropoietin may be a human erythropoietin. The therapeutic agent may be GMCSF.

Disclosed herein is the use of an immunoglobulin fusion protein for the treatment of a pathogenic infection in a subject in need thereof. The IFP may be any of the IFPs disclosed herein. The pathogenic infection may be a viral infection. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be interferon-alpha.

Disclosed herein is the use of an immunoglobulin fusion protein for the treatment of a growth disorder in a subject in need thereof. Examples of growth disorders included, but are not limited to, achondroplasia, achondroplasia in children, acromegaly, adiposogenital dystrophy, dwarfism, gigantism, Brooke Greenberg, hemihypertrophy, hypochondroplasia, Jansen's metaphyseal chondrodysplasia, Kowarski syndrome, Léri-Weill dyschondrosteosis, local gigantism, macrodystrophia lipomatosa, Majewski's polydactyly syndrome, microcephalic osteodysplastic primordial dwarfism type II, midget, overgrowth syndrome, parastremmatic dwarfism, primordial dwarfism, pseudoachondroplasia, psychosocial short stature, Seckel syndrome, short rib-polydactyly syndrome and Silver-Russell syndrome. The IFP may be any of the IFPs disclosed herein. The immunoglobulin fusion protein may comprise an antibody region attached to a non-antibody region. The non-antibody region may comprise a therapeutic agent. The non-antibody region may comprise an extender peptide. The non-antibody region may comprise a linker peptide. The non-antibody region may comprise a proteolytic cleavage site. The immunoglobulin fusion protein may comprise an antibody region attached to an extender fusion region. The extender fusion region may comprise a therapeutic agent. The extender fusion region may comprise an extender peptide. The extender fusion region may comprise a linker peptide. The extender fusion region may comprise a proteolytic cleavage site. The IFP may comprise a non-antibody region attached to an antibody region, wherein the antibody region comprises 6 or fewer amino acids of an ultralong CDR3. The non-antibody region may comprise one or more therapeutic agents. In some instances, the immunoglobulin fusion protein comprising an antibody region attached to an extender fusion region, wherein the extender fusion region comprises (a) an extender peptide comprising at least one secondary structure; and (b) a therapeutic agent. The extender fusion region may be inserted within the antibody region. The extender fusion region may be inserted within an immunoglobulin heavy chain of the antibody region. The extender fusion region may be inserted within an immunoglobulin light chain of the antibody region. The extender fusion region may be conjugated to the antibody region. The extender fusion region may be conjugated to a position within the antibody region. The antibody region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody may be a bovine antibody. The mammalian antibody may be a human antibody. In other instances, the mammalian antibody is a murine antibody. The immunoglobulin fusion protein, antibody region and/or extender fusion region may further comprise one or more linkers. The linker may attach therapeutic agent to the extender peptide. The linker may attach the extender fusion region to the antibody region. The linker may attach a proteolytic cleavage site to the antibody region, extender fusion region, extender peptide, or therapeutic agent. The therapeutic agent may be a peptide or derivative or variant thereof. Alternatively, therapeutic agent is a small molecule. The therapeutic agent may be a growth hormone. The growth hormone may be a human growth hormone (hGH).

Pharmacological Properties

Further disclosed herein are methods of improving one or more pharmacological properties of a therapeutic agent. The method may comprise producing an immunoglobulin fusion protein disclosed herein. Examples of pharmacological properties may include, but are not limited to, half-life, stability, solubility, immunogenicity, toxicity, bioavailability, absorption, liberation, distribution, metabolization, and excretion. Liberation may refer to the process of releasing of a therapeutic agent from the pharmaceutical formulation. Absorption may refer to the process of a substance entering the blood circulation. Distribution may refer to the dispersion or dissemination of substances throughout the fluids and tissues of the body. Metabolization (or biotransformation, or inactivation) may refer to the recognition by an organism that a foreign substance is present and the irreversible transformation of parent compounds into daughter metabolites. Excretion may refer to the removal of the substances from the body.

The half-life of a therapeutic agent may greater than the half-life of the non-conjugated therapeutic agent. The half-life of the therapeutic agent may be greater than 4 hours, greater than 6 hours, greater than 12 hours, greater than 24 hours, greater than 36 hours, greater than 2 days, greater than 3 days, greater than 4 days, greater than 5 days, greater than 6 days, greater than 7 days, greater than 8 days, greater than 9 days, greater than 10 days, greater than 11 days, greater than 12 days, greater than 13 days, or greater than 14 days when administered to a subject. The half-life of the therapeutic agent may be greater than 4 hours when administered to a subject. The half-life of the therapeutic agent may be greater than 6 hours when administered to a subject.

The half-life of the therapeutic agent may increase by at least about 2, 4, 6, 8, 10, 12, 14, 16, 18, or 20 or more hours. The half-life of the therapeutic agent may increase by at least about 2 hours. The half-life of the therapeutic agent may increase by at least about 4 hours. The half-life of the therapeutic agent may increase by at least about 6 hours. The half-life of the therapeutic agent may increase by at least about 8 hours.

The half-life of a therapeutic agent may be at least about 1.5, 2, 2.5, 3, 3.5, 4, 4.5, 5, 5.5, 6, 6.5, 7, 7.5, 8, 8.5, 9, 9.5, or 10-fold greater than the half-life of the non-conjugated therapeutic peptide. The half-life of a therapeutic agent an antibody described herein may be at least about 15, 16, 17, 18, 19, 20, 25, 30, 35, 40, 45, or 50-fold greater than the half-life of the non-conjugated therapeutic peptide. The half-life of a therapeutic agent an antibody described herein may be at least about 2-fold greater than the half-life of the non-conjugated therapeutic peptide. The half-life of a therapeutic agent an antibody described herein may be at least about 5-fold greater than the half-life of the non-conjugated therapeutic peptide. The half-life of a therapeutic agent an antibody described herein may be at least about 10-fold greater than the half-life of the non-conjugated therapeutic peptide.

The half-life of a therapeutic agent an antibody described herein may be at least about 5%, 10%, 15%, 20%, 25%, 30%, 35%, 40%, 45%, 55%, 60%, 65%, 70%, 75%, 80%, 85%, 90%, 95%, or 97% greater than the half-life of the non-conjugated therapeutic peptide. The half-life of a therapeutic agent an antibody described herein may be at least about 10% greater than the half-life of the non-conjugated therapeutic peptide. The half-life of a therapeutic agent an antibody described herein may be at least about 20% greater than the half-life of the non-conjugated therapeutic peptide. The half-life of a therapeutic agent an antibody described herein may be at least about 30% greater than the half-life of the non-conjugated therapeutic peptide. The half-life of a therapeutic agent an antibody described herein may be at least about 40% greater than the half-life of the non-conjugated therapeutic peptide. The half-life of a therapeutic agent an antibody described herein may be at least about 50% greater than the half-life of the non-conjugated therapeutic peptide.

EXAMPLES

Example 1: Construction of Trastuzumab-Coil-bGCSF Fusion Protein Vectors for Expression in Mammalian Cells A gene encoding bovine GCSF (bGCSF) (SEQ ID NO: 186) was synthesized by Genscript or IDT, and amplified by polymerase chain reaction (PCR). To optimize the folding and stability of the immunoglobulin fusion protein, flexible linkers of GGGGS (SEQ ID NO: 179, n=1) were added on both ends of the bGCSF fragments. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the bGCSF-linker fragment. Subsequently, PCR fragments encoding the bGCSF gene with the extender peptides and linkers was grafted into the complementarity determining region 3 of the heavy chain (CDR3H) of trastuzumab IgG antibody by exploiting overlap extension PCR, to replace the Trp99-Met107 loop. The trastuzumab-coil based bGCSF fusion protein was further modified to replace the hIgG1 CH1-CH3 constant region of trastuzumab with hIgG4 CH1-CH3 constant region containing triple mutants (S228P, F234A and L235A) to generate trastuzumab-coil bGCSF HC (SEQ ID NO: 38). The expression vectors of trastuzumab-coil based fusion proteins were generated by in-frame ligation of the amplified fusion genes to the pFuse backbone vector (InvivoGen, CA). Similarly, the gene encoding the light chain of trastuzumab IgG antibody (SEQ ID NO: 1) was cloned into the pFuse backbone vector. The obtained expression vectors were confirmed by DNA sequencing.

Example 2: Construction of Bovine-Coil-bGCSF Fusion Protein Vectors for Expression in Mammalian Cells A gene encoding bovine GCSF (bGCSF) (SEQ ID NO: 186) was synthesized by Genscript or IDT, and amplified by polymerase chain reaction (PCR). To optimize the folding and stability of the immunoglobulin fusion protein, flexible linkers of GGGGS (SEQ ID NO: 179, n=1) were added on both ends of the bGCSF fragments. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the bGCSF-linker fragment. Subsequently, PCR fragments encoding the bGCSF gene with the extender peptides and linkers was grafted into the complementarity determining region 3 of the heavy chain (CDR3H) of bovine IgG antibody (BLVIH12) by exploiting overlap extension PCR to generate bovine-coil bGCSF HC (SEQ ID NO: 39). The expression vectors of bovine-coil based fusion proteins were generated by in-frame ligation of the amplified fusion genes to the pFuse backbone vector (InvivoGen, CA). Similarly, the gene encoding the light chain of bovine IgG antibody (SEQ ID NO: 18) was cloned into the pFuse backbone vector. The obtained expression vectors were confirmed by DNA sequencing.

Example 3: Expression and Purification of Trastuzumab-Coil-bGCSF and Bovine-Coil-bGCSF Based Fusion Proteins Trastuzumab-coil-bGCSF based fusion proteins were expressed through transient transfections of free style HEK293 cells with vectors encoding trastuzumab-coil-bGCSF fusion protein heavy chain (SEQ ID NO: 38) and the trastuzumab light chain (SEQ ID NO: 1). Bovine-coil-bGCSF based fusion proteins were expressed through transient transfections of free style HEK293 cells with vectors encoding bovine-coil-bGCSF fusion protein heavy chain (SEQ ID NO: 39) and the bovine light chain (SEQ ID NO: 18). Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel. As shown in FIG. 4, Lane 1 depicts the protein ladder, Lane 2 depicts bovine-coil IgG, Lane 3 depicts bovine-coil IgG treated with DTT, Lane 4 depicts bovine-coil-bGCSF IgG, Lane 5 depicts bovine-coil-bGCSF IgG treated with DTT, Lane 6 depicts trastuzumab-coil-bGCSF IgG, Lane 7 depicts trastuzumab-coil-bGCSF IgG treated with DTT, Lane 8 depicts trastuzumab IgG and Lane 9 depicts trastuzumab IgG treated with DTT.

Example 4: In Vitro Study of Trastuzumab-Coil bGCSF Fusion Protein and Bovine-Coil bGCSF Fusion Protein Proliferative Activity on Mouse NFS-60 Cells Mouse NFS-60 cells were obtained from American Type Culture Collection (ATCC), VA, and cultured in RPMI-1640 medium supplemented with 10% fetal bovine serum (FBS), 0.05 mM 2-mercapoethanol and 62 ng/ml human macrophage colony stimulating factor (M-CSF). For proliferation assays, mouse NFS-60 cells were washed three times with RPMI-1640 medium and resuspended in RPMI-1640 medium with 10% FBS and 0.05 mM 2-mercapoethanol at a density of 1.5×10$^5$ cells/ml. In 96-well plates, 100 µl of cell suspension was added into each well, followed by the addition of varied concentrations of trastuzumab IgG (SEQ ID NOs: 22 and 19), trastuzumab-coil-bGCSF IgG (SEQ ID NOs: 69 and 19), bovine-coil IgG (SEQ ID NOs: 36 and 271), bovine-coil-bGCSF IgG (SEQ ID NOs: 70 and 36), and bGCSF (SEQ ID NO: 227). The plates were incubated at 37° C. in a 5% CO$_2$ incubator for 72 hours. Cells were then treated with AlamarBlue (Invitrogen) (1/10 volume of cell suspension) for 4 hours at 37° C. Fluorescence at 595 nm for each well was read to indicate the cell viability and is displayed in Table 13. FIG. 6 depicts a graphical representation of the data. The EC$_{50}$ of trastuzumab-coil-bGCSF IgG was 2.49±0.26 ng/mL. The EC$_{50}$ of bovine-coil-bGCSF IgG was 2.55±0.38 ng/mL. The EC$_{50}$ of bGCSF was 4.87±0.29 ng/mL.

TABLE 13

| trastuzumab IgG (ng/mL) | Fluorescence Intensity | trastuzumab-coil bGCSF IgG (ng/mL) | Fluorescence Intensity |
|---|---|---|---|
| 1000 | 1465.7345 | 1000 | 7392.629 |
| 333.33333 | 1464.256 | 333.33333 | 8058.969 |
| 111.11111 | 1497.443 | 111.11111 | 8386.5135 |
| 37.03704 | 1533.4505 | 37.03704 | 7799.397 |
| 12.34568 | 1546.9655 | 12.34568 | 7649.2075 |
| 4.11523 | 1613.3125 | 4.11523 | 6019.7085 |
| 1.37174 | 1909.983 | 1.37174 | 3517.689 |
| 0.45725 | 1751.1505 | 0.45725 | 2359.373 |
| 0.15242 | 1596.733 | 0.15242 | 1863.8285 |
| 0.05081 | 1674.4565 | 0.05081 | 1823.8255 |
| 0.01694 | 1729.6545 | 0.01694 | 1834.7485 |
| 0.00565 | 1929.9635 | 0.00565 | 1873.0145 |

Example 5: Binding of Trastuzumab-Coil-bGCSF to Her2 Receptor

The binding affinity of trastuzumab-coil-bGCSF fusion proteins to Her2 receptor was examined by ELISA. Human Her2-Fc chimera (5 ug/mL) (R&D Systems) was coated on 96-well ELISA plate overnight at 4° C., followed by blocking with 1% BSA in PBS (pH7.4) for 2 hours at 37° C. After washing with 0.05% Tween-20 in PBS (pH7.4), varied concentrations of trastuzumab IgG (SEQ ID NOs: 22 and 19) and trastuzumab-coil-bGCSF (SEQ ID NOs: 69 and 19) fusion proteins were added to each well and incubated for 2 hours at 37° C. Subsequently, goat polyclonal anti-human kappa light chain antibody with HRP conjugate (Sigma) was added and incubated for 2 hours at 37° C. Wells were subsequently washed and binding affinities were examined on the basis of fluorescence intensity at 425 nm by adding fluoregenic peroxidase substrate to each well. Table 2 displays the fluorescence intensity at 425 nm of the trastuzumab IgG and trastuzumab-coil-bGCSF IgG. FIG. 7 depicts a graphical representation of the data in Table 14. As shown in FIG. 7, Line 1 represents trastuzumab IgG and Line 2 represents trastuzumab-coil-bGCSF IgG. The EC$_{50}$ of trastuzumab IgG was 110±14 pM.

TABLE 14

| trastuzumab IgG (pM) | Fluorescence Intensity | trastuzumab-coil bGCSF IgG (pM) | Fluorescence Intensity |
|---|---|---|---|
| 4074.07407 | 13113.5475 | 4074.07407 | 1216.3565 |
| 1358.02469 | 11544.1275 | 1358.02469 | 591.2115 |
| 452.6749 | 10776.7925 | 452.6749 | 342.6245 |
| 150.89163 | 7846.828 | 150.89163 | 240.7235 |
| 50.29721 | 4164.892 | 50.29721 | 215.4655 |
| 16.76574 | 1994.7745 | 16.76574 | 215.9255 |
| 5.58858 | 1023.4985 | 5.58858 | 208.08 |
| 1.86286 | 566.8795 | 1.86286 | 198.5575 |

Example 6: Construction of BLV1H12 Betatrophin Based Fusion Protein Vectors for Expression in Mammalian Cells A gene encoding betatrophin (SEQ ID NO: 198) was synthesized by Genscript or IDT, and amplified by polymerase chain reaction (PCR). To optimize the folding and stability of fusion proteins, flexible linkers of GGGGS (SEQ ID NO: 179, n=1) were added on both ends of the betatrophin fragment. Subsequently, PCR fragments encoding genes of interest are grafted into the complementarity determining region 3 of the heavy chain (CDR3H) of a bovine IgG antibody (BLVIH12) by exploiting overlap extension PCR to generate BLV1H2-direct betatrophin fusion (SEQ ID NO: 118). To generate a BLV1H12-coil betatrophin based fusion protein, sequences encoding extender peptides GGSGAKLAALKAKLAALK (SEQ ID NO: 151) and ELAALEAELAALEAGGSG (SEQ ID NO: 161), which form antiparallel coiled coils, are added at the ends of the N- and C-terminal of the betatrophin-linker fragment. Subsequently, the PCR fragment comprising betatrophin, linkers, and extender peptides is grafted into the complementarity determining region 3 of the heavy chain (CDR3H) of a BLV1H12 antibody by exploiting overlap extension PCR to generate trastuzumab-coil betatrophin (CDRH3) HC (SEQ ID NO: 66). The expression vectors of BLV1H2-betatrophin based fusion proteins were generated by in-frame ligation of the amplified fusion genes to the pFuse backbone vector (InvivoGen, CA). Similarly, the gene encoding the light chain of BLV1H2 antibody (SEQ ID NO: 18) was cloned into the pFuse backbone vector. The obtained expression vectors were confirmed by DNA sequencing.

Example 7: Expression and Purification of BLV1H12 Betatrophin Fusion Proteins

BLV1H12-direct betatrophin fusion proteins were expressed through transient transfections of free style HEK293 cells with vectors encoding BLV1H12-direct betatrophin fusion protein heavy chain (SEQ ID NO: 140) and the BLV1H12 light chain (SEQ ID NO: 36). BLV1H12-coil betatrophin fusion proteins were expressed through transient transfections of free style HEK293 cells with vectors encoding BLVIH12-coil betatrophin fusion protein heavy chain (SEQ ID NO: 97) and the BLVIH12 light chain (SEQ ID NO: 36). Expressed fusion proteins were secreted into the culture medium and harvested at 48 and 96 hours after transfection. The fusion proteins were purified by Protein A/G chromatography (Thermo Fisher Scientific, IL), and analyzed by Western blot (FIG. 8). As shown in FIG. 8, Lane 1 contains the protein ladder; Lane 2 contains BLV1H12-coil betatrophin fusion protein (SEQ ID NOs: 97 and 36)

treated with DTT; and Lane 3 contains BLV1H12-coil betatrophin fusion protein (SEQ ID NOs: 97 and 36).

Example 8: Construction of Trastuzumab-Direct bGCSF Protein Vectors for Expression in Mammalian Cells A gene encoding bGCSF (SEQ ID NO: 186) was synthesized by Genscript or IDT, and amplified by polymerase chain reaction (PCR). To optimize the folding and stability of fusion proteins, flexible linkers of GGGGS (SEQ ID NO: 179, n=1) were added on both ends of the bGCSF fragment. Subsequently, PCR fragments encoding genes of interest are grafted into the complementarity determining region 3 of the heavy chain (CDR3H) of a trastuzumab IgG antibody by exploiting overlap extension PCR to generate trastuzumab-direct bGCSF fusion (SEQ ID NO: 101). The expression vectors of trastuzumab-bGCSF based fusion proteins were generated by in-frame ligation of the amplified fusion genes to the pFuse backbone vector (InvivoGen, CA). Similarly, the gene encoding the light chain of trastuzumab antibody (SEQ ID NO: 1) was cloned into the pFuse backbone vector. The obtained expression vectors were confirmed by DNA sequencing.

Example 9: Expression and Purification of Trastuzumab-Direct bGCSF Fusion Protein Trastuzumab-direct bGCSF fusion proteins were expressed through transient transfections of free style HEK293 cells with vectors encoding trastuzumab-direct bGCSF fusion protein heavy chain (SEQ ID NO: 123) and the trastuzumab light chain (SEQ ID NO: 19). Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel (FIG. 10). As shown in FIG. 10, Lane 1 contains the protein ladder; Lane 2 contains trastuzumab-direct bGCSF fusion protein (SEQ ID NOs: 123 and 19); and Lane 3 contains trastuzumab-direct bGCSF fusion protein (SEQ ID NOs: 123 and 19) treated with DTT.

Example 10: In Vitro Study of Trastuzumab-Direct bGCSF Fusion Protein Proliferative Activity on Mouse NFS-60 Cells Mouse NFS-60 cells were obtained from American Type Culture Collection (ATCC), VA, washed three times with RPMI-1640 medium, and resuspended in RPMI-1640 medium supplemented with 10% fetal bovine serum (FBS) and 0.05 mM 2-mercapoethanol at a density of $1.5 \times 10^5$ cells/mL. In 96-well plates, 100 µl of cell suspension was added into each well, followed by the addition of varied concentrations of trastuzumab-direct bGCSF IgG (SEQ ID NOs: 123 and 19) and bGCSF (SEQ ID NO: 227). The plates were incubated at 37° C. in a 5% $CO_2$ incubator for 72 hours. Cells were then treated with AlamarBlue (Invitrogen) (1/10 volume of cell suspension) for 4 hours at 37° C. Fluorescence at 595 nm for each well was read to indicate the cell viability. FIG. 11 depicts a graphical representation of the data. The $EC_{50}$ of trastuzumab-direct-bGCSF IgG was 1.8±0.4 ng/mL. The $EC_{50}$ of bGCSF was 1.3±0.2 ng/mL.

Example 11: Construction of Trastuzumab-Coil-Exendin-4 Fusion Protein Vectors for Expression in Mammalian Cells A gene encoding exendin-4 (Ex-4) (SEQ ID NO: 188) was synthesized by Genscript or IDT, and amplified by polymerase chain reaction (PCR). A cleavage site of Factor Xa (SEQ ID NO: 182) was placed in front of the N-terminal of Ex-4. A flexible CGGGGS linker (SEQ ID NO: 276) was added immediately before the Factor Xa protease cleavage site and a GGGGSC linker (SEQ ID NO: 277) was added at the end of C-terminal of Ex-4 gene fragment to increase folding and stability of the fusion protein. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the exendin-4 linker fragment. Subsequently, PCR fragments encoding genes of interest were grafted into the complementarity determining region 3 of the heavy chain (CDR3H) of trastuzumab IgG antibody by exploiting overlap extension PCR, to replace the Trp99-Met107 loop. The trastuzumab-coil-exendin-4 based fusion protein was modified with human hIgG1 CH1-CH3 constant region containing seven mutations (E233P, L234V, L235A, AG236, A327G, A330S, and P331S) to generate trastuzumab-coil-Ex4 HC fusion (SEQ ID NO: 40). The expression vectors of trastuzumab-coil-exendin-4 based fusion proteins were generated by in-frame ligation of the amplified fusion genes to the pFuse backbone vector (InvivoGen, CA). Similarly, the gene encoding the light chain of trastuzumab IgG antibody (SEQ ID NO: 1) was cloned into the pFuse backbone vector. The obtained expression vectors were confirmed by DNA sequencing.

Example 12: Expression and Purification of Trastuzumab-Coil-Exendin-4 Based Fusion Proteins Trastuzumab-coil-exendin-4 based fusion proteins were expressed through transient transfections of free style HEK293 cells with vectors encoding trastuzumab-coil-exendin-4 fusion protein heavy chain (SEQ ID NO: 71) and the trastuzumab light chain (SEQ ID NO: 19). Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel. trastuzumab-coil based Ex-4 fusion protein was further treated with Factor Xa protease (GE Healthcare) following manufacture's protocol to release N-terminal of fused peptide. After treatment, fusion proteins were re-purified by Protein A/G affinity column to remove protease and analyzed by SDS-PAGE gel as shown in FIG. 12. Lane 1 is a protein marker. Lane 2 is trastuzumab-coil-Ex-4 IgG (SEQ ID NOs: 71 and 19). Lane 3 is trastuzumab-coil-Ex-4 IgG (SEQ ID NOs: 71 and 19) treated with DTT. Lane 4 is a protein marker. Lane 5 is trastuzumab-coil-Ex-4 IgG (SEQ ID NOs: 71 and 19) after cleavage with Factor Xa, releasing the N-terminus of Ex-4 peptide to generate trastuzumab-coil-Ex-4 RN IgG, wherein RN is an abbreviation for released N-terminus. Lane 6 is trastuzumab-coil-Ex-4 RN IgG treated with DTT.

Example 13. Electrospray Ionization Mass Spectrometry (ESI-MS) of Trastuzumab-Coil-Exendin-4 IgG 10 µg of purified trastuzumab-coil-exendin-4 heavy chain (HC) fusion (SEQ ID NOs: 71 and 19), in PBS (pH 7.4) was treated overnight at 37° C. with 1 µL (500 units) of peptide-N-glycosidase (NEB), followed by the addition of 50 mM DTT. The fusion protein was analyzed by ESI-MS using a 6520 Q-TOF LC/MS from Agilent Technology. The chromatograph is shown in FIG. 13. The expected molecular weight for trastuzumab-coil-exendin-4 HC is 56,880 Da. The observed molecular weight for trastuzumab-coil-exendin-4 HC was 56,748 Da. The observed molecular weight correlates to the expected molecular weight without the first amino acid glutamic acid (E).

Example 14: Electrospray Ionization Mass Spectrometry (ESI-MS) of Trastuzumab-Coil-Exendin-4 RN IgG 10 μg of purified Factor Xa cleaved trastuzumab-coil-exendin-4 heavy chain (HC) fusion (SEQ ID NOs: 71 and 19) in PBS (pH 7.4) was treated overnight at 37° C. with 1 μL (500 units) of peptide-N-glycosidase (NEB), followed by the addition of 50 mM DTT. The cleaved fusion protein fragments were analyzed by ESI-MS using a 6520 Q-TOF LC/MS from Agilent Technology. The chromatograph of the N-terminal fragment is shown in FIG. 14A and the chromatograph of the C-terminal fragment is shown in FIG. 14B. The expected molecular weight for trastuzumab-coil-exendin-4 HC RN N-terminal fragment is 13,309 Da. The observed molecular weight for trastuzumab-coil-exendin-4 HC RN N-terminal fragment was 13,307 Da. The expected molecular weight for trastuzumab-coil-exendin-4 HC RN C-terminal fragment is 43,589 Da. The observed molecular weight for trastuzumab-coil-exendin-4 HC RN C-terminal fragment was 43,458 Da.

Example 15: In Vitro Study of Trastuzumab-Coil Exendin-4 Fusion Protein Activation Activities on GLP-1 Receptor (GLP-1R)

HEK293 cells overexpressing surface GLP-1R and cAMP responsive luciferase reporter gene were seeded in 384 well plates at a density of 5,000 cells per well. After 24 h incubation at 37° C. with 5% $CO_2$, cells were treated with various concentrations of exendin-4 peptide (SEQ ID NO: 228), trastuzumab (SEQ ID NOs: 19 and 22), trastuzumab-coil exendin-4 (SEQ ID NOs: 71 and 19), and trastuzumab-coil exendin-4 (SEQ ID NOs: 71 and 19) RN; and incubated for another 24 h. Subsequently, a luciferase assay was performed using One-Glo luciferase reagent according manufacture's instruction (Promega). FIG. 15 depicts a graphical representation of the data. The $EC_{50}$ of exendin-4 was 0.03±0.004 nM. The $EC_{50}$ of trastuzumab-coil exendin-4 was 3.8±0.2 nM. The $EC_{50}$ of trastuzumab-coil exendin-4 RN was 0.01±0.001 nM.

Example 16: In Vitro Study of Trastuzumab-Coil-Exendin-4 Fusion Protein Glucagon Receptor Activation Assay HEK 293 cells overexpressing glucagon receptor (GCGR) and CRE-Luc reporter were grown in DMEM with 10% FBS at 37° C. with 5% CO2. Cells were seeded in 384-well plates at a density of 5,000 cells per well and treated with various concentrations of glucagon, exendin-4 peptide (SEQ ID NO: 228), trastuzumab (SEQ ID NOs: 19 and 22), trastuzumab-coil exendin-4 (SEQ ID NOs: 71 and 19), and trastuzumab-coil exendin-4 (SEQ ID NOs: 71 and 19) RN fusion proteins for 24 hours at 37° C. with 5% CO2. Luminescence intensities were then measured using One-Glo (Promega, WI) luciferase reagent by following manufacturer's instruction. FIG. 16 depicts a graphical representation of the data.

Example 17: Pharmacokinetics of Trastuzumab-Coil-Ex-4 RN Fusion Protein in Mice Ex-4 (SEQ ID NO: 228) (1.6 mg/kg) and trastuzumab-coil-Ex-4 (SEQ ID NOs: 71 and 19) RN fusion protein (2.8 mg/kg) were administered by intravenous (i.v.) or subcutaneous (s.c.) injection into CD1 mice (N=3). Blood samples were collected from day 0 to day 8 for Ex-4 peptide and day 0 to day 14 for trastuzumab-coil-Ex-4 RN fusion protein. The remaining activities were analyzed using HEK 293-GLP-1R-CRE-Luc cells. Data were normalized by taking the maximal concentration at the first time point (30 minutes) for the intravenous injection. Data were normalized by taking the maximal concentration at the second time point (1 day) for the subcutaneous injection. Percentages of the maximal concentration were plotted versus time points of blood sample collection, and half-lives were determined by fitting data into the first-order equation, $A=A0e-kt$, where A0 is the initial concentration, t is the time, and k is the first-order rate constant. FIG. 17A and FIG. 17B depicts a graphical representation of the data. FIG. 17A depicts intravenous inject. FIG. 17B depicts subcutaneous inject. The $t_{1/2}$ of exendin-4 (i.v.) was 1.5±0.2 hours. The $t_{1/2}$ of trastuzumab-coil exendin-4 RN (i.v.) was 2.4±0.1 days. The $t_{1/2}$ of trastuzumab-coil exendin-4 RN (s.c.) was 3.9±1.2 days.

Example 18: Pharmacodynamics of Trastuzumab-Coil-Ex-4 RN Fusion Protein in Mice Single doses of Ex-4 (SEQ ID NO: 228) (20 μg/kg), trastuzumab (SEQ ID NOs: 19 and 22) (8 mg/kg), and varied concentrations of trastuzumab-coil-Ex-4 RN (SEQ ID NOs: 71 and 19) fusion protein were administered by subcutaneous (s.c.) injection into CD1 mice (N=5). Glucose (3 g/kg, p.o.) were given at 30 minutes, 24, 48, 72, 96, 120, 144, 168, and 216 hours post single-dose treatments, followed by blood glucose measurements immediately prior to and at 15, 30, 45, 60, and 120 minutes post glucose load. FIG. 18A-18D depicts a graphical representation of the data at 30 minutes (FIG. 18A), 24 (FIG. 18A), 48 (FIG. 18B), 72 (FIG. 18B), 96 (FIG. 18C), 120 (FIG. 18C), 144 (FIG. 18D), 168 (FIG. 18D), and 216 (FIG. 18D) hours post single-dose treatments.

Example 19: Pharmacodynamics of Trastuzumab-Coil-Ex-4 Fusion Protein in Mice Single doses of Ex-4 (SEQ ID NO: 228) (20 μg/kg), trastuzumab (SEQ ID NOs: 19 and 22) (8 mg/kg), and varied concentrations of trastuzumab-coil-Ex-4 (SEQ ID NOs: 71 and 19) fusion protein were administered by subcutaneous (s.c.) injection into CD1 mice (N=5). Glucose (3 g/kg, p.o.) were given at 2, 24, 48, 72, 96, 120, and 144 hours post single-dose treatments, followed by blood glucose measurements immediately prior to and at 15, 30, 45, 60, and 120 minutes post glucose load. FIG. 19A-FIG. 19C depict a graphical representation of the data at 2 (FIG. 19A), 24 (FIG. 19A), 48 (FIG. 19B), 72 (FIG. 19B), 144 (FIG. 19C), 168 (FIG. 19C), and 216 (FIG. 19C) hours post single-dose treatments.

Example 20: Binding of Trastuzumab-Coil-Exendin-4 to Her2 Receptor

The binding affinity of trastuzumab-coil-exendin-4 fusion proteins to Her2 receptor is examined by ELISA. Human Her2-Fc chimera (5 ug/mL) (R&D Systems) is coated on 96-well ELISA plate overnight at 4° C., followed by blocking with 1% BSA in PBS (pH7.4) for 2 hours at 37° C. After washing with 0.05% Tween-20 in PBS (pH7.4), varied concentrations of trastuzumab IgG (SEQ ID NOs: 19 and 22) and trastuzumab-coil-exendin-4 (SEQ ID NOs: 71 and 19) fusion proteins are added to incubate for 2 hours at 37° C. Subsequently, goat polyclonal anti-human kappa light chain antibody with HRP conjugate (Sigma) is added and incubated for 2 hours at 37° C. Wells are subsequently washed and binding affinities are examined on the basis of fluorescence intensity at 425 nm by adding fluorogenic peroxidase substrate to each well.

Example 21: Flow Cytometric Analysis of Trastuzumab-Coil-Exendin-4 Binding to HER2 Receptor HER2-overexpressing SKBR3 cells are grown in DMEM with 10% FBS and 1% penicillin and streptomycin. Cells are washed with cold PBS for three times, blocked with 2% BSA in PBS, and incubated with 10 or 100 nM of trastuzumab (SEQ ID NOs: 19 and 22) and trastuzumab-CDR fusion proteins (SEQ ID NOs: 71 and 19) for 2 hours at 4° C. with gentle mixing. Unbound antibody is removed by washing with 2% BSA in PBS. Cells are then stained with FITC anti-human IgG Fc (KPL, Inc., MD) for 1 hour at 4° C. with gentle mixing, followed by washing with PBS and analysis by flow cytometry.

Example 22: Construction of Trastuzumab-Coil-Moka Fusion Protein Vectors for Expression in Mammalian Cells A gene encoding Moka (SEQ ID NO: 189) was synthesized by Genscript or IDT, and amplified by polymerase chain reaction (PCR). To optimize the folding and stability of fusion proteins, flexible linkers of GGGGS (SEQ ID NO: 179, n=1) were added on both ends of the Moka fragment. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the Moka-Linker fragment. Subsequently, PCR fragments encoding the Moka gene with the extender peptides and linkers was grafted into the complementarity determining region 3 of the heavy chain (CDR3H) of trastuzumab IgG antibody by exploiting overlap extension PCR, to replace the Trp99-Met107 loop. The trastuzumab-coil-Moka-based fusion protein was further modified to replace the hIgG1 CH1-CH3 constant region of trastuzumab with hIgG4 CH1-CH3 constant region containing triple mutants (S228P, F234A and L235A) to generate trastuzumab-coil-Moka IgG (SEQ ID NO: 41). The expression vectors of trastuzumab-coil-Moka-based fusion proteins were generated by in-frame ligation of the amplified fusion genes to the pFuse backbone vector (InvivoGen, CA). Similarly, the gene encoding the light chain of trastuzumab IgG antibody (SEQ ID NO: 1) was cloned into the pFuse backbone vector. The obtained expression vectors were confirmed by DNA sequencing.

Example 23: Expression and Purification of Trastuzumab-Coil-Moka Based Fusion Proteins Trastuzumab-coil-Moka based fusion proteins are expressed through transient transfections of free style HEK293 cells with vectors encoding trastuzumab-coil-Moka fusion protein heavy chain (SEQ ID NO: 72) and the trastuzumab light chain (SEQ ID NO: 19). Expressed fusion proteins are secreted into the culture medium and harvested at 48 and 96 hours after transfection. The fusion proteins are purified by Protein A/G chromatography (Thermo Fisher Scientific, IL), and analyzed by SDS-PAGE gel as shown in FIG. 20. Lane 1 shows a protein molecular weight marker. Lane 2 shows purified trastuzumab-coil-Moka IgG. Lane 3 shows purified trastuzumab-coil-Moka IgG treated with DTT.

Example 24: Construction of Trastuzumab-Coil-VM24 Fusion Protein Vectors for Expression in Mammalian Cells A gene encoding VM24 (SEQ ID NO: 190) was synthesized by Genscript or IDT, and amplified by polymerase chain reaction (PCR). To optimize the folding and stability of the fusion proteins, flexible linkers of GGGGS (SEQ ID NO: 179, n=1) were added on both ends of VM24 fragments. Then, sequences encoding encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the VM24-linker fragments. Subsequently, PCR fragments encoding genes of interest were grafted into the complementarity determining region 3 of the heavy chain (CDR3H) of trastuzumab IgG antibody by exploiting overlap extension PCR, to replace the Trp99-Met107 loop. The trastuzumab-coil-VM24 based fusion protein was further modified to replace the hIgG1 CH1-CH3 constant region of trastuzumab with hIgG4 CH1-CH3 constant region containing triple mutants (S228P, F234A and L235A) to generate SEQ ID NO: 42. The expression vectors of trastuzumab-coil-VM24 based fusion proteins were generated by in-frame ligation of the amplified fusion genes to the pFuse backbone vector (InvivoGen, CA). Similarly, the gene encoding the light chain of trastuzumab IgG antibody (SEQ ID NO: 1) was cloned into the pFuse backbone vector. The obtained expression vectors were confirmed by DNA sequencing.

Example 25: Expression and Purification of Trastuzumab-Coil-VM24 Based Fusion Proteins Trastuzumab-coil-VM24 based fusion proteins are expressed through transient transfections of free style HEK293 cells with vectors encoding trastuzumab-coil-VM24 fusion protein heavy chain (SEQ ID NO: 73) and the trastuzumab light chain (SEQ ID NO: 19). Expressed fusion proteins are secreted into the culture medium and harvested at 48 and 96 hours after transfection. The fusion proteins are purified by Protein A/G chromatography (Thermo Fisher Scientific, IL), and analyzed by SDS-PAGE gel as shown in FIG. 20. Lane 1 shows a protein molecular weight marker. Lane 4 shows purified trastuzumab-coil-Vm24 IgG. Lane 5 shows purified trastuzumab-coil-Vm24 IgG treated with DTT.

Example 26: In Vitro Study of Trastuzumab-Coil-Moka Fusion Protein and Trastuzumab-Coil-Vm24 Fusion Protein Inhibitory Activities on Human Peripheral Blood Mononuclear Cells (PBMCs)/T Cells Activation Human PBMCs were isolated from fresh venous blood of healthy donors through ficoll gradient centrifugation, followed by resuspension in RPMI1640 medium with 10% FBS and plating in 96-well plates at a density of 1×10$^6$ cells/mL. Human T cells were purified from the isolated PBMCs using T cell enrichment kit. Purified PBMCs and T cells were pretreated for 1 h at 37° C. with 5% CO$_2$ with various concentrations of purified trastuzumab-coil Moka (SEQ ID NOs: 72 and 19) and trastuzumab-coil Vm24 (SEQ ID NOs: 73 and 19) fusion proteins and then activated by anti-CD3 and CD28 antibodies. After 24 h treatment, supernatant was collected for measurement of the levels of secreted TNF-α using ELISA kit. FIG. 21 depicts a graphical representation of the in vitro inhibition on T-cell activation data. The EC$_{50}$ of trastuzumab-coil Moka IgG (SEQ ID NOs: 72 and 19) was 269±46 nM. The EC$_{50}$ of trastuzumab-coil Vm24 IgG (SEQ ID NOs: 73 and 19) was 178±104 nM.

Example 27: Construction of Trastuzumab-Coil-hGCSF Fusion Protein Vectors for Expression in Mammalian Cells A gene encoding human GCSF (hGCSF) (SEQ ID NO: 187) was synthesized by Genscript or IDT, and amplified by polymerase chain reaction (PCR). To optimize the folding and stability of the fusion proteins, flexible linkers of GGGGS (SEQ ID NO: 179, n=1) were added on both ends of hGCSF fragments. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the hGCSF-linker fragments. To generate a CDRH3 fusion, PCR fragments encoding genes of interest were grafted into the complementarity determining region 3 of the heavy chain (CDRH3) of trastuzumab IgG antibody by exploiting overlap extension PCR, to replace the Trp99-Met107 loop. To generate a CDRH2 fusion, PCR fragments encoding genes of interest were grafted into the complementary determining region 2 of the heavy chain (CDRH2) of trastuzumab IgG antibody by exploiting overlap extension PCR, to replace Thr54-Asn55. To generate a CDRL3 fusion, PCR fragments encoding genes of interest were grafted into the complementary determining region 3 of the light chain (CDRL3) of trastuzumab IgG antibody by exploiting overlap extension PCR, to replace Thr93-Pro95. The trastuzumab-coil-hGCSF based fusion proteins were modified with human hIgG1 CH1-CH3 constant region containing seven mutations (E233P, L234V, L235A, AG236, A327G, A330S, and P331S). The expression vectors of trastuzumab-coil-hGCSF based fusion proteins were generated by in-frame ligation of the amplified fusion genes to the pFuse backbone vector (InvivoGen, CA). Similarly, the gene encoding the light chain of trastuzumab IgG antibody (SEQ ID NO: 1) was cloned into the pFuse backbone vector. The obtained expression vectors were confirmed by DNA sequencing.

Example 28: Expression and Purification of Trastuzumab-Coil-hGCSF Based Fusion Proteins Trastuzumab-coil-hGCSF based fusion proteins are expressed through transient transfections of free style HEK293 cells with vectors encoding trastuzumab-coil-hGCSF fusion protein (CDRH3) heavy chain (SEQ ID NO: 74) and the trastuzumab light chain (SEQ ID NO: 9), trastuzumab-coil-hGCSF fusion protein (CDRH2) heavy chain and the trastuzumab light chain, and trastuzumab-coil-hGCSF fusion protein (CDRL3) light chain and the trastuzumab heavy chain. Expressed fusion proteins are secreted into the culture medium and harvested at 48 and 96 hours after transfection. The fusion proteins are purified by Protein A/G chromatography (Thermo Fisher Scientific, IL), and analyzed by SDS-PAGE gel. FIG. 22 depicts purified trastuzumab-coil-hGCSF based fusion proteins. Lane 1 shows purified trastuzumab-coil hGCSF (CDRH2) IgG. Lane 2 shows purified trastuzumab-coil hGCSF (CDRH2) IgG treated with DTT. Lane 3 shows a protein molecular weight marker. Lane 4 shows purified trastuzumab-coil hGCSF (CDRL3) IgG. Lane 5 shows purified trastuzumab-coil hGCSF (CDRL3) IgG treated with DTT.

Example 29: Electrospray Ionization Mass Spectrometry (ESI-MS) of Trastuzumab-Coil-hGCSF Based Fusion Proteins 10 μg of purified trastuzumab-coil-hGCSF (CDRH2), in PBS (pH 7.4) was treated overnight at 37° C. with 1 μL (500 units) of peptide-N-glycosidase (NEB), followed by the addition of 50 mM DTT. The fusion protein was analyzed by ESI-MS using a 6520 Q-TOF LC/MS from Agilent Technology. The chromatograph is shown in FIG. 23A. The expected molecular weight for trastuzumab-coil-hGCSF (CDRH2) HC is 71,472 Da. The observed molecular weight for trastuzumab-coil-hGCSF (CDRH2) HC was 72,300 Da. The observed molecular weight correlates to O-glycosylation on hGCSF. 10 μg of purified trastuzumab-coil-hGCSF (CDRL3), in PBS (pH 7.4) was treated overnight at 37° C. with 1 μL (500 units) of peptide-N-glycosidase (NEB), followed by the addition of 50 mM DTT. The fusion protein was analyzed by ESI-MS using a 6520 Q-TOF LC/MS from Agilent Technology. The chromatograph is shown in FIG. 23B. The expected molecular weight for trastuzumab-coil-hGCSF (CDRL3) LC is 45,746 Da. The observed molecular weight for trastuzumab-coil-hGCSF (CDRL3) LC was 46,692 Da. The observed molecular weight correlates to O-glycosylation on hGCSF.

Example 30: Binding of Trastuzumab-Coil hGCSF Based Fusion Proteins to HER2 Receptor HER2-overexpressing SKBR3 cells were grown in DMEM with 10% FBS and 1% penicillin and streptomycin. Cells were washed with cold PBS for three times, blocked with 2% BSA in PBS, and incubated with 10 or 100 nM of trastuzumab and trastuzumab-CDR fusion proteins, trastuzumab-coil-hGCSF (CDRH2) and trastuzumab-coil-hGCSF (CDRL3), for 2 hours at 4° C. with gentle mixing. Unbound antibody was removed by washing with 2% BSA in PBS. Cells were then stained with FITC anti-human IgG Fc (KPL, Inc., MD) for 1 hour at 4° C. with gentle mixing, followed by washing with PBS and analysis by flow cytometry. FIG. 24 depicts the flow cytometry histogram.

Example 31: In Vitro Study of Trastuzumab-Coil hGCSF Fusion Protein Proliferative Activity on Mouse NFS-60 Cells Mouse NFS-60 cells were cultured in RPMI-1640 medium supplemented with 10% FBS, 0.05 mM 2-mercapoethanol and 62 ng/ml human macrophage colony stimulating factor (M-CSF). To examine the proliferative activity of trastuzumab-hGCSF fusion proteins, cells were washed three times with RPMI-1640 medium with 10% FBS, resuspended in RPMI-1640 medium with 10% FBS and 0.05 mM 2-mercapoethanol at a density of 1.5×105 cells/ml, plated in 96-well plates (1.5×104 cells per well) with various concentrations of hGCSF, trastuzumab, trastuzumab-coil-hGCSF (CDRH2), and trastuzumab-coil-hGCSF (CDRL3), and incubated for 72 hours at 37° C. with 5% CO2. Cells were then treated with AlamarBlue (Life Technologies, CA) for 4 hours at 37° C. Fluorescence intensity measured at 595 nm is proportional to cell viability. FIG. 25 depicts a graphical representation of the data. The $EC_{50}$ of hGCSF was 1.7±0.3 ng/mL. The $EC_{50}$ of trastuzumab-coil hGCSF (CDRH2) was 0.4±0.1 ng/mL. The $EC_{50}$ of trastuzumab-coil hGCSF (CDRL3) was 0.9±0.1 ng/mL.

Example 32. Construction of Trastuzumab-Coil-hEPO Fusion Protein Vectors for Expression in Mammalian Cells A gene encoding hEPO (SEQ ID NO: 192) was synthesized by Genscript or IDT, and amplified by polymerase chain reaction (PCR). To optimize the folding and stability of the immunoglobulin fusion protein, flexible linkers of GGGGS (SEQ ID NO: 179, n=1) were added on both ends of the hEPO fragments. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the hEPO-linker fragment. Subsequently, PCR fragments encoding the hEPO gene with the extender peptides and linkers was grafted into the complementarity determining region 3 of the heavy chain (CDR3H) of trastuzumab IgG antibody by exploiting overlap extension PCR, to replace the Trp99-Met107 loop. The CH1-CH3 constant regions of trastuzumab-coil hEPO (CDRH3) heavy chain were replaced with human IgG4 CH1-CH3 constant region containing triple mutations (S228P, F234A and L235A) to generate trastuzumab-coil hEPO (CDRH3) HC. The expression vectors of trastuzumab-coil based fusion proteins were generated by in-frame ligation of the amplified fusion genes to the pFuse backbone vector (InvivoGen, CA). Similarly, the gene encoding the light chain of trastuzumab IgG antibody (SEQ ID NO: 1) was cloned into the pFuse backbone vector. The obtained expression vectors were confirmed by DNA sequencing.

Example 33: Expression and Purification of Trastuzumab-Coil-hEPO Fusion Proteins Trastuzumab-coil-hEPO based fusion proteins were expressed through transient transfections of free style HEK293 cells with vectors encoding trastuzumab-coil-hEPO fusion protein heavy chain and the trastuzumab light chain (SEQ ID NO: 1). Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel. As shown in FIG. 26, Lane 1 depicts a protein ladder, Lane 2 depicts purified trastuzumab-coil-hEPO (CDRH3) and trastuzumab LC, and Lane 3 depicts trastuzumab-coil-hEPO (CDRH3) and trastuzumab LC treated with DTT.

Example 34: Electrospray Ionization Mass Spectrometry (ESI-MS) of Trastuzumab-Coil-hEPO Based Fusion Proteins 10 μg of purified trastuzumab-coil-hEPO (CDRH3), in PBS (pH 7.4) was treated overnight at 37° C. with 1 μL (500 units) of peptide-N-glycosidase (NEB), followed by the addition of 50 mM DTT. The fusion protein was analyzed by ESI-MS using a 6520 Q-TOF LC/MS from Agilent Technology. The chromatograph is shown in FIG. 27. The expected molecular weight for trastuzumab-coil-hEPO (CDRH3) HC is 70,307 Da. The observed molecular weight for trastuzumab-coil-hEPO (CDRH3) HC was 70,177 Da. The observed molecular weight correlates to O-glycosylation on hEPO and the absence of the first amino acid glutamic acid (E).

Example 35: Binding of Trastuzumab-Coil hEPO Based Fusion Proteins to HER2 Receptor HER2-overexpressing SKBR3 cells were grown in DMEM with 10% FBS and 1% penicillin and streptomycin. Cells were washed with cold PBS for three times, blocked with 2% BSA in PBS, and incubated with 10 or 100 nM of trastuzumab and trastuzumab-coil-hEPO (CDRH3), for 2 hours at 4° C. with gentle mixing. Unbound antibody was removed by washing with 2% BSA in PBS. Cells were then stained with FITC anti-human IgG Fc (KPL, Inc., MD) for 1 hour at 4° C. with gentle mixing, followed by washing with PBS and analysis by flow cytometry. FIG. 28 depicts the flow cytometry histogram.

Example 36: In Vitro Proliferative Activity Assay of Trastuzumab-Coil-hEPO Fusion Protein on TF-1 Cells Human TF-1 cells were cultured at 37° C. with 5% CO2 in RPMI-1640 medium containing 10% fetal bovine serum (FBS), penicillin and streptomycin (50 U/mL), and 2 ng/ml human granulocyte macrophage colony stimulating factor (GM-CSF). To examine the proliferative activity of trastuzumab-hEPO fusion proteins, cells were washed three times with RPMI-1640 medium with 10% FBS, resuspended in RPMI-1640 medium with 10% FBS at a density of $1.5 \times 10^5$ cells/ml, plated in 96-well plates ($1.5 \times 10^4$ cells per well) with various concentrations of hEPO, trastuzumab, and trastuzumab-coil hEPO (CDRH3) fusion protein, and then incubated for 72 hours at 37° C. with 5% CO2. Cells were then treated with Alamar Blue (Life Technologies, CA) for 4 hours at 37° C. Fluorescence intensity measured at 595 nm is proportional to cell viability. The $EC_{50}$ values were determined by fitting data into a logistic sigmoidal function: y=A2+(A1−A2)/(1+(x/x0)p), where A1 is the initial value, A2 is the final value, x0 is the inflection point of the curve, and p is the power. FIG. 29 depicts a graphical representation of the data. The $EC_{50}$ of hEPO was 0.1±0.02 nM. The $EC_{50}$ of trastuzumab-coil hEPO (CDRH3) was 0.1±0.01 nM.

Example 37: Construction of Trastuzumab hGCSF/EPO Dual Fusion Protein

A gene encoding hEPO (SEQ ID NO: 192) was synthesized by Genscript or IDT, and amplified by polymerase chain reaction (PCR). To optimize the folding and stability of the immunoglobulin fusion protein, flexible linkers of GGGGS (SEQ ID NO: 179, n=1) were added on both ends of the hEPO fragments. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the hEPO-linker fragment. Subsequently, PCR fragments encoding the hEPO gene with the extender peptides and linkers was grafted into the complementarity determining region 3 of the heavy chain (CDR3H) of trastuzumab IgG antibody by exploiting overlap extension PCR, to replace the Trp99-Met107 loop. The CH1-CH3 constant regions of trastuzumab-coil hEPO (CDRH3) heavy chain were replaced with human IgG4 CH1-CH3 constant region containing triple mutations (S228P, F234A and L235A) to generate trastuzumab-coil hEPO (CDRH3) HC (SEQ ID NO: 62).

A gene encoding human GCSF (hGCSF) (SEQ ID NO: 187) was synthesized by Genscript or IDT, and amplified by polymerase chain reaction (PCR). To optimize the folding and stability of the fusion proteins, flexible linkers of GGGGS (SEQ ID NO: 179, n=1) were added on both ends of hGCSF fragments. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the hGCSF-linker fragments. The PCR fragment encoding the hGCSF-linker-extender was grafted into the complementary determining region 3 of the light chain (CDRL3) of trastuzumab IgG antibody by exploiting overlap extension PCR, to replace Thr93-Pro95. The trastuzumab-coil-hGCSF based fusion protein was modified with human hIgG1 CH1-CH3 constant region containing seven mutations (E233P, L234V, L235A, AG236, A327G, A330S, and P331S) to generate trastuzumab-coil hGCSF (CDRL3) LC (SEQ ID NO: 63). The expression vectors of trastuzumab-coil based fusion proteins were generated by in-frame ligation of the amplified fusion genes to the pFuse backbone vector (InvivoGen, CA).

Example 38: Expression and Purification of Trastuzumab hGCSF/EPO Dual Fusion Protein Trastuzumab-coil-hGCSF/EPO dual fusion protein was expressed through transient transfections of free style HEK293 cells with a vector encoding trastuzumab-coil hEPO (CDRH3) HC (SEQ ID NO: 62) and trastuzumab-coil hGCSF (CDRL3) LC (SEQ ID NO: 63). Expressed dual fusion proteins were secreted into the culture medium and harvested at 48 and 96 hours after transfection. The fusion proteins were purified by Protein A/G chromatography (Thermo Fisher Scientific, IL), and analyzed by SDS-PAGE gel. As shown in FIG. 30, Lane 1 depicts the protein ladder, Lane 2 depicts trastuzumab-coil-hGCSF/EPO dual fusion protein, and Lane 3 depicts trastuzumab-coil-hGCSF/EPO dual fusion protein treated with DTT.

Example 39: Electrospray Ionization Mass Spectrometry (ESI-MS) of Trastuzumab hGCSF/hEPO Based Fusion Proteins 10 µg of purified Trastuzumab-coil-hGCSF/EPO dual fusion protein (SEQ ID NOs: 62, 63), in PBS (pH 7.4) was treated overnight at 37° C. with 1 µL (500 units) of peptide-N-glycosidase (NEB), followed by the addition of 50 mM DTT. The fusion protein was analyzed by ESI-MS using a 6520 Q-TOF LC/MS from Agilent Technology. The chromatograph is shown in FIG. 31A. The expected molecular weight for trastuzumab-coil hGCSF (CDRL3) LC is 45,746 Da. The observed molecular weight for trastuzumab-coil hGCSF (CDRL3) LC was 46,690 Da. The observed molecular weights correlates to O-glycosylation on hGCSF.

10 µg of purified Trastuzumab-coil-hGCSF/EPO dual fusion protein (SEQ ID NOs: 62, 63), in PBS (pH 7.4) was treated overnight at 37° C. with 1 µL (500 units) of peptide-N-glycosidase (NEB), followed by the addition of 50 mM DTT. The fusion protein was analyzed by ESI-MS using a 6520 Q-TOF LC/MS from Agilent Technology. The chromatograph is shown in FIG. 31B. The expected molecular weight for trastuzumab-coil hEPO (CDRH3) HC is 70,307 Da. The observed molecular weights for trastuzumab-coil-hEPO (CDRH3) HC was 70,179 Da (correlating to the mass of trastuzumab-coil hEPO (CDRH3) HC without the first amino acid glutamic acid) and 71,126 Da (correlating to O-glycosylation on hEPO).

Example 40: Binding of Trastuzumab hGCSF/hEPO Based Fusion Proteins to HER2 Receptor HER2-overexpressing SKBR3 cells were grown in DMEM with 10% FBS and 1% penicillin and streptomycin. Cells were washed with cold PBS for three times, blocked with 2% BSA in PBS, and incubated with 10 or 100 nM of trastuzumab and trastuzumab-coil-hGCSF/EPO dual fusion protein (SEQ ID NOs: 62, 63) for 2 hours at 4° C. with gentle mixing. Unbound antibody was removed by washing with 2% BSA in PBS. Cells were then stained with FITC anti-human IgG Fc (KPL, Inc., MD) for 1 hour at 4° C. with gentle mixing, followed by washing with PBS and analysis by flow cytometry. FIG. 32 depicts the flow cytometry histogram.

Example 41: In Vitro Proliferative Activity Assay of Trastuzumab hGCSF/hEPO Fusion Protein on TF-1 Cells Human TF-1 cells were cultured at 37° C. with 5% CO2 in RPMI-1640 medium containing 10% fetal bovine serum (FBS), penicillin and streptomycin (50 U/mL), and 2 ng/ml human granulocyte macrophage colony stimulating factor (GM-CSF). To examine the proliferative activity of trastuzumab hGCSF/hEPO fusion proteins, cells were washed three times with RPMI-1640 medium with 10% FBS, resuspended in RPMI-1640 medium with 10% FBS at a density of $1.5 \times 10^5$ cells/ml, plated in 96-well plates ($1.5 \times 10^4$ cells per well) with various concentrations of hEPO, trastuzumab, and trastuzumab hGCSF/hEPO (CDRH3) fusion protein (SEQ ID NOs: 62, 63), and then incubated for 72 hours at 37° C. with 5% CO2. Cells were then treated with Alamar Blue (Life Technologies, CA) for 4 hours at 37° C. Fluorescence intensity measured at 595 nm is proportional to cell viability. FIG. 33 depicts a graphical representation of the data. The $EC_{50}$ of hEPO was 0.1±0.02 nM. The $EC_{50}$ of trastuzumab-coil hGCSF/hEPO was 0.2±0.03 nM.

Example 42: In Vitro Study of Trastuzumab-Coil hGCSF/hEPO Fusion Protein Proliferative Activity on Mouse NFS-60 Cells Mouse NFS-60 cells were cultured in RPMI-1640 medium supplemented with 10% FBS, 0.05 mM 2-mercapoethanol and 62 ng/ml human macrophage colony stimulating factor (M-CSF). To examine the proliferative activity of trastuzumab hGCSF/hEPO fusion proteins, cells were washed three times with RPMI-1640 medium with 10% FBS, resuspended in RPMI-1640 medium with 10% FBS and 0.05 mM 2-mercapoethanol at a density of $1.5 \times 105$ cells/ml, plated in 96-well plates ($1.5 \times 104$ cells per well) with various concentrations of hGCSF, trastuzumab, and trastuzumab hGCSF/hEPO (CDRH3) fusion protein (SEQ ID NOs: 62, 63), and incubated for 72 hours at 37° C. with 5% CO2. Cells were then treated with AlamarBlue (Life Technologies, CA) for 4 hours at 37° C. Fluorescence intensity measured at 595 nm is proportional to cell viability. FIG. 34 depicts a graphical representation of the data. The $EC_{50}$ of hGCSF was 1.7±0.3 nM. The $EC_{50}$ of trastuzumab-coil hGCSF/hEPO was 3.1±0.1 nM.

Example 43. Construction of Herceptin hGH Fusion Protein Vectors for Expression in Mammalian Cells A gene encoding hGH (SEQ ID NO: 201) was synthesized by Genscript or IDT, and amplified by polymerase chain reaction (PCR). To optimize the folding and stability of the immunoglobulin fusion protein, flexible linkers of GGGGS (SEQ ID NO: 179, n=1) were added on both ends of the hGH fragments. To generate Herceptin-coil hGH fusion proteins, sequences encoding extender peptides GGS-GAKLAALKAKLAALK (SEQ ID NO: 151) and ELAALEAELAALEAGGSG (SEQ ID NO: 161), which form antiparallel coiled coils, were added at the ends of the N- and C-terminal of the hGH-linker fragment. To generate a trastuzumab-direct hGH (CDRH2) fusion protein (SEQ ID NO: 128), a PCR fragment encoding the hGH gene with the linkers was grafted into the complementarity determining region 2 of the heavy chain (CDRH2) of Herceptin IgG antibody by exploiting overlap extension PCR. To generate a trastuzumab-coil hGH (CDRH3) fusion protein (SEQ ID NO: 75), a PCR fragment encoding the hGH gene with the extender peptides and linkers was grafted into the complementary determining region 3 of the heavy chain (CDRH3) of Herceptin IgG antibody by exploiting overlap extension PCR. To generate a trastuzumab-coil hGH (CDRH2) fusion protein (SEQ ID NO: 76), a PCR fragment encoding the hGH gene with the extender peptides and linkers was grafted into the complementary determining region 2 of the heavy chain (CDRH2) of Herceptin IgG antibody by exploiting overlap extension PCR. The expression vectors of trastuzumab hGH based fusion proteins were generated by in-frame ligation of the amplified fusion genes to the pFuse backbone vector (InvivoGen, CA). The obtained expression vectors were confirmed by DNA sequencing.

Example 44: Expression and Purification of Trastuzumab hGH Based Fusion Proteins Trastuzumab-direct hGH based fusion proteins were expressed through transient transfections of free style HEK293 cells with vectors encoding trastuzumab-direct hGH (CDRH2) HC (SEQ ID NO: 128), and the trastuzumab light chain (SEQ ID NO: 19). trastuzumab-coil hGH (CDRH3) based fusion proteins were expressed through transient transfections of free style HEK293 cells with vectors encoding trastuzumab-coil hGH (CDRH3) HC (SEQ ID NO: 75), and the trastuzumab light chain (SEQ ID NO: 19). Trastuzumab-coil hGH (CDRH2) based fusion proteins were expressed through transient transfections of free style HEK293 cells with vectors encoding trastuzumab-coil hGH (CDRH2) HC (SEQ ID NO: 76), and the trastuzumab light chain (SEQ ID NO: 19). Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel. As shown in FIG. 35, Lane 1 depicts a protein ladder, Lane 2 depicts trastuzumab-coil hGH (CDRH3) (SEQ ID NOs: 75, 19), Lane 3 depicts trastuzumab-coil hGH (CDRH3) (SEQ ID NOs: 75, 19) treated with DTT, Lane 4 depicts a protein ladder, Lane 5 depicts trastuzumab-direct hGH (CDRH2) (SEQ ID NOs: 128 and 19), Lane 6 depicts trastuzumab-direct hGH (CDRH2) (SEQ ID NOs: 128 and 19) treated with DTT, Lane 7 depicts trastuzumab-coil hGH (CDRH2) (SEQ ID NOs: 76, 19), and Lane 8 depicts trastuzumab-coil hGH (CDRH2) (SEQ ID NOs: 76, 19) treated with DTT.

Example 45: Trastuzumab hGH Based Fusion Protein Activity Assays hGHR-Ba/F3 proliferation assay: Murine Ba/F3 cell lines were stably transduced with hGH receptor (hGHR) under a EF1α promoter. Clonally selected hGHR-Ba/F3 were maintained in 10% FBS, RPMI1640, and 50 ng/mL of hGH. The proliferation assay was performed in 96 well culture plates comprising 20,000 cells in 200 μL assay medium (10% FBS in RPMI1640) per well. Increasing concentrations of hGH, trastuzumab-coil hGH (CDRH3), trastuzumab-coil hGH (CDRH2), and trastuzumab-direct (CDRH2) were incubated with the cells for 72 hours. At the end of the incubation period, 20 μl of Prestoblue was added to each well, and the fluorescent signal recorded on a Spectramax fluorescence plate reader at 590 nm with 550 nm excitation. The $EC_{50}$ values for hGH and trastuzumab hGH fusions are shown in Table 15.

NB2 proliferation assay: Rat Nb2-11 cell lines (Sigma) were maintained in 10% FBS, 10% horse serum (HS) in RPMI with 55 μM β-ME. The proliferation assay was performed in 96 well culture plates comprising 50,000 cells in 200 μL assay medium (10% HS in RPMI with 55 uM β-ME) per well. Increasing concentrations of hGH, trastuzumab-coil hGH (CDRH3), trastuzumab-coil hGH (CDRH2), and trastuzumab-direct (CDRH2) were incubated with the cells for 72 hours. At the end of the incubation period, 20 μl of Prestoblue was added to each well, and the fluorescent signal recorded on a Spectramax fluorescence plate reader at 590 nm with 550 nm excitation. The $EC_{50}$ values for hGH and trastuzumab hGH fusions are shown in Table 15.

Stat5 phosphorylation assay: Human IM9 cells (ATCC) were maintained in 10% FBS in RPMI1640. The night before the phosphorylation assay, $2 \times 10e^5$ IM9 cells were seeded into V bottom 96 well plates in 200 μL assay medium (1% charcoal stripped FBS in RPMI) and starved overnight. On the day of the phosphorylation experiment, starved cells were stimulated with hGH, trastuzumab-coil hGH (CDRH3), trastuzumab-coil hGH (CDRH2), and trastuzumab-direct (CDRH2) at various concentration for 10 min at 37° C. After stimulation, cells were fixed by 4% formaldehyde at 37° C. for 10 min, and then permeablized with 90% methanol. Cells were then blocked with 5% BSA at room temperature for 10 min and stained with Alexa Fluor® 488 conjugated anti-pStat5 (Tyr694) (C71E5) Rabbit mAb (Cell Signaling Technology, Inc.) following the manufacturer's suggested protocol. Cells were washed with PBS and analyzed by a flow cytometer. The $EC_{50}$ values for hGH and trastuzumab hGH fusions are shown in Table 15. ND=not determined.

TABLE 15

| | hGH Activity Assays | | |
|---|---|---|---|
| Analyte | NB2 proliferation assay ($EC_{50}$) | hGHR-Ba/F3 proliferation assay ($EC_{50}$) | Stat5 phosphorylation assay ($EC_{50}$) |
| hGH | 0.084 ± 0.011 | 0.926 ± 0.059 | 0.353 ± 0.090 |
| trastuzumab-coil hGH (CDRH3) | 0.153 ± 0.044 | 1.792 ± 0.448 | 1.065 ± 0.116 |

TABLE 15-continued hGH Activity Assays

| Analyte | NB2 proliferation assay (EC$_{50}$) | hGHR-Ba/F3 proliferation assay (EC$_{50}$) | Stat5 phosphorylation assay (EC$_{50}$) |
|---|---|---|---|
| trastuzumab-coil hGH (CDRH2) | ND | ND | 0.524 ± 0.046 |
| trastuzumab-direct hGH (CDRH2) | ND | ND | 0.539 ± 0.034 |

Example 46: Trastuzumab-Coil hGH (CDRH3) Pharmacokinetics Studies

Trastuzumab-coil hGH (CDRH3) and genotropin were injected intravenously (i.v) or subcutaneously (s.c.) into two separate experiment groups at 2 mg/kg in PBS into SD female rats with three rats per treatment. Plasma samples were collected at the following time points: 30 min, 1 hr, 2 hr, 4 hr, 6 hr, 24 hr, 48 hr, 3 days, 4 days, 7 days, 10 days, and 14 days. The amount of genotropin was quantified by hGH Human Direct ELISA Kit (Life Technologies). Trastuzumab-coil hGH (CDRH3) was quantified using a sandwich ELISA assay. Briefly, maxisorb ELISA plates were coated with Goat Anti-Human IgG Fc (Abcam, ab98616) for 1 hour at 37° C., and then blocked with 5% BSA. A proper dilution of plasma was added to the blocked wells and the wells incubated for 1 hour at room temperature. After washing the wells, biotinylated polyclonal anti-hGH antibodies (R&D systems, BAF 1067) were applied to the wells for 1 hour. The plates were washed and incubated with high sensitivity Streptavidin-HRP conjugate (Pierce, 21130) for 1 hour at room temperature. QuantaBlu fluorogenic ELISA substrate was applied after extensive washing, and signals were obtained with Spectramax fluorescence plate reader. The amount of trastuzumab-coil hGH (CDRH3) fusion in plasma samples was quantified by extrapolating the signal into a linear range (signal vs concentration) of a standard curve. The concentrations of genotropin and trastuzumab-coil hGH (CDRH3) at each collection time point were plotted and shown in FIG. 36A-FIG. 36B. FIG. 36A shows the pharmacokinetics by intravenous injection. FIG. 36B shows the pharmacokinetics by subcutaneous injection.

Example 47: Trastuzumab-coil hGH (CDRH3) Pharmacodynamics Studies

The pharmacodynamics performance of the trastuzumab-coil hGH (CDRH3) fusion was assessed in a standard hypophysectomized rat assay. Hypophysectomized male rats were purchased from Harlan, and pre-screened for several days prior to the study to monitor body weight normalization post-surgery/travel. The rats matched by initial weights were treated with one of several therapies: daily subcutaneous injection of genotropin for 14 days (0.1 mg/kg); or biweekly administration of genotropin (0.3 mg/kg) or trastuzumab-coil hGH (CDRH3) (1.0 mg/kg). The animals were weighed daily. At the end the treatment period animals were sacrificed and epiphyses thickness was measured. The percent change in body weight from day 1 was plotted per day and is shown in FIG. 37.

Example 48: Construction of Trastuzumab-Coil hLeptin Based Fusion Protein Vectors for Expression in Mammalian Cells A gene encoding hLeptin (SEQ ID NO: 197) was synthesized by Genscript or IDT, and amplified by polymerase chain reaction (PCR). To optimize the folding and stability of the immunoglobulin fusion protein, flexible linkers of GGGGS (SEQ ID NO: 179, n=1) were added on both ends of the hLeptin fragments. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the hLeptin-linker fragment. The PCR fragment encoding the hLeptin gene with the extender peptides and linkers was grafted into the complementarity determining region 3 of the heavy chain (CDRH3) of trastuzumab IgG antibody by exploiting overlap extension PCR. The constant regions of trastuzumab were modified with human IgG CH1-CH3 constant region containing seven mutations (E233P, L234V, L235A, AG236, A327G, A330S, and P331S) to generate trastuzumab-coil hLeptin (CDRH3) HC (SEQ ID NO: 78). To generate a CDRL3 fusion, the PCR fragment encoding the hLeptin gene with the extender peptides and linkers was grafted into the complementary determining region 3 of the light chain (CDRL3) of trastuzumab IgG antibody by exploiting overlap extension PCR, to replace Thr93-Pro95 and generate trastuzumab-coil hLeptin (CDRL3) (SEQ ID NO: 49). The PCR fragment encoding the hLeptin gene with the extender peptides and linkers was grafted into the complementarity determining region 2 of the heavy chain (CDRH2) of trastuzumab IgG antibody by exploiting overlap extension PCR to generate trastuzumab-coil hLeptin (CDRH2) HC (SEQ ID NO: 79). The expression vectors of the trastuzumab-coil hLeptin based fusion proteins were generated by in-frame ligation of the amplified fusion genes to the pFuse backbone vector (InvivoGen, CA). Similarly, the gene encoding the light chain of trastuzumab IgG antibody (SEQ ID NO: 1) was cloned into the pFuse backbone vector. The obtained expression vectors were confirmed by DNA sequencing.

Example 49: Expression and Purification of Trastuzumab-Coil hLeptin Based Fusion Proteins Trastuzumab-coil hLeptin (CDRH3) based fusion proteins were expressed through transient transfections of free style HEK293 cells with vectors encoding trastuzumab-coil hLeptin (CDRH3) HC (SEQ ID NO: 78) and the trastuzumab light chain (SEQ ID NO: 19). Trastuzumab-coil hLeptin (CDRH2) based fusion proteins were expressed through transient transfections of free style HEK293 cells with vectors encoding trastuzumab-coil hLeptin (CDRH2) HC (SEQ ID NO: 79) and the trastuzumab light chain (SEQ ID NO: 19). Trastuzumab-coil hLeptin (CDRL3) based fusion proteins were expressed through transient transfections of free style HEK293 cells with vectors encoding trastuzumab-coil hLeptin (CDRL3) LC (SEQ ID NO: 49) and the trastuzumab heavy chain (SEQ ID NO: 4). Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel. As shown in FIG. 38, Lane 1 depicts trastuzumab-coil hLeptin (CDRH2) (SEQ ID NOs: 79, 19), Lane 2 depicts trastuzumab-coil hLeptin (CDRH2) (SEQ ID NOs: 79, 19) treated with DTT, Lanes 3, 4 and 7 depict protein molecular weight markers, Lane 5 depicts trastuzumab-coil hLeptin (CDRH3) (SEQ ID NOs: 78, 19), Lane 6 depicts trastuzumab-coil hLeptin (CDRH3) (SEQ ID NOs: 78, 19) treated with DTT, Lane 8 depicts trastuzumab-coil hLeptin (CDRL3) (SEQ ID NOs: 49, 4), and Lane 9 depicts trastuzumab-coil hLeptin (CDRL3) (SEQ ID NOs: 49, 4) treated with DTT.

Example 50: In Vitro Activity of Trastuzumab-Coil hLeptin Based Fusion Proteins in Activating Human Leptin Receptor (LepR)

Baf3 stable cells overexpressing human Leptin receptor (LepR) were seeded in a 96-well plate, treated with different doses of hLeptin (SEQ ID NO: 238), trastuzumab-coil hLeptin (CDRH2) (SEQ ID NOs: 79, 19), and trastuzumab-coil hLeptin (CDRH3) (SEQ ID NOs: 78, 19) for 72 hours. AlamarBlue regent was added at 1/10 volume, incubated for 2 hrs, and the fluorescent measured at 590 nm under excitation at 560 nm. The data was were analyzed using GraphPad Prism 6. FIG. 39A-FIG. 39B depicts a graphical representation of the data. The $EC_{50}$ of hLeptin was 129.4±46.09 pM (FIG. 39A). The $EC_{50}$ of trastuzumab-coil hLeptin (CDRH3) was 55.38±14.04 pM. The $EC_{50}$ of trastuzumab-coil hLeptin (CDRH2) was 99.41±18.91 pM. The $EC_{50}$ of hLeptin was 58.19±10.88 pM (FIG. 39B). The $EC_{50}$ of trastuzumab-coil hLeptin (CDRL3) was 665.1±62.70 pM.

Example 51: SKBR3 Binding of Trastuzumab-Coil hLeptin Based Fusion Proteins

SKBR3 cells were grown in DMEM with 10% FBS and 1% penicillin and streptomycin. Cells were washed with cold PBS for three times, blocked with 2% BSA in PBS, and incubated with 10 or 100 nM of trastuzumab, trastuzumab-coil hLeptin (CDRH2) (SEQ ID NOs: 79, 19), and trastuzumab-coil hLeptin (CDRH3) (SEQ ID NOs: 78, 19) for 2 hours at 4° C. with gentle mixing. Unbound antibody was removed by washing with 2% BSA in PBS. Cells were then stained with FITC anti-human IgG Fc (KPL, Inc., MD) for 1 hour at 4° C. with gentle mixing, followed by washing with PBS and analysis by flow cytometry. FIG. 40A-FIG. 40C depicts the flow cytometry histogram of (FIG. 40A) trastuzumab, (FIG. 40B) trastuzumab-coil hLeptin (CDRH2), and (FIG. 40C) trastuzumab-coil hLeptin (CDRH3).

Example 52: Construction of Trastuzumab-Coil-Elafin Fusion Protein Vectors for Expression in Mammalian Cells A gene encoding elafin (SEQ ID NO: 217) was synthesized by Genscript or IDT, and amplified by polymerase chain reaction (PCR). A flexible GGGGS linker (SEQ ID NO: 179) was added to the N-terminus and C-terminus of the elafin gene fragment to increase folding and stability of the fusion protein. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the elafin linker fragment. Subsequently, the PCR fragment encoding elafin with the linker and extender fragments were grafted into the complementarity determining region 3 of the heavy chain (CDR3H) of trastuzumab IgG antibody by exploiting overlap extension PCR, to replace the Trp99-Met107 loop. The trastuzumab-coil-elafin based fusion protein was modified with human hIgG1 CH1-CH3 constant region containing seven mutations (E233P, L234V, L235A, AG236, A327G, A330S, and P331S) to generate trastuzumab-coil-elafin HC fusion (SEQ ID NO: 54). The expression vector of trastuzumab-coil-elafin (CDRH3) was generated by in-frame ligation of the amplified fusion gene to the pFuse backbone vector (InvivoGen, CA). Similarly, the gene encoding the light chain of trastuzumab IgG antibody (SEQ ID NO: 1) was cloned into the pFuse backbone vector. The obtained expression vectors were confirmed by DNA sequencing.

Example 53: Expression and Purification of Trastuzumab-Coil-Elafin Based Fusion Proteins Trastuzumab-coil-elafin (CDRH3) based fusion proteins were expressed through transient transfections of free style HEK293 cells with vectors encoding trastuzumab-coil elafin fusion protein heavy chain (SEQ ID NO: 54) and the trastuzumab light chain (SEQ ID NO: 19). Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel as shown in FIG. 41. Lane 1 is a protein marker. Lane 2 is trastuzumab-coil-elafin (CDRH3) IgG (SEQ ID NOs: 85 and 19). Lane 3 is trastuzumab-coil-elafin (CDRH3) IgG (SEQ ID NOs: 85 and 19) treated with DTT.

Example 54: Elastase Inhibition Assay

Human elastase was purchased from Elastin Products Company, Inc. Increasing concentrations of elafin (SEQ ID NO: 258) and trastuzumab-coil elafin (CDRH3) IgG (SEQ ID NOs: 85 and 19) were incubated with elastase at room temperature, the residue activity of elastase was analyzed by the addition of fluorogenic elastase substrate MeOSuc-AAPV-AMC (EMD Millipore). The slope of the reactions were obtained by monitoring at 420 nm wavelength with 325 nm excitation on a Spectramax fluorescence plate reader. Each data point was triplicated and fit into the equation:

$$Q=(Ki*(1+(S/Km))).$$

$$Y=Vo*(1-((((Et+X+Q)-(((Et+X+Q)^2)-4*Et*X)^0.5))/(2*Et))).$$

FIG. 42A-FIG. 42B shows the inhibition of elastase by elafin (FIG. 42A) and trastuzumab-coil elafin (CDRH3) IgG (FIG. 42B).

Example 55: Construction of Trastuzumab-Coil GLP2 Fusion Protein Vectors for Expression in Mammalian Cells A gene encoding GLP2 (SEQ ID NO: 222) was synthesized by Genscript or IDT, and amplified by polymerase chain reaction (PCR). A flexible CGGGGS linker (SEQ ID NO: 276) was added to the N-terminus of GLP2 and a flexible GGGGSC (SEQ ID NO: 277) was added to the C-terminus of GLP2. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the GLP2 linker fragment. Subsequently, the PCR fragment encoding GLP2 with the linker and extender fragments were grafted into the complementarity determining region 3 of the heavy chain (CDR3H) of trastuzumab IgG antibody by exploiting overlap extension PCR, to replace the Trp99-Met107 loop. The trastuzumab-coil GLP2 based fusion protein was modified with human hIgG1 CH1-CH3 constant region containing seven mutations (E233P, L234V, L235A, AG236, A327G, A330S, and P331 S) to generate trastuzumab-coil GLP2 (CDRH3) HC fusion (SEQ ID NO: 65). The expression vector of trastuzumab-coil GLP2 (CDRH3) was generated by in-frame ligation of the amplified fusion gene to the pFuse backbone vector (InvivoGen, CA). Similarly, the gene encoding the light chain of trastuzumab IgG antibody (SEQ ID NO: 1) was cloned into the pFuse backbone vector. The obtained expression vectors were confirmed by DNA sequencing.

Example 56: Expression and Purification of Trastuzumab-Coil GLP2 Based Fusion Proteins Trastuzumab-coil GLP2 (CDRH3) based fusion proteins were expressed through transient transfections of free style HEK293 cells with vectors encoding trastuzumab-coil GLP2 fusion protein heavy chain (SEQ ID NO: 65) and the trastuzumab light chain (SEQ ID NO: 19). Expressed fusion proteins were secreted into the culture medium and har-vested at 48 and 96 hours after transfection. The fusion proteins were purified by Protein A/G chromatography (Thermo Fisher Scientific, IL), and analyzed by SDS-PAGE gel as shown in FIG. 43. Lane 1 is a protein marker. Lane 2 is trastuzumab-coil GLP2 (CDRH3) IgG (SEQ ID NOs: 96 and 19). Lane 3 is trastuzumab-coil GLP2 (CDRH3) IgG (SEQ ID NOs: 96 and 19) treated with DTT.

Example 57: Construction of Trastuzumab-Coil Relaxin (Insulin c-Peptide) Fusion Protein Vectors for Expression in Mammalian Cells A gene encoding relaxin (insulin c peptide) (SEQ ID NO: 225) was synthesized by Genscript or IDT, and amplified by polymerase chain reaction (PCR). A flexible GGGGS linker (SEQ ID NO: 179) was added to the N-terminus of relaxin and a flexible GGGGS (SEQ ID NO: 179) was added to the C-terminus of relaxin. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the relaxin linker fragment. Subsequently, the PCR fragment encoding relaxin (insulin c-peptide) with the linker and extender fragments were grafted into the complementarity determining region 3 of the heavy chain (CDR3H) of trastuzumab IgG antibody by exploiting overlap extension PCR, to replace the Trp99-Met107 loop. The trastuzumab-coil relaxin (insulin c-pep-tide) based fusion protein was modified with human hIgG1 CH1-CH3 constant region containing seven mutations (E233P, L234V, L235A, AG236, A327G, A330S, and P331S) to generate trastuzumab-coil relaxin (insulin c-pep-tide) (CDRH3) HC fusion. The expression vector of trastu-zumab-coil relaxin (insulin c-peptide) (CDRH3) was gen-erated by in-frame ligation of the amplified fusion gene to the pFuse backbone vector (InvivoGen, CA). Similarly, the gene encoding the light chain of trastuzumab IgG antibody (SEQ ID NO: 1) was cloned into the pFuse backbone vector. The obtained expression vectors were confirmed by DNA sequencing.

Example 58: Expression and Purification of Trastuzumab-Coil Relaxin (Insulin c-Peptide) Based Fusion Proteins Trastuzumab-coil relaxin (insulin c-peptide) (CDRH3) based fusion proteins were expressed through transient transfections of free style HEK293 cells with vectors encod-ing trastuzumab-coil relaxin (insulin c-peptide) fusion pro-tein heavy chain and the trastuzumab light chain. Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel as shown in FIG. 44. Lane 1 is trastuzumab-coil relaxin (insulin c-peptide) (CDRH3) IgG treated with DTT. Lane 2 is trastuzumab-coil relaxin (insulin c-peptide) (CDRH3) IgG. Lane 3 is a protein marker.

Example 59: Construction of Trastuzumab-Coil Relaxin Fusion Protein Vectors for Expression in Mammalian Cells A gene encoding relaxin comprising internal protease cleavage sites for Factor Xa and PC2 (IEGRKKR (SEQ ID NO: 278)) was synthesized by Genscript or IDT, and ampli-fied by polymerase chain reaction (PCR). A flexible GGGGS linker (SEQ ID NO: 179) was added to the N-terminus of relaxin and a flexible GGGGS (SEQ ID NO: 179) was added to the C-terminus of relaxin. Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the relaxin linker fragment. Subsequently, the PCR fragment encoding relaxin with the protease cleavage sites, linkers and extender fragments were grafted into the complementarity determining region 3 of the heavy chain (CDR3H) of trastuzumab IgG antibody by exploiting overlap extension PCR, to replace the Trp99-Met107 loop. The trastuzumab-coil relaxin based fusion protein was modified with human hIgG1 CH1-CH3 constant region containing seven mutations (E233P, L234V, L235A, AG236, A327G, A330S, and P331S) to generate a trastu-zumab-coil relaxin (CDRH3) HC fusion. The expression vector of trastuzumab-coil relaxin (CDRH3) was generated by in-frame ligation of the amplified fusion gene to the pFuse backbone vector (InvivoGen, CA). Similarly, the gene encoding the light chain of trastuzumab IgG antibody (SEQ ID NO: 1) was cloned into the pFuse backbone vector. The obtained expression vectors were confirmed by DNA sequencing.

Example 60: Expression and Purification of Trastuzumab-Coil Relaxin Based Fusion Proteins Trastuzumab-coil relaxin (CDRH3) based fusion proteins were expressed through transient transfections of free style HEK293 cells with vectors encoding trastuzumab-coil relaxin fusion protein heavy chain (SEQ ID NO: 90) and the trastuzumab light chain (SEQ ID NO: 18). Expressed fusion proteins were secreted into the culture medium and har-vested at 48 and 96 hours after transfection. The fusion proteins were purified by Protein A/G chromatography (Thermo Fisher Scientific, IL) and analyzed by SDS-PAGE gel as shown in FIG. 45. Lane 1 is a protein marker. Lane 2 is trastuzumab-coil relaxin (CDRH3) IgG. Lane 3 is trastuzumab-coil relaxin (CDRH3) IgG treated with DTT. Lane 4 is trastuzumab-coil relaxin (CDRH3) IgG co-ex-pressed with protease PC2. Lane 5 is trastuzumab-coil relaxin (CDRH3) IgG co-expressed with PC2 and treated with DTT.

Example 61: Construction of Trastuzumab-Coil Relaxin (XTEN35) Fusion Protein Vectors for Expression in Mammalian Cells A gene encoding relaxin (XTEN35) (SEQ ID NO: 224) comprising an internal 6×HIS (SEQ ID NO: 274) and a protease cleavage site for PC2 (RKKR) was synthesized by Genscript or IDT, and amplified by polymerase chain reaction (PCR). A flexible GGGGS linker (SEQ ID NO: 179) was added to the N-terminus of relaxin (XTEN35) and a flexible GGGGS (SEQ ID NO: 179) was added to the C-terminus of relaxin (XTEN35). Then, sequences encoding extender peptides GGSGAKLAALKAKLAALK (SEQ ID NO: 151) and ELAALEAELAALEAGGSG (SEQ ID NO: 161), which form antiparallel coiled coils, were added at the ends of the N- and C-terminal of the relaxin (XTEN35) linker fragment. Subsequently, the PCR fragment encoding relaxin (XTEN35) with the linkers and extender fragments were grafted into the complementarity determining region 3 of the heavy chain (CDR3H) of trastuzumab IgG antibody by exploiting overlap extension PCR, to replace the Trp99-Met107 loop. The trastuzumab-coil relaxin (XTEN35) based fusion protein was modified with human hIgG1 CH1-CH3 constant region containing seven mutations (E233P, L234V, L235A, AG236, A327G, A330S, and P331S) to generate a trastuzumab-coil relaxin (CDRH3) HC fusion. The expression vector of trastuzumab-coil relaxin (CDRH3) was generated by in-frame ligation of the amplified fusion gene to the pFuse backbone vector (InvivoGen, CA). Similarly, the gene encoding the light chain of trastuzumab IgG antibody (SEQ ID NO: 1) was cloned into the pFuse backbone vector. The obtained expression vectors were confirmed by DNA sequencing.

Example 62: Expression and Purification of Trastuzumab-Coil Relaxin (XTEN35) Based Fusion Proteins Trastuzumab-coil relaxin (XTEN35) (CDRH3) based fusion proteins were expressed through transient transfections of free style HEK293 cells with vectors encoding trastuzumab-coil relaxin (XTEN35) fusion protein heavy chain and the trastuzumab light chain. Expressed fusion proteins were secreted into the culture medium and harvested at 48 and 96 hours after transfection. The fusion proteins were purified by Protein A/G chromatography (Thermo Fisher Scientific, IL), cleaved with protease PC2, and analyzed by SDS-PAGE gel as shown in FIG. 46. Lane 1 is trastuzumab-coil relaxin (XTEN35) (CDRH3) IgG treated with DTT. Lane 2 is trastuzumab-coil relaxin (XTEN35) (CDRH3) IgG. Lane 3 is trastuzumab-coil relaxin (XTEN35) (CDRH3) IgG co-expressed with PC2 and treated with DTT. Lane 4 is trastuzumab-coil relaxin (XTEN35) (CDRH3) IgG co-expressed with PC2. Lane 5 is a protein molecular weight marker.

Example 63: Binding of Trastuzumab-Coil-hGCSF Protein to Her2 Receptor

The binding affinity of trastuzumab-coil-hGCSF fusion proteins to Her2 receptor is examined by ELISA. Human Her2-Fc chimera (5 µg/mL) (R&D Systems) is coated on 96-well ELISA plate overnight at 4° C., followed by blocking with 1% BSA in PBS (pH 7.4) for 2 hours at 37° C. After washing with 0.05% Tween-20 in PBS (pH 7.4), various concentrations of trastuzumab IgG and trastuzumab-coil-hGCSF fusion proteins are added to the plate for 2 hours of incubation at 37° C. Subsequently, goat polyclonal anti-human kappa light chain antibody with HRP conjugate (Sigma) is added to the plate and the plate is incubated for 2 hours at 37° C. Wells are subsequently washed and binding affinities are examined on the basis of fluorescence intensity at 425 nm by adding fluoregenic peroxidase substrate to each well.

Example 64: Binding of Trastuzumab-Coil-VM24 to Her2 Receptor

The binding affinity of trastuzumab-coil-VM24 fusion proteins to Her2 receptor is examined by ELISA. Human Her2-Fc chimera (5 µg/mL) (R&D Systems) is coated on 96-well ELISA plate overnight at 4° C., followed by blocking with 1% BSA in PBS (pH 7.4) for 2 hours at 37° C. After washing with 0.05% Tween-20 in PBS (pH 7.4), various concentrations of trastuzumab IgG and trastuzumab-coil-VM24 fusion proteins are added to the plate for 2 hours at 37° C. Subsequently, goat polyclonal anti-human kappa light chain antibody with HRP conjugate (Sigma) is added to the plate and the plate is incubated for 2 hours at 37° C. Wells are subsequently washed and binding affinities are examined on the basis of fluorescence intensity at 425 nm by adding fluoregenic peroxidase substrate to each well.

Example 65: Construction of Trastuzumab-Coil hLeptin-Exendin-4 Dual Fusion Protein Leptin and exendin-4 are fused to the CDR-3H and CDR-3L regions in the trastuzumab backbone with an engineered coiled coil stalk. The generated humanized biologically active fusion proteins may improve pharmacological properties for treatment of relevant diseases. In addition, the combination of hLeptin and Ex-4 may have synergistic effects. Trastuzumab-coil hLeptin/Ex4 fusions contain GGGGS linkers (SEQ ID NO: 179) at each terminal of the fused hLeptin and Ex-4 fragments and a GGSG linker (SEQ ID NO: 279) to connect the coiled coils to the base of antibody.

Example 66: Binding of Trastuzumab-Coil-Moka IgG to Her2 Receptor

The binding of trastuzumab-coil-Moka fusion protein to Her2 receptor is examined by ELISA. Human Her2-Fc chimera (5 µg/mL) (R&D Systems) is coated on 96-well ELISA plate overnight at 4° C., followed by blocking with 1% BSA in PBS (pH 7.4) for 2 hours at 37° C. After washing with 0.05% Tween-20 in PBS (pH 7.4), various concentrations of trastuzumab IgG and trastuzumab-coil-Moka fusion proteins are added to each well and the plate is incubated for 2 hours at 37° C. Subsequently, goat polyclonal anti-human kappa light chain antibody with HRP conjugate (Sigma) is added to the plate and the plate is incubated for 2 hours at 37° C. Wells are subsequently washed and binding affinities are examined on the basis of fluorescence intensity at 425 nm by adding fluoregenic peroxidase substrate to each well.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

All references cited herein are incorporated by reference in their entirety and for all purposes to the same extent as if each individual publication or patent or patent application was specifically and individually indicated to be incorporated by reference in its entirety for all purposes.

TABLE 1

Immunoglobulin Light Chain (LC) and Heavy Chain (HC)-Nucleotide Sequence

| NAME | SEQ ID NO | SEQUENCE |
|---|---|---|
| trastuzumab light chain (LC) | 1 | GACATCCAGATGACCCAGTCTCCATCCTCCCTGTCTGCATCTGT AGGAGACAGAGTCACCATCACTTGCCGGGCAAGTCAGGATGT GAATACCGCGGTCGCATGGTATCAGCAGAAACCAGGGAAAGC CCCTAAGCTCCTGATCTATTCTGCATCCTTCTTGTATAGTGGGG TCCCATCAAGGTTCAGTGGCAGTAGATCTGGGACAGATTTCAC TCTCACCATCAGCAGTCTGCAACCTGAAGATTTTGCAACTTAC TACTGTCAACAGCATTACACTACCCCTCCGACGTTCGGCCAAG GTACCAAGCTTGAGATCAAACGAACTGTGGCTGCACCATCTGT CTTCATCTTCCCGCCATCTGATGAGCAGTTGAAATCTGGAACT GCCTCTGTCGTGTGCCTGCTGAATAACTTCTATCCCAGAGAGG CCAAAGTACAGTGGAAGGTGGATAACGCCCTCCAATCGGGTA ACTCCCAGGAGAGTGTCACAGAGCAGGACAGCAAGGACAGCA CCTACAGCCTCAGCAGCACCCTGACGCTGAGCAAAGCAGACT ACGAGAAACACAAAGTCTACGCCTGCGAAGTCACCCATCAGG GCCTGTCCTCGCCCGTCACAAAGAGCTTCAACAGGGGAGAGTGT |
| trastuzumab N-terminal LC | 2 | GACATCCAGATGACCCAGTCTCCATCCTCCCTGTCTGCATCTGT AGGAGACAGAGTCACCATCACTTGCCGGGCAAGTCAG |
| trastuzumab C-terminal LC | 3 | ACCGCGGTCGCATGGTATCAGCAGAAACCAGGGAAAGCCCCT AAGCTCCTGATCTATTCTGCATCCTTCTTGTATAGTGGGGTCCC ATCAAGGTTCAGTGGCAGTAGATCTGGGACAGATTTCACTCTC ACCATCAGCAGTCTGCAACCTGAAGATTTTGCAACTTACTACT GTCAACAGCATTACACTACCCCTCCGACGTTCGGCCAAGGTAC CAAGCTTGAGATCAAACGAACTGTGGCTGCACCATCTGTCTTC ATCTTCCCGCCATCTGATGAGCAGTTGAAATCTGGAACTGCCT CTGTCGTGTGCCTGCTGAATAACTTCTATCCCAGAGAGGCCAA AGTACAGTGGAAGGTGGATAACGCCCTCCAATCGGGTAACTCC CAGGAGAGTGTCACAGAGCAGGACAGCAAGGACAGCACCTAC AGCCTCAGCAGCACCCTGACGCTGAGCAAAGCAGACTACGAG AAACACAAAGTCTACGCCTGCGAAGTCACCCATCAGGGCCTGT CCTCGCCCGTCACAAAGAGCTTCAACAGGGGAGAGTGT |
| trastuzumab heavy chain (HC) | 4 | GAAGTGCAGCTGGTGGAAAGCGGCGGCGGCCTGGTGCAGCCG GGCGGCAGCCTGCGCCTGAGCTGCGCGGCGAGCGGCTTTAAC ATTAAAGATACCTATATTCATTGGGTGCGCCAGGCGCCGGGCA AAGGCCTGGAATGGGTGGCGCGCATTTATCCGACCAACGGCTA TACCCGCTATGCGGATAGCGTGAAAGGCCGCTTTACCATTAGC GCGGATACCAGCAAAAACACCGCGTATCTGCAGATGAACAGC CTGCGCGCGGAAGATACCGCGGTGTATTATTGCAGCCGCTGGG GCGGCGATGGCTTTTATGCGATGGATTATTGGGGCCAGGGCAC CCTGGTGACCGTGAGCAGCGCGAGCACCAAAGGCCCGAGCGT GTTTCCGCTGGCGCCGAGCAGCAAAAGCACCAGCGGCGGCAC CGCGGCGCTGGGCTGCCTGGTGAAAGATTATTTTCCGGAACCG GTGACCGTGAGCTGGAACAGCGGCGCGCTGACCAGCGGCGTG CATACCTTTCCGGCGGTGCTGCAGAGCAGCGGCCTGTATAGCC TGAGCAGCGTGGTGACCGTGCCGAGCAGCAGCCTGGGCACCC AGACCTATATTTGCAACGTGAACCATAAACCGAGCAACACCA AAGTGGATAAAAAAGTGGAACCGCCGAAAAGCTGCGATAAAA CCCATACCTGCCCGCCGTGCCCGGCGCCGGAACTGCTGGGCGG CCCGAGCGTGTTTCTGTTTCCGCCGAAACCGAAAGATACCCTG ATGATTAGCCGCACCCCGGAAGTGACCTGCGTGGTGGTGGATG TGAGCCATGAAGATCCGGAAGTGAAATTTAACTGGTATGTGGA TGGCGTGGAAGTGCATAACGCGAAAACCAAACCGCGCGAAGA ACAGTATAACAGCACCTATCGCGTGGTGAGCGTGCTGACCGTG CTGCATCAGGATTGGCTGAACGGCAAAGAATATAAATGCAAA GTGAGCAACAAAGCGCTGCCGGCGCCGATTGAAAAAACCATT AGCAAAGCGAAAGGCCAGCCGCGCGAACCGCAGGTGTATACC |

TABLE 1-continued

Immunoglobulin Light Chain (LC) and
Heavy Chain (HC)-Nucleotide Sequence

| NAME | SEQ ID NO | SEQUENCE |
|---|---|---|
| | | CTGCCGCCGAGCCGCGATGAACTGACCAAAAACCAGGTGAGC
CTGACCTGCCTGGTGAAAGGCTTTTATCCGAGCGATATTGCGG
TGGAATGGGAAAGCAACGGCCAGCCGGAAAACAACTATAAAA
CCACCCCGCCGGTGCTGGATAGCGATGGCAGCTTTTTTCTGTA
TAGCAAACTGACCGTGGATAAAAGCCGCTGGCAGCAGGGCAA
CGTGTTTAGCTGCAGCGTGATGCATGAAGCGCTGCATAACCAT
TATACCCAGAAAAGCCTGAGCCTGAGCCCGGGCAAA |
| trastuzumab N-terminal HC | 5 | GAAGTGCAGCTGGTGGAAAGCGGCGGCGGCCTGGTGCAGCCG
GGCGGCAGCCTGCGCCTGAGCTGCGCGGCGAGCGGCTTTAAC
ATTAAAGATACCTATATTCATTGGGTGCGCCAGGCGCCGGGCA
AAGGCCTGGAATGGGTGGCGCGCATTTATCCGACCAACGGCTA
TACCCGCTATGCGGATAGCGTGAAAGGCCGCTTTACCATTAGC
GCGGATACCAGCAAAAACACCGCGTATCTGCAGATGAACAGC
CTGCGCGCGGAAGATACCGCGGTGTATTATTGCAGCCGC |
| trastuzumab C-terminal HC | 6 | GATTATTGGGGCCAGGGCACCCTGGTGACCGTGAGCAGCGCG
AGCACCAAAGGCCCGAGCGTGTTTCCGCTGGCGCCGAGCAGC
AAAAGCACCAGCGGCGGCACCGCGGCGCTGGGCTGCCTGGTG
AAAGATTATTTTCCGGAACCGGTGACCGTGAGCTGGAACAGCG
GCGCGCTGACCAGCGGCGTGCATACCTTTCCGGCGGTGCTGCA
GAGCAGCGGCCTGTATAGCCTGAGCAGCGTGGTGACCGTGCC
GAGCAGCAGCCTGGGCACCCAGACCTATATTTGCAACGTGAAC
CATAAACCGAGCAACACCAAAGTGGATAAAAAAGTGGAACCG
AAAAGCTGCGATAAAACCCATACCTGCCCGCCGTGCCCGG
CGCCGGAACTGCTGGGCGGCCCGAGCGTGTTTCTGTTTCCGCC
GAAACCGAAAGATACCCTGATGATTAGCCGCACCCCGGAAGT
GACCTGCGTGGTGGTGGATGTGAGCCATGAAGATCCGGAAGT
GAAATTTAACTGGTATGTGGATGGCGTGGAAGTGCATAACGCG
AAAACCAAACCGCGCGAAGAACAGTATAACAGCACCTATCGC
GTGGTGAGCGTGCTGACCGTGCTGCATCAGGATTGGCTGAACG
GCAAAGAATATAAATGCAAAGTGAGCAACAAAGCGCTGCCGG
CGCCGATTGAAAAAACCATTAGCAAAGCGAAAGGCCAGCCGC
GCGAACCGCAGGTGTATACCCTGCCGCCGAGCCGCGATGAACT
GACCAAAAACCAGGTGAGCCTGACCTGCCTGGTGAAAGGCTTT
TATCCGAGCGATATTGCGGTGGAATGGGAAAGCAACGGCCAG
CCGGAAAACAACTATAAAACCACCCCGCCGGTGCTGGATAGC
GATGGCAGCTTTTTTCTGTATAGCAAACTGACCGTGGATAAAA
GCCGCTGGCAGCAGGGCAACGTGTTTAGCTGCAGCGTGATGCA
TGAAGCGCTGCATAACCATTATACCCAGAAAAGCCTGAGCCTG
AGCCCGGGCAAA |
| trastuzumab-wt hIgG1 HC | 7 | GAGGTGCAGCTGGTGGAGTCTGGAGGAGGCTTGGTCCAGCCT
GGGGGGTCCCTGAGACTCTCCTGTGCAGCCTCTGGGTTCAATA
TTAAGGACACTTACATCCACTGGGTCCGCCAGGCTCCAGGGAA
GGGGCTGGAGTGGGTCGCACGTATTTATCCTACCAATGGTTAC
ACACGCTACGCAGACTCCGTGAAGGGCCGATTCACCATCTCCG
CAGACACTTCCAAGAACACGGCGTATCTTCAAATGAACAGCCT
GAGAGCCGAGGACACGGCCGTGTATTACTGTTCGAGATGGGG
CGGTGACGGCTTCTATGCCATGGACTACTGGGGCCAAGGAACC
CTGGTCACCGTCTCCTCAGCCTCCACCAAGGGCCCATCGGTCT
TCCCCCTGGCACCCTCCTCCAAGAGCACCTCTGGGGGCACAGC
GGCCCTGGGCTGCCTGGTCAAGGACTACTTCCCCGAACCGGTG
ACGGTGTCGTGGAACTCAGGCGCCCTGACCAGCGGCGTGCAC
ACCTTCCCGGCTGTCCTACAGTCCTCAGGACTCTACTCCCTCAG
CAGCGTGGTGACTGTGCCCTCTAGCAGCTTGGGCACCCAGACC
TACATCTGCAACGTGAATCACAAGCCCAGCAACACCAAGGTG
GACAAGAAAGTTGAACCCAAATCTTGCGACAAAACTCACACA
TGCCCACCGTGCCCAGCACCTGAACTCCTGGGGGGACCGTCAG
TCTTCCTCTTCCCCCCAAAACCCAAGGACACCCTCATGATCTCC
CGGACCCCTGAGGTCACATGCGTGGTGGTGGACGTGAGCCAC
GAAGACCCTGAGGTCAAGTTCAACTGGTACGTGGACGGCGTG
GAGGTGCATAATGCCAAGACAAAGCCGCGGGAGGAGCAGTAC
AACAGCACGTACCGTGTGGTCAGCGTCCTCACCGTCCTGCACC
AGGACTGGCTGAATGGCAAGGAGTACAAGTGCAAGGTCTCCA
ACAAAGCCCTCCCAGCCCCCATCGAGAAAACCATCTCCAAAGC
CAAAGGGCAGCCCCGAGAACCACAGGTGTACACCCTGCCCCC
ATCCCGGGATGAGCTGACCAAGAACCAGGTCAGCCTGACCTG
CCTGGTCAAAGGCTTCTATCCCAGCGACATCGCCGTGGAGTGG
GAGAGCAATGGGCAGCCGGAGAACAACTACAAGACCACGCCT
CCCGTGCTGGACTCCGACGGCTCCTTCTTCCTCTACAGCAAGCT
CACCGTGGACAAGAGCAGGTGGCAGCAGGGGAACGTCTTCTC
ATGCTCCGTGATGCATGAGGCTCTGCACAACCACTACACGCAG
AAGAGCCTCTCCCTGTCTCCGGGTAAA |

TABLE 1-continued

Immunoglobulin Light Chain (LC) and
Heavy Chain (HC)-Nucleotide Sequence

| NAME | SEQ ID NO | SEQUENCE |
|---|---|---|
| trastuzumab heptad mutation hIgG1 HC | 8 | GAGGTGCAGCTGGTGGAGTCTGGAGGAGGCTTGGTCCAGCCT
GGGGGGTCCCTGAGACTCTCCTGTGCAGCCTCTGGGTTCAATA
TTAAGGACACTTACATCCACTGGGTCCGCCAGGCTCCAGGGAA
GGGGCTGGAGTGGGTCGCACGTATTTATCCTACCAATGGTTAC
ACACGCTACGCAGACTCCGTGAAGGGCCGATTCACCATCTCCG
CAGACACTTCCAAGAACACGGCGTATCTTCAAATGAACAGCCT
GAGAGCCGAGGACACGGCCGTGTATTACTGTTCGAGATGGGG
CGGTGACGGCTTCTATGCCATGGACTACTGGGGCCAAGGAACC
CTGGTCACCGTCTCCTCAGCCTCCACCAAGGGCCCATCGGTCT
TCCCCCTGGCACCCTCCTCCAAGAGCACCTCTGGGGGCACAGC
GGCCCTGGGCTGCCTGGTCAAGGACTACTTCCCCGAACCGGTG
ACGGTGTCGTGGAACTCAGGCGCCCTGACCAGCGGCGTGCAC
ACCTTCCCGGCTGTCCTACAGTCCTCAGGACTCTACTCCCTCAG
CAGCGTGGTGACTGTGCCCTCTAGCAGCTTGGGCACCCAGACC
TACATCTGCAACGTGAATCACAAGCCCAGCAACACCAAGGTG
GACAAGAAAGTTGAACCCAAATCTTGCGACAAAACTCACACA
TGCCCACCGTGCCCAGCACCTCCAGTCGCCGGACCGTCAGTCT
TCCTCTTCCCTCCAAAACCCAAGGACACCCTCATGATCTCCCG
GACCCCTGAGGTCACATGCGTGGTGGTGGACGTGAGCCACGA
AGACCCTGAGGTCAAGTTCAACTGGTACGTGGACGGCGTGGA
GGTGCATAATGCCAAGACAAAGCCGCGGGAGGAGCAGTACAA
CAGCACGTACCGTGTGGTCAGCGTCCTCACCGTCCTGCACCAG
GACTGGCTGAATGGCAAGGAGTACAAGTGCAAGGTCTCCAAC
AAAGGCCTCCCAAGCTCCATCGAGAAAACCATCTCCAAAGCC
AAAGGGCAGCCCCGAGAACCACAGGTGTACACCCTGCCTCCA
TCCCGGGATGAGCTGACCAAGAACCAGGTCAGCCTGACCTGCC
TGGTCAAAGGCTTCTATCCCAGCGACATCGCCGTGGAGTGGGA
GAGCAATGGGCAGCCGGAGAACAACTACAAGACCACGCCTCC
CGTGCTGGACTCCGACGGCTCCTTCTTCCTCTACAGCAAGCTC
ACCGTGGACAAGAGCAGGTGGCAGCAGGGGAACGTCTTCTCA
TGCTCCGTGATGCATGAGGCTCTGCACAACCACTACACGCAGA
AGAGCCTCTCCCTGTCTCCGGGTAAA |
| trastuzumab triple mutations hIgG4 HC | 9 | GAGGTGCAGCTGGTGGAGTCTGGAGGAGGCTTGGTCCAGCCT
GGGGGGTCCCTGAGACTCTCCTGTGCAGCCTCTGGGTTCAATA
TTAAGGACACTTACATCCACTGGGTCCGCCAGGCTCCAGGGAA
GGGGCTGGAGTGGGTCGCACGTATTTATCCTACCAATGGTTAC
ACACGCTACGCAGACTCCGTGAAGGGCCGATTCACCATCTCCG
CAGACACTTCCAAGAACACGGCGTATCTTCAAATGAACAGCCT
GAGAGCCGAGGACACGGCCGTGTATTACTGTTCGAGATGGGG
CGGTGACGGCTTCTATGCCATGGACTACTGGGGCCAAGGAACC
CTGGTCACCGTCTCCTCAGCCAGCACTAAAGGTCCATCTGTGT
TCCCTCTGGCTCCTTGCAGCCGGAGCACCTCCGAGTCCACAGC
CGCTCTGGGATGTCTGGTGAAAGATTACTTCCCCGAGCCCGTC
ACCGTGAGCTGGAATAGCGGAGCACTGACCTCCGGCGTCCAC
ACATTCCCCGCCGTGCTCCAAAGCTCCGGCCTGTACAGCCTCT
CCTCCGTGGTCACCGTGCCCAGCAGCTCTCTGGGCACAAAGAC
CTATACCTGTAACGTGGATCACAAGCCTAGCAACACCAAAGTG
GATAAGCGGGTGGAGAGCAAGTACGGCCCTCCCTGTCCCCCTT
GCCCCGCTCCTGAGGCCGCTGGCGGACCTTCCGTGTTCCTGTTT
CCCCCTAAGCCCAAGGACACCCTCATGATTAGCCGGACACCCG
AAGTGACCTGCGTGGTCGTGGATGTGTCCCAGGAGGACCCTGA
AGTGCAATTTAACTGGTACGTGGACGGCGTCGAGGTGCACAAC
GCCAAGACCAAGCCTCGGGAAGAGCAGTTCAACAGCACCTAC
CGGGTGGTCAGCGTGCTGACAGTGCTGCACCAGGACTGGCTGA
ACGGCAAGGAGTACAAGTGCAAGGTGAGCAACAAGGGCCTGC
CCAGCTCCATCGAGAAGACCATCAGCAAGGCCAAGGGCCAGC
CCAGGGAACCCCAGGTGTATACCCTGCCCCCTAGCCAGGAGG
AAATGACCAAAAACCAGGTGAGCCTGACCTGCCTGGTGAAGG
GCTTCTACCCCAGCGACATCGCCGTGGAGTGGGAGAGCAACG
GCCAGCCCGAGAACAATTACAAGACCACCCCTCCTGTGCTGGA
CAGCGACGGCTCCTTCTTTCTGTATAGCCGGCTGACCGTGGAC
AAGAGCAGGTGGCAGGAGGGCAACGTGTTCTCCTGTAGCGTG
ATGCACGAGGCCCTGCACAACCATTACACCCAGAAGAGCTTG
AGCCTGAGCCTGGGCAAA |
| palivizumab LC | 10 | GACATCCAGATGACCCAGTCCCCCTCCACCCTGTCCGCCTCCG
TGGGCGACCGCGTGACCATCACCTGCAAGTGCCAGCTGTCCGT
GGGCTACATGCACTGGTACCAGCAGAAGCCCGGCAAGGCCCC
CAAGCTGCTGATCTACGACACCTCCAAGCTGGCCTCCGGCGTG
CCCTCCCGCTTCTCCGGCTCCGGCTCCGGCACCGAGTTCACCCT
GACCATCTCCTCCCTGCAGCCCGACGACTTCGCCACCTACTAC
TGCTTCCAGGGCTCCGGCTACCCCTTCACCTTCGGCGGCGGCA
CCAAGCTGGAGATCAAACGAACTGTGGCTGCACCATCTGTCTT
CATCTTCCCGCCATCTGATGAGCAGTTGAAATCTGGAACTGCC |

TABLE 1-continued

Immunoglobulin Light Chain (LC) and
Heavy Chain (HC)-Nucleotide Sequence

| NAME | SEQ ID NO | SEQUENCE |
|---|---|---|
| | | TCTGTCGTGTGCCTGCTGAATAACTTCTATCCCAGAGAGGCCA
AAGTACAGTGGAAGGTGGATAACGCCCTCCAATCGGGTAACT
CCCAGGAGAGTGTCACAGAGCAGGACAGCAAGGACAGCACCT
ACAGCCTCAGCAGCACCCTGACGCTGAGCAAAGCAGACTACG
AGAAACACAAAGTCTACGCCTGCGAAGTCACCCATCAGGGCC
TGTCCTCGCCCGTCACAAAGAGCTTCAACAGGGGAGAGTGT |
| palivizumab N-terminal HC | 11 | CAGGTGACCCTGCGCGAGTCCGGCCCTGCACTGGTGAAGCCCA
CCCAGACCCTGACCCTGACCTGCACCTTCTCCGGCTTCTCCCTG
TCCACCTCCGGCATGTCCGTGGGCTGGATCCGGCAGCCTCCCG
GCAAGGCCCTGGAGTGGCTGGCTGACATCTGGTGGGACGACA
AGAAGGACTACAACCCCTCCCTGAAGTCCCGCCTGACCATCTC
CAAGGACACCTCCAAGAACCAGGTGGTGCTGAAGGTGACCAA
CATGGACCCCGCCGACACCGCCACCTACTACTGCGCCCGC |
| palivizumab C-terminal HC | 12 | GACGTGTGGGGAGCCGGTACCACCGTGACCGTGTCTTCCGCCT
CCACCAAGGGCCCATCGGTCTTCCCCCTGGCACCCTCCTCCAA
GAGCACCTCTGGGGGCACAGCGGCCCTGGGCTGCCTGGTCAA
GGACTACTTCCCCGAACCGGTGACGGTGTCGTGGAACTCAGGC
GCCCTGACCAGCGGCGTGCACACCTTCCCGGCTGTCCTACAGT
CCTCAGGACTCTACTCCCTCAGCAGCGTGGTGACTGTGCCCTC
TAGCAGCTTGGGCACCCAGACCTACATCTGCAACGTGAATCAC
AAGCCCAGCAACACCAAGGTGGACAAGAAAGTTGAACCCAAA
TCTTGCGACAAAACTCACACATGCCCACCGTGCCCAGCACCTC
CAGTCGCCGGACCGTCAGTCTTCCTCTTCCCTCCAAAACCCAA
GGACACCCTCATGATCTCCCGGACCCCTGAGGTCACATGCGTG
GTGGTGGACGTGAGCCACGAAGACCCTGAGGTCAAGTTCAAC
TGGTACGTGGACGGCGTGGAGGTGCATAATGCCAAGACAAAG
CCGCGGGAGGAGCAGTACAACAGCACGTACCGTGTGGTCAGC
GTCCTCACCGTCCTGCACCAGGACTGGCTGAATGGCAAGGAGT
ACAAGTGCAAGGTCTCCAACAAAGGCCTCCCAAGCTCCATCGA
GAAAACCATCTCCAAAGCCAAAGGGCAGCCCCGAGAACCACA
GGTGTACACCCTGCCTCCATCCCGGGATGAGCTGACCAAGAAC
CAGGTCAGCCTGACCTGCCTGGTCAAAGGCTTCTATCCCAGCG
ACATCGCCGTGGAGTGGGAGAGCAATGGGCAGCCGGAGAACA
ACTACAAGACCACGCCTCCCGTGCTGGACTCCGACGGCTCCTT
CTTCCTCTACAGCAAGCTCACCGTGGACAAGAGCAGGTGGCAG
CAGGGGAACGTCTTCTCATGCTCCGTGATGCATGAGGCTCTGC
ACAACCACTACACGCAGAAGAGCCTCTCCCTGTCTCCGGGTAA
ATGATAAGTGCTAGCTGGCCAGA |
| palivizumab-wt hIgG1 HC | 13 | CAGGTGACCCTGCGCGAGTCCGGCCCCGCCCTGGTGAAGCCCA
CCCAGACCCTGACCCTGACCTGCACCTTCTCCGGCTTCTCCCTG
TCCACCTCCGGCATGTCCGTGGGCTGGATCCGCCAGCCCCCCG
GCAAGGCCCTGGAGTGGCTGGCCGACATCTGGTGGGACGACA
AGAAGGACTACAACCCCTCCCTGAAGTCCCGCCTGACCATCTC
CAAGGACACCTCCAAGAACCAGGTGGTGCTGAAGGTGACCAA
CATGGACCCCGCCGACACCGCCACCTACTACTGCGCCCGCTCC
ATGATCACCAACTGGTACTTCGACGTGTGGGGCGCCGGCACCA
CCGTGACCGTGTCCTCCGCCTCCACCAAGGGCCCATCGGTCTT
CCCCCTGGCACCCTCCTCCAAGAGCACCTCTGGGGGCACAGCG
GCCCTGGGCTGCCTGGTCAAGGACTACTTCCCCGAACCGGTGA
CGGTGTCGTGGAACTCAGGCGCCCTGACCAGCGGCGTGCACAC
CTTCCCGGCTGTCCTACAGTCCTCAGGACTCTACTCCCTCAGCA
GCGTGGTGACTGTGCCCTCTAGCAGCTTGGGCACCCAGACCTA
CATCTGCAACGTGAATCACAAGCCCAGCAACACCAAGGTGGA
CAAGAAAGTTGAACCCAAATCTTGCGACAAAACTCACACATG
CCCACCGTGCCCAGCACCTGAACTCCTGGGGGGACCGTCAGTC
TTCCTCTTCCCCCCAAAACCCAAGGACACCCTCATGATCTCCC
GGACCCCTGAGGTCACATGCGTGGTGGTGGACGTGAGCCACG
AAGACCCTGAGGTCAAGTTCAACTGGTACGTGGACGGCGTGG
AGGTGCATAATGCCAAGACAAAGCCGCGGGAGGAGCAGTACA
ACAGCACGTACCGTGTGGTCAGCGTCCTCACCGTCCTGCACCA
GGACTGGCTGAATGGCAAGGAGTACAAGTGCAAGGTCTCCAA
CAAAGCCCTCCCAGCCCCCATCGAGAAAACCATCTCCAAAGCC
AAAGGGCAGCCCCGAGAACCACAGGTGTACACCCTGCCCCCA
TCCCGGGATGAGCTGACCAAGAACCAGGTCAGCCTGACCTGCC
TGGTCAAAGGCTTCTATCCCAGCGACATCGCCGTGGAGTGGGA
GAGCAATGGGCAGCCGGAGAACAACTACAAGACCACGCCTCC
CGTGCTGGACTCCGACGGCTCCTTCTTCCTCTACAGCAAGCTC
ACCGTGGACAAGAGCAGGTGGCAGCAGGGGAACGTCTTCTCA
TGCTCCGTGATGCATGAGGCTCTGCACAACCACTACACGCAGA
AGAGCCTCTCCCTGTCTCCGGGTAAA |

TABLE 1-continued

Immunoglobulin Light Chain (LC) and Heavy Chain (HC)-Nucleotide Sequence

| NAME | SEQ ID NO | SEQUENCE |
|---|---|---|
| palivizumab heptad mutation hIgG4 HC | 14 | CAGGTGACCCTGCGCGAGTCCGGCCCCGCCCTGGTGAAGCCCA<br>CCCAGACCCTGACCCTGACCTGCACCTTCTCCGGCTTCTCCCTG<br>TCCACCTCCGGCATGTCCGTGGGCTGGATCCGCCAGCCCCCG<br>GCAAGGCCCTGGAGTGGCTGGCCGACATCTGGTGGGACGACA<br>AGAAGGACTACAACCCCTCCCTGAAGTCCCGCCTGACCATCTC<br>CAAGGACACCTCCAAGAACCAGGTGGTGCTGAAGGTGACCAA<br>CATGGACCCCGCCGACACCGCCACCTACTACTGCGCCCGCTCC<br>ATGATCACCAACTGGTACTTCGACGTGTGGGGCGCCGGCACCA<br>CCGTGACCGTGTCCTCCGCCTCCACCAAGGGCCCATCGGTCTT<br>CCCCCTGGCACCCTCCTCCAAGAGCACCTCTGGGGGCACAGCG<br>GCCCTGGGCTGCCTGGTCAAGGACTACTTCCCCGAACCGGTGA<br>CGGTGTCGTGGAACTCAGGCGCCCTGACCAGCGGCGTGCACAC<br>CTTCCCGGCTGTCCTACAGTCCTCAGGACTCTACTCCCTCAGCA<br>GCGTGGTGACTGTGCCCTCTAGCAGCTTGGGCACCCAGACCTA<br>CATCTGCAACGTGAATCACAAGCCCAGCAACACCAAGGTGGA<br>CAAGAAAGTTGAACCCAAATCTTGCGACAAAACTCACACATG<br>CCCACCGTGCCCAGCACCTCCAGTCGCCGGACCGTCAGTCTTC<br>CTCTTCCCTCCAAAACCCAAGGACACCCTCATGATCTCCCGGA<br>CCCCTGAGGTCACATGCGTGGTGGTGGACGTGAGCCACGAAG<br>ACCCTGAGGTCAAGTTCAACTGGTACGTGGACGGCGTGGAGGT<br>GCATAATGCCAAGACAAAGCCGCGGGAGGAGCAGTACAACAG<br>CACGTACCGTGTGGTCAGCGTCCTCACCGTCCTGCACCAGGAC<br>TGGCTGAATGGCAAGGAGTACAAGTGCAAGGTCTCCAACAAA<br>GGCCTCCCAAGCTCCATCGAGAAAACCATCTCCAAAGCCAAA<br>GGGCAGCCCCGAGAACCACAGGTGTACACCCTGCCTCCATCCC<br>GGGATGAGCTGACCAAGAACCAGGTCAGCCTGACCTGCCTGG<br>TCAAAGGCTTCTATCCCAGCGACATCGCCGTGGAGTGGGAGAG<br>CAATGGGCAGCCGGAGAACAACTACAAGACCACGCCTCCCGT<br>GCTGGACTCCGACGGCTCCTTCTTCCTCTACAGCAAGCTCACC<br>GTGGACAAGAGCAGGTGGCAGCAGGGGAACGTCTTCTCATGC<br>TCCGTGATGCATGAGGCTCTGCACAACCACTACACGCAGAAGA<br>GCCTCTCCCTGTCTCCGGGTAAA |
| palivizumab triple mutation hIgG4 HC | 15 | CAGGTGACCCTGCGCGAGTCCGGCCCCGCCCTGGTGAAGCCCA<br>CCCAGACCCTGACCCTGACCTGCACCTTCTCCGGCTTCTCCCTG<br>TCCACCTCCGGCATGTCCGTGGGCTGGATCCGCCAGCCCCCG<br>GCAAGGCCCTGGAGTGGCTGGCCGACATCTGGTGGGACGACA<br>AGAAGGACTACAACCCCTCCCTGAAGTCCCGCCTGACCATCTC<br>CAAGGACACCTCCAAGAACCAGGTGGTGCTGAAGGTGACCAA<br>CATGGACCCCGCCGACACCGCCACCTACTACTGCGCCCGCTCC<br>ATGATCACCAACTGGTACTTCGACGTGTGGGGCGCCGGCACCA<br>CCGTGACCGTGTCCTCCGCCAGCACTAAAGGTCCATCTGTGTT<br>CCCTCTGGCTCCTTGCAGCCGGAGCACCTCCGAGTCCACAGCC<br>GCTCTGGGATGTCTGGTGAAAGATTACTTCCCCGAGCCCGTCA<br>CCGTGAGCTGGAATAGCGGAGCACTGACCTCCGGCGTCCACAC<br>ATTCCCCGCCGTGCTCCAAAGCTCCGGCCTGTACAGCCTCTCCT<br>CCGTGGTCACCGTGCCCAGCAGCTCTCTGGGCACAAAGACCTA<br>TACCTGTAACGTGGATCACAAGCCTAGCAACACCAAAGTGGAT<br>AAGCGGGTGGAGAGCAAGTACGGCCCTCCCTGTCCCCCTTGCC<br>CCGCTCCTGAGGCCGCTGGCGGACCTTCCGTGTTCCTGTTTCCC<br>CCTAAGCCCAAGGACACCCTCATGATTAGCCGGACACCCGAA<br>GTGACCTGCGTGGTCGTGGATGTGTCCCAGGAGGACCCTGAAG<br>TGCAATTTAACTGGTACGTGGACGGCGTCGAGGTGCACAACGC<br>CAAGACCAAGCCTCGGGAAGAGCAGTTCAACAGCACCTACCG<br>GGTGGTCAGCGTGCTGACAGTGCTGCACCAGGACTGGCTGAAC<br>GGCAAGGAGTACAAGTGCAAGGTGAGCAACAAGGGCCTGCCC<br>AGCTCCATCGAGAAGACCATCAGCAAGGCCAAGGGCCAGCCC<br>AGGGAACCCCAGGTGTATACCCTGCCCCCTAGCCAGGAGGAA<br>ATGACCAAAAACCAGGTGAGCCTGACCTGCCTGGTGAAGGGC<br>TTCTACCCCAGCGACATCGCCGTGGAGTGGGAGAGCAACGGC<br>CAGCCCGAGAACAATTACAAGACCACCCCTCCTGTGCTGGACA<br>GCGACGGCTCCTTCTTTCTGTATAGCCGGCTGACCGTGGACAA<br>GAGCAGGTGGCAGGAGGGCAACGTGTTCCTGTAGCGTGAT<br>GCACGAGGCCCTGCACAACCATTACACCCAGAAGAGCTTGAG<br>CCTGAGCCTGGGCAAA |
| BLV1H12 N-terminal HC | 16 | CAGGTCCAGCTGAGAGAGAGCGGCCCTTCACTGGTCAAGCCAT<br>CCCAGACACTGAGCCTGACATGCACAGCAAGCGGGTTTTCACT<br>GAGCGACAAGGCAGTGGGATGGGTCCGACAGGCACCAGGAAA<br>AGCCCTGGAATGGCTGGGCAGCATCGATACCGGCGGGAACAC<br>AGGGTACAATCCCGGACTGAAGAGCAGACTGTCCATTACCAA<br>GGACAACTCTAAAAGTCAGGTGTCACTGAGCGTGAGCTCCGTC<br>ACCACAGAGGATAGTGCAACTTACTATTGCACCTCTGTGCACC<br>AG |

TABLE 1-continued

Immunoglobulin Light Chain (LC) and Heavy Chain (HC)-Nucleotide Sequence

| NAME | SEQ ID NO | SEQUENCE |
| --- | --- | --- |
| BLV1H12 C-terminal HC | 17 | TGGCATGTGGATGTCTGGGGACAGGGCCTGCTGGTGACAGTCT<br>CTAGTGCTTCCACAACTGCACCAAAGGTGTACCCCCTGTCAAG<br>CTGCTGTGGGGACAAATCCTCTAGTACCGTGACACTGGGATGC<br>CTGGTCTCAAGCTATATGCCCGAGCCTGTGACTGTCACCTGGA<br>ACTCAGGAGCCCTGAAAAGCGGAGTGCACACCTTCCCAGCTGT<br>GCTGCAGTCCTCTGGCCTGTATAGCCTGAGTTCAATGGTGACA<br>GTCCCCGGCAGTACTTCAGGGCAGACCTTCACCTGTAATGTGG<br>CCCATCCTGCCAGCTCCACCAAAGTGGACAAAGCAGTGGAAC<br>CCAAATCTTGCGACAAAACTCACACATGCCCACCGTGCCCAGC<br>ACCTGAACTCCTGGGGGGACCGTCAGTCTTCCTCTTCCCCCCA<br>AAACCCAAGGACACCCTCATGATCTCCCGGACCCCTGAGGTCA<br>CATGCGTGGTGGTGGACGTGAGCCACGAAGACCCTGAGGTCA<br>AGTTCAACTGGTACGTGGACGGCGTGGAGGTGCATAATGCCA<br>AGACAAAGCCGCGGGAGGAGCAGTACAACAGCACGTACCGTG<br>TGGTCAGCGTCCTCACCGTCCTGCACCAGGACTGGCTGAATGG<br>CAAGGAGTACAAGTGCAAGGTCTCCAACAAAGCCCTCCCAGC<br>CCCCATCGAGAAAACCATCTCCAAAGCCAAAGGGCAGCCCCG<br>AGAACCACAGGTGTACACCCTGCCCCCATCCCGGGATGAGCTG<br>ACCAAGAACCAGGTCAGCCTGACCTGCCTGGTCAAAGGCTTCT<br>ATCCCAGCGACATCGCCGTGGAGTGGGAGAGCAATGGGCAGC<br>CGGAGAACAACTACAAGACCACGCCTCCCGTGCTGGACTCCG<br>ACGGCTCCTTCTTCCTCTACAGCAAGCTCACCGTGGACAAGAG<br>CAGGTGGCAGCAGGGGAACGTCTTCTCATGCTCCGTGATGCAT<br>GAGGCTCTGCACAACCACTACACGCAGAAGAGCCTCTCCCTGT<br>CTCCGGGTAAA |
| BLV1H12 LC | 18 | CAGGCCGTCCTGAACCAGCCAAGCAGCGTCTCCGGGTCTCTGG<br>GGCAGCGGGTCTCAATCACCTGTAGCGGGTCTTCCTCCAATGT<br>CGGCAACGGCTACGTGTCTTGGTATCAGCTGATCCCTGGCAGT<br>GCCCCACGAACCCTGATCTACGGCGACACATCCAGAGCTTCTG<br>GGGTCCCCGATCGGTTCTCAGGGAGCAGATCCGGAAACACAG<br>CTACTCTGACCATCAGCTCCCTGCAGGCTGAGGACGAAGCAGA<br>TTATTTCTGCGCATCTGCCGAGGACTCTAGTTCAAATGCCGTGT<br>TTGGAAGCGGCACCACACTGACAGTCCTGGGGCAGCCCAAGA<br>GTCCCCCTTCAGTGACTCTGTTCCCACCCTCTACCGAGGAACTG<br>AACGGAAACAAGGCCACACTGGTGTGTCTGATCAGCGACTTTT<br>ACCCTGGATCCGTCACTGTGGTCTGGAAGGCAGATGGCAGCAC<br>AATTACTAGGAACGTGGAAACTACCCGCGCCTCCAAGCAGTCT<br>AATAGTAAATACGCCGCCAGCTCCTATCTGAGCCTGACCCTCTA<br>GTGATTGGAAGTCCAAAGGGTCATATAGCTGCGAAGTGACCC<br>ATGAAGGCTCAACCGTGACTAAGACTGTGAAACCATCCGAGT<br>GCTCC |

TABLE 2

Immunoglobulin Light Chain (LC) and Heavy Chain (HC)-Amino Acid Sequence

| Name | SEQ ID NO | Sequence |
| --- | --- | --- |
| trastuzumab light chain (LC) | 19 | DIQMTQSPSSLSASVGDRVTITCRASQDVNTAVAWYQQKPGKAP<br>KLLIYSASFLYSGVPSRFSGSRSGTDFTLTISSLQPEDFATYYCQQH<br>YTTPPTFGQGTKLEIKRTVAAPSVFIFPPSDEQLKSGTASVVCLLN<br>NFYPREAKVQWKVDNALQSGNSQESVTEQDSKDSTYSLSSTLTL<br>SKADYEKHKVYACEVTHQGLSSPVTKSFNRGEC |
| trastuzumab N-terminal LC | 20 | DIQMTQSPSSLSASVGDRVTITCRASQ |
| trastuzumab C-terminal LC | 21 | TAVAWYQQKPGKAPKLLIYSASFLYSGVPSRFSGSRSGTDFTLTIS<br>SLQPEDFATYYCQQHYTTPPTFGQGTKLEIKRTVAAPSVFIFPPSD<br>EQLKSGTASVVCLLNNFYPREAKVQWKVDNALQSGNSQESVTE<br>QDSKDSTYSLSSTLTLSKADYEKHKVYACEVTHQGLSSPVTKSFN<br>RGEC |
| trastuzumab heavy chain (HC) | 22 | EVQLVESGGGLVQPGGSLRLSCAASGFNIKDTYIHWVRQAPGKG<br>LEWVARIYPTNGYTRYADSVKGRFTISADTSKNTAYLQMNSLRA<br>EDTAVYYCSRWGGDGFYAMDYWGQGTLVTVSSASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPP<br>KSCDKTHTCPPCPAPELLGGPSVFLFPPKPKDTLMISRTPEVTCVV<br>VDVSHEDPEVKFNWYVDGVEVHNAKTKPREEQYNSTYRVVSVL<br>TVLHQDWLNGKEYKCKVSNKALPAPIEKTISKAKGQPREPQVYT |

TABLE 2-continued

Immunoglobulin Light Chain (LC) and Heavy Chain (HC)-Amino Acid Sequence

| Name | SEQ ID NO | Sequence |
|---|---|---|
| | | LPPSRDELTKNQVSLTCLVKGFYPSDIAVEWESNGQPENNYKTTP<br>PVLDSDGSFFLYSKLTVDKSRWQQGNVFSCSVMHEALHNHYTQ<br>KSLSLSPGK |
| trastuzumab N-terminal HC | 23 | EVQLVESGGGLVQPGGSLRLSCAASGFNIKDTYIHWVRQAPGKG<br>LEWVARIYPTNGYTRYADSVKGRFTISADTSKNTAYLQMNSLRA<br>EDTAVYYCSR |
| trastuzumab C-terminal HC | 24 | DYWGQGTLVTVSSASTKGPSVFPLAPSSKSTSGGTAALGCLVKD<br>YFPEPVTVSWNSGALTSGVHTFPAVLQSSGLYSLSSVVTVPSSSLG<br>TQTYICNVNHKPSNTKVDKKVEPPKSCDKTHTCPPCPAPELLGGP<br>SVFLFPPKPKDTLMISRTPEVTCVVVDVSHEDPEVKFNWYVDGVE<br>VHNAKTKPREEQYNSTYRVVSVLTVLHQDWLNGKEYKCKVSNK<br>ALPAPIEKTISKAKGQPREPQVYTLPPSRDELTKNQVSLTCLVKGF<br>YPSDIAVEWESNGQPENNYKTTPPVLDSDGSFFLYSKLTVDKSRW<br>QQGNVFSCSVMHEALHNHYTQKSLSLSPGK |
| trastuzumab-wt hIgG1 HC | 25 | EVQLVESGGGLVQPGGSLRLSCAASGFNIKDTYIHWVRQAPGKG<br>LEWVARIYPTNGYTRYADSVKGRFTISADTSKNTAYLQMNSLRA<br>EDTAVYYCSRWGGDGFYAMDYWGQGTLVTVSSASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPK<br>SCDKTHTCPPCPAPELLGGPSVFLFPPKPKDTLMISRTPEVTCVVV<br>DVSHEDPEVKFNWYVDGVEVHNAKTKPREEQYNSTYRVVSVLT<br>VLHQDWLNGKEYKCKVSNKALPAPIEKTISKAKGQPREPQVYTL<br>PPSRDELTKNQVSLTCLVKGFYPSDIAVEWESNGQPENNYKTTPP<br>VLDSDGSFFLYSKLTVDKSRWQQGNVFSCSVMHEALHNHYTQK<br>SLSLSPGK |
| trastuzumab heptad mutation hIgG1 HC | 26 | EVQLVESGGGLVQPGGSLRLSCAASGFNIKDTYIHWVRQAPGKG<br>LEWVARIYPTNGYTRYADSVKGRFTISADTSKNTAYLQMNSLRA<br>EDTAVYYCSRWGGDGFYAMDYWGQGTLVTVSSASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPK<br>SCDKTHTCPPCPAPPVAGPSVFLFPPKPKDTLMISRTPEVTCVVVD<br>VSHEDPEVKFNWYVDGVEVHNAKTKPREEQYNSTYRVVSVLTV<br>LHQDWLNGKEYKCKVSNKGLPSSIEKTISKAKGQPREPQVYTLPP<br>SRDELTKNQVSLTCLVKGFYPSDIAVEWESNGQPENNYKTTPPVL<br>DSDGSFFLYSKLTVDKSRWQQGNVFSCSVMHEALHNHYTQKSLS<br>LSPGK |
| trastuzumab triple mutations hIgG4 HC | 27 | EVQLVESGGGLVQPGGSLRLSCAASGFNIKDTYIHWVRQAPGKG<br>LEWVARIYPTNGYTRYADSVKGRFTISADTSKNTAYLQMNSLRA<br>EDTAVYYCSRWGGDGFYAMDYWGQGTLVTVSSASTKGPSVFPL<br>APCSRSTSESTAALGCLVKDYFPEPVTVSWNSGALTSGVHTFPAV<br>LQSSGLYSLSSVVTVPSSSLGTKTYTCNVDHKPSNTKVDKRVESK<br>YGPPCPPCPAPEAAGGPSVFLFPPKPKDTLMISRTPEVTCVVVDVS<br>QEDPEVQFNWYVDGVEVHNAKTKPREEQFNSTYRVVSVLTVLH<br>QDWLNGKEYKCKVSNKGLPSSIEKTISKAKGQPREPQVYTLPPSQ<br>EEMTKNQVSLTCLVKGFYPSDIAVEWESNGQPENNYKTTPPVLD<br>SDGSFFLYSRLTVDKSRWQEGNVFSCSVMHEALHNHYTQKSLSL<br>SLGK |
| palivizumab LC | 28 | DIQMTQSPSTLSASVGDRVTITCKCQLSVGYMHWYQQKPGKAPK<br>LLIYDTSKLASGVPSRFSGSGSGTEFTLTISSLQPDDFATYYCFQGS<br>GYPPTFGGGTKLEIKRTVAAPSVFIFPPSDEQLKSGTASVVCLLNN<br>FYPREAKVQWKVDNALQSGNSQESVTEQDSKDSTYSLSSTLTLS<br>KADYEKHKVYACEVTHQGLSSPVTKSFNRGEC |
| palivizumab N-terminal HC | 29 | QVTLRESGPALVKPTQTLTLTCTFSGFSLSTSGMSVGWIRQPPGK<br>ALEWLADIWWDDKKDYNPSLKSRLTISKDTSKNQVVLKVTNMD<br>PADTATYYCAR |
| palivizumab C-terminal HC | 30 | DVWGAGTTVTVSSASTKGPSVFPLAPSSKSTSGGTAALGCLVKD<br>YFPEPVTVSWNSGALTSGVHTFPAVLQSSGLYSLSSVVTVPSSSLG<br>TQTYICNVNHKPSNTKVDKKVEPKSCDKTHTCPPCPAPPVAGPSV<br>FLFPPKPKDTLMISRTPEVTCVVVDVSHEDPEVKFNWYVDGVEV<br>HNAKTKPREEQYNSTYRVVSVLTVLHQDWLNGKEYKCKVSNKG<br>LPSSIEKTISKAKGQPREPQVYTLPPSRDELTKNQVSLTCLVKGFY<br>PSDIAVEWESNGQPENNYKTTPPVLDSDGSFFLYSKLTVDKSRWQ<br>QGNVFSCSVMHEALHNHYTQKSLSLSPGK |
| palivizumab-wt hIgG1 HC | 31 | QVTLRESGPALVKPTQTLTLTCTFSGFSLSTSGMSVGWIRQPPGK<br>ALEWLADIWWDDKKDYNPSLKSRLTISKDTSKNQVVLKVTNMD<br>PADTATYYCARSMITNWYFDVWGAGTTVTVSSASTKGPSVFPLA<br>PSSKSTSGGTAALGCLVKDYFPEPVTVSWNSGALTSGVHTFPAVL |

TABLE 2-continued

Immunoglobulin Light Chain (LC) and Heavy Chain (HC)-Amino Acid Sequence

| Name | SEQ ID NO | Sequence |
|---|---|---|
| | | QSSGLYSLSSVVTVPSSSLGTQTYICNVNHKPSNTKVDKKVEPKS<br>CDKTHTCPPCPAPELLGGPSVFLFPPKPKDTLMISRTPEVTCVVVD<br>VSHEDPEVKFNWYVDGVEVHNAKTKPREEQYNSTYRVVSVLTV<br>LHQDWLNGKEYKCKVSNKALPAPIEKTISKAKGQPREPQVYTLPP<br>SRDELTKNQVSLTCLVKGFYPSDIAVEWESNGQPENNYKTTPPVL<br>DSDGSFFLYSKLTVDKSRWQQGNVFSCSVMHEALHNHYTQKSLS<br>LSPGK |
| palivizumab heptad mutation hIgG4 HC | 32 | QVTLRESGPALVKPTQTLTLTCTFSGFSLSTSGMSVGWIRQPPGK<br>ALEWLADIWWDDKKDYNPSLKSRLTISKDTSKNQVVLKVTNMD<br>PADTATYYCARSMITNWYFDVWGAGTTVTVSSASTKGPSVFPLA<br>PSSKSTSGGTAALGCLVKDYFPEPVTVSWNSGALTSGVHTFPAVL<br>QSSGLYSLSSVVTVPSSSLGTQTYICNVNHKPSNTKVDKKVEPKS<br>CDKTHTCPPCPAPPVAGPSVFLFPPKPKDTLMISRTPEVTCVVVDV<br>SHEDPEVKFNWYVDGVEVHNAKTKPREEQYNSTYRVVSVLTVL<br>HQDWLNGKEYKCKVSNKGLPSSIEKTISKAKGQPREPQVYTLPPS<br>RDELTKNQVSLTCLVKGFYPSDIAVEWESNGQPENNYKTTPPVLD<br>SDGSFFLYSKLTVDKSRWQQGNVFSCSVMHEALHNHYTQKSLSL<br>SPGK |
| palivizumab triple mutation hIgG4 HC | 33 | QVTLRESGPALVKPTQTLTLTCTFSGFSLSTSGMSVGWIRQPPGK<br>ALEWLADIWWDDKKDYNPSLKSRLTISKDTSKNQVVLKVTNMD<br>PADTATYYCARSMITNWYFDVWGAGTTVTVSSASTKGPSVFPLA<br>PCSRSTSESTAALGCLVKDYFPEPVTVSWNSGALTSGVHTFPAVL<br>QSSGLYSLSSVVTVPSSSLGTKTYTCNVDHKPSNTKVDKRVESKY<br>GPPCPPCPAPEAAGGPSVFLFPPKPKDTLMISRTPEVTCVVVDVSQ<br>EDPEVQFNWYVDGVEVHNAKTKPREEQFNSTYRVVSVLTVLHQ<br>DWLNGKEYKCKVSNKGLPSSIEKTISKAKGQPREPQVYTLPPSQE<br>EMTKNQVSLTCLVKGFYPSDIAVEWESNGQPENNYKTTPPVLDS<br>DGSFFLYSRLTVDKSRWQEGNVFSCSVMHEALHNHYTQKSLSLS<br>LGK |
| BLV1H12 N-terminal HC | 34 | QVQLRESGPSLVKPSQTLSLTCTASGFSLSDKAVGWVRQAPGKA<br>LEWLGSIDTGGNTGYNPGLKSRLSITKDNSKSQVSLSVSSVTTEDS<br>ATYYCTSVHQ |
| BLV1H12 C-terminal HC | 35 | WHVDVWGQGLLVTVSSASTTAPKVYPLSSCCGDKSSSTVTLGCL<br>VSSYMPEPVTVTWNSGALKSGVHTFPAVLQSSGLYSLSSMVTVP<br>GSTSGQTFTCNVAHPASSTKVDKAVEPKSCDKTHTCPPCPAPELL<br>GGPSVFLFPPKPKDTLMISRTPEVTCVVVDVSHEDPEVKFNWYVD<br>GVEVHNAKTKPREEQYNSTYRVVSVLTVLHQDWLNGKEYKCKV<br>SNKALPAPIEKTISKAKGQPREPQVYTLPPSRDELTKNQVSLTCLV<br>KGFYPSDIAVEWESNGQPENNYKTTPPVLDSDGSFFLYSKLTVDK<br>SRWQQGNVFSCSVMHEALHNHYTQKSLSLSPGK |
| BLV1H12 LC | 36 | QAVLNQPSSVSGSLGQRVSITCSGSSSNVGNGYVSWYQLIPGSAP<br>RTLIYGDTSRASGVPDRFSGSRSGNTATLTISSLQAEDEADYFCAS<br>AEDSSSNAVFGSGTTLTVLGQPKSPPSVTLFPPSTEELNGNKATLV<br>CLISDFYPGSVTVVWKADGSTITRNVETTRASKQSNSKYAASSYL<br>SLTSSDWKSKGSYSCEVTHEGSTVTKTVKPSECS |

TABLE 3

Coiled Coil Immunoglobulin Fusion Proteins-Nucleotide Sequence

| NAME | SEQ ID NO | SEQUENCE |
|---|---|---|
| trastuzumab-coil-hEPO LC | 37 | GACATCCAGATGACCCAGTCTCCATCCTCCCTGTCTGCATCTGT<br>AGGAGACAGAGTCACCATCACTTGCCGGGCAAGTCAGGGCGG<br>AAGCGGAGCAAAGCTCGCCGCACTGAAAGCCAAGCTGGCCGCTCT<br>GAAGGGGGGTGGCGGAAGCGCCCCACCACGCCTCATCTGTGACA<br>GCCGAGTCCTGGAGAGGTACCTCTTGGAGGCCAAGGAGGCCGAG<br>AATATCACGACGGGCTGTGCTGAACACTGCAGCTTGAATGAGAATA<br>TCACTGTCCCAGACACCAAAGTTAATTTCTATGCCTGGAAGAGGAT<br>GGAGGTCGGGCAGCAGGCCGTAGAAGTCTGACAGGGCCTGGCCC<br>TGCTGTCGGAAGCTGTCCTGCGGGGCCAGGCCCTGTTGGTCAACT<br>CTTCCCAGCCGTGGGAGCCCCTGCAGCTGCATGTGGATAAAGCCG<br>TCAGTGGCCTTCGCAGCCTCACCACTCTGCTTCGGGCTCTGGGAG<br>CCCAGAAGGAAGCCATCTCCCCTCCAGATGCGGCCTCAGCTGCTC<br>CACTCCGAACAATCACTGCTGACACTTTCCGCAAACTCTTCCGAGT |

TABLE 3-continued

Coiled Coil Immunoglobulin Fusion Proteins-Nucleotide Sequence

| NAME | SEQ ID NO | SEQUENCE |
|---|---|---|
| | | CTACTCCAATTTCCTCCGGGGAAAGCTGAAGCTGTACACAGGGGA GGCCTGCAGGACAGGGGACAGAGGCGGAGGTGGGAGTGAACTG GCCGCACTGGAAGCTGAGCTGGCTGCCCTCGAAGCTGGAGGCTC TGGAACCGCGGTCGCATGGTATCAGCAGAAACCAGGGAAAGC CCCTAAGCTCCTGATCTATTCTGCATCCTTCTTGTATAGTGGGG TCCCATCAAGGTTCAGTGGCAGTAGATCTGGGACAGATTTCAC TCTCACCATCAGCAGTCTGCAACCTGAAGATTTTGCAACTTAC TACTGTCAACAGCATTACACTACCCCTCCGACGTTCGGCCAAG GTACCAAGCTTGAGATCAAACGAACTGTGGCTGCACCATCTGT CTTCATCTTCCCGCCATCTGATGAGCAGTTGAAATCTGGAACT GCCTCTGTCGTGTGCCTGCTGAATAACTTCTATCCCAGAGAGG CCAAAGTACAGTGGAAGGTGGATAACGCCCTCCAATCGGGTA ACTCCCAGGAGAGTGTCACAGAGCAGGACAGCAAGGACAGCA CCTACAGCCTCAGCAGCACCCTGACGCTGAGCAAAGCAGACT ACGAGAAACACAAAGTCTACGCCTGCGAAGTCACCCATCAGG GCCTGTCCTCGCCCGTCACAAAGAGCTTCAACAGGGGAGAGTGT |
| trastuzumab-coil bGCSF HC | 38 | GAGGTGCAGCTGGTGGAGTCTGGAGGAGGCTTGGTCCAGCCT GGGGGGTCCCTGAGACTCTCCTGTGCAGCCTCTGGGTTCAATA TTAAGGACACTTACATCCACTGGGTCCGCCAGGCTCCAGGGAA GGGGCTGGAGTGGGTCGCACGTATTTATCCTACCAATGGTTAC ACACGCTACGCAGACTCCGTGAAGGGCCGATTCACCATCTCCG CAGACACTTCCAAGAACACGGCGTATCTTCAAATGAACAGCCT GAGAGCCGAGGACACGGCCGTGTATTACTGTTCGAGAGGCGG AAGCGGAGCAAAGCTCGCCGCACTGAAAGCCAAGCTGGCCGCTCT GAAGGGAGGCGGTGGCTCCACCCCCCTTGGCCCTGCCCGATCCC TGCCCCAGAGCTTCCTGCTCAAGTGCTTAGAGCAAGTGAGGAAAAT CCAGGCTGATGGCGCCGAGCTGCAGGAGAGGCTGTGTGCCGCCC ACAAGCTGTGCCACCCGGAGGAGCTGATGCTGCTCAGGCACTCTC TGGGCATCCCCCAGGCTCCCCTAAGCAGCTGCTCCAGCCAGTCCC TGCAGCTGACGAGCTGCCTGAACCAACTACACGGCGGCCTCTTTC TCTACCAGGGCCTCCTGCAGGCCCTGGCGGGCATCTCCCCAGAG CTGGCCCCCACCTTGGACACACTGCAGCTGGACGTCACTGACTTT GCCACGAACATCTGGCTGCAGATGGAGGACCTGGGGGCGGCCCC CGCTGTGCAGCCCACCCAGGGCGCCATGCCGACCTTCACTTCAGC CTTCCAACGCAGAGCAGGAGGGGTCCTGGTTGCTTCCCAGCTGCA TCGTTTCCTGGAGCTGGCATACCGTGCCTGCGCTACCTTGCTGA GCCCGGCGGTGGCGGAAGCGAACTGGCCGCACTGGAAGCTGAGC TGGCTGCCCTCGAAGCTGGAGGCTCTGGAGACTACTGGGGCCAA GGAACCCTGGTCACCGTCTCCTCAGCCTCCACCAAGGGCCCAT CGGTCTTCCCCCTGGCACCCTCCTCCAAGAGCACCTCTGGGGG CACAGCGGCCCTGGGCTGCCTGGTCAAGGACTACTTCCCCGAA CCGGTGACGGTGTCGTGGAACTCAGGCGCCCTGACCAGCGGC GTGCACACCTTCCCGGCTGTCCTACAGTCCTCAGGACTCTACTC CCTCAGCAGCGTGGTGACTGTGCCCTCTAGCAGCTTGGGCACC CAGACCTACATCTGCAACGTGAATCACAAGCCCAGCAACACC AAGGTGGACAAGAAAGTTGAACCCAAATCTTGCGACAAAACT |

TABLE 3-continued

Coiled Coil Immunoglobulin Fusion Proteins-Nucleotide Sequence

| NAME | SEQ ID NO | SEQUENCE |
|---|---|---|
| | | CACACATGCCCACCGTGCCCAGCACCTGAACTCCTGGGGGGAC |
| | | CGTCAGTCTTCCTCTTCCCCCCAAAACCCAAGGACACCCTCAT |
| | | GATCTCCCGGACCCCTGAGGTCACATGCGTGGTGGTGGACGTG |
| | | AGCCACGAAGACCCTGAGGTCAAGTTCAACTGGTACGTGGAC |
| | | GGCGTGGAGGTGCATAATGCCAAGACAAAGCCGCGGGAGGAG |
| | | CAGTACAACAGCACGTACCGTGTGGTCAGCGTCCTCACCGTCC |
| | | TGCACCAGGACTGGCTGAATGGCAAGGAGTACAAGTGCAAGG |
| | | TCTCCAACAAAGCCCTCCCAGCCCCCATCGAGAAAACCATCTC |
| | | CAAAGCCAAAGGGCAGCCCCGAGAACCACAGGTGTACACCCT |
| | | GCCCCCATCCCGGGATGAGCTGACCAAGAACCAGGTCAGCCT |
| | | GACCTGCCTGGTCAAAGGCTTCTATCCCAGCGACATCGCCGTG |
| | | GAGTGGGAGAGCAATGGGCAGCCGGAGAACAACTACAAGACC |
| | | ACGCCTCCCGTGCTGGACTCCGACGGCTCCTTCTTCCTCTACAG |
| | | CAAGCTCACCGTGGACAAGAGCAGGTGGCAGCAGGGGAACGT |
| | | CTTCTCATGCTCCGTGATGCATGAGGCTCTGCACAACCACTAC |
| | | ACGCAGAAGAGCCTCTCCCTGTCTCCGGGTAAA |
| Bovine-coil bGCSF HC (CDRH3) | 39 | CAGGTCCAGCTGAGAGAGAGCGGCCCTTCACTGGTCAAGCCAT |
| | | CCCAGACACTGAGCCTGACATGCACAGCAAGCGGGTTTTCACT |
| | | GAGCGACAAGGCAGTGGGATGGGTCCGACAGGCACCAGGAAA |
| | | AGCCCTGGAATGGCTGGGCAGCATCGATACCGGCGGGAACAC |
| | | AGGGTACAATCCCGGACTGAAGAGCAGACTGTCCATTACCAA |
| | | GGACAACTCTAAAAGTCAGGTGTCACTGAGCGTGAGCTCCGTC |
| | | ACCACAGAGGATAGTGCAACTTACTATTGCACCTCTGTGCACC |
| | | AGGGCGGAAGCGGAGCAAAGCTCGCCGCACTGAAAGCCAAGCTG |
| | | GCCGCTCTGAAGGGAGGCGGTGGCTCCACCCCCCCTTGGCCCTGC |
| | | CCGATCCCTGCCCCAGAGCTTCCTGCTCAAGTGCTTAGAGCAAGT |
| | | GAGGAAAATCCAGGCTGATGGCGCCGAGCTGCAGGAGAGGCTGT |
| | | GTGCCGCCCACAAGCTGTGCCACCCGGAGGAGCTGATGCTGCTCA |
| | | GGCACTCTCTGGGCATCCCCCAGGCTCCCCTAAGCAGCTGCTCCA |
| | | GCCAGTCCCTGCAGCTGACGAGCTGCCTGAACCAACTACACGGCG |
| | | GCCTCTTTCTCTACCAGGGCCTCCTGCAGGCCCTGGCGGGCATCT |
| | | CCCCAGAGCTGGCCCCCACCTTGGACACACTGCAGCTGGACGTCA |
| | | CTGACTTTGCCACGAACATCTGGCTGCAGATGGAGGACCTGGGGG |
| | | CGGCCCCCGCTGTGCAGCCCACCCAGGGCGCCATGCCGACCTTC |
| | | ACTTCAGCCTTCCAACGCAGAGCAGGAGGGGTCCTGGTTGCTTCC |
| | | CAGCTGCATCGTTTCCTGGAGCTGGCATACCGTGGCCTGCGCTAC |
| | | CTTGCTGAGCCCGGCGGTGGCGGAAGCGAACTGGCCGCACTGGA |
| | | AGCTGAGCTGGCTGCCCTCGAAGCTGGAGGCTCTGGATGGCATG |
| | | TGGATGTCTGGGGACAGGGCCTGCTGGTGACAGTCTCTAGTGC |
| | | TTCCACAACTGCACCAAAGGTGTACCCCCTGTCAAGCTGCTGT |
| | | GGGGACAAATCCTCTAGTACCGTGACACTGGGATGCCTGGTCT |
| | | CAAGCTATATGCCCGAGCCTGTGACTGTCACCTGGAACTCAGG |
| | | AGCCCTGAAAAGCGGAGTGCACACCTTCCCAGCTGTGCTGCAG |
| | | TCCTCTGGCCTGTATAGCCTGAGTTCAATGGTGACAGTCCCCG |
| | | GCAGTACTTCAGGGCAGACCTTCACCTGTAATGTGGCCCATCC |

TABLE 3-continued

Coiled Coil Immunoglobulin Fusion Proteins-Nucleotide Sequence

| NAME | SEQ ID NO | SEQUENCE |
|------|-----------|----------|
| | | TGCCAGCTCCACCAAAGTGGACAAAGCAGTGGAACCCAAATC |
| | | TTGCGACAAAACTCACACATGCCCACCGTGCCCAGCACCTGAA |
| | | CTCCTGGGGGGACCGTCAGTCTTCCTCTTCCCCCCAAAACCCA |
| | | AGGACACCCTCATGATCTCCCGGACCCCTGAGGTCACATGCGT |
| | | GGTGGTGGACGTGAGCCACGAAGACCCTGAGGTCAAGTTCAA |
| | | CTGGTACGTGGACGGCGTGGAGGTGCATAATGCCAAGACAAA |
| | | GCCGCGGGAGGAGCAGTACAACAGCACGTACCGTGTGGTCAG |
| | | CGTCCTCACCGTCCTGCACCAGGACTGGCTGAATGGCAAGGAG |
| | | TACAAGTGCAAGGTCTCCAACAAAGCCCTCCCAGCCCCCATCG |
| | | AGAAAACCATCTCCAAAGCCAAAGGGCAGCCCCGAGAACCAC |
| | | AGGTGTACACCCTGCCCCCATCCCGGGATGAGCTGACCAAGAA |
| | | CCAGGTCAGCCTGACCTGCCTGGTCAAAGGCTTCTATCCCAGC |
| | | GACATCGCCGTGGAGTGGGAGAGCAATGGGCAGCCGGAGAAC |
| | | AACTACAAGACCACGCCTCCCGTGCTGGACTCCGACGGCTCCT |
| | | TCTTCCTCTACAGCAAGCTCACCGTGGACAAGAGCAGGTGGCA |
| | | GCAGGGGAACGTCTTCTCATGCTCCGTGATGCATGAGGCTCTG |
| | | CACAACCACTACACGCAGAAGAGCCTCTCCCTGTCTCCGGGTAAA |
| trastuzumab-coil exendin-4 HC | 40 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGA*GGCGG* |
| | | *AAGCGGAGCAAAGCTCGCCGCACTGAAAGCCAAGCTGGCCGCTCT* |
| | | *GAAGTGCGGGGGTGGCGGAAGCATCGAAGGTCGTCACGGAGAAG* |
| | | GAACATTTACCAGCGACCTCAGCAAGCAGATGGAGGAAGAGGCCG |
| | | TGAGGCTGTTCATCGAGTGGCTGAAGAACGGCGGACCCTCCTCTG |
| | | GCGCTCCACCCCCTAGC*GGCGGAGGTGGGAGTTGCGAACTGGCC* |
| | | *GCACTGGAAGCTGAGCTGGCTGCCCTCGAAGCTGGAGGCTCTGG* |
| | | AGACTACTGGGGCCAAGGAACCCTGGTCACCGTCTCCTCAGCC |
| | | TCCACCAAGGGCCCATCGGTCTTCCCCCTGGCACCCTCCTCCA |
| | | AGAGCACCTCTGGGGGCACAGCGGCCCTGGGCTGCCTGGTCA |
| | | AGGACTACTTCCCCGAACCGGTGACGGTGTCGTGGAACTCAGG |
| | | CGCCCTGACCAGCGGCGTGCACACCTTCCCGGCTGTCCTACAG |
| | | TCCTCAGGACTCTACTCCCTCAGCAGCGTGGTGACTGTGCCCT |
| | | CTAGCAGCTTGGGCACCCAGACCTACATCTGCAACGTGAATCA |
| | | CAAGCCCAGCAACACCAAGGTGGACAAGAAAGTTGAACCCAA |
| | | ATCTTGCGACAAAACTCACACATGCCCACCGTGCCCAGCACCT |
| | | CCAGTCGCCGGACCGTCAGTCTTCCTCTTCCCTCCAAAACCCA |
| | | AGGACACCCTCATGATCTCCCGGACCCCTGAGGTCACATGCGT |

TABLE 3-continued

Coiled Coil Immunoglobulin Fusion Proteins-Nucleotide Sequence

| NAME | SEQ ID NO | SEQUENCE |
|---|---|---|
| | | GGTGGTGGACGTGAGCCACGAAGACCCTGAGGTCAAGTTCAA |
| | | CTGGTACGTGGACGGCGTGGAGGTGCATAATGCCAAGACAAA |
| | | GCCGCGGGAGGAGCAGTACAACAGCACGTACCGTGTGGTCAG |
| | | CGTCCTCACCGTCCTGCACCAGGACTGGCTGAATGGCAAGGAG |
| | | TACAAGTGCAAGGTCTCCAACAAAGGCCTCCCAAGCTCCATCG |
| | | AGAAAACCATCTCCAAAGCCAAAGGGCAGCCCCGAGAACCAC |
| | | AGGTGTACACCCTGCCTCCATCCCGGGATGAGCTGACCAAGAA |
| | | CCAGGTCAGCCTGACCTGCCTGGTCAAAGGCTTCTATCCCAGC |
| | | GACATCGCCGTGGAGTGGGAGAGCAATGGGCAGCCGGAGAAC |
| | | AACTACAAGACCACGCCTCCCGTGCTGGACTCCGACGGCTCCT |
| | | TCTTCCTCTACAGCAAGCTCACCGTGGACAAGAGCAGGTGGCA |
| | | GCAGGGGAACGTCTTCTCATGCTCCGTGATGCATGAGGCTCTG |
| | | CACAACCACTACACGCAGAAGAGCCTCTCCCTGTCTCCGGGTAAA |
| trastuzumab-coil Mokal HC | 41 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGA*GGCGG* |
| | | *AAGCGGAGCAAAGCTCGCCGCACTGAAAGCCAAGCTGGCCGCTCT* |
| | | *GAAGGGAGGCGGTGGCTCC*ATCAACGTGAAGTGCAGCCTGCCCC |
| | | AGCAGTGCATCAAGCCCTGCAAGGACGCCGGCATGCGGTTCGGC |
| | | AAGTGCATGAACAAGAAGTGCAGGTGCTACAGC*GGCGGTGGCGG* |
| | | *AAGCGAACTGGCCGCACTGGAAGCTGAGCTGGCTGCCCTCGAAG* |
| | | *CTGGAGGCTCTGGA*GACTACTGGGGCCAAGGAACCCTGGTCAC |
| | | CGTCTCCTCAGCCTCCACCAAGGGCCCATCGGTCTTCCCCCTG |
| | | GCACCCTCCTCCAAGAGCACCTCTGGGGGCACAGCGGCCCTGG |
| | | GCTGCCTGGTCAAGGACTACTTCCCCGAACCGGTGACGGTGTC |
| | | GTGGAACTCAGGCGCCCTGACCAGCGGCGTGCACACCTTCCCG |
| | | GCTGTCCTACAGTCCTCAGGACTCTACTCCCTCAGCAGCGTGG |
| | | TGACTGTGCCCTCTAGCAGCTTGGGCACCCAGACCTACATCTG |
| | | CAACGTGAATCACAAGCCCAGCAACACCAAGGTGGACAAGAA |
| | | AGTTGAACCCAAATCTTGCGACAAAACTCACACATGCCCACCG |
| | | TGCCCAGCACCTGAACTCCTGGGGGGACCGTCAGTCTTCCTCT |
| | | TCCCCCCAAAACCCAAGGACACCCTCATGATCTCCCGGACCCC |
| | | TGAGGTCACATGCGTGGTGGTGGACGTGAGCCACGAAGACCC |
| | | TGAGGTCAAGTTCAACTGGTACGTGGACGGCGTGGAGGTGCAT |
| | | AATGCCAAGACAAAGCCGCGGGAGGAGCAGTACAACAGCACG |
| | | TACCGTGTGGTCAGCGTCCTCACCGTCCTGCACCAGGACTGGC |
| | | TGAATGGCAAGGAGTACAAGTGCAAGGTCTCCAACAAAGCCC |

TABLE 3-continued

Coiled Coil Immunoglobulin Fusion Proteins-Nucleotide Sequence

| NAME | SEQ ID NO | SEQUENCE |
|------|-----------|----------|
| | | TCCCAGCCCCCATCGAGAAAACCATCTCCAAAGCCAAAGGGC |
| | | AGCCCCGAGAACCACAGGTGTACACCCTGCCCCCATCCCGGA |
| | | TGAGCTGACCAAGAACCAGGTCAGCCTGACCTGCCTGGTCAAA |
| | | GGCTTCTATCCCAGCGACATCGCCGTGGAGTGGGAGAGCAATG |
| | | GGCAGCCGGAGAACAACTACAAGACCACGCCTCCCGTGCTGG |
| | | ACTCCGACGGCTCCTTCTTCCTCTACAGCAAGCTCACCGTGGA |
| | | CAAGAGCAGGTGGCAGCAGGGGAACGTCTTCTCATGCTCCGTG |
| | | ATGCATGAGGCTCTGCACAACCACTACACGCAGAAGAGCCTCT |
| | | CCCTGTCTCCGGGTAAA |
| trastuzumab-coil VM24 HC | 42 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGA<u>GGCGG</u> |
| | | <u>AAGCGGAGCAAAGCTCGCCGCACTGAAAGCCAAGCTGGCCGCTCT</u> |
| | | <u>GAAGGGAGGCGGTGGCTCCGCCGCTGCAATCTCCTGCGTCGGCA</u> |
| | | GCCCCGAATGTCCTCCCAAGTGCCGGGCTCAGGGATGCAAGAACG |
| | | GCAAGTGTATGAACCGGAAGTGCAAGTGCTACTATTGC<u>GGCGGTG</u> |
| | | <u>GCGGAAGC</u>GAACTGGCCGCACTGGAAGCTGAGCTGGCTGCCCTC |
| | | <u>GAAGCTGGAGGCTCTGGA</u>GACTACTGGGGCCAAGGAACCCTGG |
| | | TCACCGTCTCCTCAGCCTCCACCAAGGGCCCATCGGTCTTCCCC |
| | | CTGGCACCCTCCTCCAAGAGCACCTCTGGGGGCACAGCGGCCC |
| | | TGGGCTGCCTGGTCAAGGACTACTTCCCCGAACCGGTGACGGT |
| | | GTCGTGGAACTCAGGCGCCCTGACCAGCGGCGTGCACACCTTC |
| | | CCGGCTGTCCTACAGTCCTCAGGACTCTACTCCCTCAGCAGCG |
| | | TGGTGACTGTGCCCTCTAGCAGCTTGGGCACCCAGACCTACAT |
| | | CTGCAACGTGAATCACAAGCCCAGCAACACCAAGGTGGACAA |
| | | GAAAGTTGAACCCAAATCTTGCGACAAAACTCACACATGCCCA |
| | | CCGTGCCCAGCACCTGAACTCCTGGGGGGACCGTCAGTCTTCC |
| | | TCTTCCCCCCAAAACCCAAGGACACCCTCATGATCTCCCGGAC |
| | | CCCTGAGGTCACATGCGTGGTGGTGGACGTGAGCCACGAAGA |
| | | CCCTGAGGTCAAGTTCAACTGGTACGTGGACGGCGTGGAGGTG |
| | | CATAATGCCAAGACAAAGCCGCGGGAGGAGCAGTACAACAGC |
| | | ACGTACCGTGTGGTCAGCGTCCTCACCGTCCTGCACCAGGACT |
| | | GGCTGAATGGCAAGGAGTACAAGTGCAAGGTCTCCAACAAAG |
| | | CCCTCCCAGCCCCCATCGAGAAAACCATCTCCAAAGCCAAAGG |
| | | GCAGCCCCGAGAACCACAGGTGTACACCCTGCCCCCATCCCGG |
| | | GATGAGCTGACCAAGAACCAGGTCAGCCTGACCTGCCTGGTCA |
| | | AAGGCTTCTATCCCAGCGACATCGCCGTGGAGTGGGAGAGCA |

TABLE 3-continued

Coiled Coil Immunoglobulin Fusion Proteins-Nucleotide Sequence

| NAME | SEQ ID NO | SEQUENCE |
|---|---|---|
| | | ATGGGCAGCCGGAGAACAACTACAAGACCACGCCTCCCGTGC |
| | | TGGACTCCGACGGCTCCTTCTTCCTCTACAGCAAGCTCACCGT |
| | | GGACAAGAGCAGGTGGCAGCAGGGGAACGTCTTCTCATGCTC |
| | | CGTGATGCATGAGGCTCTGCACAACCACTACACGCAGAAGAG |
| | | CCTCTCCCTGTCTCCGGGTAAA |
| trastuzumab-coil hGCSF HC | 43 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGCGG |
| | | AAGCGGAGCAAAGCTCGCCGCACTGAAAGCCAAGCTGGCCGCTCT |
| | | GAAGGGGGGTGGCGGAAGCGCCACACCTCTGGGCCCCGCCTCCT |
| | | CCCTGCCTCAGAGCTTTCTGCTCAAATGTCTGGAGCAGGTGCGGA |
| | | AGATCCAGGGCGACGGCGCCGCTCTGCAAGAGAAACTGGTCAGC |
| | | GAATGCGCCACATATAAGCTGTGTCACCCCGAGGAACTGGTCCTCT |
| | | TGGGCCACAGCCTGGGCATCCCCTGGGCCCCTCTCAGCTCCTGCC |
| | | CCTCCCAAGCTCTCCAACTGGCTGGATGTCTGTCCCAACTGCACTC |
| | | CGGCCTCTTCCTGTACCAGGGACTCCTCCAGGCTCTCGAAGGGAT |
| | | CAGCCCCGAACTGGGCCCCACACTGGACACCTTGCAACTCGATGT |
| | | GGCCGATTTCGCCACAACCATCTGGCAGCAGATGGAAGAACTCGG |
| | | AATGGCTCCTGCTCTCCAGCCCACACAGGGAGCTATGCCTGCTTTC |
| | | GCCTCTGCTTTCCAGCGGAGAGCTGGTGGTGTGCTCGTCGCATCC |
| | | CACCTCCAGAGCTTCTTGGAGGTGTCCTATCGGGTGCTCCGGCAT |
| | | CTGGCCCAACCCGGCGGAGGTGGGAGTGAACTGGCCGCACTGGA |
| | | AGCTGAGCTGGCTGCCCTCGAAGCTGGAGGCTCTGGAGACTACT |
| | | GGGGCCAAGGAACCCTGGTCACCGTCTCCTCAGCCAGCACTAA |
| | | AGGTCCATCTGTGTTCCCTCTGGCTCCTTGCAGCCGGAGCACCT |
| | | CCGAGTCCACAGCCGCTCTGGGATGTCTGGTGAAAGATTACTT |
| | | CCCCGAGCCCGTCACCGTGAGCTGGAATAGCGGAGCACTGAC |
| | | CTCCGGCGTCCACACATTCCCCGCCGTGCTCCAAAGCTCCGGC |
| | | CTGTACAGCCTCTCCTCCGTGGTCACCGTGCCCAGCAGCTCTCT |
| | | GGGCACAAAGACCTATACCTGTAACGTGGATCACAAGCCTAG |
| | | CAACACCAAAGTGGATAAGCGGGTGGAGAGCAAGTACGGCCC |
| | | TCCCTGTCCCCCTTGCCCCGCTCCTGAGGCCGCTGGCGGACCTT |
| | | CCGTGTTCCTGTTTCCCCCTAAGCCCAAGGACACCCTCATGATT |
| | | AGCCGGACACCCGAAGTGACCTGCGTGGTCGTGGATGTGTCCC |
| | | AGGAGGACCCTGAAGTGCAATTTAACTGGTACGTGGACGGCG |
| | | TCGAGGTGCACAACGCCAAGACCAAGCCTCGGGAAGAGCAGT |
| | | TCAACAGCACCTACCGGGTGGTCAGCGTGCTGACAGTGCTGCA |
| | | CCAGGACTGGCTGAACGGCAAGGAGTACAAGTGCAAGGTGAG |
| | | CAACAAGGGCCTGCCCAGCTCCATCGAGAAGACCATCAGCAA |
| | | GGCCAAGGGCCAGCCCAGGGAACCCCAGGTGTATACCCTGCC |
| | | CCCTAGCCAGGAGGAAATGACCAAAAACCAGGTGAGCCTGAC |

TABLE 3-continued

Coiled Coil Immunoglobulin Fusion Proteins-Nucleotide Sequence

| NAME | SEQ ID NO | SEQUENCE |
|---|---|---|
| | | CTGCCTGGTGAAGGGCTTCTACCCCAGCGACATCGCCGTGGAG |
| | | TGGGAGAGCAACGGCCAGCCCGAGAACAATTACAAGACCACC |
| | | CCTCCTGTGCTGGACAGCGACGGCTCCTTCTTTCTGTATAGCCG |
| | | GCTGACCGTGGACAAGAGCAGGTGGCAGGAGGGCAACGTGTT |
| | | CTCCTGTAGCGTGATGCACGAGGCCCTGCACAACCATTACACC |
| | | CAGAAGAGCTTGAGCCTGAGCCTGGGCAAA |
| trastuzumab-coil hGH HC (CDRH3) | 44 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGA<u>GGCGG</u> |
| | | <u>AAGCGGAGCAAAGCTCGCCGCACTGAAAGCCAAGCTGGCCGCTCT</u> |
| | | <u>GAAGGGGGGTGGCGG</u>AAGCTTCCCAACCATTCCCTTATCCAGGCT |
| | | *TTTTGACAACGCTATGCTCCGCGCCCATCGTCTGCACCAGCTGGC* |
| | | *CTTTGACACCTACCAGGAGTTTGAAGAAGCCTATATCCCAAAGGAA* |
| | | *CAGAAGTATTCATTCCTGCAGAACCCCCAGACCTCCCTCTGTTTCT* |
| | | *CAGAGTCTATTCCGACACCCTCCAACAGGGAGGAAACACAACAGA* |
| | | *AATCCAACCTAGAGCTGCTCCGCATCTCCCTGCTGCTCATCCAGTC* |
| | | *GTGGCTGGAGCCCGTGCAGTTCCTCAGGAGTGTCTTCGCCAACAG* |
| | | *CCTGGTGTACGGCGCCTCTGACAGCAACGTCTATGACCTCCTAAA* |
| | | *GGACCTAGAGGAAGGCATCCAAACGCTGATGGGGAGGCTGGAAG* |
| | | *ATGGCAGCCCCCGGACTGGGCAGATCTTCAAGCAGACCTACAGCA* |
| | | *AGTTCGACACAAACTCACACAACGATGACGCACTACTAAGAACTA* |
| | | *CGGGCTGCTCTACTGCTTCAGGAAGGACATGGACAAGGTCGAGAC* |
| | | *ATTCCTGCGCATCGTGCAGTGCCGCTCTGTGGAGGGCAGCTGTGG* |
| | | *CTTCGGCGGAGGTGGGAGT*<u>GAACTGGCCGCACTGGAAGCTGAGC</u> |
| | | <u>TGGCTGCCCTCGAAGCTGGAGGCTCTGGA</u>GACTACTGGGGCCAA |
| | | GGAACCCTGGTCACCGTCTCCTCAGCCAGCACTAAAGGTCCAT |
| | | CTGTGTTCCCTCTGGCTCCTTGCAGCCGGAGCACCTCCGAGTCC |
| | | ACAGCCGCTCTGGGATGTCTGGTGAAAGATTACTTCCCCGAGC |
| | | CCGTCACCGTGAGCTGGAATAGCGGAGCACTGACCTCCGGCGT |
| | | CCACACATTCCCCGCCGTGCTCCAAAGCTCCGGCCTGTACAGC |
| | | CTCTCCTCCGTGGTCACCGTGCCCAGCAGCTCTCTGGGCACAA |
| | | AGACCTATACCTGTAACGTGGATCACAAGCCTAGCAACACCAA |
| | | AGTGGATAAGCGGGTGGAGAGCAAGTACGGCCCTCCCTGTCC |
| | | CCCTTGCCCCGCTCCTGAGGCCGCTGGCGGACCTTCCGTGTTCC |
| | | TGTTTCCCCCTAAGCCCAAGGACACCCTCATGATTAGCCGGAC |
| | | ACCCGAAGTGACCTGCGTGGTCGTGGATGTGTCCCAGGAGGAC |
| | | CCTGAAGTGCAATTTAACTGGTACGTGGACGGCGTCGAGGTGC |
| | | ACAACGCCAAGACCAAGCCTCGGGAAGAGCAGTTCAACAGCA |
| | | CCTACCGGGTGGTCAGCGTGCTGACAGTGCTGCACCAGGACTG |
| | | GCTGAACGGCAAGGAGTACAAGTGCAAGGTGAGCAACAAGGG |
| | | CCTGCCCAGCTCCATCGAGAAGACCATCAGCAAGGCCAAGGG |
| | | CCAGCCCAGGGAACCCCAGGTGTATACCCTGCCCCCTAGCCAG |

TABLE 3-continued

Coiled Coil Immunoglobulin Fusion Proteins-Nucleotide Sequence

| NAME | SEQ ID NO | SEQUENCE |
|---|---|---|
| | | GAGGAAATGACCAAAAACCAGGTGAGCCTGACCTGCCTGGTG |
| | | AAGGGCTTCTACCCCAGCGACATCGCCGTGGAGTGGGAGAGC |
| | | AACGGCCAGCCCGAGAACAATTACAAGACCACCCCTCCTGTGC |
| | | TGGACAGCGACGGCTCCTTCTTTCTGTATAGCCGGCTGACCGT |
| | | GGACAAGAGCAGGTGGCAGGAGGGCAACGTGTTCTCCTGTAG |
| | | CGTGATGCACGAGGCCCTGCACAACCATTACACCCAGAAGAG |
| | | CTTGAGCCTGAGCCTGGGCAAA |
| trastuzumab-coil hGH HC (CDRH2) | 45 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCT<u>GGCGGAAGCGGA</u> |
| | | <u>GCAAAGCTCGCCGCACTGAAAGCCAAGCTGGCCGCTCTGAAGGGT</u> |
| | | <u>GGTGGCGGAAGC</u>TTCCCAACCATTCCCTTATCCAGGCTTTTTGACA |
| | | ACGCTATGCTCCGCGCCCATCGTCTGCACCAGCTGGCCTTTGACA |
| | | CCTACCAGGAGTTTGAAGAAGCCTATATCCCAAAGGAACAGAAGTA |
| | | TTCATTCCTGCAGAACCCCCAGACCTCCCTCTGTTTCTCAGAGTCT |
| | | ATTCCGACACCCTCCAACAGGGAGGAAACACAACAGAAATCCAACC |
| | | TAGAGCTGCTCCGCATCTCCCTGCTGCTCATCCAGTCGTGGCTGG |
| | | AGCCCGTGCAGTTCCTCAGGAGTGTCTTCGCCAACAGCCTGGTGT |
| | | ACGGCGCCTCTGACAGCAACGTCTATGACCTCCTAAAGGACCTAG |
| | | AGGAAGGCATCCAAACGCTGATGGGGAGGCTGGAAGATGGCAGC |
| | | CCCCGGACTGGGCAGATCTTCAAGCAGACCTACAGCAAGTTCGAC |
| | | ACAAACTCACACAACGATGACGCACTACTCAAGAACTACGGGCTGC |
| | | TCTACTGCTTCAGGAAGGACATGGACAAGGTCGAGACATTCCTGC |
| | | GCATCGTGCAGTGCCGCTCTGTGGAGGGCAGCTGTGGCTTC<u>GGC</u> |
| | | <u>GGAGGTGGGAGTGAACTGGCCGCACTGGAAGCTGAGCTGGCTGC</u> |
| | | <u>CCTCGAAGCTGGAGGCTCTGGAG</u>GTTACACACGCTACGCAGACT |
| | | CCGTGAAGGGCCGATTCACCATCTCCGCAGACACTTCCAAGAA |
| | | CACGGCGTATCTTCAAATGAACAGCCTGAGAGCCGAGGACAC |
| | | GGCCGTGTATTACTGTTCGAGATGGGGCGGTGACGGCTTCTAT |
| | | GCCATGGACTACTGGGGCCAAGGAACCCTGGTCACCGTCTCCT |
| | | CAGCCTCCACCAAGGGCCCATCGGTCTTCCCCCTGGCACCCTC |
| | | CTCCAAGAGCACCTCTGGGGGCACAGCGGCCCTGGGCTGCCTG |
| | | GTCAAGGACTACTTCCCCGAACCGGTGACGGTGTCGTGGAACT |
| | | CAGGCGCCCTGACCAGCGGCGTGCACACCTTCCCGGCTGTCCT |
| | | ACAGTCCTCAGGACTCTACTCCCTCAGCAGCGTGGTGACTGTG |
| | | CCCTCTAGCAGCTTGGGCACCCAGACCTACATCTGCAACGTGA |
| | | ATCACAAGCCCAGCAACACCAAGGTGGACAAGAAAGTTGAAC |
| | | CCAAATCTTGCGACAAAACTCACACATGCCCACCGTGCCCAGC |
| | | ACCTCCAGTCGCCGGACCGTCAGTCTTCCTCTTCCCTCCAAAAC |
| | | CCAAGGACACCCTCATGATCTCCCGGACCCCTGAGGTCACATG |
| | | CGTGGTGGTGGACGTGAGCCACGAAGACCCTGAGGTCAAGTT |
| | | CAACTGGTACGTGGACGGCGTGGAGGTGCATAATGCCAAGAC |
| | | AAAGCCGCGGGAGGAGCAGTACAACAGCACGTACCGTGTGGT |
| | | CAGCGTCCTCACCGTCCTGCACCAGGACTGGCTGAATGGCAAG |

TABLE 3-continued

Coiled Coil Immunoglobulin Fusion Proteins-Nucleotide Sequence

| NAME | SEQ ID NO | SEQUENCE |
|------|-----------|----------|
| | | GAGTACAAGTGCAAGGTCTCCAACAAAGGCCTCCCAAGCTCC |
| | | ATCGAGAAAACCATCTCCAAAGCCAAAGGGCAGCCCCGAGAA |
| | | CCACAGGTGTACACCCTGCCTCCATCCCGGGATGAGCTGACCA |
| | | AGAACCAGGTCAGCCTGACCTGCCTGGTCAAAGGCTTCTATCC |
| | | CAGCGACATCGCCGTGGAGTGGGAGAGCAATGGGCAGCCGGA |
| | | GAACAACTACAAGACCACGCCTCCCGTGCTGGACTCCGACGGC |
| | | TCCTTCTTCCTCTACAGCAAGCTCACCGTGGACAAGAGCAGGT |
| | | GGCAGCAGGGGAACGTCTTCTCATGCTCCGTGATGCATGAGGC |
| | | TCTGCACAACCACTACACGCAGAAGAGCCTCTCCCTGTCTCCG |
| | | GGTAAATGATAA |
| BLV1H12 coil-hGH HC | 46 | CAGGTCCAGCTGAGAGAGAGCGGCCCTTCACTGGTCAAGCCAT |
| | | CCCAGACACTGAGCCTGACATGCACAGCAAGCGGGTTTTCACT |
| | | GAGCGACAAGGCAGTGGGATGGGTCCGACAGGCACCAGGAAA |
| | | AGCCCTGGAATGGCTGGGCAGCATCGATACCGGCGGGAACAC |
| | | AGGGTACAATCCCGGACTGAAGAGCAGACTGTCCATTACCAA |
| | | GGACAACTCTAAAAGTCAGGTGTCACTGAGCGTGAGCTCCGTC |
| | | ACCACAGAGGATAGTGCAACTTACTATTGC*GGCGGAAGCGGAG* |
| | | *CAAAGCTCGCCGCACTGAAAGCCAAGCTGGCCGCTCTGAAGGGG* |
| | | *GGTGGCGGAAGC*TTCCCAACCATTCCCTTATCCAGGCTTTTTGACA |
| | | ACGCTATGCTCCGCGCCCATCGTCTGCACCAGCTGGCCTTTGACA |
| | | CCTACCAGGAGTTTGAAGAAGCCTATATCCCAAAGGAACAGAAGTA |
| | | TTCATTCCTGCAGAACCCCCAGACCTCCCTCTGTTTCTCAGAGTCT |
| | | ATTCCGACACCCTCCAACAGGGAGGAAACACAACAGAAATCCAACC |
| | | TAGAGCTGCTCCGCATCTCCCTGCTGCTCATCCAGTCGTGGCTGG |
| | | AGCCCGTGCAGTTCCTCAGGAGTGTCTTCGCCAACAGCCTGGTGT |
| | | ACGGCGCCTCTGACAGCAACGTCTATGACCTCCTAAAGGACCTAG |
| | | AGGAAGGCATCCAAACGCTGATGGGGAGGCTGGAAGATGGCAGC |
| | | CCCCGGACTGGGCAGATCTTCAAGCAGACCTACAGCAAGTTCGAC |
| | | ACAAACTCACACAACGATGACGCACTACTCAAGAACTACGGGCTGC |
| | | TCTACTGCTTCAGGAAGGACATGGACAAGGTCGAGACATTCCTGC |
| | | GCATCGTGCAGTGCCGCTCTGTGGAGGGCAGCTGTGGCTTC*GGC* |
| | | *GGAGGTGGGAGTGAACTGGCCGCACTGGAAGCTGAGCTGGCTGC* |
| | | *CCTCGAAGCTGGAGGCTCTGGA*CATGTGGATGTCTGGGGACAG |
| | | GGCCTGCTGGTGACAGTCTCTAGTGCTTCCACAACTGCACCAA |
| | | AGGTGTACCCCCTGTCAAGCTGCTGTGGGACAAATCCTCTAG |
| | | TACCGTGACACTGGGATGCCTGGTCTCAAGCTATATGCCCGAG |
| | | CCTGTGACTGTCACCTGGAACTCAGGAGCCCTGAAAAGCGGA |
| | | GTGCACACCTTCCCAGCTGTGCTGCAGTCCTCTGGCCTGTATA |
| | | GCCTGAGTTCAATGGTGACAGTCCCCGGCAGTACTTCAGGGCA |
| | | GACCTTCACCTGTAATGTGGCCCATCCTGCCAGCTCCACCAAA |
| | | GTGGACAAAGCAGTGGAACCCAAATCTTGCGACAAAACTCAC |
| | | ACATGCCCACCGTGCCCAGCACCTGAACTCCTGGGGGGACCGT |
| | | CAGTCTTCCTCTTCCCCCCAAAACCCAAGGACACCCTCATGAT |
| | | CTCCCGGACCCCTGAGGTCACATGCGTGGTGGTGGACGTGAGC |
| | | CACGAAGACCCTGAGGTCAAGTTCAACTGGTACGTGGACGGC |
| | | GTGGAGGTGCATAATGCCAAGACAAAGCCGCGGGAGGAGCAG |

TABLE 3-continued

Coiled Coil Immunoglobulin Fusion Proteins-Nucleotide Sequence

| NAME | SEQ ID NO | SEQUENCE |
|---|---|---|
| | | TACAACAGCACGTACCGTGTGGTCAGCGTCCTCACCGTCCTGC |
| | | ACCAGGACTGGCTGAATGGCAAGGAGTACAAGTGCAAGGTCT |
| | | CCAACAAAGCCCTCCCAGCCCCCATCGAGAAAACCATCTCCAA |
| | | AGCCAAAGGGCAGCCCCGAGAACCACAGGTGTACACCCTGCC |
| | | CCCATCCCGGGATGAGCTGACCAAGAACCAGGTCAGCCTGAC |
| | | CTGCCTGGTCAAAGGCTTCTATCCCAGCGACATCGCCGTGGAG |
| | | TGGGAGAGCAATGGGCAGCCGGAGAACAACTACAAGACCACG |
| | | CCTCCCGTGCTGGACTCCGACGGCTCCTTCTTCCTCTACAGCAA |
| | | GCTCACCGTGGACAAGAGCAGGTGGCAGCAGGGGAACGTCTT |
| | | CTCATGCTCCGTGATGCATGAGGCTCTGCACAACCACTACACG |
| | | CAGAAGAGCCTCTCCCTGTCTCCGGGTAAA |
| trastuzumab-coil hLeptin HC (CDRH3) | 47 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGCGG |
| | | AAGCGGAGCAAAGCTCGCCGCACTGAAAGCCAAGCTGGCCGCTCT |
| | | GAAGGGGGGTGGCGGAAGCGTTCCAATTCAAAAGGTTCAAGATGA |
| | | TACCAAAACTCTGATTAAAACTATTGTCACGCGTATAAACGACATCA |
| | | GCCATACCCAGTCGGTTAGCTCAAAGCAAAAAGTTACCGGTTTGGA |
| | | CTTTATTCCGGGACTGCACCCGATCCTGACCCTTAGTAAAATGGAC |
| | | CAGACACTGGCCGTCTACCAGCAAATCCTGACATCGATGCCATCCA |
| | | GAAATGTGATACAAATTAGCAACGATTTGGAAAACCTTCGCGATCT |
| | | GCTGCACGTGCTGGCCTTCAGTAAGTCCTGTCATCTGCCGTGGGC |
| | | GTCGGGACTGGAGACTCTTGACTCGCTGGGTGGAGTGTTAGAGGC |
| | | CTCTGGCTATTCTACTGAAGTCGTTGCGCTGTCACGCCTCCAGGG |
| | | GAGCCTGCAGGACATGCTGTGGCAGCTGGACCTGTCACCTGGCTG |
| | | CGGCGGAGGTGGGAGTGAACTGGCCGCACTGGAAGCTGAGCTGG |
| | | CTGCCCTCGAAGCTGGAGGCTCTGGAGACTACTGGGGCCAAGG |
| | | AACCCTGGTCACCGTCTCCTCAGCCTCCACCAAGGGCCCATCG |
| | | GTCTTCCCCCTGGCACCCTCCTCCAAGAGCACCTCTGGGGGCA |
| | | CAGCGGCCCTGGGCTGCCTGGTCAAGGACTACTTCCCCGAACC |
| | | GGTGACGGTGTCGTGGAACTCAGGCGCCCTGACCAGCGGCGT |
| | | GCACACCTTCCCGGCTGTCCTACAGTCCTCAGGACTCTACTCCC |
| | | TCAGCAGCGTGGTGACTGTGCCCTCTAGCAGCTTGGGCACCCA |
| | | GACCTACATCTGCAACGTGAATCACAAGCCCAGCAACACCAA |
| | | GGTGGACAAGAAAGTTGAACCCAAATCTTGCGACAAAACTCA |
| | | CACATGCCCACCGTGCCCAGCACCTCCAGTCGCCGGACCGTCA |
| | | GTCTTCCTCTTCCCTCCAAAACCCAAGGACACCCTCATGATCTC |
| | | CCGGACCCCTGAGGTCACATGCGTGGTGGTGGACGTGAGCCAC |
| | | GAAGACCCTGAGGTCAAGTTCAACTGGTACGTGGACGGCGTG |
| | | GAGGTGCATAATGCCAAGACAAAGCCGCGGGAGGAGCAGTAC |

TABLE 3-continued

Coiled Coil Immunoglobulin Fusion Proteins-Nucleotide Sequence

| NAME | SEQ ID NO | SEQUENCE |
|---|---|---|
| | | AACAGCACGTACCGTGTGGTCAGCGTCCTCACCGTCCTGCACC |
| | | AGGACTGGCTGAATGGCAAGGAGTACAAGTGCAAGGTCTCCA |
| | | ACAAAGGCCTCCCAAGCTCCATCGAGAAAACCATCTCCAAAG |
| | | CCAAAGGGCAGCCCCGAGAACCACAGGTGTACACCCTGCCTC |
| | | CATCCCGGGATGAGCTGACCAAGAACCAGGTCAGCCTGACCT |
| | | GCCTGGTCAAAGGCTTCTATCCCAGCGACATCGCCGTGGAGTG |
| | | GGAGAGCAATGGGCAGCCGGAGAACAACTACAAGACCACGCC |
| | | TCCCGTGCTGGACTCCGACGGCTCCTTCTTCCTCTACAGCAAGC |
| | | TCACCGTGGACAAGAGCAGGTGGCAGCAGGGGAACGTCTTCT |
| | | CATGCTCCGTGATGCATGAGGCTCTGCACAACCACTACACGCA |
| | | GAAGAGCCTCTCCCTGTCTCCGGGTAAA |
| trastuzumab-coil hLeptin HC (CDRH2) | 48 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATT*GGCGGAAGCGGAGCAAAG* |
| | | *CTCGCCGCACTGAAAGCCAAGCTGGCCGCTCTGAAGGGGGGTGG* |
| | | *CGGAAGCGTTCCAATTCAAAAGGTTCAAGATGATACCAAAACTCTG* |
| | | *ATTAAAACTATTGTCACGCGTATAAACGACATCTCACATACCCAGTC* |
| | | *GGTTAGCTCAAAGCAAAAAGTTACCGGTTTGGACTTTATTCCGGGA* |
| | | *CTGCACCCGATCCTGACCCTTAGTAAAATGGACCAGACACTGGCC* |
| | | *GTCTACCAGCAAATCCTGACATCGATGCCATCCAGAAATGTGATAC* |
| | | *AAATTAGCAACGATTTGGAAAACCTTCGCGATCTGCTGCACGTGCT* |
| | | *GGCCTTCAGTAAGTCCTGTCATCTGCCGTGGGCGTCGGGACTGGA* |
| | | *GACTCTTGACTCGCTGGGTGGAGTGTTAGAGGCCTCTGGCTATTCT* |
| | | *ACTGAAGTCGTTGCGCTGTCACGCCTCCAGGGGAGCCTGCAGGAC* |
| | | *ATGCTGTGGCAGCTGGACCTGTCACCTGGCTGC*GGCGGAGGTGG |
| | | GAGTGAACTGGCCGCACTGGAAGCTGAGCTGGCTGCCCTCGAAG |
| | | *CTGGAGGCTCTGGA*ACACGCTACGCAGACTCCGTGAAGGGCCG |
| | | ATTCACCATCTCCGCAGACACTTCCAAGAACACGGCGTATCTT |
| | | CAAATGAACAGCCTGAGAGCCGAGGACACGGCCGTGTATTAC |
| | | TGTTCGAGATGGGGCGGTGACGGCTTCTATGCCATGGACTACT |
| | | GGGGCCAAGGAACCCTGGTCACCGTCTCCTCAGCCTCCACCAA |
| | | GGGCCCATCGGTCTTCCCCCTGGCACCCTCCTCCAAGAGCACC |
| | | TCTGGGGGCACAGCGGCCCTGGGCTGCCTGGTCAAGGACTACT |
| | | TCCCCGAACCGGTGACGGTGTCGTGGAACTCAGGCGCCCTGAC |
| | | CAGCGGCGTGCACACCTTCCCGGCTGTCCTACAGTCCTCAGGA |
| | | CTCTACTCCCTCAGCAGCGTGGTGACTGTGCCCTCTAGCAGCTT |
| | | GGGCACCCAGACCTACATCTGCAACGTGAATCACAAGCCCAG |
| | | CAACACCAAGGTGGACAAGAAAGTTGAACCCAAATCTTGCGA |
| | | CAAAACTCACACATGCCCACCGTGCCCAGCACCTCCAGTCGCC |
| | | GGACCGTCAGTCTTCCTCTTCCCTCCAAAACCCAAGGACACCC |
| | | TCATGATCTCCCGGACCCCTGAGGTCACATGCGTGGTGGTGGA |
| | | CGTGAGCCACGAAGACCCTGAGGTCAAGTTCAACTGGTACGTG |
| | | GACGGCGTGGAGGTGCATAATGCCAAGACAAAGCCGCGGGAG |

TABLE 3-continued

Coiled Coil Immunoglobulin Fusion Proteins-Nucleotide Sequence

| NAME | SEQ ID NO | SEQUENCE |
|---|---|---|
| | | GAGCAGTACAACAGCACGTACCGTGTGGTCAGCGTCCTCACCG |
| | | TCCTGCACCAGGACTGGCTGAATGGCAAGGAGTACAAGTGCA |
| | | AGGTCTCCAACAAAGGCCTCCCAAGCTCCATCGAGAAAACCAT |
| | | CTCCAAAGCCAAAGGGCAGCCCCGAGAACCACAGGTGTACAC |
| | | CCTGCCTCCATCCCGGGATGAGCTGACCAAGAACCAGGTCAGC |
| | | CTGACCTGCCTGGTCAAAGGCTTCTATCCCAGCGACATCGCCG |
| | | TGGAGTGGGAGAGCAATGGGCAGCCGGAGAACAACTACAAGA |
| | | CCACGCCTCCCGTGCTGGACTCCGACGGCTCCTTCTTCCTCTAC |
| | | AGCAAGCTCACCGTGGACAAGAGCAGGTGGCAGCAGGGGAAC |
| | | GTCTTCTCATGCTCCGTGATGCATGAGGCTCTGCACAACCACT |
| | | ACACGCAGAAGAGCCTCTCCCTGTCTCCGGGTAAATGATAA |
| trastuzumab-coil hLeptin LC (CDRL3) | 49 | GACATCCAGATGACCCAGTCTCCATCCTCCCTGTCTGCATCTGT |
| | | AGGAGACAGAGTCACCATCACTTGCCGGGCAAGTCAGGATGT |
| | | GAATACCGCGGTCGCATGGTATCAGCAGAAACCAGGGAAAGC |
| | | CCCTAAGCTCCTGATCTATTCTGCATCCTTCTTGTATAGTGGGG |
| | | TCCCATCAAGGTTCAGTGGCAGTAGATCTGGGACAGATTTCAC |
| | | TCTCACCATCAGCAGTCTGCAACCTGAAGATTTTGCAACTTAC |
| | | TACTGTCAACAGCATTAC*GGCGGAAGCGGAGCAAAGCTCGCCG* |
| | | *CACTGAAAGCCAAGCTGGCCGCTCTGAAGGGGGGTGGCGGAAGC* |
| | | GTTCCAATTCAAAAGGTTCAAGATGATACCAAAACTCTGATTAAAAC |
| | | TATTGTCACGCGTATAAACGACATCTCACATACCCAGTCGGTTAGC |
| | | TCAAAGCAAAAAGTTACCGGTTTGGACTTTATTCCGGGACTGCACC |
| | | CGATCCTGACCCTTAGTAAAATGGACCAGACACTGGCCGTCTACCA |
| | | GCAAATCCTGACATCGATGCCATCCAGAAATGTGATACAAATTAGC |
| | | AACGATTTGGAAAACCTTCGCGATCTGCTGCACGTGCTGGCCTTCA |
| | | GTAAGTCCTGTCATCTGCCGTGGGCGTCGGGACTGGAGACTCTTG |
| | | ACTCGCTGGGTGGAGTGTTAGAGGCCTCTGGCTATTCTACTGAAGT |
| | | CGTTGCGCTGTCACGCCTCCAGGGGAGCCTGCAGGACATGCTGTG |
| | | GCAGCTGGACCTGTCACCTGGCTGC*GGCGGAGGTGGGAGTGAAC* |
| | | *TGGCCGCACTGGAAGCTGAGCTGGCTGCCCTCGAAGCTGGAGGC* |
| | | *TCTGGA*CCGACGTTCGGCCAAGGTACCAAGCTTGAGATCAAAC |
| | | GAACTGTGGCTGCACCATCTGTCTTCATCTTCCCGCCATCTGAT |
| | | GAGCAGTTGAAATCTGGAACTGCCTCTGTCGTGTGCCTGCTGA |
| | | ATAACTTCTATCCCAGAGAGGCCAAAGTACAGTGGAAGGTGG |
| | | ATAACGCCCTCCAATCGGGTAACTCCCAGGAGAGTGTCACAGA |
| | | GCAGGACAGCAAGGACAGCACCTACAGCCTCAGCAGCACCCT |
| | | GACGCTGAGCAAAGCAGACTACGAGAAACACAAAGTCTACGC |
| | | CTGCGAAGTCACCCATCAGGGCCTGTCCTCGCCCGTCACAAAG |
| | | AGCTTCAACAGGGGAGAGTGT |
| trastuzumab-coil-hIFN-alpha HC | 50 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |

TABLE 3-continued

Coiled Coil Immunoglobulin Fusion Proteins-Nucleotide Sequence

| NAME | SEQ ID NO | SEQUENCE |
|---|---|---|
| | | CAGACACTTCCAAGAACACGGCGTATCTTCAAATGAACAGCCT |
| | | GAGAGCCGAGGACACGGCCGTGTATTACTGTTCGAGA<u>GGCGG</u> |
| | | <u>AAGCGGAGCAAAGCTCGCCGCACTGAAAGCCAAGCTGGCCGCTCT</u> |
| | | <u>GAAGGGTGGTGGCGGAAGC</u>TGTGATCTGCCTCAAACCCACAGCCT |
| | | *GGGTAGCAGGAGGACCTTGATGCTCCTGGCACAGATGAGGAGAAT* |
| | | *CTCTCTTTTCTCCTGCTTGAAGGACAGACATGACTTTGGATTTCCCC* |
| | | *AGGAGGAGTTTGGCAACCAGTTCCAAAAGGCTGAAACCATCCCTGT* |
| | | *CCTCCATGAGATGATCCAGCAGATCTTCAATCTCTTCAGCACAAAG* |
| | | *GACTCATCTGCTGCTTGGGATGAGACCCTCCTAGACAAATTCTACA* |
| | | *CTGAACTCTACCAGCAGCTGAATGACCTGGAAGCCTGTGTGATACA* |
| | | *GGGGGTGGGGGTGACAGAGACTCCCCTGATGAAGGAGGACTCCA* |
| | | *TTCTGGCTGTGAGGAAATACTTCCAAAGAATCACTCTCTATCTGAAA* |
| | | *GAGAAGAAATACAGCCCTTGTGCCTGGGAGGTTGTCAGAGCAGAA* |
| | | *ATCATGAGATCTTTTTCTTTGTCAACAAACTTGCAAGAAAGTTTAAGA* |
| | | *AGTAAGGAAGGCGGAGGTGGGAG*<u>TGAACTGGCCGCACTGGAAGC</u> |
| | | <u>TGAGCTGGCTGCCCTCGAAGCTGGAGGCTCTGGA</u>GACTACTGGG |
| | | GCCAAGGAACCCTGGTCACCGTCTCCTCAGCCAGCACTAAAGG |
| | | TCCATCTGTGTTCCCTCTGGCTCCTTGCAGCCGGAGCACCTCCG |
| | | AGTCCACAGCCGCTCTGGGATGTCTGGTGAAAGATTACTTCCC |
| | | CGAGCCCGTCACCGTGAGCTGGAATAGCGGAGCACTGACCTCC |
| | | GGCGTCCACACATTCCCCGCCGTGCTCCAAAGCTCCGGCCTGT |
| | | ACAGCCTCTCCTCCGTGGTCACCGTGCCCAGCAGCTCTCTGGG |
| | | CACAAAGACCTATACCTGTAACGTGGATCACAAGCCTAGCAAC |
| | | ACCAAAGTGGATAAGCGGGTGGAGAGCAAGTACGGCCCCTCCC |
| | | TGTCCCCCTTGCCCCGCTCCTGAGGCCGCTGGCGGACCTTCCGT |
| | | GTTCCTGTTTCCCCCTAAGCCCAAGGACACCCTCATGATTAGC |
| | | CGGACACCCGAAGTGACCTGCGTGGTCGTGGATGTGTCCCAGG |
| | | AGGACCCTGAAGTGCAATTTAACTGGTACGTGGACGGCGTCGA |
| | | GGTGCACAACGCCAAGACCAAGCCTCGGGAAGAGCAGTTCAA |
| | | CAGCACCTACCGGGTGGTCAGCGTGCTGACAGTGCTGCACCAG |
| | | GACTGGCTGAACGGCAAGGAGTACAAGTGCAAGGTGAGCAAC |
| | | AAGGGCCTGCCCAGCTCCATCGAGAAGACCATCAGCAAGGCC |
| | | AAGGGCCAGCCCAGGGAACCCCAGGTGTATACCCTGCCCCCTA |
| | | GCCAGGAGGAAATGACCAAAAACCAGGTGAGCCTGACCTGCC |
| | | TGGTGAAGGGCTTCTACCCCAGCGACATCGCCGTGGAGTGGGA |
| | | GAGCAACGGCCAGCCCGAGAACAATTACAAGACCACCCCTCC |
| | | TGTGCTGGACAGCGACGGCTCCTTCTTTCTGTATAGCCGGCTG |
| | | ACCGTGGACAAGAGCAGGTGGCAGGAGGGCAACGTGTTCTCC |
| | | TGTAGCGTGATGCACGAGGCCCTGCACAACCATTACACCCAGA |
| | | AGAGCTTGAGCCTGAGCCTGGGCAAA |
| trastuzumab-coil hIFN-B1 HC | 51 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |

TABLE 3-continued

Coiled Coil Immunoglobulin Fusion Proteins-Nucleotide Sequence

| NAME | SEQ ID NO | SEQUENCE |
|------|-----------|----------|
| | | CAGACACTTCCAAGAACACGGCGTATCTTCAAATGAACAGCCT |
| | | GAGAGCCGAGGACACGGCCGTGTATTACTGTTCGAGA<u>GGCGG</u> |
| | | <u>AAGCGGAGCAAAGCTCGCCGCACTGAAAGCCAAGCTGGCCGCTCT</u> |
| | | <u>GAAGGGTGGTGGCGGAAGC</u>ATGAGCTACAACTTGCTTGGATTCCT |
| | | ACAAAGAAGCAGCAATTTTCAGTGTCAGAAGCTCCTGTGGCAATTG<br>AATGGGAGGCTTGAATACTGCCTCAAGGACAGGATGAACTTTGACA<br>TCCCTGAGGAGATTAAGCAGCTGCAGCAGTTCCAGAAGGAGGACG<br>CCGCATTGACCATCTATGAGATGCTCCAGAACATCTTTGCTATTTTC<br>AGACAAGATTCATCTAGCACTGGCTGGAATGAGACTATTGTTGAGA<br>ACCTCCTGGCTAATGTCTATCATCAGATAAACCATCTGAAGACAGTC<br>CTGGAAGAAAAACTGGAGAAAGAAGATTTCACCAGGGGAAAACTCA<br>TGAGCAGTCTGCACCTGAAAAGATATTATGGGAGGATTCTGCATTA<br>CCTGAAGGCCAAGGAGTACAGTCACTGTGCCTGGACCATAGTCAG<br>AGTGGAAATCCTAAGGAACTTTTACTTCATTAACAGACTTACAGGTT<br>ACCTCCGAAA<u>CGGCGGAGGTGGGAGTGAACTGGCCGCACTGGAA</u> |
| | | <u>GCTGAGCTGGCTGCCCTCGAAGCTGGAGGCTCTGGA</u>GACTACTG |
| | | GGGCCAAGGAACCCTGGTCACCGTCTCCTCAGCCTCCACCAAG |
| | | GGCCCATCGGTCTTCCCCCTGGCACCCTCCTCCAAGAGCACCT |
| | | CTGGGGGCACAGCGGCCCTGGGCTGCCTGGTCAAGGACTACTT |
| | | CCCCGAACCGGTGACGGTGTCGTGGAACTCAGGCGCCCTGACC |
| | | AGCGGCGTGCACACCTTCCCGGCTGTCCTACAGTCCTCAGGAC |
| | | TCTACTCCCTCAGCAGCGTGGTGACTGTGCCCTCTAGCAGCTT |
| | | GGGCACCCAGACCTACATCTGCAACGTGAATCACAAGCCCAG |
| | | CAACACCAAGGTGGACAAGAAAGTTGAACCCAAATCTTGCGA |
| | | CAAAACTCACACATGCCCACCGTGCCCAGCACCTCCAGTCGCC |
| | | GGACCGTCAGTCTTCCTCTTCCCTCCAAAACCCAAGGACACCC |
| | | TCATGATCTCCCGGACCCCTGAGGTCACATGCGTGGTGGTGGA |
| | | CGTGAGCCACGAAGACCCTGAGGTCAAGTTCAACTGGTACGTG |
| | | GACGGCGTGGAGGTGCATAATGCCAAGACAAAGCCGCGGGAG |
| | | GAGCAGTACAACAGCACGTACCGTGTGGTCAGCGTCCTCACCG |
| | | TCCTGCACCAGGACTGGCTGAATGGCAAGGAGTACAAGTGCA |
| | | AGGTCTCCAACAAAGGCCTCCCAAGCTCCATCGAGAAAACCAT |
| | | CTCCAAAGCCAAAGGGCAGCCCCGAGAACCACAGGTGTACAC |
| | | CCTGCCTCCATCCCGGGATGAGCTGACCAAGAACCAGGTCAGC |
| | | CTGACCTGCCTGGTCAAAGGCTTCTATCCCAGCGACATCGCCG |
| | | TGGAGTGGGAGAGCAATGGGCAGCCGGAGAACAACTACAAGA |
| | | CCACGCCTCCCGTGCTGGACTCCGACGGCTCCTTCTTCCTCTAC |
| | | AGCAAGCTCACCGTGGACAAGAGCAGGTGGCAGCAGGGGAAC |
| | | GTCTTCTCATGCTCCGTGATGCATGAGGCTCTGCACAACCACT |
| | | ACACGCAGAAGAGCCTCTCCCTGTCTCCGGGTAAATGATAA |
| BLV1H12-coil-<br>IFNB HC | 52 | CAGGTCCAGCTGAGAGAGAGCGGCCCTTCACTGGTCAAGCCAT |
| | | CCCAGACACTGAGCCTGACATGCACAGCAAGCGGGTTTTCACT |
| | | GAGCGACAAGGCAGTGGGATGGGTCCGACAGGCACCAGGAAA |
| | | AGCCCTGGAATGGCTGGGCAGCATCGATACCGGCGGGAACAC |
| | | AGGGTACAATCCCGGACTGAAGAGCAGACTGTCCATTACCAA |

TABLE 3-continued

Coiled Coil Immunoglobulin Fusion Proteins-Nucleotide Sequence

| NAME | SEQ ID NO | SEQUENCE |
|------|-----------|----------|
| | | GGACAACTCTAAAAGTCAGGTGTCACTGAGCGTGAGCTCCGTC |
| | | ACCACAGAGGATAGTGCAACTTACTATTGC*GGCGGAAGCGGAG* |
| | | *CAAAGCTCGCCGCACTGAAAGCCAAGCTGGCCGCTCTGAAGGGG* |
| | | *GGTGGCGGAAGC*ATGAGCTACAACTTGCTTGGATTCCTACAAAGAA |
| | | GCAGCAATTTTCAGTGTCAGAAGCTCCTGTGGCAATTGAATGGGAG |
| | | GCTTGAATACTGCCTCAAGGACAGGATGAACTTTGACATCCCTGAG |
| | | GAGATTAAGCAGCTGCAGCAGTTCCAGAAGGAGGACGCCGCATTG |
| | | ACCATCTATGAGATGCTCCAGAACATCTTTGCTATTTTCAGACAAGA |
| | | TTCATCTAGCACTGGCTGGAATGAGACTATTGTTGAGAACCTCCTG |
| | | GCTAATGTCTATCATCAGATAAACCATCTGAAGACAGTCCTGGAAG |
| | | AAAAAACTGGAGAAAGAAGATTTCACCAGGGGAAAACTCATGAGCAG |
| | | TCTGCACCTGAAAAGATATTATGGGAGGATTCTGCATTACCTGAAG |
| | | GCCAAGGAGTACAGTCACTGTGCCTGGACCATAGTCAGAGTGGAA |
| | | ATCCTAAGGAACTTTTACTTCATTAACAGACTTACAGGTTACCTCCG |
| | | AAAC*GGCGGAGGTGGGAGTGAA*CTGGCCGCACTGGAAGCTGAGC |
| | | *TGGCTGCCCTCGAAGCTGGAGGCTCTGGA*CATGTGGATGTCTGG |
| | | GGACAGGGCCTGCTGGTGACAGTCTCTAGTGCTTCCACAACTG |
| | | CACCAAAGGTGTACCCCCTGTCAAGCTGCTGTGGGGACAAATC |
| | | CTCTAGTACCGTGACACTGGGATGCCTGGTCTCAAGCTATATG |
| | | CCCGAGCCTGTGACTGTCACCTGGAACTCAGGAGCCCTGAAAA |
| | | GCGGAGTGCACACCTTCCCAGCTGTGCTGCAGTCCTCTGGCCT |
| | | GTATAGCCTGAGTTCAATGGTGACAGTCCCCGGCAGTACTTCA |
| | | GGGCAGACCTTCACCTGTAATGTGGCCCATCCTGCCAGCTCCA |
| | | CCAAAGTGGACAAAGCAGTGGAACCCAAATCTTGCGACAAAA |
| | | CTCACACATGCCCACCGTGCCCAGCACCTGAACTCCTGGGGGG |
| | | ACCGTCAGTCTTCCTCTTCCCCCCAAAACCCAAGGACACCCTC |
| | | ATGATCTCCCGGACCCCTGAGGTCACATGCGTGGTGGTGGACG |
| | | TGAGCCACGAAGACCCTGAGGTCAAGTTCAACTGGTACGTGG |
| | | ACGGCGTGGAGGTGCATAATGCCAAGACAAAGCCGCGGGAGG |
| | | AGCAGTACAACAGCACGTACCGTGTGGTCAGCGTCCTCACCGT |
| | | CCTGCACCAGGACTGGCTGAATGGCAAGGAGTACAAGTGCAA |
| | | GGTCTCCAACAAAGCCCTCCCAGCCCCCATCGAGAAAACCATC |
| | | TCCAAAGCCAAAGGGCAGCCCCGAGAACCACAGGTGTACACC |
| | | CTGCCCCCATCCCGGGATGAGCTGACCAAGAACCAGGTCAGCC |
| | | TGACCTGCCTGGTCAAAGGCTTCTATCCCAGCGACATCGCCGT |
| | | GGAGTGGGAGAGCAATGGGCAGCCGGAGAACAACTACAAGAC |
| | | CACGCCTCCCGTGCTGGACTCCGACGGCTCCTTCTTCCTCTACA |
| | | GCAAGCTCACCGTGGACAAGAGCAGGTGGCAGCAGGGGAACG |
| | | TCTTCTCATGCTCCGTGATGCATGAGGCTCTGCACAACCACTA |
| | | CACGCAGAAGAGCCTCTCCCTGTCTCCGGGTAAA |
| trastuzumab-coil GLP1 HC | 53 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |

TABLE 3-continued

Coiled Coil Immunoglobulin Fusion Proteins-Nucleotide Sequence

| NAME | SEQ ID NO | SEQUENCE |
|---|---|---|
| | | CAGACACTTCCAAGAACACGGCGTATCTTCAAATGAACAGCCT |
| | | GAGAGCCGAGGACACGGCCGTGTATTACTGTTCGAGAGGCGG |
| | | AAGCGGAGCAAAGCTCGCCGCACTGAAAGCCAAGCTGGCCGCTCT |
| | | GAAGTGCGGGGGTGGCGGAAGCATCGAAGGTCGTCACGCTGAGG |
| | | GAACATTCACTTCCGATGTGTCCTCCTACCTGGAGGGCCAGGCTG |
| | | CCAAAGAGTTCATCGCTTGGCTCGTCAAGGGCAGGGGCGGAGGT |
| | | GGGAGTTGCGAACTGGCCGCACTGGAAGCTGAGCTGGCTGCCCT |
| | | CGAAGCTGGAGGCTCTGGAGACTACTGGGGCCAAGGAACCCTG |
| | | GTCACCGTCTCCTCAGCCTCCACCAAGGGCCCATCGGTCTTCC |
| | | CCCTGGCACCCTCCTCCAAGAGCACCTCTGGGGGCACAGCGGC |
| | | CCTGGGCTGCCTGGTCAAGGACTACTTCCCCGAACCGGTGACG |
| | | GTGTCGTGGAACTCAGGCGCCCTGACCAGCGGCGTGCACACCT |
| | | TCCCGGCTGTCCTACAGTCCTCAGGACTCTACTCCCTCAGCAG |
| | | CGTGGTGACTGTGCCCTCTAGCAGCTTGGGCACCCAGACCTAC |
| | | ATCTGCAACGTGAATCACAAGCCCAGCAACACCAAGGTGGAC |
| | | AAGAAAGTTGAACCCAAATCTTGCGACAAAACTCACACATGC |
| | | CCACCGTGCCCAGCACCTCCAGTCGCCGGACCGTCAGTCTTCC |
| | | TCTTCCCTCCAAAACCCAAGGACACCCTCATGATCTCCCGGAC |
| | | CCCTGAGGTCACATGCGTGGTGGTGGACGTGAGCCACGAAGA |
| | | CCCTGAGGTCAAGTTCAACTGGTACGTGGACGGCGTGGAGGTG |
| | | CATAATGCCAAGACAAAGCCGCGGGAGGAGCAGTACAACAGC |
| | | ACGTACCGTGTGGTCAGCGTCCTCACCGTCCTGCACCAGGACT |
| | | GGCTGAATGGCAAGGAGTACAAGTGCAAGGTCTCCAACAAAG |
| | | GCCTCCCAAGCTCCATCGAGAAAACCATCTCCAAAGCCAAAG |
| | | GGCAGCCCCGAGAACCACAGGTGTACACCCTGCCTCCATCCCG |
| | | GGATGAGCTGACCAAGAACCAGGTCAGCCTGACCTGCCTGGTC |
| | | AAAGGCTTCTATCCCAGCGACATCGCCGTGGAGTGGGAGAGC |
| | | AATGGGCAGCCGGAGAACAACTACAAGACCACGCCTCCCGTG |
| | | CTGGACTCCGACGGCTCCTTCTTCCTCTACAGCAAGCTCACCGT |
| | | GGACAAGAGCAGGTGGCAGCAGGGGAACGTCTTCTCATGCTC |
| | | CGTGATGCATGAGGCTCTGCACAACCACTACACGCAGAAGAG |
| | | CCTCTCCCTGTCTCCGGGTAAA |
| trastuzumab-coil elafin HC | 54 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGCGG |
| | | AAGCGGAGCAAAGCTCGCCGCACTGAAAGCCAAGCTGGCCGCTCT |
| | | GAAGGGGGGTGGCGGAAGCGCGCAAGAGCCAGTCAAAGGTCCAG |

TABLE 3-continued

Coiled Coil Immunoglobulin Fusion Proteins-Nucleotide Sequence

| NAME | SEQ ID NO | SEQUENCE |
|---|---|---|
| | | *TCTCCACTAAGCCTGGCTCCTGCCCCATTATCTTGATCCGGTGCGC* |
| | | *CATGTTGAATCCCCCTAACCGCTGCTTGAAAGATACTGACTGCCCA* |
| | | *GGAATCAAGAAGTGCTGTGAAGGCTCTTGCGGGATGGCCTGTTTC* |
| | | *GTTCCCCAGG*GCGGAGGTGGGAGTGAACTGGCCGCACTGGAAGC |
| | | TGAGCTGGCTGCCCTCGAAGCTGGAGGCTCTGGAGACTACTGGG |
| | | GCCAAGGAACCCTGGTCACCGTCTCCTCAGCCTCCACCAAGGG |
| | | CCCATCGGTCTTCCCCCTGGCACCCTCCTCCAAGAGCACCTCTG |
| | | GGGGCACAGCGGCCCTGGGCTGCCTGGTCAAGGACTACTTCCC |
| | | CGAACCGGTGACGGTGTCGTGGAACTCAGGCGCCCTGACCAG |
| | | CGGCGTGCACACCTTCCCGGCTGTCCTACAGTCCTCAGGACTC |
| | | TACTCCCTCAGCAGCGTGGTGACTGTGCCCTCTAGCAGCTTGG |
| | | GCACCCAGACCTACATCTGCAACGTGAATCACAAGCCCAGCA |
| | | ACACCAAGGTGGACAAGAAAGTTGAACCCAAATCTTGCGACA |
| | | AAACTCACACATGCCCACCGTGCCCAGCACCTCCAGTCGCCGG |
| | | ACCGTCAGTCTTCCTCTTCCCTCCAAAACCCAAGGACACCCTC |
| | | ATGATCTCCCGGACCCCTGAGGTCACATGCGTGGTGGTGGACG |
| | | TGAGCCACGAAGACCCTGAGGTCAAGTTCAACTGGTACGTGG |
| | | ACGGCGTGGAGGTGCATAATGCCAAGACAAAGCCGCGGGAGG |
| | | AGCAGTACAACAGCACGTACCGTGTGGTCAGCGTCCTCACCGT |
| | | CCTGCACCAGGACTGGCTGAATGGCAAGGAGTACAAGTGCAA |
| | | GGTCTCCAACAAAGGCCTCCCAAGCTCCATCGAGAAAACCATC |
| | | TCCAAAGCCAAAGGGCAGCCCCGAGAACCACAGGTGTACACC |
| | | CTGCCTCCATCCCGGGATGAGCTGACCAAGAACCAGGTCAGCC |
| | | TGACCTGCCTGGTCAAAGGCTTCTATCCCAGCGACATCGCCGT |
| | | GGAGTGGGAGAGCAATGGGCAGCCGGAGAACAACTACAAGAC |
| | | CACGCCTCCCGTGCTGGACTCCGACGGCTCCTTCTTCCTCTACA |
| | | GCAAGCTCACCGTGGACAAGAGCAGGTGGCAGCAGGGGAACG |
| | | TCTTCTCATGCTCCGTGATGCATGAGGCTCTGCACAACCACTA |
| | | CACGCAGAAGAGCCTCTCCCTGTCTCCGGGTAAA |
| trastuzumab-coil-relaxin2 (insulin c peptide) HC | 55 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGCGG |
| | | AAGCGGAGCAAAGCTCGCCGCACTGAAAGCCAAGCTGGCCGCTCT |
| | | GAAGGGAGGTGGCGGGAGCGACTCTTGGATGGAAGAAGTTATCAA |
| | | *ACTGTGCGGTCGTGAACTGGTTCGTGCTCAGATCGCTATCTGCGG* |
| | | *TATGTCTACCTGGTCTAAACGTGAGGCAGAGGACCTGCAGGTGGG* |
| | | *GCAGGTGGAGCTGGGCGGGGGCCCTGGTGCAGGCAGCCTGCAG* |
| | | *CCCTTGGCCCTGGAGGGGTCCCTGCAGAAGCGTCGTAAAAAACGT* |
| | | *CAGCTGTACTCTGCTCTGGCTAACAAATGCTGCCACGTTGGTTGCA* |
| | | *CCAAACGTTCTCTGGCTCGTTTCTGC*GGCGGAGGTGGGAGTGAAC |

TABLE 3-continued

Coiled Coil Immunoglobulin Fusion Proteins-Nucleotide Sequence

| NAME | SEQ ID NO | SEQUENCE |
|---|---|---|
| | | *TGGCCGCACTGGAAGCTGAGCTGGCTGCCCTCGAAGCTGGAGGC* |
| | | *TCTGGA*GACTACTGGGGCCAAGGAACCCTGGTCACCGTCTCCT |
| | | CAGCCTCCACCAAGGGCCCATCGGTCTTCCCCCTGGCACCCTC |
| | | CTCCAAGAGCACCTCTGGGGGCACAGCGGCCCTGGGCTGCCTG |
| | | GTCAAGGACTACTTCCCCGAACCGGTGACGGTGTCGTGGAACT |
| | | CAGGCGCCCTGACCAGCGGCGTGCACACCTTCCCGGCTGTCCT |
| | | ACAGTCCTCAGGACTCTACTCCCTCAGCAGCGTGGTGACTGTG |
| | | CCCTCTAGCAGCTTGGGCACCCAGACCTACATCTGCAACGTGA |
| | | ATCACAAGCCCAGCAACACCAAGGTGGACAAGAAAGTTGAAC |
| | | CCAAATCTTGCGACAAAACTCACACATGCCCACCGTGCCCAGC |
| | | ACCTCCAGTCGCCGGACCGTCAGTCTTCCTCTTCCCTCCAAAAC |
| | | CCAAGGACACCCTCATGATCTCCCGGACCCCTGAGGTCACATG |
| | | CGTGGTGGTGGACGTGAGCCACGAAGACCCTGAGGTCAAGTT |
| | | CAACTGGTACGTGGACGGCGTGGAGGTGCATAATGCCAAGAC |
| | | AAAGCCGCGGGAGGAGCAGTACAACAGCACGTACCGTGTGGT |
| | | CAGCGTCCTCACCGTCCTGCACCAGGACTGGCTGAATGGCAAG |
| | | GAGTACAAGTGCAAGGTCTCCAACAAAGGCCTCCCAAGCTCC |
| | | ATCGAGAAAACCATCTCCAAAGCCAAAGGGCAGCCCCGAGAA |
| | | CCACAGGTGTACACCCTGCCTCCATCCCGGGATGAGCTGACCA |
| | | AGAACCAGGTCAGCCTGACCTGCCTGGTCAAAGGCTTCTATCC |
| | | CAGCGACATCGCCGTGGAGTGGGAGAGCAATGGGCAGCCGGA |
| | | GAACAACTACAAGACCACGCCTCCCGTGCTGGACTCCGACGGC |
| | | TCCTTCTTCCTCTACAGCAAGCTCACCGTGGACAAGAGCAGGT |
| | | GGCAGCAGGGGAACGTCTTCTCATGCTCCGTGATGCATGAGGC |
| | | TCTGCACAACCACTACACGCAGAAGAGCCTCTCCCTGTCTCCG |
| | | GGTAAATGATAA |
| trastuzumab-coil mambalgin HC | 56 | GAAGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTC*GGGCGGAAGC* |
| | | *GGAGCAAAGCTCGCCGCACTGAAAGCCAAGCTGGCCGCTCTGAAG* |
| | | *GGGGGTGGCGGAAGCCTGAAATGTTACCAACATGGTAAAGTTGTG* |
| | | *ACTTGTCATCGAGATATGAAGTTTTGCTATCATAACACTGGCATGCC* |
| | | *TTTTCGAAATCTCAAGCTCATCCTACAGGGATGTTCTTCTTCGTGCA* |
| | | *GTGAAACAGAAAACAATAAGTGTTGCTCAACAGACAGATGCAACAA* |
| | | *AGGCGGAGGTGGGAGT*GAACTGGCCGCACTGGAAGCTGAGCTGG |
| | | CTGCCCTCGAAGCTGGAGGCTCTGGATGGGGCCAAGGAACCCTG |
| | | GTCACCGTCTCCTCAGCCTCCACCAAGGGCCCATCGGTCTTCC |
| | | CCCTGGCACCCTCCTCCAAGAGCACCTCTGGGGGCACAGCGGC |

TABLE 3-continued

Coiled Coil Immunoglobulin Fusion Proteins-Nucleotide Sequence

| NAME | SEQ ID NO | SEQUENCE |
|---|---|---|
| | | CCTGGGCTGCCTGGTCAAGGACTACTTCCCCGAACCGGTGACG<br>GTGTCGTGGAACTCAGGCGCCCTGACCAGCGGCGTGCACACCT<br>TCCCGGCTGTCCTACAGTCCTCAGGACTCTACTCCCTCAGCAG<br>CGTGGTGACTGTGCCCTCTAGCAGCTTGGGCACCCAGACCTAC<br>ATCTGCAACGTGAATCACAAGCCCAGCAACACCAAGGTGGAC<br>AAGAAAGTTGAACCCAAATCTTGCGACAAAACTCACACATGC<br>CCACCGTGCCCAGCACCTCCAGTCGCCGGACCGTCAGTCTTCC<br>TCTTCCCTCCAAAACCCAAGGACACCCTCATGATCTCCCGGAC<br>CCCTGAGGTCACATGCGTGGTGGTGGACGTGAGCCACGAAGA<br>CCCTGAGGTCAAGTTCAACTGGTACGTGGACGGCGTGGAGGTG<br>CATAATGCCAAGACAAAGCCGCGGGAGGAGCAGTACAACAGC<br>ACGTACCGTGTGGTCAGCGTCCTCACCGTCCTGCACCAGGACT<br>GGCTGAATGGCAAGGAGTACAAGTGCAAGGTCTCCAACAAAG<br>GCCTCCCAAGCTCCATCGAGAAAACCATCTCCAAAGCCAAAG<br>GGCAGCCCCGAGAACCACAGGTGTACACCCTGCCTCCATCCCG<br>GGATGAGCTGACCAAGAACCAGGTCAGCCTGACCTGCCTGGTC<br>AAAGGCTTCTATCCCAGCGACATCGCCGTGGAGTGGGAGAGC<br>AATGGGCAGCCGGAGAACAACTACAAGACCACGCCTCCCGTG<br>CTGGACTCCGACGGCTCCTTCTTCCTCTACAGCAAGCTCACCGT<br>GGACAAGAGCAGGTGGCAGCAGGGGAACGTCTTCTCATGCTC<br>CGTGATGCATGAGGCTCTGCACAACCACTACACGCAGAAGAG<br>CCTCTCCCTGTCTCCGGGTAAATGATAA |
| palivizumab-coil<br>mambalgin HC | 57 | CAGGTGACCCTGCGCGAGTCCGGCCCTGCACTGGTGAAGCCCA<br>CCCAGACCCTGACCCTGACCTGCACCTTCTCCGGCTTCTCCCTG<br>TCCACCTCCGGCATGTCCGTGGGCTGGATCCGGCAGCCTCCCG<br>GCAAGGCCCTGGAGTGGCTGGCTGACATCTGGTGGGACGACA<br>AGAAGGACTACAACCCCTCCCTGAAGTCCCGCCTGACCATCTC<br>CAAGGACACCTCCAAGAACCAGGTGGTGCTGAAGGTGACCAA<br>CATGGACCCCGCCGACACCGCCACCTACTACTGCGCCCGCTCT<br>*TCTGAAACTAAGAAAGGGGGTGGCGGAAGCCTGAAATGTTACCAA*<br>*CATGGTAAAGTTGTGACTTGTCATCGAGATATGAAGTTTTGCTATCA*<br>*TAACACTGGCATGCCTTTTCGAAATCTCAAGCTCATCCTACAGGGA*<br>*TGTTCTTCTTCGTGCAGTGAAACAGAAAACAATAAGTGTTGCTCAAC*<br>*AGACAGATGCAACAAAGGCGGAGGTGGGAGTTACAATTATGAA*TA<br>CTTTGACGTGTGGGGAGCCGGTACCACCGTGACCGTGTCTTCC<br>GCCTCCACCAAGGGCCCATCGGTCTTCCCCCTGGCACCCTCCT<br>CCAAGAGCACCTCTGGGGGCACAGCGGCCCTGGGCTGCCTGGT<br>CAAGGACTACTTCCCCGAACCGGTGACGGTGTCGTGGAACTCA<br>GGCGCCCTGACCAGCGGCGTGCACACCTTCCCGGCTGTCCTAC<br>AGTCCTCAGGACTCTACTCCCTCAGCAGCGTGGTGACTGTGCC<br>CTCTAGCAGCTTGGGCACCCAGACCTACATCTGCAACGTGAAT<br>CACAAGCCCAGCAACACCAAGGTGGACAAGAAAGTTGAACCC |

TABLE 3-continued

Coiled Coil Immunoglobulin Fusion Proteins-Nucleotide Sequence

| NAME | SEQ ID NO | SEQUENCE |
|---|---|---|
| | | AAATCTTGCGACAAAACTCACACATGCCCACCGTGCCCAGCAC |
| | | CTCCAGTCGCCGGACCGTCAGTCTTCCTCTTCCCTCCAAAACCC |
| | | AAGGACACCCTCATGATCTCCCGGACCCCTGAGGTCACATGCG |
| | | TGGTGGTGGACGTGAGCCACGAAGACCCTGAGGTCAAGTTCA |
| | | ACTGGTACGTGGACGGCGTGGAGGTGCATAATGCCAAGACAA |
| | | AGCCGCGGGAGGAGCAGTACAACAGCACGTACCGTGTGGTCA |
| | | GCGTCCTCACCGTCCTGCACCAGGACTGGCTGAATGGCAAGGA |
| | | GTACAAGTGCAAGGTCTCCAACAAAGGCCTCCCAAGCTCCATC |
| | | GAGAAAACCATCTCCAAAGCCAAAGGGCAGCCCCGAGAACCA |
| | | CAGGTGTACACCCTGCCTCCATCCCGGGATGAGCTGACCAAGA |
| | | ACCAGGTCAGCCTGACCTGCCTGGTCAAAGGCTTCTATCCCAG |
| | | CGACATCGCCGTGGAGTGGGAGAGCAATGGGCAGCCGGAGAA |
| | | CAACTACAAGACCACGCCTCCCGTGCTGGACTCCGACGGCTCC |
| | | TTCTTCCTCTACAGCAAGCTCACCGTGGACAAGAGCAGGTGGC |
| | | AGCAGGGGAACGTCTTCTCATGCTCCGTGATGCATGAGGCTCT |
| | | GCACAACCACTACACGCAGAAGAGCCTCTCCCTGTCTCCGGGT |
| | | AAATGATAA |
| trastuzumab-coil-relaxin2 short HC | 58 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGCGG |
| | | AAGCGGAGCAAAGCTCGCCGCACTGAAAGCCAAGCTGGCCGCTCT |
| | | GAAGGGAGGTGGCGGGAGCGACTCTTGGATGGAAGAAGTTATCAA |
| | | ACTGTGCGGTCGTGAACTGGTTCGTGCTCAGATCGCTATCTGCGG |
| | | TATGTCTACCTGGTCTAAACGTTCTCTGTCTCAGGAAATCGAGGGC |
| | | CGTAAAAAACGTCAGCTGTACTCTGCTCTGGCTAACAAATGCTGCC |
| | | ACGTTGGTTGCACCAAACGTTCTCTGGCTCGTTTCTGCGGCGGAG |
| | | GTGGGAGTGAACTGGCCGCACTGGAAGCTGAGCTGGCTGCCCTC |
| | | GAAGCTGGAGGCTCTGGAGACTACTGGGGCCAAGGAACCCTGG |
| | | TCACCGTCTCCTCAGCCTCCACCAAGGGCCCATCGGTCTTCCCC |
| | | CTGGCACCCTCCTCCAAGAGCACCTCTGGGGGCACAGCGGCCC |
| | | TGGGCTGCCTGGTCAAGGACTACTTCCCCGAACCGGTGACGGT |
| | | GTCGTGGAACTCAGGCGCCCTGACCAGCGGCGTGCACACCTTC |
| | | CCGGCTGTCCTACAGTCCTCAGGACTCTACTCCCTCAGCAGCG |
| | | TGGTGACTGTGCCCTCTAGCAGCTTGGGCACCCAGACCTACAT |
| | | CTGCAACGTGAATCACAAGCCCAGCAACACCAAGGTGGACAA |
| | | GAAAGTTGAACCCAAATCTTGCGACAAAACTCACACATGCCCA |
| | | CCGTGCCCAGCACCTCCAGTCGCCGGACCGTCAGTCTTCCTCTT |
| | | CCCTCCAAAACCCAAGGACACCCTCATGATCTCCCGGACCCCT |

TABLE 3-continued

Coiled Coil Immunoglobulin Fusion Proteins-Nucleotide Sequence

| NAME | SEQ ID NO | SEQUENCE |
|------|-----------|----------|
| | | GAGGTCACATGCGTGGTGGTGGACGTGAGCCACGAAGACCCT |
| | | GAGGTCAAGTTCAACTGGTACGTGGACGGCGTGGAGGTGCAT |
| | | AATGCCAAGACAAAGCCGCGGGAGGAGCAGTACAACAGCACG |
| | | TACCGTGTGGTCAGCGTCCTCACCGTCCTGCACCAGGACTGGC |
| | | TGAATGGCAAGGAGTACAAGTGCAAGGTCTCCAACAAAGGCC |
| | | TCCCAAGCTCCATCGAGAAAACCATCTCCAAAGCCAAAGGGC |
| | | AGCCCCGAGAACCACAGGTGTACACCCTGCCTCCATCCCGGGA |
| | | TGAGCTGACCAAGAACCAGGTCAGCCTGACCTGCCTGGTCAAA |
| | | GGCTTCTATCCCAGCGACATCGCCGTGGAGTGGGAGAGCAATG |
| | | GGCAGCCGGAGAACAACTACAAGACCACGCCTCCCGTGCTGG |
| | | ACTCCGACGGCTCCTTCTTCCTCTACAGCAAGCTCACCGTGGA |
| | | CAAGAGCAGGTGGCAGCAGGGGAACGTCTTCTCATGCTCCGTG |
| | | ATGCATGAGGCTCTGCACAACCACTACACGCAGAAGAGCCTCT |
| | | CCCTGTCTCCGGGTAAAT |
| trastuzumab-coil-relaxin2 long HC | 59 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGA<u>GGCGG</u> |
| | | <u>AAGCGGAGCAAAGCTCGCCGCACTGAAAGCCAAGCTGGCCGCTCT</u> |
| | | <u>GAAGGGAGGTGGCGGGAGC</u>GACTCTTGGATGGAAGAAGTTATCAA |
| | | *ACTGTGCGGTCGTGAACTGGTTCGTGCTCAGATCGCTATCTGCGG* |
| | | *TATGTCTACCTGGTCTAAACGTTCTCTGTCTCAGGAAGACGCTCCG* |
| | | *CAGACCCCGCGTCCGGTT*<u>ATCGAGGGCCGTAAAAAAACGTCAGCTG</u> |
| | | *TACTCTGCTCTGGCTAACAAATGCTGCCACGTTGGTTGCACCAAAC* |
| | | *GTTCTCTGGCTCGTTTCTGC*<u>GGCGGAGGTGGGAGT</u><u>GAACTGGCCG</u> |
| | | <u>CACTGGAAGCTGAGCTGGCTGCCCTCGAAGCTGGAGGCTCTGGA</u> |
| | | GACTACTGGGGCCAAGGAACCCTGGTCACCGTCTCCTCAGCCT |
| | | CCACCAAGGGCCCATCGGTCTTCCCCCTGGCACCCTCCTCCAA |
| | | GAGCACCTCTGGGGGCACAGCGGCCCTGGGCTGCCTGGTCAA |
| | | GGACTACTTCCCCGAACCGGTGACGGTGTCGTGGAACTCAGGC |
| | | GCCCTGACCAGCGGCGTGCACACCTTCCCGGCTGTCCTACAGT |
| | | CCTCAGGACTCTACTCCCTCAGCAGCGTGGTGACTGTGCCCTC |
| | | TAGCAGCTTGGGCACCCAGACCTACATCTGCAACGTGAATCAC |
| | | AAGCCCAGCAACACCAAGGTGGACAAGAAAGTTGAACCCAAA |
| | | TCTTGCGACAAAACTCACACATGCCCACCGTGCCCAGCACCTC |
| | | CAGTCGCCGGACCGTCAGTCTTCCTCTTCCCTCCAAAACCCAA |
| | | GGACACCCTCATGATCTCCCGGACCCCTGAGGTCACATGCGTG |
| | | GTGGTGGACGTGAGCCACGAAGACCCTGAGGTCAAGTTCAAC |
| | | TGGTACGTGGACGGCGTGGAGGTGCATAATGCCAAGACAAAG |

TABLE 3-continued

Coiled Coil Immunoglobulin Fusion Proteins-Nucleotide Sequence

| NAME | SEQ ID NO | SEQUENCE |
|---|---|---|
| | | CCGCGGGAGGAGCAGTACAACAGCACGTACCGTGTGGTCAGC |
| | | GTCCTCACCGTCCTGCACCAGGACTGGCTGAATGGCAAGGAGT |
| | | ACAAGTGCAAGGTCTCCAACAAAGGCCTCCCAAGCTCCATCGA |
| | | GAAAACCATCTCCAAAGCCAAAGGGCAGCCCCGAGAACCACA |
| | | GGTGTACACCCTGCCTCCATCCCGGGATGAGCTGACCAAGAAC |
| | | CAGGTCAGCCTGACCTGCCTGGTCAAAGGCTTCTATCCCAGCG |
| | | ACATCGCCGTGGAGTGGGAGAGCAATGGGCAGCCGGAGAACA |
| | | ACTACAAGACCACGCCTCCCGTGCTGGACTCCGACGGCTCCTT |
| | | CTTCCTCTACAGCAAGCTCACCGTGGACAAGAGCAGGTGGCAG |
| | | CAGGGGAACGTCTTCTCATGCTCCGTGATGCATGAGGCTCTGC |
| | | ACAACCACTACACGCAGAAGAGCCTCTCCCTGTCTCCGGGTAAA |
| trastuzumab-coil ZP fusion HC (CDRH3) | 60 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGCGG |
| | | AAGCGGAGCAAAGCTCGCCGCACTGAAAGCCAAGCTGGCCGCTCT |
| | | GAAGTGCGGGGGTGGCGGAAGCATCGAAGGTCGTCACAGCCAGG |
| | | GCACATTCACTAGCGATTATAGTAAATATCTGGATTCCAAGGCAGC |
| | | GCACGATTTTGTAGAGTGGCTCTTGAACGGAGGCCCTTCCTCCGG |
| | | AGCTCCACCTCCGTCCGGCGGAGGTGGGAGTTGCGAACTGGCCG |
| | | CACTGGAAGCTGAGCTGGCTGCCCTCGAAGCTGGAGGCTCTGGA |
| | | GACTACTGGGGCCAAGGAACCCTGGTCACCGTCTCCTCAGCCT |
| | | CCACCAAGGGCCCATCGGTCTTCCCCCTGGCACCCTCCTCCAA |
| | | GAGCACCTCTGGGGGCACAGCGGCCCTGGGCTGCCTGGTCAA |
| | | GGACTACTTCCCCGAACCGGTGACGGTGTCGTGGAACTCAGGC |
| | | GCCCTGACCAGCGGCGTGCACACCTTCCCGGCTGTCCTACAGT |
| | | CCTCAGGACTCTACTCCCTCAGCAGCGTGGTGACTGTGCCCTC |
| | | TAGCAGCTTGGGCACCCAGACCTACATCTGCAACGTGAATCAC |
| | | AAGCCCAGCAACACCAAGGTGGACAAGAAAGTTGAACCCAAA |
| | | TCTTGCGACAAAACTCACACATGCCCACCGTGCCCAGCACCTC |
| | | CAGTCGCCGGACCGTCAGTCTTCCTCTTCCCTCCAAAACCCAA |
| | | GGACACCCTCATGATCTCCCGGACCCCTGAGGTCACATGCGTG |
| | | GTGGTGGACGTGAGCCACGAAGACCCTGAGGTCAAGTTCAAC |
| | | TGGTACGTGGACGGCGTGGAGGTGCATAATGCCAAGACAAAG |
| | | CCGCGGGAGGAGCAGTACAACAGCACGTACCGTGTGGTCAGC |
| | | GTCCTCACCGTCCTGCACCAGGACTGGCTGAATGGCAAGGAGT |
| | | ACAAGTGCAAGGTCTCCAACAAAGGCCTCCCAAGCTCCATCGA |
| | | GAAAACCATCTCCAAAGCCAAAGGGCAGCCCCGAGAACCACA |

TABLE 3-continued

Coiled Coil Immunoglobulin Fusion Proteins-Nucleotide Sequence

| NAME | SEQ ID NO | SEQUENCE |
|---|---|---|
| | | GGTGTACACCCTGCCTCCATCCCGGGATGAGCTGACCAAGAAC |
| | | CAGGTCAGCCTGACCTGCCTGGTCAAAGGCTTCTATCCCAGCG |
| | | ACATCGCCGTGGAGTGGGAGAGCAATGGGCAGCCGGAGAACA |
| | | ACTACAAGACCACGCCTCCCGTGCTGGACTCCGACGGCTCCTT |
| | | CTTCCTCTACAGCAAGCTCACCGTGGACAAGAGCAGGTGGCAG |
| | | CAGGGGAACGTCTTCTCATGCTCCGTGATGCATGAGGCTCTGC |
| | | ACAACCACTACACGCAGAAGAGCCTCTCCCTGTCTCCGGGTAAA |
| trastuzumab-coil ZP mutant (S-G) fusion HC | 61 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGCGG |
| | | AAGCGGAGCAAAGCTCGCCGCACTGAAAGCCAAGCTGGCCGCTCT |
| | | GAAGTGCGGGGGTGGCGGAAGCATCGAAGGTCGTCACGGCCAG |
| | | GGCACATTCACTAGCGATTATAGTAAATATCTGGATTCCAAGG |
| | | CAGCGCACGATTTTGTAGAGTGGCTCTTGAACGGAGGCCCTTC |
| | | CTCCGGAGCTCCACCTCCGTCCGGCGGAGGTGGGAGTTGCGAAC |
| | | TGGCCGCACTGGAAGCTGAGCTGGCTGCCCTCGAAGCTGGAGGC |
| | | TCTGGAGACTACTGGGGCCAAGGAACCCTGGTCACCGTCTCCT |
| | | CAGCCTCCACCAAGGGCCCATCGGTCTTCCCCCTGGCACCCTC |
| | | CTCCAAGAGCACCTCTGGGGGCACAGCGGCCCTGGGCTGCCTG |
| | | GTCAAGGACTACTTCCCCGAACCGGTGACGGTGTCGTGGAACT |
| | | CAGGCGCCCTGACCAGCGGCGTGCACACCTTCCCGGCTGTCCT |
| | | ACAGTCCTCAGGACTCTACTCCCTCAGCAGCGTGGTGACTGTG |
| | | CCCTCTAGCAGCTTGGGCACCCAGACCTACATCTGCAACGTGA |
| | | ATCACAAGCCCAGCAACACCAAGGTGGACAAGAAAGTTGAAC |
| | | CCAAATCTTGCGACAAAACTCACACATGCCCACCGTGCCCAGC |
| | | ACCTCCAGTCGCCGGACCGTCAGTCTTCCTCTTCCCTCCAAAAC |
| | | CCAAGGACACCCTCATGATCTCCCGGACCCCTGAGGTCACATG |
| | | CGTGGTGGTGGACGTGAGCCACGAAGACCCTGAGGTCAAGTT |
| | | CAACTGGTACGTGGACGGCGTGGAGGTGCATAATGCCAAGAC |
| | | AAAGCCGCGGGAGGAGCAGTACAACAGCACGTACCGTGTGGT |
| | | CAGCGTCCTCACCGTCCTGCACCAGGACTGGCTGAATGGCAAG |
| | | GAGTACAAGTGCAAGGTCTCCAACAAAGGCCTCCCAAGCTCC |
| | | ATCGAGAAAACCATCTCCAAAGCCAAAGGGCAGCCCCGAGAA |
| | | CCACAGGTGTACACCCTGCCTCCATCCCGGGATGAGCTGACCA |
| | | AGAACCAGGTCAGCCTGACCTGCCTGGTCAAAGGCTTCTATCC |
| | | CAGCGACATCGCCGTGGAGTGGGAGAGCAATGGGCAGCCGGA |
| | | GAACAACTACAAGACCACGCCTCCCGTGCTGGACTCCGACGGC |

TABLE 3-continued

Coiled Coil Immunoglobulin Fusion Proteins-Nucleotide Sequence

| NAME | SEQ ID NO | SEQUENCE |
|---|---|---|
| | | TCCTTCTTCCTCTACAGCAAGCTCACCGTGGACAAGAGCAGGT |
| | | GGCAGCAGGGGAACGTCTTCTCATGCTCCGTGATGCATGAGGC |
| | | TCTGCACAACCACTACACGCAGAAGAGCCTCTCCCTGTCTCCG |
| | | GGTAAA |
| trastuzumab-coil hEPO HC (CDRH3) | 62 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGCGG |
| | | AAGCGGAGCAAAGCTCGCCGCACTGAAAGCCAAGCTGGCCGCTCT |
| | | GAAGGGGGTGGCGGAAGCGCCCCACCACGCCTCATCTGTGACA |
| | | GCCGAGTCCTGGAGAGGTACCTCTTGGAGGCCAAGGAGGCCGAG |
| | | AATATCACGACGGGCTGTGCTGAACACTGCAGCTTGAATGAGAATA |
| | | TCACTGTCCCAGACACCAAAGTTAATTTCTATGCCTGGAAGAGGAT |
| | | GGAGGTCGGGCAGCAGGCCGTAGAAGTCTGGCAGGGCCTGGCCC |
| | | TGCTGTCGGAAGCTGTCCTGCGGGGCCAGGCCCTGTTGGTCAACT |
| | | CTTCCCAGCCGTGGGAGCCCCTGCAGCTGCATGTGGATAAAGCCG |
| | | TCAGTGGCCTTCGCAGCCTCACCACTCTGCTTCGGGCTCTGGGAG |
| | | CCCAGAAGGAAGCCATCTCCCCTCCAGATGCGGCCTCAGCTGCTC |
| | | CACTCCGAACAATCACTGCTGACACTTTCCGCAAACTCTTCCGAGT |
| | | CTACTCCAATTTCCTCCGGGGAAAGCTGAAGCTGTACACAGGGGA |
| | | GGCCTGCAGGACAGGGGACAGAGGCGGAGGTGGGAGTGAACTG |
| | | GCCGCACTGGAAGCTGAGCTGGCTGCCCTCGAAGCTGGAGGCTC |
| | | TGGAGACTACTGGGGCCAAGGAACCCTGGTCACCGTCTCCTCA |
| | | GCCAGCACTAAAGGTCCATCTGTGTTCCCTCTGGCTCCTTGCA |
| | | GCCGGAGCACCTCCGAGTCCACAGCCGCTCTGGGATGTCTGGT |
| | | GAAAGATTACTTCCCCGAGCCCGTCACCGTGAGCTGGAATAGC |
| | | GGAGCACTGACCTCCGGCGTCCACACATTCCCCGCCGTGCTCC |
| | | AAAGCTCCGGCCTGTACAGCCTCTCCTCCGTGGTCACCGTGCC |
| | | CAGCAGCTCTCTGGGCACAAAGACCTATACCTGTAACGTGGAT |
| | | CACAAGCCTAGCAACACCAAAGTGGATAAGCGGGTGGAGAGC |
| | | AAGTACGGCCCTCCCTGTCCCCCTTGCCCCGCTCCTGAGGCCG |
| | | CTGGCGGACCTTCCGTGTTCCTGTTTCCCCCTAAGCCCAAGGA |
| | | CACCCTCATGATTAGCCGGACACCCGAAGTGACCTGCGTGGTC |
| | | GTGGATGTGTCCCAGGAGGACCCTGAAGTGCAATTTAACTGGT |
| | | ACGTGGACGGCGTCGAGGTGCACAACGCCAAGACCAAGCCTC |
| | | GGGAAGAGCAGTTCAACAGCACCTACCGGGTGGTCAGCGTGC |
| | | TGACAGTGCTGCACCAGGACTGGCTGAACGGCAAGGAGTACA |
| | | AGTGCAAGGTGAGCAACAAGGGCCTGCCCAGCTCCATCGAGA |
| | | AGACCATCAGCAAGGCCAAGGGCCAGCCCAGGGAACCCCAGG |
| | | TGTATACCCTGCCCCCTAGCCAGGAGGAAATGACCAAAAACC |
| | | AGGTGAGCCTGACCTGCCTGGTGAAGGGCTTCTACCCCAGCGA |
| | | CATCGCCGTGGAGTGGGAGAGCAACGGCCAGCCCGAGAACAA |

TABLE 3-continued

Coiled Coil Immunoglobulin Fusion Proteins-Nucleotide Sequence

| NAME | SEQ ID NO | SEQUENCE |
|---|---|---|
| | | TTACAAGACCACCCCTCCTGTGCTGGACAGCGACGGCTCCTTC |
| | | TTTCTGTATAGCCGGCTGACCGTGGACAAGAGCAGGTGGCAGG |
| | | AGGGCAACGTGTTCTCCTGTAGCGTGATGCACGAGGCCCTGCA |
| | | CAACCATTACACCCAGAAGAGCTTGAGCCTGAGCCTGGGCAAA |
| trastuzumab-coil hGCSF (CDRL3) LC | 63 | GACATCCAGATGACCCAGTCTCCATCCTCCCTGTCTGCATCTGT |
| | | AGGAGACAGAGTCACCATCACTTGCCGGGCAAGTCAGGATGT |
| | | GAATACCGCGGTCGCATGGTATCAGCAGAAACCAGGGAAAGC |
| | | CCCTAAGCTCCTGATCTATTCTGCATCCTTCTTGTATAGTGGGG |
| | | TCCCATCAAGGTTCAGTGGCAGTAGATCTGGGACAGATTTCAC |
| | | TCTCACCATCAGCAGTCTGCAACCTGAAGATTTTGCAACTTAC |
| | | TACTGTCAACAGCATTAC*GGCGGAAGCGGAGCAAAGCTCGCCG* |
| | | *CACTGAAAGCCAAGCTGGCCGCTCTGAAGGGGGGTGGCGGAAGC* |
| | | ACACCTCTGGGCCCCGCCTCCTCCCTGCCTCAGAGCTTTCTGCTC |
| | | AAATGTCTGGAGCAGGTGCGGAAGATCCAGGGCGACGGCGCCGC |
| | | TCTGCAAGAGAAACTGTGCGCCACATATAAGCTGTGTCACCCCGAG |
| | | GAACTGGTCCTCTTGGGCCACAGCCTGGGCATCCCCTGGGCCCCT |
| | | CTCAGCTCCTGCCCCTCCCAAGCTCTCCAACTGGCTGGATGTCTGT |
| | | CCCAACTGCACTCCGGCCTCTTCCTGTACCAGGGACTCCTCCAGG |
| | | CTCTCGAAGGGATCAGCCCCGAACTGGGCCCCACACTGGACACCT |
| | | TGCAACTCGATGTGGCCGATTTCGCCACAACCATCTGGCAGCAGAT |
| | | GGAAGAACTCGGAATGGCTCCTGCTCTCCAGCCCACACAGGGAGC |
| | | TATGCCTGCTTTCGCCTCTGCTTTCCAGCGGAGAGCTGGTGGTGT |
| | | GCTCGTCGCATCCCACCTCCAGAGCTTCTTGGAGGTGTCCTATCG |
| | | GGTGCTCCGGCATCTGGCCCAACCC*GGCGGAGGTGGGAGT*GAAC |
| | | *TGGCCGCACTGGAAGCTGAGCTGGCTGCCCTCGAAGCTGGAGGC* |
| | | *TCTGGA*CCGACGTTCGGCCAAGGTACCAAGCTTGAGATCAAAC |
| | | GAACTGTGGCTGCACCATCTGTCTTCATCTTCCCGCCATCTGAT |
| | | GAGCAGTTGAAATCTGGAACTGCCTCTGTCGTGTGCCTGCTGA |
| | | ATAACTTCTATCCCAGAGAGGCCAAAGTACAGTGGAAGGTGG |
| | | ATAACGCCCTCCAATCGGGTAACTCCCAGGAGAGTGTCACAGA |
| | | GCAGGACAGCAAGGACAGCACCTACAGCCTCAGCAGCACCCT |
| | | GACGCTGAGCAAAGCAGACTACGAGAAACACAAAGTCTACGC |
| | | CTGCGAAGTCACCCATCAGGGCCTGTCCTCGCCCGTCACAAAG |
| | | AGCTTCAACAGGGGAGAGTGT |
| trastuzumab-coil Ssam6a HC (CDRH3) | 64 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGA*GGCGG* |
| | | *AAGCGGAGCAAAGCTCGCCGCACTGAAAGCCAAGCTGGCCGCTCT* |
| | | *GAAGGGGGGTGGCGGAAGCGC*TGACAACAAATGCGAAAACTCTCT |
| | | GCGTCGTGAAATCGCTTGCGGTCAGTGCCGTGACAAAGTTAAAAC |
| | | CGACGGTTACTTCTACGAATGCTGCACCTCTGACTCTACCTTCAAA |
| | | AAATGCCAGGACCTGCTGCACGGCGGAGGTGGGAGTGAACTGGC |

TABLE 3-continued

Coiled Coil Immunoglobulin Fusion Proteins-Nucleotide Sequence

| NAME | SEQ ID NO | SEQUENCE |
|------|-----------|----------|
| | | CGCACTGGAAGCTGAGCTGGCTGCCCTCGAAGCTGGAGGCTCTG |
| | | GAGACTACTGGGGCCAAGGAACCCTGGTCACCGTCTCCTCAGC |
| | | CTCCACCAAGGGCCCATCGGTCTTCCCCCTGGCACCCTCCTCC |
| | | AAGAGCACCTCTGGGGGCACAGCGGCCCTGGGCTGCCTGGTC |
| | | AAGGACTACTTCCCCGAACCGGTGACGGTGTCGTGGAACTCAG |
| | | GCGCCCTGACCAGCGGCGTGCACACCTTCCCGGCTGTCCTACA |
| | | GTCCTCAGGACTCTACTCCCTCAGCAGCGTGGTGACTGTGCCC |
| | | TCTAGCAGCTTGGGCACCCAGACCTACATCTGCAACGTGAATC |
| | | ACAAGCCCAGCAACACCAAGGTGGACAAGAAAGTTGAACCCA |
| | | AATCTTGCGACAAAACTCACACATGCCCACCGTGCCCAGCACC |
| | | TCCAGTCGCCGGACCGTCAGTCTTCCTCTTCCCTCCAAAACCCA |
| | | AGGACACCCTCATGATCTCCCGGACCCCTGAGGTCACATGCGT |
| | | GGTGGTGGACGTGAGCCACGAAGACCCTGAGGTCAAGTTCAA |
| | | CTGGTACGTGGACGGCGTGGAGGTGCATAATGCCAAGACAAA |
| | | GCCGCGGGAGGAGCAGTACAACAGCACGTACCGTGTGGTCAG |
| | | CGTCCTCACCGTCCTGCACCAGGACTGGCTGAATGGCAAGGAG |
| | | TACAAGTGCAAGGTCTCCAACAAAGGCCTCCCAAGCTCCATCG |
| | | AGAAAACCATCTCCAAAGCCAAAGGGCAGCCCCGAGAACCAC |
| | | AGGTGTACACCCTGCCTCCATCCCGGGATGAGCTGACCAAGAA |
| | | CCAGGTCAGCCTGACCTGCCTGGTCAAAGGCTTCTATCCCAGC |
| | | GACATCGCCGTGGAGTGGGAGAGCAATGGGCAGCCGGAGAAC |
| | | AACTACAAGACCACGCCTCCCGTGCTGGACTCCGACGGCTCCT |
| | | TCTTCCTCTACAGCAAGCTCACCGTGGACAAGAGCAGGTGGCA |
| | | GCAGGGGAACGTCTTCTCATGCTCCGTGATGCATGAGGCTCTG |
| | | CACAACCACTACACGCAGAAGAGCCTCTCCCTGTCTCCGGGTA |
| | | AATGATAA |
| trastuzumab-coil GLP2 HC (CDRH3) | 65 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGCGG |
| | | AAGCGGAGCAAAGCTCGCCGCACTGAAAGCCAAGCTGGCCGCTCT |
| | | GAAGTGCGGGGGTGGCGGAAGCATCGAAGGTCGTCACGGCGACG |
| | | GTTCATTCTCTGACGAAATGAATACAATACTCGACAACCTCGCCGC |
| | | CAGGGACTTTATCAATTGGCTCATTCAAACTAAAATCACCGACGGA |
| | | GGCCCTTCCTCCGGAGCTCCACCTCCGTCCGGCCGGAGGTGGGAG |
| | | TTGCGAACTGGCCGCACTGGAAGCTGAGCTGGCTGCCCTCGAAGC |
| | | TGGAGGCTCTGGAGACTACTGGGGCCAAGGAACCCTGGTCACC |
| | | GTCTCCTCAGCCTCCACCAAGGGCCCATCGGTCTTCCCCCTGG |

TABLE 3-continued

Coiled Coil Immunoglobulin Fusion Proteins-Nucleotide Sequence

| NAME | SEQ ID NO | SEQUENCE |
|---|---|---|
| | | CACCCTCCTCCAAGAGCACCTCTGGGGGCACAGCGGCCCTGGG |
| | | CTGCCTGGTCAAGGACTACTTCCCCGAACCGGTGACGGTGTCG |
| | | TGGAACTCAGGCGCCCTGACCAGCGGCGTGCACACCTTCCCGG |
| | | CTGTCCTACAGTCCTCAGGACTCTACTCCCTCAGCAGCGTGGT |
| | | GACTGTGCCCTCTAGCAGCTTGGGCACCCAGACCTACATCTGC |
| | | AACGTGAATCACAAGCCCAGCAACACCAAGGTGGACAAGAAA |
| | | GTTGAACCCAAATCTTGCGACAAAACTCACACATGCCCACCGT |
| | | GCCCAGCACCTCCAGTCGCCGGACCGTCAGTCTTCCTCTTCCCT |
| | | CCAAAACCCAAGGACACCCTCATGATCTCCCGGACCCCTGAGG |
| | | TCACATGCGTGGTGGTGGACGTGAGCCACGAAGACCCTGAGG |
| | | TCAAGTTCAACTGGTACGTGGACGGCGTGGAGGTGCATAATGC |
| | | CAAGACAAAGCCGCGGGAGGAGCAGTACAACAGCACGTACCG |
| | | TGTGGTCAGCGTCCTCACCGTCCTGCACCAGGACTGGCTGAAT |
| | | GGCAAGGAGTACAAGTGCAAGGTCTCCAACAAAGGCCTCCCA |
| | | AGCTCCATCGAGAAAACCATCTCCAAAGCCAAAGGGCAGCCC |
| | | CGAGAACCACAGGTGTACACCCTGCCTCCATCCCGGGATGAGC |
| | | TGACCAAGAACCAGGTCAGCCTGACCTGCCTGGTCAAAGGCTT |
| | | CTATCCCAGCGACATCGCCGTGGAGTGGGAGAGCAATGGGCA |
| | | GCCGGAGAACAACTACAAGACCACGCCTCCCGTGCTGGACTCC |
| | | GACGGCTCCTTCTTCCTCTACAGCAAGCTCACCGTGGACAAGA |
| | | GCAGGTGGCAGCAGGGGAACGTCTTCTCATGCTCCGTGATGCA |
| | | TGAGGCTCTGCACAACCACTACACGCAGAAGAGCCTCTCCCTG |
| | | TCTCCGGGTAAATGATAA |
| trastuzumab-coil betatrophin HC (CDRH3) | 66 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTCGAGA<u>GGCGG</u> |
| | | <u>AAGCGGAGCAAAGCTCGCCGCACTGAAAGCCAAGCTGGCCGCTCT</u> |
| | | <u>GAAGGGAGGTGGCGGGAGC</u>GCTCCTCTGGGCGGTCCTGAACCAG |
| | | CACAGTACGAGGAACTGACACTGTTGTTCCATGGAGCCTTGCAGCT |
| | | GGGCCAGGCCCTCAACGGCGTGTACCGCGCCACAGAGGCACGTT |
| | | TGACCGAGGCCGGACACAGCCTGGGTTTGTACAGACAGAGCCCTG |
| | | GAGTTTCTGGGTACCGAAGTGCGTCAGGGCCAGGACGCAACTCAG |
| | | GAGCTGAGAACCTCCCTCTCTGAGATCCAGGTGGAGGAGGACGCC |
| | | CTGCACCTGCGCGCCGAGGCGACAGCACGCTCTTTGGGAGAAGTT |
| | | GCTCGCGCTCAGCAGGCCCTGCGTGATACCGTGCGGAGACTCCAA |
| | | GTTCAGCTCAGAGGCGCTTGGCTCGGACAGGCGCATCAGGAGTTC |
| | | GAGACCCTGAAAGCTCGTGCCGACAAACAGTCCCACCTGCTGTGG |
| | | GCGCTCACCGGTCACGTCCAGCGCCAGCAACGCGAAATGGCCGA |
| | | GCAGCAGCAATGGCTGCGCCAAATCCAGCAGCGCCTGCATACCGC |
| | | GGCCCTGCCAGCGGGCGGAGGTGGGAGTGAACTGGCCGCACTG |
| | | <u>GAAGCTGAGCTGGCTGCCCTCGAAGCTGGAGGCTCTGGAGACTA</u> |

TABLE 3-continued

Coiled Coil Immunoglobulin Fusion Proteins-Nucleotide Sequence

| NAME | SEQ ID NO | SEQUENCE |
|---|---|---|
| | | CTGGGGCCAAGGAACCCTGGTCACCGTCTCCTCAGCCTCCACC |
| | | AAGGGCCCATCGGTCTTCCCCCTGGCACCCTCCTCCAAGAGCA |
| | | CCTCTGGGGGCACAGCGGCCCTGGGCTGCCTGGTCAAGGACTA |
| | | CTTCCCCGAACCGGTGACGGTGTCGTGGAACTCAGGCGCCCTG |
| | | ACCAGCGGCGTGCACACCTTCCCGGCTGTCCTACAGTCCTCAG |
| | | GACTCTACTCCCTCAGCAGCGTGGTGACTGTGCCCTCTAGCAG |
| | | CTTGGGCACCCAGACCTACATCTGCAACGTGAATCACAAGCCC |
| | | AGCAACACCAAGGTGGACAAGAAAGTTGAACCCAAATCTTGC |
| | | GACAAAACTCACACATGCCCACCGTGCCCAGCACCTCCAGTCG |
| | | CCGGACCGTCAGTCTTCCTCTTCCCTCCAAAACCCAAGGACAC |
| | | CCTCATGATCTCCCGGACCCCTGAGGTCACATGCGTGGTGGTG |
| | | GACGTGAGCCACGAAGACCCTGAGGTCAAGTTCAACTGGTAC |
| | | GTGGACGGCGTGGAGGTGCATAATGCCAAGACAAAGCCGCGG |
| | | GAGGAGCAGTACAACAGCACGTACCGTGTGGTCAGCGTCCTC |
| | | ACCGTCCTGCACCAGGACTGGCTGAATGGCAAGGAGTACAAG |
| | | TGCAAGGTCTCCAACAAAGGCCTCCCAAGCTCCATCGAGAAA |
| | | ACCATCTCCAAAGCCAAAGGGCAGCCCCGAGAACCACAGGTG |
| | | TACACCCTGCCTCCATCCCGGGATGAGCTGACCAAGAACCAGG |
| | | TCAGCCTGACCTGCCTGGTCAAAGGCTTCTATCCCAGCGACAT |
| | | CGCCGTGGAGTGGGAGAGCAATGGGCAGCCGGAGAACAACTA |
| | | CAAGACCACGCCTCCCGTGCTGGACTCCGACGGCTCCTTCTTC |
| | | CTCTACAGCAAGCTCACCGTGGACAAGAGCAGGTGGCAGCAG |
| | | GGGAACGTCTTCTCATGCTCCGTGATGCATGAGGCTCTGCACA |
| | | ACCACTACACGCAGAAGAGCCTCTCCCTGTCTCCGGGTAAA |
| trastuzumab-coil exendin-4 LC | 67 | GACATCCAGATGACCCAGTCTCCATCCTCCCTGTCTGCATCTGT |
| | | AGGAGACAGAGTCACCATCACTTGCCGGGCAAGTCAGGATGT |
| | | GAATACCGCGGTCGCATGGTATCAGCAGAAACCAGGGAAAGC |
| | | CCCTAAGCTCCTGATCTATTCTGCATCCTTCTTGTATAGTGGGG |
| | | TCCCATCAAGGTTCAGTGGCAGTAGATCTGGGACAGATTTCAC |
| | | TCTCACCATCAGCAGTCTGCAACCTGAAGATTTTGCAACTTAC |
| | | TACTGTCAACAGGGCGGAAGCGGAGCAAAGCTCGCCGCACTGAA |
| | | AGCCAAGCTGGCCGCTCTGAAGTGCGGGGGTGGCGGAAGCATCG |
| | | AAGGTCGTCACGGAGAAGGAACATTTACCAGCGACCTCAGCAAGC |
| | | AGATGGAGGAAGAGGCCGTGAGGCTGTTCATCGAGTGGCTGAAGA |
| | | ACGGCGGACCCTCCTCTGGCGCTCCACCCCCTAGCGGCGGAGGT |
| | | GGGAGTTGCGAACTGGCCGCACTGGAAGCTGAGCTGGCTGCCCT |
| | | CGAAGCTGGAGGCTCTGGACCGACGTTCGGCCAAGGTACCAAG |
| | | CTTGAGATCAAACGAACTGTGGCTGCACCATCTGTCTTCATCTT |
| | | CCCGCCATCTGATGAGCAGTTGAAATCTGGAACTGCCTCTGTC |
| | | GTGTGCCTGCTGAATAACTTCTATCCCAGAGAGGCCAAAGTAC |
| | | AGTGGAAGGTGGATAACGCCCTCCAATCGGGTAACTCCCAGG |

TABLE 3-continued

Coiled Coil Immunoglobulin Fusion Proteins-Nucleotide Sequence

| NAME | SEQ ID NO | SEQUENCE |
|------|-----------|----------|
| | | AGAGTGTCACAGAGCAGGACAGCAAGGACAGCACCTACAGCC |
| | | TCAGCAGCACCCTGACGCTGAGCAAAGCAGACTACGAGAAAC |
| | | ACAAAGTCTACGCCTGCGAAGTCACCCATCAGGGCCTGTCCTC |
| | | GCCCGTCACAAAGAGCTTCAACAGGGGAGAGTGT |

For SEQ ID NOs: 37-67
Antibody region = dashed underline
Non-antibody region = italic
Extender peptide = thick underline
Linker = *italic, squiggly underline*; protease site: underline

TABLE 4

Coiled Coil Immunoglobulin Fusion Proteins-Amino Acid Sequence

| Name | SEQ ID NO | Sequence |
|------|-----------|----------|
| trastuzumab-coil-hEPO LC | 68 | DIQMTQSPSSLSASVGDRVTITCRASQ*GGSGAKLAALKAKLAALKG GGGS*APPRLICDSRVLERYLLEAKEAENITTGCAEHCSLNENITVPDTK VNFYAWKRMEVGQQAVEVWQGLALLSEAVLRGQALLVNSSQPWEPL QLHVDKAVSGLRSLTTLLRALGAQKEAISPPDAASAAPLRTITADTFRK LFRVYSNFLRGKLKLYTGEACRTGDR*GGGGS*ELAALEAEIEAALEAGG *SG*TAVAWYQQKPGKAPKLLYSASFLYSGVPSRFSGSRSGTDFTL TISSLQPEDFATYYCQQHYTTPPTFGQGTKLEIKRTVAAPSVFIFPP SDEQLKSGTASVVCLLNNFYPREAKVQWKVDNALQSGNSQESVT EQDSKDSTYSLSSTLTLSKADYEKHKVYACEVTHQGLSSPVTKSF NRGEC |
| trastuzumab-coil-bGCSF HC | 69 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGSGAKLAALKAKLAALKGGGGS*TPLGPARSLPQSF LLKCLEQVRKIQADGAELQERLCAAHKLCHPEELMLLRHSLGIPQAP LSSCSSQSLQLTSCLNQLHGGLFLYQGLLQALAGISPELAPTLDTLQLD VTDFATNIWLQMEDLGAAPAVQPTQGAMPTFTSAFQRRAGGVLVAS QLHRFLELAYRGLRYLAEP*GGGGS*ELAALEAEIEAALEAGGSGDYWG QGTLVTVSSASTKGPSVFPLAPSSKSTSGGTAALGCLVKDYFPEPV TVSWNSGALTSGVHTFPAVLQSSGLYSLSSVVTVPSSSLGTQTYIC NVNHKPSNTKVDKKVEPKSCDKT HTCPPCPAPELLGGPSVFLFPPKPKDTLMISRTPEVTCVVVDVSHE DPEVKFNWYVDGVEVHNAKTKPREEQYNSTYRVVSVLTVLHQD WLNGKEYKCKVSNKALPAPIEKTISKAKGQPREPQVYTLPPSRDE LTKNQVSLTCLVKGFYPSDIAVEWESNGQPENNYKTTPPVLDSDG SFFLYSKLTVDKSRWQQGNVFSCSVMHEALHNHYTQKSLSLSPGK |
| Bovine-coil bGCSF HC (CDRH3) | 70 | QVQLRESGPSLVKPSQTLSLTCTASGFSLSDKAVGWVRQAPGKA LEWLGSIDTGGNTGYNPGLKSRLSITKDNSKSQVSLSVSSVTTEDS ATYYCTSVHQGGSGAKLAALKAKLAALK*GGGGS*TPLGPARSLPQSF LLKCLEQVRKIQADGAELQERLCAAHKLCHPEELMLLRHSLGIPQAP LSSCSSQSLQLTSCLNQLHGGLFLYQGLLQALAGISPELAPTLDTLQLD VTDFATNIWLQMEDLGAAPAVQPTQGAMPTFTSAFQRRAGGVLVAS |

TABLE 4-continued

Coiled Coil Immunoglobulin Fusion Proteins-Amino Acid Sequence

| Name | SEQ ID NO | Sequence |
|---|---|---|
| | | QLHRFLELAYRGLRYLAEPGGGGSELAALEAELAALEAGGSGWHVD VWGQGLLVTVSSASTTAPKVYPLSSCCGDKSSSTVTLGCLVSSY MPEPVTVTWNSGALKSGVHTFPAVLQSSGLYSLSSMVTVPGSTS GQTFTCNVAHPASSTKVDKAVEPKSCDKTHTCPPCPAPELLGGPS VFLFPPKPKDTLMISRTPEVTCVVVDVSHEDPEVKFNWYVDGVE VHNAKTKPREEQYNSTYRVVSVLTVLHQDWLNGKEYKCKVSNK ALPAPIEKTISKAKGQPREPQVYTLPPSRDELTKNQVSLTCLVKGF YPSDIAVEWESNGQPENNYKTTPPVLDSDGSFFLYSKLTVDKSRW QQGNVFSCSVMHEALHNHYTQKSLSLSPGK |
| trastuzumab-coil exendin-4 HC | 71 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSRGGSGAKLAALKAKLAALKCGGGGSIEGRHGEGTFTS DLSKQMEEEAVRLFIEWLKNGGPSSGAPPPSGGGGSCELAALEAELA ALEAGGSGDYWGQGTLVTVSSASTKGPSVFPLAPSSKSTSGGTAA LGCLVKDYFPEPVTVSWNSGALTSGVHTFPAVLQSSGLYSLSSVV TVPSSSLGTQTYICNVNHKPSNTKVDKKVEPKSCDKTHTCPPCPA PPVAGPSVFLFPPKPKDTLMISRTPEVTCVVVDVSHEDPEVKFNW YVDGVEVHNAKTKPREEQYNSTYRVVSVLTVLHQDWLNGKEYK CKVSNKGLPSSIEKTISKAKGQPREPQVYTLPPSRDELTKNQVSLT CLVKGFYPSDIAVEWESNGQPENNYKTTPPVLDSDGSFFLYSKLT VDKSRWQQGNVFSCSVMHEALHNHYTQKSLSLSPGK |
| trastuzumab-coil Moka1 HC | 72 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSRGGSGAKLAALKAKLAALKGGGGSINVKCSLPQQCIK PCKDAGMRFGKCMNKKCRCYSGGGGSELAALEAELAALEAGGSGD YWGQGTLVTVSSASTKGPSVFPLAPSSKSTSGGTAALGCLVKDYF PEPVTVSWNSGALTSGVHTFPAVLQSSGLYSLSSVVTVPSSSLGTQ TYICNVNHKPSNTKVDKKVEPKSCDKTHTCPPCPAPELLGGPSVF LFPPKPKDTLMISRTPEVTCVVVDVSHEDPEVKFNWYVDGVEVH NAKTKPREEQYNSTYRVVSVLTVLHQDWLNGKEYKCKVSNKAL PAPIEKTISKAKGQPREPQVYTLPPSRDELTKNQVSLTCLVKGFYP SDIAVEWESNGQPENNYKTTPPVLDSDGSFFLYSKLTVDKSRWQ QGNVFSCSVMHEALHNHYTQKSLSLSPGK |
| trastuzumab-coil VM24 HC | 73 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSRGGSGAKLAALKAKLAALKGGGGSAAAISCVGSPECP PKCRAQGCKNGKCMNRKCKCYYCGGGGSELAALEAELAALEAGGS GDYWGQGTLVTVSSASTKGPSVFPLAPSSKSTSGGTAALGCLVK DYFPEPVTVSWNSGALTSGVHTFPAVLQSSGLYSLSSVVTVPSSSL |

TABLE 4-continued

Coiled Coil Immunoglobulin Fusion Proteins-Amino Acid Sequence

| Name | SEQ ID NO | Sequence |
|---|---|---|
| | | GTQTYICNVNHKPSNTKVDKKVEPKSCDKTHTCPPCPAPELLGGP |
| | | SVFLFPPKPKDTLMISRTPEVTCVVVDVSHEDPEVKFNWYVDGVE |
| | | VHNAKTKPREEQYNSTYRVVSVLTVLHQDWLNGKEYKCKVSNK |
| | | ALPAPIEKTISKAKGQPREPQVYTLPPSRDELTKNQVSLTCLVKGF |
| | | YPSDIAVEWESNGQPENNYKTTPPVLDSDGSFFLYSKLTVDKSRW |
| | | QQGNVFSCSVMHEALHNHYTQKSLSLSPGK |
| trastuzumab-coil hGCSF HC | 74 | EVQLVESGGGLVQPGGSLRLSCAASGFNIKDTYIHWVRQAPGKG |
| | | LEWVARIYPTNGYTRYADSVKGRFTISADTSKNTAYLQMNSLRA |
| | | EDTAVYYCSR*GGSGAKLAALKAKLAALKGGGGS*ATPLGPASSLPQS |
| | | *FLLKCLEQVRKIQGDGAALQEKLVSECATYKLCHPEELVLLGHSLGIP* |
| | | *WAPLSSCPSQALQLAGCLSQLHSGLFLYQGLLQALEGISPELGPTLDT* |
| | | *LQLDVADFATTIWQQMEELGMAPALQPTQGAMPAFASAFQRRAGGV* |
| | | *LVASHLQSFLEVSYRVLRHLAQPGGGGSELAALEAELAALEAGGSGD* |
| | | YWGQGTLVTVSSASTKGPSVFPLAPCSRSTSESTAALGCLVKDYF |
| | | PEPVTVSWNSGALTSGVHTFPAVLQSSGLYSLSSVVTVPSSSLGTK |
| | | TYTCNVDHKPSNTKVDKRVESKYGPPCPPCPAPEAAGGPSVFLFP |
| | | PKPKDTLMISRTPEVTCVVVDVSQEDPEVQFNWYVDGVEVHNA |
| | | KTKPREEQFNSTYRVVSVLTVLHQDWLNGKEYKCKVSNKGLPSS |
| | | IEKTISKAKGQPREPQVYTLPPSQEEMTKNQVSLTCLVKGFYPSDI |
| | | AVEWESNGQPENNYKTTPPVLDSDGSFFLYSRLTVDKSRWQEGN |
| | | VFSCSVMHEALHNHYTQKSLSLSLGK |
| trastuzumab-coil hGH HC (CDRH3) | 75 | EVQLVESGGGLVQPGGSLRLSCAASGFNIKDTYIHWVRQAPGKG |
| | | LEWVARIYPTNGYTRYADSVKGRFTISADTSKNTAYLQMNSLRA |
| | | EDTAVYYCSR*GGSGAKLAALKAKLAALKGGGGS*FPTIPLSRLFDNA |
| | | *MLRAHRLHQLAFDTYQEFEEAYIPKEQKYSFLQNPQTSLCFSESIPTPS* |
| | | *NREETQQKSNLELLRISLLLIQSWLEPVQFLRSVFANSLVYGASDSNVY* |
| | | *DLLKDLEEGIQTLMGRLEDGSPRTGQIFKQTYSKFDTNSHNDDALLK* |
| | | *NYGLLYCFRKDMDKVETFLRIVQCRSVEGSCGFGGGGSELAALEAEL* |
| | | *AALEAGGSGD*YWGQGTLVTVSSASTKGPSVFPLAPCSRSTSESTA |
| | | ALGCLVKDYFPEPVTVSWNSGALTSGVHTFPAVLQSSGLYSLSSV |
| | | VTVPSSSLGTKTYTCNVDHKPSNTKVDKRVESKYGPPCPPCPAPE |
| | | AAGGPSVFLFPPKPKDTLMISRTPEVTCVVVDVSQEDPEVQFNWY |
| | | VDGVEVHNAKTKPREEQFNSTYRVVSVLTVLHQDWLNGKEYKC |
| | | KVSNKGLPSSIEKTISKAKGQPREPQVYTLPPSQEEMTKNQVSLTC |
| | | LVKGFYPSDIAVEWESNGQPENNYKTTPPVLDSDGSFFLYSRLTV |
| | | DKSRWQEGNVFSCSVMHEALHNHYTQKSLSLSLGK |
| trastuzumab-coil hGH HC (CDRH2) | 76 | EVQLVESGGGLVQPGGSLRLSCAASGFNIKDTYIHWVRQAPGKG |
| | | LEWVARIYP*GGSGAKLAALKAKLAALKGGGGS*FPTIPLSRLFDNAML |
| | | *RAHRLHQLAFDTYQEFEEAYIPKEQKYSFLQNPQTSLCFSESIPTPSNR* |
| | | *EETQQKSNLELLRISLLLIQSWLEPVQFLRSVFANSLVYGASDSNVYDL* |
| | | *LKDLEEGIQTLMGRLEDGSPRTGQIFKQTYSKFDTNSHNDDALLKNY* |
| | | *GLLYCFRKDMDKVETFLRIVQCRSVEGSCGFGGGGSELAALEAELAA* |
| | | *LEAGGSGG*YTRYADSVKGRFTISADTSKNTAYLQMNSLRAEDTA |

TABLE 4-continued

Coiled Coil Immunoglobulin Fusion Proteins-Amino Acid Sequence

| Name | SEQ ID NO | Sequence |
|------|-----------|----------|
| | | VYYCSRWGGDGFYAMDYWGQGTLVTVSSASTKGPSVFPLAPSS |
| | | KSTSGGTAALGCLVKDYFPEPVTVSWNSGALTSGVHTFPAVLQSS |
| | | GLYSLSSVVTVPSSSLGTQTYICNVNHKPSNTKVDKKVEPKSCDK |
| | | THTCPPCPAPPVAGPSVFLFPPKPKDTLMISRTPEVTCVVVDVSHE |
| | | DPEVKFNWYVDGVEVHNAKTKPREEQYNSTYRVVSVLTVLHQD |
| | | WLNGKEYKCKVSNKGLPSSIEKTISKAKGQPREPQVYTLPPSRDE |
| | | LTKNQVSLTCLVKGFYPSDIAVEWESNGQPENNYKTTPPVLDSDG |
| | | SFFLYSKLTVDKSRWQQGNVFSCSVMHEALHNHYTQKSLSLSPGK |
| BLV1H12 coil-hGH HC | 77 | QVQLRESGPSLVKPSQTLSLTCTASGFSLSDKAVGWVRQAPGKA |
| | | LEWLGSIDTGGNTGYNPGLKSRLSITKDNSKSQVSLSVSSVTTEDS |
| | | ATYYCGGSGAKLAALKAKLAALKGGGGSFPTIPLSRLFDNAMLRAHR |
| | | LHQLAFDTYQEFEEAYIPKEQKYSFLQNPQTSLCFSESIPTPSNREETQ |
| | | QKSNLELLRISLLLIQSWLEPVQFLRSVFANSLVYGASDSNVYDLLKDL |
| | | EEGIQTLMGRLEDGSPRTGQIFKQTYSKFDTNSHNDDALLKNYGLLY |
| | | CFRKDMDKVETFLRIVQCRSVEGSCGFGGGGSELAALEAELAALEAG |
| | | GSGHVDVWGQGLLVTVSSASTTAPKVYPLSSCCGDKSSSTVTLG |
| | | CLVSSYMPEPVTVTWNSGALKSGVHTFPAVLQSSGLYSLSSMVT |
| | | VPGSTSGQTFTCNVAHPASSTKVDKAVEPKSCDKTHTCPPCPAPE |
| | | LLGGPSVFLFPPKPKDTLMISRTPEVTCVVVDVSHEDPEVKFNWY |
| | | VDGVEVHNAKTKPREEQYNSTYRVVSVLTVLHQDWLNGKEYKC |
| | | KVSNKALPAPIEKTISKAKGQPREPQVYTLPPSRDELTKNQVSLTC |
| | | LVKGFYPSDIAVEWESNGQPENNYKTTPPVLDSDGSFFLYSKLTV |
| | | DKSRWQQGNVFSCSVMHEALHNHYTQKSLSLSPGK |
| trastuzumab-coil hLeptin HC (CDRH3) | 78 | EVQLVESGGGLVQPGGSLRLSCAASGFNIKDTYIHWVRQAPGKG |
| | | LEWVARIYPTNGYTRYADSVKGRFTISADTSKNTAYLQMNSLRA |
| | | EDTAVYYCSRGGSGAKLAALKAKLAALKGGGGSVPIQKVQDDTKTL |
| | | IKTIVTRINDISHTQSVSSKQKVTGLDFIPGLHPILTLSKMDQTLAVYQQ |
| | | ILTSMPSRNVIQISNDLENLRDLLHVLAFSKSCHLPWASGLETLDSLGG |
| | | VLEASGYSTEVVALSRLQGSLQDMLWQLDLSPGCGGGGSELAALEAE |
| | | LAALEAGGSGDYWGQGTLVTVSSASTKGPSVFPLAPSSKSTSGGT |
| | | AALGCLVKDYFPEPVTVSWNSGALTSGVHTFPAVLQSSGLYSLSS |
| | | VVTVPSSSLGTQTYICNVNHKPSNTKVDKKVEPKSCDKTHTCPPC |
| | | PAPPVAGPSVFLFPPKPKDTLMISRTPEVTCVVVDVSHEDPEVKFN |
| | | WYVDGVEVHNAKTKPREEQYNSTYRVVSVLTVLHQDWLNGKE |
| | | YKCKVSNKGLPSSIEKTISKAKGQPREPQVYTLPPSRDELTKNQVS |
| | | LTCLVKGFYPSDIAVEWESNGQPENNYKTTPPVLDSDGSFFLYSK |
| | | LTVDKSRWQQGNVFSCSVMHEALHNHYTQKSLSLSPGK |
| trastuzumab-coil hLeptin HC (CDRH2) | 79 | EVQLVESGGGLVQPGGSLRLSCAASGFNIKDTYIHWVRQAPGKG |
| | | LEWVARIGGSGAKLAALKAKLAALKGGGGSVPIQKVQDDTKTLIKTI |
| | | VTRINDISHTQSVSSKQKVTGLDFIPGLHPILTLSKMDQTLAVYQQILTS |
| | | MPSRNVIQISNDLENLRDLLHVLAFSKSCHLPWASGLETLDSLGGVLE |
| | | ASGYSTEVVALSRLQGSLQDMLWQLDLSPGCGGGGSELAALEAELAA |

TABLE 4-continued

Coiled Coil Immunoglobulin Fusion Proteins-Amino Acid Sequence

| Name | SEQ ID NO | Sequence |
|---|---|---|
| | | *LEAGGSG*TRYADSVKGRFTISADTSKNTAYLQMNSLRAEDTAVY |
| | | YCSRWGGDGFYAMDYWGQGTLVTVSSASTKGPSVFPLAPSSKST |
| | | SGGTAALGCLVKDYFPEPVTVSWNSGALTSGVHTFPAVLQSSGL |
| | | YSLSSVVTVPSSSLGTQTYICNVNHKPSNTKVDKKVEPKSCDKTH |
| | | TCPPCPAPPVAGPSVFLFPPKPKDTLMISRTPEVTCVVVDVSHEDP |
| | | EVKFNWYVDGVEVHNAKTKPREEQYNSTYRVVSVLTVLHQDW |
| | | LNGKEYKCKVSNKGLPSSIEKTISKAKGQPREPQVYTLPPSRDELT |
| | | KNQVSLTCLVKGFYPSDIAVEWESNGQPENNYKTTPPVLDSDGSF |
| | | FLYSKLTVDKSRWQQGNVFSCSVMHEALHNHYTQKSLSLSPGK |
| trastuzumab-coil hLeptin LC (CDRL3) | 80 | DIQMTQSPSSLSASVGDRVTITCRASQDVNTAVAWYQQKPGKAP KLLIYSASFLYSGVPSRFSGSRSGTDFTLTISSLQPEDFATYYCQQH *Y*GGSGAKLAALKAKLAALKGGGGS*VPIQKVQDDTKTLIKTIVTRINDI SHTQSVSSKQKVTGLDFIPGLHPILTLSKMDQTLAVYQQILTSMPSRNV IQISNDLENLRDLLHVLAFSKSCHLPWASGLETLDSLGGVLEASGYSTE VVALSRLQGSLQDMLWQLDLSPGC*GGGGSELAALEAELAALEAGGS *GPTFGQGTKLEIKRTVAAPSVFIFPPSDEQLKSGTASVVCLLNNFY PREAKVQWKVDNALQSGNSQESVTEQDSKDSTYSLSSTLTLSKA DYEKHKVYACEVTHQGLSSPVTKSFNRGEC |
| trastuzumab-coil hIFN-alpha HC | 81 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGSGAKLAALKAKLAALKGGGGS*CDLPQTHSLGSRR TLMLLAQMRRISLFSCLKDRHDFGFPQEEFGNQFQKAETIPVLHEMI QQIFNLFSTKDSSAAWDETLLDKFYTELYQQLNDLEACVIQGVGVTET PLMKEDSILAVRKYFQRITLYLKEKKYSPCAWEVVRAEIMRSFSLSTNL QESLRSKEG*GGGSELAALEAELAALEAGGSG*DYWGQGTLVTVSSAS TKGPSVFPLAPCSRSTSESTAALGCLVKDYFPEPVTVSWNSGALTS GVHTFPAVLQSSGLYSLSSVVTVPSSSLGTKTYTCNVDHKPSNTK VDKRVESKYGPPCPPCPAPEAAGGPSVFLFPPKPKDTLMISRTPEV TCVVVDVSQEDPEVQFNWYVDGVEVHNAKTKPREEQFNSTYRV VSVLTVLHQDWLNGKEYKCKVSNKGLPSSIEKTISKAKGQPREPQ VYTLPPSQEEMTKNQVSLTCLVKGFYPSDIAVEWESNGQPENNY KTTPPVLDSDGSFFLYSRLTVDKSRWQEGNVFSCSVMHEALHNH YTQKSLSLSLGK |
| trastuzumab-coil hIFN-B1 HC | 82 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGSGAKLAALKAKLAALKGGGGS*MSYNLLGFLQRSS NFQCQKLLWQLNGRLEYCLKDRMNFDIPEEIKQLQQFQKEDAALTIY EMLQNIFAIFRQDSSSTGWNETIVENLLANVYHQINHLKTVLEEKLEK EDFTRGKLMSSLHLKRYYGRILHYLKAKEYSHCAWTIVRVEILRNFYFI NRLTGYLRN*GGGGSELAALEAELAALEAGGSG*DYWGQGTLVTVSSA STKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPPVAGPSVFLFPPKPKDTLMISRT |

TABLE 4-continued

Coiled Coil Immunoglobulin Fusion Proteins-Amino Acid Sequence

| Name | SEQ ID NO | Sequence |
|---|---|---|
| | | PEVTCVVVDVSHEDPEVKFNWYVDGVEVHNAKTKPREEQYNST |
| | | YRVVSVLTVLHQDWLNGKEYKCKVSNKGLPSSIEKTISKAKGQP |
| | | REPQVYTLPPSRDELTKNQVSLTCLVKGFYPSDIAVEWESNGQPE |
| | | NNYKTTPPVLDSDGSFFLYSKLTVDKSRWQQGNVFSCSVMHEAL |
| | | HNHYTQKSLSLSPGK |
| BLV1H12 coil-IFNB HC | 83 | QVQLRESGPSLVKPSQTLSLTCTASGFSLSDKAVGWVRQAPGKA |
| | | LEWLGSIDTGGNTGYNPGLKSRLSITKDNSKSQVSLSVSSVTTEDS |
| | | ATYYCGGSGAKLAALKAKLAALKGGGGSMSYNLLGFLQRSSNFQCQ |
| | | KLLWQLNGRLEYCLKDRMNFDIPEEIKQLQQFQKEDAALTIYEMLQN |
| | | IFAIFRQDSSSTGWNETIVENLLANVYHQINHLKTVLEEKLEKEDFTRG |
| | | KLMSSLHLKRYYGRILHYLKAKEYSHCAWTIVRVEILRNFYFINRLTGY |
| | | LRNGGGGSELAALEAELAALEAGGSGHVDVWGQGLLVTVSSASTT |
| | | APKVYPLSSCCGDKSSSTVTLGCLVSSYMPEPVTVTWNSGALKSG |
| | | VHTFPAVLQSSGLYSLSSMVTVPGSTSGQTFTCNVAHPASSTKVD |
| | | KAVEPKSCDKTHTCPPCPAPELLGGPSVFLFPPKPKDTLMISRTPE |
| | | VTCVVVDVSHEDPEVKFNWYVDGVEVHNAKTKPREEQYNSTYR |
| | | VVSVLTVLHQDWLNGKEYKCKVSNKALPAPIEKTISKAKGQPRE |
| | | PQVYTLPPSRDELTKNQVSLTCLVKGFYPSDIAVEWESNGQPENN |
| | | YKTTPPVLDSDGSFFLYSKLTVDKSRWQQGNVFSCSVMHEALHN |
| | | HYTQKSLSLSPGK |
| trastuzumab-coil GLP1 HC | 84 | EVQLVESGGGLVQPGGSLRLSCAASGFNIKDTYIHWVRQAPGKG |
| | | LEWVARIYPTNGYTRYADSVKGRFTISADTSKNTAYLQMNSLRA |
| | | EDTAVYYCSRGGSGAKLAALKAKLAALKCGGGGSIEGRHAEGTFTS |
| | | DVSSYLEGQAAKEFIAWLVKGRGGGGSCELAALEAELAALEAGGSGD |
| | | YWGQGTLVTVSSASTKGPSVFPLAPSSKSTSGGTAALGCLVKDYF |
| | | PEPVTVSWNSGALTSGVHTFPAVLQSSGLYSLSSVVTVPSSSLGTQ |
| | | TYICNVNHKPSNTKVDKKVEPKSCDKTHTCPPCPAPPVAGPSVFL |
| | | FPPKPKDTLMISRTPEVTCVVVDVSHEDPEVKFNWYVDGVEVHN |
| | | AKTKPREEQYNSTYRVVSVLTVLHQDWLNGKEYKCKVSNKGLP |
| | | SSIEKTISKAKGQPREPQVYTLPPSRDELTKNQVSLTCLVKGFYPS |
| | | DIAVEWESNGQPENNYKTTPPVLDSDGSFFLYSKLTVDKSRWQQ |
| | | GNVFSCSVMHEALHNHYTQKSLSLSPGK |
| trastuzumab-coil elafin HC | 85 | EVQLVESGGGLVQPGGSLRLSCAASGFNIKDTYIHWVRQAPGKG |
| | | LEWVARIYPTNGYTRYADSVKGRFTISADTSKNTAYLQMNSLRA |
| | | EDTAVYYCSRGGSGAKLAALKAKLAALKGGGGSAQEPVKGPVSTKP |
| | | GSCPIILIRCAMLNPPNRCLKDTDCPGIKKCCEGSCGMACFVPQGGG |
| | | GSELAALEAELAALEAGGSGDYWGQGTLVTVSSASTKGPSVFPLAP |
| | | SSKSTSGGTAALGCLVKDYFPEPVTVSWNSGALTSGVHTFPAVLQ |
| | | SSGLYSLSSVVTVPSSSLGTQTYICNVNHKPSNTKVDKKVEPKSC |
| | | DKTHTCPPCPAPPVAGPSVFLFPPKPKDTLMISRTPEVTCVVVDVS |
| | | HEDPEVKFNWYVDGVEVHNAKTKPREEQYNSTYRVVSVLTVLH |

TABLE 4-continued

Coiled Coil Immunoglobulin Fusion Proteins-Amino Acid Sequence

| Name | SEQ ID NO | Sequence |
|---|---|---|
| | | QDWLNGKEYKCKVSNKGLPSSIEKTISKAKGQPREPQVYTLPPSR |
| | | DELTKNQVSLTCLVKGFYPSDIAVEWESNGQPENNYKTTPPVLDS |
| | | DGSFFLYSKLTVDKSRWQQGNVFSCSVMHEALHNHYTQKSLSLS |
| | | PGK |
| trastuzumab-coil-relaxin2 (insulin c peptide) HC | 86 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGSGAKLAALKAKLAALKGGGGS*DSWMEEVIKLCG RELVRAQIAICGMSTWSKREAEDLQVGQVELGGGPGAGSLQPLALEG SLQKRRKKRQLYSALANKCCHVGCTKRSLARFCGGGG*SELAALEAEL AALEAGGSG*DYWGQGTLVTVSSASTKGPSVFPLAPSSKSTSGGTA ALGCLVKDYFPEPVTVSWNSGALTSGVHTFPAVLQSSGLYSLSSV VTVPSSSLGTQTYICNVNHKPSNTKVDKKVEPKSCDKTHTCPPCP APPVAGPSVFLFPPKPKDTLMISRTPEVTCVVVDVSHEDPEVKFN WYVDGVEVHNAKTKPREEQYNSTYRVVSVLTVLHQDWLNGKE YKCKVSNKGLPSSIEKTISKAKGQPREPQVYTLPPSRDELTKNQVS LTCLVKGFYPSDIAVEWESNGQPENNYKTTPPVLDSDGSFFLYSK LTVDKSRWQQGNVFSCSVMHEALHNHYTQKSLSLSPGK |
| trastuzumab-coil mambalgin HC | 87 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCS*GGSGAKLAALKAKLAALKGGGGS*LKCYQHGKVVTCH RDMKFCYHNTGMPFRNLKLILQGCSSSCSETENNKCCSTDRCNK*GG GGSELAALEAELAALEAGGSG*WGQGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKKVEPKSCD KTHTCPPCPAPPVAGPSVFLFPPKPKDTLMISRTPEVTCVVVDVSH EDPEVKFNWYVDGVEVHNAKTKPREEQYNSTYRVVSVLTVLHQ DWLNGKEYKCKVSNKGLPSSIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPGK |
| palivizumab-coil mambalgin HC | 88 | QVTLRESGPALVKPTQTLTLTCTFSGFSLSTSGMSVGWIRQPPGK ALEWLADIWWDDKKDYNPSLKSRLTISKDTSKNQVVLKVTNMD PADTATYYCARS*GGSGAKLAALKAKLAALKGGGGS*LKCYQHGKVV TCHRDMKFCYHNTGMPFRNLKLILQGCSSSCSETENNKCCSTDRCNK *GGGGSELAALEAELAALEAGGSG*YFDVWGAGTTVTVSSASTKGPS VFPLAPSSKSTSGGTAALGCLVKDYFPEPVTVSWNSGALTSGVHT FPAVLQSSGLYSLSSVVTVPSSSLGTQTYICNVNHKPSNTKVDKK VEPKSCDKTHTCPPCPAPPVAGPSVFLFPPKPKDTLMISRTPEVTC VVVDVSHEDPEVKFNWYVDGVEVHNAKTKPREEQYNSTYRVVS VLTVLHQDWLNGKEYKCKVSNKGLPSSIEKTISKAKGQPREPQV YTLPPSRDELTKNQVSLTCLVKGFYPSDIAVEWESNGQPENNYKT |

TABLE 4-continued

Coiled Coil Immunoglobulin Fusion Proteins-Amino Acid Sequence

| Name | SEQ ID NO | Sequence |
|---|---|---|
| | | TPPVLDSDGSFFLYSKLTVDKSRWQQGNVFSCSVMHEALHNHYT QKSLSLSPGK |
| Trastuzumab-coil relaxin2 short HC | 89 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGSGAKLAALKAKLAALKGGGGS*DSWMEEVIKLCG RELVRAQIAICGMSTWSKRSLSQE*IEGRKKR*QLYSALANKCCHVGCTK RSLARFC*GGGGSELAALEAELAALEAGGSG*DYWGQGTLVTVSSAST KGPSVFPLAPSSKSTSGGTAALGCLVKDYFPEPVTVSWNSGALTS GVHTFPAVLQSSGLYSLSSVVTVPSSSLGTQTYICNVNHKPSNTK VDKKVEPKSCDKTHTCPPCPAPPVAGPSVFLFPPKPKDTLMISRTP EVTCVVVDVSHEDPEVKFNWYVDGVEVHNAKTKPREEQYNSTY RVVSVLTVLHQDWLNGKEYKCKVSNKGLPSSIEKTISKAKGQPR EPQVYTLPPSRDELTKNQVSLTCLVKGFYPSDIAVEWESNGQPEN NYKTTPPVLDSDGSFFLYSKLTVDKSRWQQGNVFSCSVMHEALH NHYTQKSLSLSPGK |
| Trastuzumab-coil relaxin2 long HC | 90 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGSGAKLAALKAKLAALKGGGGS*DSWMEEVIKLCG RELVRAQIAICGMSTWSKRSLSQEDAPQTPRPV*IEGRKKR*QLYSALAN KCCHVGCTKRSLARFC*GGGGSELAALEAELAALEAGGSG*DYWGQG TLVTVSSASTKGPSVFPLAPSSKSTSGGTAALGCLVKDYFPEPVTV SWNSGALTSGVHTFPAVLQSSGLYSLSSVVTVPSSSLGTQTYICNV NHKPSNTKVDKKVEPKSCDKTHTCPPCPAPPVAGPSVFLFPPKPK DTLMISRTPEVTCVVVDVSHEDPEVKFNWYVDGVEVHNAKTKP REEQYNSTYRVVSVLTVLHQDWLNGKEYKCKVSNKGLPSSIEKTI SKAKGQPREPQVYTLPPSRDELTKNQVSLTCLVKGFYPSDIAVEW ESNGQPENNYKTTPPVLDSDGSFFLYSKLTVDKSRWQQGNVFSCS VMHEALHNHYTQKSLSLSPGK |
| trastuzumab-coil ZP HC (CDRH3) | 91 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGSGAKLAALKAKLAALKCGGGGS*IEGRHSQGTFTS DYSKYLDSKAAHDFVEWLLNGGPSSGAPPPSGGGGSC*ELAALEAELA ALEAGGSG*DYWGQGTLVTVSSASTKGPSVFPLAPSSKSTSGGTAA LGCLVKDYFPEPVTVSWNSGALTSGVHTFPAVLQSSGLYSLSSVV TVPSSSLGTQTYICNVNHKPSNTKVDKKVEPKSCDKTHTCPPCPA PPVAGPSVFLFPPKPKDTLMISRTPEVTCVVVDVSHEDPEVKFNW YVDGVEVHNAKTKPREEQYNSTYRVVSVLTVLHQDWLNGKEYK CKVSNKGLPSSIEKTISKAKGQPREPQVYTLPPSRDELTKNQVSLT CLVKGFYPSDIAVEWESNGQPENNYKTTPPVLDSDGSFFLYSKLT VDKSRWQQGNVFSCSVMHEALHNHYTQKSLSLSPGK |

TABLE 4-continued

Coiled Coil Immunoglobulin Fusion Proteins-Amino Acid Sequence

| Name | SEQ ID NO | Sequence |
|---|---|---|
| trastuzumab-coil ZP mutant (S-G) HC | 92 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSRGGSGAKLAALKAKLAALKCGGGGSIEGRHGQGTFTS DYSKYLDSKAAHDFVEWLLNGGPSSGAPPPSGGGGSCELAALEAELA ALEAGGSGDYWGQGTLVTVSSASTKGPSVFPLAPSSKSTSGGTAA LGCLVKDYFPEPVTVSWNSGALTSGVHTFPAVLQSSGLYSLSSVV TVPSSSLGTQTYICNVNHKPSNTKVDKKVEPKSCDKTHTCPPCPA PPVAGPSVFLFPPKPKDTLMISRTPEVTCVVVDVSHEDPEVKFNW YVDGVEVHNAKTKPREEQYNSTYRVVSVLTVLHQDWLNGKEYK CKVSNKGLPSSIEKTISKAKGQPREPQVYTLPPSRDELTKNQVSLT CLVKGFYPSDIAVEWESNGQPENNYKTTPPVLDSDGSFFLYSKLT VDKSRWQQGNVFSCSVMHEALHNHYTQKSLSLSPGK |
| trastuzumab-coil hEPO (CDRH3) HC | 93 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSRGGSGAKLAALKAKLAALKGGGGSAPPRLICDSRVLER YLLEAKEAENITTGCAEHCSLNENITVPDTKVNFYAWKRMEVGQQAV EVWQGLALLSEAVLRGQALLVNSSQPWEPLQLHVDKAVSGLRSLTTLL RALGAQKEAISPPDAASAAPLRTITADTFRKLFRVYSNFLRGKLKLYTG EACRTGDRGGGGSELAALEAELAALEAGGSGDYWGQGTLVTVSSA STKGPSVFPLAPCSRSTSESTAALGCLVKDYFPEPVTVSWNSGALT SGVHTFPAVLQSSGLYSLSSVVTVPSSSLGTKTYTCNVDHKPSNT KVDKRVESKYGPPCPPCPAPEAAGGPSVFLFPPKPKDTLMISRTPE VTCVVVDVSQEDPEVQFNWYVDGVEVHNAKTKPREEQFNSTYR VVSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLGK |
| trastuzumab-coil hGCSF (CDRL3) LC | 94 | DIQMTQSPSSLSASVGDRVTITCRASQDVNTAVAWYQQKPGKAP KLLIYSASFLYSGVPSRFSGSRSGTDFTLTISSLQPEDFATYYCQQH YGGSGAKLAALKAKLAALKGGGGSTPLGPASSLPQSFLLKCLEQVRKI QGDGAALQEKLCATYKLCHPEELVLLGHSLGIPWAPLSSCPSQALQL AGCLSQLHSGLFLYQGLLQALEGISPELGPTLDTLQLDVADFATTIWQ QMEELGMAPALQPTQGAMPAFASAFQRRAGGVLVASHLQSFLEVSY RVLRHLAQPGGGGSELAALEAELAALEAGGSGPTFGQGTKLEIKRTV AAPSVFIFPPSDEQLKSGTASVVCLLNNFYPREAKVQWKVDNAL QSGNSQESVTEQDSKDSTYSLSSTLTLSKADYEKHKVYACEVTH QGLSSPVTKSFNRGEC |
| trastuzumab-coil Ssam6a HC (CDRH3) | 95 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSRGGSGAKLAALKAKLAALKGGGGSADNKCENSLRREI ACGQCRDKVKTDGYFYECCTSDSTFKKCQDLLHGGGGSELAALEAE LAALEAGGSGDYWGQGTLVTVSSASTKGPSVFPLAPSSKSTSGGT |

TABLE 4-continued

Coiled Coil Immunoglobulin Fusion Proteins-Amino Acid Sequence

| Name | SEQ ID NO | Sequence |
|---|---|---|
| | | AALGCLVKDYFPEPVTVSWNSGALTSGVHTFPAVLQSSGLYSLSS |
| | | VVTVPSSSLGTQTYICNVNHKPSNTKVDKKVEPKSCDKTHTCPPC |
| | | PAPPVAGPSVFLFPPKPKDTLMISRTPEVTCVVVDVSHEDPEVKFN |
| | | WYVDGVEVHNAKTKPREEQYNSTYRVVSVLTVLHQDWLNGKE |
| | | YKCKVSNKGLPSSIEKTISKAKGQPREPQVYTLPPSRDELTKNQVS |
| | | LTCLVKGFYPSDIAVEWESNGQPENNYKTTPPVLDSDGSFFLYSK |
| | | LTVDKSRWQQGNVFSCSVMHEALHNHYTQKSLSLSPGK |
| trastuzumab-coil GLP2 (CDRH3) HC | 96 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGSGAKLAALKAKLAALKC*GGGGS*IEGRHGDGSFSD EMNTILDNLAARDFINWLIQTKITDGGPSSGAPPPS*GGGGS*CELAALE AELAALEAGGSG*DYWGQGTLVTVSSASTKGPSVFPLAPSSKSTSGG TAALGCLVKDYFPEPVTVSWNSGALTSGVHTFPAVLQSSGLYSLS SVVTVPSSSLGTQTYICNVNHKPSNTKVDKKVEPKSCDKTHTCPP CPAPPVAGPSVFLFPPKPKDTLMISRTPEVTCVVVDVSHEDPEVKF NWYVDGVEVHNAKTKPREEQYNSTYRVVSVLTVLHQDWLNGK EYKCKVSNKGLPSSIEKTISKAKGQPREPQVYTLPPSRDELTKNQV SLTCLVKGFYPSDIAVEWESNGQPENNYKTTPPVLDSDGSFFLYS KLTVDKSRWQQGNVFSCSVMHEALHNHYTQKSLSLSPGK |
| trastuzumab-coil betatrophin HC (CDRH3) | 97 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGSGAKLAALKAKLAALK*GGGGS*APLGGPEPAQYEE LTLLFHGALQLGQALNGVYRATEARLTEAGHSLGLYDRALEFLGTEVR QGQDATQELRTSLSEIQVEEDALHLRAEATARSLGEVARAQQALRDTV RRLQVQLRGAWLGQAHQEFETLKARADKQSHLLWALTGHVQRQQR EMAEQQQWLRQIQQRLHTAALPAGGGGS*ELAALEAELAALEAGGSSG DYWGQGTLVTVSSASTKGPSVFPLAPSSKSTSGGTAALGCLVKD YFPEPVTVSWNSGALTSGVHTFPAVLQSSGLYSLSSVVTVPSSSLG TQTYICNVNHKPSNTKVDKKVEPKSCDKTHTCPPCPAPPVAGPSV FLFPPKPKDTLMISRTPEVTCVVVDVSHEDPEVKFNWYVDGVEV HNAKTKPREEQYNSTYRVVSVLTVLHQDWLNGKEYKCKVSNKG LPSSIEKTISKAKGQPREPQVYTLPPSRDELTKNQVSLTCLVKGFY PSDIAVEWESNGQPENNYKTTPPVLDSDGSFFLYSKLTVDKSRWQ QGNVFSCSVMHEALHNHYTQKSLSLSPGK |
| trastuzumab-coil exendin-4 LC | 98 | DIQMTQSPSSLSASVGDRVTITCRASQ*GGSGAKLAALKAKLAALKC GGGGS*IEGRHGEGTFTSDLSKQMEEEAVRLFIEWLKNGGPSSGAPPP SGGGGS*CELAALEAELAALEAGGSG*TAVAWYQQKPGKAPKLLIYS ASFLYSGVPSRFSGSRSGTDFTLTISSLQPEDFATYYCQQHYTTPPT FGQGTKLEIKRTVAAPSVFIFPPSDEQLKSGTASVVCLLNNFYPRE AKVQWKVDNALQSGNSQESVTEQDSKDSTYSLSSTLTLSKADYE KHKVYACEVTHQGLSSPVTKSFNRGEC |

TABLE 4-continued

Coiled Coil Immunoglobulin Fusion Proteins-Amino Acid Sequence

| Name | SEQ ID NO | Sequence |
|---|---|---|
| BLV1H12 coil-relaxin HC | 99 | QVQLRESGPSLVKPSQTLSLTCTASGFSLSDKAVGWVRQAPGKA LEWLGSIDTGGNTGYNPGLKSRLSITKDNSKSQVSLSVSSVTTEDS ATYYC*GGSGAKLAALKAKLAALKGGGGS*DSWMEEVIKLCGRELVRA *QIAICGMSTWSIEGRSLSQEDAPQTPRPVAEIVPSFINKDTETINMMSE FVANLPQELKLTLSEMQPALPQLQQHVPVLKDSSLLFEEFKKLIRNRQ SEAADSSPSELKYLGLDTHSIEGRQLYSALANKCCHVGCTKRSLARFC GGGGS*ELAALEAELAALEAGGSGHVDVWGQGLLVTVSSASTTAPK VYPLSSCCGDKSSSTVTLGCLVSSYMPEPVTVTWNSGALKSGVH TFPAVLQSSGLYSLSSMVTVPGSTSGQTFTCNVAHPASSTKVDKA VEPKSCDKTHTCPPCPAPELLGGPSVFLFPPKPKDTLMISRTPEVT CVVVDVSHEDPEVKFNWYVDGVEVHNAKTKPREEQYNSTYRVV SVLTVLHQDWLNGKEYKCKVSNKALPAPIEKTISKAKGQPREPQ VYTLPPSRDELTKNQVSLTCLVKGFYPSDIAVEWESNGQPENNYK TTPPVLDSDGSFFLYSKLTVDKSRWQQGNVFSCSVMHEALHNHY TQKSLSLSPGK |

For SEQ ID NOs: 68-99
Antibody region = dashed underline
Non-antibody region = *italic*
Extender peptide = thick underline
Linker = *italic, squiggly underline*; protease site: underline

TABLE 5

Direct Immunoglobulin Fusion Proteins—Nucleotide Sequence

| NAME | SEQ ID NO | SEQUENCE |
|---|---|---|
| trastuzumab-direct-hEPO LC | 100 | GACATCCAGATGACCCAGTCTCCATCCTCCCTGTCTGCATCTGT AGGAGACAGAGTCACCATCACTTGCCGGGCAAGTCAG*GGGGG TGGCGGAAGC*GCCCCACCACGCCTCATCTGTGACAGCCGAGTCCT *GGAGAGGTACCTCTTGGAGGCCAAGGAGGCCGAGAATATCACGAC GGGCTGTGCTGAACACTGCAGCTTGAATGAGAATATCACTGTCCCA GACACCAAAGTTAATTTCTATGCCTGGAAGAGGATGGAGGTCGGG CAGCAGGCCGTAGAAGTCTGGCAGGGCCTGGCCCTGCTGTCGGA AGCTGTCCTGCGGGGCCAGGCCCTGTTGGTCAACTCTTCCCAGCC GTGGGAGCCCCTGCAGCTGCATGTGGATAAAGCCGTCAGTGGCCT TCGCAGCCTCACCACTCTGCTTCGGGCTCTGGGAGCCCAGAAGGA AGCCATCTCCCCTCCAGATGCGGCCTCAGCTGCTCCACTCCGAAC AATCACTGCTGACACTTTCCGCAAACTCTTCCGAGTCTACTCCAATT TCCTCCGGGGAAAGCTGAAGCTGTACACAGGGGAGGCCTGCAGG ACAGGGGACAGAGGCGGAGGTGGGAGTACCGCGGTCGCATGGT* ATCAGCAGAAACCAGGGAAAGCCCCTAAGCTCCTGATCTATTC TGCATCCTTCTTGTATAGTGGGGTCCCATCAAGGTTCAGTGGC AGTAGATCTGGGACAGATTTCACTCTCACCATCAGCAGTCTGC AACCTGAAGATTTTGCAACTTACTACTGTCAACAGCATTACAC TACCCCTCCGACGTTCGGCCAAGGTACCAAGCTTGAGATCAAA CGAACTGTGGCTGCACCATCTGTCTTCATCTTCCCGCCATCTGA TGAGCAGTTGAAATCTGGAACTGCCTCTGTCGTGTGCCTGCTG AATAACTTCTATCCCAGAGAGGCCAAAGTACAGTGGAAGGTG GATAACGCCCTCCAATCGGGTAACTCCCAGGAGAGTGTCACAG |

TABLE 5-continued

Direct Immunoglobulin Fusion Proteins—Nucleotide Sequence

| NAME | SEQ ID NO | SEQUENCE |
|---|---|---|
| | | AGCAGGACAGCAAGGACAGCACCTACAGCCTCAGCAGCACCC |
| | | TGACGCTGAGCAAAGCAGACTACGAGAAACACAAAGTCTACG |
| | | CCTGCGAAGTCACCCATCAGGGCCTGTCCTCGCCCGTCACAAA |
| | | GAGCTTCAACAGGGGAGAGTGT |
| trastuzumab-direct bGCSF HC (CDRH3) | 101 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGATGGGG |
| | | CGGTGAC*GGAGGCGGTGGCTCC*ACCCCCCTTGGCCCTGCCCGAT |
| | | *CCCTGCCCCAGAGCTTCCTGCTCAAGTGCTTAGAGCAAGTGAGGA* |
| | | *AAATCCAGGCTGATGGCGCCGAGCTGCAGGAGAGGCTGTGTGCC* |
| | | *GCCCACAAGCTGTGCCACCCGGAGGAGCTGATGCTGCTCAGGCA* |
| | | *CTCTCTGGGCATCCCCCAGGCTCCCCTAAGCAGCTGCTCCAGCCA* |
| | | *GTCCCTGCAGCTGACGAGCTGCCTGAACCAACTACACGGCGGCCT* |
| | | *CTTTCTCTACCAGGGCCTCCTGCAGGCCCTGGCGGGCATCTCCCC* |
| | | *AGAGCTGGCCCCCACCTTGGACACACTGCAGCTGGACGTCACTGA* |
| | | *CTTTGCCACGAACATCTGGCTGCAGATGGAGGACCTGGGGGCGG* |
| | | *CCCCCGCTGTGCAGCCCACCCAGGGCGCCATGCCGACCTTCACTT* |
| | | *CAGCCTTCCAACGCAGAGCAGGAGGGGTCCTGGTTGCTTCCCAGC* |
| | | *TGCATCGTTTCCTGGAGCTGGCATACCGTGGCCTGCGCTACCTTG* |
| | | *CTGAGCCC*GGCGGTGGCGGAAGCGGCTTCTATGCCATGGACTA |
| | | CTGGGGCCAAGGAACCCTGGTCACCGTCTCCTCAGCCTCCACC |
| | | AAGGGCCCATCGGTCTTCCCCCTGGCACCCTCCTCCAAGAGCA |
| | | CCTCTGGGGGCACAGCGGCCCTGGGCTGCCTGGTCAAGGACTA |
| | | CCTCTGGGGGCACAGCGGCCCTGGGCTGCCTGGTCAAGGACTA |
| | | CTTCCCCGAACCGGTGACGGTGTCGTGGAACTCAGGCGCCCTG |
| | | ACCAGCGGCGTGCACACCTTCCCGGCTGTCCTACAGTCCTCAG |
| | | GACTCTACTCCCTCAGCAGCGTGGTGACTGTGCCCTCTAGCAG |
| | | CTTGGGCACCCAGACCTACATCTGCAACGTGAATCACAAGCCC |
| | | AGCAACACCAAGGTGGACAAGAAAGTTGAACCCAAATCTTGC |
| | | GACAAAACTCACACATGCCCACCGTGCCCAGCACCTGAACTCC |
| | | TGGGGGGACCGTCAGTCTTCCTCTTCCCCCCAAAACCCAAGGA |
| | | CACCCTCATGATCTCCCGGACCCCTGAGGTCACATGCGTGGTG |
| | | GTGGACGTGAGCCACGAAGACCCTGAGGTCAAGTTCAACTGG |
| | | TACGTGGACGGCGTGGAGGTGCATAATGCCAAGACAAAGCCG |
| | | CGGGAGGAGCAGTACAACAGCACGTACCGTGTGGTCAGCGTC |
| | | CTCACCGTCCTGCACCAGGACTGGCTGAATGGCAAGGAGTACA |
| | | AGTGCAAGGTCTCCAACAAAGCCCTCCCAGCCCCCATCGAGAA |
| | | AACCATCTCCAAAGCCAAAGGGCAGCCCCGAGAACCACAGGT |

TABLE 5-continued

Direct Immunoglobulin Fusion Proteins—Nucleotide Sequence

| NAME | SEQ ID NO | SEQUENCE |
|---|---|---|
| | | GTACACCCTGCCCCCATCCCGGGATGAGCTGACCAAGAACCAG |
| | | GTCAGCCTGACCTGCCTGGTCAAAGGCTTCTATCCCAGCGACA |
| | | TCGCCGTGGAGTGGGAGAGCAATGGGCAGCCGGAGAACAACT |
| | | ACAAGACCACGCCTCCCGTGCTGGACTCCGACGGCTCCTTCTT |
| | | CCTCTACAGCAAGCTCACCGTGGACAAGAGCAGGTGGCAGCA |
| | | GGGGAACGTCTTCTCATGCTCCGTGATGCATGAGGCTCTGCAC |
| | | AACCACTACACGCAGAAGAGCCTCTCCCTGTCTCCGGGTAAA |
| trastuzumab-direct exendin-4 HC | 102 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGATGCGG |
| | | GGGTGGCGGAAGCATCGAAGGTCGTCACGGAGAAGGAACATTTAC |
| | | CAGCGACCTCAGCAAGCAGATGGAGGAAGAGGCCGTGAGGCTGT |
| | | TCATCGAGTGGCTGAAGAACGGCGGACCCTCCTCTGGCGCTCCAC |
| | | CCCCTAGCGGCGGAGGTGGGAGTTGCGACTACTGGGGCCAAGG |
| | | AACCCTGGTCACCGTCTCCTCAGCCTCCACCAAGGGCCCATCG |
| | | GTCTTCCCCCTGGCACCCTCCTCCAAGAGCACCTCTGGGGGCA |
| | | CAGCGGCCCTGGGCTGCCTGGTCAAGGACTACTTCCCCGAACC |
| | | GGTGACGGTGTCGTGGAACTCAGGCGCCCTGACCAGCGGCGT |
| | | GCACACCTTCCCGGCTGTCCTACAGTCCTCAGGACTCTACTCCC |
| | | TCAGCAGCGTGGTGACTGTGCCCTCTAGCAGCTTGGGCACCCA |
| | | GACCTACATCTGCAACGTGAATCACAAGCCCAGCAACACCAA |
| | | GGTGGACAAGAAAGTTGAACCCAAATCTTGCGACAAAACTCA |
| | | CACATGCCCACCGTGCCCAGCACCTGAACTCCTGGGGGGACCG |
| | | TCAGTCTTCCTCTTCCCCCCAAAACCCAAGGACACCCTCATGA |
| | | TCTCCCGGACCCCTGAGGTCACATGCGTGGTGGTGGACGTGAG |
| | | CCACGAAGACCCTGAGGTCAAGTTCAACTGGTACGTGGACGG |
| | | CGTGGAGGTGCATAATGCCAAGACAAAGCCGCGGGAGGAGCA |
| | | GTACAACAGCACGTACCGTGTGGTCAGCGTCCTCACCGTCCTG |
| | | CACCAGGACTGGCTGAATGGCAAGGAGTACAAGTGCAAGGTC |
| | | TCCAACAAAGCCCTCCCAGCCCCCATCGAGAAAACCATCTCCA |
| | | AAGCCAAAGGGCAGCCCCGAGAACCACAGGTGTACACCCTGC |
| | | CCCCATCCCGGGATGAGCTGACCAAGAACCAGGTCAGCCTGA |
| | | CCTGCCTGGTCAAAGGCTTCTATCCCAGCGACATCGCCGTGGA |
| | | GTGGGAGAGCAATGGGCAGCCGGAGAACAACTACAAGACCAC |
| | | GCCTCCCGTGCTGGACTCCGACGGCTCCTTCTTCCTCTACAGCA |
| | | AGCTCACCGTGGACAAGAGCAGGTGGCAGCAGGGGAACGTCT |

TABLE 5-continued

Direct Immunoglobulin Fusion Proteins—Nucleotide Sequence

| NAME | SEQ ID NO | SEQUENCE |
|---|---|---|
| | | TCTCATGCTCCGTGATGCATGAGGCTCTGCACAACCACTACAC |
| | | GCAGAAGAGCCTCTCCCTGTCTCCGGGTAAA |
| trastuzumab-direct Moka1 HC | 103 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGA*GGAGG* |
| | | *CGGTGGCTCC*ATCAACGTGAAGTGCAGCCTGCCCCAGCAGTGCAT |
| | | CAAGCCCTGCAAGGACGCCGGCATGCGGTTCGGCAAGTGCATGAA |
| | | CAAGAAGTGCAGGTGCTACAGC*GGCGGTGGCGGAAGC*GACTACT |
| | | GGGGCCAAGGAACCCTGGTCACCGTCTCCTCAGCCTCCACCAA |
| | | GGGCCCATCGGTCTTCCCCCTGGCACCCTCCTCCAAGAGCACC |
| | | TCTGGGGGCACAGCGGCCCTGGGCTGCCTGGTCAAGGACTACT |
| | | TCCCCGAACCGGTGACGGTGTCGTGGAACTCAGGCGCCCTGAC |
| | | CAGCGGCGTGCACACCTTCCCGGCTGTCCTACAGTCCTCAGGA |
| | | CTCTACTCCCTCAGCAGCGTGGTGACTGTGCCCTCTAGCAGCTT |
| | | GGGCACCCAGACCTACATCTGCAACGTGAATCACAAGCCCAG |
| | | CAACACCAAGGTGGACAAGAAAGTTGAACCCAAATCTTGCGA |
| | | CAAAACTCACACATGCCCACCGTGCCCAGCACCTGAACTCCTG |
| | | GGGGGACCGTCAGTCTTCCTCTTCCCCCCAAAACCCAAGGACA |
| | | CCCTCATGATCTCCCGGACCCCTGAGGTCACATGCGTGGTGGT |
| | | GGACGTGAGCCACGAAGACCCTGAGGTCAAGTTCAACTGGTA |
| | | CGTGACGGCGTGGAGGTGCATAATGCCAAGACAAAGCCGCG |
| | | GGAGGAGCAGTACAACAGCACGTACCGTGTGGTCAGCGTCCT |
| | | CACCGTCCTGCACCAGGACTGGCTGAATGGCAAGGAGTACAA |
| | | GTGCAAGGTCTCCAACAAAGCCCTCCCAGCCCCCATCGAGAAA |
| | | ACCATCTCCAAAGCCAAAGGGCAGCCCCGAGAACCACAGGTG |
| | | TACACCCTGCCCCCATCCCGGGATGAGCTGACCAAGAACCAGG |
| | | TCAGCCTGACCTGCCTGGTCAAAGGCTTCTATCCCAGCGACAT |
| | | CGCCGTGGAGTGGGAGAGCAATGGGCAGCCGGAGAACAACTA |
| | | CAAGACCACGCCTCCCGTGCTGGACTCCGACGGCTCCTTCTTC |
| | | CTCTACAGCAAGCTCACCGTGGACAAGAGCAGGTGGCAGCAG |
| | | GGGAACGTCTTCTCATGCTCCGTGATGCATGAGGCTCTGCACA |
| | | ACCACTACACGCAGAAGAGCCTCTCCCTGTCTCCGGGTAAA |
| trastuzumab-direct VM24 HC | 104 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |

TABLE 5-continued

Direct Immunoglobulin Fusion Proteins—Nucleotide Sequence

| NAME | SEQ ID NO | SEQUENCE |
|---|---|---|
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGAGG |
| | | CGGTGGCTCCGCCGCTGCAATCTCCTGCGTCGGCAGCCCCGAAT |
| | | GTCCTCCCAAGTGCCGGGCTCAGGGATGCAAGAACGGCAAGTGTA |
| | | TGAACCGGAAGTGCAAGTGCTACTATTGCGGCGGTGGCGGAAGCG |
| | | ACTACTGGGGCCAAGGAACCCTGGTCACCGTCTCCTCAGCCTC |
| | | CACCAAGGGCCCATCGGTCTTCCCCCTGGCACCCTCCTCCAAG |
| | | AGCACCTCTGGGGGCACAGCGGCCCTGGGCTGCCTGGTCAAG |
| | | GACTACTTCCCCGAACCGGTGACGGTGTCGTGGAACTCAGGCG |
| | | CCCTGACCAGCGGCGTGCACACCTTCCCGGCTGTCCTACAGTC |
| | | CTCAGGACTCTACTCCCTCAGCAGCGTGGTGACTGTGCCCTCT |
| | | AGCAGCTTGGGCACCCAGACCTACATCTGCAACGTGAATCACA |
| | | AGCCCAGCAACACCAAGGTGGACAAGAAAGTTGAACCCAAAT |
| | | CTTGCGACAAAACTCACACATGCCCACCGTGCCCAGCACCTGA |
| | | ACTCCTGGGGGGACCGTCAGTCTTCCTCTTCCCCCCAAAACCC |
| | | AAGGACACCCTCATGATCTCCCGGACCCCTGAGGTCACATGCG |
| | | TGGTGGTGGACGTGAGCCACGAAGACCCTGAGGTCAAGTTCA |
| | | ACTGGTACGTGGACGGCGTGGAGGTGCATAATGCCAAGACAA |
| | | AGCCGCGGGAGGAGCAGTACAACAGCACGTACCGTGTGGTCA |
| | | GCGTCCTCACCGTCCTGCACCAGGACTGGCTGAATGGCAAGGA |
| | | GTACAAGTGCAAGGTCTCCAACAAAGCCCTCCCAGCCCCCATC |
| | | GAGAAAACCATCTCCAAAGCCAAAGGGCAGCCCCGAGAACCA |
| | | CAGGTGTACACCCTGCCCCCATCCCGGGATGAGCTGACCAAGA |
| | | ACCAGGTCAGCCTGACCTGCCTGGTCAAAGGCTTCTATCCCAG |
| | | CGACATCGCCGTGGAGTGGGAGAGCAATGGGCAGCCGGAGAA |
| | | CAACTACAAGACCACGCCTCCCGTGCTGGACTCCGACGGCTCC |
| | | TTCTTCCTCTACAGCAAGCTCACCGTGGACAAGAGCAGGTGGC |
| | | AGCAGGGGAACGTCTTCTCATGCTCCGTGATGCATGAGGCTCT |
| | | GCACAACCACTACACGCAGAAGAGCCTCTCCCTGTCTCCGGGT |
| | | AAA |
| Herceptin-direct hGCSF HC | 105 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGGGG |
| | | TGGCGGAAGCGCCACACCTCTGGGCCCCGCCTCCTCCCTGCCTCA |
| | | GAGCTTTCTGCTCAAATGTCTGGAGCAGGTGCGGAAGATCCAGGG |
| | | CGACGGCGCCGCTCTGCAAGAGAAACTGGTCAGCGAATGCGCCA |
| | | CATATAAGCTGTGTCACCCCGAGGAACTGGTCCTCTTGGGCCACA |

TABLE 5-continued

Direct Immunoglobulin Fusion Proteins—Nucleotide Sequence

| NAME | SEQ ID NO | SEQUENCE |
|---|---|---|
| | | GCCTGGGCATCCCCTGGGCCCCTCTCAGCTCCTGCCCCTCCCAAG<br>CTCTCCAACTGGCTGGATGTCTGTCCCAACTGCACTCCGGCCTCTT<br>CCTGTACCAGGGACTCCTCCAGGCTCTCGAAGGGATCAGCCCCGA<br>ACTGGGCCCCACACTGGACACCTTGCAACTCGATGTGGCCGATTT<br>CGCCACAACCATCTGGCAGCAGATGGAAGAACTCGGAATGGCTCC<br>TGCTCTCCAGCCCACACAGGGAGCTATGCCTGCTTTCGCCTCTGCT<br>TTCCAGCGGAGAGCTGGTGGTGTGCTCGTCGCATCCCACCTCCAG<br>AGCTTCTTGGAGGTGTCCTATCGGGTGCTCCGGCATCTGGCCCAA<br>CCCGGCGGAGGTGGGAGTGACTACTGGGGCCAAGGAACCCTGG<br>TCACCGTCTCCTCAGCCAGCACTAAAGGTCCATCTGTGTTCCCT<br>CTGGCTCCTTGCAGCCGGAGCACCTCCGAGTCCACAGCCGCTC<br>TGGGATGTCTGGTGAAAGATTACTTCCCCGAGCCCGTCACCGT<br>GAGCTGGAATAGCGGAGCACTGACCTCCGGCGTCCACACATTC<br>CCCGCCGTGCTCCAAAGCTCCGGCCTGTACAGCCTCTCCTCCG<br>TGGTCACCGTGCCCAGCAGCTCTCTGGGCACAAAGACCTATAC<br>CTGTAACGTGGATCACAAGCCTAGCAACACCAAAGTGGATAA<br>GCGGGTGGAGAGCAAGTACGGCCCTCCCTGTCCCCCTTGCCCC<br>GCTCCTGAGGCCGCTGGCGGACCTTCCGTGTTCCTGTTTCCCCC<br>TAAGCCCAAGGACACCCTCATGATTAGCCGGACACCCGAAGT<br>GACCTGCGTGGTCGTGGATGTGTCCCAGGAGGACCCTGAAGTG<br>CAATTTAACTGGTACGTGGACGGCGTCGAGGTGCACAACGCCA<br>AGACCAAGCCTCGGGAAGAGCAGTTCAACAGCACCTACCGGG<br>TGGTCAGCGTGCTGACAGTGCTGCACCAGGACTGGCTGAACGG<br>CAAGGAGTACAAGTGCAAGGTGAGCAACAAGGGCCTGCCCAG<br>CTCCATCGAGAAGACCATCAGCAAGGCCAAGGGCCAGCCCAG<br>GGAACCCCAGGTGTATACCCTGCCCCCTAGCCAGGAGGAAAT<br>GACCAAAAACCAGGTGAGCCTGACCTGCCTGGTGAAGGGCTT<br>CTACCCCAGCGACATCGCCGTGGAGTGGGAGAGCAACGGCCA<br>GCCCGAGAACAATTACAAGACCACCCCTCCTGTGCTGGACAGC<br>GACGGCTCCTTCTTTCTGTATAGCCGGCTGACCGTGGACAAGA<br>GCAGGTGGCAGGAGGGCAACGTGTTCTCCTGTAGCGTGATGCA<br>CGAGGCCCTGCACAACCATTACACCCAGAAGAGCTTGAGCCTG<br>AGCCTGGGCAAA |
| trastuzumab-<br>direct hGH HC | 106 | GAGGTGCAGCTGGTGGAGTCTGGAGGAGGCTTGGTCCAGCCT<br>GGGGGGTCCCTGAGACTCTCCTGTGCAGCCTCTGGGTTCAATA<br>TTAAGGACACTTACATCCACTGGGTCCGCCAGGCTCCAGGGAA<br>GGGGCTGGAGTGGGTCGCACGTATTTATCCTACCAATGGTTAC<br>ACACGCTACGCAGACTCCGTGAAGGGCCGATTCACCATCTCCG<br>CAGACACTTCCAAGAACACGGCGTATCTTCAAATGAACAGCCT<br>GAGAGCCGAGGACACGGCCGTGTATTACTGTTCGAGAGGGGG<br>TGGCGGAAGCTTCCCAACCATTCCCTTATCCAGGCTTTTTGACAAC<br>GCTATGCTCCGCGCCCATCGTCTGCACCAGCTGGCCTTTGACACC<br>TACCAGGAGTTTGAAGAAGCCTATATCCCAAAGGAACAGAAGTATT<br>CATTCCTGCAGAACCCCCAGACCTCCCTCTGTTTCTCAGAGTCTAT<br>TCCGACACCCTCCAACAGGGAGGAAACACAACAGAAATCCAACCTA<br>GAGCTGCTCCGCATCTCCCTGCTGCTCATCCAGTCGTGGCTGGAG<br>CCCGTGCAGTTCCTCAGGAGTGTCTTCGCCAACAGCCTGGTGTAC |

TABLE 5-continued

Direct Immunoglobulin Fusion Proteins—Nucleotide Sequence

| NAME | SEQ ID NO | SEQUENCE |
|---|---|---|
| | | *GGCGCCTCTGACAGCAACGTCTATGACCTCCTAAAGGACCTAGAG*<br>*GAAGGCATCCAAACGCTGATGGGGAGGCTGGAAGATGGCAGCCC*<br>*CCGGACTGGGCAGATCTTCAAGCAGACCTACAGCAAGTTCGACAC*<br>*AAACTCACACAACGATGACGCACTACTCAAGAACTACGGGCTGCTC*<br>*TACTGCTTCAGGAAGGACATGGACAAGGTCGAGACATTCCTGCGC*<br>*ATCGTGCAGTGCCGCTCTGTGGAGGGCAGCTGTGGCTTC*GGCGG<br><br>AGGTGGGAGTGACTACTGGGGCCAAGGAACCCTGGTCACCGTC<br><br>TCCTCAGCCAGCACTAAAGGTCCATCTGTGTTCCCTCTGGCTCC<br><br>TTGCAGCCGGAGCACCTCCGAGTCCACAGCCGCTCTGGGATGT<br><br>CTGGTGAAAGATTACTTCCCCGAGCCCGTCACCGTGAGCTGGA<br><br>ATAGCGGAGCACTGACCTCCGGCGTCCACACATTCCCCGCCGT<br><br>GCTCCAAAGCTCCGGCCTGTACAGCCTCTCCTCCGTGGTCACC<br><br>GTGCCCAGCAGCTCTCTGGGCACAAAGACCTATACCTGTAACG<br><br>TGGATCACAAGCCTAGCAACACCAAAGTGGATAAGCGGGTGG<br><br>AGAGCAAGTACGGCCCTCCCTGTCCCCCTTGCCCCGCTCCTGA<br><br>GGCCGCTGGCGGACCTTCCGTGTTCCTGTTTCCCCCTAAGCCCA<br><br>AGGACACCCTCATGATTAGCCGGACACCCGAAGTGACCTGCGT<br><br>GGTCGTGGATGTGTCCCAGGAGGACCCTGAAGTGCAATTTAAC<br><br>TGGTACGTGGACGGCGTCGAGGTGCACAACGCCAAGACCAAG<br><br>CCTCGGGAAGAGCAGTTCAACAGCACCTACCGGGTGGTCAGC<br><br>GTGCTGACAGTGCTGCACCAGGACTGGCTGAACGGCAAGGAG<br><br>TACAAGTGCAAGGTGAGCAACAAGGGCCTGCCCAGCTCCATC<br><br>GAGAAGACCATCAGCAAGGCCAAGGGCCAGCCCAGGGAACCC<br><br>CAGGTGTATACCCTGCCCCCTAGCCAGGAGGAAATGACCAAA<br><br>AACCAGGTGAGCCTGACCTGCCTGGTGAAGGGCTTCTACCCCA<br><br>GCGACATCGCCGTGGAGTGGGAGAGCAACGGCCAGCCCGAGA<br><br>ACAATTACAAGACCACCCCTCCTGTGCTGGACAGCGACGGCTC<br><br>CTTCTTTCTGTATAGCCGGCTGACCGTGGACAAGAGCAGGTGG<br><br>CAGGAGGGCAACGTGTTCTCCTGTAGCGTGATGCACGAGGCCC<br><br>TGCACAACCATTACACCCAGAAGAGCTTGAGCCTGAGCCTGGG<br><br>CAAA |
| trastuzumab-direct hLeptin HC | 107 | GAGGTGCAGCTGGTGGAGTCTGGAGGAGGCTTGGTCCAGCCT<br><br>GGGGGGTCCCTGAGACTCTCCTGTGCAGCCTCTGGGTTCAATA<br><br>TTAAGGACACTTACATCCACTGGGTCCGCCAGGCTCCAGGGAA<br><br>GGGGCTGGAGTGGGTCGCACGTATTTATCCTACCAATGGTTAC<br><br>ACACGCTACGCAGACTCCGTGAAGGGCCGATTCACCATCTCCG<br><br>CAGACACTTCCAAGAACACGGCGTATCTTCAAATGAACAGCCT<br><br>GAGAGCCGAGGACACGGCCGTGTATTACTGTTCGAGA*GGTGG*<br><br>*CGGAGGATCTGTT*CCAATTCAAAAGGTTCAAGATGATACCAAAACT<br>CTGATTAAAACTATTGTCACGCGTATAAACGACATCAGCCATACCCA<br>GTCGGTTAGCTCAAAGCAAAAAGTTACCGGTTTGGACTTTATTCCG<br>GGACTGCACCCGATCCTGACCCTTAGTAAAATGGACCAGACACTG<br>GCCGTCTACCAGCAAATCCTGACATCGATGCCATCCAGAAATGTGA<br>TACAAATTAGCAACGATTTGGAAAACCTTCGCGATCTGCTGCACGT<br>GCTGGCCTTCAGTAAGTCCTGTCATCTGCCGTGGGCGTCGGGACT<br>GGAGACTCTTGACTCGCTGGGTGGAGTGTTAGAGGCCTCTGGCTA |

TABLE 5-continued

Direct Immunoglobulin Fusion Proteins—Nucleotide Sequence

| NAME | SEQ ID NO | SEQUENCE |
|---|---|---|
| | | TTCTACTGAAGTCGTTGCGCTGTCACGCCTCCAGGGGAGCCTGCA |
| | | GGACATGCTGTGGCAGCTGGACCTGTCACCTGGCTGCGGAGGTG |
| | | GTGGTTCAGACTACTGGGGCCAAGGAACCCTGGTCACCGTCTC |
| | | CTCAGCCAGCACTAAAGGTCCATCTGTGTTCCCTCTGGCTCCTT |
| | | GCAGCCGGAGCACCTCCGAGTCCACAGCCGCTCTGGGATGTCT |
| | | GGTGAAAGATTACTTCCCCGAGCCCGTCACCGTGAGCTGGAAT |
| | | AGCGGAGCACTGACCTCCGGCGTCCACACATTCCCCGCCGTGC |
| | | TCCAAAGCTCCGGCCTGTACAGCCTCTCCTCCGTGGTCACCGT |
| | | GCCCAGCAGCTCTCTGGGCACAAAGACCTATACCTGTAACGTG |
| | | GATCACAAGCCTAGCAACACCAAAGTGGATAAGCGGGTGGAG |
| | | AGCAAGTACGGCCCTCCCTGTCCCCCTTGCCCCGCTCCTGAGG |
| | | CCGCTGGCGGACCTTCCGTGTTCCTGTTTCCCCCTAAGCCCAAG |
| | | GACACCCTCATGATTAGCCGGACACCCGAAGTGACCTGCGTGG |
| | | TCGTGGATGTGTCCCAGGAGGACCCTGAAGTGCAATTTAACTG |
| | | GTACGTGGACGGCGTCGAGGTGCACAACGCCAAGACCAAGCC |
| | | TCGGGAAGAGCAGTTCAACAGCACCTACCGGGTGGTCAGCGT |
| | | GCTGACAGTGCTGCACCAGGACTGGCTGAACGGCAAGGAGTA |
| | | CAAGTGCAAGGTGAGCAACAAGGGCCTGCCCAGCTCCATCGA |
| | | GAAGACCATCAGCAAGGCCAAGGGCCAGCCCAGGGAACCCCA |
| | | GGTGTATACCCTGCCCCCTAGCCAGGAGGAAATGACCAAAAA |
| | | CCAGGTGAGCCTGACCTGCCTGGTGAAGGGCTTCTACCCCAGC |
| | | GACATCGCCGTGGAGTGGGAGAGCAACGGCCAGCCCGAGAAC |
| | | AATTACAAGACCACCCCTCCTGTGCTGGACAGCGACGGCTCCT |
| | | TCTTTCTGTATAGCCGGCTGACCGTGGACAAGAGCAGGTGGCA |
| | | GGAGGGCAACGTGTTCTCCTGTAGCGTGATGCACGAGGCCCTG |
| | | CACAACCATTACACCCAGAAGAGCTTGAGCCTGAGCCTGGGC |
| | | AAA |
| trastuzumab-direct-hIFN-alpha HC | 108 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGTGGT |
| | | GGCGGAAGCTGTGATCTGCCTCAAACCCACAGCCTGGGTAGCAGG |
| | | AGGACCTTGATGCTCCTGGCACAGATGAGGAGAATCTCTCTTTTCT |
| | | CCTGCTTGAAGGACAGACATGACTTTGGATTTCCCCAGGAGGAGTT |
| | | TGGCAACCAGTTCCAAAAGGCTGAAACCATCCCTGTCCTCCATGAG |
| | | ATGATCCAGCAGATCTTCAATCTCTTCAGCACAAAGGACTCATCTG |
| | | CTGCTTGGGATGAGACCCTCCTAGACAAATTCTACACTGAACTCTA |
| | | CCAGCAGCTGAATGACCTGGAAGCCTGTGTGATACAGGGGGTGGG |
| | | GGTGACAGAGACTCCCCTGATGAAGGAGGACTCCATTCTGGCTGT |
| | | GAGGAAATACTTCCAAAGAATCACTCTCTATCTGAAAGAAGAAAT |
| | | ACAGCCCTTGTGCCTGGGAGGTTGTCAGAGCAGAAATCATGAGAT |
| | | CTTTTTCTTTGTCAACAAACTTGCAAGAAAGTTTAAGAAGTAAGGAA |

TABLE 5-continued

Direct Immunoglobulin Fusion Proteins—Nucleotide Sequence

| NAME | SEQ ID NO | SEQUENCE |
|------|-----------|----------|
| | | *GGCGGAGGTGGGAGT*GACTACTGGGGCCAAGGAACCCTGGTCA |
| | | CCGTCTCCTCAGCCAGCACTAAAGGTCCATCTGTGTTCCCTCTG |
| | | GCTCCTTGCAGCCGGAGCACCTCCGAGTCCACAGCCGCTCTGG |
| | | GATGTCTGGTGAAAGATTACTTCCCCGAGCCCGTCACCGTGAG |
| | | CTGGAATAGCGGAGCACTGACCTCCGGCGTCCACACATTCCCC |
| | | GCCGTGCTCCAAAGCTCCGGCCTGTACAGCCTCTCCTCCGTGG |
| | | TCACCGTGCCCAGCAGCTCTCTGGGCACAAAGACCTATACCTG |
| | | TAACGTGGATCACAAGCCTAGCAACACCAAAGTGGATAAGCG |
| | | GGTGGAGAGCAAGTACGGCCCTCCCTGTCCCCCTTGCCCCGCT |
| | | CCTGAGGCCGCTGGCGGACCTTCCGTGTTCCTGTTTCCCCCTAA |
| | | GCCCAAGGACACCCTCATGATTAGCCGGACACCCGAAGTGAC |
| | | CTGCGTGGTCGTGGATGTGTCCCAGGAGGACCCTGAAGTGCAA |
| | | TTTAACTGGTACGTGGACGGCGTCGAGGTGCACAACGCCAAG |
| | | ACCAAGCCTCGGGAAGAGCAGTTCAACAGCACCTACCGGGTG |
| | | GTCAGCGTGCTGACAGTGCTGCACCAGGACTGGCTGAACGGC |
| | | AAGGAGTACAAGTGCAAGGTGAGCAACAAGGGCCTGCCCAGC |
| | | TCCATCGAGAAGACCATCAGCAAGGCCAAGGGCCAGCCCAGG |
| | | GAACCCCAGGTGTATACCCTGCCCCCTAGCCAGGAGGAAATG |
| | | ACCAAAAACCAGGTGAGCCTGACCTGCCTGGTGAAGGGCTTCT |
| | | ACCCCAGCGACATCGCCGTGGAGTGGGAGAGCAACGGCCAGC |
| | | CCGAGAACAATTACAAGACCACCCCTCCTGTGCTGGACAGCGA |
| | | CGGCTCCTTCTTTCTGTATAGCCGGCTGACCGTGGACAAGAGC |
| | | AGGTGGCAGGAGGGCAACGTGTTCTCCTGTAGCGTGATGCACG |
| | | AGGCCCTGCACAACCATTACACCCAGAAGAGCTTGAGCCTGA |
| | | GCCTGGGCAAA |
| trastuzumab-direct GLP1 HC | 109 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGA*TGCGG* |
| | | *GGGTGGCGG*AAGCATCGAAGGTCGTCACGCTGAGGGAACATTCAC |
| | | TTCCGATGTGTCCTCCTACCTGGAGGGCCAGGCTGCCAAAGAGTT |
| | | CATCGCTTGGCTCGTCAAGGGCAGG*GGCGGAGGTGGGAGT*TGCG |
| | | ACTACTGGGGCCAAGGAACCCTGGTCACCGTCTCCTCAGCCTC |
| | | CACCAAGGGCCCATCGGTCTTCCCCCTGGCACCCTCCTCCAAG |
| | | AGCACCTCTGGGGGCACAGCGGCCCTGGGCTGCCTGGTCAAG |
| | | GACTACTTCCCCGAACCGGTGACGGTGTCGTGGAACTCAGGCG |
| | | CCCTGACCAGCGGCGTGCACACCTTCCCGGCTGTCCTACAGTC |

TABLE 5-continued

Direct Immunoglobulin Fusion Proteins—Nucleotide Sequence

| NAME | SEQ ID NO | SEQUENCE |
|---|---|---|
| | | CTCAGGACTCTACTCCCTCAGCAGCGTGGTGACTGTGCCCTCT |
| | | AGCAGCTTGGGCACCCAGACCTACATCTGCAACGTGAATCACA |
| | | AGCCCAGCAACACCAAGGTGGACAAGAAAGTTGAACCCAAAT |
| | | CTTGCGACAAAACTCACACATGCCCACCGTGCCCAGCACCTCC |
| | | AGTCGCCGGACCGTCAGTCTTCCTCTTCCCTCCAAAACCCAAG |
| | | GACACCCTCATGATCTCCCGGACCCCTGAGGTCACATGCGTGG |
| | | TGGTGGACGTGAGCCACGAAGACCCTGAGGTCAAGTTCAACT |
| | | GGTACGTGGACGGCGTGGAGGTGCATAATGCCAAGACAAAGC |
| | | CGCGGGAGGAGCAGTACAACAGCACGTACCGTGTGGTCAGCG |
| | | TCCTCACCGTCCTGCACCAGGACTGGCTGAATGGCAAGGAGTA |
| | | CAAGTGCAAGGTCTCCAACAAAGGCCTCCCAAGCTCCATCGAG |
| | | AAAACCATCTCCAAAGCCAAGGGCAGCCCCGAGAACCACAG |
| | | GTGTACACCCTGCCTCCATCCCGGGATGAGCTGACCAAGAACC |
| | | AGGTCAGCCTGACCTGCCTGGTCAAAGGCTTCTATCCCAGCGA |
| | | CATCGCCGTGGAGTGGGAGAGCAATGGGCAGCCGGAGAACAA |
| | | CTACAAGACCACGCCTCCCGTGCTGGACTCCGACGGCTCCTTC |
| | | TTCCTCTACAGCAAGCTCACCGTGGACAAGAGCAGGTGGCAGC |
| | | AGGGGAACGTCTTCTCATGCTCCGTGATGCATGAGGCTCTGCA |
| | | CAACCACTACACGCAGAAGAGCCTCTCCCTGTCTCCGGGTAAA |
| trastuzumab-direct elafin HC | 110 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGGGG |
| | | TGGCGGAAGCGCGCAAGAGCCAGTCAAAGGTCCAGTCTCCACTAA |
| | | GCCTGGCTCCTGCCCCATTATCTTGATCCGGTGCGCCATGTTGAAT |
| | | CCCCCTAACCGCTGCTTGAAAGATACTGACTGCCCAGGAATCAAGA |
| | | AGTGCTGTGAAGGCTCTTGCGGGATGGCCTGTTTCGTTCCCCAGG |
| | | GCGGAGGTGGGAGTGACTACTGGGGCCAAGGAACCCTGGTCAC |
| | | CGTCTCCTCAGCCTCCACCAAGGGCCCATCGGTCTTCCCCCTG |
| | | GCACCCTCCTCCAAGAGCACCTCTGGGGGCACAGCGGCCCTGG |
| | | GCTGCCTGGTCAAGGACTACTTCCCCGAACCGGTGACGGTGTC |
| | | GTGGAACTCAGGCGCCCTGACCAGCGGCGTGCACACCTTCCCG |
| | | GCTGTCCTACAGTCCTCAGGACTCTACTCCCTCAGCAGCGTGG |
| | | TGACTGTGCCCTCTAGCAGCTTGGGCACCCAGACCTACATCTG |
| | | CAACGTGAATCACAAGCCCAGCAACACCAAGGTGGACAAGAA |
| | | AGTTGAACCCAAATCTTGCGACAAAACTCACACATGCCCACCG |
| | | TGCCCAGCACCTCCAGTCGCCGGACCGTCAGTCTTCCTCTTCCC |
| | | TCCAAAACCCAAGGACACCCTCATGATCTCCCGGACCCCTGAG |

TABLE 5-continued

Direct Immunoglobulin Fusion Proteins—Nucleotide Sequence

| NAME | SEQ ID NO | SEQUENCE |
|---|---|---|
| | | GTCACATGCGTGGTGGTGGACGTGAGCCACGAAGACCCTGAG |
| | | GTCAAGTTCAACTGGTACGTGGACGGCGTGGAGGTGCATAATG |
| | | CCAAGACAAAGCCGCGGGAGGAGCAGTACAACAGCACGTACC |
| | | GTGTGGTCAGCGTCCTCACCGTCCTGCACCAGGACTGGCTGAA |
| | | TGGCAAGGAGTACAAGTGCAAGGTCTCCAACAAAGGCCTCCC |
| | | AAGCTCCATCGAGAAAACCATCTCCAAAGCCAAAGGGCAGCC |
| | | CCGAGAACCACAGGTGTACACCCTGCCTCCATCCCGGGATGAG |
| | | CTGACCAAGAACCAGGTCAGCCTGACCTGCCTGGTCAAAGGCT |
| | | TCTATCCCAGCGACATCGCCGTGGAGTGGGAGAGCAATGGGC |
| | | AGCCGGAGAACAACTACAAGACCACGCCTCCCGTGCTGGACT |
| | | CCGACGGCTCCTTCTTCCTCTACAGCAAGCTCACCGTGGACAA |
| | | GAGCAGGTGGCAGCAGGGGAACGTCTTCTCATGCTCCGTGATG |
| | | CATGAGGCTCTGCACAACCACTACACGCAGAAGAGCCTCTCCC |
| | | TGTCTCCGGGTAAA |
| trastuzumab-direct mambalgin HC | 111 | GAAGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCG*GGGGGTGG* |
| | | *CGGAAGCCTGAAATGTTACCAACATGGTAAAGTTGTGACTTGTCAT* |
| | | *CGAGATATGAAGTTTTGCTATCATAACACTGGCATGCCTTTTCGAAA* |
| | | *TCTCAAGCTCATCCTACAGGGATGTTCTTCTTCGTGCAGTGAAACA* |
| | | *GAAAACAATAAGTGTTGCTCAACAGACAGATGCAACAAAGGCGGAG* |
| | | *GTGGGAGT*TGGGGCCAAGGAACCCTGGTCACCGTCTCCTCAGC |
| | | CTCCACCAAGGGCCCATCGGTCTTCCCCCTGGCACCCTCCTCC |
| | | AAGAGCACCTCTGGGGGCACAGCGGCCCTGGGCTGCCTGGTC |
| | | AAGGACTACTTCCCCGAACCGGTGACGGTGTCGTGGAACTCAG |
| | | GCGCCCTGACCAGCGGCGTGCACACCTTCCCGGCTGTCCTACA |
| | | GTCCTCAGGACTCTACTCCCTCAGCAGCGTGGTGACTGTGCCC |
| | | TCTAGCAGCTTGGGCACCCAGACCTACATCTGCAACGTGAATC |
| | | ACAAGCCCAGCAACACCAAGGTGGACAAGAAAGTTGAACCCA |
| | | AATCTTGCGACAAAACTCACACATGCCCACCGTGCCCAGCACC |
| | | TCCAGTCGCCGGACCGTCAGTCTTCCTCTTCCCTCCAAAACCCA |
| | | AGGACACCCTCATGATCTCCCGGACCCCTGAGGTCACATGCGT |
| | | GGTGGTGGACGTGAGCCACGAAGACCCTGAGGTCAAGTTCAA |
| | | CTGGTACGTGGACGGCGTGGAGGTGCATAATGCCAAGACAAA |
| | | GCCGCGGGAGGAGCAGTACAACAGCACGTACCGTGTGGTCAG |
| | | CGTCCTCACCGTCCTGCACCAGGACTGGCTGAATGGCAAGGAG |
| | | TACAAGTGCAAGGTCTCCAACAAAGGCCTCCCAAGCTCCATCG |

TABLE 5-continued

Direct Immunoglobulin Fusion Proteins—Nucleotide Sequence

| NAME | SEQ ID NO | SEQUENCE |
|---|---|---|
| | | AGAAAACCATCTCCAAAGCCAAAGGGCAGCCCCGAGAACCAC |
| | | AGGTGTACACCCTGCCTCCATCCCGGGATGAGCTGACCAAGAA |
| | | CCAGGTCAGCCTGACCTGCCTGGTCAAAGGCTTCTATCCCAGC |
| | | GACATCGCCGTGGAGTGGGAGAGCAATGGGCAGCCGGAGAAC |
| | | AACTACAAGACCACGCCTCCCGTGCTGGACTCCGACGGCTCCT |
| | | TCTTCCTCTACAGCAAGCTCACCGTGGACAAGAGCAGGTGGCA |
| | | GCAGGGGAACGTCTTCTCATGCTCCGTGATGCATGAGGCTCTG |
| | | CACAACCACTACACGCAGAAGAGCCTCTCCCTGTCTCCGGGTA |
| | | AATGATAA |
| trastuzumab-direct relaxin2 short HC | 112 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGAGGT |
| | | GGCGGGAGCGACTCTTGGATGGAAGAAGTTATCAAACTGTGCGGT |
| | | CGTGAACTGGTTCGTGCTCAGATCGCTATCTGCGGTATGTCTACCT |
| | | GGTCTAAACGTTCTCTGTCTCAGGAAATCGAGGGCCGTAAAAAACG |
| | | TCAGCTGTACTCTGCTCTGGCTAACAAATGCTGCCACGTTGGTTGC |
| | | ACCAAACGTTCTCTGGCTCGTTTCTGCGGCGGAGGTGGGAGTGAC |
| | | TACTGGGGCCAAGGAACCCTGGTCACCGTCTCCTCAGCCTCCA |
| | | CCAAGGGCCCATCGGTCTTCCCCCTGGCACCCTCCTCCAAGAG |
| | | CACCTCTGGGGGCACAGCGGCCCTGGGCTGCCTGGTCAAGGAC |
| | | TACTTCCCCGAACCGGTGACGGTGTCGTGGAACTCAGGCGCCC |
| | | TGACCAGCGGCGTGCACACCTTCCCGGCTGTCCTACAGTCCTC |
| | | AGGACTCTACTCCCTCAGCAGCGTGGTGACTGTGCCCTCTAGC |
| | | AGCTTGGGCACCCAGACCTACATCTGCAACGTGAATCACAAGC |
| | | CCAGCAACACCAAGGTGGACAAGAAAGTTGAACCCAAATCTT |
| | | GCGACAAAACTCACACATGCCCACCGTGCCCAGCACCTCCAGT |
| | | CGCCGGACCGTCAGTCTTCCTCTTCCCTCCAAAACCCAAGGAC |
| | | ACCCTCATGATCTCCCGGACCCCTGAGGTCACATGCGTGGTGG |
| | | TGGACGTGAGCCACGAAGACCCTGAGGTCAAGTTCAACTGGT |
| | | ACGTGGACGGCGTGGAGGTGCATAATGCCAAGACAAAGCCGC |
| | | GGGAGGAGCAGTACAACAGCACGTACCGTGTGGTCAGCGTCC |
| | | TCACCGTCCTGCACCAGGACTGGCTGAATGGCAAGGAGTACA |
| | | AGTGCAAGGTCTCCAACAAAGGCCTCCCAAGCTCCATCGAGA |
| | | AAACCATCTCCAAAGCCAAAGGGCAGCCCCGAGAACCACAGG |
| | | TGTACACCCTGCCTCCATCCCGGGATGAGCTGACCAAGAACCA |
| | | GGTCAGCCTGACCTGCCTGGTCAAAGGCTTCTATCCCAGCGAC |

TABLE 5-continued

Direct Immunoglobulin Fusion Proteins—Nucleotide Sequence

| NAME | SEQ ID NO | SEQUENCE |
|---|---|---|
| | | ATCGCCGTGGAGTGGGAGAGCAATGGGCAGCCGGAGAACAAC |
| | | TACAAGACCACGCCTCCCGTGCTGGACTCCGACGGCTCCTTCT |
| | | TCCTCTACAGCAAGCTCACCGTGGACAAGAGCAGGTGGCAGC |
| | | AGGGGAACGTCTTCTCATGCTCCGTGATGCATGAGGCTCTGCA |
| | | CACCACTACACGCAGAAGAGCCTCTCCCTGTCTCCGGGTAAA |
| | | T |
| trastuzumab-direct relaxin2 long HC | 113 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGAGGT |
| | | GGCGGGAGCGACTCTTGGATGGAAGAAGTTATCAAACTGTGCGGT |
| | | CGTGAACTGGTTCGTGCTCAGATCGCTATCTGCGGTATGTCTACCT |
| | | GGTCTAAACGTTCTCTGTCTCAGGAAGACGCTCCGCAGACCCCGC |
| | | GTCCGGTTATCGAGGGCCGTAAAAAACGTCAGCTGTACTCTGCTCT |
| | | GGCTAACAAATGCTGCCACGTTGGTTGCACCAAACGTTCTCTGGCT |
| | | CGTTTCTGCGGCGGAGGTGGGAGTGACTACTGGGGCCAAGGAA |
| | | CCCTGGTCACCGTCTCCTCAGCCTCCACCAAGGGCCCATCGGT |
| | | CTTCCCCCTGGCACCCTCCTCCAAGAGCACCTCTGGGGGCACA |
| | | GCGGCCCTGGGCTGCCTGGTCAAGGACTACTTCCCCGAACCGG |
| | | TGACGGTGTCGTGGAACTCAGGCGCCCTGACCAGCGGCGTGCA |
| | | CACCTTCCCGGCTGTCCTACAGTCCTCAGGACTCTACTCCCTCA |
| | | GCAGCGTGGTGACTGTGCCCTCTAGCAGCTTGGGCACCCAGAC |
| | | CTACATCTGCAACGTGAATCACAAGCCCAGCAACACCAAGGT |
| | | GGACAAGAAAGTTGAACCCAAATCTTGCGACAAAACTCACAC |
| | | ATGCCCACCGTGCCCAGCACCTCCAGTCGCCGGACCGTCAGTC |
| | | TTCCTCTTCCCTCCAAAACCCAAGGACACCCTCATGATCTCCCG |
| | | GACCCCTGAGGTCACATGCGTGGTGGTGGACGTGAGCCACGA |
| | | AGACCCTGAGGTCAAGTTCAACTGGTACGTGGACGGCGTGGA |
| | | GGTGCATAATGCCAAGACAAAGCCGCGGGAGGAGCAGTACAA |
| | | CAGCACGTACCGTGTGGTCAGCGTCCTCACCGTCCTGCACCAG |
| | | GACTGGCTGAATGGCAAGGAGTACAAGTGCAAGGTCTCCAAC |
| | | AAAGGCCTCCCAAGCTCCATCGAGAAAACCATCTCCAAAGCC |
| | | AAAGGGCAGCCCCGAGAACCACAGGTGTACACCCTGCCTCCA |
| | | TCCCGGGATGAGCTGACCAAGAACCAGGTCAGCCTGACCTGCC |
| | | TGGTCAAAGGCTTCTATCCCAGCGACATCGCCGTGGAGTGGGA |
| | | GAGCAATGGGCAGCCGGAGAACAACTACAAGACCACGCCTCC |
| | | CGTGCTGGACTCCGACGGCTCCTTCTTCCTCTACAGCAAGCTC |

TABLE 5-continued

Direct Immunoglobulin Fusion Proteins—Nucleotide Sequence

| NAME | SEQ ID NO | SEQUENCE |
|---|---|---|
| | | ACCGTGGACAAGAGCAGGTGGCAGCAGGGGAACGTCTTCTCA |
| | | TGCTCCGTGATGCATGAGGCTCTGCACAACCACTACACGCAGA |
| | | AGAGCCTCTCCCTGTCTCCGGGTAAA |
| trastuzumab-direct hGH HC | 114 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGA<u>GGTGGT</u> |
| | | <u>GGCGGAAGCTTCCCAACCATTCCCTTATCCAGGCTTTTTGACAACG</u> |
| | | CTATGCTCCGCGCCCATCGTCTGCACCAGCTGGCCTTTGACACCTA |
| | | CCAGGAGTTTGAAGAAGCCTATATCCCAAAGGAACAGAAGTATTCA |
| | | TTCCTGCAGAACCCCCAGACCTCCCTCTGTTTCTCAGAGTCTATTC |
| | | CGACACCCTCCAACAGGGAGGAAACACAACAGAAATCCAACCTAG |
| | | AGCTGCTCCGCATCTCCCTGCTGCTCATCCAGTCGTGGCTGGAGC |
| | | CCGTGCAGTTCCTCAGGAGTGTCTTCGCCAACAGCCTGGTGTACG |
| | | GCGCCTCTGACAGCAACGTCTATGACCTCCTAAAGGACCTAGAGG |
| | | AAGGGCATCCAAACGCTGATGGGGAGGCTGGAAGATGGCAGCCCC |
| | | CGGACTGGGCAGATCTTCAAGCAGACCTACAGCAAGTTCGACACA |
| | | AACTCACACAACGATGACGCACTACTCAAGAACTACGGGCTGCTCT |
| | | ACTGCTTCAGGAAGGACATGGACAAGGTCGAGACATTCCTGCGCA |
| | | TCGTGCAGTGCCGCTCTGTGGAGGGCAGCTGTGGCTTC<u>GGCGGA</u> |
| | | <u>GGTGGGAGT</u>GACTACTGGGGCCAAGGAACCCTGGTCACCGTCT |
| | | CCTCAGCCTCCACCAAGGGCCCATCGGTCTTCCCCCTGGCACC |
| | | CTCCTCCAAGAGCACCTCTGGGGGCACAGCGGCCCTGGGCTGC |
| | | CTCCTCCAAGAGCACCTCTGGGGGCACAGCGGCCCTGGGCTGC |
| | | ACTCAGGCGCCCTGACCAGCGGCGTGCACACCTTCCCGGCTGT |
| | | CCTACAGTCCTCAGGACTCTACTCCCTCAGCAGCGTGGTGACT |
| | | GTGCCCTCTAGCAGCTTGGGCACCCAGACCTACATCTGCAACG |
| | | TGAATCACAAGCCCAGCAACACCAAGGTGGACAAGAAAGTTG |
| | | AACCCAAATCTTGCGACAAAACTCACACATGCCCACCGTGCCC |
| | | AGCACCTCCAGTCGCCGGACCGTCAGTCTTCCTCTTCCCTCCAA |
| | | AACCCAAGGACACCCTCATGATCTCCCGGACCCCTGAGGTCAC |
| | | ATGCGTGGTGGTGGACGTGAGCCACGAAGACCCTGAGGTCAA |
| | | GTTCAACTGGTACGTGGACGGCGTGGAGGTGCATAATGCCAA |
| | | GACAAAGCCGCGGGAGGAGCAGTACAACAGCACGTACCGTGT |
| | | GGTCAGCGTCCTCACCGTCCTGCACCAGGACTGGCTGAATGGC |
| | | AAGGAGTACAAGTGCAAGGTCTCCAACAAAGGCCTCCCAAGC |
| | | TCCATCGAGAAAACCATCTCCAAAGCCAAAGGGCAGCCCCGA |
| | | GAACCACAGGTGTACACCCTGCCTCCATCCCGGGATGAGCTGA |
| | | CCAAGAACCAGGTCAGCCTGACCTGCCTGGTCAAAGGCTTCTA |
| | | TCCCAGCGACATCGCCGTGGAGTGGGAGAGCAATGGGCAGCC |
| | | GGAGAACAACTACAAGACCACGCCTCCCGTGCTGGACTCCGA |
| | | CGGCTCCTTCTTCCTCTACAGCAAGCTCACCGTGGACAAGAGC |

TABLE 5-continued

Direct Immunoglobulin Fusion Proteins—Nucleotide Sequence

| NAME | SEQ ID NO | SEQUENCE |
|---|---|---|
| | | AGGTGGCAGCAGGGGAACGTCTTCTCATGCTCCGTGATGCATG |
| | | AGGCTCTGCACAACCACTACACGCAGAAGAGCCTCTCCCTGTC |
| | | TCCGGGTAAATGATAA |
| trastuzumab-direct hIFN-B1 HC | 115 | GAGGTGCAGCTGGTGGAGTCTGGAGGAGGCTTGGTCCAGCCT |
| | | GGGGGGTCCCTGAGACTCTCCTGTGCAGCCTCTGGGTTCAATA |
| | | TTAAGGACACTTACATCCACTGGGTCCGCCAGGCTCCAGGGAA |
| | | GGGGCTGGAGTGGGTCGCACGTATTTATCCTACCAATGGTTAC |
| | | ACACGCTACGCAGACTCCGTGAAGGGCCGATTCACCATCTCCG |
| | | CAGACACTTCCAAGAACACGGCGTATCTTCAAATGAACAGCCT |
| | | GAGAGCCGAGGACACGGCCGTGTATTACTGTTCGAGAGGGTG |
| | | GTGGCGGAAGCATGAGCTACAACTTGCTTGGATTCCTACAAAGAAG |
| | | CAGCAATTTTCAGTGTCAGAAGCTCCTGTGGCAATTGAATGGGAGG |
| | | CTTGAATACTGCCTCAAGGACAGGATGAACTTTGACATCCCTGAGG |
| | | AGATTAAGCAGCTGCAGCAGTTCCAGAAGGAGGACGCCGCATTGA |
| | | CCATCTATGAGATGCTCCAGAACATCTTTGCTATTTTCAGACAAGAT |
| | | TCATCTAGCACTGGCTGGAATGAGACTATTGTTGAGAACCTCCTGG |
| | | CTAATGTCTATCATCAGATAAACCATCTGAAGACAGTCCTGGAAGAA |
| | | AAACTGGAGAAAGAAGATTTCACCAGGGGAAAACTCATGAGCAGTC |
| | | TGCACCTGAAAAGATATTATGGGAGGATTCTGCATTACCTGAAGGC |
| | | CAAGGAGTACAGTCACTGTGCCTGGACCATAGTCAGAGTGGAAAT |
| | | CCTAAGGAACTTTTACTTCATTAACAGACTTACAGGTTACCTCCGAA |
| | | ACGGCGGAGGTGGGAGTGACTACTGGGGCCAAGGAACCCTGGT |
| | | CACCGTCTCCTCAGCCTCCACCAAGGGCCCATCGGTCTTCCCC |
| | | CTGGCACCCTCCTCCAAGAGCACCTCTGGGGGCACAGCGGCCC |
| | | TGGGCTGCCTGGTCAAGGACTACTTCCCCGAACCGGTGACGGT |
| | | GTCGTGGAACTCAGGCGCCCTGACCAGCGGCGTGCACACCTTC |
| | | CCGGCTGTCCTACAGTCCTCAGGACTCTACTCCCTCAGCAGCG |
| | | TGGTGACTGTGCCCTCTAGCAGCTTGGGCACCCAGACCTACAT |
| | | CTGCAACGTGAATCACAAGCCCAGCAACACCAAGGTGGACAA |
| | | GAAAGTTGAACCCAAATCTTGCGACAAAACTCACACATGCCCA |
| | | CCGTGCCCAGCACCTCCAGTCGCCGGACCGTCAGTCTTCCTCTT |
| | | CCCTCCAAAACCCAAGGACACCCTCATGATCTCCCGGACCCCT |
| | | GAGGTCACATGCGTGGTGGTGGACGTGAGCCACGAAGACCCT |
| | | GAGGTCAAGTTCAACTGGTACGTGGACGGCGTGGAGGTGCAT |
| | | AATGCCAAGACAAAGCCGCGGGAGGAGCAGTACAACAGCACG |
| | | TACCGTGTGGTCAGCGTCCTCACCGTCCTGCACCAGGACTGGC |
| | | TGAATGGCAAGGAGTACAAGTGCAAGGTCTCCAACAAAGGCC |
| | | TCCCAAGCTCCATCGAGAAAACCATCTCCAAAGCCAAAGGGC |
| | | AGCCCCGAGAACCACAGGTGTACACCCTGCCTCCATCCCGGGA |
| | | TGAGCTGACCAAGAACCAGGTCAGCCTGACCTGCCTGGTCAAA |
| | | GGCTTCTATCCCAGCGACATCGCCGTGGAGTGGGAGAGCAATG |
| | | GGCAGCCGGAGAACAACTACAAGACCACGCCTCCCGTGCTGG |
| | | ACTCCGACGGCTCCTTCTTCCTCTACAGCAAGCTCACCGTGGA |
| | | CAAGAGCAGGTGGCAGCAGGGGAACGTCTTCTCATGCTCCGTG |

TABLE 5-continued

Direct Immunoglobulin Fusion Proteins—Nucleotide Sequence

| NAME | SEQ ID NO | SEQUENCE |
|---|---|---|
| | | ATGCATGAGGCTCTGCACAACCACTACACGCAGAAGAGCCTCT |
| | | CCCTGTCTCCGGGTAAATGATAA |
| palivizumab-direct mambalgin HC | 116 | CAGGTGACCCTGCGCGAGTCCGGCCCTGCACTGGTGAAGCCCA |
| | | CCCAGACCCTGACCCTGACCTGCACCTTCTCCGGCTTCTCCCTG |
| | | TCCACCTCCGGCATGTCCGTGGGCTGGATCCGGCAGCCTCCCG |
| | | GCAAGGCCCTGGAGTGGCTGGCTGACATCTGGTGGGACGACA |
| | | AGAAGGACTACAACCCCTCCCTGAAGTCCCGCCTGACCATCTC |
| | | CAAGGACACCTCCAAGAACCAGGTGGTGCTGAAGGTGACCAA |
| | | CATGGACCCCGCCGACACCGCCACCTACTACTGCGCCCGCTCT |
| | | *GGGGGTGGCGGAAGC*CTGAAATGTTACCAACATGGTAAAGTTGTG |
| | | *ACTTGTCATCGAGATATGAAGTTTTGCTATCATAACACTGGCATGCC* |
| | | *TTTTCGAAATCTCAAGCTCATCCTACAGGGATGTTCTTCTTCGTGCA* |
| | | *GTGAAACAGAAAACAATAAGTGTTGCTCAACAGACAGATGCAACAA* |
| | | *AGGCGGAGGTGGGAGTT*ACTTTGACGTGTGGGGAGCCGGTACC |
| | | ACCGTGACCGTGTCTTCCGCCTCCACCAAGGGCCCATCGGTCT |
| | | TCCCCCTGGCACCCTCCTCCAAGAGCACCTCTGGGGGCACAGC |
| | | GGCCCTGGGCTGCCTGGTCAAGGACTACTTCCCCGAACCGGTG |
| | | ACGGTGTCGTGGAACTCAGGCGCCCTGACCAGCGGCGTGCAC |
| | | ACCTTCCCGGCTGTCCTACAGTCCTCAGGACTCTACTCCCTCAG |
| | | CAGCGTGGTGACTGTGCCCTCTAGCAGCTTGGGCACCCAGACC |
| | | TACATCTGCAACGTGAATCACAAGCCCAGCAACACCAAGGTG |
| | | GACAAGAAAGTTGAACCCAAATCTTGCGACAAAACTCACACA |
| | | TGCCCACCGTGCCCAGCACCTCCAGTCGCCGGACCGTCAGTCT |
| | | TCCTCTTCCCTCCAAAACCCAAGGACACCCTCATGATCTCCCG |
| | | GACCCCTGAGGTCACATGCGTGGTGGTGGACGTGAGCCACGA |
| | | AGACCCTGAGGTCAAGTTCAACTGGTACGTGGACGGCGTGGA |
| | | GGTGCATAATGCCAAGACAAAGCCGCGGGAGGAGCAGTACAA |
| | | CAGCACGTACCGTGTGGTCAGCGTCCTCACCGTCCTGCACCAG |
| | | GACTGGCTGAATGGCAAGGAGTACAAGTGCAAGGTCTCCAAC |
| | | AAAGGCCTCCCAAGCTCCATCGAGAAAACCATCTCCAAAGCC |
| | | AAAGGGCAGCCCCGAGAACCACAGGTGTACACCCTGCCTCCA |
| | | TCCCGGGATGAGCTGACCAAGAACCAGGTCAGCCTGACCTGCC |
| | | TGGTCAAAGGCTTCTATCCCAGCGACATCGCCGTGGAGTGGGA |
| | | GAGCAATGGGCAGCCGGAGAACAACTACAAGACCACGCCTCC |
| | | CGTGCTGGACTCCGACGGCTCCTTCTTCCTCTACAGCAAGCTC |
| | | ACCGTGGACAAGAGCAGGTGGCAGCAGGGGAACGTCTTCTCA |
| | | TGCTCCGTGATGCATGAGGCTCTGCACAACCACTACACGCAGA |
| | | AGAGCCTCTCCCTGTCTCCGGGTAAATGATAA |
| BLV1H12 direct-L2-betatrophin HC | 117 | CAGGTCCAGCTGAGAGAGAGCGGCCCTTCACTGGTCAAGCCAT |
| | | CCCAGACACTGAGCCTGACATGCACAGCAAGCGGGTTTTCACT |
| | | GAGCGACAAGGCAGTGGGATGGGTCCGACAGGCACCAGGAAA |

TABLE 5-continued

Direct Immunoglobulin Fusion Proteins—Nucleotide Sequence

| NAME | SEQ ID NO | SEQUENCE |
|---|---|---|
| | | AGCCCTGGAATGGCTGGGCAGCATCGATACCGGCGGGAACAC |
| | | AGGGTACAATCCCGGACTGAAGAGCAGACTGTCCATTACCAA |
| | | GGACAACTCTAAAAGTCAGGTGTCACTGAGCGTGAGCTCCGTC |
| | | ACCACAGAGGATAGTGCAACTTACTATTGCGGGGGTGGCGGAA |
| | | GCGGGGGTGGCGGAAGCGCTCCTCTGGGCGGTCCTGAACCAGCA |
| | | CAGTACGAGGAACTGACACTGTTGTTCCATGGAGCCTTGCAGCTG GGCCAGGCCCTCAACGGCGTGTACCGCGCCACAGAGGCACGTTT GACCGAGGCCGGACACAGCCTGGGTTTGTACGACAGAGCCCTGG AGTTTCTGGGTACCGAAGTGCGTCAGGGCCAGGACGCAACTCAGG AGCTGAGAACCTCCCTCTCTGAGATCCAGGTGGAGGAGGACGCCC TGCACCTGCGCGCCGAGGCGACAGCACGCTCTTTGGGAGAAGTTG CTCGCGCTCAGCAGGCCCTGCGTGATACCGTGCGGAGACTCCAAG TTCAGCTCAGAGGCGCTTGGCTCGGACAGGCGCATCAGGAGTTCG AGACCCTGAAAGCTCGTGCCGACAAACAGTCCCACCTGCTGTGGG CGCTCACCGGTCACGTCCAGCGCCAGCAACGCGAAATGGCCGAG CAGCAGCAATGGCTGCGCCAAATCCAGCAGCGCCTGCATACCGCG GCCCTGCCAGCGTAAGGCGGAGGTGGGAGTGGCGGAGGTGGGA |
| | | GTCATGTGGATGTCTGGGGACAGGGCCTGCTGGTGACAGTCTC |
| | | TAGTGCTTCCACAACTGCACCAAAGGTGTACCCCCTGTCAAGC |
| | | TGCTGTGGGACAAATCCTCTAGTACCGTGACACTGGGATGCC |
| | | TGGTCTCAAGCTATATGCCCGAGCCTGTGACTGTCACCTGGAA |
| | | CTCAGGAGCCCTGAAAAGCGGAGTGCACACCTTCCCAGCTGTG |
| | | CTGCAGTCCTCTGGCCTGTATAGCCTGAGTTCAATGGTGACAG |
| | | TCCCCGGCAGTACTTCAGGGCAGACCTTCACCTGTAATGTGGC |
| | | CCATCCTGCCAGCTCCACCAAAGTGGACAAAGCAGTGGAACC |
| | | CAAATCTTGCGACAAAACTCACACATGCCCACCGTGCCCAGCA |
| | | CCTGAACTCCTGGGGGGACCGTCAGTCTTCCTCTTCCCCCCAA |
| | | AACCCAAGGACACCCTCATGATCTCCCGGACCCCTGAGGTCAC |
| | | ATGCGTGGTGGTGGACGTGAGCCACGAAGACCCTGAGGTCAA |
| | | GTTCAACTGGTACGTGGACGGCGTGGAGGTGCATAATGCCAA |
| | | GACAAAGCCGCGGGAGGAGCAGTACAACAGCACGTACCGTGT |
| | | GGTCAGCGTCCTCACCGTCCTGCACCAGGACTGGCTGAATGGC |
| | | AAGGAGTACAAGTGCAAGGTCTCCAACAAAGCCCTCCCAGCC |
| | | CCCATCGAGAAAACCATCTCCAAAGCCAAAGGGCAGCCCCGA |
| | | GAACCACAGGTGTACACCCTGCCCCCATCCCGGGATGAGCTGA |
| | | CCAAGAACCAGGTCAGCCTGACCTGCCTGGTCAAAGGCTTCTA |
| | | TCCCAGCGACATCGCCGTGGAGTGGGAGAGCAATGGGCAGCC |
| | | GGAGAACAACTACAAGACCACGCCTCCCGTGCTGGACTCCGA |
| | | CGGCTCCTTCTTCCTCTACAGCAAGCTCACCGTGGACAAGAGC |
| | | AGGTGGCAGCAGGGGAACGTCTTCTCATGCTCCGTGATGCATG |
| | | AGGCTCTGCACAACCACTACACGCAGAAGAGCCTCTCCCTGTC |
| | | TCCGGGTAAA |
| BLV1H12 direct-L1-betatrophin HC | 118 | CAGGTCCAGCTGAGAGAGAGCGGCCCTTCACTGGTCAAGCCAT |
| | | CCCAGACACTGAGCCTGACATGCACAGCAAGCGGGTTTTCACT |
| | | GAGCGACAAGGCAGTGGGATGGGTCCGACAGGCACCAGGAAA |

TABLE 5-continued

Direct Immunoglobulin Fusion Proteins-Nucleotide Sequence

| NAME | SEQ ID NO | SEQUENCE |
|---|---|---|
| | | AGCCCTGGAATGGCTGGGCAGCATCGATACCGGCGGGAACAC |
| | | AGGGTACAATCCCGGACTGAAGAGCAGACTGTCCATTACCAA |
| | | GGACAACTCTAAAAGTCAGGTGTCACTGAGCGTGAGCTCCGTC |
| | | ACCACAGAGGATAGTGCAACTTACTATTGC*GGGGGTGGCGGAA* |
| | | *GCGCTCCTCTGGGCGGTCCTGAACCAGCACAGTACGAGGAACTGA* |
| | | *CACTGTTGTTCCATGGAGCCTTGCAGCTGGGCCAGGCCCTCAACG* |
| | | *GCGTGTACCGCGCCACAGAGGCACGTTTGACCGAGGCCGGACAC* |
| | | *AGCCTGGGTTTGTACGACAGAGCCCTGGAGTTTCTGGGTACCGAA* |
| | | *GTGCGTCAGGGCCAGGACGCAACTCAGGAGCTGAGAACCTCCCTC* |
| | | *TCTGAGATCCAGGTGGAGGAGGACGCCCTGCACCTGCCGCCGA* |
| | | *GGCGACAGCACGCTCTTTGGGAGAAGTTGCTCGCGCTCAGCAGGC* |
| | | *CCTGCGTGATACCGTGCGGAGACTCCAAGTTCAGCTCAGAGGCGC* |
| | | *TTGGCTCGGACAGGCGCATCAGGAGTTCGAGACCCTGAAAGCTCG* |
| | | *TGCCGACAAACAGTCCCACCTGCTGTGGGCGCTCACCGGTCACGT* |
| | | *CCAGCGCCAGCAACGCGAAATGGCCGAGCAGCAGCAATGGCTGC* |
| | | *GCCAAATCCAGCAGCGCCTGCATACCGCGGCCCTGCCAGCGTAAG* |
| | | *GCGGAGGTGGGAGT*CATGTGGATGTCTGGGGACAGGGCCTGCT |
| | | GGTGACAGTCTCTAGTGCTTCCACAACTGCACCAAAGGTGTAC |
| | | CCCCTGTCAAGCTGCTGTGGGACAAATCCTCTAGTACCGTGA |
| | | CACTGGGATGCCTGGTCTCAAGCTATATGCCCGAGCCTGTGAC |
| | | TGTCACCTGGAACTCAGGAGCCCTGAAAAGCGGAGTGCACAC |
| | | CTTCCCAGCTGTGCTGCAGTCCTCTGGCCTGTATAGCCTGAGTT |
| | | CAATGGTGACAGTCCCCGGCAGTACTTCAGGGCAGACCTTCAC |
| | | CTGTAATGTGGCCCATCCTGCCAGCTCCACCAAAGTGGACAAA |
| | | GCAGTGGAACCCAAATCTTGCGACAAAACTCACACATGCCCAC |
| | | CGTGCCCAGCACCTGAACTCCTGGGGGGACCGTCAGTCTTCCT |
| | | CTTCCCCCCAAAACCCAAGGACACCCTCATGATCTCCCGGACC |
| | | CCTGAGGTCACATGCGTGGTGGTGGACGTGAGCCACGAAGAC |
| | | CCTGAGGTCAAGTTCAACTGGTACGTGGACGGCGTGGAGGTGC |
| | | ATAATGCCAAGACAAAGCCGCGGGAGGAGCAGTACAACAGCA |
| | | CGTACCGTGTGGTCAGCGTCCTCACCGTCCTGCACCAGGACTG |
| | | GCTGAATGGCAAGGAGTACAAGTGCAAGGTCTCCAACAAAGC |
| | | CCTCCCAGCCCCCATCGAGAAAACCATCTCCAAAGCCAAAGG |
| | | GCAGCCCCGAGAACCACAGGTGTACACCCTGCCCCCATCCCGG |
| | | GATGAGCTGACCAAGAACCAGGTCAGCCTGACCTGCCTGGTCA |
| | | AAGGCTTCTATCCCAGCGACATCGCCGTGGAGTGGGAGAGCA |
| | | ATGGGCAGCCGGAGAACAACTACAAGACCACGCCTCCCGTGC |
| | | TGGACTCCGACGGCTCCTTCTTCCTCTACAGCAAGCTCACCGT |
| | | GGACAAGAGCAGGTGGCAGCAGGGGAACGTCTTCTCATGCTC |
| | | CGTGATGCATGAGGCTCTGCACAACCACTACACGCAGAAGAG |
| | | CCTCTCCCTGTCTCCGGGTAAA |
| BLV1H12-direct hGH HC | 119 | CAGGTCCAGCTGAGAGAGAGCGGCCCTTCACTGGTCAAGCCAT |
| | | CCCAGACACTGAGCCTGACATGCACAGCAAGCGGGTTTTCACT |
| | | GAGCGACAAGGCAGTGGGATGGGTCCGACAGGCACCAGGAAA |
| | | AGCCCTGGAATGGCTGGGCAGCATCGATACCGGCGGGAACAC |

TABLE 5-continued

Direct Immunoglobulin Fusion Proteins—Nucleotide Sequence

| NAME | SEQ ID NO | SEQUENCE |
|---|---|---|
| | | AGGGTACAATCCCGGACTGAAGAGCAGACTGTCCATTACCAA |
| | | GGACAACTCTAAAAGTCAGGTGTCACTGAGCGTGAGCTCCGTC |
| | | ACCACAGAGGATAGTGCAACTTACTATTGCGGGGGTGGCGGAA |
| | | GCTTCCCAACCATTCCCTTATCCAGGCTTTTTGACAACGCTATGCTC |
| | | CGCGCCCATCGTCTGCACCAGCTGGCCTTTGACACCTACCAGGAG<br>TTTGAAGAAGCCTATATCCCAAAGGAACAGAAGTATTCATTCCTGCA<br>GAACCCCCAGACCTCCCTCTGTTTCTCAGAGTCTATTCCGACACCC<br>TCCAACAGGGAGGAAACACAACAGAAATCCAACCTAGAGCTGCTC<br>CGCATCTCCCTGCTGCTCATCCAGTCGTGGCTGGAGCCCGTGCAG<br>TTCCTCAGGAGTGTCTTCGCCAACAGCCTGGTGTACGGCGCCTCT<br>GACAGCAACGTCTATGACCTCCTAAAGGACCTAGAGGAAGGCATC<br>CAAACGCTGATGGGGAGGCTGGAAGATGGCAGCCCCCGGACTGG<br>GCAGATCTTCAAGCAGACCTACAGCAAGTTCGACACAAACTCACAC<br>AACGATGACGCACTACTCAAGAACTACGGGCTGCTCTACTGCTTCA<br>GGAAGGACATGGACAAGGTCGAGACATTCCTGCGCATCGTGCAGT<br>GCCGCTCTGTGGAGGGCAGCTGTGGCTTCGGCGGAGGTGGGAGT |
| | | CATGTGGATGTCTGGGGACAGGGCCTGCTGGTGACAGTCTCTA |
| | | GTGCTTCCACAACTGCACCAAAGGTGTACCCCCTGTCAAGCTG |
| | | CTGTGGGACAAATCCTCTAGTACCGTGACACTGGGATGCCTG |
| | | GTCTCAAGCTATATGCCCGAGCCTGTGACTGTCACCTGGAACT |
| | | CAGGAGCCCTGAAAAGCGGAGTGCACACCTTCCCAGCTGTGCT |
| | | GCAGTCCTCTGGCCTGTATAGCCTGAGTTCAATGGTGACAGTC |
| | | CCCGGCAGTACTTCAGGGCAGACCTTCACCTGTAATGTGGCCC |
| | | ATCCTGCCAGCTCCACCAAAGTGGACAAAGCAGTGGAACCCA |
| | | AATCTTGCGACAAAACTCACACATGCCCACCGTGCCCAGCACC |
| | | TGAACTCCTGGGGGGACCGTCAGTCTTCCTCTTCCCCCCAAAA |
| | | CCCAAGGACACCCTCATGATCTCCCGGACCCCTGAGGTCACAT |
| | | GCGTGGTGGTGGACGTGAGCCACGAAGACCCTGAGGTCAAGT |
| | | TCAACTGGTACGTGGACGGCGTGGAGGTGCATAATGCCAAGA |
| | | CAAAGCCGCGGGAGGAGCAGTACAACAGCACGTACCGTGTGG |
| | | TCAGCGTCCTCACCGTCCTGCACCAGGACTGGCTGAATGGCAA |
| | | GGAGTACAAGTGCAAGGTCTCCAACAAAGCCCTCCCAGCCCCC |
| | | ATCGAGAAAACCATCTCCAAAGCCAAAGGGCAGCCCCGAGAA |
| | | CCACAGGTGTACACCCTGCCCCCATCCCGGGATGAGCTGACCA |
| | | AGAACCAGGTCAGCCTGACCTGCCTGGTCAAAGGCTTCTATCC |
| | | CAGCGACATCGCCGTGGAGTGGGAGAGCAATGGGCAGCCGGA |
| | | GAACAACTACAAGACCACGCCTCCCGTGCTGGACTCCGACGGC |
| | | TCCTTCTTCCTCTACAGCAAGCTCACCGTGGACAAGAGCAGGT |
| | | GGCAGCAGGGGAACGTCTTCTCATGCTCCGTGATGCATGAGGC |
| | | TCTGCACAACCACTACACGCAGAAGAGCCTCTCCCTGTCTCCG |
| | | GGTAAA |
| BLV1H12-direct IFNB HC | 120 | CAGGTCCAGCTGAGAGAGAGCGGCCCTTCACTGGTCAAGCCAT |
| | | CCCAGACACTGAGCCTGACATGCACAGCAAGCGGGTTTTCACT |
| | | GAGCGACAAGGCAGTGGGATGGGTCCGACAGGCACCAGGAAA |
| | | AGCCCTGGAATGGCTGGGCAGCATCGATACCGGCGGGAACAC |

TABLE 5-continued

Direct Immunoglobulin Fusion Proteins—Nucleotide Sequence

| NAME | SEQ ID NO | SEQUENCE |
|---|---|---|
| | | AGGGTACAATCCCGGACTGAAGAGCAGACTGTCCATTACCAA |
| | | GGACAACTCTAAAAGTCAGGTGTCACTGAGCGTGAGCTCCGTC |
| | | ACCACAGAGGATAGTGCAACTTACTATTGC*GGGGGTGGCGGAA* |
| | | *GC*ATGAGCTACAACTTGCTTGGATTCCTACAAAGAAGCAGCAATTTT |
| | | CAGTGTCAGAAGCTCCTGTGGCAATTGAATGGGAGGCTTGAATACT |
| | | GCCTCAAGGACAGGATGAACTTTGACATCCCTGAGGAGATTAAGCA |
| | | GCTGCAGCAGTTCCAGAAGGAGGACGCCGCATTGACCATCTATGA |
| | | GATGCTCCAGAACATCTTTGCTATTTTCAGACAAGATTCATCTAGCA |
| | | CTGGCTGGAATGAGACTATTGTTGAGAACCTCCTGGCTAATGTCTA |
| | | TCATCAGATAAACCATCTGAAGACAGTCCTGGAAGAAAAACTGGAG |
| | | AAAGAAGATTTCACCAGGGGAAAACTCATGAGCAGTCTGCACCTGA |
| | | AAAGATATTATGGGAGGATTCTGCATTACCTGAAGGCCAAGGAGTA |
| | | CAGTCACTGTGCCTGGACCATAGTCAGAGTGGAAATCCTAAGGAAC |
| | | TTTTACTTCATTAACAGACTTACAGGTTACCTCCGAAAC*GGCGGAG* |
| | | *GTGGGAGT*CATGTGGATGTCTGGGACAGGGCCTGCTGGTGAC |
| | | AGTCTCTAGTGCTTCCACAACTGCACCAAAGGTGTACCCCCTG |
| | | TCAAGCTGCTGTGGGACAAATCCTCTAGTACCGTGACACTGG |
| | | GATGCCTGGTCTCAAGCTATATGCCCGAGCCTGTGACTGTCAC |
| | | CTGGAACTCAGGAGCCCTGAAAAGCGGAGTGCACACCTTCCC |
| | | AGCTGTGCTGCAGTCCTCTGGCCTGTATAGCCTGAGTTCAATG |
| | | GTGACAGTCCCCGGCAGTACTTCAGGGCAGACCTTCACCTGTA |
| | | ATGTGGCCCATCCTGCCAGCTCCACCAAAGTGGACAAAGCAGT |
| | | GGAACCCAAATCTTGCGACAAAACTCACACATGCCCACCGTGC |
| | | CCAGCACCTGAACTCCTGGGGGGACCGTCAGTCTTCCTCTTCC |
| | | CCCCAAAACCCAAGGACACCCTCATGATCTCCCGGACCCCTGA |
| | | GGTCACATGCGTGGTGGTGGACGTGAGCCACGAAGACCCTGA |
| | | GGTCAAGTTCAACTGGTACGTGGACGGCGTGGAGGTGCATAAT |
| | | GCCAAGACAAAGCCGCGGGAGGAGCAGTACAACAGCACGTAC |
| | | CGTGTGGTCAGCGTCCTCACCGTCCTGCACCAGGACTGGCTGA |
| | | ATGGCAAGGAGTACAAGTGCAAGGTCTCCAACAAAGCCCTCC |
| | | CAGCCCCCATCGAGAAAACCATCTCCAAAGCCAAAGGGCAGC |
| | | CCCGAGAACCACAGGTGTACACCCTGCCCCCATCCCGGGATGA |
| | | GCTGACCAAGAACCAGGTCAGCCTGACCTGCCTGGTCAAAGG |
| | | CTTCTATCCCAGCGACATCGCCGTGGAGTGGGAGAGCAATGGG |
| | | CAGCCGGAGAACAACTACAAGACCACGCCTCCCGTGCTGGAC |
| | | TCCGACGGCTCCTTCTTCCTCTACAGCAAGCTCACCGTGGACA |
| | | AGAGCAGGTGGCAGCAGGGGAACGTCTTCTCATGCTCCGTGAT |
| | | GCATGAGGCTCTGCACAACCACTACACGCAGAAGAGCCTCTCC |
| | | CTGTCTCCGGGTAAA |
| Bovine-direct hGH HC (CDRH3) | 121 | CAGGTCCAGCTGAGAGAGAGCGGCCCTTCACTGGTCAAGCCAT |
| | | CCCAGACACTGAGCCTGACATGCACAGCAAGCGGGTTTTCACT |
| | | GAGCGACAAGGCAGTGGGATGGGTCCGACAGGCACCAGGAAA |
| | | AGCCCTGGAATGGCTGGGCAGCATCGATACCGGCGGGAACAC |
| | | AGGGTACAATCCCGGACTGAAGAGCAGACTGTCCATTACCAA |

TABLE 5-continued

Direct Immunoglobulin Fusion Proteins—Nucleotide Sequence

| NAME | SEQ ID NO | SEQUENCE |
|------|-----------|----------|

GGACAACTCTAAAAGTCAGGTGTCACTGAGCGTGAGCTCCGTC

ACCACAGAGGATAGTGCAACTTACTATTGCACCTCTGTGCACC

AGGGAGGTGGCGGAAGCTTCCCAACCATTCCCTTATCCAGGCTTT

*TTGACAACGCTATGCTCCGCGCCCATCGTCTGCACCAGCTGGCCT*
*TTGACACCTACCAGGAGTTTGAAGAAGCCTATATCCCAAAGGAACA*
*GAAGTATTCATTCCTGCAGAACCCCCAGACCTCCCTCTGTTTCTCA*
*GAGTCTATTCCGACACCCTCCAACAGGGAGGAAACACAACAGAAAT*
*CCAACCTAGAGCTGCTCCGCATCTCCCTGCTGCTCATCCAGTCGTG*
*GCTGGAGCCCGTGCAGTTCCTCAGGAGTGTCTTCGCCAACAGCCT*
*GGTGTACGGCGCCTCTGACAGCAACGTCTATGACCTCCTAAAGGA*
*CCTAGAGGAAGGCATCCAAACGCTGATGGGGAGGCTGGAAGATG*
*GCAGCCCCCGGACTGGGCAGATCTTCAAGCAGACCTACAGCAAGT*
*TCGACACAAACTCACACAACGATGACGCACTACTCAAGAACTACGG*
*GCTGCTCTACTGCTTCAGGAAGGACATGGACAAGGTCGAGACATT*
*CCTGCGCATCGTGCAGTGCCGCTCTGTGGAGGGCAGCTGTGGCTT*
*CGGCGGAGGTGGGAGTTGGCATGTGGATGTCTGGGGACAGGGC*

CTGCTGGTGACAGTCTCTAGTGCTTCCACAACTGCACCAAAGG

TGTACCCCCTGTCAAGCTGCTGTGGGACAAATCCTCTAGTAC

CGTGACACTGGGATGCCTGGTCTCAAGCTATATGCCCGAGCCT

GTGACTGTCACCTGGAACTCAGGAGCCCTGAAAAGCGGAGTG

CACACCTTCCCAGCTGTGCTGCAGTCCTCTGGCCTGTATAGCCT

GAGTTCAATGGTGACAGTCCCCGGCAGTACTTCAGGGCAGACC

TTCACCTGTAATGTGGCCCATCCTGCCAGCTCCACCAAAGTGG

ACAAAGCAGTGGAACCCAAATCTTGCGACAAAACTCACACAT

GCCCACCGTGCCCAGCACCTGAACTCCTGGGGGGACCGTCAGT

CTTCCTCTTCCCCCCAAAACCCAAGGACACCCTCATGATCTCCC

GGACCCCTGAGGTCACATGCGTGGTGGTGGACGTGAGCCACG

AAGACCCTGAGGTCAAGTTCAACTGGTACGTGGACGGCGTGG

AGGTGCATAATGCCAAGACAAAGCCGCGGGAGGAGCAGTACA

ACAGCACGTACCGTGTGGTCAGCGTCCTCACCGTCCTGCACCA

GGACTGGCTGAATGGCAAGGAGTACAAGTGCAAGGTCTCCAA

CAAAGCCCTCCCAGCCCCCATCGAGAAAACCATCTCCAAAGCC

AAAGGGCAGCCCCGAGAACCACAGGTGTACACCCTGCCCCCA

TCCCGGGATGAGCTGACCAAGAACCAGGTCAGCCTGACCTGCC

TGGTCAAAGGCTTCTATCCCAGCGACATCGCCGTGGAGTGGGA

GAGCAATGGGCAGCCGGAGAACAACTACAAGACCACGCCTCC

CGTGCTGGACTCCGACGGCTCCTTCTTCCTCTACAGCAAGCTC

ACCGTGGACAAGAGCAGGTGGCAGCAGGGGAACGTCTTCTCA

TGCTCCGTGATGCATGAGGCTCTGCACAACCACTACACGCAGA

AGAGCCTCTCCCTGTCTCCGGGTAAATGATAA

For SEQ ID NOs: 100-121

Antibody region = dashed underline

Non-antibody region = *italic*

Extender peptide = thick underline

Linker = *italic, squiggly underline*; protease site: underline

TABLE 6

Direct Immmunoglobulin Immunoglobulin Fusion Proteins-Amino Acid Sequence

| Name | SEQ ID NO | Sequence |
|---|---|---|
| trastuzumab-direct-hEPO LC | 122 | DIQMTQSPSSLSASVGDRVTITCRASQGGGGSAPPRLICDSRVLERY LLEAKEAENITTGCAEHCSLNENITVPDTKVNFYAWKRMEVGQQAVE VWQGLALLSEAVLRGQALLVNSSQPWEPLQLHVDKAVSGLRSLTTLLR ALGAQKEAISPPDAASAAPLRTITADTFRKLFRVYSNFLRGKLKLYTGE ACRTGDRGGGGSTAVAWYQQKPGKAPKLLIYSASFLYSGVPSRFS GSRSGTDFTLTISSLQPEDFATYYCQQHYTTPPTFGQGTKLEIKRT VAAPSVFIFPPSDEQLKSGTASVVCLLNNFYPREAKVQWKVDNA LQSGNSQESVTEQDSKDSTYSLSSTLTLSKADYEKHKVYACEVTH QGLSSPVTKSFNRGEC |
| trastuzumab-direct bGCSF HC (CDRH3) | 123 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSRWGGDGGGGSTPLGPARSLPQSFLLKCLEQVRKIQA DGAELQERLCAAHKLCHPEELMLLRHSLGIPQAPLSSCSSQSLQLTSC LNQLHGGLFLYQGLLQALAGISPELAPTLDTLQLDVTDFATNIWLQM EDLGAAPAVQPTQGAMPTFTSAFQRRAGGVLVASQLHRFLELAYRGL RYLAEPGGGGSGFYAMDYWGQGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKKVEPKSCDKT HTCPPCPAPELLGGPSVFLFPPKPKDTLMISRTPEVTCVVVDVSHE DPEVKFNWYVDGVEVHNAKTKPREEQYNSTYRVVSVLTVLHQD WLNGKEYKCKVSNKALPAPIEKTISKAKGQPREPQVYTLPPSRDE LTKNQVSLTCLVKGFYPSDIAVEWESNGQPENNYKTTPPVLDSDG SFFLYSKLTVDKSRWQQGNVFSCSVMHEALHNHYTQKSLSLSPG K |
| trastuzumab-direct exendin-4 HC | 124 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSRCGGGGSIEGRHGEGTFTSDLSKQMEEEAVRLFIEWL KNGGPSSGAPPPSGGGGSCDYWGQGTLVTVSSASTKGPSVFPLAP SSKSTSGGTAALGCLVKDYFPEPVTVSWNSGALTSGVHTFPAVLQ SSGLYSLSSVVTVPSSSLGTQTYICNVNHKPSNTKVDKKVEPKSC DKTHTCPPCPAPELLGGPSVFLFPPKPKDTLMISRTPEVTCVVVDV SHEDPEVKFNWYVDGVEVHNAKTKPREEQYNSTYRVVSVLTVL HQDWLNGKEYKCKVSNKALPAPIEKTISKAKGQPREPQVYTLPPS RDELTKNQYSLTCLVKGFYPSDIAVEWESNGQPENNYKTTPPVLD SDGSFFLYSKLTVDKSRWQQGNVFSCSVMHEALHNHYTQKSLSL SPGK |
| trastuzumab-direct Mokal HC | 125 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSRGGGGSINVKCSLPQQCIKPCKDAGMRFGKCMNKKC RCYSGGGGSDYWGQGTLVTVSSASTKGPSVFPLAPSSKSTSGGTA ALGCLVKDYFPEPVTVSWNSGALTSGVHTFPAVLQSSGLYSLSSV VTVPSSSLGTQTYICNVNHKPSNTKVDKKVEPKSCDKTHTCPPCP |

TABLE 6-continued

```
                        APELLGGPSVFLFPPKPKDTLMISRTPEVTCVVVDVSHEDPEVKFN
                        WYVDGVEVHNAKTKPREEQYNSTYRVVSVLTVLHQDWLNGKE
                        YKCKVSNKALPAPIEKTISKAKGQPREPQVYTLPPSRDELTKNQV
                        SLTCLVKGFYPSDIAVEWESNGQPENNYKTTPPVLDSDGSFFLYS
                        KLTVDKSRWQQGNVFSCSVMHEALHNHYTQKSLSLSPGK
``` trastuzumab-direct VM24 HC    126
```
EVQLVESGGGLVQPGGSLRLSCAASGFNIKDTYIHWVRQAPGKG
LEWVARIYPTNGYTRYADSVKGRFTISADTSKNTAYLQMNSLRA
EDTAVYYCSRGGGGSAAAISCVGSPECPPKCRAQGCKNGKCMNRK
CKCYYCGGGGSDYWGQGTLVTVSSASTKGPSVFPLAPSSKSTSGG
TAALGCLVKDYFPEPVTVSWNSGALTSGVHTFPAVLQSSGLYSLS
SVVTVPSSSLGTQTYICNVNHKPSNTKVDKKVEPKSCDKTHTCPP
CPAPELLGGPSVFLFPPKPKDTLMISRTPEVTCVVVDVSHEDPEVK
FNWYVDGVEVHNAKTKPREEQYNSTYRVVSVLTVLHQDWLNG
KEYKCKVSNKALPAPIEKTISKAKGQPREPQVYTLPPSRDELTKN
QVSLTCLVKGFYPSDIAVEWESNGQPENNYKTTPPVLDSDGSFFL
YSKLTVDKSRWQQGNVFSCSVMHEALHNHYTQKSLSLSPGK
```

Herceptin-direct hGCSF HC    127
```
EVQLVESGGGLVQPGGSLRLSCAASGFNIKDTYIHWVRQAPGKG
LEWVARIYPTNGYTRYADSVKGRFTISADTSKNTAYLQMNSLRA
EDTAVYYCSRGGGGSATPLGPASSLPQSFLLKCLEQVRKIQGDGAA
LQEKLVSECATYKLCHPEELVLLGHSLGIPWAPLSSCPSQALQLAGCL
SQLHSGLFLYQGLLQALEGISPELGPTLDTLQLDVADFATTIWQQME
ELGMAPALQPTQGAMPAFASAFQRRAGGVLVASHLQSFLEVSYRVLR
HLAQPGGGGSDYWGQGTLVTVSSASTKGPSVFPLAPCSRSTSEST
AALGCLVKDYFPEPVTVSWNSGALTSGVHTFPAVLQSSGLYSLSS
VVTVPSSSLGTKTYTCNVDHKPSNTKVDKRVESKYGPPCPPCPAP
EAAGGPSVFLFPPKPKDTLMISRTPEVTCVVVDVSQEDPEVQFNW
YVDGVEVHNAKTKPREEQFNSTYRVVSVLTVLHQDWLNGKEYK
CKVSNKGLPSSIEKTISKAKGQPREPQVYTLPPSQEEMTKNQVSLT
CLVKGFYPSDIAVEWESNGQPENNYKTTPPVLDSDGSFFLYSRLT
VDKSRWQEGNVFSCSVMHEALHNHYTQKSLSLSLGK
``` trastuzumab-direct hGH HC    128
```
EVQLVESGGGLVQPGGSLRLSCAASGFNIKDTYIHWVRQAPGKG
LEWVARIYPTNGYTRYADSVKGRFTISADTSKNTAYLQMNSLRA
EDTAVYYCSRGGGGSFPTIPLSRLFDNAMLRAHRLHQLAFDTYQEF
EEAYIPKEQKYSFLQNPQTSLCFSESIPTPSNREETQQKSNLELLRISLL
LIQSWLEPVQFLRSVFANSLVYGASDSNVYDLLKDLEEGIQTLMGRLE
DGSPRTGQIFKQTYSKFDTNSHNDDALLKNYGLLYCFRKDMDKVETF
LRIVQCRSVEGSCGFGGGGSDYWGQGTLVTVSSASTKGPSVFPLAP
CSRSTSESTAALGCLVKDYFPEPVTVSWNSGALTSGVHTFPAVLQ
SSGLYSLSSVVTVPSSSLGTKTYTCNVDHKPSNTKVDKRVESKYG
PPCPPCPAPEAAGGPSVFLFPPKPKDTLMISRTPEVTCVVVDVSQE
DPEVQFNWYVDGVEVHNAKTKPREEQFNSTYRVVSVLTVLHQD
WLNGKEYKCKVSNKGLPSSIEKTISKAKGQPREPQVYTLPPSQEE
MTKNQVSLTCLVKGFYPSDIAVEWESNGQPENNYKTTPPVLDSD
```

TABLE 6-continued

| | | |
|---|---|---|
| | | GSFFLYSRLTVDKSRWQEGNVFSCSVMHEALHNHYTQKSLSLSL GK |
| trastuzumab-direct hLeptin HC | 129 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGGGS*VPIQKVQDDTKTLIKTIVTRINDISHTQSVSSK QKVTGLDFIPGLHPILTLSKMDQTLAVYQQILTSMPSRNVIQISNDLEN LRDLLHVLAFSKSCHLPWASGLETLDSLGGVLEASGYSTEVVALSRLQ GSLQDMLWQLDLSPGCG*GGGS*DYWGQGTLVTVSSASTKGPSVFP LAPCSRSTSESTAALGCLVKDYFPEPVTVSWNSGALTSGVHTFPA VLQSSGLYSLSSVVTVPSSSLGTKTYTCNVDHKPSNTKVDKRVES KYGPPCPPCPAPEAAGGPSVFLFPPKPKDTLMISRTPEVTCVVVDV SQEDPEVQFNWYVDGVEVHNAKTKPREEQFNSTYRVVSVLTVL HQDWLNGKEYKCKVSNKGLPSSIEKTISKAKGQPREPQVYTLPPS QEEMTKNQVSLTCLVKGFYPSDIAVEWESNGQPENNYKTTPPVL DSDGSFFLYSRLTVDKSRWQEGNVFSCSVMHEALHNHYTQKSLS LSLGK |
| trastuzumab-direct hIFN-alpha HC | 130 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGGGS*CDLPQTHSLGSRRTLMLLAQMRRISLFSCLK DRHDFGFPQEEFGNQFQKAETIPVLHEMIQQIFNLFSTKDSSAAWDE TLLDKFYTELYQQLNDLEACVIQGVGVTETPLMKEDSILAVRKYFQRI TLYLKEKKYSPCAWEVVRAEIMRSFSLSTNLQESLRSKEGGG*GGS*DYW GQGTLVTVSSASTKGPSVFPLAPCSRSTSESTAALGCLVKDYFPEP VTVSWNSGALTSGVHTFPAVLQSSGLYSLSSVVTVPSSSLGTKTY TCNVDHKPSNTKVDKRVESKYGPPCPPCPAPEAAGGPSVFLFPPK PKDTLMISRTPEVTCVVVDVSQEDPEVQFNWYVDGVEVHNAKT KPREEQFNSTYRVVSVLTVLHQDWLNGKEYKCKVSNKGLPSSIE KTISKAKGQPREPQVYTLPPSQEEMTKNQVSLTCLVKGFYPSDIA VEWESNGQPENNYKTTPPVLDSDGSFFLYSRLTVDKSRWQEGNV FSCSVMHEALHNHYTQKSLSLSLGK |
| trastuzumab-direct GLP1 HC | 131 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*CGGGGSIEGRHAEGTFTSDVSSYLEGQAAKEFIAWLV KGRGGGGSC*DYWGQGTLVTVSSASTKGPSVFPLAPSSKSTSGGTA ALGCLVKDYFPEPVTVSWNSGALTSGVHTFPAVLQSSGLYSLSSV VTVPSSSLGTQTYICNVNHKPSNTKVDKKVEPKSCDKTHTCPPCP APPVAGPSVFLFPPKPKDTLMISRTPEVTCVVVDVSHEDPEVKFN WYVDGVEVHNAKTKPREEQYNSTYRVVSVLTVLHQDWLNGKE YKCKVSNKGLPSSIEKTISKAKGQPREPQVYTLPPSRDELTKNQVS LTCLVKGFYPSDIAVEWESNGQPENNYKTTPPVLDSDGSFFLYSK LTVDKSRWQQGNVFSCSVMHEALHNHYTQKSLSLSPGK |
| trastuzumab-direct elafin HC | 132 | EVQLVESGGGLVQPGGSLRLSCAASGFNIKDTYIHWVRQAPGKG LEWVARIYPTNGYTRYADSVKGRFTISADTSKNTAYLQMNSLRA |

TABLE 6-continued

| | | |
|---|---|---|
| | | EDTAVYYCSR*GGGGS*AQEPVKGPVSTKPGSCPIILIRCAMLNPPNRC
LKDTDCPGIKKCCEGSCGMACFVPQG*GGGS*DYWGQGTLVTVSSA
STKGPSVFPLAPSSKSTSGGTAALGCLVKDYFPEPVTVSWNSGAL
TSGVHTFPAVLQSSGLYSLSSVVTVPSSSLGTQTYICNVNHKPSNT
KVDKKVEPKSCDKTHTCPPCPAPPVAGPSVFLFPPKPKDTLMISRT
PEVTCVVVDVSHEDPEVKFNWYVDGVEVHNAKTKPREEQYNST
YRVVSVLTVLHQDWLNGKEYKCKVSNKGLPSSIEKTISKAKGQP
REPQVYTLPPSRDELTKNQVSLTCLVKGFYPSDIAVEWESNGQPE
NNYKTTPPVLDSDGSFFLYSKLTVDKSRWQQGNVFSCSVMHEAL
HNHYTQKSLSLSPGK |
| trastuzumab-
direct
mambalgin HC | 133 | EVQLVESGGGLVQPGGSLRLSCAASGFNIKDTYIHWVRQAPGKG
LEWVARIYPTNGYTRYADSVKGRFTISADTSKNTAYLQMNSLRA
EDTAVYYCS*GGGGS*LKCYQHGKVVTCHRDMKFCYHNTGMPFRNL
KLILQGCSSSCSETENNKCCSTDRCNKGGGGSWGQGTLVTVSSAST
KGPSVFPLAPSSKSTSGGTAALGCLVKDYFPEPVTVSWNSGALTS
GVHTFPAVLQSSGLYSLSSVVTVPSSSLGTQTYICNVNHKPSNTK
VDKKVEPKSCDKTHTCPPCPAPPVAGPSVFLFPPKPKDTLMISRTP
EVTCVVVDVSHEDPEVKFNWYVDGVEVHNAKTKPREEQYNSTY
RVVSVLTVLHQDWLNGKEYKCKVSNKGLPSSIEKTISKAKGQPR
EPQVYTLPPSRDELTKNQVSLTCLVKGFYPSDIAVEWESNGQPEN
NYKTTPPVLDSDGSFFLYSKLTVDKSRWQQGNVFSCSVMHEALH
NHYTQKSLSLSPGK |
| trastuzumab-
direct relaxin2
short HC | 134 | EVQLVESGGGLVQPGGSLRLSCAASGFNIKDTYIHWVRQAPGKG
LEWVARIYPTNGYTRYADSVKGRFTISADTSKNTAYLQMNSLRA
EDTAVYYCSR*GGGGS*DSWMEEVIKLCGRELVRAQIAICGMSTWSKR
SLSQE*IEGRKKR*QLYSALANKCCHVGCTKRSLARFCGGGGSDYWGQ
GTLVTVSSASTKGPSVFPLAPSSKSTSGGTAALGCLVKDYFPEPVT
VSWNSGALTSGVHTFPAVLQSSGLYSLSSVVTVPSSSLGTQTYICN
VNHKPSNTKVDKKVEPKSCDKTHTCPPCPAPPVAGPSVFLFPPKP
KDTLMISRTPEVTCVVVDVSHEDPEVKFNWYVDGVEVHNAKTK
PREEQYNSTYRVVSVLTVLHQDWLNGKEYKCKVSNKGLPSSIEK
TISKAKGQPREPQVYTLPPSRDELTKNQVSLTCLVKGFYPSDIAVE
WESNGQPENNYKTTPPVLDSDGSFFLYSKLTVDKSRWQQGNVFS
CSVMHEALHNHYTQKSLSLSPGK |
| trastuzumab-
direct relaxin2
long HC | 135 | EVQLVESGGGLVQPGGSLRLSCAASGFNIKDTYIHWVRQAPGKG
LEWVARIYPTNGYTRYADSVKGRFTISADTSKNTAYLQMNSLRA
LEWVARIYPTNGYTRYADSVKGRFTISADTSKNTAYLQMNSLRA
SLSQEDAPQTPRPV*IEGRKKR*QLYSALANKCCHVGCTKRSLARFCGG
GGSDYWGQGTLVTVSSASTKGPSVFPLAPSSKSTSGGTAALGCLV
KDYFPEPVTVSWNSGALTSGVHTFPAVLQSSGLYSLSSVVTVPSS
SLGTQTYICNVNHKPSNTKVDKKVEPKSCDKTHTCPPCPAPPVAG
PSVFLFPPKPKDTLMISRTPEVTCVVVDVSHEDPEVKFNWYVDGV |

TABLE 6-continued

| | | |
|---|---|---|
| | | EVHNAKTKPREEQYNSTYRVVSVLTVLHQDWLNGKEYKCKVSN |
| | | KGLPSSIEKTISKAKGQPREPQVYTLPPSRDELTKNQVSLTCLVKG |
| | | FYPSDIAVEWESNGQPENNYKTTPPVLDSDGSFFLYSKLTVDKSR |
| | | WQQGNVFSCSVMHEALHNHYTQKSLSLSPGK |
| trastuzumab-direct hGH HC | 136 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGGGS*FPTIPLSRLFDNAMLRAHRLHQLAFDTYQEF EEAYIPKEQKYSFLQNPQTSLCFSESIPTPSNREETQQKSNLELLRISLL LIQSWLEPVQFLRSVFANSLVYGASDSNVYDLLKDLEEGIQTLMGRLE DGSPRTGQIFKQTYSKFDTNSHNDDALLKNYGLLYCFRKDMDKVETF GRILHYLKAKEYSHCAWTIVRVEILRNFYFINRLTGYLRNGGGG*S*WHV SSKSTSGGTAALGCLVKDYFPEPVTVSWNSGALTSGVHTFPAVLQ SSGLYSLSSVVTVPSSSLGTQTYICNVNHKPSNTKVDKKVEPKSC DKTHTCPPCPAPPVAGPSVFLFPPKPKDTLMISRTPEVTCVVVDVS HEDPEVKFNWYVDGVEVHNAKTKPREEQYNSTYRVVSVLTVLH QDWLNGKEYKCKVSNKGLPSSIEKTISKAKGQPREPQVYTLPPSR DELTKNQVSLTCLVKGFYPSDIAVEWESNGQPENNYKTTPPVLDS DGSFFLYSKLTVDKSRWQQGNVFSCSVMHEALHNHYTQKSLSLS PGK |
| trastuzumab-direct hIFN-B1 HC | 137 | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSR*GGGGS*MSYNLLGFLQRSSNFQCQKLLWQLNGRLEY CLKDRMNFDIPEEIKQLQQFQKEDAALTIYEMLQNIFAIFRQDSSSTG WNETIVENLLANVYHQINHLKTVLEEKLEKEDFTRGKLMSSLHLKRYY GRILHYLKAKEYSHCAWTIVRVEILRNFYFINRLTGYLRNGGGG*S*DYW GQGTLVTVSSASTKGPSVFPLAPSSKSTSGGTAALGCLVKDYFPEP VTVSWNSGALTSGVHTFPAVLQSSGLYSLSSVVTVPSSSLGTQTYI CNVNHKPSNTKVDKKVEPKSCDKTHTCPPCPAPPVAGPSVFLFPP KPKDTLMISRTPEVTCVVVDVSHEDPEVKFNWYVDGVEVHNAK TKPREEQYNSTYRVVSVLTVLHQDWLNGKEYKCKVSNKGLPSSI EKTISKAKGQPREPQVYTLPPSRDELTKNQVSLTCLVKGFYPSDIA VEWESNGQPENNYKTTPPVLDSDGSFFLYSKLTVDKSRWQQPNV FSCSVMHEALHNHYTQKSLSLSPGK |
| palivizumab-direct mambalgin HC | 138 | QVTLRESGPALVKPTQTLTLTCTFSGFSLSTSGMSVGWIRQPPGK ALEWLADIWWDDKKDYNPSLKSRLTISKDTSKNQVVLKVTNMD PADTATYYCARS*GGGGS*LKCYQHGKVVTCHRDMKFCYHNTGMPF RNLKLILQGCSSSCSETENNKCCSTDRCNKGGGG*S*YFDVWGAGTTV TVSSASTKGPSVFPLAPSSKSTSGGTAALGCLVKDYFPEPVTVSW NSGALTSGVHTFPAVLQSSGLYSLSSVVTVPSSSLGTQTYICNVNH KPSNTKVDKKVEPKSCDKTHTCPPCPAPPVAGPSVFLFPPKPKDT LMISRTPEVTCVVVDVSHEDPEVKFNWYVDGVEVHNAKTKPREE QYNSTYRVVSVLTVLHQDWLNGKEYKCKVSNKGLPSSIEKTISK AKGQPREPQVYTLPPSRDELTKNQVSLTCLVKGFYPSDIAVEWES |

TABLE 6-continued

```
                        NGQPENNYKTTPPVLDSDGSFFLYSKLTVDKSRWQQGNVFSCSV
                        MHEALHNHYTQKSLSLSPGK
```

BLV1H12-direct betatrophin HC    139    QVQLRESGPSLVKPSQTLSLTCTASGFSLSDKAVGWVRQAPGKA
LEWLGSIDTGGNTGYNPGLKSRLSITKDNSKSQVSLSVSSVTTEDS
ATYYCTSVHQ*GGGGSGGGGS*APLGGPEPAQYEELTLLFHGALQLG
*QALNGVYRATEARLTEAGHSLGLYDRALEFLGTEVRQGQDATQELRT
SLSEIQVEEDALHLRAEATARSLGEVARAQQALRDTVRRLQVQLRGAW
LGQAHQEFETLKARADKQSHLLWALTGHVQRQQREMAEQQQWLRQ
IQQRLHTAALPAGGGGSGGGGS*WHVDVWGQGLLVTVSSASTTAP
KVYPLSSCCGDKSSSTVTLGCLVSSYMPEPVTVTWNSGALKSGV
HTFPAVLQSSGLYSLSSMVTVPGSTSGQTFTCNVAHPASSTKVDK
AVEPKSCDKTHTCPPCPAPELLGGPSVFLFPPKPKDTLMISRTPEV
TCVVVDVSHEDPEVKFNWYVDGVEVHNAKTKPREEQYNSTYRV
VSVLTVLHQDWLNGKEYKCKVSNKALPAPIEKTISKAKGQPREP
QVYTLPPSRDELTKNQVSLTCLVKGFYPSDIAVEWESNGQPENNY
KTTPPVLDSDGSFFLYSKLTVDKSRWQQGNVFSCSVMHEALHNH
YTQKSLSLSPGK BLV1H12-direct betatrophin HC    140    QVQLRESGPSLVKPSQTLSLTCTASGFSLSDKAVGWVRQAPGKA
LEWLGSIDTGGNTGYNPGLKSRLSITKDNSKSQVSLSVSSVTTEDS
ATYYCTSVHQ*GGGGS*APLGGPEPAQYEELTLLFHGALQLGQALNG
*VYRATEARLTEAGHSLGLYDRALEFLGTEVRQGQDATQELRTSLSEIQ
VEEDALHLRAEATARSLGEVARAQQALRDTVRRLQVQLRGAWLGQA
HQEFETLKARADKQSHLLWALTGHVQRQQREMAEQQQWLRQIQQR
LHTAALPAGGGGS*WHVDVWGQGLLVTVSSASTTAPKVYPLSSCC
GDKSSSTVTLGCLVSSYMPEPVTVTWNSGALKSGVHTFPAVLQSS
GLYSLSSMVTVPGSTSGQTFTCNVAHPASSTKVDKAVEPKSCDKT
HTCPPCPAPELLGGPSVFLFPPKPKDTLMISRTPEVTCVVVDVSHE
DPEVKFNWYVDGVEVHNAKTKPREEQYNSTYRVVSVLTVLHQD
WLNGKEYKCKVSNKALPAPIEKTISKAKGQPREPQVYTLPPSRDE
LTKNQVSLTCLVKGFYPSDIAVEWESNGQPENNYKTTPPVLDSDG
SFFLYSKLTVDKSRWQQGNVFSCSVMHEALHNHYTQKSLSLSPG
K BLV1H12-direct hGH HC    141    QVQLRESGPSLVKPSQTLSLTCTASGFSLSDKAVGWVRQAPGKA
LEWLGSIDTGGNTGYNPGLKSRLSITKDNSKSQVSLSVSSVTTEDS
ATYYCTSVHQ*GGGGS*FPTIPLSRLFDNAMLRAHRLHQLAFDTYQEF
*EEAYIPKEQKYSFLQNPQTSLCFSESIPTPSNREETQQKSNLELLRISLL
LIQSWLEPVQFLRSVFANSLVYGASDSNVYDLLKDLEEGIQTLMGRLE
DGSPRTGQIFKQTYSKFDTNSHNDDALLKNYGLLYCFRKDMDKVETF
LRIVQCRSVEGSCGF*GGGGS*WHVDVWGQGLLVTVSSASTTAPKV
YPLSSCCGDKSSSTVTLGCLVSSYMPEPVTVTWNSGALKSGVHTF
PAVLQSSGLYSLSSMVTVPGSTSGQTFTCNVAHPASSTKVDKAVE
PKSCDKTHTCPPCPAPELLGGPSVFLFPPKPKDTLMISRTPEVTCV
VVDVSHEDPEVKFNWYVDGVEVHNAKTKPREEQYNSTYRVVSV
LTVLHQDWLNGKEYKCKVSNKALPAPIEKTISKAKGQPREPQVY
TLPPSRDELTKNQVSLTCLVKGFYPSDIAVEWESNGQPENNYKTT TABLE 6-continued

| | | |
|---|---|---|
| | | PPVLDSDGSFFLYSKLTVDKSRWQQGNVFSCSVMHEALHNHYTQ KSLSLSPGK |
| BLV1H12-direct IFNB HC | 142 | QVQLRESGPSLVKPSQTLSLTCTASGFSLSDKAVGWVRQAPGKA LEWLGSIDTGGNTGYNPGLKSRLSITKDNSKSQVSLSVSSVTTEDS ATYYCTSVHQ*GGGGS*MSYNLLGFLQRSSNFQCQKLLWQLNGRLEY CLKDRMNFDIPEEIKQLQQFQKEDAALTIYEMLQNIFAIFRQDSSSTG WNETIVENLLANVYHQINHLKTVLEEKLEKEDFTRGKLMSSLHLKRYY GRILHYLKAKEYSHCAWTIVRVEILRNFYFINRLTGYLRNG*GGGS*WHV DVWGQGLLVTVSSASTTAPKVYPLSSCCGDKSSSTVTLGCLVSSY MPEPVTVTWNSGALKSGVHTFPAVLQSSGLYSLSSMVTVPGSTS GQTFTCNVAHPASSTKVDKAVEPKSCDKTHTCPPCPAPELLGGPS VFLFPPKPKDTLMISRTPEVTCVVVDVSHEDPEVKFNWYVDGVE VHNAKTKPREEQYNSTYRVVSVLTVLHQDWLNGKEYKCKVSNK ALPAPIEKTISKAKGQPREPQVYTLPPSRDELTKNQVSLTCLVKGF YPSDIAVEWESNGQPENNYKTTPPVLDSDGSFFLYSKLTVDKSRW QQGNVFSCSVMHEALHNHYTQKSLSLSPGK |
| Bovine-direct hGH HC (CDRH3) | 143 | QVQLRESGPSLVKPSQTLSLTCTASGFSLSDKAVGWVRQAPGKA LEWLGSIDTGGNTGYNPGLKSRLSITKDNSKSQVSLSVSSVTTEDS ATYYCTSVHQ*GGGGS*FPTIPLSRLFDNAMLRAHRLHQLAFDTYQEF EEAYIPKEQKYSFLQNPQTSLCFSESIPTPSNREETQQKSNLELLRISLL LIQSWLEPVQFLRSVFANSLVYGASDSNVYDLLKDLEEGIQTLMGRLE DGSPRTGQIFKQTYSKFDTNSHNDDALLKNYGLLYCFRKDMDKVETF LRIVQCRSVEGSCGFG*GGGS*WHVDWGQGLLVTVSSASTTAPKV YPLSSCCGDKSSSTVTLGCLVSSYMPEPVTVTWNSGALKSGVHTF PAVLQSSGLYSLSSMVTVPGSTSGQTFTCNVAHPASSTKVDKAVE PKSCDKTHTCPPCPAPELLGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQVY TLPPSRDELTKNQVSLTCLVKGFYPSDIAVEWESNGQPENNYKTT PPVLDSDGSFFLYSKLTVDKSRWQQGNVFSCSVMHEALHNHYTQ KSLSLSPGK |

For SEQ ID NOs: 122-143
Antibody region = dashed underline
Non-antibody region = italic
Extender peptide = thick underline
Linker = *italic, squiggly underline*; protease site: underline

TABLE 7

Extender Peptide Sequences

| Name | SEQ ID NO | Sequence |
|---|---|---|
| Alpha Helix 1A | 144 | $X^1X^2X^3X^4X^5X^6X^7X^8X^9X^{10}X^{11}X^{12}X^{13}X^{14}$ |
| Alpha Helix 1B | 145 | $(X^1X^2X^3X^4X^5X^6X^7)_n$ |
| Alpha Helix 1C | 146 | $X^aX^bX^cX^d(X^1X^2X^3X^4X^5X^6X^7)_n$ |
| Alpha Helix 1D | 147 | $X^aX^bX^cX^d(AKLAALK)_n$ |
| Alpha Helix 1E | 148 | $(AKLAALK)_n$ |

TABLE 7-continued

Extender Peptide Sequences

| Name | SEQ ID NO | Sequence |
|---|---|---|
| Alpha Helix 1F | 149 | GGSG(AKLAALK)$_n$ |
| Alpha Helix 1G | 150 | AKLAALKAKLAALK |
| Alpha Helix 1H | 151 | GGSGAKLAALKAKLAALK |
| Alpha Helix 1I | 152 | CAALKSKVSALKSKVASLKSKVAAL |
| Alpha Helix 1J | 153 | ALKKELQANKKELAQLKKELQALKKELAQ |
| Alpha Helix 2A | 154 | $X^1X^2X^3X^4X^5X^6X^7X^8X^9X^{10}X^{11}X^{12}X^{13}X^{14}$ |
| Alpha Helix 2B | 155 | $(X^1X^2X^3X^4X^5X^6X^7)_n$ |
| Alpha Helix 2C | 156 | $(X^1X^2X^3X^4X^5X^6X^7)_n\ X^aX^bX^cX^d$ |
| Alpha Helix 2D | 157 | $(ELAALEA)_n\ X^aX^bX^cX^d$ |
| Alpha Helix 2E | 158 | $(ELAALEA)_n$ |
| Alpha Helix 2F | 159 | $(ELAALEA)_n$GGSG |
| Alpha Helix 2G | 160 | ELAALEAELAALEA |
| Alpha Helix 2H | 161 | ELAALEAELAALEAGGSG |
| Alpha Helix 2I | 162 | LAAVESELSAVESELASVESELAAC |
| Alpha Helix 2J | 163 | QLEKKLQALEKKLAQLEKKNQALEKKLAQ |
| Alpha Helix 3 | 164 | CAALKSKVSALKSKVASLKSKVAAL |
| Alpha Helix 4 | 165 | LAAVESELSAVESELASVESELAAC |
| Alpha Helix 5 | 166 | ALKKELQANKKELAQLKKELQALKKELAQ |
| Alpha Helix 6 | 167 | QLEKKLQALEKKLAQLEKKNQALEKKLAQ |
| Alpha Helix 7 | 168 | LKLELQLIKQYREAL |
| Alpha Helix 8 | 169 | LAKILEDEEKHIEWL |
| Alpha Helix 9 | 170 | LSDLHRQVSRLV |
| Alpha Helix 10 | 171 | LQDAKVLLEAAL |
| Alpha Helix 11 | 172 | LQQKIHELEGLIAQH |
| Alpha Helix 12 | 173 | AAQIRDQLHQLRELF |
| Alpha Helix 13 | 174 | ELARLIRLYFAL |
| Alpha Helix 14 | 175 | QESLYVDLFDKF |

TABLE 8

Linker sequences

| Name | SEQ ID NO | Sequence |
|---|---|---|
| Linker 1 | 176 | $(X^eX^fX^gX^h)_n$ |
| Linker 2 | 177 | $CX^eX^fX^gX^h$ |
| Linker 3 | 178 | $X^eX^fX^gX^hC$ |
| Linker 4 | 179 | $(GGGGS)_n$ |
| Linker 5 | 180 | GGGSGGGGS |
| Linker 6 | 181 | GGGGSGGGS |

TABLE 9

Miscellaneous sequences

| Name | SEQ ID NO | Sequence |
|---|---|---|
| Factor Xa nucleotide | 182 | ATCGAAGGTCGT |
| Factor Xa peptide | 183 | IEGR |
| PC2 Cleavage Site -Nucleotide | 184 | CGTAAAAAACGT |
| PC2 Cleavage Site -Amino acid | 185 | RKKR |

TABLE 10

| Therapeutic agents -Nucleic acid sequence | | |
|---|---|---|
| Name | SEQ ID NO | Sequence |
| bGCSF | 186 | ACCCCCCTTGGCCCTGCCCGATCCCTGCCCCAGAGCTTCCTGCT<br>CAAGTGCTTAGAGCAAGTGAGGAAAATCCAGGCTGATGGCGCC<br>GAGCTGCAGGAGAGGCTGTGTGCCGCCCACAAGCTGTGCCACC<br>CGGAGGAGCTGATGCTGCTCAGGCACTCTCTGGGCATCCCCCA<br>GGCTCCCCTAAGCAGCTGCTCCAGCCAGTCCCTGCAGCTGACGA<br>GCTGCCTGAACCAACTACACGGCGGCCTCTTTCTCTACCAGGGC<br>CTCCTGCAGGCCCTGGCGGGCATCTCCCCAGAGCTGGCCCCCAC<br>CTTGGACACACTGCAGCTGGACGTCACTGACTTTGCCACGAACA<br>TCTGGCTGCAGATGGAGGACCTGGGGGCGGCCCCCGCTGTGCA<br>GCCCACCCAGGGCGCCATGCCGACCTTCACTTCAGCCTTCCAAC<br>GCAGAGCAGGAGGGGTCCTGGTTGCTTCCCAGCTGCATCGTTTC<br>CTGGAGCTGGCATACCGTGGCCTGCGCTACCTTGCTGAGCCC |
| hGCSF | 187 | GCCACACCTCTGGGCCCCGCCTCCTCCCTGCCTCAGAGCTTTCT<br>GCTCAAATGTCTGGAGCAGGTGCGGAAGATCCAGGGCGACGGC<br>GCCGCTCTGCAAGAGAAACTGGTCAGCGAATGCGCCACATATA<br>AGCTGTGTCACCCCGAGGAACTGGTCCTCTTGGGCCACAGCCTG<br>GGCATCCCCTGGGCCCCTCTCAGCTCCTGCCCCTCCCAAGCTCT<br>CCAACTGGCTGGATGTCTGTCCCAACTGCACTCCGGCCTCTTCC<br>TGTACCAGGGACTCCTCCAGGCTCTCGAAGGGATCAGCCCCGA<br>ACTGGGCCCCACACTGGACACCTTGCAACTCGATGTGGCCGATT<br>TCGCCACAACCATCTGGCAGCAGATGGAAGAACTCGGAATGGC<br>TCCTGCTCTCCAGCCCACACAGGGAGCTATGCCTGCTTTCGCCT<br>CTGCTTTCCAGCGGAGAGCTGGTGGTGTGCTCGTCGCATCCCAC<br>CTCCAGAGCTTCTTGGAGGTGTCCTATCGGGTGCTCCGGCATCT<br>GGCCCAACCC |
| exendin-4 | 188 | CACGGAGAAGGAACATTTACCAGCGACCTCAGCAAGCAGATGG<br>AGGAAGAGGCCGTGAGGCTGTTCATCGAGTGGCTGAAGAACGG<br>CGGACCCTCCTCTGGCGCTCCACCCCCTAGC |
| Mokal | 189 | ATCAACGTGAAGTGCAGCCTGCCCCAGCAGTGCATCAAGCCCT<br>GCAAGGACGCCGGCATGCGGTTCGGCAAGTGCATGAACAAGAA<br>GTGCAGGTGCTACAGC |
| VM24 | 190 | GCCGCTGCAATCTCCTGCGTCGGCAGCCCCGAATGTCCTCCCAA<br>GTGCCGGGCTCAGGGATGCAAGAACGGCAAGTGTATGAACCGG<br>AAGTGCAAGTGCTACTATTGC |
| hGLP-1 | 191 | CATGCGGAAGGCACCTTTACCAGCGATGTGAGCAGCTATCTGG<br>AAGGCCAGGCGGCGAAAGAATTTATTGCGTGGCTGGTGAAAGG<br>CCGC |
| hEPO | 192 | GCCCCACCACGCCTCATCTGTGACAGCCGAGTCCTGGAGAGGT<br>ACCTCTTGGAGGCCAAGGAGGCCGAGAATATCACGACGGGCTG<br>TGCTGAACACTGCAGCTTGAATGAGAATATCACTGTCCCAGAC<br>ACCAAAGTTAATTTCTATGCCTGGAAGAGGATGGAGGTCGGGC<br>AGCAGGCCGTAGAAGTCTGGCAGGGCCTGGCCCTGCTGTCGGA<br>AGCTGTCCTGCGGGGCCAGGCCCTGTTGGTCAACTCTTCCCAGC<br>CGTGGGAGCCCCTGCAGCTGCATGTGGATAAAGCCGTCAGTGG<br>CCTTCGCAGCCTCACCACTCTGCTTCGGGCTCTGGGAGCCCAGA<br>AGGAAGCCATCTCCCCTCCAGATGCGGCCTCAGCTGCTCCACTC<br>CGAACAATCACTGCTGACACTTTCCGCAAACTCTTCCGAGTCTA<br>CTCCAATTTCCTCCGGGGAAAGCTGAAGCTGTACACAGGGGAG<br>GCCTGCAGGACAGGGGACAGA |
| hFGF21 | 193 | CATCCGATTCCGGATAGCAGCCCGCTGCTGCAGTTTGGCGGCCA<br>GGTGCGCCAGCGCTATCTGTATACCGATGATGCGCAGCAGACC<br>GAAGCGCATCTGGAAATTCGCGAAGATGGCACCGTGGGCGGCG<br>CGGCGGATCAGAGCCCGGAAAGCCTGCTGCAGCTGAAAGCGCT<br>GAAACCGGGCGTGATTCAGATTCTGGGCGTGAAAACCAGCCGC<br>TTTCTGTGCCAGCGCCCGGATGGCGCGCTGTATGGCAGCCTGCA<br>TTTTGATCCGGAAGCGTGCAGCTTTCGCGAACTGCTGCTGGAAG<br>ATGGCTATAACGTGTATCAGAGCGAAGCGCATGGCCTGCCGCT<br>GCATCTGCCGGGCAACAAAAGCCCGCATCGCGATCCGGCGCCG<br>CGCGGCCCGGCGCGCTTTCTGCCGCTGCCGGGCCTGCCGCCGGC<br>GCCGCCGGAACCGCCGGGCATTCTGGCGCCGCAGCCGCCGGAT<br>GTGGGCAGCAGCGATCCGCTGAGCATGGTGGGCCCGAGCCAGG<br>GCCGCAGCCCGAGCTATGCGAGC |
| GMCSF | 194 | GCGCCGGCGCGCAGCCCGAGCCCGAGCACCCAGCCGTGGGAAC<br>ATGTGAACGCGATTCAGGAAGCGCGCCGCCTGCTGAACCTGAG<br>CCGCGATACCGCGGCGGAAATGAACGAAACCGTGGAAGTGATT<br>AGCGAAATGTTTGATCTGCAGGAACCGACCTGCCTGCAGACCC<br>GCCTGGAACTGTATAAACAGGGCCTGCGCGGCAGCCTGACCAA<br>ACTGAAAGGCCCGCTGACCATGATGGCGAGCCATTATAAACAG |

TABLE 10-continued

Therapeutic agents -Nucleic acid sequence

| Name | SEQ ID NO | Sequence |
|---|---|---|
| | | CATTGCCCGCCGACCCCGGAAACCAGCTGCGCGACCCAGATTA<br>TTACCTTTGAAAGCTTTAAAGAAAACCTGAAAGATTTTCTGCTG<br>GTGATTCCGTTTGATTGCTGGGAACCGGTGCAGGAA |
| IFN-beta | 195 | ATGAGCTATAACCTGCTGGGCTTTCTGCAGCGCAGCAGCAACTT<br>TCAGTGCCAGAAACTGCTGTGGCAGCTGAACGGCCGCCTGGAA<br>TATTGCCTGAAAGATCGCATGAACTTTGATATTCCGGAAGAAAT<br>TAAACAGCTGCAGCAGTTTCAGAAAGAAGATGCGGCGCTGACC<br>ATTTATGAAATGCTGCAGAACATTTTTGCGATTTTTCGCCAGGA<br>TAGCAGCAGCACCGGCTGGAACGAAACCATTGTGGAAAACCTG<br>CTGGCCGAACGTGTATCATCAGATTAACCATCTGAAAACCGTGCT<br>GGAAGAAAAACTGGAAAAAGAAGATTTTACCCGCGGCAAACTG<br>ATGAGCAGCCTGCATCTGAAACGCTATTATGGCCGCATTCTGCA<br>TTATCTGAAAGCGAAAGAATATAGCCATTGCGCGTGGACCATT<br>GTGCGCGTGGAAATTCTGCGCAACTTTTATTTTATTAACCGCCT<br>GACCGGCTATCTGCGCAAC |
| oxyntomodulin | 196 | CACTCTCAGGGTACCTTCACCTCTGACTACTCTAAATACCTGGA<br>CTCTCGTCGTGCTCAGGACTTCGTTCAGTGGCTGATGAACACCA<br>AACGTAACCGTAACAACATCGCT |
| hLeptin | 197 | GTTCCAATTCAAAAGGTTCAAGATGATACCAAAACTCTGATTAA<br>AACTATTGTCACGCGTATAAACGACATCAGCCATACCCAGTCG<br>GTTAGCTCAAAGCAAAAAGTTACCGGTTTGGACTTTATTCCGGG<br>ACTGCACCCGATCCTGACCCTTAGTAAAATGGACCAGACACTG<br>GCCGTCTACCAGCAAATCCTGACATCGATGCCATCCAGAAATGT<br>GATACAAATTAGCAACGATTTGGAAAACCTTCGCGATCTGCTGC<br>ACGTGCTGGCCTTCAGTAAGTCCTGTCATCTGCCGTGGGCGTCG<br>GGACTGGAGACTCTTGACTCGCTGGGTGGAGTGTTAGAGGCCT<br>CTGGCTATTCTACTGAAGTCGTTGCGCTGTCACGCCTCCAGGGG<br>AGCCTGCAGGACATGCTGTGGCAGCTGGACCTGTCACCTGGCT<br>GC |
| betatrophin | 198 | GCTCCTCTGGGCGGTCCTGAACCAGCACAGTACGAGGAACTGA<br>CACTGTTGTTCCATGGAGCCTTGCAGCTGGGCCAGGCCCTCAAC<br>GGCGTGTACCGCGCCACAGAGGCACGTTTGACCGAGGCCGGAC<br>ACAGCCTGGGTTTGTACGACAGAGCCCTGGAGTTTCTGGGTACC<br>GAAGTGCGTCAGGGCCAGGACGCAACTCAGGAGCTGAGAACCT<br>CCCTCTCTGAGATCCAGGTGGAGGAGGACGCCCTGCACCTGCG<br>CGCCGAGGCGACAGCACGCTCTTTGGGAGAAGTTGCTCGCGCT<br>CAGCAGGCCCTGCGTGATACCGTGCGGAGACTCCAAGTTCAGC<br>TCAGAGGGCGCTTGGCTCGGACAGGCGCATCAGGAGTTCGAGAC<br>CCTGAAAGCTCGTGCCGACAAACAGTCCCACCTGCTGTGGGCG<br>CTCACCGGTCACGTCCAGCGCCAGCAACGCGAAATGGCCGAGC<br>AGCAGCAATGGCTGCGCCAAATCCAGCAGCGCCTGCATACCGC<br>GGCCCTGCCAGCGTAA |
| GDF11 | 199 | AACCTGGGTCTGGACTGCGACGAACACTCTTCTGAATCTCGTTG<br>CTGCCGTTACCCGCTGACCGTTGACTTCGAGGCGTTCGGTTGGG<br>ACTGGATCATCGCTCCGAAACGTTACAAAGCTAACTACTGCTCT<br>GGTCAGTGCGAATACATGTTCATGCAGAAATACCCGCACACCC<br>ACCTGGTTCAGCAGGCTAACCCGCGTGGTTCTGCTGGTCCGTGC<br>TGCACCCCGACCAAAATGTCTCCGATCAACATGCTGTACTTCAA<br>CGACAAACAGCAGATCATCTACGGTAAAATCCCGGGTATGGTT<br>GTTGACCGTTGCGGTTGCTCTTAA |
| ANGPTL3 | 200 | GGATCCGGTGGTTTCACCATCAAACTGCTGCTGTTCATCGTTCC<br>GCTGGTTATCTCTTCTCGTATCGACCAGGACAACTCTTCTTTCGA<br>CTCTCTGTCTCCGGAACCGAAATCTCGTTTCGCTATGCTGGACG<br>ACGTTAAAATCCTGGCTAACGGTCTGCTGCAGCTGGGTCACGGT<br>CTGAAAGACTTCGTTCACAAAACCAAAGGTCAGATCAACGACA<br>TCTTCCAGAAACTGAACATCTTCGACCAGTCTTTCTACGACCTG<br>TCTCTGCAGACCTCTGAAATCAAAGAAGAAGAAAAAGAACTGC<br>GTCGTACCACCTACAAACTGCAGGTTAAAAACGAAGAAGTTAA<br>AAACATGTCTCTGGAACTGAACTCTAAACTGGAATCTCTGCTGG<br>AAGAAAAAATCCTGCTGCAGCAGAAAGTTAAATACCTGGAAGA<br>ACAGCTGACCAACCTGATCCAGAACCAGCCGGAAACCCCGGAA<br>CACCCGGAAGTTACCTCTCTGAAAACCTTCGTTGAAAAACAGG<br>ACAACTCTATCAAAGACCTGCTGCAGACCGTTGAAGACCAGTA<br>CAAACAGCTGAACCAGCAGCACTCTCAGATCAAAGAAATCGAA<br>AACCAGCTGCGTCGTACCTCTATCCAGGAACCGACCGAAATCTC<br>TCTGTCTTCTAAACCGCGTGCTCCGCGTACCACCCCGTTCCTGC<br>AGCTGAACGAAATCCGTAACGTTAAACACGACGGTATCCCGGC<br>TGAATGCACCACCATCTACAACCGTGGTGAACACACCTCTGGTA<br>TGTACGCTATCCGTCCGTCTAACTCTCAGGTTTTCCACGTTTACT<br>GCGACGTTATCTCTGGTTCTCCGTGGACCCTGATCCAGCACCGT |

TABLE 10-continued

Therapeutic agents -Nucleic acid sequence

| Name | SEQ ID NO | Sequence |
|---|---|---|
| | | ATCGACGGTTCTCAGAACTTCAACGAAACCTGGGAAAACTACA<br>AATACGGTTTCGGTCGTCTGGACGGTGAATTCTGGCTGGGTCTG<br>GAAAAAATCTACTCTATCGTTAAACAGTCTAACTACGTTCTGCG<br>TATCGAACTGGAAGACTGGAAAGACAACAAACACTACATCGAA<br>TACTCTTTCTACCTGGGTAACCACGAAACCAACTACACCCTGCA<br>CCTGGTTGCTATCACCGGTAACGTTCCGAACGCTATCCCGAAGA<br>AGAAGAAGAAAAAAAGAAGAAGAAAT |
| hGH | 201 | TTCCCAACCATTCCCTTATCCAGGCTTTTTGACAACGCTATGCTC<br>CGCGCCCATCGTCTGCACCAGCTGGCCTTTGACACCTACCAGGA<br>GTTTGAAGAAGCCTATATCCCAAAGGAACAGAAGTATTCATTC<br>CTGCAGAACCCCCAGACCTCCCTCTGTTTCTCAGAGTCTATTCC<br>GACACCCTCCAACAGGGAGGAAACACAACAGAAATCCAACCTA<br>GAGCTGCTCCGCATCTCCCTGCTGCTCATCCAGTCGTGGCTGGA<br>GCCCGTGCAGTTCCTCAGGAGTGTCTTCGCCAACAGCCTGGTGT<br>ACGGCGCCTCTGACAGCAACGTCTATGACCTCCTAAAGGACCT<br>AGAGGAAGGCATCCAAACGCTGATGGGGAGGCTGGAAGATGG<br>CAGCCCCCGGACTGGGCAGATCTTCAAGCAGACCTACAGCAAG<br>TTCGACACAAACTCACACAACGATGACGCACTACTCAAGAACT<br>ACGGGCTGCTCTACTGCTTCAGGAAGGACATGGACAAGGTCGA<br>GACATTCCTGCGCATCGTGCAGTGCCGCTCTGTGGAGGGCAGCT<br>GTGGCTTC |
| hIFN-alpha | 202 | TGTGATCTGCCTCAAACCCACAGCCTGGGTAGCAGGAGGACCT<br>TGATGCTCCTGGCACAGATGAGGAGAATCTCTCTTTTCTCCTGC<br>TTGAAGGACAGACATGACTTTGGATTTCCCCAGGAGGAGTTTG<br>GCAACCAGTTCCAAAAGGCTGAAACCATCCCTGTCCTCCATGA<br>GATGATCCAGCAGATCTTCAATCTCTTCAGCACAAAGGACTCAT<br>CTGCTGCTTGGGATGAGACCCTCCTAGACAAATTCTACACTGAA<br>CTCTACCAGCAGCTGAATGACCTGGAAGCCTGTGTGATACAGG<br>GGGTGGGGGTGACAGAGACTCCCCTGATGAAGGAGGACTCCAT<br>TCTGGCTGTGAGGAAATACTTCCAAAGAATCACTCTCTATCTGA<br>AAGAGAAGAAATACAGCCCTTGTGCCTGGGAGGTTGTCAGAGC<br>AGAAATCATGAGATCTTTTTCTTTGTCAACAAACTTGCAAGAAA<br>GTTTAAGAAGTAAGGAA |
| Mamba | 203 | CTGAAATGTTACCAACATGGTAAAGTTGTGACTTGTCATCGAGA<br>TATGAAGTTTTGCTATCATAACACTGGCATGCCTTTTCGAAATC<br>TCAAGCTCATCCTACAGGGATGTTCTTCTTCGTGCAGTGAAACA<br>GAAAACAATAAGTGTTGCTCAACAGACAGATGCAACAA |
| Parathyroid<br>hormone | 204 | TCTGTGAGTGAAATACAGCTTATGCATAACCTGGGAAAACATCT<br>GAACTCGATGGAGAGAGTAGAATGGCTGCGTAAGAAGCTGCAG<br>GATGTGCACAATTTTGTTGCCCTTGGAGCTCCTCTAGCTCCCAG<br>AGATGCTGGTTCCCAGAGGCCCCGAAAAAAGGAAGACAATGTC<br>TTGGTTGAGAGCCATGAAAAAAGTCTTGGAGAGGCAGACAAAG<br>CTGATGTGAATGTATTAACTAAAGCTAAATCCCAG |
| IL-11 | 205 | ATGAACTGCGTGTGCCGCCTGGTGCTGGTGGTGCTGAGCCTGTG<br>GCCGGATACCGCGGTGGCGCCGGGCCCGCCGCCGGGCCCGGCC<br>CGCGTGAGCCCGGATCCGCGCGCGGGAACTGGATAGCACCGTGC<br>TGCTGACCCGCAGCCTGCTGGCGGATACCCGCCAGCTGGCGGC<br>GCAGCTGCGCGATAAATTTCCGGCGGATGGCGATCATAACCTG<br>GATAGCCTGCCGACCCTGGCGATGAGCGCGGGCGCGCTGGGCG<br>CGCTGCAGCTGCCGGGCGTGCTGACCCGCCTGCGCGCGGATCT<br>GCTGAGCTATCTGCGCCATGTGCAGTGGCTGCGCCGCGCGGGC<br>GGCAGCAGCCTGAAAACCCTGGAACCGGAACTGGGCACCCTGC<br>AGGCGCGCCTGGATCGCCTGCTGCGCCGCCTGCAGCTGCTGATG<br>AGCCGCCTGGCGCTGCCGCAGCCGCCGCCGGATCCGCCGGCGC<br>CGCCGCTGGCGCCGCCGAGCAGCGCGTGGGGCGGCATTCGCGC<br>GGCGCTGGCGATTCTGGGCGGCCTGCATCTGACCCTGGATTGGG<br>CGGTGCGCGGCCTGCTGCTGCTGAAAACCCGCCTG |
| relaxin | 206 | GACTCTTGGATGGAAGAAGTTATCAAACTGTGCGGTCGTGAAC<br>TGGTTCGTGCTCAGATCGCTATCTGCGGTATGTCTACCTGGTCT<br>GGTGGCGGTCGTGGCGGTCGTCAGCTGTACTCTGCTCTGGCTAA<br>CAAATGCTGCCACGTTGGTTGCACCAAACGTTCTCTGGCTCGTT<br>TCTGCTAA |
| relaxin-<br>Factor Xa | 207 | GATAGCTGGATGGAAGAAGTGATTAAACTGTGCGGCCGCGAAC<br>TGGTGCGCGCGCAGATTGCGATTTGCGGCATGAGCACCTGGAG<br>CATTGAAGGCCGCAGCCTGAGCCAGGAAGATGCGCCGCAGACC<br>CCGCGCCCGGTGGCGGAAATTGTGCCGAGCTTTATTAACAAAG<br>ATACCGAAACCATTAACATGATGAGCGAATTTGTGGCGAACCT<br>GCCGCAGGAACTGAAACTGACCCTGAGCGAAATGCAGCCGGCG<br>CTGCCGCAGCTGCAGCAGCATGTGCCGGTGCTGAAAGATAGCA |

TABLE 10-continued

Therapeutic agents -Nucleic acid sequence

| Name | SEQ ID NO | Sequence |
|---|---|---|
| | | GCCTGCTGTTTGAAGAATTTAAAAAACTGATTCGCAACCGCCAG<br>AGCGAAGCGGCGGATAGCAGCCCGAGCGAACTGAAATATCTGG<br>GCCTGGATACCCATAGCATTGAAGGCCGCCAGCTGTATAGCGC<br>GCTGGCGAACAAATGCTGCCATGTGGGCTGCACCAAACGCAGC<br>CTGGCGCGCTTTTGC |
| relaxin fragment | 208 | AGCCTGAGCCAGGAAGATGCGCCGCAGACCCCGCGCCCGGTGG<br>CGGAAATTGTGCCGAGCTTTATTAACAAAGATACCGAAACCAT<br>TAACATGATGAGCGAATTTGTGGCGAACCTGCCGCAGGAACTG<br>AAACTGACCCTGAGCGAAATGCAGCCGGCGCTGCCGCAGCTGC<br>AGCAGCATGTGCCGGTGCTGAAAGATAGCAGCCTGCTGTTTGA<br>AGAATTTAAAAAACTGATTCGCAACCGCCAGAGCGAAGCGGCG<br>GATAGCAGCCCGAGCGAACTGAAATATCTGGGCCTGGATACCC<br>ATAGC |
| relaxin2 A chain | 209 | GACTCTTGGATGGAAGAAGTTATCAAACTGTGCGGTCGTGAAC<br>TGGTTCGTGCTCAGATCGCTATCTGCGGTATGTCTACCTGGTCT<br>AAACGTTCTCTGTCTCAGGAAGACGCTCCGCAGACCCCGCGTCC<br>GGTT |
| relaxin2 B chain | 210 | CAGCTGTACTCTGCTCTGGCTAACAAATGCTGCCACGTTGGTTG<br>CACCAAACGTTCTCTGGCTCGTTTCTGC |
| IL8 | 211 | CCGCGCAGCGCGAAAGAACTGCGCTGCCAGTGCATTAAAACCT<br>ATAGCAAACCGTTTCATCCGAAATTTATTAAAGAACTGCGCGTG<br>ATTGAAAGCGGCCCGCATTGCGCGAACACCGAAATTATTGTGA<br>AACTGAGCGATGGCCGCGAACTGTGCCTGGATCCGAAAGAAAA<br>CTGGGTGCAGCGCGTGGTGGAAAAATTTCTGAAACGCGCGGAA<br>AACAGC |
| ziconotide | 212 | TGCAAAGGCAAAGGCGCGAAATGCAGCCGCCTGATGTATGATT<br>GCTGCACCGGCAGCTGCCGCAGCGGCAAATGC |
| somatostatin | 213 | GCGGGCTGCAAAAACTTTTTTTGGAAAACCTTTACCAGCTGCGGC |
| chlorotoxin | 214 | ATGTGCATGCCGTGCTTTACCACCGATCATCAGATGGCGCGCAA<br>ATGCGATGATTGCTGCGGCGGCAAAGGCCGCGGCAAATGCTAT<br>GGCCCGCAGTGCCTG |
| SDF1(alpha) | 215 | AAACCGGTGAGCCTGAGCTATCGCTGCCCGTGCCGCTTTTTTGA<br>AAGCCATGTGGCGCGCGCGAACGTGAAACATCTGAAAATTCTG<br>AACACCCCGAACTGCGCGCTGCAGATTGTGGCGCGCCTGAAAA<br>ACAACAACCGCCAGGTGTGCATTGATCCGAAACTGAAATGGAT<br>TCAGGAATATCTGGAAAAAGCGCTGAACAAA |
| IL21 | 216 | CAGGGCCAGGATCGCCATATGATTCGCATGCGCCAGCTGATTG<br>ATATTGTGGATCAGCTGAAAAACTATGTGAACGATCTGGTGCC<br>GGAATTTCTGCCGGCGCCGGAAGATGTGGAAACCAACTGCGAA<br>TGGAGCGCGTTTAGCTGCTTTCAGAAAGCGCAGCTGAAAAGCG<br>CGAACACCGGCAACAACGAACGCATTATTAACGTGAGCATTAA<br>AAAACTGAAACGCAAACCGCCGAGCACCAACGCGGGCCGCCGC<br>CAGAAACATCGCCTGACCTGCCCGAGCTGCGATAGCTATGAAA<br>AAAAACCGCCGAAAGAATTTCTGGAACGCTTTAAAAGCCTGCT<br>GCAGAAAATGATTCATCAGCATCTGAGCAGCCGCACCCATGGC<br>AGCGAAGATAGC |
| elafin | 217 | GCGCAAGAGCCAGTCAAAGGTCCAGTCTCCACTAAGCCTGGCT<br>CCTGCCCCATTATCTTGATCCGGTGCGCCATGTTGAATCCCCCT<br>AACCGCTGCTTGAAAGATACTGACTGCCCAGGAATCAAGAAGT<br>GCTGTGAAGGCTCTTGCGGGATGGCCTGTTTCGTTCCCCAG |
| elastase inhibitor | 218 | ATGTGTACCGCAAGCATACCACCCCAATGCTAC |
| ZP | 219 | CACAGCCAGGGCACATTCACTAGCGATTATAGTAAATATCTGG<br>ATTCCAAGGCAGCGCACGATTTTGTAGAGTGGCTCTTGAACGG<br>AGGCCCTTCCTCCGGAGCTCCACCTCCGTCC |
| ZP mutant (S-G) | 220 | CACGGCCAGGGCACATTCACTAGCGATTATAGTAAATATCTGG<br>ATTCCAAGGCAGCGCACGATTTTGTAGAGTGGCTCTTGAACGG<br>AGGCCCTTCCTCCGGAGCTCCACCTCCGTCC |
| Ssam6a | 221 | GCTGACAACAAATGCGAAAACTCTCTGCGTCGTGAAATCGCTT<br>GCGGTCAGTGCCGTGACAAAGTTAAAACCGACGGTTACTTCTA<br>CGAATGCTGCACCTCTGACTCTACCTTCAAAAAATGCCAGGACC<br>TGCTGCAC |

TABLE 10-continued

Therapeutic agents -Nucleic acid sequence

| Name | SEQ ID NO | Sequence |
|---|---|---|
| GLP2 | 222 | CACGGCGACGGTTCATTCTCTGACGAAATGAATACAATACTCG ACAACCTCGCCGCCAGGGACTTTATCAATTGGCTCATTCAAACT AAAATCACCGACGGAGGCCCTTCCTCCGGAGCTCCACCTCCGTCC |
| relaxin2 (XTEN100) | 223 | GACTCTTGGATGGAAGAAGTTATCAAACTGTGCGGTCGTGAAC TGGTTCGTGCTCAGATCGCTATCTGCGGTATGTCTACCTGGTCT AAACGTGGAGGTGGCGGGAGCGGCACTTCTGAGTCTGCTACTC CAGAAAGCGGCCCAGGTTCTGAACCAGCAACTTCTGGCTCTGA GACTCCAGGCACTTCTGAGTCCGCAACGCCTGAATCCGGTCCTG GTTCTGAACCAGCTACTTCCGGCAGCGAAACCCCAGGTACCGG AGGTGGCGGGAGCCACCATCACCACCACCACGGAGGTGGCGGG AGCTCTGAGTCTGCGACTCCAGAGTCTGGTCCTGGTACTTCCAC TGAGCCTAGCGAGGGTTCCGCACCAGGTTCTCCGGCTGGTAGCC CGACCAGCACGGAGGAGGGTACGTCTGAATCTGCAACGCCGGA ATCGGGCCCAGGTTCGGAGGGAGGAGGTGGCGGGAGCCGTAA AAAACGTCAGCTGTACTCTGCTCTGGCTAACAAATGCTGCCACG TTGGTTGCACCAAACGTTCTCTGGCTCGTTTCTGC |
| relaxin2 (XTEN35) | 224 | GACTCTTGGATGGAAGAAGTTATCAAACTGTGCGGTCGTGAAC TGGTTCGTGCTCAGATCGCTATCTGCGGTATGTCTACCTGGTCT AAACGTGGAGGTGGCGGGAGCTCTGGCAGCGAAACCCCGGGTA CCTCCGAATCTGCTACACCGGAAAGCGGTGGAGGTGGCGGGAG CCACCATCACCACCACCACGGAGGTGGCGGGAGCCCTGGCAGC CCTGGTCCGGGCACTAGCACCGAGCCATCGGAGGGCTCCGCAC CAGGAGGTGGCGGGAGCCGTAAAAAACGTCAGCTGTACTCTGC TCTGGCTAACAAATGCTGCCACGTTGGTTGCACCAAACGTTCTC TGGCTCGTTTCTGC |
| relaxin2 (insulin c peptide) | 225 | GACTCTTGGATGGAAGAAGTTATCAAACTGTGCGGTCGTGAAC TGGTTCGTGCTCAGATCGCTATCTGCGGTATGTCTACCTGGTCT AAACGTGAGGCAGAGGACCTGCAGGTGGGCAGGTGGAGCTG GGCGGGGGCCCTGGTGCAGGCAGCCTGCAGCCCTTGGCCCTGG AGGGGTCCCTGCAGAAGCGTCGTAAAAAACGTCAGCTGTACTC TGCTCTGGCTAACAAATGCTGCCACGTTGGTTGCACCAAACGTT CTCTGGCTCGTTTCTGC |
| relaxin2 (XTEN21) | 226 | GACTCTTGGATGGAAGAAGTTATCAAACTGTGCGGTCGTGAAC TGGTTCGTGCTCAGATCGCTATCTGCGGTATGTCTAC CTGGTCTTCTGGCAGCGAAACCCCGGGTACCTCCGAATCTGCTA CACCGGAAAGCGGTCCTGGCAGCCCTCAGCTGTACT CTGCTCTGGCTAACAAATGCTGCCACGTTGGTTGCACCAAACGT TCTCTGGCTCGTTTCTGC |

TABLE 11

Therapeutic agents -Amino, acid sequences

| Name | SEQ ID NO | Sequence |
|---|---|---|
| bGCSF | 227 | TPLGPARSLPQSFLLKCLEQVRKIQADGAELQERLCAAHKLCHPEE LMLLRHSLGIPQAPLSSCSSQSLQLTSCLNQLHGGLFLYQGLLQAL AGISPELAPTLDTLQLDVTDFATNIWLQMEDLGAAPAVQPTQGAM PTFTSAFQRRAGGVLVASQLHRFLELAYRGLRYLAEP |
| exendin-4 | 228 | HGEGTFTSDLSKQMEEEAVRLFIEWLKNGGPSSGAPPPS |
| Moka1 | 229 | INVKCSLPQQCIKPCKDAGMRFGKCMNKKCRCYS |
| VM24 | 230 | AAAISCVGSPECPPKCRAQGCKNGKCMNRKCKCYYC |
| hGCSF | 231 | ATPLGPASSLPQSFLLKCLEQVRKIQGDGAALQEKLVSECATYKLC HPEELVLLGHSLGIPWAPLSSCPSQALQLAGCLSQLHSGLFLYQGL LQALEGISPELGPTLDTLQLDVADFATTIWQQMEELGMAPALQPT QGAMPAFASAFQRRAGGVLVASHLQSFLEVSYRVLRHLAQP |
| hGLP-1 | 232 | HAEGTFTSDVSSYLEGQAAKEFIAWLVKGR |
| hEPO | 233 | PPRLICDSRVLERYLLEAKEAENITTGCAEHCSLNENITVPDTKVNF YAWKRMEVGQQAVEVWQGLALLSEAVLRGQALLVNSSQPWEPL QLHVDKAVSGLRSLTTLLRALGAQKEAISPPDAASAAPLRTITADT FRKLFRVYSNFLRGKLKLYTGEACRTGDR |

TABLE 11-continued

Therapeutic agents -Amino, acid sequences

| Name | SEQ ID NO | Sequence |
|---|---|---|
| hFGF21 | 234 | HPIPDSSPLLQFGGQVRQRYLYTDDAQQTEAHLEIREDGTVGGAA<br>DQSPESLLQLKALKPGVIQILGVKTSRFLCQRPDGALYGSLHFDPE<br>ACSFRELLLEDGYNVYQSEAHGLPLHLPGNKSPHRDPAPRGPARFL<br>PLPGLPPAPPEPPGILAPQPPDVGSSDPLSMVGPSQGRSPSYAS |
| GMCSF | 235 | APARSPSPSTQPWEHVNAIQEARRLLNLSRDTAAEMNETVEVISEM<br>FDLQEPTCLQTRLELYKQGLRGSLTKLKGPLTMMASHYKQHCPPT<br>PETSCATQIITFESFKENLKDFLLVIPFDCWEPVQE |
| IFN-beta | 236 | MSYNLLGFLQRSSNFQCQKLLWQLNGRLEYCLKDRMNFDIPEEIK<br>QLQQFQKEDAALTIYEMLQNIFAIFRQDSSSTGWNETIVENLLANV<br>YHQINHLKTVLEEKLEKEDFTRGKLMSSLHLKRYYGRILHYLKAK<br>EYSHCAWTIVRVEILRNFYFINRLTGYLRN |
| oxyntomodulin | 237 | HSQGTFTSDYSKYLDSRRAQDFVQWLMNTKRNRNNIA |
| hLeptin | 238 | VPIQKVQDDTKTLIKTIVTRINDISHTQSVSSKQKVTGLDFIPGLHPI<br>LTLSKMDQTLAVYQQILTSMPSRNVIQISNDLENLRDLLHVLAFSK<br>SCHLPWASGLETLDSLGGVLEASGYSTEVVALSRLQGSLQDMLW<br>QLDLSPGC |
| betatrophin | 239 | APLGGPEPAQYEELTLLFHGALQLGQALNGVYRATEARLTEAGHS<br>LGLYDRALEFLGTEVRQGQDATQELRTSLSEIQVEEDALHLRAEAT<br>ARSLGEVARAQQALRDTVRRLQVQLRGAWLGQAHQEFETLKAR<br>ADKQSHLLWALTGHVQRQQREMAEQQQWLRQIQQRLHTAALPA |
| GDF11 | 240 | NLGLDCDEHSSESRCCRYPLTVDFEAFGWDWIIAPKRYKANYCSG<br>QCEYMFMQKYPHTHLVQQANPRGSAGPCCTPTKMSPINMLYFND<br>KQQIIYGKIPGMVVDRCGCS |
| ANGPTL3 | 241 | GSGGFTIKLLLFIVPLVISSRIDQDNSSFDSLSPEPKSRFAMLDDVKIL<br>ANGLLQLGHGLKDFVHKTKGQINDIFQKLNIFDQSFYDLSLQTSEI<br>KEEEKELRRTTYKLQVKNEEVKNMSLELNSKLESLLEEKILLQQK<br>VKYLEEQLTNLIQNQPETPEHPEVTSLKTFVEKQDNSIKDLLQTVE<br>DQYKQLNQQHSQIKEIENQLRRTSIQEPTEISLSSKPRAPRTTPFLQL<br>NEIRNVKHDGIPAECTTIYNRGEHTSGMYAIRPSNSQVFHVYCDVI<br>SGSPWTLIQHRIDSQNFNETWENYKYGFGRLDGEFWLGLEKIYSI<br>VKQSNYVLRIELEDWKDNKHYIEYSFYLGNHETNYTLHLVAITGN<br>VPNAIPKKKKKKKKK |
| hGH | 242 | FPTIPLSRLFDNAMLRAHRLHQLAFDTYQEFEEAYIPKEQKYSFLQ<br>NPQTSLCFSESIPTPSNREETQQKSNLELLRISLLLIQSWLEPVQFLRS<br>VFANSLVYGASDSNVYDLLKDLEEGIQTLMGRLEDGSPRTGQIFK<br>QTYSKFDTNSHNDDALLKNYGLLYCFRKDMDKVETFLRIVQCRSV<br>EGSCGF |
| hIFN-alpha | 243 | CDLPQTHSLGSRRTLMLLAQMRRISLFSCLKDRHDFGFPQEEFGNQ<br>FQKAETIPVLHEMIQQIFNLFSTKDSSAAWDETLLDKFYTELYQQL<br>NDLEACVIQGVGVTETPLMKEDSILAVRKYFQRITLYLKEKKYSPC<br>AWEVVRAEIMRSFSLSTNLQESLRSKE |
| Mamba | 244 | LKCYQHGKVVTCHRDMKFCYHNTGMPFRNLKLILQGCSSSCSETE<br>NNKCCSTDRCN |
| Parathyroid Hormone | 245 | SVSEIQLMHNLGKHLNSMERVEWLRKKLQDVHNFVALGAPLAPR<br>DAGSQRPRKKEDNVLVESHEKSLGEADKADVNVLTKAKSQ |
| IL-11 | 243 | MNCVCRLVLVVLSLWPDTAVAPGPPPGPPRVSPDPRAELDSTVLL<br>TRSLLADTRQLAAQLRDKFPADGDHNLDSLPTLAMSAGALGALQ<br>LPGVLTRLRADLLSYLRHVQWLRRAGGSSLKTLEPELGTLQARLD<br>RLLRRLQLLMSRLALPQPPPDPPAPPLAPPSSAWGGIRAALAILGGL<br>HLTLDWAVRGLLLLKTRL |
| relaxin | 247 | DSWMEEVIKLCGRELVRAQIAICGMSTWSGGGRGGRQLYSALAN<br>KCCHVGCTKRSLARFC |
| relaxin-Factor Xa | 248 | DSWMEEVIKLCGRELVRAQIAICGMSTWS<u>IEGR</u>SLSQEDAPQTPRP<br>VAEIVPSFINKDTETINMMSEFVANLPQELKLTLSEMQPALPQLQQ<br>HVPVLKDSSLLFEEFKKLIRNRQSEAADSSPSELKYLGLDTHS<u>IEGR</u><br>QLYSALANKCCHVGCTKRSLARFC |
| relaxin fragment | 249 | SLSQEDAPQTPRPVAEIVPSFINKDTETINMMSEFVANLPQELKLTL<br>SEMQPALPQLQQHVPVLKDSSLLFEEFKKLIRNRQSEAADSSPSEL<br>KYLGLDTHS |

TABLE 11-continued

Therapeutic agents -Amino, acid sequences

| Name | SEQ ID NO | Sequence |
|---|---|---|
| relaxin2 A chain | 250 | DSWMEEVIKLCGRELVRAQIAICGMSTWS |
| relaxin2 B chain | 251 | QLYSALANKCCHVGCTKRSLARFC |
| IL8 | 252 | PRSAKELRCQCIKTYSKPFHPKFIKELRVIESGPHCANTEIIVKLSDG RELCLDPKENWVQRVVEKFLKRAENS |
| ziconotide | 253 | CKGKGAKCSRLMYDCCTGSCRSGKC |
| somatostatin | 254 | AGCKNFFWKTFTSCG |
| chlorotoxin | 255 | MCMPCFTTDHQMARKCDDCCGGKGRGKCYGPQCL |
| SDF1(alpha) | 256 | KPVSLSYRCPCRFFESHVARANVKHLKILNTPNCALQIVARLKNNN RQVCIDPKLKWIQEYLEKALNK |
| IL21 | 257 | QGQDRHMIRMRQLIDIVDQLKNYVNDLVPEFLPAPEDVETNCEWS AFSCFQKAQLKSANTGNNERIINVSIKKLKRKPPSTNAGRRQKHRL TCPSCDSYEKKPPKEFLERFKSLLQKMIHQHLSSRTHGSEDS |
| elafin | 258 | AQEPVKGPVSTKPGSCPIILIRCAMLNPPNRCLKDTDCPGIKKCCEG SCGMACFVPQ |
| elastase inhibitor | 259 | MCTASIPPQCY |
| ZP | 260 | IEGRHSQGTFTSDYSKYLDSKAAHDFVEWLLNGGPSSGAPPPS |
| ZP mutant (S-G) | 261 | IEGRHGQGTFTSDYSKYLDSKAAHDFVEWLLNGGPSSGAPPPS |
| Ssam6a | 262 | ADNKCENSLRREIACGQCRDKVKTDGYFYECCTSDSTFKKCQDLLH |
| GLP2 | 263 | IEGRHGDGSFSDEMNTILDNLAARDFINWLIQTKITDGGPSSGAPPPS |
| relaxin2 (XTEN100) | 264 | DSWMEEVIKLCGRELVRAQIAICGMSTWSKRGGGGSGTSESATPE SGPGSEPATSGSETPGTSESATPESGPGSEPATSGSETPGTGGGGSH HHHHHGGGGSSESATPESGPGTSTEPSEGSAPGSPAGSPTSTEEGTS ESATPESGPGSEGGGGGSRKKRQLYSALANKCCHVGCTKRSLARFC |
| relaxin2 (XTEN35) | 265 | DSWMEEVIKLCGRELVRAQIAICGMSTWSKRGGGGSSGSETPGTS ESATPESGGGGGSHHHHHGGGGSPGSPGPGTSTEPSEGSAPGGG GSRKKRQLYSALANKCCHVGCTKRSLARFC |
| relaxin2 (insulin c peptide) | 266 | DSWMEEVIKLCGRELVRAQIAICGMSTWSKREAEDLQVGQVELG GGPGAGSLQPLALEGSLQKRRKKRQLYSALANKCCHVGCTKRSL ARFC |
| relaxin2 (XTEN21) | 267 | DSWMEEVIKLCGRELVRAQIAICGMSTWSSGSETPGTSESATPESG PGSPQLYSALANKCCHVGCTKRSLARFC |

TABLE 12

Bovine IgG sequences

| Name | SEQ ID NO | Sequence |
|---|---|---|
| BLV1H12 FAB HC | 268 | CAGGTCCAGCTGAGAGAGAGCGGCCCTTCACTGGTCAAGCCAT CCCAGACACTGAGCCTGACATGCACAGCAAGCGGGTTTTCACT GAGCGACAAGGCAGTGGATGGGTCCGACAGGCACCAGGAAA AGCCCTGGAATGGCTGGGCAGCATCGATACCGGCGGAACACA GGGTACAATCCCGGACTGAAGAGCAGACTGTCCATTACCAAGG ACAACTCTAAAAGTCAGGTGTCACTGAGCGTGAGCTCCGTCAC CACAGAGGATAGTGCAACTTACTATTGCACCTCTGTGCACCAGG AAACTAAGAAATACCAGAGCTGTCCTGACGGCTATCGGGAGAG ATCTGATTGCAGTAATAGGCCAGCTTGTGGCACATCCGACTGTT GTCGCGTGTCTGTCTTCGGGAACTGCCTGACTACCCTGCCTGTG TCCTACTCTTATACCTACAATTATGAATGGCATGTGGATGTCTG GGGACAGGGCCTGCTGGTGACAGTCTCTAGTGCTTCCAACTG CACCAAAGGTGTACCCCTGTCAAGCTGCTGTGGGACAAATC CTCTAGTACCGTGACACTGGGATGCCTGGTCTCAAGCTATATGC |

TABLE 12-continued

Bovine IgG sequences

| Name | SEQ ID NO | Sequence |
|---|---|---|
| | | CCGAGCCTGTGACTGTCACCTGGAACTCAGGAGCCCTGAAAAG<br>CGGAGTGCACACCTTCCCAGCTGTGCTGCAGTCCTCTGGCCTGT<br>ATAGCCTGAGTTCAATGGTGACAGTCCCCGGCAGTACTTCAGG<br>GCAGACCTTCACCTGTAATGTGGCCCATCCTGCCAGCTCCACCA<br>AAGTGGACAAAGCAGTGGAACCCAAATCTTGCGACGGCAGCCA<br>TCACCATCATCATCAC |
| BLV5B8<br>FAB HC | 269 | CAGGTCCAGCTGAGAGAGAGCGGGCCTTCACTGGTCCAGCCTT<br>CACAGACACTGAGCCTGACTTGTACTGCCTCCGGGTTTTCACTG<br>TCTGACAAGGCTGTGGGATGGGTCCGACAGGCACCAGGGAAAG<br>CTCTGGAGTGGCTGGGAAGTATCGATACCGGCGGGTCAACAGG<br>GTACAACCCTGGACTGAAGTCCAGACTGTCTATTACTAAGGAC<br>AATTCTAAAAGTCAGGTGTCACTGAGCGTGAGCTCCGTCACCAC<br>AGAGGATTCTGCAACATACTATTGCACTACCGTGCACCAGGAA<br>ACAAGGAAAACTTGTAGTGACGGCTATATCGCAGTGGATAGCT<br>GCGGACGAGGACAGTCCGACGGATGCGTGAACGATTGCAATAG<br>CTGTTACTATGGATGGCGAAACTGCCGGAGACAGCCAGCAATT<br>CATTCATACGAGTTTCATGTGGATGCTTGGGGGCGGGGCTGCT<br>GGTCACCGTCTCCTCAGCTTCCACAACTGCACCAAAGGTGTACC<br>CCTGTCAAGCTGCTGTGGGGACAAATCCTCTAGTACCGTGACA<br>CTGGGATGCCTGGTCTCAAGCTATATGCCCGAGCCTGTGACTGT<br>CACCTGGAACTCAGGAGCCCTGAAAAGCGGAGTGCACACCTTC<br>CCAGCTGTGCTGCAGTCCTCTGGCCTGTATAGCCTGAGTTCAAT<br>GGTGACAGTCCCCGGCAGTACTTCAGGGCAGACCTTCACCTGTA<br>ATGTGGCCCATCCTGCCAGCTCCACCAAAGTGGACAAAGCAGT<br>GGAACCCAAATCTTGCGACGGCAGCCATCACCATCATCATCAC |
| BLV5D3<br>FAB HC | 270 | CAGGTCCAGCTGAGGGAATCCGGCCCATCACTGGTCAAGCCTT<br>CACAGACACTGAGCCTGACATGTACTGCAAGCGGGTTTTCACTG<br>AGTGACAAGGCAGTGGGATGGGTCCGGACAGCACCAGGAAAA<br>GCCCTGGAGTGGCTGGGAACCACAGATACTGGAGGATCCGCCG<br>CTTACAACCCTGGCCTGAAGTCCCGGCTGTCTATCACCAAGGAC<br>AACTCTAAAAGTCAGGTGTCACTGAGCGTGTCCAATGTCGCTAC<br>AGAAGATTCTGCAACTTACTATTGTAGCTCCGTGACTCAGAGGA<br>CCCACGTCTCTCGCAGTTGTCCAGACGGGTGCAGTGACGGAGA<br>TGGCTGCGTGGATGGATGCTGTTGCTCAGCTTACCGATGTTATA<br>CACCCCGGGGTCAGAGACCTGAGCTGCACCTCATATAGCATTAC<br>ATACACTTACGAATGGAATGTGGATGCTTGGGGACAGGGACTG<br>CTGGTGACCGTCTCTTCAGCTTCCACAACTGCACCAAAGGTGTA<br>CCCCCTGTCAAGCTGCTGTGGGGACAAATCCTCTAGTACCGTGA<br>CACTGGGATGCCTGGTCTCAAGCTATATGCCCGAGCCTGTGACT<br>GTCACCTGGAACTCAGGAGCCCTGAAAAGCGGAGTGCACACCT<br>TCCCAGCTGTGCTGCAGTCCTCTGGCCTGTATAGCCTGAGTTCA<br>ATGGTGACAGTCCCCGGCAGTACTTCAGGGCAGACCTTCACCTG<br>TAATGTGGCCCATCCTGCCAGCTCCACCAAAGTGGACAAAGCA<br>GTGGAACCCAAATCTTGCGACGGCAGCCATCACCATCATCATC<br>AC |
| BLV1H12<br>FAB HC | 271 | QVQLRESGPSLVKPSQTLSLTCTASGFSLSDKAVGWVRQAPGKAL<br>EWLGSIDTGGNTGYNPGLKSRLSITKDNSKSQVSLSVSSVTTEDSA<br>TYYCTSVHQETKKYQSCPDGYRERSDCSNRPACGTSDCCRVSVFG<br>NCLTTLPVSYSYTYNYEWHVDVWGQGLLVTVSSASTTAPKVYPL<br>SSCCGDKSSSTVTLGCLVSSYMPEPVTVTWNSGALKSGVHTFPAV<br>LQSSGLYSLSSMVTVPGSTSGQTFTCNVAHPASSTKVDKAVEPKSC<br>DGSHHHHHH |
| BLV5B8<br>FAB HC | 272 | QVQLRESGPSLVQPSQTLSLTCTASGFSLSDKAVGWVRQAPGKAL<br>EWLGSIDTGGSTGYNPGLKSRLSITKDNSKSQVSLSVSSVTTEDSAT<br>YYCTTVHQETRKTCSDGYIAVDSCGRGQSDGCVNDCNSCYYGWR<br>NCRRQPAIHSYEFHVDAWGRGLLVTVSSASTTAPKVYPLSSCCG<br>DKSSSTVTLGCLVSSYMPEPVTVTWNSGALKSGVHTFPAVLQSSG<br>LYSLSSMVTVPGSTSGQTFTCNVAHPASSTKVDKAVEPKSCDGSH<br>HHHHH |
| BLV5D3<br>FAB HC | 273 | QVQLRESGPSLVKPSQTLSLTCTASGFSLSDKAVGWVRRAPGKAL<br>EWLGTTDTGGSAAYNPGLKSRLSITKDNSKSQVSLSVSNVATEDS<br>ATYYCSSVTQRTHVSRSCPDGCSDGDGCVDGCCCSAYRCYTPGV<br>RDLSCTSYSITYTYEWNVDAWGQGLLVTVSSASTTAPKVYPLSSC<br>CGDKSSSTVTLGCLVSSYMPEPVTVTWNSGALKSGVHTFPAVLQS<br>SGLYSLSSMVTVPGSTSGQTFTCNVAHPASSTKVDKAVEPKSCDG<br>SHHHHHH |

What is claimed is:

1. An immunoglobulin fusion protein comprising a human or humanized antibody domain, a first therapeutic agent, a first extender peptide comprising a first alpha helical secondary structure, and a second extender peptide comprising a second alpha helical secondary structure; wherein the first extender peptide and the second extender peptide form an anti-parallel coiled coil; and wherein the first extender peptide, the first therapeutic agent, and the second extender peptide are positioned within the antibody domain, and the first therapeutic agent is positioned between the first extender peptide and the second extender peptide.

2. The immunoglobulin fusion protein of claim 1, further comprising a second therapeutic agent.

3. The immunoglobulin fusion protein of claim 1, wherein the first extender peptide, the first therapeutic agent, and the second extender peptide replace a portion of a light chain of the antibody domain or a portion of a heavy chain of the antibody domain.

4. The immunoglobulin fusion protein of claim 1, wherein the antibody domain comprises an amino acid sequence selected from any one of SEQ ID NOs: 19-36 and 271-273, and wherein the first extender peptide, the first therapeutic agent, and the second extender peptide replace a portion of a light chain of the antibody domain or a portion of a heavy chain of the antibody domain.

5. The immunoglobulin fusion protein of claim 1, wherein the first antibody domain comprises an amino acid sequence selected from amino acid sequences at least 90% homologous to any one of SEQ ID NOs: 19-36 and 271-273, and wherein the first extender peptide, the first therapeutic agent, and the second extender peptide replace a portion of a light chain of the antibody domain or a portion of a heavy chain of the antibody domain.

6. The immunoglobulin fusion protein of claim 1, wherein the antibody domain comprises a trastuzumab antibody or antigen binding fragment thereof, and wherein the first extender peptide, the first therapeutic agent, and the second extender peptide replace a portion of a light chain of the trastuzumab antibody or antigen binding fragment thereof or a portion of a heavy chain of the trastuzumab antibody or antigen binding fragment thereof.

7. The immunoglobulin fusion protein of claim 1, wherein the first antibody domain comprises a palivizumab antibody or antigen binding fragment thereof, and wherein the first extender peptide, the first therapeutic agent, and the second extender peptide replace a portion of a light chain of the palivizumab antibody or antigen binding fragment thereof or a portion of a heavy chain of the palivizumab antibody or antigen binding fragment thereof.

8. The immunoglobulin fusion protein of claim 1, further comprising a second antibody domain.

9. The immunoglobulin fusion protein of claim 1, wherein
   a) the first antibody domain comprises trastuzumab or an antigen binding fragment thereof; and
   b) the first therapeutic agent comprises an elafin peptide.

10. The immunoglobulin fusion protein of claim 9, wherein the first extender peptide, the elafin peptide, and the second extender peptide replace a portion of a trastuzumab heavy chain.

11. The immunoglobulin fusion protein of claim 9, wherein:
   a) a light chain of trastuzumab is represented by an amino acid sequence at least 90% homologous to SEQ ID NOS: 19;
   b) an amino terminal region of a heavy chain of trastuzumab is represented by an amino acid sequence at least 90% homologous to SEQ ID NO: 23;
   c) a carboxy terminal region of a heavy chain of trastuzumab is represented by an amino acid sequence at least 90% homologous to SEQ ID NO: 24; and
   d) the elafin peptide is represented by an amino acid sequence of SEQ ID NO: 258, or an amino acid sequence at least 90% homologous to SEQ ID NO: 258, wherein the elafin peptide is grafted between the amino terminal region of the heavy chain of trastuzumab and the carboxy terminal region of the heavy chain of trastuzumab to produce a trastuzumab heavy chain fusion that pairs with the light chain of trastuzumab.

12. The immunoglobulin fusion protein of claim 9, comprising a polypeptide represented by a sequence that is at least 90% homologous to SEQ ID NO: 85.

13. The immunoglobulin fusion protein of claim 1, wherein the antibody domain comprises a variable domain.

* * * * *

UNITED STATES PATENT AND TRADEMARK OFFICE
CERTIFICATE OF CORRECTION

Page 1 of 1

PATENT NO. : 10,683,353 B2
APPLICATION NO. : 14/903492
DATED : June 16, 2020
INVENTOR(S) : Feng Wang It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 142 days.

Signed and Sealed this
Sixth Day of December, 2022

Katherine Kelly Vidal
*Director of the United States Patent and Trademark Office*